US011066459B2

(12) United States Patent
Capon

(10) Patent No.: US 11,066,459 B2
(45) Date of Patent: Jul. 20, 2021

(54) HYBRID IMMUNOGLOBULIN CONTAINING NON-PEPTIDYL LINKAGE

(71) Applicant: Biomolecular Holdings LLC, Burlingame, CA (US)

(72) Inventor: Daniel J. Capon, Hillsborough, CA (US)

(73) Assignee: BIOMOLECULAR HOLDINGS LLC, Burlingame, CA (US)

( * ) Notice: Subject to any disclaimer, the term of this patent is extended or adjusted under 35 U.S.C. 154(b) by 0 days.

(21) Appl. No.: 15/125,774

(22) PCT Filed: Mar. 13, 2015

(86) PCT No.: PCT/US2015/020458
§ 371 (c)(1),
(2) Date: Sep. 13, 2016

(87) PCT Pub. No.: WO2015/138907
PCT Pub. Date: Sep. 17, 2015

(65) Prior Publication Data
US 2017/0008950 A1    Jan. 12, 2017

Related U.S. Application Data

(60) Provisional application No. 61/953,650, filed on Mar. 14, 2014.

(51) Int. Cl.
| | |
|---|---|
| *C07K 16/00* | (2006.01) |
| *C07K 16/24* | (2006.01) |
| *A61K 47/68* | (2017.01) |
| *C07K 16/46* | (2006.01) |

(52) U.S. Cl.
CPC .......... *C07K 16/00* (2013.01); *A61K 47/6801* (2017.08); *A61K 47/6855* (2017.08); *A61K 47/6875* (2017.08); *A61K 47/6889* (2017.08); *C07K 16/241* (2013.01); *C07K 16/46* (2013.01); *C07K 2317/21* (2013.01); *C07K 2317/52* (2013.01); *C07K 2317/55* (2013.01); *C07K 2317/76* (2013.01)

(58) Field of Classification Search
CPC ................ A61K 47/68; A61K 47/6801; A61K 47/6855; A61K 47/6875; A61K 47/6889
See application file for complete search history.

(56) References Cited

U.S. PATENT DOCUMENTS

| | | | |
|---|---|---|---|
| 9,725,503 B2 | 8/2017 | Capon | |
| 2005/0027109 A1* | 2/2005 | Mezo | C07K 14/475 530/391.1 |
| 2008/0254512 A1 | 10/2008 | Capon | |
| 2009/0042291 A1 | 2/2009 | Chu et al. | |
| 2010/0104589 A1 | 4/2010 | Govindan et al. | |
| 2011/0178242 A1 | 7/2011 | Harris et al. | |
| 2011/0268654 A1* | 11/2011 | Hilderbrand | A61K 49/0019 424/1.11 |
| 2011/0293632 A1 | 12/2011 | Presta | |
| 2012/0034161 A1* | 2/2012 | Robillard | A61K 51/0495 424/1.49 |
| 2012/0308584 A1 | 12/2012 | Kim et al. | |
| 2013/0164286 A1 | 6/2013 | Chou et al. | |
| 2015/0183858 A1 | 7/2015 | Capon | |
| 2016/0024226 A1 | 1/2016 | Capon | |
| 2016/0376601 A1 | 12/2016 | Capon | |
| 2017/0342142 A1* | 11/2017 | Capon | C07K 7/06 |

FOREIGN PATENT DOCUMENTS

| | | |
|---|---|---|
| WO | WO 99/02711 A2 | 1/1999 |
| WO | WO 2006/063042 A2 | 6/2006 |
| WO | WO 2007/048127 A2 | 4/2007 |
| WO | WO 2010/045193 A1 | 4/2010 |
| WO | WO 2012/012612 A2 | 1/2012 |
| WO | WO 2012/125973 A2 | 9/2012 |
| WO | WO 2012/153193 A2 | 11/2012 |
| WO | WO 2012/156918 A1 | 11/2012 |
| WO | WO 2013/003555 A1 | 1/2013 |
| WO | WO 2013/006706 A1 | 1/2013 |

(Continued)

OTHER PUBLICATIONS

Stöckmann et al. (Chem. Common., 2011 46: 7203-7205) (Year: 2011).*
PCT International Search Report dated Oct. 10, 2014 in connection with PCT International Application No. PCT/US14/29511, filed Mar. 13, 2014.
Written Opinion of the International Searching Authority, dated Oct. 10, 2014 in connection with PCT International Application No. PCT/US14/29511, filed Mar. 13, 2014.
Jain, P. K., Karunakaran, D., & Friedman, S. H. (2013). Construction of a photoactivated insulin depot. *Angewandte Chemie*, 125(5), 1444-1449.
Extended European Search Report dated Oct. 11, 2016 in connection with European Patent Application No. 14763801.9.

(Continued)

*Primary Examiner* — Peter J Reddig
(74) *Attorney, Agent, or Firm* — John P. White

(57) ABSTRACT

The present invention provides a compound having the structure:

A-B - - - Z wherein A is a biologically active structure of the compound; wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a sequence selected from the group consisting of a cysteine or selenocysteine; wherein the dashed line between B and Z represents a peptidyl linkage; and wherein the solid line between A and B represents a nonpeptidyl linkage, as well as intermediates dimers thereof, and processes of producing the compounds of the invention.

15 Claims, 67 Drawing Sheets

Specification includes a Sequence Listing.

(56) References Cited

FOREIGN PATENT DOCUMENTS

| WO | WO 2013/065343 | | 5/2013 | | |
|----|----|----|----|----|----|
| WO | WO-2013065343 | A1 * | 5/2013 | ............... | C07K 7/06 |
| WO | WO 2014/014563 | A1 | 1/2014 | | |
| WO | WO 2014/144911 | A2 | 9/2014 | | |
| WO | WO 2015/138907 | A2 | 9/2015 | | |

OTHER PUBLICATIONS

Debets, M. F., Van Berkel, S. S., Dommerholt, J., Dirks, A. T. J., Rutjes, F. P., & Van Delft, F. L. (2011). Bioconjugation with strained alkenes and alkynes. *Accounts of chemical research*, 44(9), 805-815.
Capon, D. J. et al (2011). Flexible antibodies with nonprotein hinges. *Proceedings of the Japan Academy, Series B*, 87(9), 603-616.
Elias, D. R., Cheng, Z., & Tsourkas, A. (2010). An Intein-Mediated Site-Specific Click Conjugation Strategy for Improved Tumor Targeting of Nanoparticle Systems. *Small*, 6(21), 2460-2468.
Communication pursuant to Rule 70(2) and 70a(2) EPC dated Oct. 28, 2016 in connection with European Patent Application No. 14763801.9.
Response to Communication pursuant to Rule 70(2) and 70a(2) EPC filed May 5, 2017 in connection with European Patent Application No. 14763801.9.
Communication pursuant to Rule 94(3) EPC dated Dec. 22, 2017 in connection with European Patent Application No. 14763801.9.
First Office Action dated Mar. 13, 2018 in connection with Japanese Patent Application 2016-503119 and its English translation.
Response to First Office Action filed Aug. 2, 2018 in connection with Japanese Patent Application 2016-503119 including English language version thereof.
Thomas et al. (2012). Application of Strain-Promoted Azide-Alkyne Cycloaddition and Tetrazine Ligation to Targeted Fc-Drug Conjugates. Bioconjug Chem. 23(10):2007-2013.
Oct. 6, 2017 Extended European Search Report issued in connection with European Patent Application No. 15760986.8.
Oct. 24, 2017 Communication pursuant to Rules 70(2)and 70a(2) EPC issued in connection with European Patent Application No. 15760986.8.
Response dated Oct. 24, 2017 Communication pursuant to Rule 70(2) and 70a(2) EPC filed May 3, 2018 in connection with European Patent Application No. 15760986.8.
Communication pursuant to Rule 94(3) EPC dated Aug. 2, 2018 in connection with European Patent Application No. 15760986.8.

PCT International Search Report dated Mar. 13, 2015 in connection with PCT International Application No. PCT/US2015/020458.
Debets, M. F., van Berkel, S. S., Schoffelen, S., Rutjes, F. P., van Hest, J. C., & van Delft, F. L. (2010). Aza-dibenzocyclooctynes for fast and efficient enzyme PEGylation via copper-free (3+2) cycloaddition. Chemical communications, 46(1), 97-99.
Van Geel, R. et al. (2012). Preventing thiol-yne addition improves the specificity of strain-promoted azide-alkyne cycloaddition. Bioconjugate chemistry, 23(3), 392-398.
Second Office Action dated Dec. 11, 2019 in connection with Japanese Patent Application 2016-503119 and its English translation.
Uniprot database entry for IGHG1_Human, [online], Jan. 9, 2013, AC P01857, URL, https://www.uniprot.org/uniprot/P01857.txt?version=139.
Response to Second Office Action filed Jun. 10, 2019 in connection with Japanese Patent Application 2016-503119 including English language version.
Feb. 19, 2019 First Office Action issued in connection with Japanese Patent Application No. 2016-575635 including English translation thereof.
Apr. 1, 2019 Office Action issued in connection with Chinese Patent Application No. 2015800262346 including English translation thereof.
Aug. 19, 2019 Response to First Office Action filed in connection with Japanese Patent Application No. 2016-575635 including English version thereof.
Jan. 14, 2020 Second Office Action issued in connection with Japanese Patent Application No. 2016-575635 including English translation thereof.
Oct. 12, 2019 Response to Apr. 1, 2019 Office Action filed in connection with Chinese Patent Application No. 2015800262346 including English version thereof.
Jan. 22, 2020 First Examination Report issued in connection with Australian Patent Application No. 2015229186.
Jun. 18, 2020 Office Action issued in connection with Israeli application No. 270364, including English language translation thereof.
Official Communication 6437 issued in connection with Mexican application No. MX/a/2016/011934 and English summary thereof.
Jun. 22, 2020 Extended European Search Report issued in connection with European Patent application No. 19213331.2.
Selvaraj R and Fox J. "Trans-Cyclooctene—a stable, voracious dienophile for bioorthogonal labeling" Current Opinions in Chemical Biology 17.5 (2013): 753-760.
Oct. 20, 2020 Office Action issued in connection with Chinese Patent Application No. 201580026234.6, including English language translation thereof.

* cited by examiner

TNR1B (SEQ ID NO: 204)
LPAQVAFTPY APEPGSTCRL REYYDQTAQM CCSKCSPGQH
AKVFCTKTSD TVCDSCEDST YTQLWNWVPE CLSCGSRCSS
DQVETQACTR EQNRICTCRP GWYCALSKQE GCRLCAPLRK
CRPGFGVARP GTETSDVVCK PCAPGTFSNT TSSTDICRPH
QICNVVAIPG NASMDAVCTS TSPTRSMAPG AVHLPQPVST
RSQHTQPTPE PSTAPSTSFL LPMGPSPPAE GSTGDGC

Fc6 (SEQ ID NO: 205)
CPPCPAPELL GGPSVFLFPP KPKDTLMISR TPEVTCVVVD
VSHEDPEVKF NWYVDGVEVH NAKTKPREEQ YNSTYRVVSV
LTVLHQDWLN GKEYKCKVSN KALPAPIEKT ISKAKGQPRE
PQVYTLPPSR DELTKNQVSL TCLVKGFYPS DIAVEWESNG
QPENNYKTTP PVLDSDGSFF LYSKLTVDKS RWQQGNVFSC
SVMHEALHNH YTQKSLSLSP GK

TNR1B-Alk-Az-DKTHT-Fc6

Figure 11

Exhibit A

Fab'-PEGy-Alk + Az-PEGx-DKTHT-Fc6

(DKTHT = SEQ ID NO:220)

HYBRID IMMUNOGLOBULIN CONTAINING NON-PEPTIDYL LINKAGE

CROSS-REFERENCE TO RELATED APPLICATIONS

This application is a § 371 national stage of PCT International Application No. PCT/US2015/020458, filed Mar. 13, 2015, claiming the benefit of U.S. Provisional Application No. 61/953,650, filed Mar. 14, 2014, the content of each of which is hereby incorporated by reference into the application.

REFERENCE TO A SEQUENCE LISTING

This application incorporates-by-reference nucleotide and/or amino acid sequences which are present in the file named "201110_86150-PCT-US_Substitute_Sequence_Listing_DH.txt", which is 507 kilobytes in size, and which was created Nov. 10, 2020 in the IBM-PC machine format, having an operating system compatibility with MS-Windows, which is contained in the text file filed Nov. 10, 2020 as part of this application.

Throughout this application, various publications are referenced. The disclosures of all referenced publications in their entireties are hereby incorporated by reference into this application in order to more fully describe the state of the art to which this invention pertains.

BACKGROUND OF THE INVENTION

Proteins prefer to form compact globular or fibrous structures, minimizing their exposure to solvent. This tendency is inherent both in the polypeptide backbone with its propensity for hydrogen-bonded secondary structure, and in side chain interactions that promote tertiary folding. Thus, previous efforts to introduce "flexibility" into antibodies using peptides have been largely inadequate. For example, it is common to employ combinations of an amino acid that favors solvent interactions (e.g., serine) with one that breaks up helical structure (e.g., glycine). While this approach is useful in making fusion proteins such as single-chain antibody fragments (scFv), the resulting structures are actually quite compact with no evidence of extendibility (for example, see Robert et al, (2009) Engineered antibody intervention strategies for Alzheimer's disease and related dementias by targeting amyloid and toxic oligomers. Protein Eng. Des. Sel. 22, 199-208). Furthermore, such sequences are likely to create additional problems due to their intrinsic immunogenicity and proteolytic susceptibility.

There is a need for new protein compounds, incorporating nonprotein chains, that are both flexible and extendible, as well as processes for producing such compounds.

SUMMARY OF THE INVENTION

The present invention provides a compound having the structure:

wherein A is a biologically active structure of the compound;

wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a cysteine or a selenocysteine;

wherein B is a chemical structure linking A and Z;

wherein the dashed line between B and Z represents a peptidyl linkage; and wherein the solid line between A and B represents a nonpeptidyl linkage.

The present invention also provides a compound having the structure:

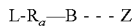

wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a cysteine or a selenocysteine;

wherein B is a chemical structure linking $R_a$ and C;

wherein the dashed line between B and Z represents a peptidyl linkage;

wherein L is selected from the group consisting of: —$N_3$, an alkyne, a

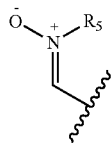

group in which $R_5$ is an alkyl or aryl group, a

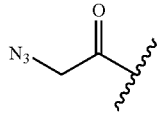

group, a tetrazine and a trans-cyclooctene; and wherein $R_a$ is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

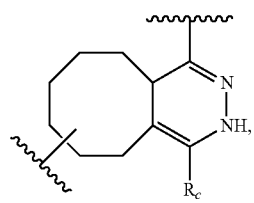

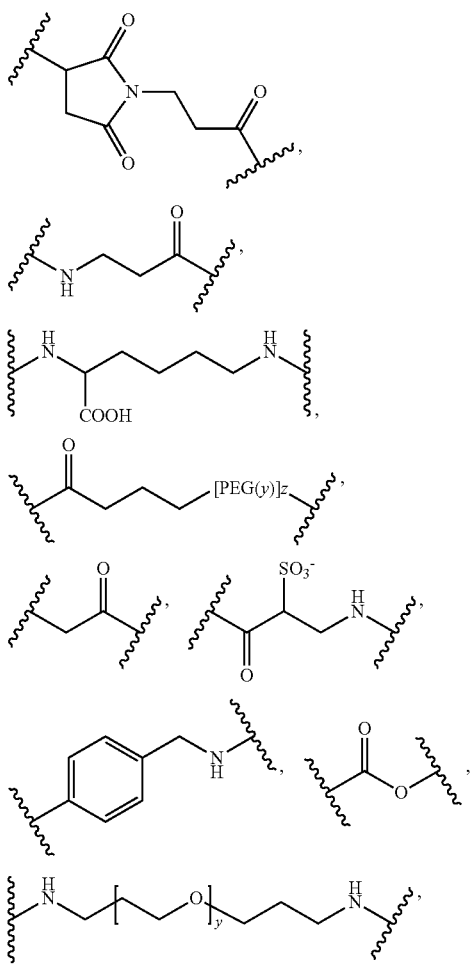

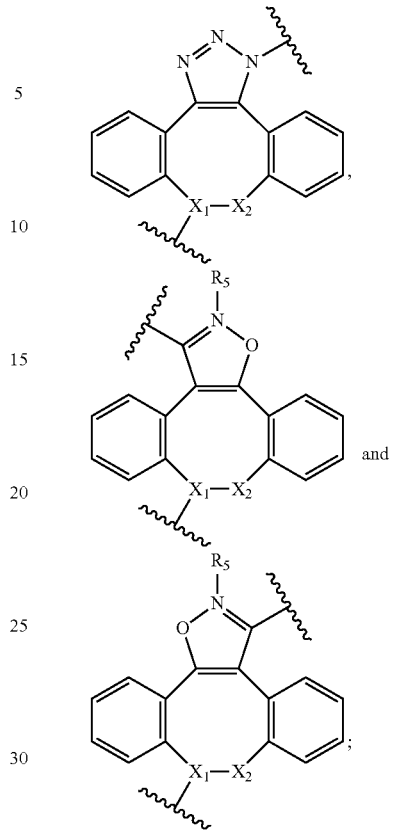

wherein $X_1$ is CH or N, $X_2$ is $CH_2$ or a carbonyl group, and $R_5$ is an aryl or alkyl group;

wherein [PEG(y)]z is:

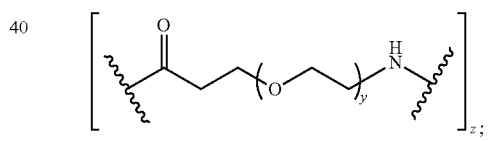

wherein y=1-100 and z=1-10.

The present invention also provides a process for producing a compound having the structure:

A-B - - - Z wherein A is a biologically active structure of the compound;

wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a cysteine or a selenocysteine;

wherein B is a chemical structure linking A and Z;

wherein the dashed line between B and Z represents a peptidyl linkage;

wherein the solid line between A and B represents a nonpeptidyl linkage;

which comprises the following steps:

a) obtaining an A' which comprises A or a derivative of A, and a first terminal reactive group;

b) obtaining a B' which comprises B or a derivative of B, a second terminal reactive group and a third terminal reactive group, wherein the second terminal reactive group is capable of reacting with the first terminal reactive group to form a non-peptidyl linkage;

c) obtaining a Z' which comprises Z or a derivative of Z, and a fourth terminal reactive group, wherein the fourth terminal reactive group is capable of reacting with the third terminal reactive group to form a peptidyl linkage; and d) reacting A', B' and Z' in any order to produce the compound.

BRIEF DESCRIPTION OF THE DRAWINGS

FIG. 11 shows tryptic peptides identified by LC/MS in the TNR1B-alkyne-azide-DKTHT-Fc6 product (Mr ~75,000) of FIG. 10. The underlined peptide sequences are those identified by LC/MS that are derived from the parent TNR1B (upper, SEQ ID NO: 204) and Fc6 (lower, SEQ ID NO: 205) sequences. DKTHT is SEQ ID NO: 220.

DETAILED DESCRIPTION OF THE INVENTION

Figure 1:
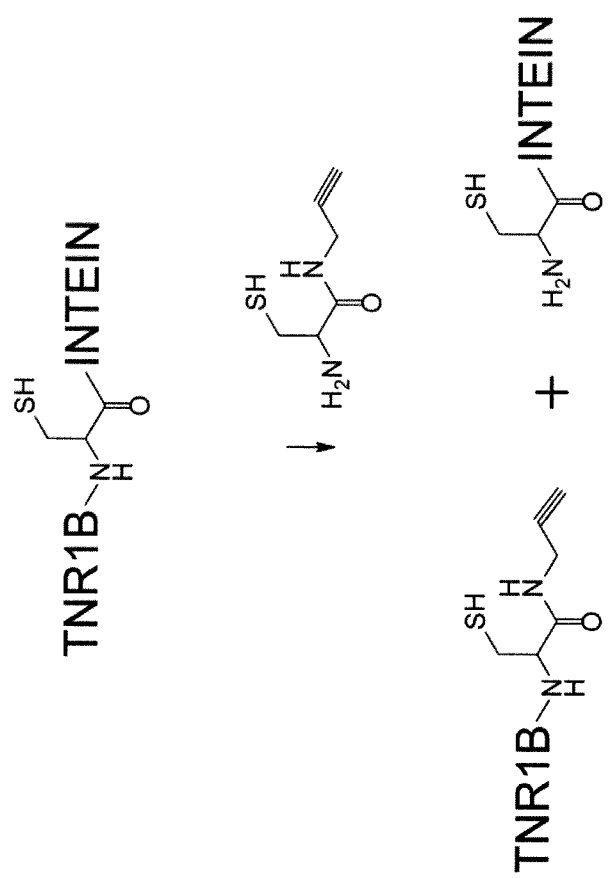
FIG. 1 shows the preparation of alkyne-modified TNR1B by cleavage of a TNR1B-intein fusion protein with cystyl-propargylamide. The intein by-product is removed by chitin chromatography. Azide-modified TNR1B and cycloalkyne-modified TNR1B are similarly prepared using cystyl-3-azidopropylamide, and various cyclooctyne (eg. DIBAC) derivatives of cysteine, respectively.

The present invention provides a compound having the structure:

A-B - - - Z wherein A is a biologically active structure of the compound;

wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a cysteine or a selenocysteine;

wherein B is a chemical structure linking A and Z;

wherein the dashed line between B and Z represents a peptidyl linkage; and wherein the solid line between A and B represents a nonpeptidyl linkage.

In some embodiments, the cysteine or selenocysteine naturally occurs in the stretch of consecutive amino acids. In some embodiments, the cysteine or selenocysteine does not naturally occur in the stretch of consecutive amino acids.

In some embodiments, the consecutive amino acids have at their N-terminus a sequence selected from the group consisting of a cysteine, selenocysteine, CP, CPXCP (where X=P, R, or S) (SEQ ID NOs: 206-208), CDKTHTCPPCP (SEQ ID NO: 209), CVECPPCP (SEQ ID NO: 210), CCVECPPCP (SEQ ID NO: 211) and CDTPPPCPRCP (SEQ ID NO: 212).

In some embodiments, the $F_c$ domain of an antibody is a naturally occurring $F_c$ domain of an antibody.

In some embodiments, the $F_c$ domain of an antibody is a variant $F_c$ domain of an antibody.

In some embodiments, the variant $F_c$ domain of an antibody is a mutated $F_c$ domain of an antibody.

In some embodiments, the mutated $F_c$ domain is a substitution mutant.

In some embodiments, the substitution mutant has an amino acid substitution at the N-terminus, the C-terminus, or at a position of the $F_c$ domain other than the N-terminus or the C-terminus.

In some embodiments, the substitution mutant has 1, 2, 3, 4, 5, 6, 7, 8, 9, 10, 10-15, 15-20, 10-20, or 20-50 amino acid sustitutions in the stretch of consecutive amino acids thereof.

In some embodiments, the substitutions are conservative amino acid substitutions.

In some embodiments, the mutated mutated $F_c$ domain is an amino acid addition mutant.

In some embodiments, the amino acid addition mutant has 1, 2, 3, 4, 5, 6, 7, 8, 9, 10, 10-15, 15-20, 10-20, or 20-50 added amino acids in the stretch of consecutive amino acids thereof.

In some embodiments, the mutated $F_c$ domain is an amino acid deletion mutant.

In some embodiments, the amino acid deletion mutant has 1, 2, 3, 4, 5, 6, 7, 8, 9, 10, 10-15, 15-20, 10-20, or 20-50 deleted amino acids in the stretch of consecutive amino acids thereof.

In some embodiments, the consecutive amino acids are identical to a stretch of at least 0, 20, 30, 40, 50, 60, 70, 80, 90, 100, 110, 120, 130, 140, 150, 160, 170, 180, or 190 consecutive amino acids present in the chain of the $F_c$ domain of the antibody.

In some embodiments, the consecutive amino acids are identical to the stretch of amino acids in the hinge region, the CH2 region or the CH3 region of the Fc domain, or a portion thereof.

In some embodiments, the solid line between A and B represents a nonpeptidyl linkage comprising the structure:

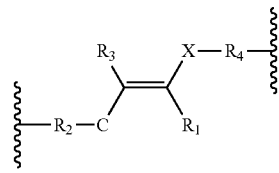

wherein

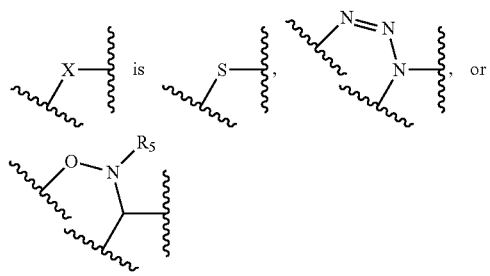

in which $R_5$ is an alkyl or aryl group wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond;

with the proviso that if

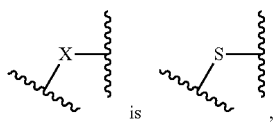

$R_3$ is a H; if

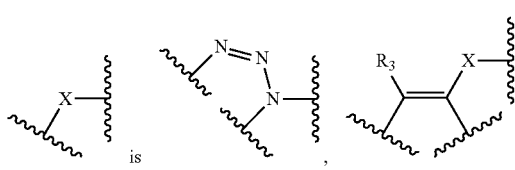

is a triazole ring that comprises

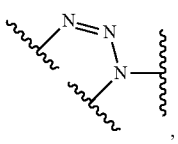 [SMILES: */N=N\N(*)*]

and if

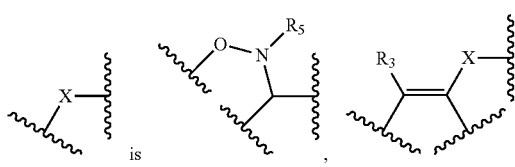

is a N-alkyl or aryl substituted isoxazoline ring that comprises

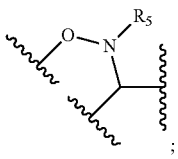

and wherein $R_2$ represents an organic structure which connects to one of A or B and $R_4$ represents an organic structure which connects to the other of A or B.

In some embodiments, the solid line between A and B represents a nonpeptidyl linkage comprising the structure:

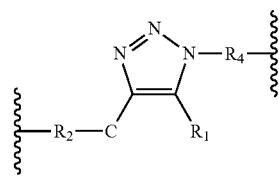

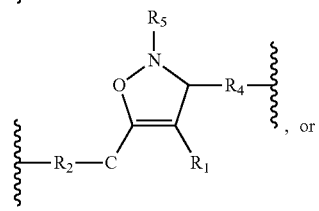

, or

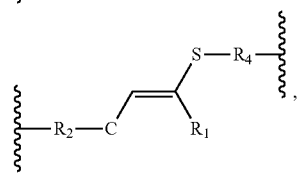

, wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, the solid line between A and B represents a nonpeptidyl linkage comprising the structure:

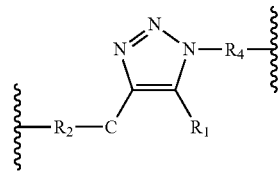

wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, the solid line between A and B represents a nonpeptidyl linkage comprising the structure:

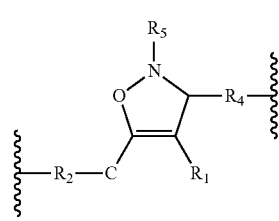

wherein $R_1$ is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, the solid line between A and B represents a nonpeptidyl linkage comprising the structure:

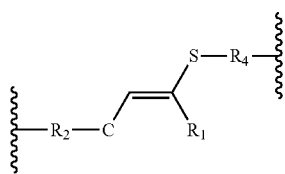

wherein $R_1$ is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond.

In some embodiments, $R_1$ and $R_2$ are linked via at least one direct bond so as to form a cyclic structure comprising i) a portion of $R_1$, ii) a portion of $R_2$, iii) the carbon between $R_2$ and the alkene double bond, and iv) the alkene double bond.

In some embodiments, $R_1$ is selected from the group consisting of:

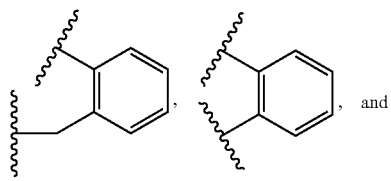

which is optionally substituted at any position.

In some embodiments, $R_1$ is

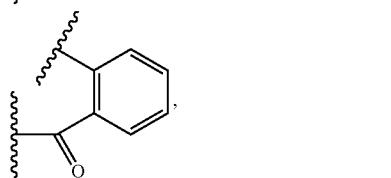

which is optionally substituted at any position.

In some embodiments, $R_1$ is

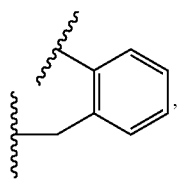 [SMILES: *Cc1ccccc1*]

which is optionally substituted at any position.

In some embodiments, $R_1$ is

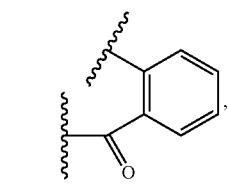 [SMILES: *C(=O)c1ccccc1*]

which is optionally substituted at any position.

In some embodiments, the carbon between $R_2$ and the alkene double bond is:

(i) directly bonded to $R_2$ with a single bond and substituted with two substituents independently selected from the group consisting of hydrogen, halogen, optionally substituted benzyl, optionally substituted alkyl or optionally substituted alkoxy; or (ii) directly bonded to $R_2$ via a double bond and a single bond.

In some embodiments, the carbon between $R_2$ and the alkene double bond is substituted with two hydrogens and directly bonded to $R_2$ with a single bond.

In some embodiments, the carbon between $R_2$ and the alkene double bond is directly bonded to $R_2$ via a double bond and a single bond.

In some embodiments, the carbon between $R_2$ and the alkene double bond is directly bonded to $R_2$ via a double bond and a single bond so as to form a phenyl ring which is optionally substituted at any position.

In some embodiments, $R_2$ is

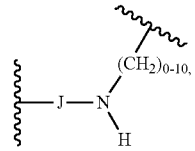

wherein $R_2$ is attached to A or B via J, and wherein J is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

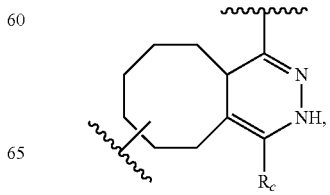

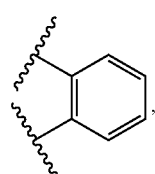

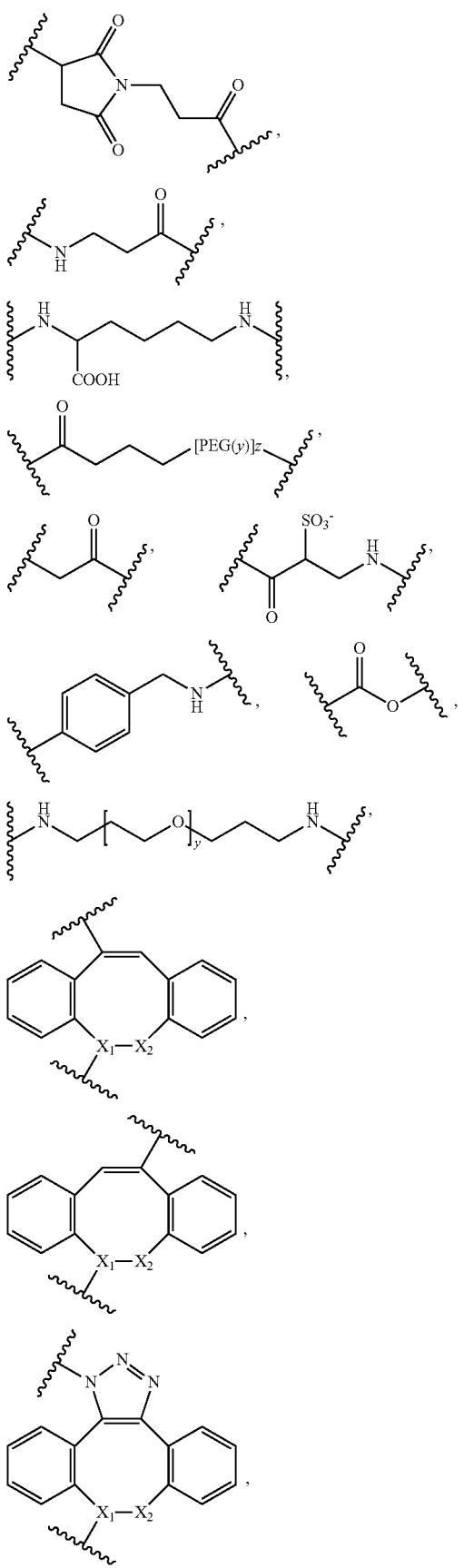

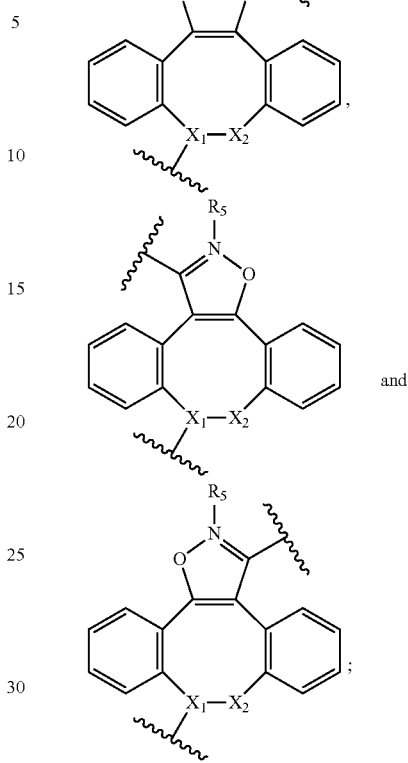

wherein $X_1$ is CH or N, $X_2$ is $CH_2$ or a carbonyl group, and $R_5$ is an aryl or alkyl group;

wherein $[PEG(y)]z$ is:

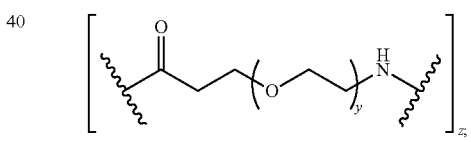

wherein y=1-100 and z=1-10.

In some embodiments, $R_2$ is

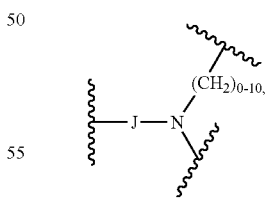

wherein $R_2$ is attached to A or B via J, and wherein $R_2$ is attached to $R_1$ via the nitrogen atom of $R_2$, and wherein J is a bond or an organic structure comprising or consisting of a chain of 1, 2, 3, 4, 5, 6, 7, 8, 9, 10 or more moieties, wherein each moiety is independently selected from the group consisting of $[PEG(y)]z$, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

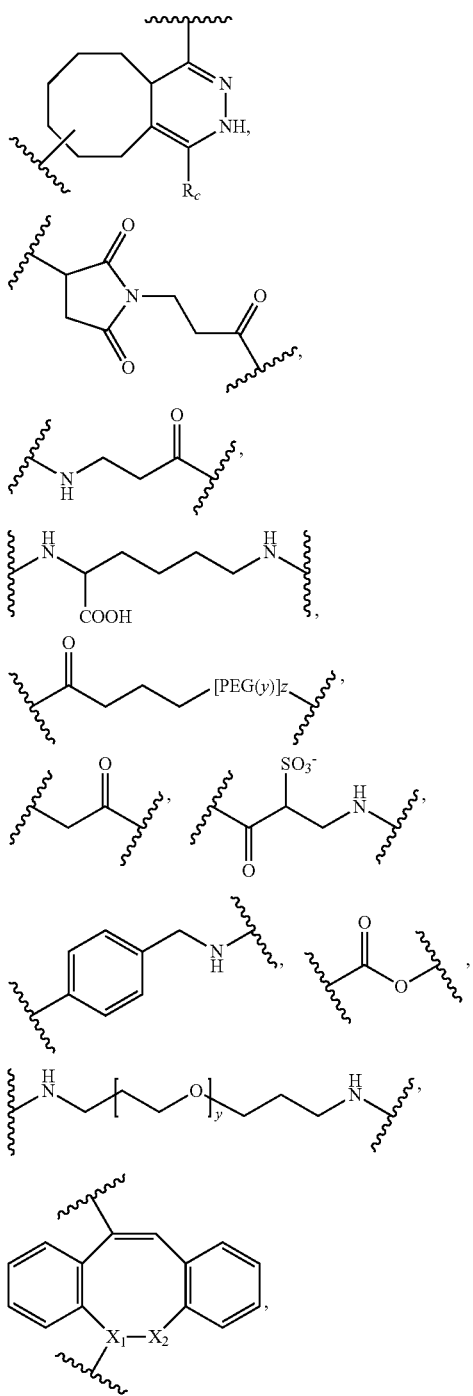

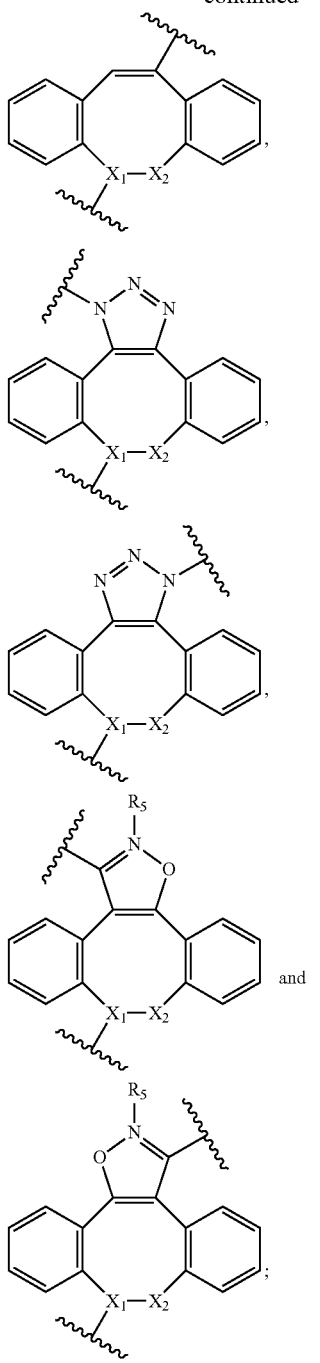

wherein $X_1$ is CH or N, $X_2$ is $CH_2$ or a carbonyl group, and $R_5$ is an aryl or alkyl group;

wherein [PEG(y)]z is:

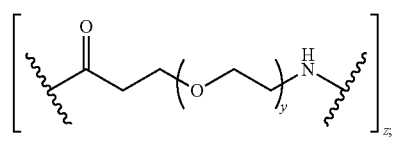

wherein y=1-100 and z=1-10.

In some embodiments, $R_2$ is

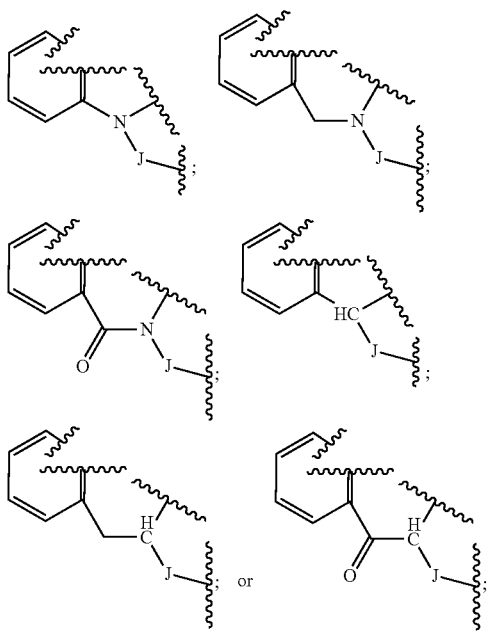

which is optionally substituted at any position,
wherein $R_2$ is attached to $R_1$ via the nitrogen or carbon atom of $R_2$,
wherein $R_2$ is attached to A or B via J,
and
wherein J is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

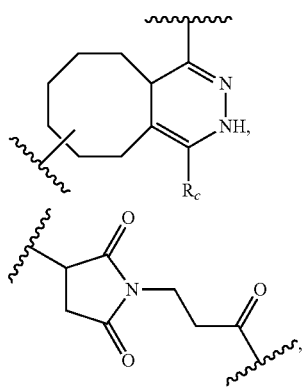

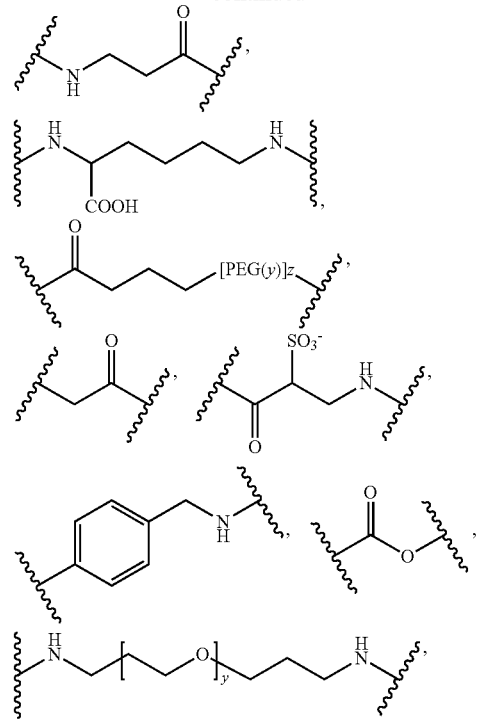

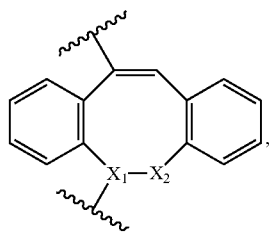

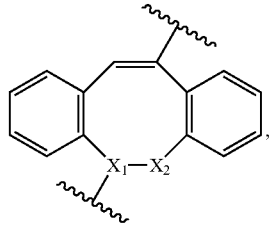

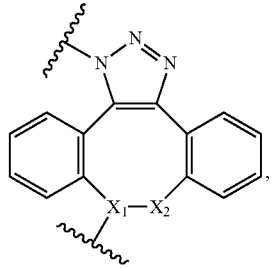

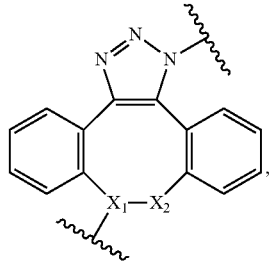

-continued

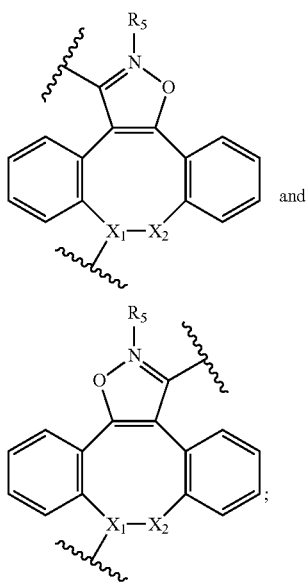

and wherein $X_1$ is CH or N, $X_2$ is $CH_2$ or a carbonyl group, and $R_5$ is an aryl or alkyl group;

wherein [PEG(y)]z is:

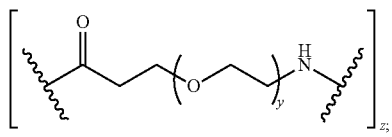

wherein y=1-100 and z=1-10.

In some embodiments, $R_2$ is

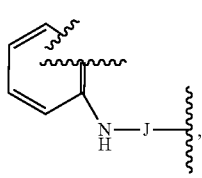

which is optionally substituted at any position.

In some embodiments, $R_2$ is

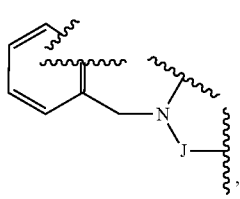

which is optionally substituted at any position.

In some embodiments, $R_2$ is

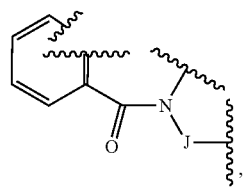

which is optionally substituted at any position.

In some embodiments, $R_2$ is

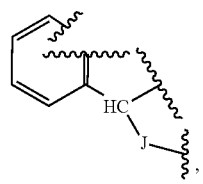

which is optionally substituted at any position.

In some embodiments, $R_2$ is

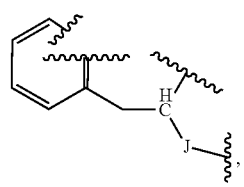

which is optionally substituted at any position.

In some embodiments, $R_2$ is

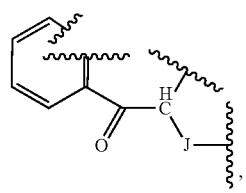

which is optionally substituted at any position.

In some embodiments, $R_1$ and $R_2$ taken together are:

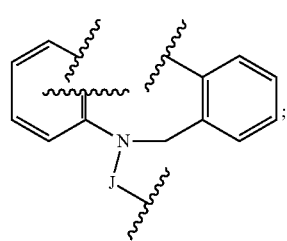

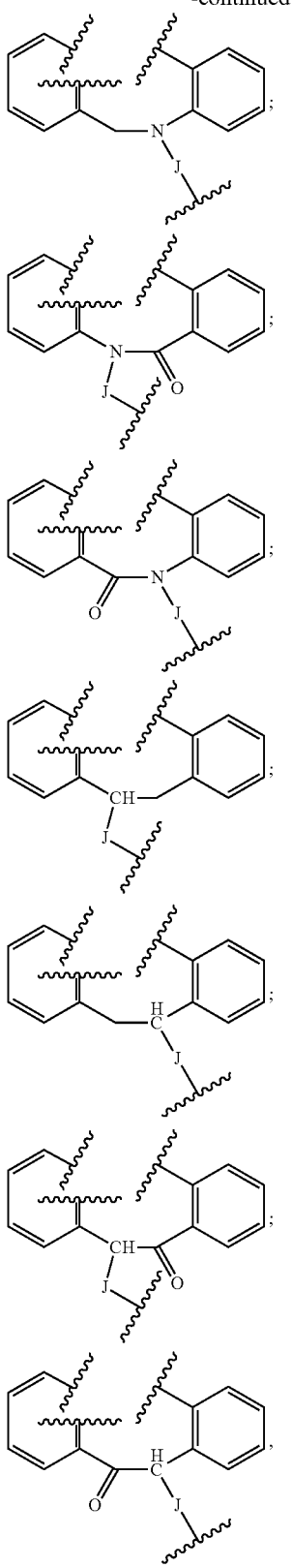

which is optionally substituted at any position,
wherein J is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

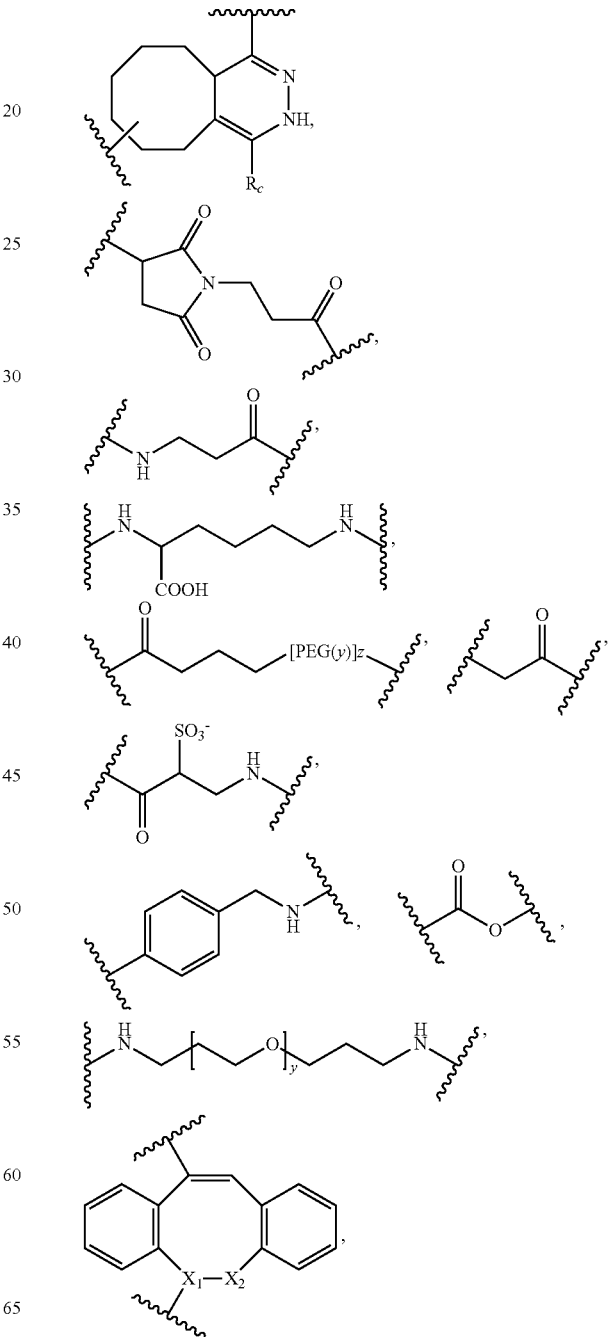

-continued

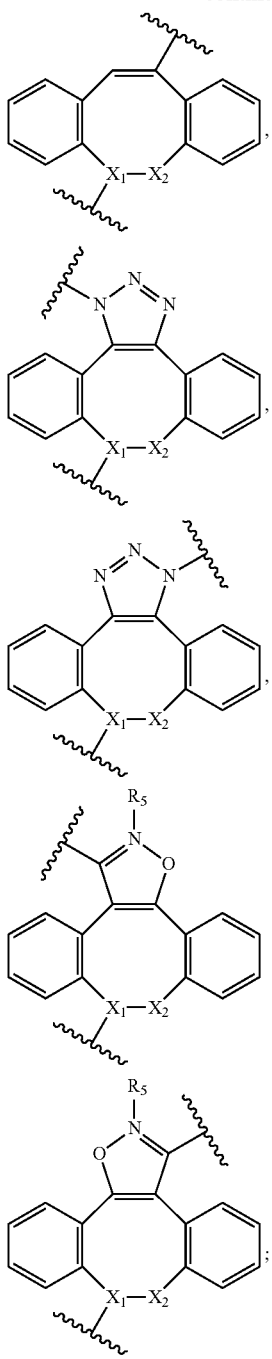

wherein $X_1$ is CH or N, $X_2$ is $CH_2$ or a carbonyl group, and $R_5$ is an aryl or alkyl group;

wherein [PEG(y)]z is:

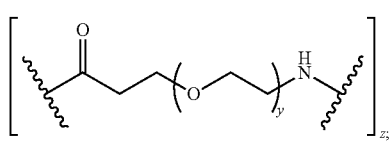

wherein y=1-100 and z=1-10.

In some embodiments, $R_1$ and $R_2$ taken together are

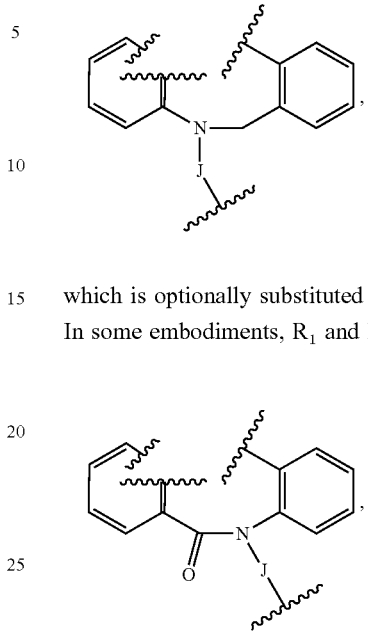

which is optionally substituted at any position.

In some embodiments, $R_1$ and $R_2$ taken together are

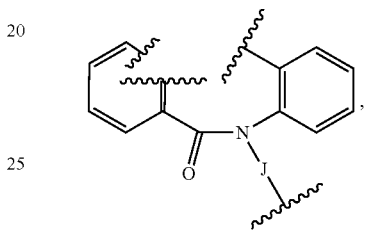

which is optionally substituted at any position.

In some embodiments, the solid line between A and B represents a nonpeptidyl linkage comprising the structure:

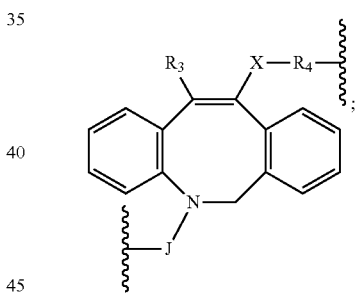

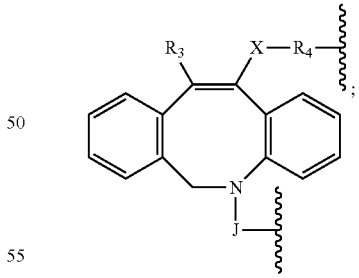

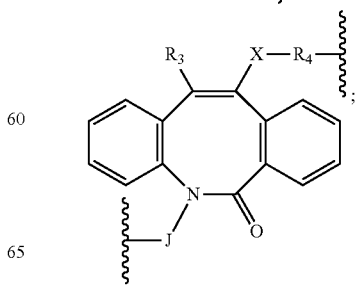

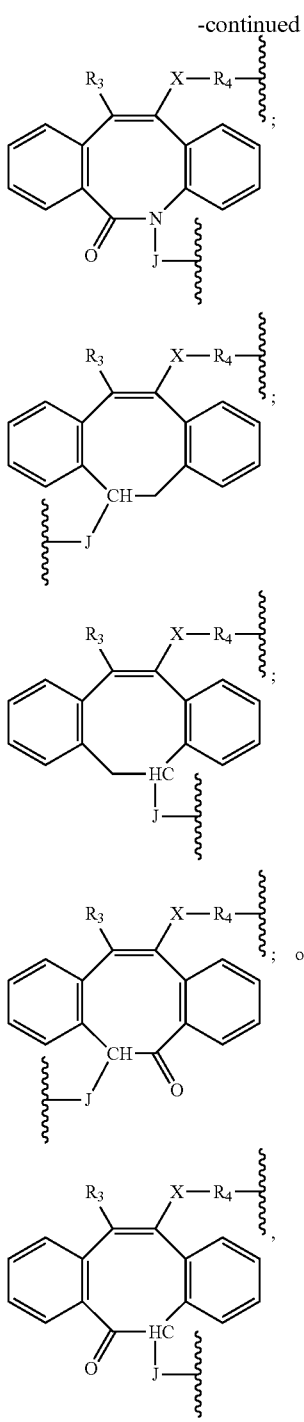

which is optionally substituted at any position, wherein J is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

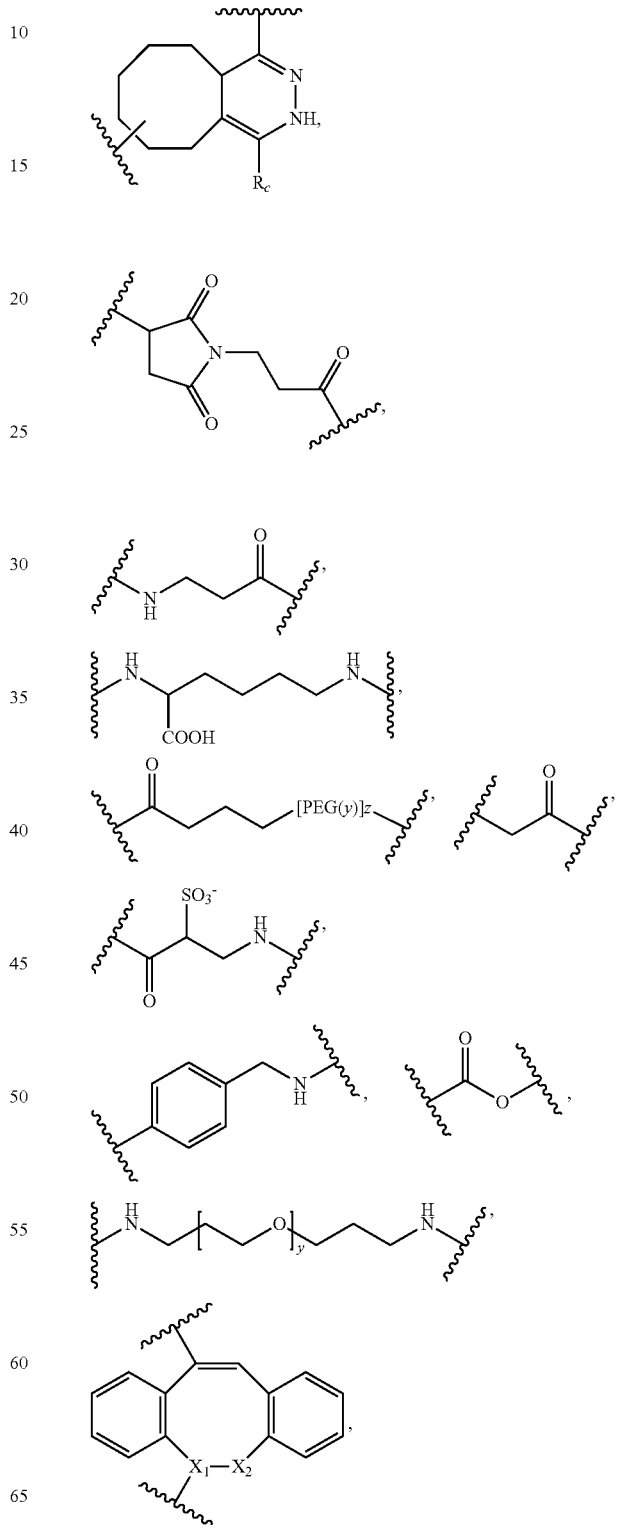

-continued

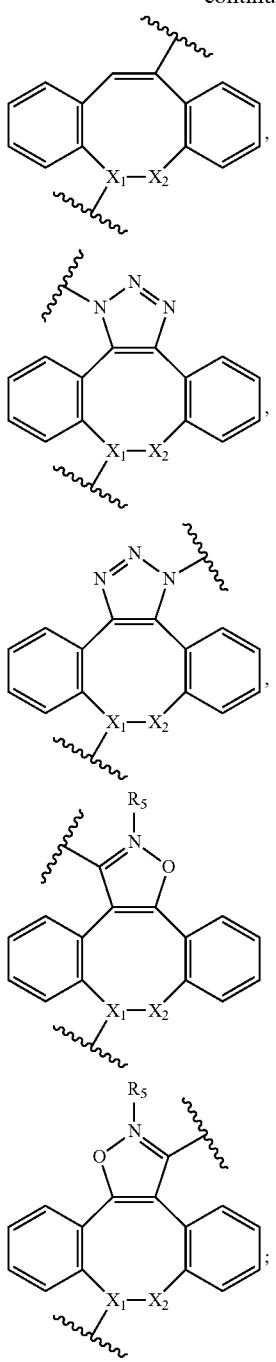

wherein $X_1$ is CH or N, $X_2$ is $CH_2$ or a carbonyl group, and $R_5$ is an aryl or alkyl group;
wherein [PEG(y)]z is:

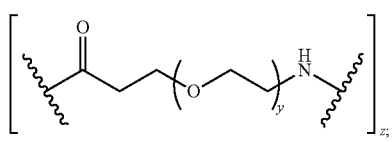

wherein y=1-100 and z=1-10.

In some embodiments, the solid line between A and B represents a nonpeptidyl linkage comprising the structure:

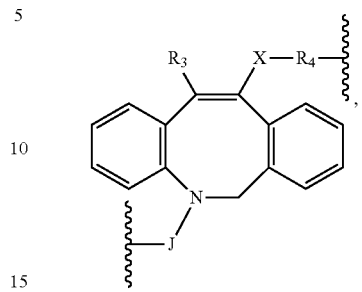

which is optionally substituted at any position.

In some embodiments, the solid line between A and B represents a nonpeptidyl linkage comprising the structure:

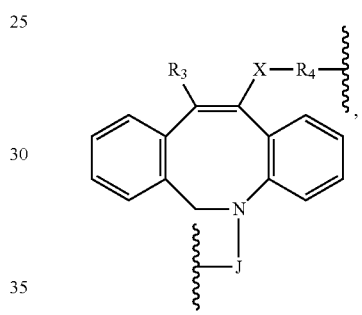

which is optionally substituted at any position.

In some embodiments, the solid line between A and B represents a nonpeptidyl linkage comprising the structure:

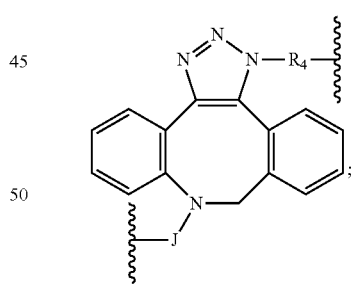

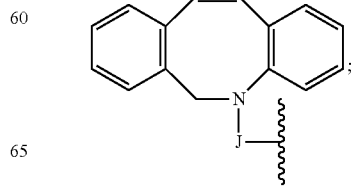

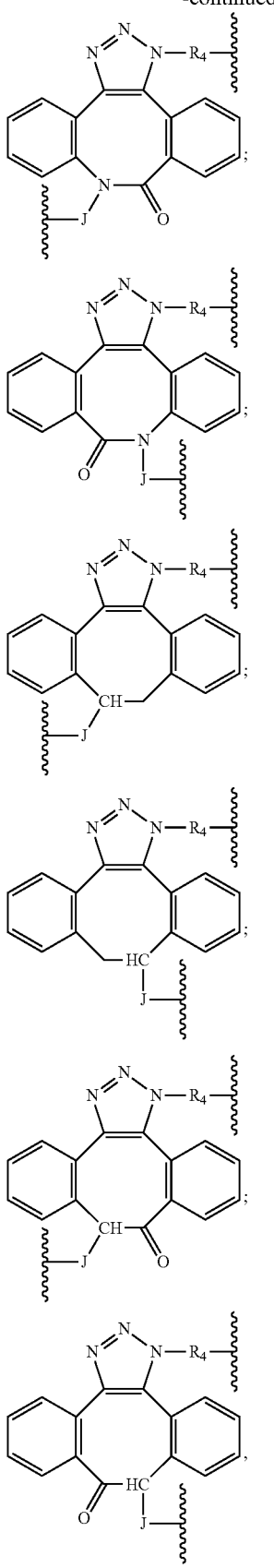

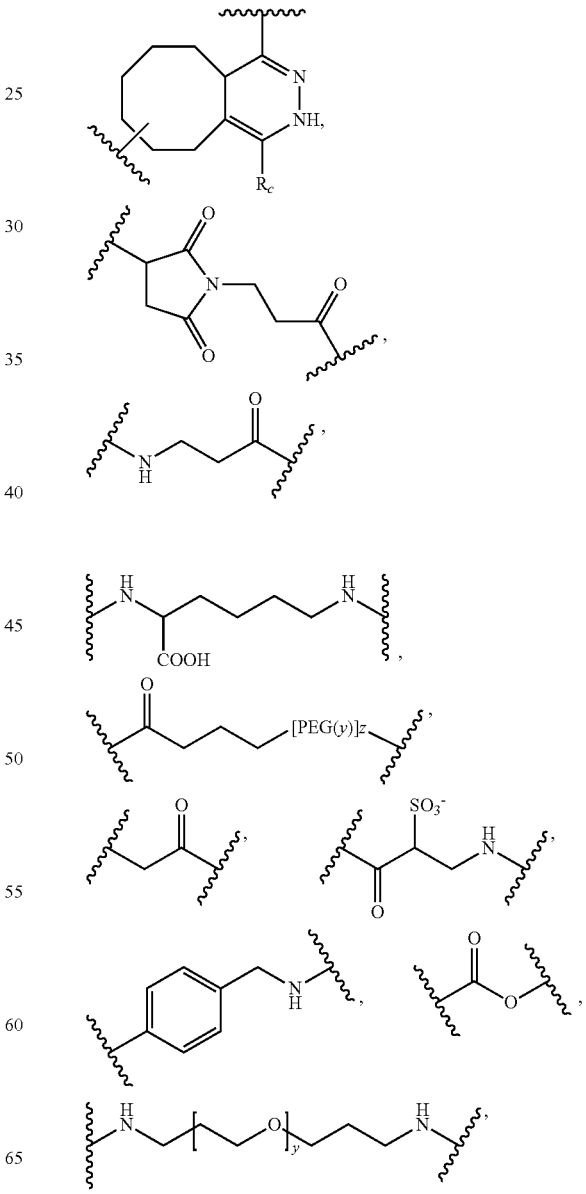

which is optionally substituted at any position, wherein J is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene, -continued

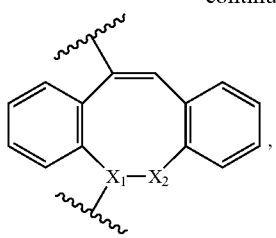
,

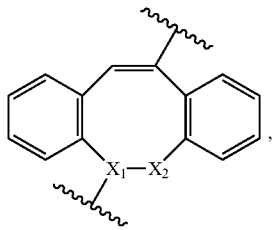
,

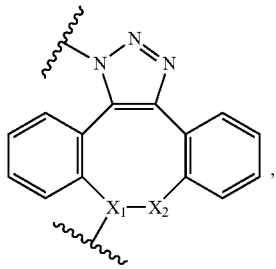
,

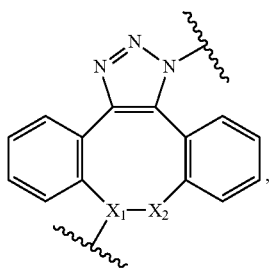
,

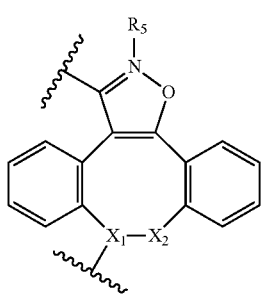
and

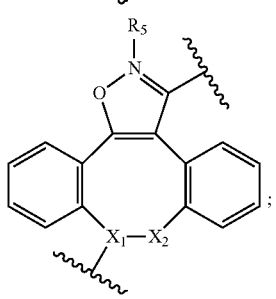
;

wherein $X_1$ is CH or N, $X_2$ is $CH_2$ or a carbonyl group, and $R_5$ is an aryl or alkyl group;

wherein [PEG(y)]z is:

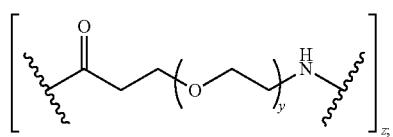

wherein y=1-100 and z=1-10.

In some embodiments, the solid line between A and B represents a nonpeptidyl linkage comprising the structure:

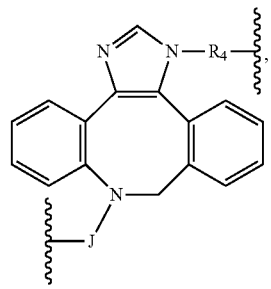

which is optionally substituted at any position.

In some embodiments, the solid line between A and B represents a nonpeptidyl linkage comprising the structure:

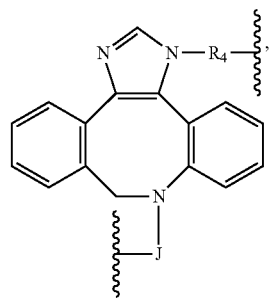

which is optionally substituted at any position.

In some embodiments, the solid line between A and B represents a nonpeptidyl linkage comprising the structure:

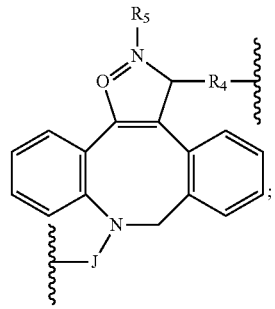
;

-continued

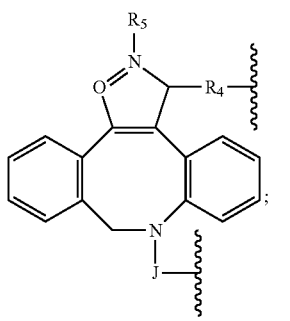

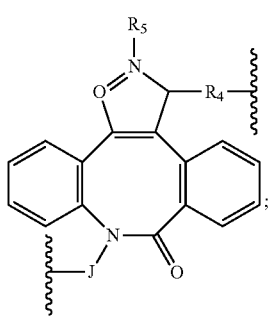

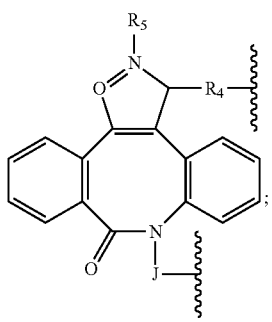

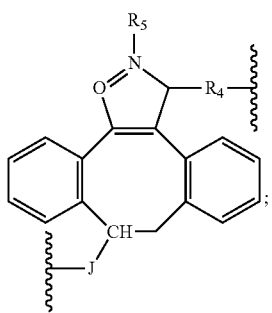

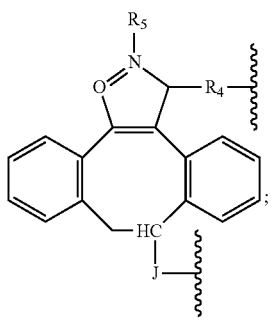

-continued

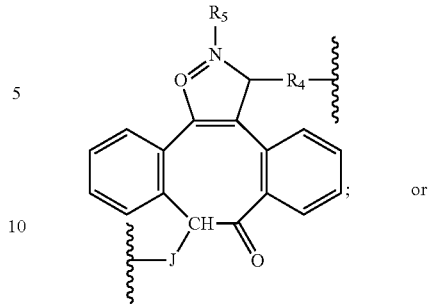

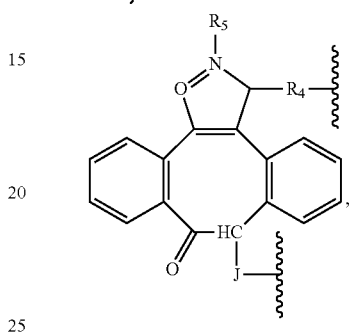

which is optionally substituted at any position, wherein J is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

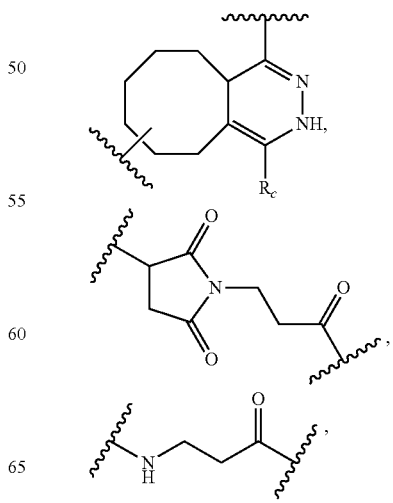

-continued
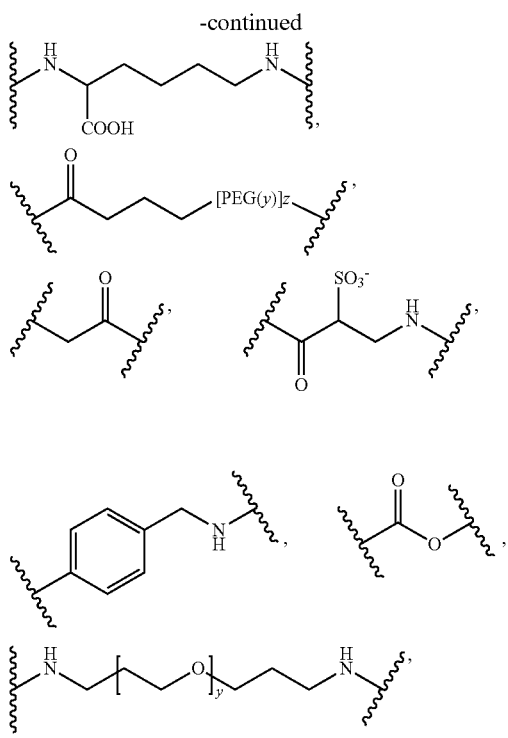
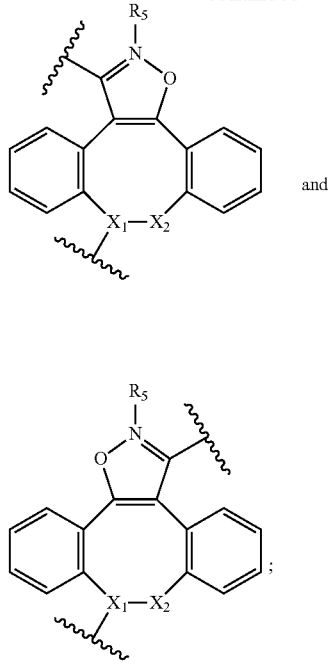
wherein $X_1$ is CH or N, $X_2$ is $CH_2$ or a carbonyl group, and $R_5$ is an aryl or alkyl group;
wherein [PEG(y)]z is:
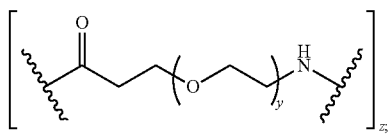
wherein y=1-100 and z=1-10.
In some embodiments, the solid line between A and B represents a nonpeptidyl linkage comprising the structure:
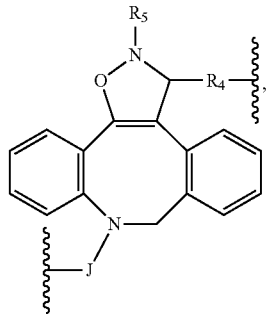
which is optionally substituted at any position.

In some embodiments, the solid line between A and B represents a nonpeptidyl linkage comprising the structure:

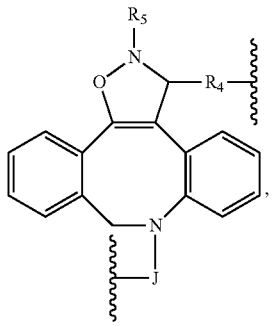

which is optionally substituted at any position.

In some embodiments, the solid line between A and B represents a nonpeptidyl linkage comprising the structure:

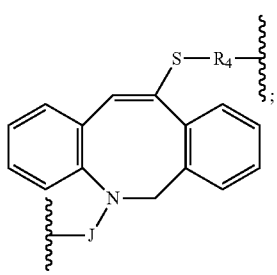

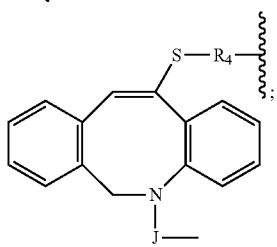

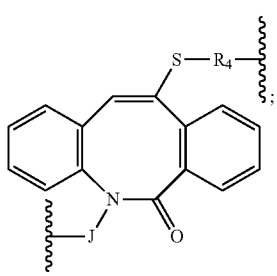

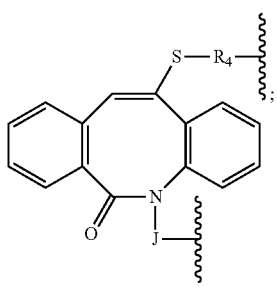

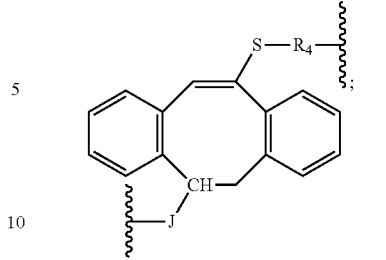

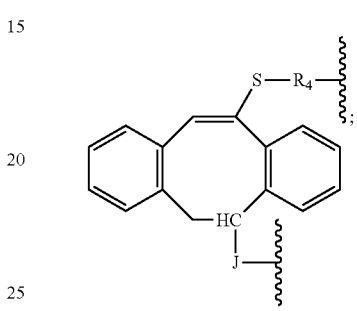

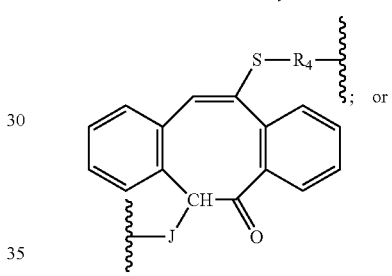

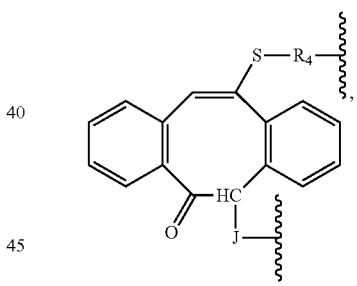

which is optionally substituted at any position, wherein J is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

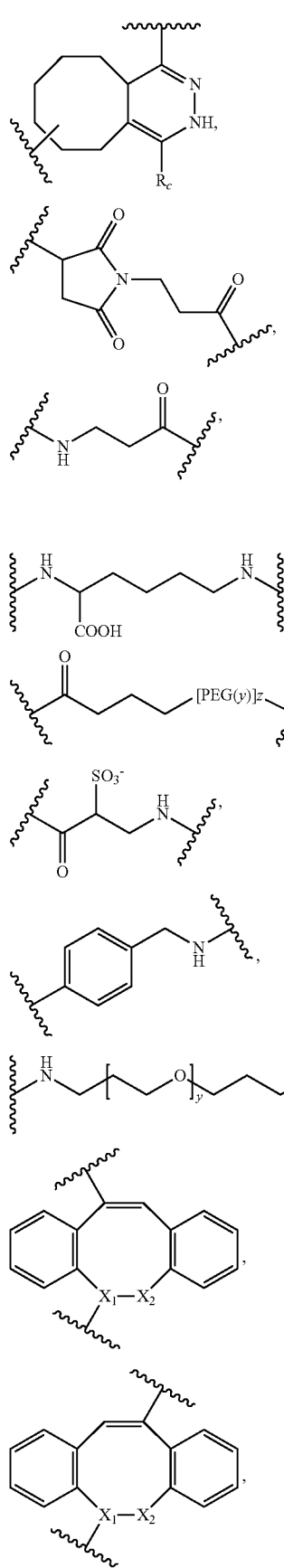
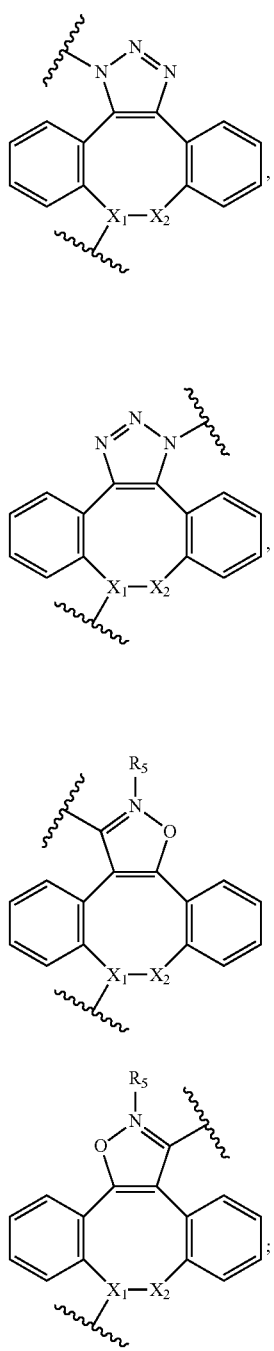
wherein $X_1$ is CH or N, $X_2$ is $CH_2$ or a carbonyl group, and $R_5$ is an aryl or alkyl group;
wherein [PEG(y)]z is:
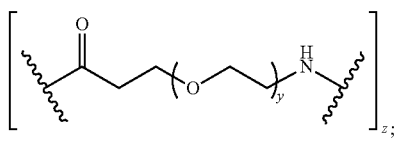
wherein y=1-100 and z=1-10.

In some embodiments, the solid line between A and B represents a nonpeptidyl linkage comprising the structure:

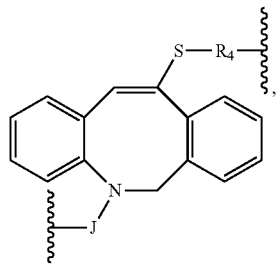

which is optionally substituted at any position.

In some embodiments, the solid line between A and B represents a nonpeptidyl linkage comprising the structure:

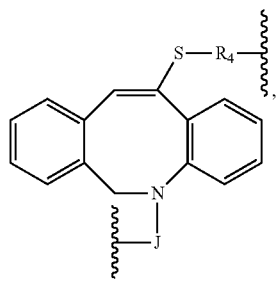

which is optionally substituted at any position.

In some embodiments, the solid line between A and B represents a nonpeptidyl linkage comprising the structure:

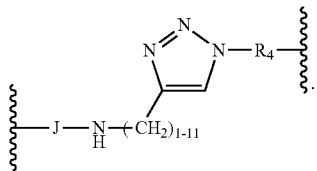

In some embodiments, $R_1$ is H.

In some embodiments, wherein J is an organic structure comprising a [PEG(y)]z group.

In some embodiments, wherein J is an organic structure comprising a polyalkylene glycol, polyoxyalkylated polyol, polyvinyl alcohol, polyvinyl alkyl ether, poly(lactic acid), poly(lactic-glycolic acid), or polysaccharide group.

In some embodiments, J is an organic structure comprising a $C_1$-$C_4$ alkyl group.

In some embodiments, J is an organic structure comprising a succinimide.

In some embodiments, J is an organic structure comprising amine.

In some embodiments, J is an organic structure comprising a succinyl, malonyl, glutaryl, phthalyl or adipoyl.

In some embodiments, J is an organic structure comprising a malonyl.

In some embodiments, J is an organic structure comprising an amino acid.

In some embodiments, J is an organic structure comprising a cysteine.

In some embodiments, J is an organic structure comprising a lysine.

In some embodiments, J is an organic structure consisting of a chain of 3 moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

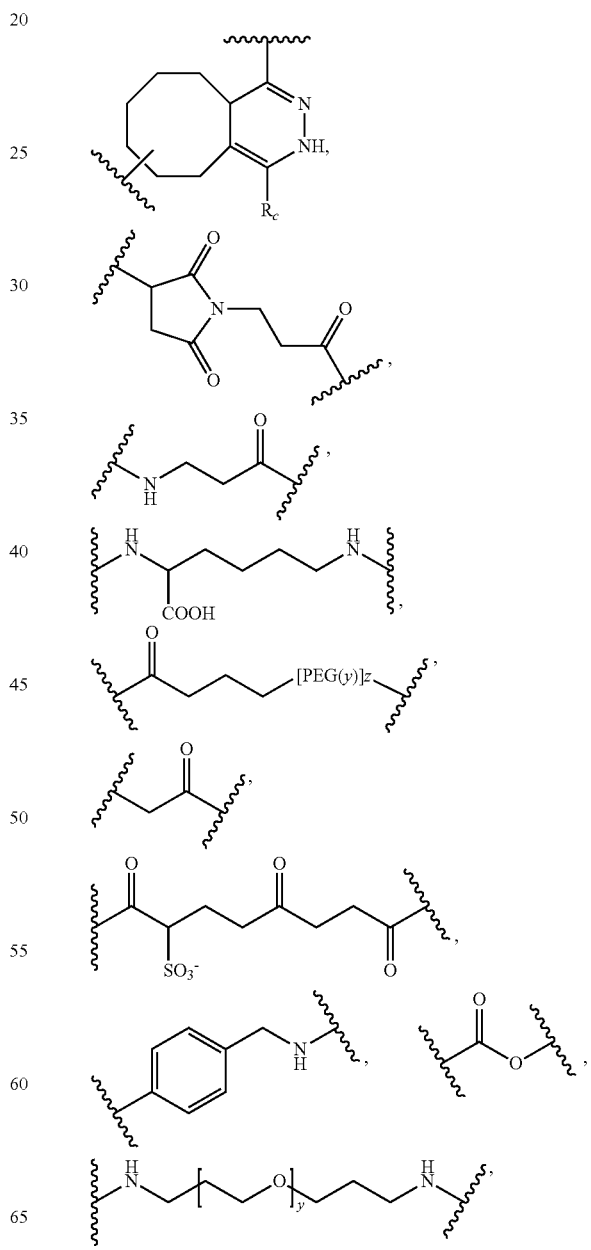

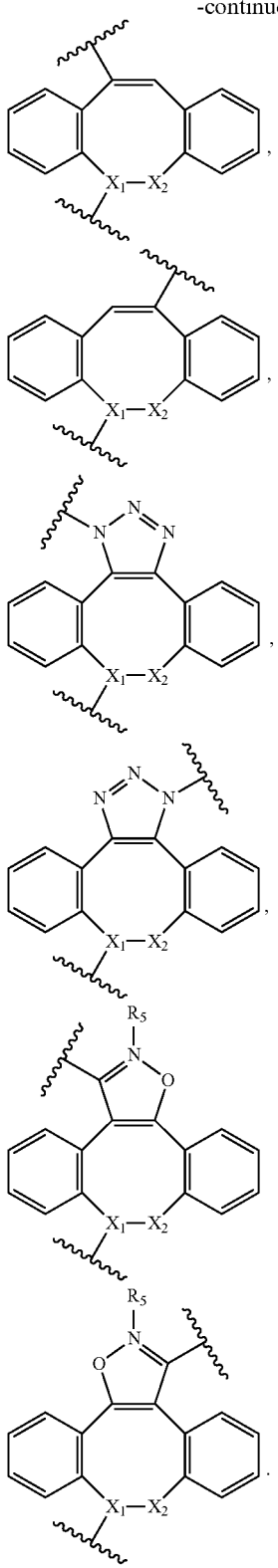

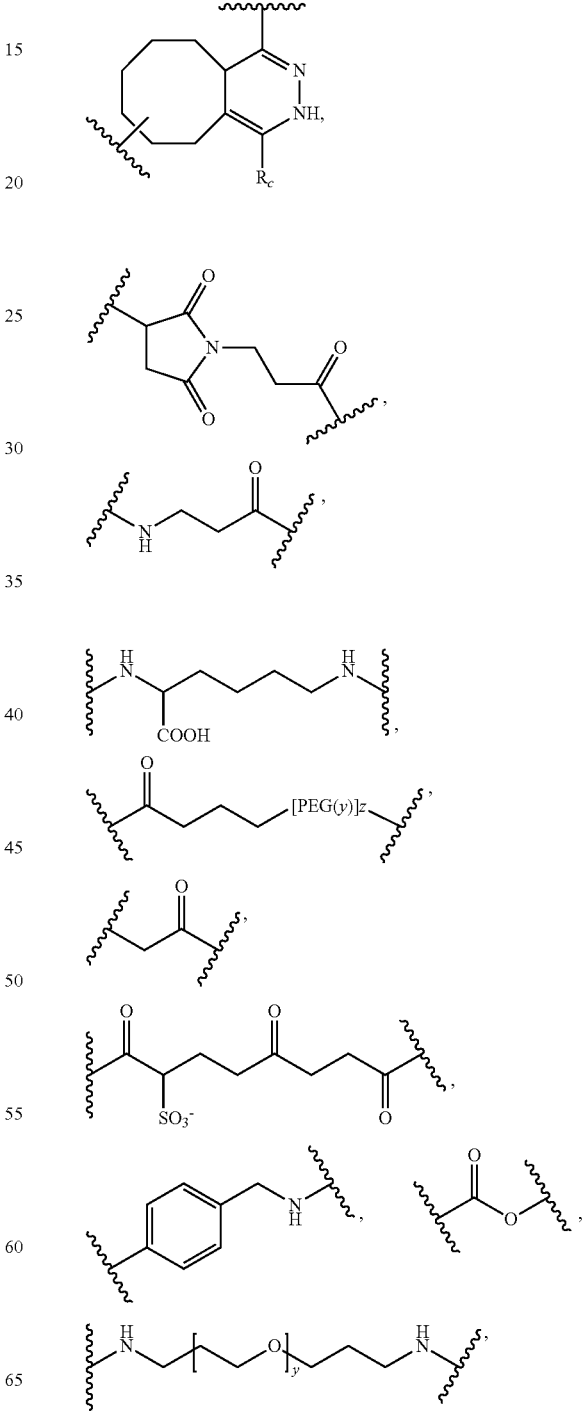

$C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene, In some embodiments, J is an organic structure consisting of a chain of four moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene,

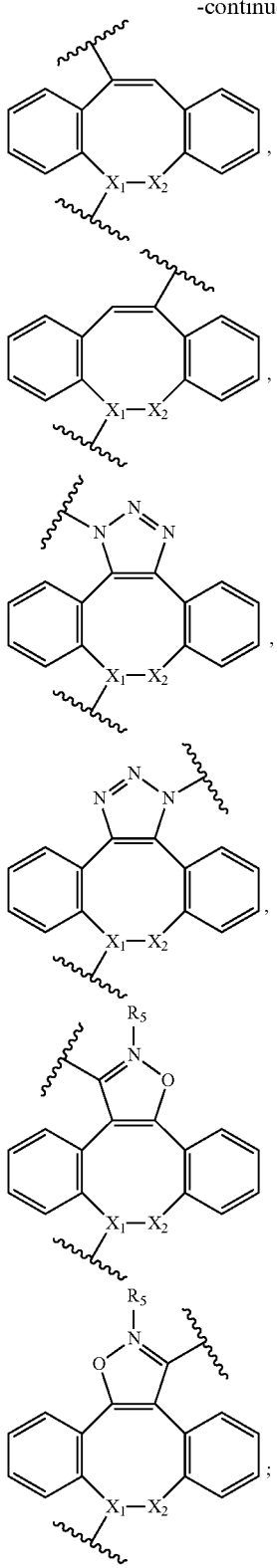

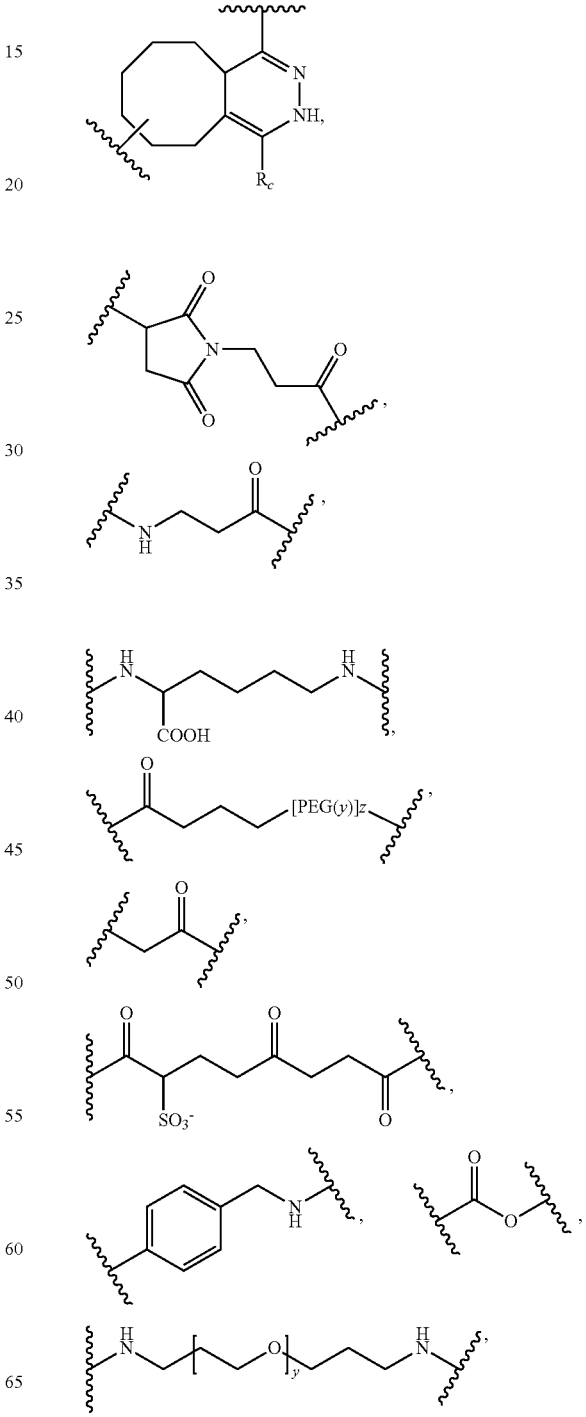

$C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene, In some embodiments, J is an organic structure consisting of a chain of five moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, -continued

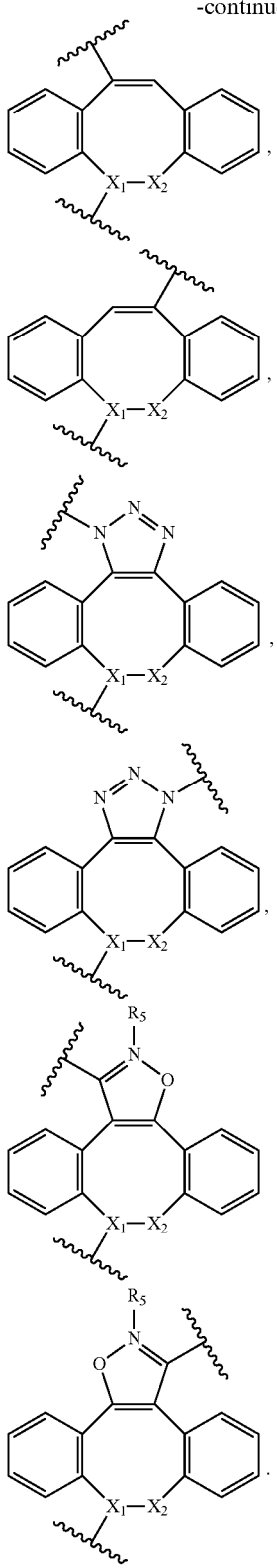

and

In some embodiments, J comprises a [PEG(y)]z group bonded to a lysine.

In some embodiments, J comprises a $C_1$-$C_4$ acyl group bonded to a succinimide group.

In some embodiments, J comprises a lysine bonded to a $C_1$-$C_4$ acyl.

In some embodiments, J comprises a [PEG(y)]z group, which is bonded to a glutaryl.

In some embodiments, J is an organic structure consisting of a chain of five moieties selected from the group consisting of [PEG(y)]z, $C_2$-$C_5$ acyl, succinyl, malonyl, glutaryl, an amino acid, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

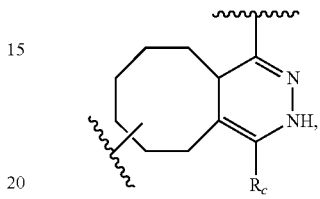

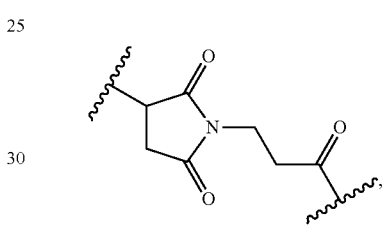

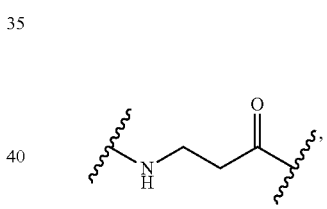

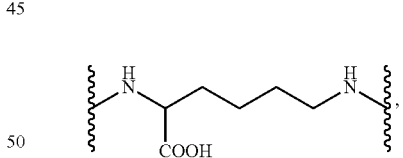

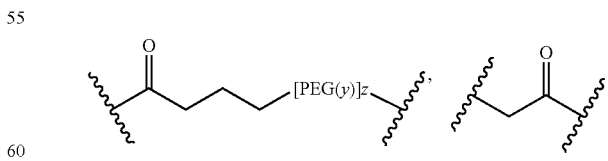

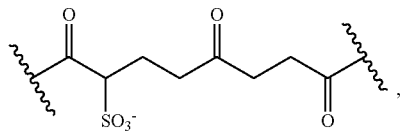

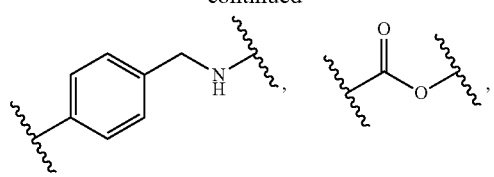
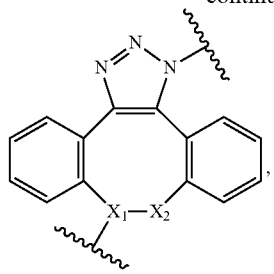
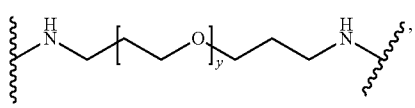
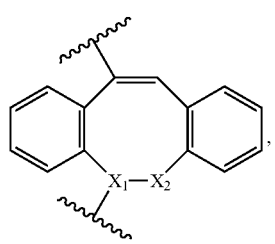
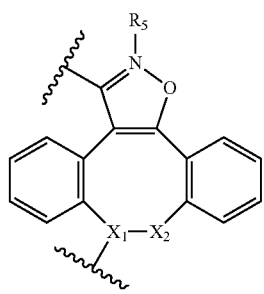
and
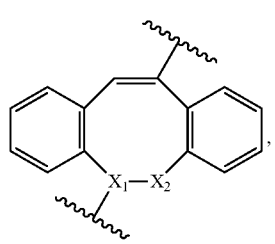
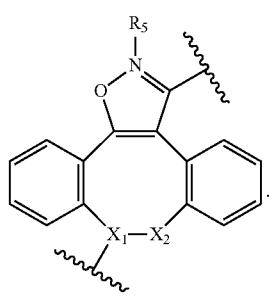
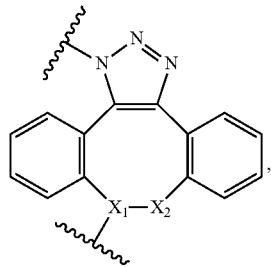
In some embodiments, J is a bond.
In some embodiments, J is a cysteine.
In some embodiments, J has the structure:
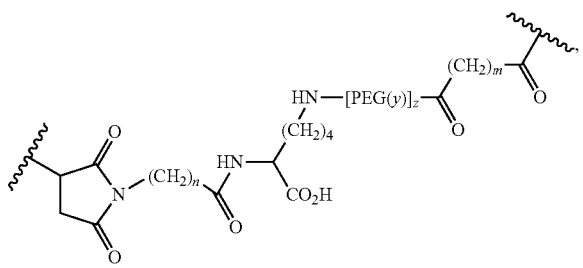
wherein n 1-3, m is 1-4, y is 1-100 and z is 1-10.
In some embodiments, J has a linear structure.
In some embodiments, J has a branched structure.

In some embodiments, $R_2$ is
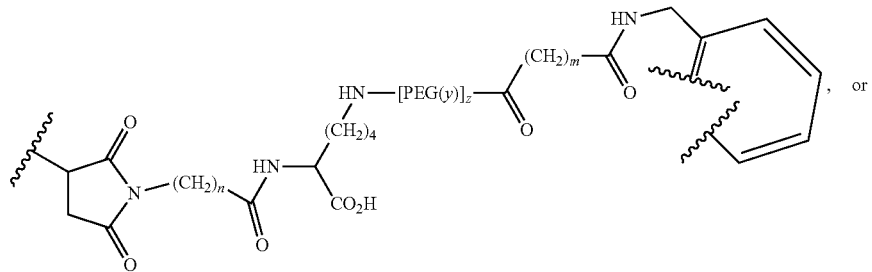, or
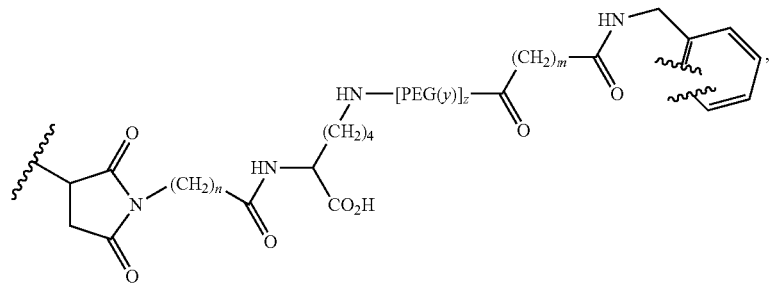,
wherein n 1-3, m is 1-4, y is 1-100 and z is 1-10.
In some embodiments, $R_2$ is
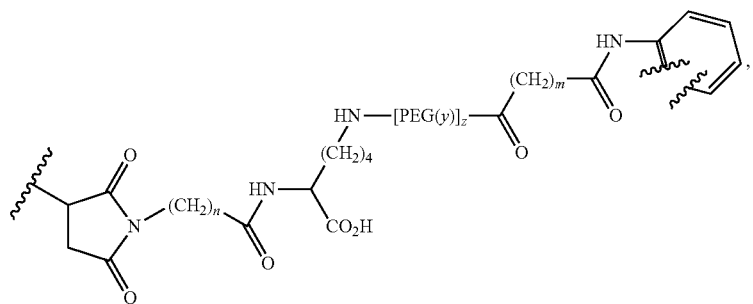,
wherein n 1-3, m is 1-4, y is 1-100 and z is 1-10.
In some embodiments, $R_2$ is
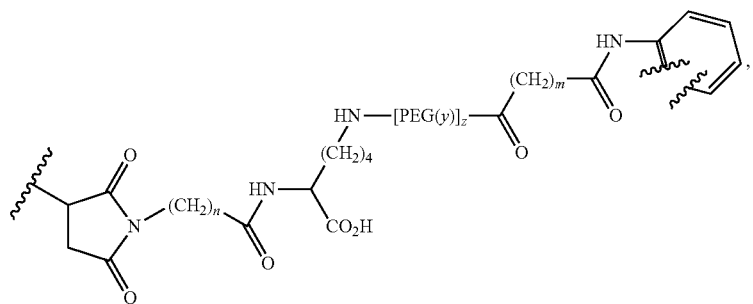,
wherein n 1-3, m is 1-4, y is 1-100 and z is 1-10.

In some embodiments, $R_1$ and $R_2$ taken together are:
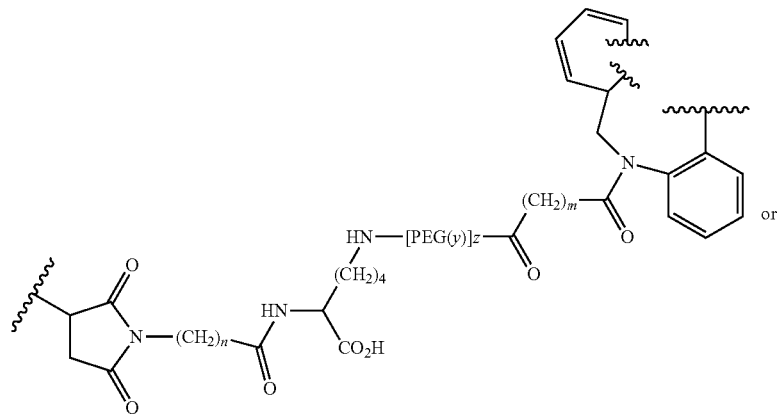
or
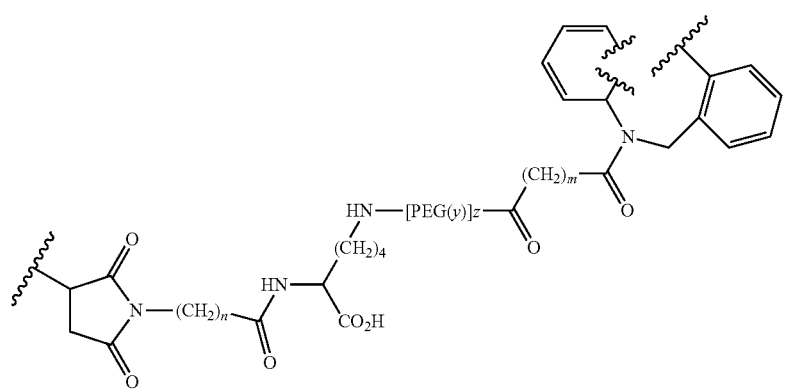
wherein n 1-3, m is 1-4, y is 1-100 and z is 1-10.
In some embodiments, $R_1$ and $R_2$ taken together are:
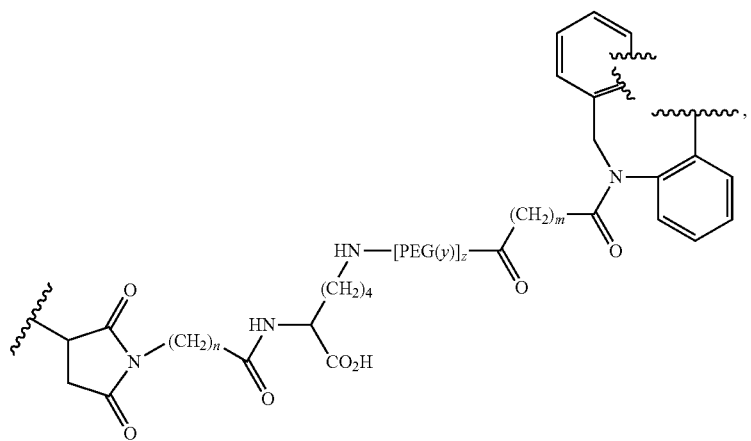
wherein n 1-3, m is 1-4, y is 1-100 and z is 1-10.

In some embodiments, $R_1$ and $R_2$ taken together are:
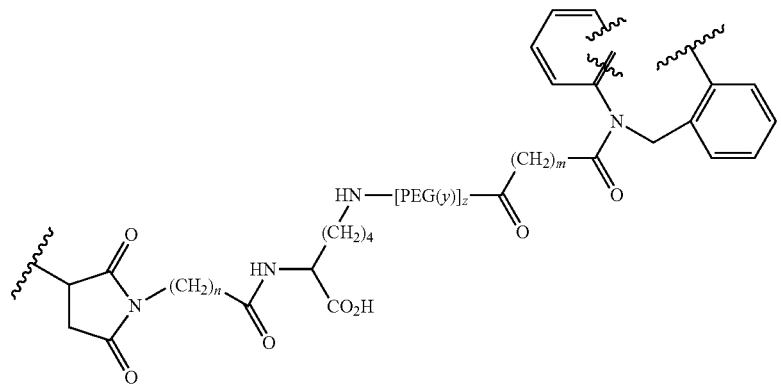
wherein n 1-3, m is 1-4, y is 1-100 and z is 1-10.
In some embodiments, the solid line between A and B represents a nonpeptidyl linkage comprising the structure:
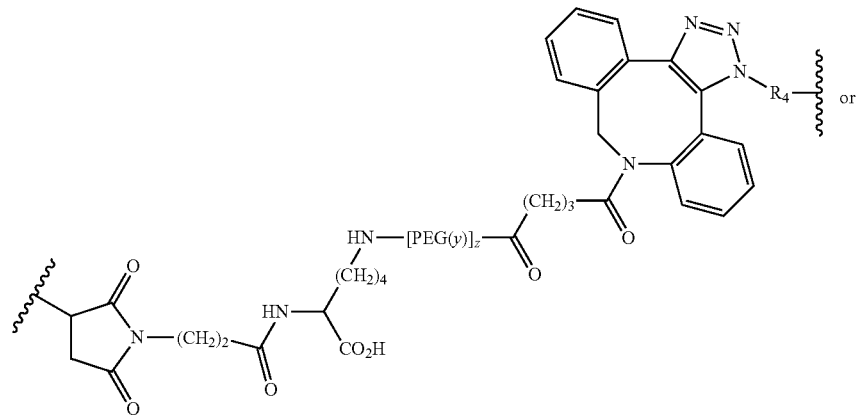
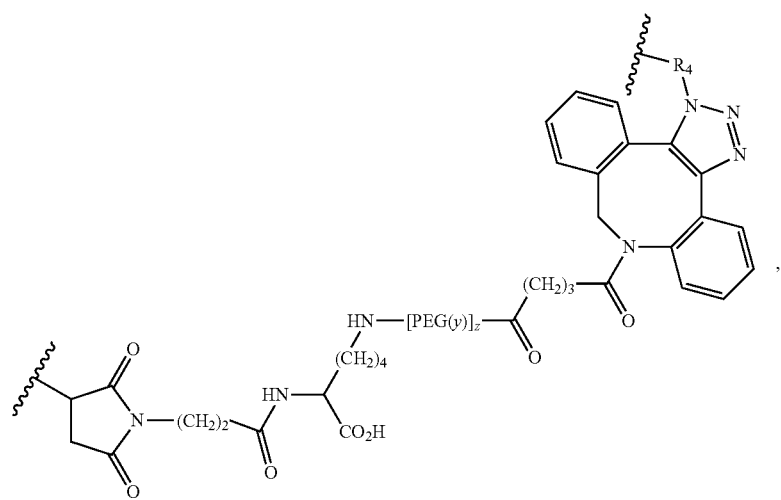

wherein [PEG(y)]z is:
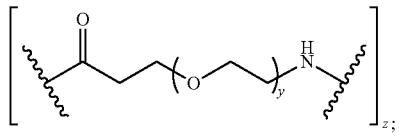
wherein y=1-100 and z=1-10.
In some embodiments, the solid line between A and B represents a nonpeptidyl linkage comprising the structure:
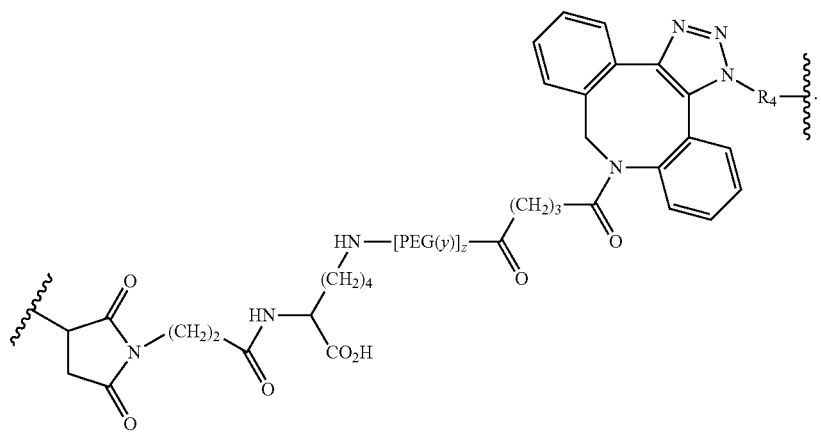
In some embodiments, the solid line between A and B represents a nonpeptidyl linkage comprising the structure:
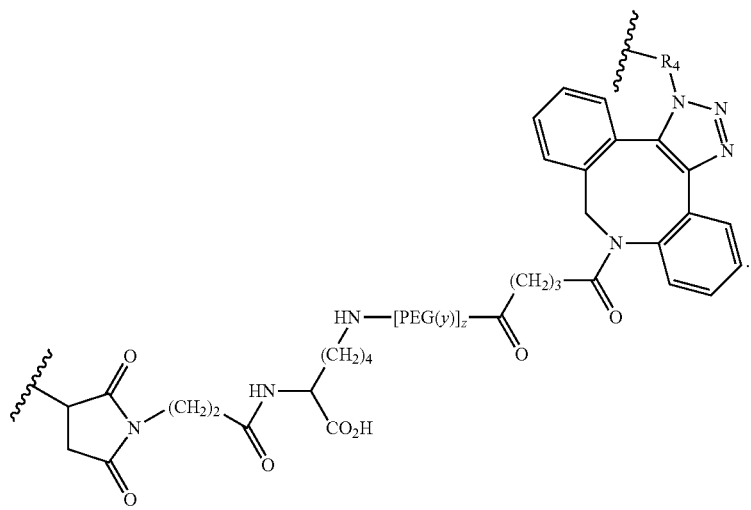

In some embodiments, the solid line between A and B represents a nonpeptidyl linkage comprising the structure:

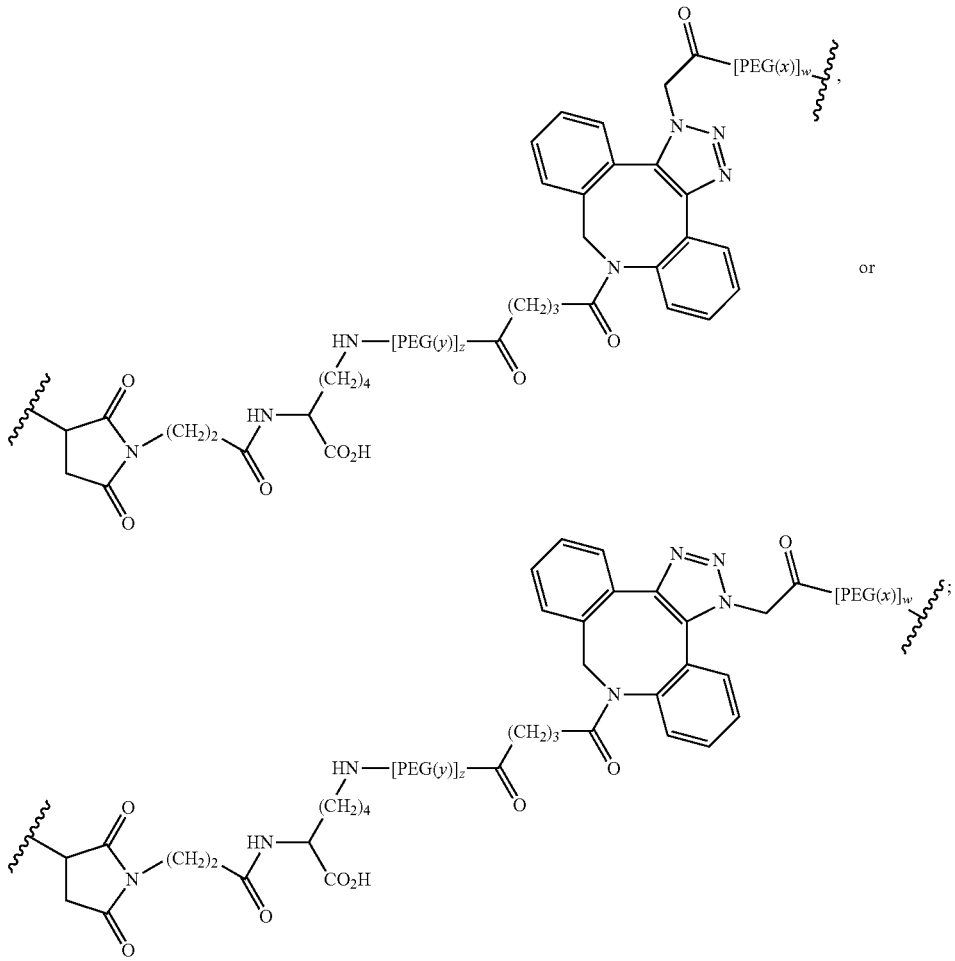

or wherein [PEG(y)]z is:

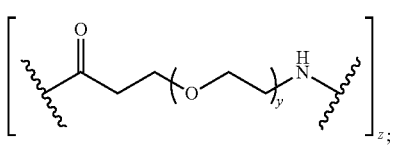

wherein y=1-100 and z=1-10;
wherein [PEG(x)]w is:

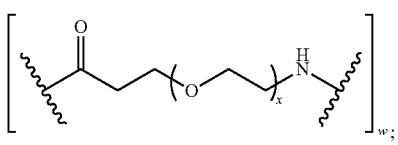

wherein x=1-100 and w=1-10.

In some embodiments, y is 1-20. In some embodiments, y is 21-40. In some embodiments, y is 41-60. In some embodiments, y is 61-80. In some embodiments, y is 30-50.

In some embodiments, y is 12, 24, 36 or 48. In some embodiments, z is 1. In some embodiments, z is 0.

In some embodiments, the terminal carbonyl is of the [PEG(y)]z group is part of an amide bond.

In some embodiments, the terminal amine of the [PEG(y)]z group is part of an amide bond.

In some embodiments, $R_4$ is

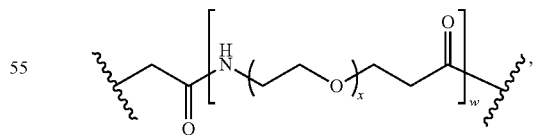

wherein x is 1-100, and w is 0-5.

In some embodiments, x is 1-20. In some embodiments, x is 21-40. In some embodiments, x is 41-60. In some embodiments, x is 61-80. In some embodiments, x is 30-50. In some embodiments, x is 12, 24, 36 or 48.

In some embodiments, w is 1. In some embodiments, w is 0.

In some embodiments, $R_4$ has the structure:

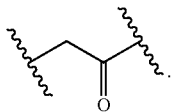

In some embodiments, $R_2$ is attached A to via J, and $R_4$ is attached to B.

In some embodiments, $R_2$ is attached B to via J, and $R_4$ is attached to A.

In some embodiments, $R_4$ is attached to B via the terminal carbonyl carbon.

In some embodiments, the solid line between A and B represents a nonpeptidyl linkage comprising the structure:

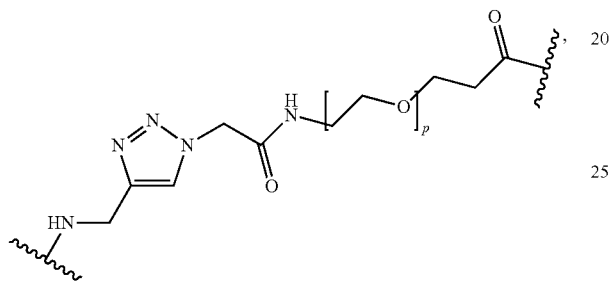

wherein p=0-5, 0-10, 0-50, or 0-100.

In some embodiments, erein $R_2$ is attached to A via a carbon-nitrogen bond or a carbon-sulfur bond.

In some embodiments, $R_2$ is attached to A via a carbon-nitrogen bond.

In some embodiments, the carbon-nitrogen bond is an amide bond.

In some embodiments, $R_2$ is attached to A via a biologically labile bond.

In some embodiments, $R_2$ is attached to A via an amide bond between the C-terminal amino acid of A and an amino group in B.

In some embodiments, the terminal amino acid is cysteine.

In some embodiments, $R_2$ is attached to A via a carbon-sulfur bond.

In some embodiments, $R_2$ is attached to A via a carbon-sulfur bond formed between $R_2$ and a free thiol.

In some embodiments, $R_2$ is attached to A via a succinimide-sulfur bond.

In some embodiments, J comprises a branched residue.

In some embodiments, J is attached to more than one A via the branched residue.

In some embodiments, B comprises a branched residue.

In some embodiments, B is linked to more than one A, each via a nonpeptidyl linkage with the branched residue.

In some embodiments, the solid line between A and B represents a nonpeptidyl linkage comprising the structure:

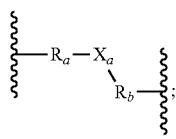

wherein $X_a$ is a chemical structure containing a cyclooctane fused to a dihydropyridazine; and wherein $R_a$ represents an organic structure which connects to one of A or B and $R_b$ represents an organic structure which connects to the other of A or B.

In some embodiments, $X_a$ has the structure:

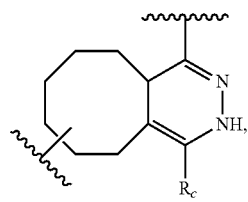

wherein $R_c$ is H, alkyl or aryl;
or a tautomer thereof.

In some embodiments, $X_a$ has the structure:

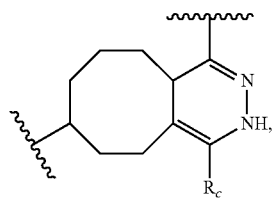

wherein $R_c$ is H, alkyl or aryl;
or a tautomer thereof.

In some embodiments, $R_a$ is connected to the cyclooctane and $R_b$ is connected to the dihydropyridazine.

In some embodiments, the solid line between A and B represents a nonpeptidyl linkage comprising the structure:

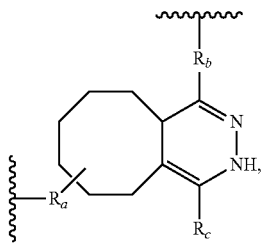

wherein $R_c$ is H, alkyl or aryl;
or a tautomer thereof.

In some embodiments, $X_a$ has the structure:

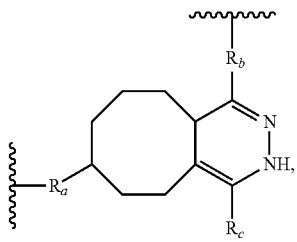

wherein $R_c$ is H, alkyl or aryl;
or a tautomer thereof.

In some embodiments, $R_c$ is methyl.

In some embodiments, $R_a$ and $R_b$ are independently a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

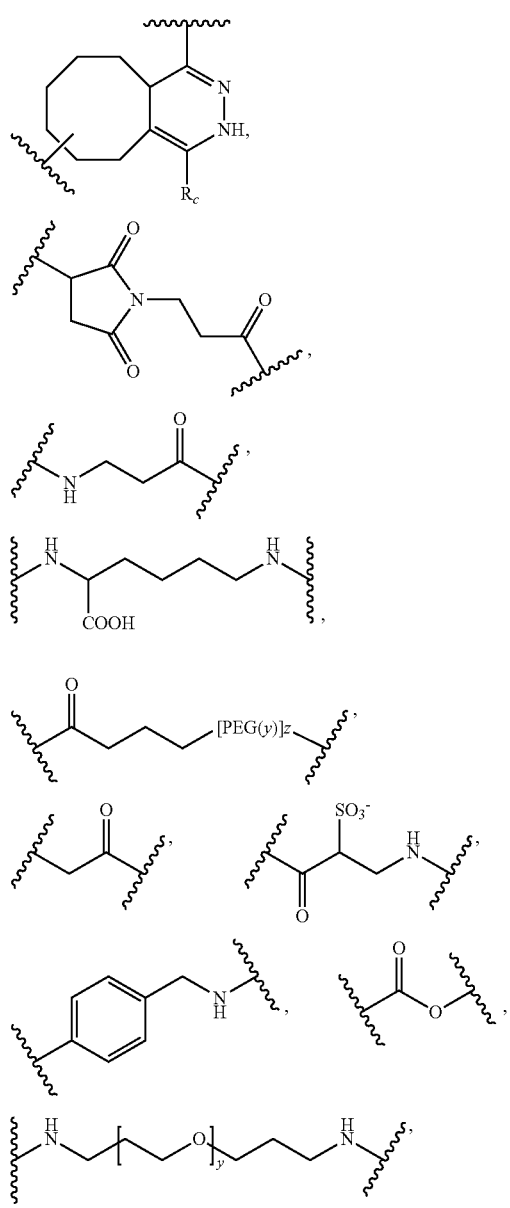

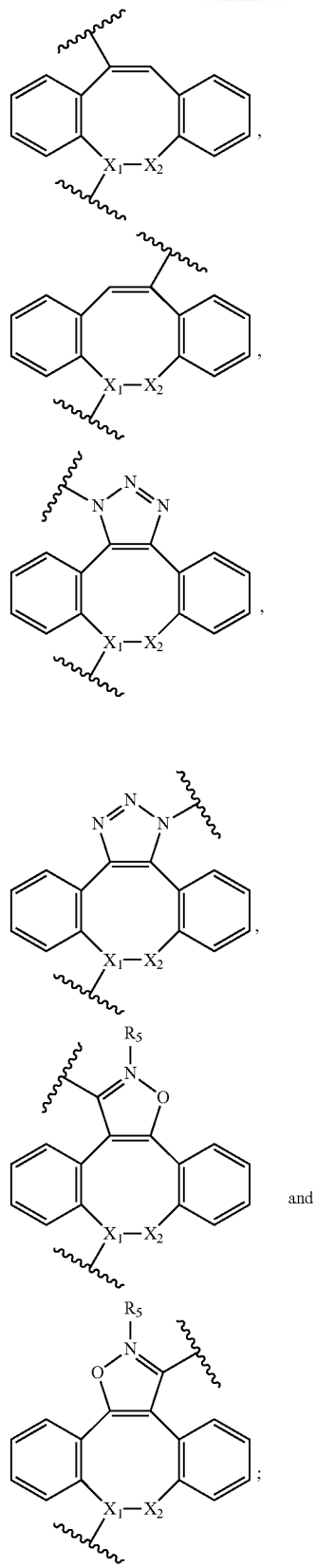

wherein $X_1$ is CH or N, $X_2$ is $CH_2$ or a carbonyl group, and $R_5$ is an aryl or alkyl group;

wherein [PEG(y)]z is:

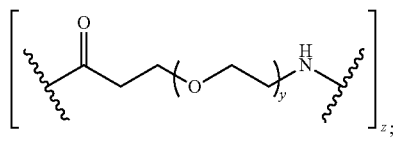

wherein y=1-100 and z=1-10.

In some embodiments, R and $R_b$ are independently a bond or an organic structure comprising or consisting of a chain of 1, 2, 3, 4, 5, 6, 7, 8, 9, 10 or more moieties, wherein each moiety is independently selected from the group consisting of [PEG(y)]z, $C_2$-$C_5$ acyl, succinyl, malonyl, glutaryl, an amino acid, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

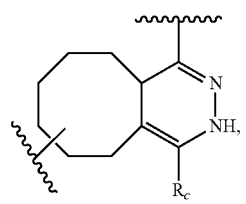

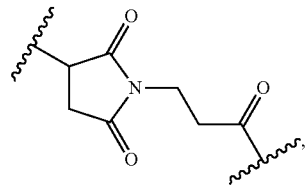

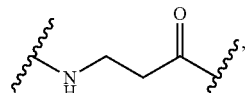

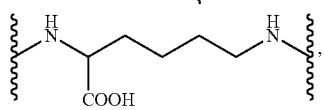

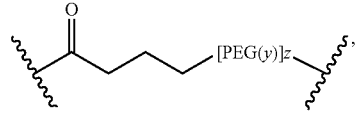

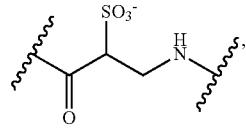

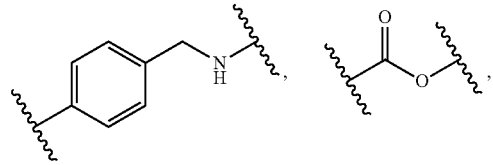

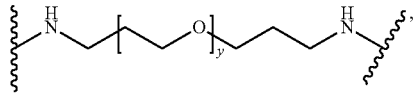

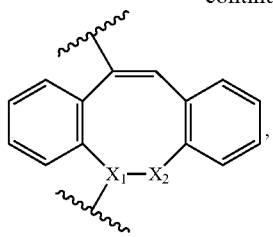

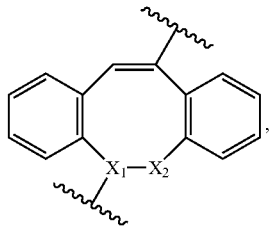

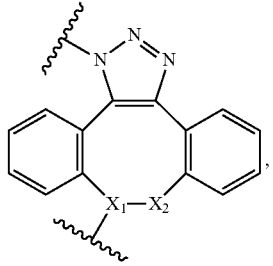

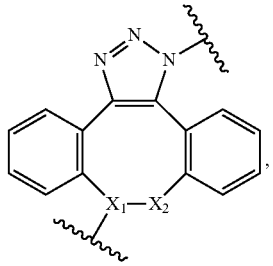

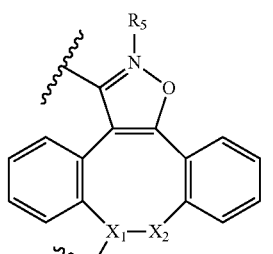

and

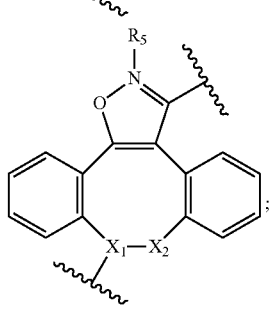

wherein $X_1$ is CH or N, $X_2$ is $CH_2$ or a carbonyl group, and $R_5$ is an aryl or alkyl group;

wherein [PEG(y)]z is:

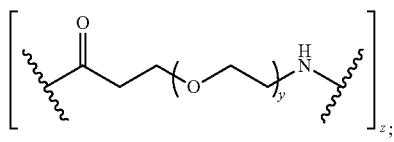

wherein y=1-100 and z=1-10.

In some embodiments, Ra or Rb is attached to A via a carbon-nitrogen bond or a carbon-sulfur bond.

In some embodiments, Ra or Rb is attached to A via a carbon-nitrogen bond.

In some embodiments, the carbon-nitrogen bond is an amide bond.

In some embodiments, Ra or Rb is attached to A via a biologically labile bond.

In some embodiments, Ra or Rb is is attached to A via an amide bond between the C-terminal amino acid of A and an amino group in B.

In some embodiments, the terminal amino acid is cysteine.

In some embodiments, Ra or Rb is is attached to A via a carbon-sulfur bond.

In some embodiments, Ra or Rb is is attached to A via a carbon-sulfur bond formed between $R_2$ and a free thiol.

In some embodiments, wherein Ra or Rb is is attached to A via a succinimide-sulfur bond.

In some embodiments, Ra or Rb comprises a branched residue.

In some embodiments, Ra or Rb is is attached to more than one A via the branched residue.

In some embodiments, the biological activity of A is increased when it is part of a compound or dimer of the invention compared to the biological activity of A when it is not linked to any other structure.

In some embodiments, A comprises the structure of a compound that is a drug approved for treating a subject afflicted with a disease.

In some embodiments, the subject is a mammalian subject.

In some embodiments, the mammalian subject is a human subject.

In some embodiments, A comprises the structure of an organic compound having a molecular weight less than 1000 Daltons, a DNA aptamer, an RNA aptamer, an oligonucleotide, or a protein that is biologically active.

In some embodiments, the oligonucleotide is an antisense oligonucleotide.

In some embodiments, the oligonucleotide is an RNA interference inducing molecule.

In some embodiments, the oligonucleotide encodes an RNA interference inducing molecule.

In some embodiments, A comprises a primary or a secondary amine.

In some embodiments, A is linked to B via the primary or secondary amine.

In some embodiments, A comprises a primary amine.

In some embodiments, A is aripiprazole or oseltamivir.

In some embodiments, A comprises a secondary amine.

In some embodiments, A is a respiratory drug, an antiasthmatic agent, an analgesic agent, an antidepressant, an antianginal agent, an antiarrhythmic agent, an antihypertensive agent, an antidiabetic agent, an antihistamine, an antiinfective agent, an antibiotic, an antiinflamatory agent, an antiparkinsonism drug, an antipsychotics, an antipyretic agent, an antiulcer agent, an attention deficit hyperactivity disorder (ADHD) drug, a central nervous system stimulant, a decongestant, or a psychostimulant.

In some embodiments, A is alprenolol, acebutolol, amidephrine, amineptine, amosulalol, amoxapine, amphetaminil, atenolol, atomoxetine, balofloxacin, bamethan, befunolol, benazepril, benfluorex, benzoctamine, betahistine, betaxolol, bevantolol, bifemelane, bisoprolol, brinzolamide, bufeniode, butethamine, camylofine, carazolol, carticaine, carvedilol, cephaeline, ciprofloxacin, cloZapine, clobenZorex, clorprenaline, cyclopentamine, delapril, demexiptiline, denopamine, desipramine, desloratadine, diclofenac, dimetofrine, dioxadrol, dobutamine, dopexamine, doripenem, dorzolamide, droprenilamine, duloxetine, eltopraZine, enalapril, enoxacin, epinephrine, ertapenem, esapraZole, esmolol, etoxadrol, fasudil, fendiline, fenethylline, fenfluramine, fenoldopam, fenoterol, fenproporex, flecamide, fluoxetine, formoterol, frovatriptan, gaboxadol, garenoxacin, gatifloxacin, grepafloxacin, hexoprenaline, imidapril, indalpine, indecainide, indeloxazine hydrochloride, isoxsuprine, ispronicline, labetalol, landiolol, lapatinib, levophacetoperane, lisinopril, lomefloxacin, lotrafiban, maprotiline, mecamylamine, mefloquine, mepindolol, meropenem, metapramine, metaproterenol, methoxyphenamine, dextrorotary methylphenidate, methylphenidate, metipranolol, metoprolol, mitoxantrone, mivazerol, moexipril, moprolol, moxifloxacin, nebivolol, nifenalol, nipradilol, norfloxacin, nortriptyline, nylidrin, olanZapine, oxamniquine, oxprenolol, oxyfedrine, paroxetine, perhexyline, phenmetrazine, phenylephrine, phenylpropylmethylamine, pholedrine, picilorex, pimethylline, pindolol, pipemidic acid, piridocaine, practolol, pradofloxacin, pramipexole, pramiverin, prenalterol, prenylamine, prilocalne, procaterol, pronethalol, propafenone, propranolol, propylhexedrine, protokylol, protriptyline, pseudoephedrine, reboxetine, rasagiline, (r)-rasagiline, repinotan, reproterol, rimiterol, ritodrine, safinamide, salbutamol/albuterol, salmeterol, sarizotan, sertraline, silodosin, sotalol, soterenol, sparfloxacin, spirapril, sulfinalol, synephrine, tamsulosin, tebanicline, tianeptine, tirofiban, tretoquinol, trimetazidine, troxipide, varenicline, vildagliptin, viloxazine, viquidil or xamoterol.

In some embodiments, A comprises a protein that is biologically active.

In some embodiments, A comprises a secreted protein.

In some embodiments, A comprises an extracellular domain of a protein.

In some embodiments, A is biologically active such that it has target-binding activity.

In some embodiments, the A is an independently-folding protein or a portion thereof.

In some embodiments, A is a glycosylated protein.

In some embodiments, A comprises intra-chain disulfide bonds.

In some embodiments, A binds a cytokine.

In some embodiments, the cytokine is TNFα.

In some embodiments, A comprises Atrial Natriuretic Peptide (ANP), Calcitonin, Corticotropin Releasing Hormone (CRH), Endothelin, Exenatide, Gastric Inhibitory Peptide (GIP), Glucagon-Like Peptide-1 (GLP-1), Glucagon-Like Peptide-2 (GLP-2), an analog of GLP-1 or GLP-2, Glucagon Vasoactive Intestinal Peptide (GVIP), Ghrelin, Peptide YY or Secretin, or a portion thereof.

In some embodiments, A comprises a stretch of consecutive amino acids in the sequence HGEGTFTSDVSSYLE-EQAAKEFIAWLVKGRG (SEQ ID NO:202).

In some embodiments, A comprises at least one stretch of consecutive amino acids which are identical to a stretch of consecutive amino acids present in the heavy chain of a Fab or a Fab' of an antibody.

In some embodiments, A comprises at least one at least one stretch of consecutive amino acids which are identical to a stretch of consecutive amino acids present in the light chain of a Fab or a Fab' of an antibody.

In some embodiments, A comprises at least one Fab or Fab' of an antibody, or a portion of the at least one Fab or Fab'.

In some embodiments, A comprises at least 2, 3, 4, 5, 6, 7, 8, 9, or 10 copies of the Fab or Fab' or portion thereof.

In some embodiments, A comprises Fab-1 or Fab'1, or a portion thereof of the antibody.

In some embodiments, A comprises Fab-2 or Fab'2, or a portion thereof of the antibody.

In some embodiments, A comprises two Fab or Fab' hands of the antibody.

In some embodiments, the Fab or Fab' is present in adalimumab

In some embodiments, A comprises at least one stretch of consecutive amino acids which are identical to a stretch of consecutive amino acids present in a single chain antibody.

In some embodiments, A comprises at least one stretch of consecutive amino acids which are identical to a stretch of consecutive amino acids present in a TNFα receptor.

In some embodiments, the TNFα receptor is TNR1B.

In some embodiments, a compound of the invention forms part of a homodimer.

In some embodiments, a compound of the invention forms part of a heterodimer.

The present invention provides homodimers comprising compounds of the invention.

The present invention provides heterodimers comprising compounds of the invention.

In some embodiments, each compound of the dimer is capable of binding to the other by at least one disulfide bond.

In some embodiments, each compound of the dimer is capable of binding to the other by at least one disulfide bond between the Z of each compound.

In some embodiments, each compound of the dimer is bound to the other by at least one disulfide bond.

In some embodiments, each compound of the dimer is bound to the other by at least one disulfide bond between the Z of each compound.

In some embodiments, each compound of the dimer is non-covalently bound to the other.

The present invention provides a compound having the structure:

L-$R_a$—B - - - Z wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a cysteine or a selenocysteine;

wherein B is a chemical structure linking $R_a$ and C;

wherein the dashed line between B and Z represents a peptidyl linkage;

wherein L is selected from the group consisting of: —$N_3$, an alkyne, a group in which $R_5$ is an alkyl or aryl group, a group, a tetrazine and a trans-cyclooctene; and wherein $R_a$ is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

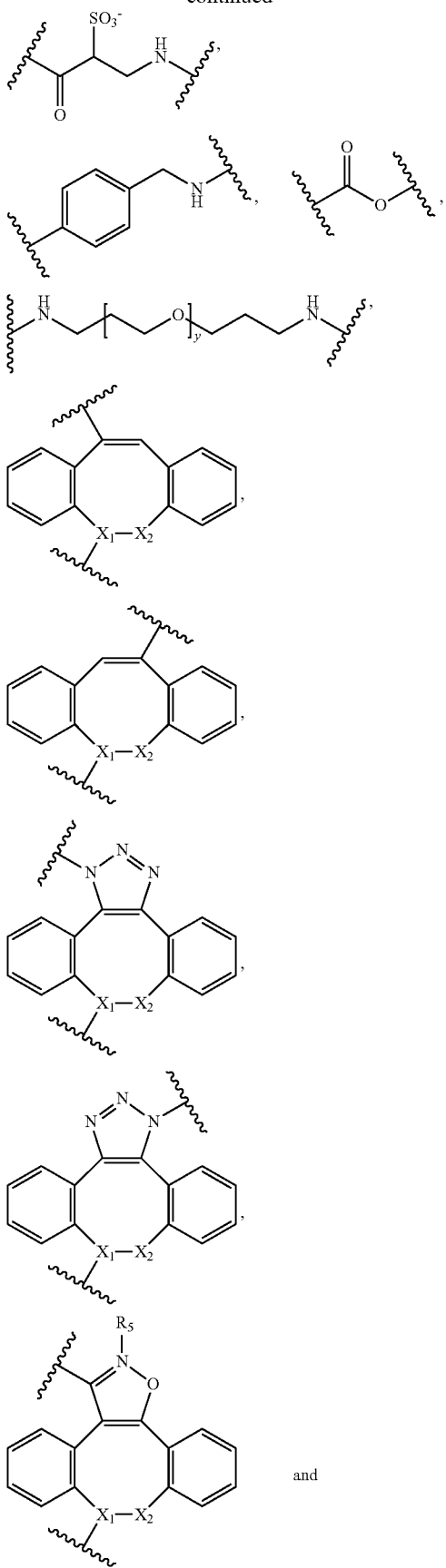

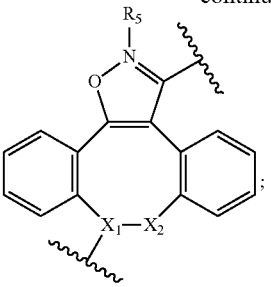

wherein $X_1$ is CH or N, $X_2$ is $CH_2$ or a carbonyl group, and $R_5$ is an aryl or alkyl group;

wherein [PEG(y)]z is:

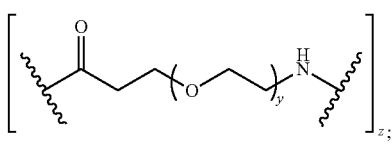

wherein y=1-100 and z=1-10.

In some embodiments, the cysteine or selenocysteine naturally occurs in the stretch of consecutive amino acids. In some embodiments, the cysteine or selenocysteine does not naturally occur in the stretch of consecutive amino acids.

In some embodiments, the consecutive amino acids have at their N-terminus a sequence selected from the group consisting of a cysteine, selenocysteine, CP, CPXCP (where X=P, R, or S) (SEQ ID NOs: 206-208), CDKTHTCPPCP (SEQ ID NO: 209), CVECPPCP (SEQ ID NO: 210), CCVECPPCP (SEQ ID NO: 211) and CDTPPPCPRCP (SEQ ID NO: 212).

In some embodiments, the $F_c$ domain of an antibody is a naturally occurring $F_c$ domain of an antibody.

In some embodiments, the $F_c$ domain of an antibody is a variant $F_c$ domain of an antibody.

In some embodiments, the variant $F_c$ domain of an antibody is a mutated $F_c$ domain of an antibody.

In some embodiments, the mutated $F_c$ domain is a substitution mutant.

In some embodiments, the substitution mutant has an amino acid substitution at the N-terminus, the C-terminus, or at a position of the $F_c$ domain other than the N-terminus or the C-terminus.

In some embodiments, the substitution mutant has 1, 2, 3, 4, 5, 6, 7, 8, 9, 10, 10-15, 15-20, 10-20, or 20-50 amino acid sustitutions in the stretch of consecutive amino acids thereof.

In some embodiments, the substitutions are conservative amino acid substitutions.

In some embodiments, the mutated mutated $F_c$ domain is an amino acid addition mutant.

In some embodiments, the amino acid addition mutant has 1, 2, 3, 4, 5, 6, 7, 8, 9, 10, 10-15, 15-20, 10-20, or 20-50 added amino acids in the stretch of consecutive amino acids thereof.

In some embodiments, the mutated $F_c$ domain is an amino acid deletion mutant.

In some embodiments, the amino acid deletion mutant has 1, 2, 3, 4, 5, 6, 7, 8, 9, 10, 10-15, 15-20, 10-20, or 20-50 deleted amino acids in the stretch of consecutive amino acids thereof.

In some embodiments, the consecutive amino acids are identical to a stretch of at least 0, 20, 30, 40, 50, 60, 70, 80, 90, 100, 110, 120, 130, 140, 150, 160, 170, 180, or 190 consecutive amino acids present in the chain of the $F_c$ domain of the antibody.

In some embodiments, the consecutive amino acids are identical to the stretch of amino acids in the hinge region, the CH2 region or the CH3 region of the Fc domain, or a portion thereof.

In some embodiments, L is —$N_3$.

In some embodiments, L is

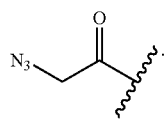

In some embodiments, L is an alkyne.

In some embodiments, the alkyne is a propargyl group.

In some embodiments, the alkyne is a cyclooctyne group.

In some embodiments, the alkyne has the structure:

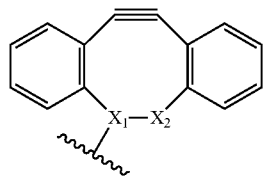

wherein $X_1$ is CH or N, $X_2$ is $CH_2$ or a carbonyl group, and R5 is an aryl or alkyl group.

In some embodiments, the alkyne has the structure:

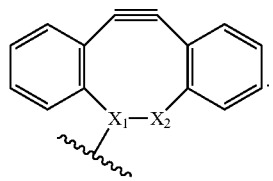

In some embodiments, L is a tetrazine.

In some embodiments, the tetrazine has the structure:

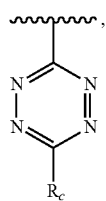

wherein Rc is H, alkyl or aryl.

In some embodiments, the tetrazine has the structure:

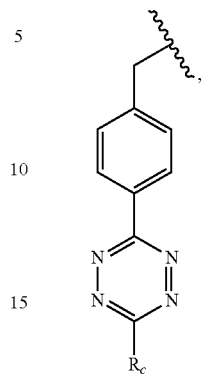

wherein Rc is H, alkyl or aryl.

In some embodiments, the tetrazine has the structure:

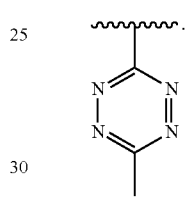

In some embodiments, the tetrazine has the structure:

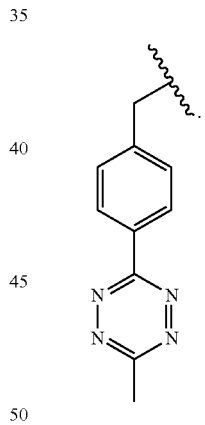

In some embodiments, L is trans-cyclooctene.

In some embodiments, the trans-cyclooctene has the structure:

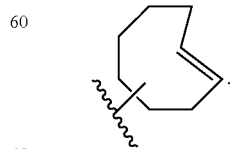

In some embodiments, the trans-cyclooctene has the structure:

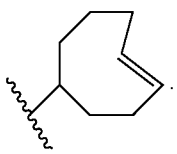 [SMILES: *C1CC/C=C/CCC1]

In some embodiments, Ra or Rb is an organic structure comprising a [PEG(y)]z group.

In some embodiments, Ra or Rb is an organic structure comprising a polyalkylene glycol, polyoxyalkylated polyol, polyvinyl alcohol, polyvinyl alkyl ether, poly(lactic acid), poly(lactic-glycolic acid), or polysaccharide group.

In some embodiments, Ra or Rb is an organic structure comprising a $C_1$-$C_4$ alkyl group.

In some embodiments, Ra or Rb is an organic structure comprising a succinimide.

In some embodiments, Ra or Rb is an organic structure comprising an amine.

In some embodiments, Ra or Rb is an organic structure comprising a succinyl, malonyl, glutaryl, phthalyl or adipoyl.

In some embodiments, Ra or Rb is an organic structure comprising a malonyl.

In some embodiments, Ra or Rb is an organic structure comprising an amino acid.

In some embodiments, Ra or Rb is an organic structure comprising a cysteine.

In some embodiments, Ra or Rb is an organic structure comprising a lysine.

In some embodiments, Ra or Rb is an organic structure consisting of a chain of 3 moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

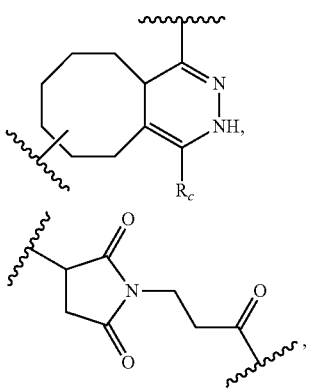

-continued

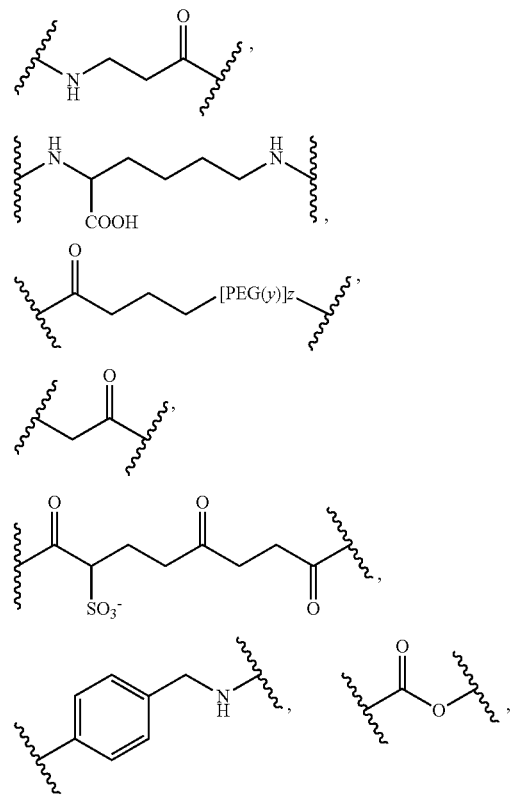

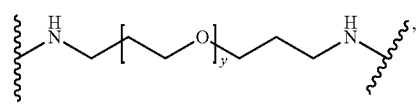

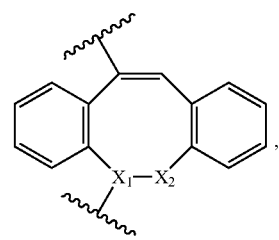

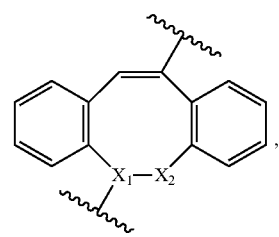

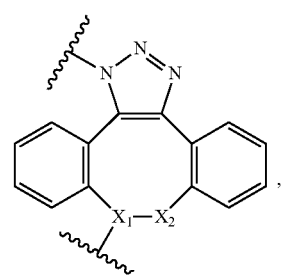

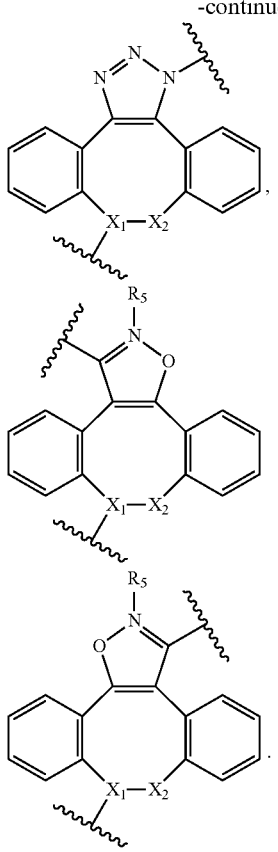

and

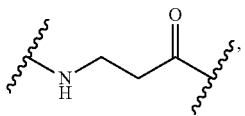

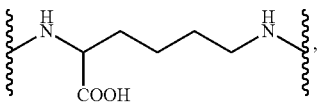

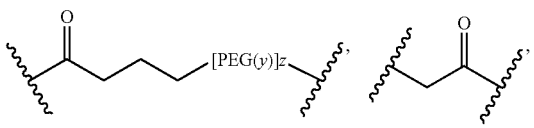

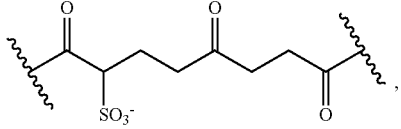

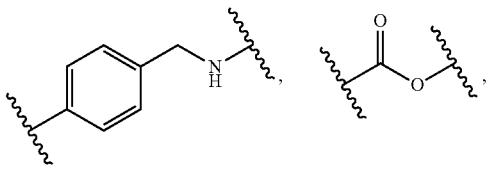

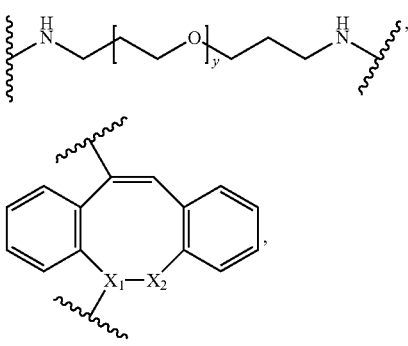

In some embodiments, Ra or Rb is an organic structure consisting of a chain of four moieties selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

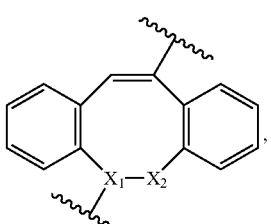

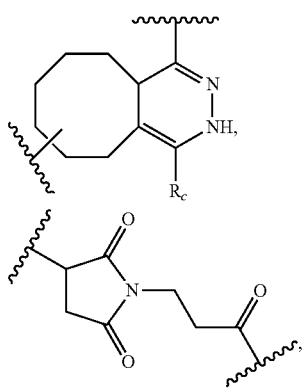

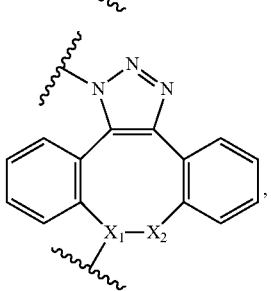

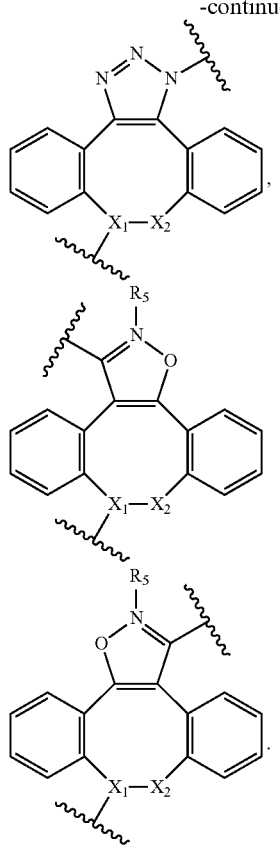

In some embodiments, Ra or Rb is an organic structure consisting of a chain of five moieties selected from the group consisting of [PEG(y)]z, polyalkylene glycol, polyoxyalkylated polyol, polyvinyl alcohol, polyvinyl alkyl ether, poly (lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

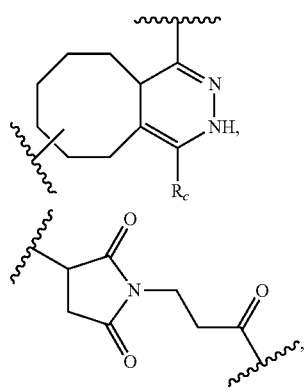

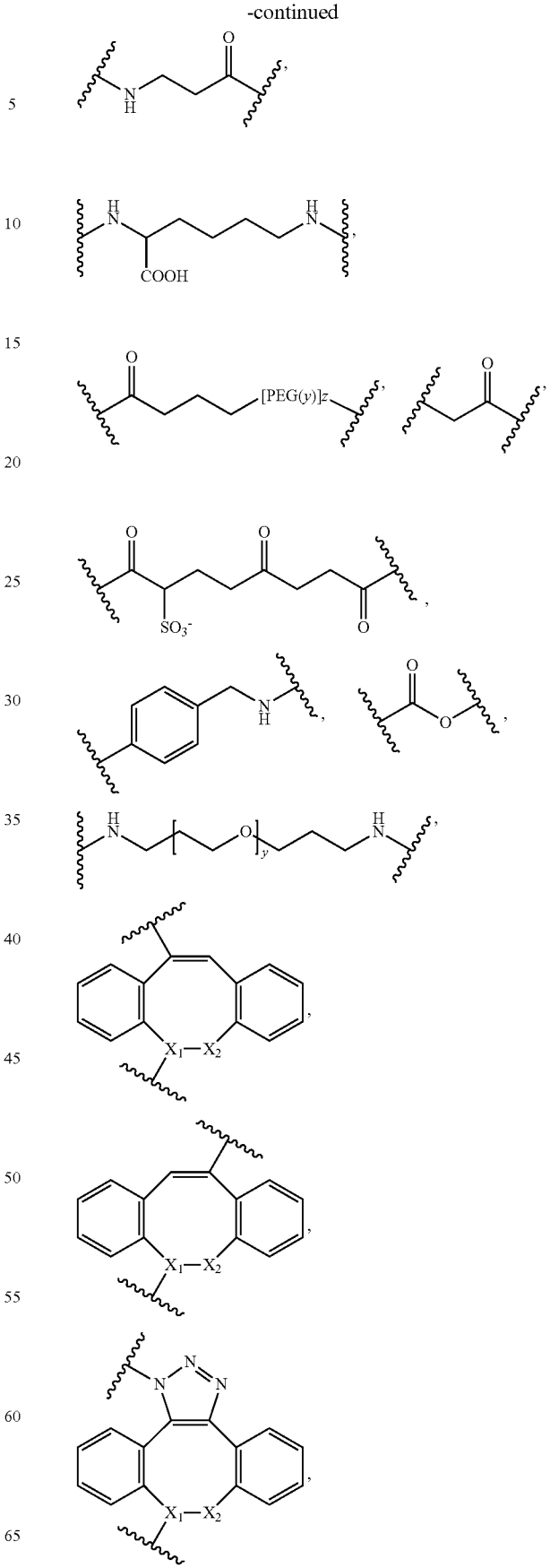

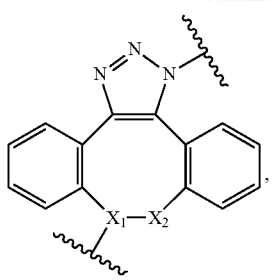

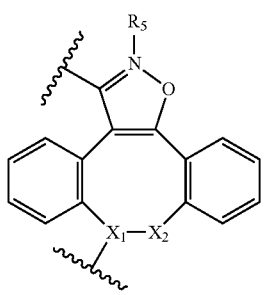

and

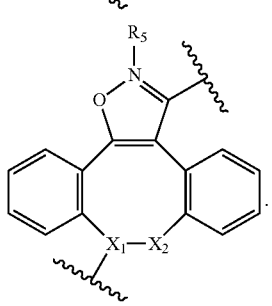

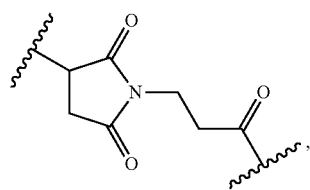

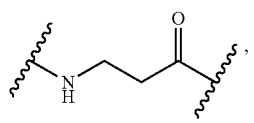

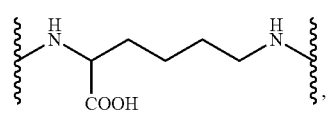

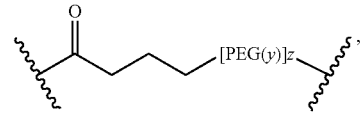

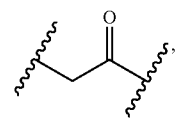

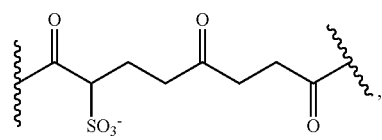

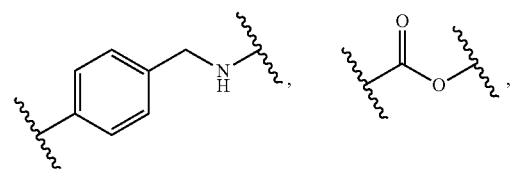

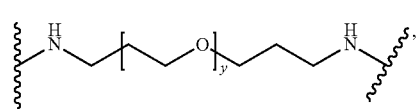

In some embodiments, Ra or Rb comprises a [PEG(y)]z group bonded to a lysine.

In some embodiments, Ra or Rb comprises a $C_1$-$C_4$ acyl group bonded to a succinimide group.

In some embodiments, Ra or Rb comprises a lysine bonded to a $C_1$-$C_4$ acyl.

In some embodiments, Ra or Rb comprises a [PEG(y)]z group, which is bonded to a glutaryl.

In some embodiments, Ra or Rb is an organic structure consisting of a chain of three, four or five moieties selected from the group consisting of [PEG(y)]z, $C_2$-$C_5$ acyl, succinyl, malonyl, glutaryl, an amino acid, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

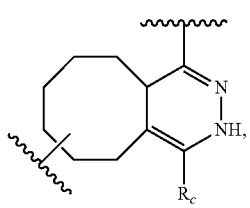

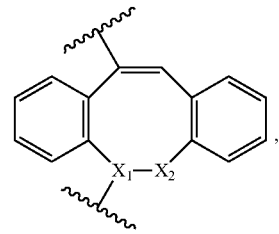

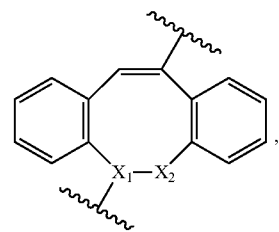

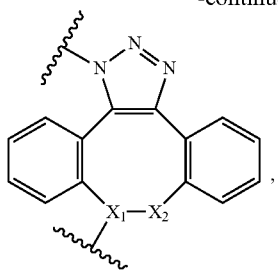

,

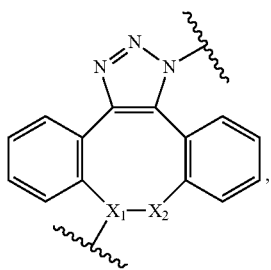

,

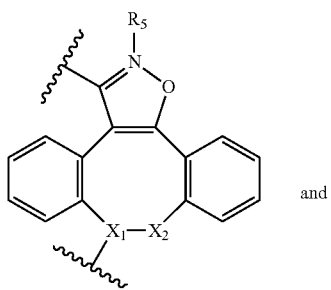

and

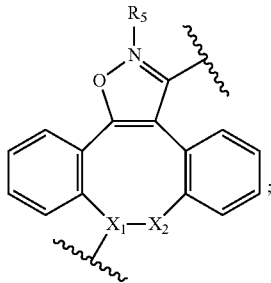

;

wherein $X_1$ is CH or N, $X_2$ is $CH_2$ or a carbonyl group, and $R_5$ is an aryl or alkyl group;

wherein [PEG(y)]z is:

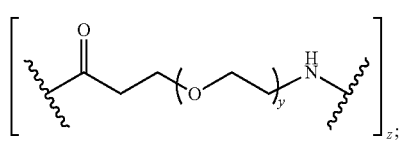

wherein y=1-100 and z=1-10.

In some embodiments, Ra or Rb is a bond.

In some embodiments, Ra or Rb is a cysteine.

In some embodiments, Ra or Rb has a linear structure.

In some embodiments, Ra or Rb has a branched structure.

In some embodiments, y is 1-20. In some embodiments, y is 21-40. In some embodiments, y is 41-60. In some embodiments, y is 61-80. In some embodiments, y is 30-50. In some embodiments, y is 12, 24, 36 or 48.

In some embodiments, z is 1.

In some embodiments, the terminal carbonyl of the [PEG(y)]z group is part of an amide bond.

In some embodiments, the terminal amine of the [PEG(y)]z group is part of an amide bond.

In some embodiments, Ra or Rb is

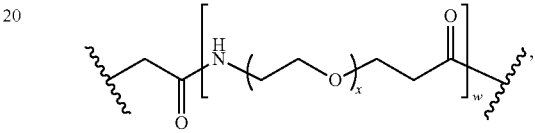

wherein x is 1-100, and w is 0-5.

In some embodiments, x is 1-20. In some embodiments, x is 21-40. In some embodiments, x is 41-60. In some embodiments, x is 61-80. In some embodiments, x is 30-50. In some embodiments, x is 12, 24, 36 or 48.

In some embodiments, w is 1. In some embodiments, w is 0.

In some embodiments, Ra or Rb has the structure:

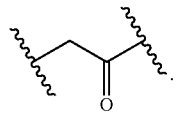 [SMILES: *CC(*)=O]

In some embodiments, Ra or Rb is:

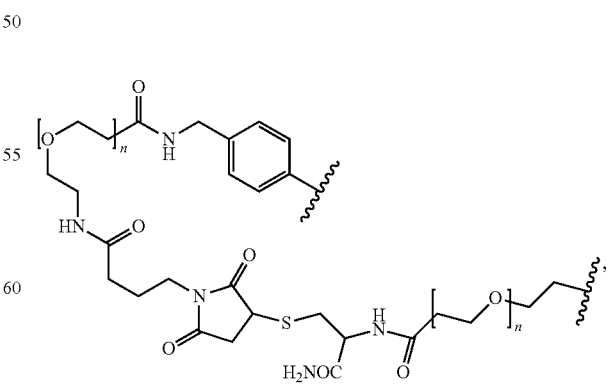

wherein n is 1, 2, 3, 4, 5, 6, 7, 8, 9, 10, 11, 12, 13, 14, 15, 16, 17, 18, 19, 20, 1-30, 1-40, or 1-50.

In some embodiments, Ra or Rb is:
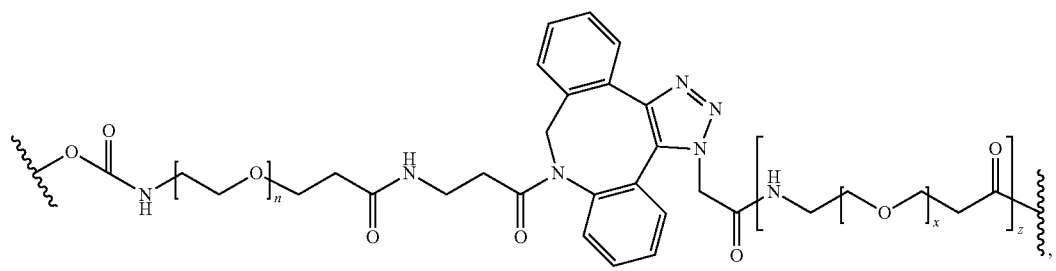
wherein n is 1, 2, 3, 4, 5, 6, 7, 8, 9, 10, 11, 12, 13, 14, 15, 16, 17, 18, 19, 20, 1-30, 1-40, or 1-50, x is 1, 2, 3, 4, 5, 6, 7, 8, 9, 10, 11, 12, 13, 14, 15, 16, 17, 18, 19, 20, 1-30, 1-40, or 1-50 and z is 1, 2, 3, 4, 5, 6, 7, 8, 9, 10, 11, 12, 13, 14, 15, 16, 17, 18, 19, 20, 1-30, 1-40, or 1-50.
In some embodiments, Ra or Rb is:
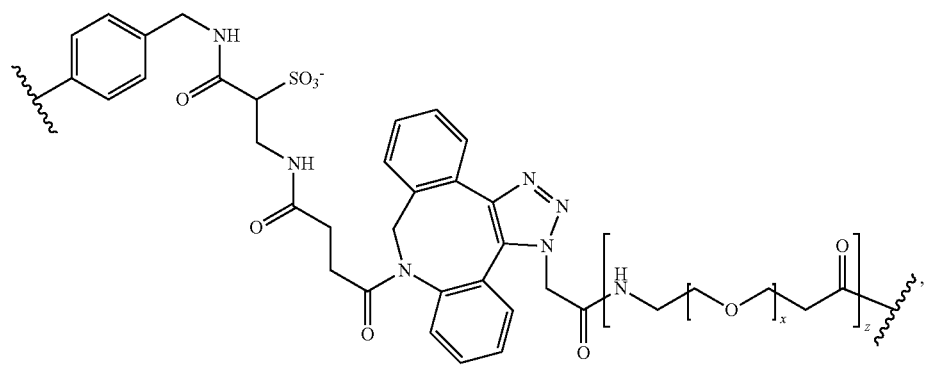

wherein x is 1, 2, 3, 4, 5, 6, 7, 8, 9, 10, 11, 12, 13, 14, 15, 16, 17, 18, 19, 20, 1-30, 1-40, or 1-50 and z is 1, 2, 3, 4, 5, 6, 7, 8, 9, 10, 11, 12, 13, 14, 15, 16, 17, 18, 19, 20, 1-30, 1-40, or 1-50.
In some embodiments, Ra or Rb is:
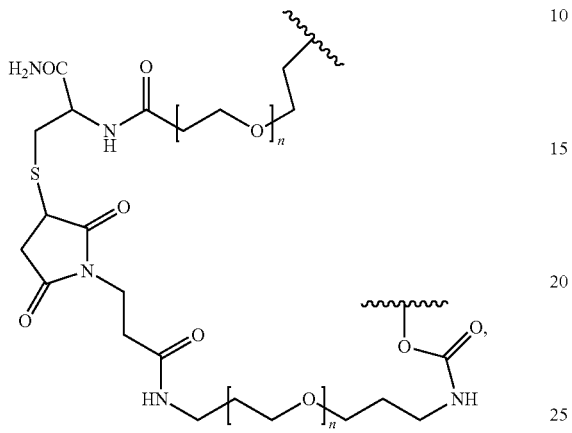
wherein n is 1, 2, 3, 4, 5, 6, 7, 8, 9, 10, 11, 12, 13, 14, 15, 16, 17, 18, 19, 20, 1-30, 1-40, or 1-50.
In some embodiments, the solid line between A and B represents a nonpeptidyl linkage comprising the structure:
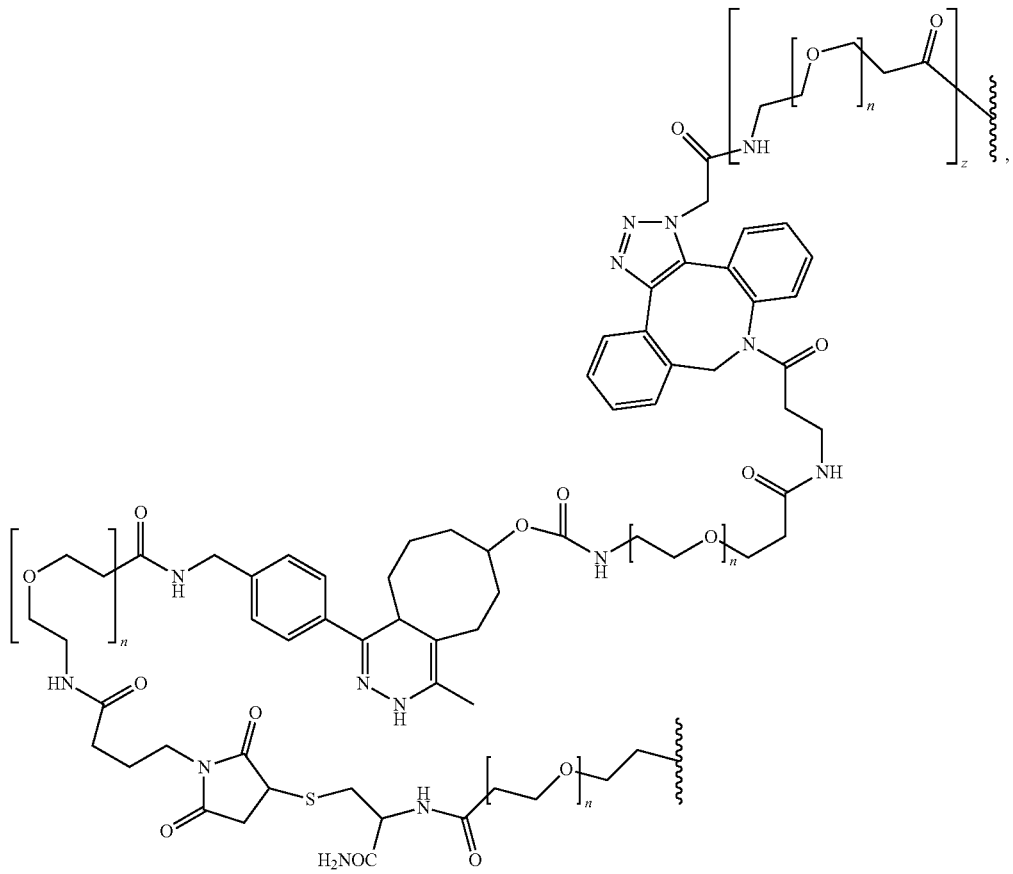

wherein n is 1, 2, 3, 4, 5, 6, 7, 8, 9, 10, 11, 12, 13, 14, 15, 16, 17, 18, 19, 20, 1-30, 1-40, or 1-50, x is 1, 2, 3, 4, 5, 6, 7, 8, 9, 10, 11, 12, 13, 14, 15, 16, 17, 18, 19, 20, 1-30, 1-40, or 1-50 and z is 1, 2, 3, 4, 5, 6, 7, 8, 9, 10, 11, 12, 13, 14, 15, 16, 17, 18, 19, 20, 1-30, 1-40, or 1-50.

In some embodiments, the solid line between A and B represents a nonpeptidyl linkage comprising the structure:

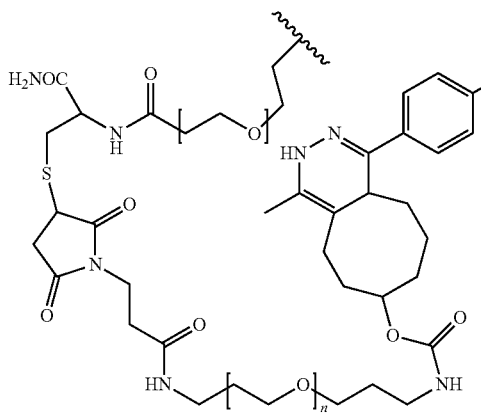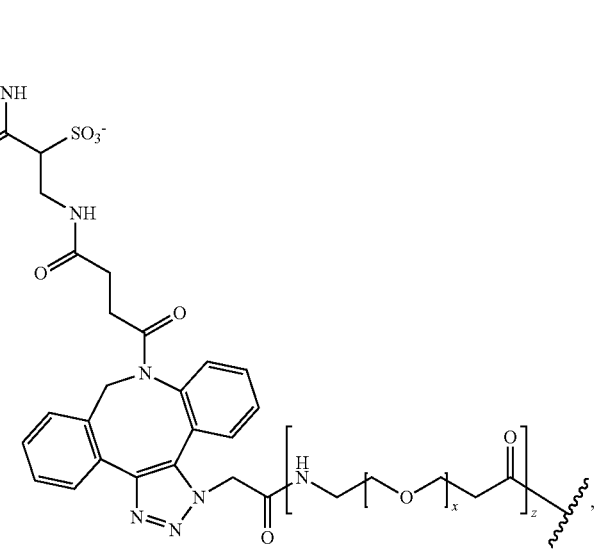

d) reacting A', B' and Z' in any order to produce the compound.

In some embodiments, the cysteine or selenocysteine naturally occurs in the stretch of consecutive amino acids. In some embodiments, the cysteine or selenocysteine does not naturally occur in the stretch of consecutive amino acids.

wherein n is 1, 2, 3, 4, 5, 6, 7, 8, 9, 10, 11, 12, 13, 14, 15, 16, 17, 18, 19, 20, 1-30, 1-40, or 1-50, x is 1, 2, 3, 4, 5, 6, 7, 8, 9, 10, 11, 12, 13, 14, 15, 16, 17, 18, 19, 20, 1-30, 1-40, or 1-50 and x is 1, 2, 3, 4, 5, 6, 7, 8, 9, 10, 11, 12, 13, 14, 15, 16, 17, 18, 19, 20, 1-30, 1-40, or 1-50.

The present invention provides a process for producing a compound having the structure:

A-B - - - Z wherein A is a biologically active structure of the compound;

wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a cysteine or a selenocysteine;

wherein B is a chemical structure linking A and Z;

wherein the dashed line between B and Z represents a peptidyl linkage;

wherein the solid line between A and B represents a nonpeptidyl linkage;

which comprises the following steps:

a) obtaining an A' which comprises A or a derivative of A, and a first terminal reactive group;

b) obtaining a B' which comprises B or a derivative of B, a second terminal reactive group and a third terminal reactive group, wherein the second terminal reactive group is capable of reacting with the first terminal reactive group to form a non-peptidyl linkage;

c) obtaining a Z' which comprises Z or a derivative of Z, and a fourth terminal reactive group, wherein the fourth terminal reactive group is capable of reacting with the third terminal reactive group to form a peptidyl linkage; and In some embodiments, the consecutive amino acids have at their N-terminus a sequence selected from the group consisting of a cysteine, selenocysteine, CP, CPXCP (where X=P, R, or S) (SEQ ID NOs: 206-208), CDKTHTCPPCP (SEQ ID NO: 209), CVECPPCP (SEQ ID NO: 210), CCVECPPCP (SEQ ID NO: 211) and CDTPPPCPRCP (SEQ ID NO: 212).

In some embodiments, the $F_c$ domain of an antibody is a naturally occurring $F_c$ domain of an antibody.

In some embodiments, the $F_c$ domain of an antibody is a variant $F_c$ domain of an antibody.

In some embodiments, the variant $F_c$ domain of an antibody is a mutated $F_c$ domain of an antibody.

In some embodiments, the mutated $F_c$ domain is a substitution mutant.

In some embodiments, the substitution mutant has an amino acid substitution at the N-terminus, the C-terminus, or at a position of the $F_c$ domain other than the N-terminus or the C-terminus.

In some embodiments, the substitution mutant has 1, 2, 3, 4, 5, 6, 7, 8, 9, 10, 10-15, 15-20, 10-20, or 20-50 amino acid substitutions in the stretch of consecutive amino acids thereof.

In some embodiments, the substitutions are conservative amino acid substitutions.

In some embodiments, the mutated mutated $F_c$ domain is an amino acid addition mutant.

In some embodiments, the amino acid addition mutant has 1, 2, 3, 4, 5, 6, 7, 8, 9, 10, 10-15, 15-20, 10-20, or 20-50 added amino acids in the stretch of consecutive amino acids thereof.

In some embodiments, the mutated $F_c$ domain is an amino acid deletion mutant.

In some embodiments, the amino acid deletion mutant has 1, 2, 3, 4, 5, 6, 7, 8, 9, 10, 10-15, 15-20, 10-20, or 20-50 deleted amino acids in the stretch of consecutive amino acids thereof.

In some embodiments, the consecutive amino acids are identical to a stretch of at least 0, 20, 30, 40, 50, 60, 70, 80, 90, 100, 110, 120, 130, 140, 150, 160, 170, 180, or 190 consecutive amino acids present in the chain of the $F_c$ domain of the antibody.

In some embodiments, the consecutive amino acids are identical to the stretch of amino acids in the hinge region, the CH2 region or the CH3 region of the Fc domain, or a portion thereof.

In some embodiments, the solid line between A and B represents a nonpeptidyl linkage comprising the structure:

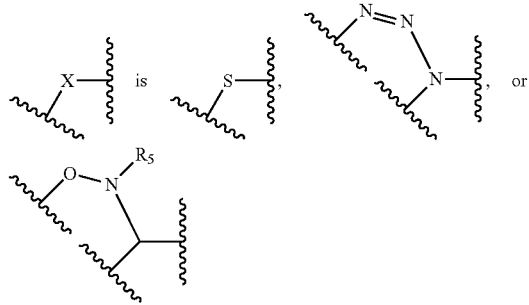

wherein

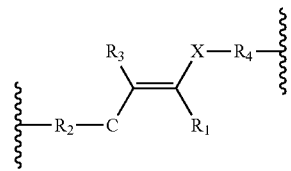

in which $R_5$ is an alkyl or aryl group wherein $R_1$ is H or is part of an additional structure that is a cyclic structure, wherein the additional cyclic structure comprises $R_1$ or a portion of $R_1$, and may also comprise $R_2$ or a portion of $R_2$, and the carbon between $R_2$ and the alkene double bond;

with the proviso that if

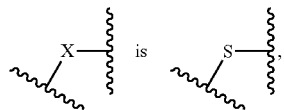

$R_3$ is a H; if

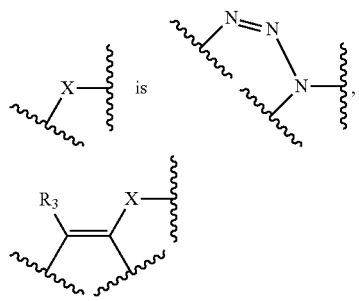

is a triazole ring that comprises

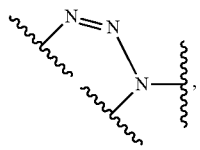 [SMILES: */N=N\N(*)*]

and if

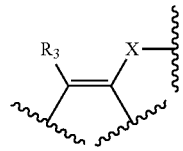

is

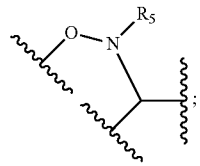

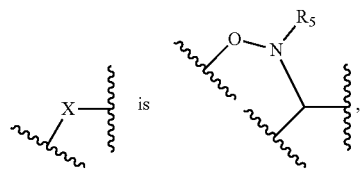

a N-alkyl or aryl substituted isoxazoline ring that comprises

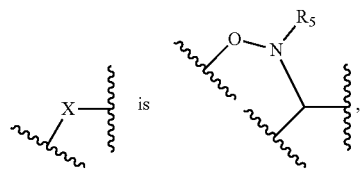

and wherein $R_2$ represents an organic structure which connects to one of A or B and $R_4$ represents an organic structure which connects to the other of A or B;

which comprises the following steps:

a) obtaining an A' which comprises A or a derivative of A, and a first terminal reactive group;

b) obtaining a B' which comprises B or a derivative of B, a second terminal reactive group and a third terminal reactive group, wherein the second terminal reactive group is capable of reacting with the first terminal reactive group to form a non-peptidyl linkage;

c) obtaining a C' which comprises C or a derivative of C, and a fourth terminal reactive group, wherein the fourth terminal reactive group is capable of reacting with the third terminal reactive group to form a peptidyl linkage; and d) reacting A', B' and C' in any order to produce the compound.

In some embodiments, step d) is performed by first reacting A' and B' to produce $$\overset{A}{\underset{B''}{|}}$$

wherein B" comprises B and the third terminal reactive group, and the solid line between B" and represents a non-peptidyl linkage; and then reacting

with C' to produce the compound.

In some embodiments, step d) is performed by first reacting C' and B' to produce

wherein B" comprises B and the second terminal reactive group, and the dashed line between B" and C represents a peptidyl linkage; and then reacting

with A' to produce the compound.

In some embodiments, the first terminal reactive group is an azide, a thiol, a nitrone or an alkyne.

In some embodiments, the first terminal reactive group is an alkyne.

In some embodiments, the alkyne is a cycloalkyne

In some embodiments, the alkyne is an eight-membered ring.

In some embodiments, the alkyne is an azacyclooctyne.

In some embodiments, the cycloalkyne is a biarylazacyclooctyne.

In some embodiments, the cycloalkyne is a cyclooctyne.

In some embodiments, the alkyne is a terminal alkyne.

In some embodiments, the first terminal reactive group is an azide, thiol or nitrone.

In some embodiments, the first terminal reactive group is an azide.

In some embodiments, the first terminal reactive group is a thiol.

In some embodiments, the first terminal reactive group is a nitrone.

In some embodiments, the first terminal reactive group is an N-alkyl nitrone.

In some embodiments, the first terminal reactive group is an N-aryl nitrone.

In some embodiments, the second terminal reactive group is an azide, a thiol, a nitrone or an alkyne.

In some embodiments, the second terminal reactive group is an alkyne.

In some embodiments, the alkyne is a cycloalkyne

In some embodiments, the alkyne is an eight-membered ring.

In some embodiments, the alkyne is an azacyclooctyne.

In some embodiments, the cycloalkyne is a biarylazacyclooctyne.

In some embodiments, the cycloalkyne is a cyclooctyne.

In some embodiments, the alkyne is a terminal alkyne.

In some embodiments, the second terminal reactive group is an azide, thiol or nitrone.

In some embodiments, the second terminal reactive group is an azide.

In some embodiments, the second terminal reactive group is a thiol.

In some embodiments, the second terminal reactive group is a nitrone.

In some embodiments, the second terminal reactive group is an N-alkyl nitrone.

In some embodiments, the second terminal reactive group is an N-aryl nitrone.

In some embodiments, the first terminal reactive group is a terminal alkyne and the second terminal reactive group is an azide, thiol or nitrone.

In some embodiments, the second terminal reactive group is an azide.

In some embodiments, the second terminal reactive group is a thiol.

In some embodiments, the second terminal reactive group is a nitrone.

In some embodiments, the nitrone is an N-alkyl or N-aryl nitrone.

In some embodiments, the first terminal reactive group is an azide, thiol or nitrone, and the second terminal reactive group is a terminal alkyne.

In some embodiments, the first terminal reactive group is an azide.

In some embodiments, the first terminal reactive group is a thiol.

In some embodiments, the first terminal reactive group is a nitrone.

In some embodiments, the nitrone is an N-alkyl or N-aryl nitrone.

In some embodiments, the first terminal reactive group is a cycloalkyne and the second terminal reactive group is an azide, thiol or nitrone.

In some embodiments, the first terminal reactive group is an azide.

In some embodiments, the first terminal reactive group is a thiol.

In some embodiments, the first terminal reactive group is a nitrone.

In some embodiments, the nitrone is an N-alkyl or N-aryl nitrone.

In some embodiments, the first terminal reactive group is an azide, thiol or nitrone, and the second terminal reactive group is a cycloalkyne.

In some embodiments, the first terminal reactive group is an azide.

In some embodiments, the first terminal reactive group is a thiol.

In some embodiments, the first terminal reactive group is a nitrone.

In some embodiments, the nitrone is an N-alkyl or N-aryl nitrone.

In some embodiments, the cycloalkyne is an eight-membered ring.

In some embodiments, the cycloalkyne is an azacyclooctyne.

In some embodiments, the cycloalkyne is a biarylazacyclooctyne.

In some embodiments, the cycloalkyne is a cyclooctyne.

In some embodiments, the first terminal reactive group is an azide and the second terminal reactive group is a terminal alkyne; or the first terminal reactive group is an azide and the second terminal reactive group is a cycloalkyne; or the first terminal reactive group is a thiol and the second terminal reactive group is a cycloalkyne; or the first terminal reactive group is a N-alkyl nitrone or N-aryl nitrone and the second terminal reactive group is a cyclooctyne.

In some embodiments, the second terminal reactive group is an azide and the first terminal reactive group is a terminal alkyne; or the second terminal reactive group is an azide and the first terminal reactive group is a cycloalkyne; or the second terminal reactive group is a thiol and the first terminal reactive group is a cycloalkyne; or the second terminal reactive group is a N-alkyl nitrone or N-aryl nitrone and the first terminal reactive group is a cyclooctyne.

In some embodiments, the first terminal reactive group and the second terminal reactive group react to produce a triazole, thiolene, N-alkyl isoxazoline or N-aryl isoxazoline.

In some embodiments, the first terminal reactive group and the second terminal reactive group react to produce a triazole.

In some embodiments, the first terminal reactive group and the second terminal reactive group react to produce a thiolene.

In some embodiments, the first terminal reactive group and the second terminal reactive group react to produce a N-alkyl isoxazoline or N-aryl isoxazoline.

In some embodiments, reacting the first reactive group with the second reactive group results in at least an 80%, 85% or 90% yield of the reaction in less than 3, 6, 12, 18, 24, 30, 36, 42, 48 or 72 hours.

In some embodiments, the solid line between A and B represents a nonpeptidyl linkage comprising the structure:

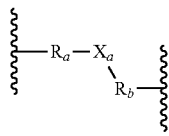

wherein $X_a$ is a chemical structure containing a cyclooctane fused to a dihydropyridazine; and
wherein $R_a$ represents an organic structure which connects to one of A or B and $R_b$ represents an organic structure which connects to the other of A or B.

In some embodiments, the first terminal reactive group is a trans-cyclooctene or a tetrazine.

In some embodiments, the first terminal reactive group is a trans-cyclooctene.

In some embodiments, the alkyne is a tetrazine.

In some embodiments, the second terminal reactive group is a trans-cyclooctene or a tetrazine.

In some embodiments, the second terminal reactive group is a trans-cyclooctene.

In some embodiments, the second terminal reactive group has the structure:

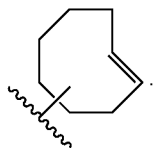

In some embodiments, the second terminal reactive group has the structure:

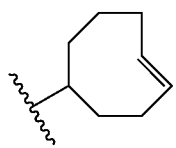

In some embodiments, the second terminal reactive group is a tetrazine.

In some embodiments, the second terminal reactive group has the structure:

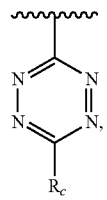

wherein $R_c$ is H, alkyl or aryl.

In some embodiments, the second terminal reactive group has the structure:

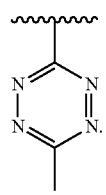

In some embodiments, the first terminal reactive group is a trans-cyclooctene and the second terminal reactive group is a tetrazine.

In some embodiments, the first terminal reactive group is a tetrazine and the second terminal reactive group is a trans-cyclooctene.

In some embodiments, the first terminal reactive group and the second terminal reactive group react to produce a chemical structure containing a cyclooctane fused to a dihydropyridazine.

In some embodiments, the first terminal reactive group and the second terminal reactive group react to produce the chemical structure:

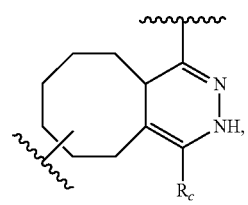

wherein $R_c$ is H, alkyl or aryl;
or a tautomer thereof.

In some embodiments, the the third reactive group and the fourth terminal reactive group are each independently an amino acid or amino acid derivative.

In some embodiments, the third reactive group is a threonine or threonine derivative.

In some embodiments, the third reactive group is a thioester derivative of an amino acid.

In some embodiments, the fourth reactive group is cysteine, selenocysteine, homocysteine, or homoselenosysteine, or a derivative of cysteine, selenocysteine, homocysteine, or homoselenosysteine.

In some embodiments, the fourth reactive group is cysteine or a derivative of cysteine.

In some embodiments, the fourth reactive group is cysteine.

In some embodiments, A' is prepared by the following steps:
i) obtaining an A" which comprises A or a derivative of A, and a stretch of consecutive amino acids comprising an intein;
ii) obtaining a substituted cysteine, selenocysteine, homocysteine, or homoselenosysteine residue, or a substituted derivative of a cysteine, selenocysteine, homocysteine, or homoselenosysteine residue, wherein the cysteine residue is substituted at the C-terminus with an organic structure containing an alkyne, an azide, a thiol, or a nitrone; and
iii) reacting A" with the substituted cysteine residue to produce A'.

In some embodiments, the organic structure containing an alkyne is N-propargyl amine.

In some embodiments, A' is prepared by the following steps:
i) obtaining an A" which comprises A or a derivative of A, and which comprises at least one free thiol group;
ii) obtaining a compound which comprises a first terminal reactive group and a terminal maleimide; and
iii) reacting A" with the compound of step ii) to produce A'.

In some embodiments, A" is prepared by the following steps:
a) obtaining an A''', wherein A''' is a polypeptide which comprises A or a derivative of A, and which comprises at least one disulfide bond; and
b) treating A''' with mercaptoethylamine (MEA) to produce A".

In some embodiments, the A''' is prepared by the following steps:
a) obtaining a monoclonal antibody which comprises A or derivative of A, and which comprises at least one disulfide bond; and
b) treating the polypeptide of step a) with IdeS to produce A'''.

In some embodiments, the monoclonal antibody binds TNFα.

In some embodiments, the monoclonal antibody is adalimumab.

In some embodiments, if R1 is hydrogen and the first terminal reactive group is alkyne, then in step d) B' is reacted in the presence of a metal catalyst.

In some embodiments, if R1 is hydrogen and the second terminal reactive group is alkyne, then in step d) B' is reacted in the presence of a metal catalyst.

In some embodiments, the metal catalyst is Ag(I) or Cu(I).

In some embodiments, A' comprises one or more branched residue, wherein each branched residue comprises an additional first terminal reactive group.

In some embodiments, B' comprises one or more branched residue, wherein each branched residue comprises an additional second terminal reactive group.

In some embodiments, B' comprises one or more branched residue, wherein each branched residue comprises an additional third terminal reactive group.

In some embodiments, the branched residue is an amino acid residue.

In some embodiments, the amino acid residue is a lysine or a lysine derivative, arginine or an arginine derivative, aspartic acid or an aspartic acid derivative, glutamic acid or a glutamic acid derivative, asparagines or a asparagines derivative, glutamine or glutamine derivative, tyrosine or tyrosine derivative, cysteine or cysteine derivative or ornithine or ornithine derivative.

In some embodiments, the amino acid residue is substituted at the N-position with a residue containing a terminal amino or carbony reactive group.

In some embodiments, the branched residue is an organic residue containing two or more terminal amino groups or two or more terminal carbonyl groups.

In some embodiments, the organic residue is iminodipropionic acid, iminodiacetic acid, 4-amino-pimelic acid, 4-amino-heptanedioic acid, 3-aminohexanedioic acid, 3-aminoadipic acid, 2-aminooctanedioic acid, or 2-amino-6-carbonyl-heptanedioic acid.

In some embodiments, the process is performed in the absence of a non-thiol reducing agent.

In some embodiments, the process is performed in the absence of a thiol reducing agent.

In some embodiments, the process is performed in the presence of a thiol reducing agent.

In some embodiments, the process is performed at an overall yield of 80% or higher.

In some embodiments, the process is performed at an overall yield of 90% or higher.

In some embodiments, reacting the first reactive group with the second reactive group results in at least a 50%, 55%, 60%, 65%, 70%, 80%, 85% or 90% yield of the reaction in less than 1, 2, 3, 4, 5, 6, 7, 8, 9, 10, or 60 minutes.

In some embodiments, B is an organic acid residue.

In some embodiments, B is a stretch of 1-50 amino acid residues, and optionally, an organic acid residue.

In some embodiments, B is a stretch of 1-10 consecutive amino acids.

In some embodiments, B comprises a stretch of consecutive amino acids in the sequence, or a portion thereof,

```
                                              (SEQ ID NO: 213)
    EPKSCDKTHTCPPCP, (SEQ ID NO: 214)
    ERKCCVECPPCP, (SEQ ID NO: 215)
    ELKTPLGDTTHTCPRCP(EPKSCDTPPPCPRCP)3, (SEQ ID NO: 216)
    ESKYGPPCPSCP.
```

In some embodiments, B has a threonine at its C-terminus.

In some embodiments, Z comprises one C, wherein C is a first polypeptide, which first polypeptide comprises consecutive amino acids which (i) are identical to a stretch of consecutive amino acids present in a chain of an $F_c$ domain of an antibody; (ii) bind to an $F_c$ receptor; and (iii) have at their N-terminus a sequence selected from the group consisting of a cysteine, selenocysteine, CP, CPXCP (where X=P, R, or S) (SEQ ID NOs: 206-208), CDKTHTCPPCP (SEQ ID NO: 209), CVECPPCP (SEQ ID NO: 210), CCVECPPCP (SEQ ID NO: 211) and CDTPPPCPRCP (SEQ ID NO: 212).

In some embodiments, C comprises consecutive amino acids which (i) are identical to a stretch of consecutive amino acids present in a chain of an $F_c$ domain of an antibody; (ii) bind to an $F_c$ receptor; and (iii) have at their N-terminus a sequence comprising a naturally occurring cysteine selected from the group consisting of CP, CPXCP (where X=P, R, or S) (SEQ ID NOs: 206-208), CDKTH-TCPPCP (SEQ ID NO: 209), CVECPPCP (SEQ ID NO: 210), CCVECPPCP (SEQ ID NO: 211) and CDTPPPCPRCP (SEQ ID NO: 212).

In some embodiments, C is a polypeptide component of the compound, which polypeptide component comprises consecutive amino acids which (i) are identical to a stretch of consecutive amino acids present in a chain of an $F_c$ domain of an antibody; (ii) bind to an $F_c$ receptor; and (iii) have at their N-terminus a sequence comprising a non-naturally occurring cysteine or selenocysteine.

In some embodiments, C comprises consecutive amino acids which are identical to a stretch of consecutive amino acids present in the chain of an Fc domain of an antibody selected from the group consisting of IgG, IgM, IgA, IgD, and IgE.

In some embodiments, C comprises consecutive amino acids which are identical to a stretch of consecutive amino acids present in the chain of an Fc6 domain of an antibody.

In some embodiments, C further comprises consecutive amino acids which are identical to a stretch of consecutive amino acids present in a chain of an antibody other than a chain of a Fc domain of the antibody.

In some embodiments, C comprises consecutive amino acids which are identical to a stretch of consecutive amino acids present in a heavy chain of a Fab or a Fab' of an antibody.

In some embodiments, C comprises consecutive amino acids which are identical to a stretch of consecutive amino acids present in the light chain of a Fab or a Fab' of an antibody.

In some embodiments, Z further comprises a second polypeptide, which second polypeptide comprises consecutive amino acids which are identical to a stretch of consecutive amino acids present in a chain of an antibody other than a chain of a Fc domain of the antibody.

In some embodiments, the second polypeptide comprises consecutive amino acids which are identical to a stretch of consecutive amino acids present in a heavy chain of a Fab or a Fab' of an antibody.

In some embodiments, the second polypeptide comprises consecutive amino acids which are identical to a stretch of consecutive amino acids present in the light chain of a Fab or a Fab' of an antibody.

In some embodiments, Z comprises an antibody or a portion thereof.

In some embodiments, Z comprises at least one Fab or Fab' of an antibody, or a portion of the at least one Fab or Fab'.

In some embodiments, Z comprises at least 2, 3, 4, 5, 6, 7, 8, 9, or 10 copies of the Fab or Fab' or portion thereof.

In some embodiments, Z comprises Fab-1 or Fab'1, or a portion thereof of an antibody.

In some embodiments, Z comprises Fab-2 or Fab'2, or a portion thereof of an antibody.

In some embodiments, Z comprises two Fab or Fab' hands of an antibody.

In some embodiments, the antibody is an IgG, IgM, IgA, IgD or IgE antibody.

In some embodiments, the Fab or Fab' is present in adalimumab.

In some embodiments, Z comprises at least one stretch of consecutive amino acids which are identical to a stretch of consecutive amino acids present in a single chain antibody.

In some embodiments, the C-terminus of C comprises a stretch of consecutive amino acids present in a chain of an $F_c$ domain of an antibody that has been modified.

In some embodiments, the C-terminus of C is a cysteine, selenocysteine, homocysteine, or homoselenosysteine, or a derivative of cysteine, selenocysteine, homocysteine, or homoselenosysteine.

In some embodiments, B is linked to Z via a peptidyl linkage between an N-terminal cysteine or selenocysteine of a polypeptide of Z and an amino acid residue or an organic acid residue of B.

In some embodiments, Z comprises a second polypeptide, and B is linked to Z via a peptidyl linkage between the N-terminal cysteine or selenocysteine of the second polypeptide of Z and an amino acid residue or an organic acid residue of B.

In some embodiments, B is linked to C via a peptidyl linkage between the N-terminal cysteine or selenocysteine of C and an amino acid residue or an organic acid residue of B.

In some embodiments, Z comprises one polypeptide, which is C.

In some embodiments, Z comprises two polypeptides, which are C and a second polypeptide.

The present invention provides homodimers and heterodimers comprising compounds of the invention.

In some embodiments, each compound of the dimer is capable of binding to the other by at least one disulfide bond.

In some embodiments, each compound of the dimer is capable of binding to the other by at least one disulfide bond between the C or the second polypeptide of each compound.

In some embodiments, each compound of the dimer is bound to the other by at least one disulfide bond.

In some embodiments, each compound of the dimer is bound to the other by at least one disulfide bond between the C or the second polypeptide of each compound.

In some embodiments, each compound of the dimer is non-covalently bound to the other.

In some embodiments, the dimer is:
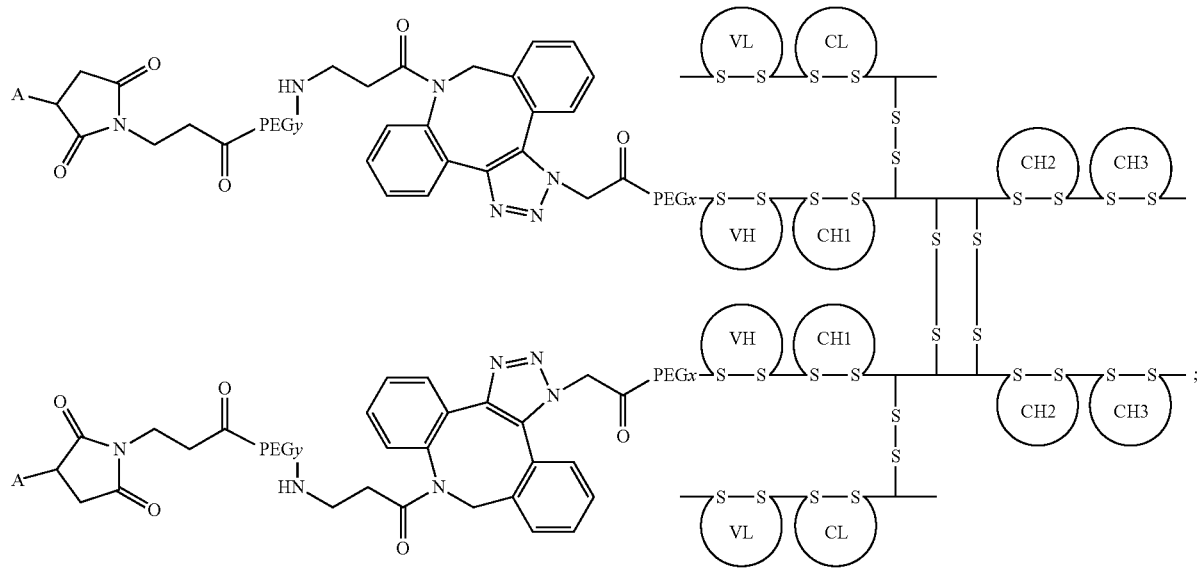
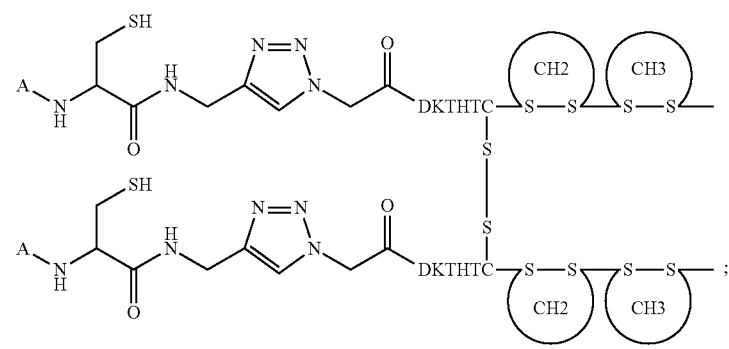
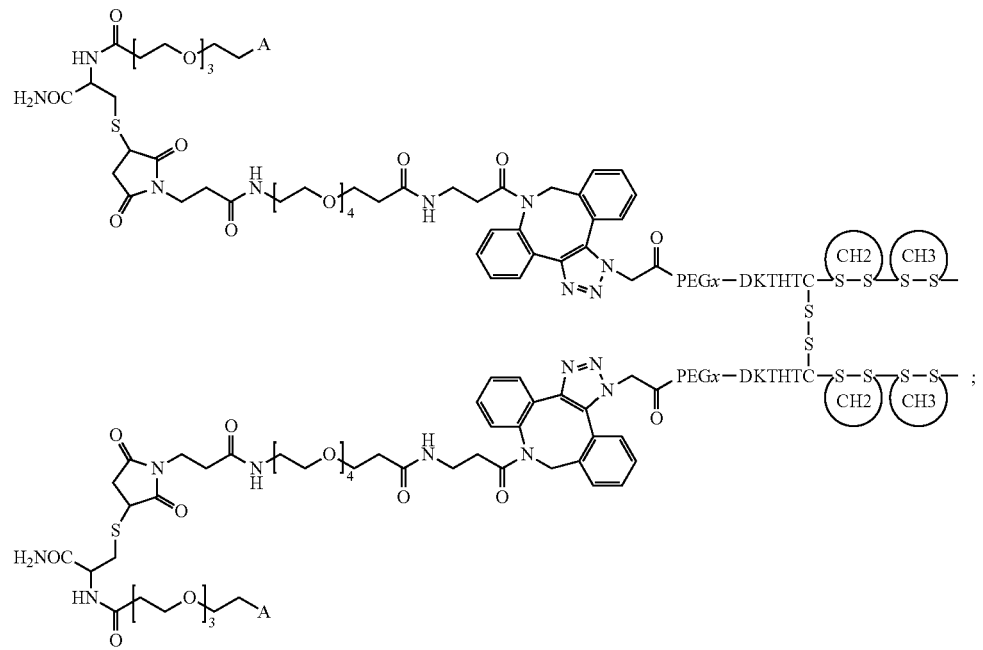

-continued
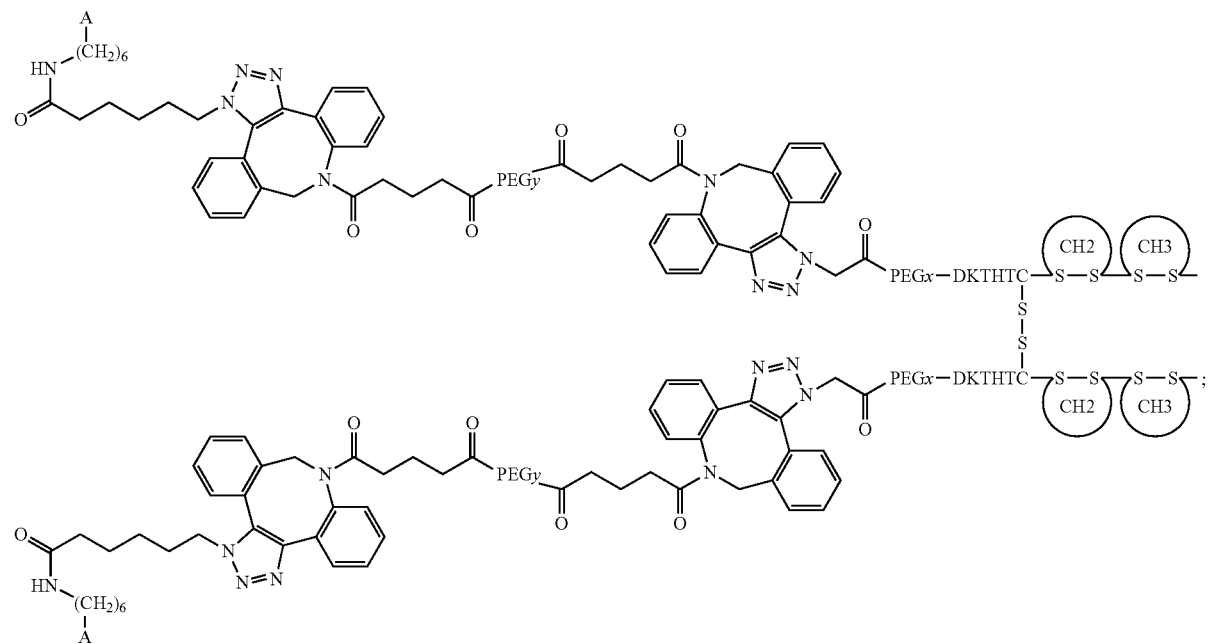
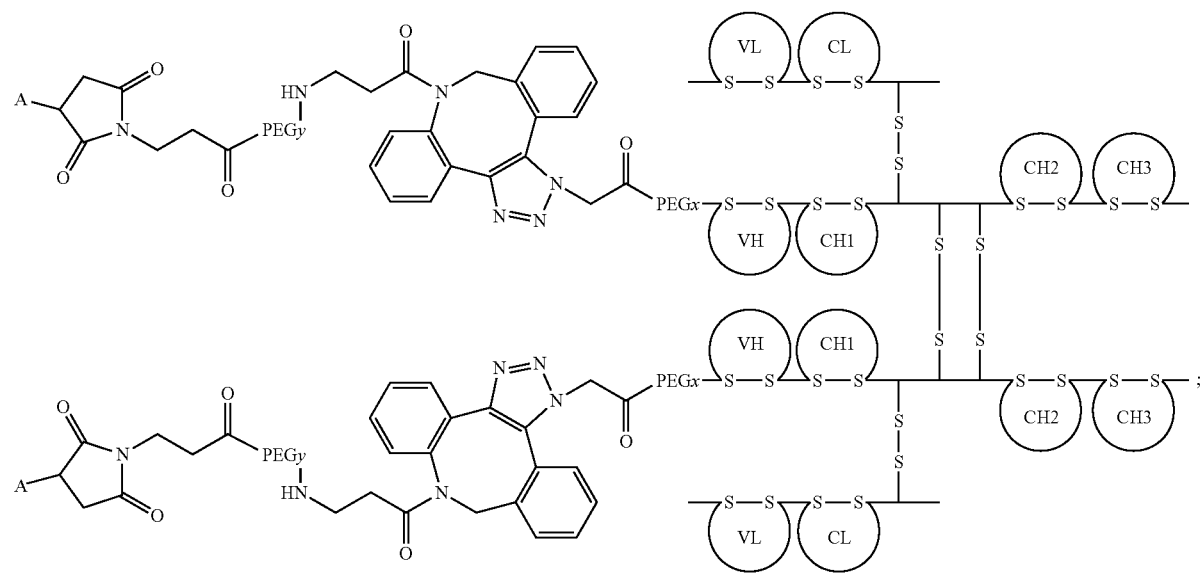

-continued
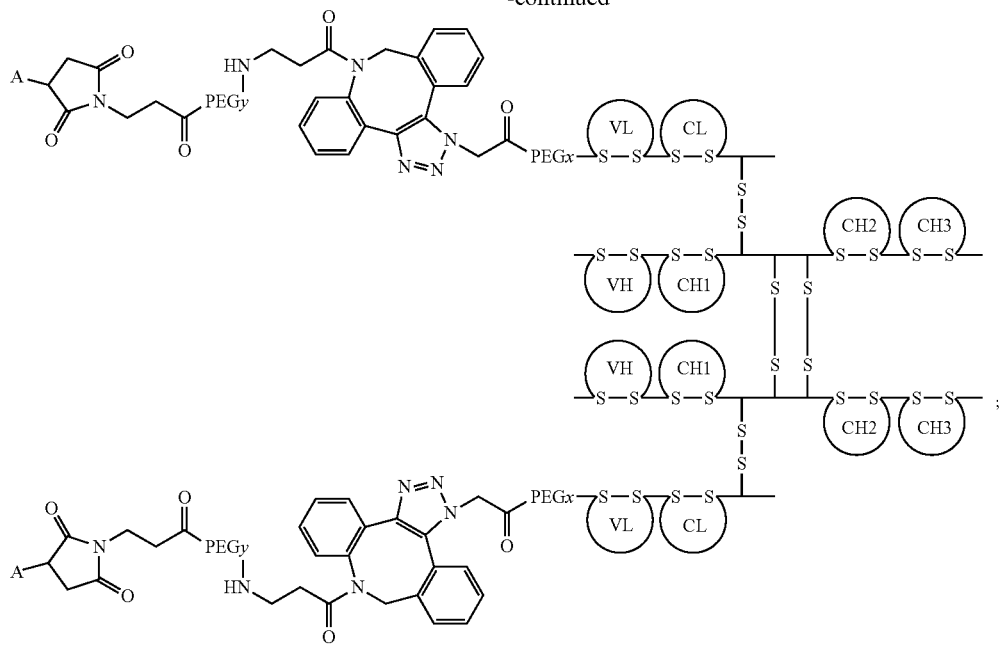
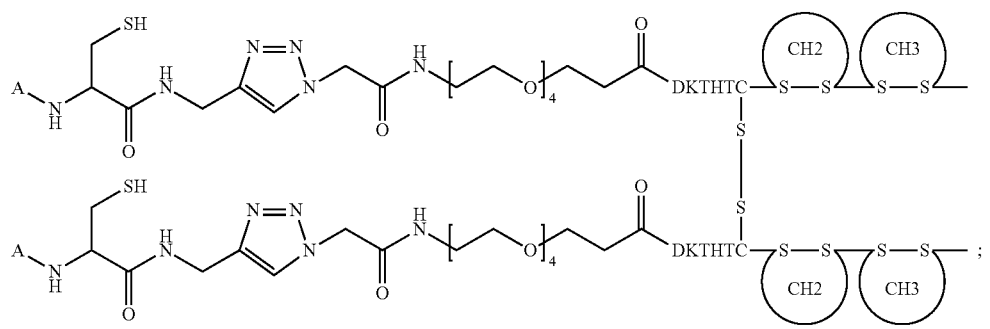
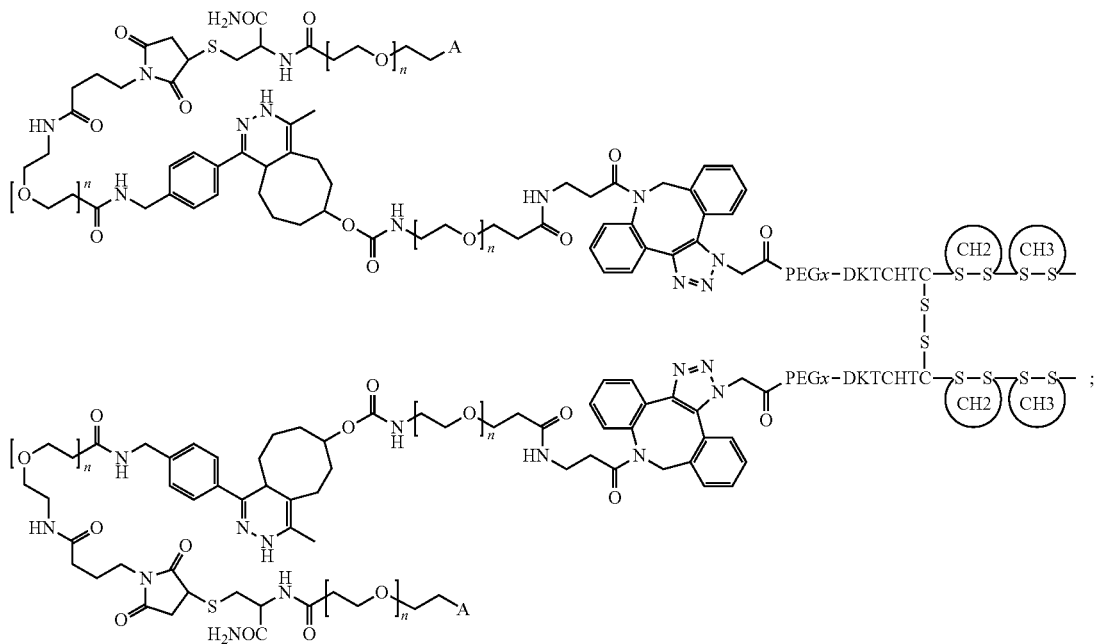

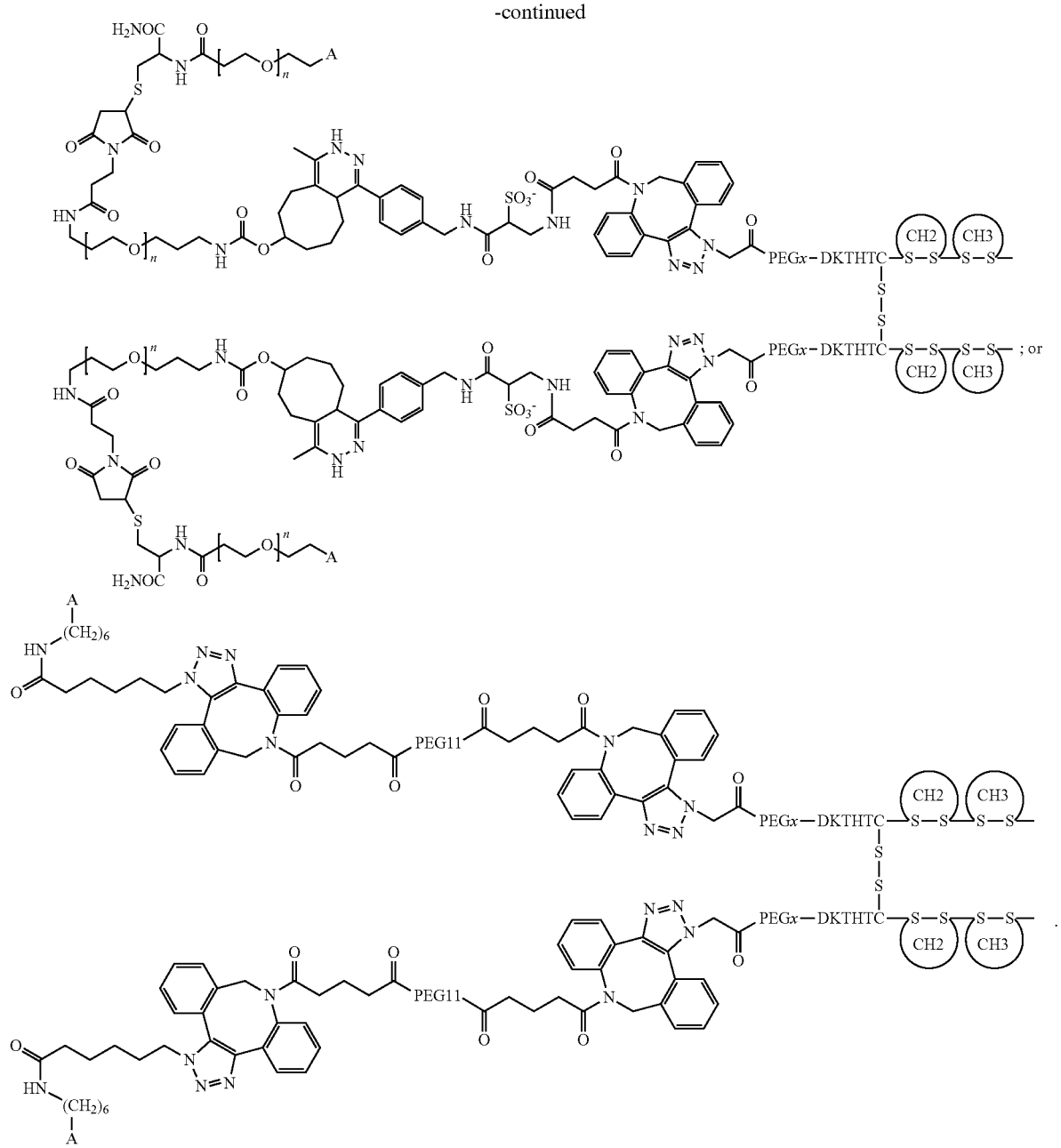

Additional non-limiting examples of dimers of compounds of the present invention are shown in the Figures.

In some embodiments, the branched residue is a lysine or a lysine derivative, arginine or an arginine derivative, aspartic acid or an aspartic acid derivative, glutamic acid or a glutamic acid derivative, asparagines or a asparagines derivative, glutamine or glutamine derivative, tyrosine or tyrosine derivative, cysteine or cysteine derivative or ornithine or ornithine derivative.

In some embodiments, the branched residue is an amino acid substituted at the N-position with a residue containing a terminal amino or carbonyl reactive group. In some embodiments, the branched residue is an organic residue containing two or more terminal amino groups or two or more terminal carbonyl groups.

In some embodiments, the branched residue is an organic residue containing two or more terminal amino groups. In some embodiments, the branched residue is an organic residue containing two or more terminal carbonyl groups. In some embodiments, the branched residue is a diaminopropionic acid. In some embodiments, the branched residue is a diaminopropionic carbonyl compound.

In some embodiments, the branched residue is 4-(carbonylmethoxy)phenylalanine, 2-amino-6-(carbonylmethylamino)hexanoic acid, S-(carbonylpropyl)cysteine, S-(carbonylethyl)cysteine, S-(carbonylmethyl)cysteine, N-(carbonylethyl)glycine, N-(carbonylmethyl)glycine, iminodipropionic acid, iminodiacetic acid, 4-amino-pimelic acid, 4-amino-heptanedioic acid, 3-aminohexanedioic acid, 3-aminoadipic acid, 2-aminooctanedioic acid, or 2-amino-6-carbonyl-heptanedioic acid.

In some embodiments, the branched residue is prepared from Fmoc-L-Asp-AMC, Fmoc-L-Asp-pNA, Fmoc-L-Glu-AMC, Fmoc-L-Glu-pNA, Fmoc-L-Glu(Edans)-OH, Fmoc-L-Glu(PEG-biotinyl)-OH, (S)-Fmoc-2-amino-hexanedioic acid-6-tert-butyl ester, (S)-Fmoc-2-amino-adipic acid-6-tert-butyl ester, (S)-Fmoc-Aad(OtBu)—OH, (S)-Fmoc-2-amino-5-tert-butoxycarbonyl-hexanedioic acid-6-tert-butyl ester, (S)-Fmoc-2-amino-heptanedioic acid-7-tert-butyl ester, (S)-Fmoc-2-amino-pimelic acid-7-tert-butyl ester, (S)-Fmoc-2-amino-6-tert-butoxycarbonyl-heptanedioic acid-7-tert-butyl ester, (S)-Fmoc-2-amino-octanedioic acid-8-tert-butyl ester, (S)-Fmoc-2-amino-suberic acid-8-tert-butyl ester, (S)-Fmoc-Asu(OtBu)—OH, (R)-Fmoc-3-amino-hexanedioic acid-1-tert-butyl ester, (R)-Fmoc-3-amino-adipic acid-1-tert-butyl ester, (R)-Fmoc-4-amino-heptanedioic acid-1-tert-butyl ester, (R)-Fmoc-4-amino-pimelic acid-1-tert-butyl ester, Boc-iminodiacetic acid, Fmoc-iminodiacetic acid, Boc-iminodipropionic acid, Fmoc-iminodipropionic acid, Fmoc-N-(tert-butoxycarbonylmethyl)-glycine, Fmoc-N-(tert-butoxycarbonylethyl)-glycine, Fmoc-L-Cys(tert-butoxycarbonylmethyl)-OH (R)-Fmoc-2-amino-3-(tert-butoxycarbonylmethylsulfanyl)-propionic acid, Fmoc-L-Cys(tert-butoxycarbonylpropyl)-OH (R)-Fmoc-2-amino-3-(3-tert-butoxycarbonylpropylsulfanyl)-propionic acid, Fmoc-L-Cys(tert-butoxycarbonylethyl)-OH (R)-Fmoc-2-amino-3-(2-tert-butoxycarbonylethylsulfanyl)-propionic acid, Fmoc-4-(tert-butoxycarbonylmethoxy)-L-phenylalanine, or (S)-Fmoc-2-amino-6-(Boc-tert-butoxycarbonylmethylamino)-hexanoic acid.

In some embodiments, the branched residue is prepared from N-α-Boc-DL-diaminopropionic acid, N-α-Boc-D-diaminopropionic acid, N-α-Boc-L-diaminopropionic acid, N-α-Fmoc-L-diaminopropionic acid, N-α-Boc-N-β-Alloc-D-diaminopropionic acid, N-α-Boc-N-β-Alloc-L-diaminopropionic acid, N-α-Fmoc-N-β-alloc-L-diaminopropionic acid, N-α-N-α-Bis-Boc-L-diaminopropionic acid, N-α-Fmoc-N-β-Boc-D-diaminopropionic acid, N-α-Fmoc-N-β-Boc-L-diaminopropionic acid, N-α-Z—N-β-Boc-L-diaminopropionic acid, N-α-Boc-N-β-Fmoc-D-diaminopropionic acid, N-α-Boc-N-β-Fmoc-L-diaminopropionic acid, N-α-N-β-Bis-Fmoc-L-diaminopropionic acid, N-α-Z—N-β-Fmoc-L-diaminopropionic acid, N-α-Boc-N-β-Z-L-diaminopropionic acid, N-α-Fmoc-N-β-Z-L-diaminopropionic acid, N-α-Fmoc-N-β-(Boc-aminooxyacetyl)-L-diaminopropionic acid, N-α-Boc-N-gamma-Fmoc-D-diaminobutyric acid, N-α-Boc-N-gamma-Fmoc-L-diaminobutyric acid, N-α-Boc-N-gamma-Fmoc-L-diaminobutyric acid, N-α-Fmoc-N-gamma-Boc-D-diaminobutyric acid, N-α-Fmoc-N-gamma-Boc-L-diaminobutyric acid, N-α-Fmoc-N-gamma-Alloc-L-diaminobutyric acid, (S)—N-b-Fmoc-N-gamma-Boc-3,4-diaminobutyric acid, H-L-ornithine, N-α-Boc-N-delta-Alloc-L-ornithine, N-α-Fmoc-N-delta-Alloc-L-ornithine, N-α-Fmoc-N-delta-Boc-L-ornithine, (S)-Boc-2-amino-5-azido-pentanoic acid. DCHA, (S)-Fmoc-2-amino-5-azido-pentanoic acid, N-a-N-delta-bis-Boc-N-a-N-delta-bis(3-Boc-aminopropyl)-L-ornithine, N-α-Boc-N-β-N-delta-N-delta-tris(3-Boc-aminopropyl)-L-ornithine, Fmoc-L-Lys(Biotin)-OH, Fmoc-L-Lys(Dabcyl)-OH, Fmoc-L-Lys(Boc)(Me)-OH, Fmoc-L-Lys(Boc)(iPr)—OH, (2S,5R)-Fmoc-2-amino-4-(3-Boc-2,2-dimethyl-oxazolidin-5-yl)-butyric acid, (S)-Fmoc-2-amino-6-(Boc-tert-butoxycarbonylmethyl-amino)-hexanoic acid, (S)-Fmoc-2-amino-7-(Boc-amino)-heptanoic acid, Fmoc-L-Arg(Me)(Pbf)-OH, Fmoc-L-Arg(Me)2(Pbf)-OH, Fmoc-L-Arg(Me)2-OH, (S)-Fmoc-3-amino-5-[(N'-Pbf-pyrrolidine-1-carboximidoyl)-amino]-pentanoic acid, Fmoc-L-Homoarg(Et)2-OH, Boc-3-amino-5-(Fmoc-amino)-benzoic acid, 3,5-bis[2-(Boc-amino)ethoxy]-benzoic acid, Fmoc-4-[2-(Boc-amino)ethoxy]-L-phenylalanine, N,N-bis(N'-Fmoc-3-aminopropyl)-glycine potassium hemisulfate, N,N-bis(N'-Fmoc-3-aminopropyl)-glycine potassium hemisulfate, Fmoc-N-(2-Boc-amino-ethyl)-glycine, Fmoc-N-(3-Boc-aminopropyl)-glycine, Fmoc-N-(4-Boc-aminobutyl)-glycine, (R,S)—N-α-Fmoc-N-a'-Boc-diaminoacetic acid, N,N'-bis-Fmoc-diaminoacetic acid, (S)—N-4-Fmoc-N-8-Boc-diaminooctanoic acid, (R,S)—N-Fmoc-N'-Boc-imidazolidine-2-carboxylic acid, Fmoc-p(NH-Boc)-L-Phe-OH, Boc-p(NH-Fmoc)-L-Phe-OH, or Boc-p(NH—Z)—L-Phe-OH.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Terms

As used herein, and unless stated otherwise, each of the following terms shall have the definition set forth below.
Peptidyl linkage: the structure

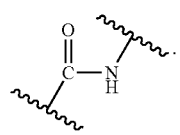 [SMILES: *NC(*)=O]

A peptidyl linkage may be a peptide bond.

Stretch of consecutive amino acids: a plurality of amino acids arranged in a chain, each of which is joined to a preceding amino acid by a peptide bond, excepting that the first amino acid in the chain may optionally not be joined to a preceding amino acid. The amino acids of the chain may be naturally or non-naturally occurring, or may comprise a mixture thereof. The amino acids, unless otherwise indicated, may be genetically encoded, naturally-occurring but not genetically encoded, or non-naturally occurring, and any selection thereof.

N-terminal amino acid residue: the terminal residue of a stretch of two or more consecutive amono acids having a free α-amino (NH$_2$) functional group, or a derivative of an α-amino (NH$_2$) functional group.

N-terminus: the free α-amino (NH$_2$) group (or derivative thereof) of a N-terminal amino acid residue.

C-terminal amino acid residue: the terminal residue of a stretch of two or more consecutive amono acids having a free α-carboxyl (COOH) functional group, or a derivative of a α-carboxyl (COOH) functional group.

C-terminus: the free α-carboxyl (COOH) group (or derivative thereof) of a C-terminal amino acid residue.

A "biologically active structure", as used herein, means a structure of a molecule or fragment thereof, capable of treating a disease or condition or localizing or targeting a compound of the invention to a site of a disease or condition in the body by performing a function or an action, or stimulating or responding to a function, an action or a reaction, in a biological context (e.g. in an organism, a cell, or an in vitro model thereof). Biologically active structures may comprise a structure of at least one of polypeptides, nucleic acids, small molecules such as small organic or inorganic molecules.

A "bond", unless otherwise specified, or contrary to context, is understood to include a covalent bond, a dipole-dipole interaction such as a hydrogen bond, and intermolecular interactions such as van der Waals forces.

A "Signal Sequence" is a short (3-60 amino acids long) peptide chain that directs the post-translational transport of a polypeptide.

"Amino acid" as used herein, in one embodiment, means a L or D isomer of the genetically encoded amino acids, i.e. isoleucine, alanine, leucine, asparagine, lysine, aspartate, methionine, cysteine, phenylalanine, glutamate, threonine, glutamine, tryptophan, glycine, valine, proline, arginine, serine, histidine, tyrosine, selenocysteine, pyrrolysine and also includes homocysteine and homoselenocysteine.

Other examples of amino acids include an L or D isomer of taurine, gaba, dopamine, lanthionine, 2-aminoisobutyric acid, dehydroalanine, ornithine and citrulline, as well as non-natural homologues and synthetically modified forms thereof including amino acids having alkylene chains shortened or lengthened by up to two carbon atoms, amino acids comprising optionally substituted aryl groups, and amino acids comprising halogenated groups, including halogenated alkyl and aryl groups as well as beta or gamma amino acids, and cyclic analogs.

Due to the presence of ionizable amino and carboxyl groups, the amino acids in these embodiments may be in the form of acidic or basic salts, or may be in neutral forms. Individual amino acid residues may also be modified by oxidation or reduction. Other contemplated modifications include hydroxylation of proline and lysine, phosphorylation of hydroxyl groups of seryl or threonyl residues, and methylation of the alpha-amino groups of lysine, arginine, and histidine side chains.

Covalent derivatives may be prepared by linking particular functional groups to the amino acid side chains or at the N- or C-termini.

Compounds comprising amino acids with R-group substitutions are within the scope of the invention. It is understood that substituents and substitution patterns on the compounds of the instant invention can be selected by one of ordinary skill in the art to provide compounds that are chemically stable from readily available starting materials.

"Natural amino acid" as used herein means a L or D isomer of the genetically encoded amino acids, i.e. isoleucine, alanine, leucine, asparagine, lysine, aspartate, methionine, cysteine, phenylalanine, glutamate, threonine, glutamine, tryptophan, glycine, valine, proline, arginine, serine, histidine, tyrosine, selenocysteine, pyrrolysine and homocysteine and homoselenocysteine.

"Non-natural amino acid" as used herein means a chemically modified L or D isomer of isoleucine, alanine, leucine, asparagine, lysine, aspartate, methionine, cysteine, phenylalanine, glutamate, threonine, glutamine, tryptophan, glycine, valine, proline, arginine, serine, histidine, tyrosine, selenocysteine, pyrrolysine, homocysteine, homoselenocysteine, taurine, gaba, dopamine, lanthionine, 2-aminoisobutyric acid, dehydroalanine, ornithine or citrulline, including cysteine and selenocysteine derivatives having $C_3$-$C_{10}$ aliphatic side chains between the alpha carbon and the S or Se. In one embodiment the aliphatic side chain is an alkylene. In another embodiment, the aliphatic side chain is an alkenylene or alkynylene.

In addition to the stretches of consecutive amino acid sequences described herein, it is contemplated that variants thereof can be prepared by introducing appropriate nucleotide changes into the encoding DNA, and/or by synthesis of the desired consecutive amino acid sequences. Those skilled in the art will appreciate that amino acid changes may alter post-translational processes of the stretches of consecutive amino acids described herein when expression is the chosen method of synthesis (rather than chemical synthesis for example), such as changing the number or position of glycosylation sites or altering the membrane anchoring characteristics.

Variations in the sequences described herein, can be made, for example, using any of the techniques and guidelines for conservative and non-conservative mutations set forth, for instance, in U.S. Pat. No. 5,364,934. Variations may be a substitution, deletion or insertion of one or more codons encoding the consecutive amino acid sequence of interest that results in a change in the amino acid sequence as compared with the native sequence. Optionally the variation is by substitution of at least one amino acid with any other amino acid in one or more of the domains. Guidance in determining which amino acid residue may be inserted, substituted or deleted without adversely affecting the desired activity may be found by comparing the sequence with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements.

Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence. It is understood that any terminal variations are made within the context of the invention disclosed herein.

Amino acid sequence variants of the binding partner are prepared with various objectives in mind, including increasing the affinity of the binding partner for its ligand, facilitating the stability, purification and preparation of the binding partner, modifying its plasma half life, improving therapeutic efficacy, and lessening the severity or occurrence of side effects during therapeutic use of the binding partner.

Amino acid sequence variants of these sequences are also contemplated herein including insertional, substitutional, or deletional variants. Such variants ordinarily can prepared by site-specific mutagenesis of nucleotides in the DNA encoding the target-binding monomer, by which DNA encoding the variant is obtained, and thereafter expressing the DNA in recombinant cell culture. Fragments having up to about 100-150 amino acid residues can also be prepared conveniently by in vitro synthesis. Such amino acid sequence variants are predetermined variants and are not found in nature. The variants exhibit the qualitative biological activity (including target-binding) of the nonvariant form, though not necessarily of the same quantative value. While the site for introducing an amino acid sequence variation is predetermined, the mutation per se need not be predetermined. For example, in order to optimize the performance of a mutation at a given site, random or saturation mutagenesis (where all 20 possible residues are inserted) is conducted at the target codon and the expressed variant is screened for the optimal combination of desired activities. Such screening is within the ordinary skill in the art.

Amino acid insertions usually will be on the order of about from 1 to 10 amino acid residues; substitutions are typically introduced for single residues; and deletions will range about from 1 to 30 residues. Deletions or insertions preferably are made in adjacent pairs, i.e. a deletion of 2 residues or insertion of 2 residues. It will be amply apparent from the following discussion that substitutions, deletions, insertions or any combination thereof are introduced or combined to arrive at a final construct.

In an aspect, the invention concerns a compound comprising a stretch of consecutive amino acids having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence disclosed in the specification, a figure, a SEQ ID NO. or a sequence listing of the present application.

The % amino acid sequence identity values can be readily obtained using, for example, the WU-BLAST-2 computer program (Altschul et al., Methods in Enzymology 266:460-480 (1996)).

Fragments of native sequences are provided herein. Such fragments may be truncated at the N-terminus or C-terminus, or may lack internal residues, for example, when compared with a full length native protein. Again, it is understood that any terminal variations are made within the context of the invention disclosed herein.

Certain fragments lack amino acid residues that are not essential for a desired biological activity of the sequence of interest.

Any of a number of conventional techniques may be used. Desired peptide fragments or fragments of stretches of consecutive amino acids may be chemically synthesized. An alternative approach involves generating fragments by enzymatic digestion, e.g. by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide/sequence fragment, by polymerase chain reaction (PCR). Oligonucleotides that define the desired termini of the DNA fragment are employed at the 5' and 3' primers in the PCR.

In particular embodiments, conservative substitutions of interest are shown in Table A under the heading of preferred substitutions. If such substitutions result in a change in biological activity, then more substantial changes, denominated exemplary substitutions in Table A, or as further described below in reference to amino acid classes, are introduced and the products screened.

TABLE 1

| Original | Exemplary | Preferred |
|---|---|---|
| Ala (A) | val; leu; ile | val |
| Arg (R) | lys; gln; asn | lye |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the sequence are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro;
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-1085 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Covalent modifications: The stretch of consecutive amino acids may be covalently modified. One type of covalent modification includes reacting targeted amino acid residues with an organic derivatizing agent that is capable of reacting with selected side chains or the N- or C-terminal residues that are not involved in an -x-x- bond. Derivatization with bifunctional agents is useful, for instance, for crosslinking to a water-insoluble support matrix or surface for use in the method for purifying anti-sequence of interest antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-((p-azidophenyl)dithio)propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification comprises altering the native glycosylation pattern of the stretch of consecutive amino acids. "Altering the native glycosylation pattern" is intended for purposes herein to mean deleting one or more carbohydrate moieties found in amino acid sequences (either by removing the underlying glycosylation site or by deleting the glycosylation by chemical and/or enzymatic means), and/or adding one or more glycosylation sites that are not present in the native sequence. In addition, the phrase includes qualitative changes in the glycosylation of the native proteins, involving a change in the nature and proportions of the various carbohydrate moieties present.

Addition of glycosylation sites to the amino acid sequence may be accomplished by altering the amino acid sequence. The alteration may be made, for example, by the addition of, or substitution by, one or more serine or threonine residues to the native sequence (for O-linked glycosylation sites). The amino acid sequence may optionally be altered through changes at the DNA level, particularly by mutating the DNA encoding the amino acid sequence at preselected bases such that codons are generated that will translate into the desired amino acids.

Another means of increasing the number of carbohydrate moieties on the amino acid sequence is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259-306 (1981).

Removal of carbohydrate moieties present on the amino acid sequence may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification comprises linking the amino acid sequence to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The term "substitution", "substituted" and "substituent" refers to a functional group in which one or more bonds to a hydrogen atom contained therein are replaced by a bond to non-hydrogen atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include halogens (i.e., F, Cl, Br, and I); alkyl groups, such as methyl, ethyl, n-propyl, isopropryl, n-butyl, tert-butyl, and trifluoromethyl; aryl groups, such as phenyl; heteroaryl groups, such as triazole, dihydropyridazine and tetrazole; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as sulfonate, trifluoromethanesulfonyl, methanesulfonyl, and p-toluenesulfonyl; sulfnitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. In the compounds used in the method of the present invention, alkyl, heteroalkyl, monocycle, bicycle, aryl, heteroaryl and heterocycle groups can be substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, and hexyl. Unless otherwise specified contains one to twelve carbons. Alkyl groups can be unsubstituted or substituted with one or more substituents, including but not limited to halogen, alkoxy, alkylthio, trifluoromethyl, difluoromethyl, methoxy, and hydroxyl. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. Alkyl is intended to include moieties that are monovalent, divalent, trivalent, etc.

As used herein, "$C_1$-$C_4$ alkyl" includes both branched and straight-chain $C_1$-$C_4$ alkyl.

As used herein, the term "cycloalkane" refers to a monocyclic or bicyclic ring system, which may be unsaturated or partially unsaturated, i.e. possesses one or more double bonds. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclopentenyl, cyclohexyl, cyclohexenyl, cycloheptyl and cyclooctyl. Bicyclic fused ring systems are exemplified by a cycloalkyl ring fused to another cycloalkyl ring. Examples of bicyclic fused ring systems include, but are not limited to, decalin, 1,2,3, 7,8,8a-hexahydro-naphthalene, and the like. Thus, $C_3$-$C_{10}$ cycloalkane includes cyclic rings of alkanes of three to eight total carbon atoms, (e.g., cyclopropyl, cyclobutyl, cyclopentyl, cyclohexyl, cycloheptyl or cyclooctyl and so on). Cycloalkane groups can be unsubstituted or substituted with one or more substituents, including but not limited to halogen, alkoxy, alkylthio, trifluoromethyl, difluoromethyl, methoxy, and hydroxyl. Cycloalkane is intended to include moieties that are monovalent, divalent, trivalent, etc.

As used herein, the term "cycloalkene" refers to a cycloalkane which possesses one or more double bonds. Thus, $C_5$-$C_{10}$ cycloalkene includes cyclic rings of alkanes of five to ten total carbon atoms, (e.g., cyclopentenyl, cyclohexenyl, cycloheptenyl, cyclohexadienyl, cyclooctenyl or cyclooctadienyl and so on). Cycloalkene is intended to moieties that are monovalent, divalent, trivalent, etc. Cycloalkene is intended to include moieties that are monovalent, divalent, trivalent, etc.

As used herein, "alkene" includes both branched and straight-chain aliphatic hydrocarbon groups having one or more double bond and the specified number of carbon atoms and may be unsubstituted or substituted. Thus, $C_2$-$C_n$ as in "C2-$C_n$ alkene" is defined to include groups having 2, 3, . . . , n−1 or n carbons in a linear or branched arrangement. For example, $C_2$-$C_{10}$, as in "$C_2$-$C_{10}$ alkene" is defined to include groups having 2, 3, 4, 5 . . . 10 carbons in a linear or branched arrangement, and specifically includes vinyl, allyl, 1-butene, 2-butene, iso-butene, 1-pentene, 2-pentene, etc. Alkyene groups can be unsubstituted or substituted with one or more substituents, including but not limited to halogen, alkoxy, alkylthio, trifluoromethyl, difluoromethyl, methoxy, and hydroxyl. An embodiment can be $C_2$-$C_3$ alkene, $C_2$-$C_4$ alkene, $C_2$-$C_5$ alkene, and so on. Alkene is intended to include moieties that are monovalent, divalent, trivalent, etc.

As used herein, an "acyl" refers to an alkyl group having a ketone at the first position. For example, an "acyl" embodiment can be acetyl, propionyl, butyryl and valeryl. As another example, an "acyl" embodiment can be:

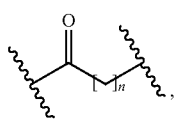

wherein n is 1-10. In another embodiment, n is 1-4. Thus, a "$C_2$-$C_5$ acyl" can be acetyl, propionyl, butyryl, or and valeryl. Acyl is intended to include moieties that are monovalent, divalent, trivalent, etc.

$C_2$-$C_5$ acylamino is an acyl group as defined above further substituted with an amine. The amine may be linked to the carbonyl portion of the acyl group so as to form an amide or the amine may linked to a non-carbonyl portion of the acyl group. For example, the amino group may be at the alpha-position, the beta-position, the gamma-position, the delta-position, etc. As further examples, acylamino includes both alpha-aminoacetyl and acetamido groups. Acylamino includes beta-aminopropionyl).

$C_2$-$C_5$ acyloxy is an acyl group as defined above further substituted with an oxygen. The oxygen may be linked to the carbonyl portion of the acyl group so as to form an amide or the oxygen may linked to a non-carbonyl portion of the acyl group. For example, the oxygen group may be at the alpha-position, the beta-position, the gamma-position, the delta-position, etc. As further examples, acyloxy includes both alpha-oxyacetyl and acetate groups. Acyloxy includes beta-oxypropionyl).

As used herein, "amino" includes primary, secondary, tertiary and quarternary amines. Thus, amino includes a —NH— group, a —NH$_2$ group, a —NR— group, a —NR$_2^+$— group, a —NRH$^+$— group, a —NH$_2^+$— group, a —NH$_3^+$ group and a —NR$_3^+$ group, wherein R is alkyl or aryl. Amino is intended to include moieties that are monovalent, divalent, trivalent, etc.

As used herein, "sulfur" includes a —S— group and a —SH group. The term sulfur is intended to include moieties that are monovalent, divalent, trivalent, etc.

As used herein, "oxygen" includes a —O— group and a —OH group. The term sulfur is intended to moieties that are monovalent and divalent.

As used herein, "succinyl" is derived from succinic acid by removal of one or both hydroxyl groups. An embodiment can be —C(O)—CH$_2$—CH$_2$—C(O)—. Succinyl is intended to include moieties that are monovalent, divalent, trivalent, etc.

As used herein, a "malonyl" is derived from malonic acid by removal of one or both hydroxyl groups. An embodiment can be —C(O)—CH$_2$—C(O)—. Malonyl is intended to include moieties that are monovalent, divalent, trivalent, etc.

As used herein, a "glutaryl" is derived from glutaric acid by removal of one or both hydroxyl groups. An embodiment can be —C(O)—CH$_2$—CH$_2$—CH$_2$—C(O)—. Glutaryl is intended to include moieties that are monovalent, divalent, trivalent, etc.

As used herein, an "adipoyl" is derived from adipic acid by removal of one or both hydroxyl groups. An embodiment can be —C(O)—CH$_2$—CH$_2$—CH$_2$—CH$_2$—(O)—. Adipoyl is intended to include moieties that are monovalent, divalent, trivalent, etc.

A "polyalkylene glycol" is derived from polyalkylene glycol by removal of both hydrogens from the hydroxyl groups. An embodiment can be derived from polyethylene glycol, polypropylene glycol, or polybutylene glycol.

An "polyalkylene glycol" embodiment can be

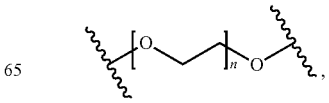

-continued

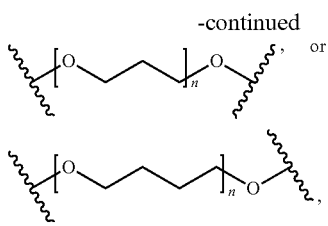

wherein n is 1-10.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from 0, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, dihydropyridizine, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "phenyl" is intended to mean an aromatic six membered ring containing six carbons, and any substituted derivative thereof.

The term "benzyl" is intended to mean a methylene attached directly to a benzene ring. A benzyl group is a methyl group wherein a hydrogen is replaced with a phenyl group, and any substituted derivative thereof.

The term "triazole" is intended to mean a hetaryl having a five-membered ring containing two carbon atoms and three nitrogen atoms, and any substituted derivative thereof.

Dihydropyradizine is optionally substituted and includes 1,2-dihydropyridazines,

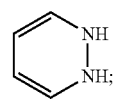

1,4-dihydropyridazines,

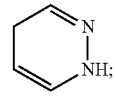

1,6-dihydropyridazines,

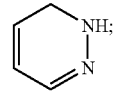

and 4,5-dihydropyridazines,

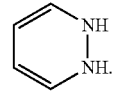

A chemical structure containing a cyclooctane fused to a dihydropyridazine includes, but is not limited to, a chemical structure which contains a cyclooctane fused to the 3rd and 4th position of a dihydropyridazine or a chemical structure which contains a saturated cycloocta[d]pyridazine, any of which are optionally substituted. For example, the chemical structure containing a cyclooctane fused to a dihydropyridazine includes, but is not limited to, a chemical structure which contains a 2,4a,5,6,7,8,9,10-octahydrocycloocta[d]pyridazine,

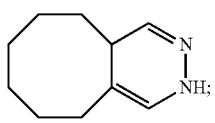 [SMILES: C1=NNC=C2CCCCCCC12]

a 4a,5,6,7,8,9,10,10a-octahydrocycloocta[d]pyridazine,

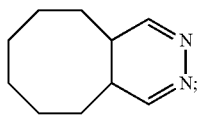 [SMILES: C1=NN=CC2CCCCCCC12]

a 2,3,5,6,7,8,9,10-octahydrocycloocta[d]pyridazine,

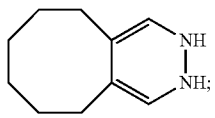 [SMILES: C1=C2CCCCCCC2=CNN1]

a 1,2,5,6,7,8,9,10-octahydrocycloocta[d]pyridazine,

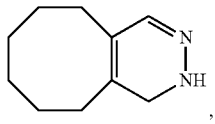

or a 1,2,5,6,7,8,9,10-octahydrocycloocta[d]pyridazine, each of which may be optionally substituted. Tautomers of include, but are not limited to:

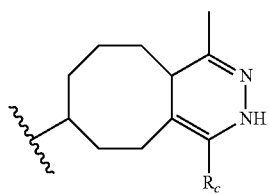

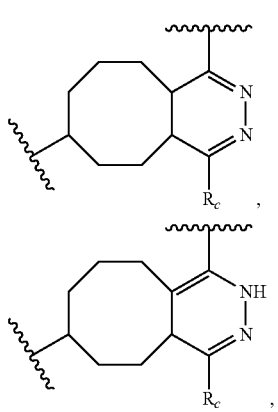

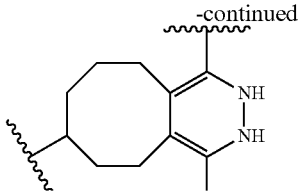

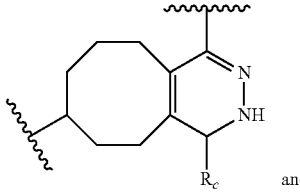

and

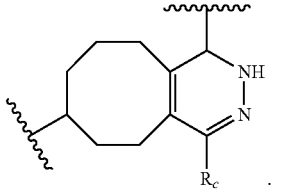

.

In some embodiments, the dihydropyridazine is oxidized to a pyridazine.

In some embodiments, the dihydropyridazine is reduced to result in an open ring structure having a 1,4-dicarbonyl compound.

The compounds used in the method of the present invention may be prepared by techniques well know in organic synthesis and familiar to a practitioner ordinarily skilled in the art. However, these may not be the only means by which to synthesize or obtain the desired compounds.

Compounds of the subject invention can be converted to prodrugs to optimize absorption and bioavailability. Formation of a prodrug include, but is not limited to, reaction of a free hydroxyl group with a carboxylic acid to form an ester, reaction of a free hydroxyl group with an phosphorus oxychloride followed by hydrolysis to form a phosphate, or reaction of a free hydroxyl group with an amino acid to form an amino acid ester, the process of which has been described previously by Chandran in WO 2005/046575. The substituents are chosen and resulting analogs are evaluated according to principles well known in the art of medicinal and pharmaceutical chemistry, such as quantification of structure-activity relationships, optimization of biological activity and ADMET (absorption, distribution, metabolism, excretion, and toxicity) properties.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incoporated by reference.

The compounds of present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

A person having ordinary skill in the art will immediately understand that the definitions of the substituents and moieties (e.g. the moieties of J, Ra and Rb) provided herein are intended to obey the standard rules of chemical valency. For example, where a structure provided herein requires a particular substituent or moiety to be divalent, (e.g. a moiety in a linear chain of moieties) a person having ordinary skill in the art will immediately understand that the definitions of that substituent or moiety are divalent in order to obey the standard rules of chemical valency.

A person having ordinary skill in the art will immediately understand that some divalent moieties depicted in the present invention may be linked to other chemical structures in more than one way, e.g., the depicted structures may be linked to other chemical structures when rotated or flipped.

In some embodiments of the present invention, a compound comprises a nonproteinaceous polymer. In some embodiments, the nonproteinaceous polymer may be is a hydrophilic synthetic polymer, i.e., a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturontc acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; and heparin or heparon.

Salts

Salts of the compounds disclosed herein are within the scope of the invention. As used herein, a "salt" is salt of the instant compounds which has been modified by making acid or base salts of the compounds.

Fc Domains

The term "Fc domain", as used herein, generally refers to a monomer or dimer complex, comprising the C-terminal polypeptide sequences of an immunoglobulin heavy chain. The Fc domain may comprise native or variant Fc sequences. Although the boundaries of the Fc domain of an immunoglobulin heavy chain might vary, the human IgG heavy chain Fc domain is usually defined to stretch from an amino acid residue in the hinge region to the carboxyl terminus of the Fc sequence. The Fc sequence of an immunoglobulin generally comprises two constant regions, a CH2 region and a CH3 region, and optionally comprises a CH4 region. A human Fc domain may be obtained from any suitable immunoglobulin, such as the IgG1, IgG2, IgG3, or IgG4 subtypes, IgA, IgE, IgD or IgM.

Suitable Fc domains are prepared by recombinant DNA expression of pre-Fc chimeric polypeptides comprising 1) a signal peptide, obtained from a secreted or transmembrane protein, that is cleaved in front of a mature polypeptide having an N-terminal cysteine residue, contiguous with 2) an Fc domain polypeptide having an N-terminal cysteine residue.

Suitable examples of signal peptides are sonic hedgehog (SHH) (GenBank Acc. No. NM000193), IFNalpha-2 (IFN) (GenBank Acc. No. NP000596), and cholesterol ester transferase (CETP) (GenBank Accession No. NM000078). Other suitable examples include Indian hedgehog (Genbank Acc. No. NM002181), desert hedgehog (Genbank Acc. No. NM021044), IFNalpha-1 (Genbank Acc. No. NP076918), IFNalpha-4 (Genbank Acc. No. NM021068), IFNalpha-5 (Genbank Acc. No. NM002169), IFNalpha-6 (Genbank Acc. No. NM021002), IFNalpha-7 (Genbank Acc. No. NM021057), IFNalpha-8 (Genbank Acc. No. NM002170), IFNalpha-10 (Genbank Acc. No. NM002171), IFNalpha-13 (Genbank Acc. No. NM006900), IFNalpha-14 (Genbank Acc. No. NM002172), IFNalpha-16 (Genbank Acc. No. NM002173), IFNalpha-17 (Genbank Acc. No. NM021268) and IFNalpha-21 (Genbank Acc. No. NM002175).

Suitable examples of Fc domains and their pre-Fc chimeric polypeptides are shown in SEQ ID NO: 1 through SEQ ID NO: 96. The Fc domains are obtained by expressing the pre-Fc chimeric polypeptides in cells under conditions leading to their secretion and cleavage of the signal peptide. The pre-Fc polypeptides may be expressed in either prokaryotic or eukaryotic host cells. Preferably, mammalian host cells are transfected with expression vectors encoding the pre-Fc polypeptides.

Human IgG1 Fc domains having the N-terminal sequence CDKTHTCPPCPAPE, CPPCPAPE, and CPAPE are shown in SEQ ID NO: 1, SEQ ID NO: 9, and SEQ ID NO: 17, respectively, and the DNA sequences encoding them are shown in SEQ ID NO: 2, SEQ ID NO: 10, and SEQ ID NO: 18, respectively. The IgG1 domain of SEQ ID NO: 1 is obtained by expressing the pre-Fc chimeric polypeptides shown in SEQ ID NO: 3 (SHH signal peptide), SEQ ID NO: 5 (IFN signal peptide), and SEQ ID NO: 7 (CETP signal peptide), using the DNA sequences shown in SEQ ID NO: 4, SEQ ID NO: 6, and SEQ ID NO: 8, respectively. The IgG1 domain of SEQ ID NO: 9 is obtained by expressing the pre-Fc chimeric polypeptides shown in SEQ ID NO: 11 (SHH signal peptide), SEQ ID NO: 13 (IFN signal peptide), and SEQ ID NO: 15 (CETP signal peptide), using the DNA sequences shown in SEQ ID NO: 12, SEQ ID NO: 14, and SEQ ID NO: 16, respectively. The IgG1 domain of SEQ ID NO: 17 is obtained by expressing the pre-Fc chimeric polypeptides shown in SEQ ID NO: 19 (SHH signal peptide), SEQ ID NO: 21 (IFN signal peptide), and SEQ ID NO: 23 (CETP signal peptide), using the DNA sequences shown in SEQ ID NO: 20, SEQ ID NO: 22, and SEQ ID NO: 24, respectively.

Human IgG2 Fc domains having the N-terminal sequence CCVECPPCPAPE, CVECPPCPAPE, CPPCPAPE, and CPAPE are shown in SEQ ID NO: 25, SEQ ID NO: 33, SEQ ID NO: 41, and SEQ ID NO: 49, respectively, and the DNA sequences encoding them are shown in SEQ ID NO: 26, SEQ ID NO: 34, SEQ ID NO: 42, and SEQ ID NO: 50, respectively. The IgG2 domain of SEQ ID NO: 25 is obtained by expressing the pre-Fc chimeric polypeptides shown in SEQ ID NO: 27 (SHH signal peptide), SEQ ID NO: 29 (IFN signal peptide), and SEQ ID NO: 31 (CETP signal peptide), using the DNA sequences shown in SEQ ID NO: 28, SEQ ID NO: 30, and SEQ ID NO: 32, respectively. The IgG2 domain of SEQ ID NO: 33 is obtained by expressing the pre-Fc chimeric polypeptides shown in SEQ ID NO: 35 (SHH signal peptide), SEQ ID NO: 37 (IFN signal peptide), and SEQ ID NO: 39 (CETP signal peptide)

using the DNA sequences shown in SEQ ID NO: 36, SEQ ID NO: 38, and SEQ ID NO: 40, respectively. The IgG2 domain of SEQ ID NO: 41 is obtained from the pre-Fc chimeric polypeptides shown in SEQ ID NO: 43 (SHH signal peptide), SEQ ID NO: 45 (IFN signal peptide), and SEQ ID NO: 47 (CETP signal peptide), using the DNA sequences shown in SEQ ID NO: 44, SEQ ID NO: 46, and SEQ ID NO: 48, respectively. The IgG2 domain of SEQ ID NO: 49 is obtained from the pre-Fc chimeric polypeptides shown in SEQ ID NO: 51 (SHH signal peptide), SEQ ID NO: 53 (IFN signal peptide), and SEQ ID NO: 55 (CETP signal peptide), using the DNA sequences shown in SEQ ID NO: 52, SEQ ID NO: 54, and SEQ ID NO: 56, respectively.

Human IgG3 Fc domains having the N-terminal sequence (CPRCPEPKSDTPPP)$_3$—CPRCPAPE, CPRCPAPE, and CPAPE are shown in SEQ ID NO: 57, SEQ ID NO: 65, and SEQ ID NO: 73, respectively, and the DNA sequences encoding them are shown in SEQ ID NO: 58, SEQ ID NO: 66, SEQ ID NO: 42, and SEQ ID NO: 74, respectively. The IgG3 domain of SEQ ID NO: 57 is obtained by expressing the pre-Fc chimeric polypeptides shown in SEQ ID NO: 59 (SHH signal peptide), SEQ ID NO: 61 (IFN signal peptide), and SEQ ID NO: 63 (CETP signal peptide), using the DNA sequences shown in SEQ ID NO: 60, SEQ ID NO: 62, and SEQ ID NO: 64, respectively. The IgG3 domain of SEQ ID NO: 65 is obtained by expressing the pre-Fc chimeric polypeptides shown in SEQ ID NO: 67 (SHH signal peptide), SEQ ID NO: 69 (IFN signal peptide), and SEQ ID NO: 71 (CETP signal peptide), using the DNA sequences shown in SEQ ID NO: 68, SEQ ID NO: 70, and SEQ ID NO: 72, respectively. The IgG3 domain of SEQ ID NO: 73 is obtained by expressing the pre-Fc chimeric polypeptides shown in SEQ ID NO: 75 (SHH signal peptide), SEQ ID NO: 77 (IFN signal peptide), and SEQ ID NO: 79 (CETP signal peptide), using the DNA sequences shown in SEQ ID NO: 76, SEQ ID NO: 78, and SEQ ID NO: 80, respectively.

The sequences of human IgG4 Fc domains having the N-terminal sequence CPSCPAPE and CPAPE are shown in SEQ ID NO: 81 and SEQ ID NO: 89, respectively, and the DNA sequences encoding them are shown in SEQ ID NO: 82 and SEQ ID NO: 90, respectively. The IgG4 domain of SEQ ID NO: 81 is obtained by expressing the pre-Fc chimeric polypeptides shown in SEQ ID NO: 83 (SHH signal peptide), SEQ ID NO: 85 (IFN signal peptide), and SEQ ID NO: 87 (CETP signal peptide), using the DNA sequences shown in SEQ ID NO: 84, SEQ ID NO: 86, and SEQ ID NO: 88, respectively. The IgG4 domain of SEQ ID NO: 89 is obtained by expressing the pre-Fc chimeric polypeptides shown in SEQ ID NO: 91 (SHH signal peptide), SEQ ID NO: 93 (IFN signal peptide), and SEQ ID NO: 95 (CETP signal peptide), using the DNA sequences shown in SEQ ID NO: 92, SEQ ID NO: 94, and SEQ ID NO: 96, respectively.

Suitable antibody variants having at their heavy chain N-terminus a cysteine residue are prepared by recombinant DNA expression of pre-heavy chain chimeric polypeptides comprising 1) a signal peptide, obtained from a secreted or transmembrane protein, that is cleaved in front of a mature polypeptide having an N-terminal cysteine residue, contiguous with 2) a antibody heavy chain polypeptide having an N-terminal cysteine residue.

Suitable antibody variants having at their light chain N-terminus a cysteine residue are prepared by recombinant DNA expression of pre-light chain chimeric polypeptides comprising 1) a signal peptide, obtained from a secreted or transmembrane protein, that is cleaved in front of a mature polypeptide having an N-terminal cysteine residue, contiguous with 2) a antibody light chain polypeptide having an N-terminal cysteine residue.

Trastuzumab heavy and light chains are obtained by expressing the pre-heavy and pre-light chimeric polypeptides in cells under conditions leading to their secretion and cleavage of the signal peptide. The pre-heavy chain and pre-light chain polypeptides may be expressed in either prokaryotic or eukaryotic host cells. Preferably, mammalian host cells are transfected with expression vectors encoding the pre-heavy chain and pre-light chain polypeptides.

Protein sequences added to the N-terminus of the aforementioned antibody heavy chain, pre-heavy chain, light chain, and pre-light chain variants are illustrated herein for the recombinant antibody trastuzumab, but are generally applicable to any recombinant antibody. DNA sequences encoding trastuzumab and its variants may be constructed and expressed in mammalian cells by cotransfecting DNA vectors for its heavy and light chains, and variants derived thereof, as described in U.S. Pat. No. 5,821,337 ("Immunoglobulin Variants") which is hereby incorporated by reference. The amino acid sequence of the wild-type trastuzumab light and heavy chains are shown in SEQ ID NO: 128 and SEQ ID NO: 129, respectively.

Suitable examples of trastuzumab light chains with N-terminal cysteine residues and their pre-Fc chimeric polypeptides are shown in SEQ ID NO: 130 through SEQ ID NO: 165. Suitable examples of trastuzumab heavy chains with N-terminal cysteine residues and their pre-Fc chimeric polypeptides are shown in SEQ ID NO: 166 through SEQ ID NO: 201.

Trastuzumab light chains having the N-terminal sequence C, CP, CPP, CPR, CPS, CDKT, CDKTHT, CVE, and CDTPPP are shown in SEQ ID NO: 130, SEQ ID NO: 134, SEQ ID NO: 138, SEQ ID NO: 142, SEQ ID NO: 146, SEQ ID NO: 150, SEQ ID NO: 154, SEQ ID NO: 158, and SEQ ID NO: 162, respectively. The light chain of SEQ ID NO: 130 is obtained by expressing the pre-light chimeric polypeptides shown in SEQ ID NO: 131 (SHH signal peptide), SEQ ID NO: 132 (IFN signal peptide), and SEQ ID NO: 133 (CETP signal peptide). The light chain of SEQ ID NO: 134 is obtained by expressing the pre-light chain chimeric polypeptides shown in SEQ ID NO: 135 (SHH signal peptide), SEQ ID NO: 136 (IFN signal peptide), and SEQ ID NO: 137 (CETP signal peptide). The light chain of SEQ ID NO: 138 is obtained by expressing the pre-light chimeric polypeptides shown in SEQ ID NO: 139 (SHH signal peptide), SEQ ID NO: 140 (IFN signal peptide), and SEQ ID NO: 141 (CETP signal peptide). The light chain of SEQ ID NO: 142 is obtained by expressing the pre-light chimeric polypeptides shown in SEQ ID NO: 143 (SHH signal peptide), SEQ ID NO: 144 (IFN signal peptide), and SEQ ID NO: 145 (CETP signal peptide). The light chain of SEQ ID NO: 146 is obtained by expressing the pre-heay light chimeric polypeptides shown in SEQ ID NO: 147 (SHH signal peptide), SEQ ID NO: 148 (IFN signal peptide), and SEQ ID NO: 149 (CETP signal peptide). The light chain of SEQ ID NO: 150 is obtained by expressing the pre-light chimeric polypeptides shown in SEQ ID NO: 151 (SHH signal peptide), SEQ ID NO: 152 (IFN signal peptide), and SEQ ID NO: 153 (CETP signal peptide). The light chain of SEQ ID NO: 154 is obtained by expressing the pre-light chimeric polypeptides shown in SEQ ID NO: 155 (SHH signal peptide), SEQ ID NO: 156 (IFN signal peptide), and SEQ ID NO: 157 (CETP signal peptide). The light chain of SEQ ID NO: 158 is obtained by expressing the pre-light chimeric polypeptides shown in SEQ ID NO: 159 (SHH signal peptide), SEQ ID NO: 160 (IFN signal peptide), and SEQ ID NO: 161 (CETP signal peptide). The light chain of SEQ ID NO: 162 is obtained by expressing the pre-light chimeric polypeptides shown in SEQ ID NO: 163 (SHH signal peptide), SEQ ID NO: 164 (IFN signal peptide), and SEQ ID NO: 165 (CETP signal peptide).

Trastuzumab heavy chains having the N-terminal sequence C, CP, CPP, CPR, CPS, CDKT, CDKTHT, CVE, and CDTPPP are shown in SEQ ID NO: 166, SEQ ID NO: 170, SEQ ID NO: 174, SEQ ID NO: 178, SEQ ID NO: 182, SEQ ID NO: 186, SEQ ID NO: 190, SEQ ID NO: 194, and SEQ ID NO: 198, respectively. The heavy chain of SEQ ID NO: 166 is obtained by expressing the pre-heavy chain chimeric polypeptides shown in SEQ ID NO: 167 (SHH signal peptide), SEQ ID NO: 168 (IFN signal peptide), and SEQ ID NO: 169 (CETP signal peptide). The heavy chain of SEQ ID NO: 170 is obtained by expressing the pre-heavy chain chimeric polypeptides shown in SEQ ID NO: 171 (SHH signal peptide), SEQ ID NO: 172 (IFN signal peptide), and SEQ ID NO: 173 (CETP signal peptide). The heavy chain of SEQ ID NO: 174 is obtained from the pre-heavy chain chimeric polypeptides shown in SEQ ID NO: 175 (SHH signal peptide), SEQ ID NO: 176 (IFN signal peptide), and SEQ ID NO: 177 (CETP signal peptide). The heavy chain of SEQ ID NO: 178 is obtained from the pre-heavy chain chimeric polypeptides shown in SEQ ID NO: 179 (SHH signal peptide), SEQ ID NO: 180 (IFN signal peptide), and SEQ ID NO: 181 (CETP signal peptide). The heavy chain of SEQ ID NO: 182 is obtained by expressing the pre-heavy chain chimeric polypeptides shown in SEQ ID NO: 183 (SHH signal peptide), SEQ ID NO: 184 (IFN signal peptide), and SEQ ID NO: 185 (CETP signal peptide). The heavy chain of SEQ ID NO: 186 is obtained by expressing the pre-heavy chain chimeric polypeptides shown in SEQ ID NO: 187 (SHH signal peptide), SEQ ID NO: 188 (IFN signal peptide), and SEQ ID NO: 189 (CETP signal peptide). The heavy chain of SEQ ID NO: 190 is obtained from the pre-heavy chain chimeric polypeptides shown in SEQ ID NO: 191 (SHH signal peptide), SEQ ID NO: 192 (IFN signal peptide), and SEQ ID NO: 193 (CETP signal peptide). The heavy chain of SEQ ID NO: 194 is obtained from the pre-heavy chain chimeric polypeptides shown in SEQ ID NO: 195 (SHH signal peptide), SEQ ID NO: 196 (IFN signal peptide), and SEQ ID NO: 197 (CETP signal peptide). The heavy chain of SEQ ID NO: 198 is obtained from the pre-heavy chain chimeric polypeptides shown in SEQ ID NO: 199 (SHH signal peptide), SEQ ID NO: 200 (IFN signal peptide), and SEQ ID NO: 201 (CETP signal peptide).

Suitable host cells include 293 human embryonic cells (ATCC CRL-1573) and CHO-K1 hamster ovary cells (ATCC CCL-61) obtained from the American Type Culture Collection (Rockville, Md.). Cells are grown at 37° C. in an atmosphere of air, 95%; carbon dioxide, 5%. 293 cells are maintained in Minimal essential medium (Eagle) with 2 mM L-glutamine and Earle's BSS adjusted to contain 1.5 g/L sodium bicarbonate, 0.1 mM non-essential amino acids, and 1.0 mM sodium pyruvate, 90%; fetal bovine serum, 10%. CHO-K1 cells are maintained in Ham's F12K medium with 2 mM L-glutamine adjusted to contain 1.5 g/L sodium bicarbonate, 90%; fetal bovine serum, 10%. Other suitable host cells include CV1 monkey kidney cells (ATCC CCL-70), COS-7 monkey kidney cells (ATCC CRL-1651), VERO-76 monkey kidney cells (ATCC CRL-1587), HELA human cervical cells (ATCC CCL-2), W138 human lung cells (ATCC CCL-75), MDCK canine kidney cells (ATCC CCL-34), BRL3A rat liver cells (ATCC CRL-1442), BHK hamster kidney cells (ATCC CCL-10), MMT060562 mouse mammary cells (ATCC CCL-51), and human CD8.sup.+T lymphocytes (described in U.S. Ser. No. 08/258,152 incorporated herein in its entirety by reference).

Examples of a suitable expression vectors are pCDNA3.1 (+) shown in SEQ ID NO: 97 and pSA shown in SEQ ID NO: 98. Plasmid pSA contains the following DNA sequence elements: 1) pBluescriptIIKS(+) (nucleotides 912-2941/1-619, GenBank Accession No. X52327), 2) a human cytomegalovirus promoter, enhancer, and first exon splice donor (nucleotides 63-912, GenBank Accession No. K03104), 3) a human alpha1-globin second exon splice acceptor (nucleotides 6808-6919, GenBank Accession No. J00153), 4) an SV40 T antigen polyadenylation site (nucleotides 2770-2533, Reddy et al. (1978) Science 200, 494-502), and 5) an SV40 origin of replication (nucleotides 5725-5578, Reddy et al., ibid). Other suitable expression vectors include plasmids pSVeCD4DHFR and pRKCD4 (U.S. Pat. No. 5,336,603), plasmid pIK.1.1 (U.S. Pat. No. 5,359,046), plasmid pVL-2 (U.S. Pat. No. 5,838,464), plasmid pRT43.2F3 (described in U.S. Ser. No. 08/258,152 incorporated herein in its entirety by reference).

Suitable expression vectors for human IgG pre-Fc polypeptides may be constructed by the ligation of a HindIII-PspOM1 vector fragment prepared from SEQ ID NO: 98, with a HindIII-EagI insert fragment prepared from SEQ ID NOS: 4, 6, 8, 12, 14, 16, 20, 22, 24, 28, 30, 32, 36, 38, 40, 44, 46, 48, 52, 54, 56, 60, 62, 64, 68, 70, 72, 76, 78, 80, 84, 86, 88, 92, 94, and 96.

Suitable selectable markers include the Tn5 transposon neomycin phosphotransferase (NEO) gene (Southern and Berg (1982) J. Mol. Appl. Gen. 1, 327-341), and the dihydrofolate reductase (DHFR) cDNA (Lucas et al. (1996) Nucl. Acids Res. 24, 1774-1779). One example of a suitable expression vector that incorporates a NEO gene is plasmid pSA-NEO, which is constructed by ligating a first DNA fragment, prepared by digesting SEQ ID NO: 99 with EcoRI and BglII, with a second DNA fragment, prepared by digesting SEQ ID NO:98 with EcoRI and BglII. SEQ ID NO:99 incorporates a NEO gene (nucleotides 1551 to 2345, Genbank Accession No. U00004) preceded by a sequence for translational initiation (Kozak (1991) J. Biol. Chem, 266, 19867-19870). Another example of a suitable expression vector that incorporates a NEO gene and a DHFR cDNA is plasmid pSVe-NEO-DHFR, which is constructed by ligating a first DNA fragment, prepared by digesting SEQ ID NO:99 with EcoRI and BglII, with a second DNA fragment, prepared by digesting pSVeCD4DHFR with EcoRI and BglII. Plasmid pSVe-NEO-DHFR uses SV40 early promoter/enhancers to drive expression of the NEO gene and the DHFR cDNA. Other suitable selectable markers include the XPGT gene (Mulligan and Berg (1980) Science 209, 1422-1427) and the hygromycin resistance gene (Sugden et al. (1985) Mol. Cell. Biol. 5, 410-413).

In one embodiment, cells are transfected by the calcium phosphate method of Graham et al. (1977) J. Gen. Virol. 36, 59-74. A DNA mixture (10 ug) is dissolved in 0.5 ml of 1 mM Tris-HCl, 0.1 mM EDTA, and 227 mM $CaCl_2$. The DNA mixture contains (in a ratio of 10:1:1) the expression vector DNA, the selectable marker DNA, and a DNA encoding the VA RNA gene (Thimmappaya et al. (1982) Cell 31, 543-551). To this mixture is added, dropwise, 0.5 mL of 50 mM Hepes (pH 7.35), 280 mM NaCl, and 1.5 mM $NaPO_4$. The DNA precipitate is allowed to form for 10 minutes at 25° C., then suspended and added to cells grown to confluence on 100 mm plastic tissue culture dishes. After 4 hours at 37° C., the culture medium is aspirated and 2 ml of 20% glycerol in PBS is added for 0.5 minutes. The cells are then washed with serum-free medium, fresh culture medium is added, and the cells are incubated for 5 days.

In another embodiment, cells are transiently transfected by the dextran sulfate method of Somparyrac et al. (1981) Proc. Nat. Acad. Sci. 12, 7575-7579. Cells are grown to maximal density in spinner flasks, concentrated by centrifugation, and washed with PBS. The DNA-dextran precipitate is incubated on the cell pellet. After 4 hours at 37° C., the DEAE-dextran is aspirated and 20% glycerol in PBS is added for 1.5 minutes. The cells are then washed with serum-free medium, re-introduced into spinner flasks containing fresh culture medium with 5 micrograms/ml bovine insulin and 0.1 micrograms/ml bovine transferring, and incubated for 4 days.

Following transfection by either method, the conditioned media is centrifuged and filtered to remove the host cells and debris. The sample contained the Fc domain is then concentrated and purified by any selected method, such as dialysis and/or column chromatography (see below). To identify the Fc domain in the cell culture supernatant, the culture medium is removed 24 to 96 hours after transfection, concentrated, and analyzed by SDS-polyacrylamide gel electrophoresis (SDS-PAGE) in the presence or absence of a reducing agent such as dithiothreitol.

For unamplified expression, plasmids are transfected into human 293 cells (Graham et al., J. Gen. Virol. 36:59 74 (1977)), using a high efficiency procedure (Gorman et al., DNA Prot. Eng. Tech. 2:3 10 (1990)). Media is changed to serum-free and harvested daily for up to five days. For unamplified expression, plasmids are transfected into human 293 cells (Graham et al., J. Gen. Virol. 36:59 74 (1977)), using a high efficiency procedure (Gorman et al., DNA Prot. Eng. Tech. 2:3 10 (1990)). Media is changed to serum-free and harvested daily for up to five days. The Fc domains are purified from the cell culture supernatant using HiTrap Protein A HP (Pharmacia). The eluted Fc domains are buffer-exchanged into PBS using a Centricon-30 (Amicon), concentrated to 0.5 ml, sterile filtered using a Millex-GV (Millipore) at 4° C.

Stretches of Consecutive Amino Acids

Examples of stretches of consecutive amino acids as referred to herein include, but are not limited to, consecutive amino acids including binding domains such as secreted or transmembrane proteins, intracellular binding domains and antibodies (whole or portions thereof) and modififed versions thereof. The following are some non-limiting examples:

1) Immunoglobulins

The term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity (e.g., Fab and/or single-armed antibodies).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

A "blocking" antibody or an "antagonist" antibody is one which significantly inhibits (either partially or completely) a biological activity of the antigen it binds.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The phrase "N-terminally truncated heavy chain", as used herein, refers to a polypeptide comprising parts but not all of a full length immunoglobulin heavy chain, wherein the missing parts are those normally located on the N terminal region of the heavy chain. Missing parts may include, but are not limited to, the variable domain, CH1, and part or all of a hinge sequence. Generally, if the wild type hinge sequence is not present, the remaining constant domain(s) in the N-terminally truncated heavy chain would comprise a component that is capable of linkage to another Fc sequence (i.e., the "first" Fc polypeptide as described herein). For example, said component can be a modified residue or an added cysteine residue capable of forming a disulfide linkage.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daeron, Annu. Rev. Imnunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Imnunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001).

The "hinge region," "hinge sequence", and variations thereof, as used herein, includes the meaning known in the art, which is illustrated in, for example, Janeway et al., Immuno Biology: the immune system in health and disease, (Elsevier Science Ltd., NY) (4th ed., 1999); Bloom et al., Protein Science (1997), 6:407-415; Humphreys et al., J. Imnunol. Methods (1997), 209:193-202.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab') 2 antibody fragments comprise a pair of Fab fragments which are generally covalently linked near their carboxy termini by hinge cysteines between them. Other chemical couplings of antibody fragments are also known in the art.

The phrase "antigen binding arm", as used herein, refers to a component part of an antibody fragment that has an ability to specifically bind a target molecule of interest. Generally and preferably, the antigen binding arm is a complex of immunoglobulin polypeptide sequences, e.g., HVR and/or variable domain sequences of an immunoglobulin light and heavy chain.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8(10):1057-1062 (1995). Briefly, these antibodies comprise a pair of tandem Fd segments (V.sub.H-C.sub.H1-V.sub.H-C.sub.H1) which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more HVRs, compared to a parent antibody which does not possess such alterations, such alterations resulting in an improvement in the affinity of the antibody for antigen.

An antibody having a "biological characteristic" of a designated antibody is one which possesses one or more of the biological characteristics of that antibody which distinguish it from other antibodies that bind to the same antigen.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis as described in Example 2 of U.S. Patent Application Publication No. 20050186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above. In some embodiments, the species-dependent antibody is a humanized or human antibody.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

2) Extracellular Proteins

Extracellular proteins play important roles in, among other things, the formation, differentiation and maintenance of multicellular organisms. A discussion of various intracellular proteins of interest is set forth in U.S. Pat. No. 6,723,535, Ashkenazi et al., issued Apr. 20, 2004, hereby incorporated by reference.

The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature (see, for example, Klein et al., Proc. Natl. Acad. Sci. 93:7108-7113 (1996); U.S. Pat. No. 5,536,637)).

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

3) Intein-Based C-Terminal Syntheses

As described, for example, in U.S. Pat. No. 6,849,428, issued Feb. 1, 2005, inteins are the protein equivalent of the self-splicing RNA introns (see Perler et al., Nucleic Acids Res. 22:1125-1127 (1994)), which catalyze their own excision from a precursor protein with the concomitant fusion of the flanking protein sequences, known as exteins (reviewed in Perler et al., Curr. Opin. Chem. Biol. 1:292-299 (1997); Perler, F. B. Cell 92(1):1-4 (1998); Xu et al., EMBO J. 15(19):5146-5153 (1996)).

Studies into the mechanism of intein splicing led to the development of a protein purification system that utilized thiol-induced cleavage of the peptide bond at the N-terminus of the Sce VMA intein (Chong et al., Gene 192(2):271-281 (1997)). Purification with this intein-mediated system generates a bacterially-expressed protein with a C-terminal thioester (Chong et al., (1997)). In one application, where it is described to isolate a cytotoxic protein, the bacterially expressed protein with the C-terminal thioester is then fused to a chemically-synthesized peptide with an N-terminal cysteine using the chemistry described for "native chemical ligation" (Evans et al., Protein Sci. 7:2256-2264 (1998); Muir et al., Proc. Natl. Acad. Sci. USA 95:6705-6710 (1998)).

This technique, referred to as "intein-mediated protein ligation" (IPL), represents an important advance in protein semi-synthetic techniques. However, because chemically-synthesized peptides of larger than about 100 residues are difficult to obtain, the general application of IPL was limited by the requirement of a chemically-synthesized peptide as a ligation partner.

IPL technology was significantly expanded when an expressed protein with a predetermined N-terminus, such as cysteine, was generated, as described for example in U.S. Pat. No. 6,849,428. This allows the fusion of one or more expressed proteins from a host cell, such as bacterial, yeast or mammalian cells. In one non-limiting example the intein a modified RIR1 *Methanobacterium thermoautotrophicum* is that cleaves at either the C-terminus or N-terminus is used which allows for the release of a bacterially expressed protein during a one-column purification, thus eliminating the need proteases entirely.

Intein technology is one example of one route to obtain components. In one embodiment, the subunits of the compounds of the invention are obtained by transfecting suitable cells, capable of expressing and secreting mature chimeric polypeptides, wherein such polypeptides comprise, for example, an adhesin domain contiguous with an isolatable c-terminal intein domain (see U.S. Pat. No. 6,849,428, Evans et al., issued Feb. 1, 2005, hereby incorporated by reference). The cells, such as mammalian cells or bacterial cells, are transfected using known recombinant DNA techniques. The secreted chimeric polypeptide can then be isolated, e.g. using a chitin-derivatized resin in the case of an intein-chitin binding domain (see U.S. Pat. No. 6,897,285, Xu et al., issued May 24, 2005, hereby incorporated by reference), and is then treated under conditions permitting thiol-mediated cleavage and release of the now C-terminal thioester-terminated subunit. The thioester-terminated adhesion subunit is readily converted to a C-terminal cysteine terminated subunit.

For example, following an intein autocleavage reaction, a thioester intermediate is generated that permits the facile addition of cysteine, selenocysteine, homocysteine, or homoselenocysteine, or a derivative of cysteine, selenocysteine, homocysteine, homoselenocysteine, to the C-terminus by native chemical ligation. Methods of adding a cysteine, selenocysteine, homocysteine, or homoselenocysteine, or a derivative of cysteine, selenocysteine, homocysteine, homoselenocysteine, to the C-terminus by native chemical ligation which are useful in aspects of the present invention are described in U.S. Patent Application No. 2008/0254512, Capon, published Oct. 16, 2008, the entire contents of which are hereby incorporated herein by reference.

Kits

Another aspect of the present invention provides kits comprising the compounds disclosed herein and the pharmaceutical compositions comprising these compounds. A kit may include, in addition to the compound or pharmaceutical composition, diagnostic or therapeutic agents. A kit may also include instructions for use in a diagnostic or therapeutic method. In a diagnostic embodiment, the kit includes the compound or a pharmaceutical composition thereof and a diagnostic agent. In a therapeutic embodiment, the kit includes the antibody or a pharmaceutical composition thereof and one or more therapeutic agents, such as an additional antineoplastic agent, anti-tumor agent or chemotherapeutic agent.

General Techniques

The description below relates primarily to production of stretches of consecutive amino acids or polypeptides of interest by culturing cells transformed or transfected with a vector containing an encoding nucleic acid. It is, of course, contemplated that alternative methods, which are well known in the art, may be employed. For instance, the amino acid sequence, or portions thereof, may be produced by direct peptide synthesis using solid-phase techniques (see, e.g., Stewart et al., Solid-Phase Peptide Synthesis, W.H. Freeman Co., San Francisco, Calif. (1969); Merrifield, J. Am. Chem. Soc., 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the stretches of consecutive amino acids or polypeptides of interest may be chemically synthesized separately and combined using chemical or enzymatic methods to produce the full-length stretches of consecutive amino acids or polypeptides of interest.

1. Selection and Transformation of Host Cells

Host cells are transfected or transformed with expression or cloning vectors described herein for production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published Jun. 29, 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946(1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain $27C_7$ (ATCC 55,244), which has the complete genotype tonAptr3phoA E15 (argF-lac)169 degP ompT kan.sup.r; *E. coli* W3110 strain 37D6, which has the complete genotype tonA ptr3 phoA E15 (argF-lac)169 degP ompT rbs7 ilvG kan.sup.r, *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for encoding vectors. *Saccharomyces cerevisiae* is a commonly used lower eukaryotic host microorganism. Others include *Schizosaccharomyces pombe* (Beach and Nurse, Nature, 290:140 (1981); EP 139,383 published May 2, 1985); *Kluyveromyces* hosts (U.S. Pat. No. 4,943,529; Fleer et al., Bio/Technology, 9:968-975 (1991)) such as, e.g., *K. lactis* (MW98-8C, CBS683, CBS4574; Louvencourt et al., J. Bacteriol., 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265-278 (1988)); *Candida*; *Trichoderma reesia* (EP 244,234); *Neurospora crassa* (Case et al., Proc. Natl. Acad. Sci. USA, 76:5259-5263 (1979)); *Schwanniomyces* such as *Schwanniomyces occidentalis* (EP 394,538 published Oct. 31, 1990); and filamentous fungi such as, e.g., *Neurospora*, *Penicillium*, *Tolypocladium* (WO 91/00357 published Jan. 10, 1991), and *Aspergillus* hosts such as *A. nidulans* (Ballance et al., Biochem. Biophys. Res. Commun., 112:284-289 (1983); Tilburn et al., Gene, 26:205-

221 (1983); Yelton et al., Proc. Natl. Acad. Sci. USA, 81:1470-1474 (1984)) and *A. niger* (Kelly and Hynes, EMBO J., 4:475479 (1985)). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated stretches of consecutive amino acids or polypeptides of interest are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

2. Selection and Use of a Replicable Vector

The nucleic acid (e.g., cDNA or genomic DNA) encoding the stretch of consecutive amino acids or polypeptides of interest may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The stretches of consecutive amino acids or polypeptides of interest may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the encoding DNA that is inserted into the vector. The signal sequence may be a prokaryotic signal sequence selected, for example, from the group of the alkaline phosphatase, penicillinase, 1pp, or heat-stable enterotoxin II leaders. For yeast secretion the signal sequence may be, e.g., the yeast invertase leader, alpha factor leader (including *Saccharomyces* and *Kluyveromyces* alpha-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 mu plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trpl gene present in the yeast plasmid YRp7 (Stinchcomb et al., Nature, 282:39 (1979); Kingsman et al., Gene, 7:141 (1979); Tschemper et al., Gene, 10:157 (1980)). The trpl gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the encoding nucleic acid sequence to direct mRNA synthesis. Promoters recognized by a variety of potential host cells are well known. Promoters suitable for use with prokaryotic hosts include the beta-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980); EP 36,776), and hybrid promoters such as the tac promoter (deBoer et al., Proc. Natl. Acad. Sci. USA, 80:21-25 (1983)). Promoters for use in bacterial systems also will contain a Shine-Dalgarno (S. D.) sequence operably linked to the encoding DNA.

Examples of suitable promoting sequences for use with yeast hosts include the promoters for 3-phosphoglycerate kinase (Hitzeman et al., J. Biol. Chem., 255:2073 (1980)) or other glycolytic enzymes (Hess et al., J. Adv. Enzyme Re.g., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the stretches of consecutive amino acids or polypeptides of interest by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding stretches of consecutive amino acids or polypeptides of interest.

Still other methods, vectors, and host cells suitable for adaptation to the synthesis of stretches of consecutive amino acids or polypeptides in recombinant vertebrate cell culture are described in Gething et al., Nature 293:620-625 (1981); Mantei et al., Nature, 281:4046 (1979); EP 117,060; and EP 117,058.

3. Detecting Gene Amplification/Expression

Gene amplification and/or expression may be measured in a sample directly, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence stretches of consecutive amino acids or polypeptides of interest or against a synthetic peptide based on the DNA sequences provided herein or against exogenous sequence fused to DNA encoding a stretch of consecutive amino acids or polypeptide of interest and encoding a specific antibody epitope.

4. Purification of Polypeptide

Forms of the stretches of consecutive amino acids or polypeptides of interest may be recovered from culture medium or from host cell lysates. If membrane-bound, it can be released from the membrane using a suitable detergent solution (e.g. Triton-X 100) or by enzymatic cleavage. Cells employed in expression of the stretches of consecutive amino acids or polypeptides of interest can be disrupted by various physical or chemical means, such as freeze-thaw cycling, sonication, mechanical disruption, or cell lysing agents.

It may be desired to purify the stretches of consecutive amino acids or polypeptides of interest from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular stretches of consecutive amino acids or polypeptides of interest produced.

Example of Expression of Stretch of Consecutive Amino Acids or Polypeptide Component of Interest in *E. coli*

The DNA sequence encoding the desired amino acid sequence of interest or polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the specific amino acid sequence of interest/polypeptide coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized amino acid sequence of interest or polypeptide can then be purified using a metal chelating column under conditions that allow tight binding of the protein.

The primers can contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences can be ligated into an expression vector used to transform an E. coli host based on, for example, strain 52 (W3110 fuhA(tonA) lon galE rpoHts(htpRts) clpP(lacIq). Transformants can first be grown in LB containing 50 mg/ml carbenicillin at 30° C. with shaking until an O.D.600 of 3-5 is reached. Cultures are then diluted 50-100 fold into C RAP media (prepared by mixing 3.57 g $(NH_4)_2$ $SO_4$, 0.71 g sodium citrate-$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples were removed to verify expression by SDS-PAGE analysis, and the bulk culture is centrifuged to pellet the cells. Cell pellets were frozen until purification and refolding.

E. coli paste from 0.5 to 1 L fermentations (6-10 g pellets) was resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution was stirred overnight at 4° C. This step results in a denatured protein with all cysteine residues blocked by sulfitolization. The solution was centrifuged at 40,000 rpm in a Beckman Ultracentifuge for 30 min. The supernatant was diluted with 3-5 volumes of metal chelate column buffer (6 M guanidine, 20 mM Tris, pH 7.4) and filtered through 0.22 micron filters to clarify. Depending the clarified extract was loaded onto a 5 mil Qiagen Ni-NTA metal chelate column equilibrated in the metal chelate column buffer. The column was washed with additional buffer containing 50 mM imidazole (Calbiochem, Utrol grade), pH 7.4. The protein was eluted with buffer containing 250 mM imidazole. Fractions containing the desired protein were pooled and stored at 4.degree. C. Protein concentration was estimated by its absorbance at 280 nm using the calculated extinction coefficient based on its amino acid sequence.

Expression of Stretch of Consecutive Amino Acids or Polypeptides in Mammalian Cells This general example illustrates a preparation of a glycosylated form of a desired amino acid sequence of interest or polypeptide component by recombinant expression in mammalian cells.

The vector pRK5 (see EP 307,247, published Mar. 15, 1989) can be employed as the expression vector. Optionally, the encoding DNA is ligated into pRK5 with selected restriction enzymes to allow insertion of the DNA using ligation methods such as described in Sambrook et al., supra.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg of the ligated vector DNA is mixed with about 1 µg DNA encoding the VA RNA gene [Thimmappaya et al., Cell 31:543 (1982)] and dissolved in 500 µl of I mM Tris-HCl, 0.1 mM EDTA, 0.227 M $CaCl_2$ To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of amino acid sequence of interest or polypeptide component. The cultures containing transfected cells may undergo further incubation (in serum free medium) and the medium is tested in selected bioassays.

In an alternative technique, the nucleic acid amino acid sequence of interest or polypeptide component may be introduced into 293 cells transiently using the dextran sulfate method described by Somparyrac et al., Proc. Natl. Acad. Sci., 12:7575 (1981). 293 cells are grown to maximal density in a spinner flask and 700 µg of the ligated vector is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed amino acid sequence of interest or polypeptide component can then be concentrated and purified by any selected method, such as dialysis and/or column chromatography.

In another embodiment, the amino acid sequence of interest or polypeptide component can be expressed in CHO cells. The amino acid sequence of interest or polypeptide component can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of amino acid sequence of interest or polypeptide component, the culture medium may be replaced with serum free medium. Preferably, the cultures are incubated for about 6 days, and then the conditioned medium is harvested. The medium containing the expressed amino acid sequence of interest or polypeptide component can then be concentrated and purified by any selected method.

Epitope-tagged amino acid sequence of interest or polypeptide component may also be expressed in host CHO cells. The amino acid sequence of interest or polypeptide component may be subcloned out of a pRK5 vector. The subclone insert can undergo PCR to fuse in frame with a selected epitope tag such as a poly-his tag into a Baculovirus expression vector. The poly-his tagged amino acid sequence of interest or polypeptide component insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged amino acid sequence of interest or polypeptide component can then be concentrated and purified by any selected method, such as by $Ni^{2+}$-chelate affinity chromatography.

In an embodiment the amino acid sequence of interest or polypeptide component are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used in expression in CHO cells is as described in Lucas et al., Nucl. Acids Res. 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Expression of Stretch of Consecutive Amino Acids or Polypeptides in Yeast

The following method describes recombinant expression of a desired amino acid sequence of interest or polypeptide component in yeast.

First, yeast expression vectors are constructed for intracellular production or secretion of a stretch of consecutive amino acids from the ADH2/GAPDH promoter. DNA encoding a desired amino acid sequence of interest or polypeptide component, a selected signal peptide and the promoter is inserted into suitable restriction enzyme sites in the selected plasmid to direct intracellular expression of the amino acid sequence of interest or polypeptide component. For secretion, DNA encoding the stretch of consecutive amino acids can be cloned into the selected plasmid, together with DNA encoding the ADH2/GAPDH promoter, the yeast alpha-factor secretory signal/leader sequence, and linker sequences (if needed) for expression of the stretch of consecutive amino acids.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant amino acid sequence of interest or polypeptide component can subsequently be isolated and purified by removing the yeast cells from the fermentation medium by centrifugation and then concentrating the medium using selected cartridge filters. The concentrate containing the amino acid sequence of interest or polypeptide component may further be purified using selected column chromatography resins.

Expression of Stretches of Stretch of Consecutive Amino Acids or Polypeptides in Baculovirus-Infected Insect Cells The following method describes recombinant expression of stretches of consecutive amino acids in Baculovirus-infected insect cells.

The desired nucleic acid encoding the stretch of consecutive amino acids is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the amino acid sequence of interest or polypeptide component or the desired portion of the amino acid sequence of interest or polypeptide component (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged amino acid sequence of interest or polypeptide component can then be purified, for example, by $Ni^{2+}$-chelate affinity chromatography as follows. Extracts are prepared from recombinant virus-infected Sf9 cells as described by Rupert et al., Nature, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged sequence are pooled and dialyzed against loading buffer.

Alternatively, purification of the IgG tagged (or Fc tagged) amino acid sequence can be performed using known chromatography techniques, including for instance, Protein A or Protein G column chromatography.

Fc containing constructs of proteins can be purified from conditioned media as follows. The conditioned media is pumped onto a 5 ml Protein A column (Pharmacia) which is equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 mL of 1 M Tris buffer, pH 9. The highly purified protein is subsequently desalted into storage buffer as described above for the poly-His tagged proteins. The homogeneity of the proteins is verified by SDS polyacrylamide gel (PEG) electrophoresis and N-terminal amino acid sequencing by Edman degradation.

Examples of Pharmaceutical Compositions

Non-limiting examples of such compositions and dosages are set forth as follows:

Compositions comprising a compound comprising a stretch of consecutive amino acids which comprises consecutive amino acids having the sequence of etanercept (e.g. Enbrel) may comprise mannitol, sucrose, and tromethamine. In an embodiment, the composition is in the form of a lyophilizate. In an embodiment, the composition is reconstituted with, for example, Sterile Bacteriostatic Water for Injection (BWFI), USP (containing 0.9% benzyl alcohol). In an embodiment the compound is administered to a subject for reducing signs and symptoms, inducing major clinical response, inhibiting the progression of structural damage, and improving physical function in subjects with moderately to severely active rheumatoid arthritis. The compound may be initiated in combination with methotrexate (MTX) or used alone. In an embodiment the compound is administered to a subject for reducing signs and symptoms of moderately to severely active polyarticular-course juvenile rheumatoid arthritis in subjects who have had an inadequate response to one or more DMARDs. In an embodiment the compound is administered to a subject for reducing signs and symptoms, inhibiting the progression of structural damage of active arthritis, and improving physical function in subjects with psoriatic arthritis. In an embodiment the compound is administered to a subject for reducing signs and symptoms in subjects with active ankylosing spondylitis. In an embodiment the compound is administered to a subject for the treatment of chronic moderate to severe plaque psoriasis. In an embodiment wherein the subject has rheumatoid arthritis, psoriatic arthritis, or ankylosing spondylitis the compound is administered at 25-75 mg per week given as one or more subcutaneous (SC) injections. In a further embodiment the compound is administered at 50 mg per week in a single SC injection. In an embodiment wherein the subject has plaque psoriasis the compound is administered at 25-75 mg twice weekly or 4 days apart for 3 months followed by a reduction to a maintenance dose of 25-75 mg per week. In a further embodiment the compound is administered at a dose of at 50 mg twice weekly or 4 days apart for 3 months followed by a reduction to a maintenance dose of 50 mg per week. In an embodiment the dose is between 2× and 100× less than the doses set forth herein. In an embodiment wherein the subject has active polyarticular-course JRA the compound may be administered at a dose of 0.2-1.2 mg/kg per week (up to a maximum of 75 mg per week). In a further embodiment the compound is administered at a dose of 0.8 mg/kg per week (up to a maximum of 50 mg per week). In some embodiments the dose is between 2× and 100× less than the doses set forth hereinabove.

Compositions comprising a compound comprising a stretch of consecutive amino acids which comprises consecutive amino acids having the sequence of infliximab (e.g. Remicade) may comprise sucrose, polysorbate 80, monobasic sodium phosphate, monohydrate, and dibasic sodium phosphate, dihydrate. Preservatives are not present in one embodiment. In an embodiment, the composition is in the form of a lyophilizate. In an embodiment, the composition is reconstituted with, for example, Water for Injection (BWFI), USP. In an embodiment the pH of the composition is 7.2 or is about 7.2. In one embodiment the compound is administered is administered to a subject with rheumatoid arthritis in a dose of 2-4 mg/kg given as an intravenous infusion followed with additional similar doses at 2 and 6 weeks after the first infusion then every 8 weeks thereafter. In a further embodiment the compound is administered in a dose of 3 mg/kg given as an intravenous infusion followed with additional similar doses at 2 and 6 weeks after the first infusion then every 8 weeks thereafter. In an embodiment the dose is adjusted up to 10 mg/kg or treating as often as every 4 weeks. In an embodiment the compound is administered in combination with methotrexate. In one embodiment the compound is administered is administered to a subject with Crohn's disease or fistulizing Crohn's disease at dose of 2-7 mg/kg given as an induction regimen at 0, 2 and 6 weeks followed by a maintenance regimen of 4-6 mg/kg every 8 weeks thereafter for the treatment of moderately to severely active Crohn's disease or fistulizing disease. In a further embodiment the compound is administered at a dose of 5 mg/kg given as an induction regimen at 0, 2 and 6 weeks followed by a maintenance regimen of 5 mg/kg every 8 weeks thereafter for the treatment of moderately to severely active Crohn's disease or fistulizing disease. In an embodiment the dose is adjusted up to 10 mg/kg. In one embodiment the compound is administered to a subject with ankylosing spondylitis at a dose of 2-7 mg/kg given as an intravenous infusion followed with additional similar doses at 2 and 6 weeks after the first infusion, then every 6 weeks thereafter. In a further embodiment the compound is administered at a dose of 5 mg/kg given as an intravenous infusion followed with additional similar doses at 2 and 6 weeks after the first infusion, then every 6 weeks thereafter. In one embodiment the compound is administered to a subject with psoriatic arthritis at a dose of 2-7 mg/kg given as an intravenous infusion followed with additional similar doses at 2 and 6 weeks after the first infusion then every 8 weeks thereafter. In a further embodiment the compound is administered at a dose of 5 mg/kg given as an intravenous infusion followed with additional similar doses at 2 and 6 weeks after the first infusion then every 8 weeks thereafter. In an embodiment the compound is administered with methotrexate. In one embodiment the compound is administered to a subject with ulcerative colitis at a dose of 2-7 mg/kg given as an induction regimen at 0, 2 and 6 weeks followed by a maintenance regimen of 2-7 mg/kg every 8 weeks thereafter for the treatment of moderately to severely active ulcerative colitis. In a further embodiment the compound is administered to a subject with ulcerative colitis at a dose of 5 mg/kg given as an induction regimen at 0, 2 and 6 weeks followed by a maintenance regimen of 5 mg/kg every 8 weeks thereafter. In some embodiments the dose is between 2× and 100× less than the doses set forth hereinabove for treating the indivisual diseases.

In each of the embodiments of the compositions described herein, the compositions, when in the form of a lyophilizate, may be reconstituted with, for example, sterile aqueous solutions, sterile water, Sterile Water for Injections (USP), Sterile Bacteriostatic Water for Injections (USP), and equivalents thereof known to those skilled in the art.

It is understood that in administration of any of the instant compounds, the compound may be administered in isolation, in a carrier, as part of a pharmaceutical composition, or in any appropriate vehicle.

Dosage

It is understood that where a dosage range is stated herein, e.g. 1-10 mg/kg per week, the invention disclosed herein also contemplates each integer dose, and tenth thereof, between the upper and lower limits. In the case of the example given, therefore, the invention contemplates 1.0, 1.1, 1.2, 1.3, 1.4, 1.5, 1.6, 1.7, 1.8, 1.9, 2.0, 2.1, 2.2, 2.3, 2.4 etc. mg/kg up to 10 mg/kg.

In embodiments, the compounds of the present invention can be administered as a single dose or may be administered as multiple doses.

In general, the daily dosage for treating a disorder or condition according to the methods described above will generally range from about 0.01 to about 10.0 mg/kg body weight of the subject to be treated.

Variations based on the aforementioned dosage ranges may be made by a physician of ordinary skill taking into account known considerations such as the weight, age, and condition of the person being treated, the severity of the affliction, and the particular route of administration chosen.

It is also expected that the compounds disclosed will effect cooperative binding with attendant consequences on effective dosages required.

Pharmaceuticals

The term "pharmaceutically acceptable carrier" is understood to include excipients, carriers or diluents. The particular carrier, diluent or excipient used will depend upon the means and purpose for which the active ingredient is being applied.

For parenteral administration, solutions containing a compound of this invention or a pharmaceutically acceptable salt thereof in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The compositions of this invention may be in a variety of forms. These include, for example, liquid, semi-solid and solid dosage forms, such as liquid solutions (e.g., injectable and infusible solutions), dispersions or suspensions. The preferred form depends on the intended mode of administration and therapeutic application. Some compositions are in the form of injectable or infusible solutions. A mode of administration is parenteral (e.g., intravenous, subcutaneous, intraperitoneal, intramuscular). In an embodiment, the compound is administered by intravenous infusion or injection. In another embodiment, the compound is administered by intramuscular or subcutaneous injection.

For therapeutic use, the compositions disclosed here can be administered in various manners, including soluble form by bolus injection, continuous infusion, sustained release from implants, oral ingestion, local injection (e.g. intracrdiac, intramuscular), systemic injection, or other suitable techniques well known in the pharmaceutical arts. Other methods of pharmaceutical administration include, but are not limited to, oral, subcutaneously, transdermal, intravenous, intramuscular and parenteral methods of administration. Typically, a soluble composition will comprise a purified compound in conjunction with physiologically acceptable carriers, excipients or diluents. Such carriers will be nontoxic to recipients at the dosages and concentrations employed. The preparation of such compositions can entail combining a compound with buffers, antioxidants, carbohydrates including glucose, sucrose or dextrins, chelating agents such as EDTA, glutathione and other stabilizers and excipients. Neutral buffered saline or saline mixed with conspecific serum albumin are exemplary appropriate diluents. The product can be formulated as a lyophilizate using appropriate excipient solutions (e.g., sucrose) as diluents.

Other derivatives comprise the compounds/compositions of this invention covalently bonded to a nonproteinaceous polymer. The bonding to the polymer is generally conducted so as not to interfere with the preferred biological activity of the compound, e.g. the binding activity of the compound to a target. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturontc acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; as well as heparin or heparon.

The pharmaceutical compositions of the invention may include a "therapeutically effective amount" or a "prophylactically effective amount" of a compound of the invention. A "therapeutically effective amount" refers to an amount effective, at dosages and for periods of time necessary, to achieve the desired therapeutic result. A therapeutically effective amount of the compound may vary according to factors such as the disease state, age, sex, and weight of the individual. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

All combinations of the various elements disclosed herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: TNR1B-alkyne-azide-Fc6

TNR1B-alkyne-azide-Fc6 was prepared via the reaction of alkyne-modified TNR1B (TNF receptor 1B) with azide-modified Fc6 as follows. TNR1B-azide-alkyne-Fc6 is prepared using the same principles via the reaction of azide-modified TNR1B with alkyne-modified Fc6.

Alkyne-modified TNFR1B (TNR1B-Alk) was prepared by cleavage of TNR1B-intein (TNR1B-Mth fusion protein) with cystyl-propargylamide, $HSCH_2CH[NH_2]CONHCH_2C\equiv CH_3$ (FIG. 1) and azide-modified TNR1B (TNR1B-Az) was prepared by cleavage of TNR1B-intein with cystyl-3-azidopropylamide, $HSCH_2CH[NH_2]CONH(CH_2)_3NH_2$.

TNR1B-intein and Fc6 are described in U.S. Ser. No. 11/982,085, published Oct. 16, 2008, the whole of which is incorporated herein by reference.

TNR1B-intein fusion protein was produced using vector pCDNA3-TNR1B-Mth, the sequence of which is shown in SEQ ID NO: 100.

The pre-TNR1B-intein chimeric polypeptide that is initially expressed, containing the TNR1B extracellular domain joined at its C-terminus by a peptide bond to the N-terminus of an Mth RIR1 self-splicing intein at the autocleavage site, is shown in SEQ ID NO: 101. Cleavage of the homologous TNR signal sequences by the cellular signal peptidase provides the mature TNR1B-intein fusion protein that is secreted into the cell culture fluid, the sequence of which is shown in SEQ ID NO: 102.

Fc6 protein was expressed using vector pCDNA3-SHH-IgG1-Fcll, the sequence of which is shown in SEQ ID NO: 103. The pre-Fc6 polypeptide that is initially expressed is shown in SEQ ID NO: 104. Cleavage of the heterologous sonic hedgehog (SHH) signal sequences by the cellular signal peptidase provides the mature Fc6 protein that is secreted into the cell culture fluid, the sequence of which is shown in SEQ ID NO: 105.

Protein production was executed by transient expression in CHO-DG44 cells, adapted to serum-free suspension culture. Transient transfections were done with polyethylenimine as transfection agent, complexed with DNA, under high density conditions as described by Rajendra et al., J. Biotechnol. 153, 22-26 (2011). Seed train cultures were maintained in TubeSpin® bioreactor 50 tubes obtained from TPP (Trasadingen, CH) and scaled up in volume to generate sufficient biomass for transfection. Transfections were carried out in cultures of 0.5-1.0 L. Cultures at this scale were maintained in 2 L or 5 L Schott-bottles with a ventilated cap. The bottles were shaken at 180 rpm in a Kihner incubator shaker with humidification and $CO_2$ control at 5%. The cell culture fluid was harvested after 10 days, centrifuged and sterile-filtered, prior to purification.

Cystyl-propargylamide and cystyl-3-azidopropylamide were prepared as follows. Boc-Cys(Trt)-OH, $(C_6H_5)_3CSCH_2CH[NHCO_2C(CH_3)]CO_2H$; propargylamine, $HC{\equiv}CCH_2NH$; 3-azidopropylamine, $NH_2CH_2CH_2CH_2N_3$; EDC, N-(3-Dimethylaminopropyl)-N'-ethylcarbodiimide hydrochloride; and HOBt, 1-Hydroxybenzotriazole, and were obtained from AnaSpec (Freemont, Calif.) or CPC Scientific (San Jose, Calif.). All other chemicals were obtained from Sigma-Aldrich (St. Louis, Mo.). For the synthesis of cystyl-propargylamide, a solution of Boc-Cys(Trt)-OH (100 mM) and propargylamine (100 mM) in CH2Cl2 was made 100 mM each in EDC, HOBt, and triethylamine. For the synthesis of cystyl-3-azidopropylamide, 3-azidopropylamine (100 mM) was substituted for propargylamine. Both reactions were worked up by the following procedure. After stirring overnight at room temperature, the reaction was stopped with an excess of saturated $NaHCO_3$ in water, extracted with CH2Cl2, dried over $MgSO_4$, filtered, evaporated, and purified by column chromatography. To remove the Boc/Trt protecting groups, the intermediate product was dissolved at a concentration of 0.05M in TFA/triisopropylsilane/H2O (90:5:5) and stirred for 30 minutes at room temperature. The reaction was then dried by evaporation and extracted with CH2Cl2. The organic layer was then extracted with water, yielding the final cystyl-propargylamide product as a yellowish oil, and the final cystyl-3-azidopropylamide product as a yellowish solid.

To prepare the alkyne-modified TNR1B (FIG. 1) or the azide-modified TNR1B, the TNR1B-intein protein in the cell culture fluid was applied to a column packed with chitin beads obtained from New England BioLabs (Beverley, Mass.) that was pre-equilibrated with buffer A (20 M Tris-HCl, 500 mM NaCl, pH 7.5). Unbound protein was washed from the column with buffer A. Cleavage was initiated by rapidly equilibrating the chitin resin in buffer B (20 mM Tris-HCl, 500 mM NaCl, pH 8.0) containing either 50 mM cystyl-propargylamide (for alkyne-modified TNR1B) or 50 mM cystyl-3-azidopropylamide (for azide-modified TNR1B) and incubation was carried out for 24 to 96 hours at room temperature. The cleaved alkyne-modified TNR1B (SEQ ID NO: 106) or azide-modified TNR1B proteins (SEQ ID NO: 107) were eluted from the column with buffer A, concentrated using an Amicon Ultracel-3 Centrifugal Filter Unit from Millipore (Billerica, Mass.), dialyzed against Dulbecco's phosphate buffered saline without Ca or Mg salts (PBS) obtained from the UCSF Cell Culture Facility (San Francisco, Calif.), and stored at 4° C. prior to use.

Figure 2:
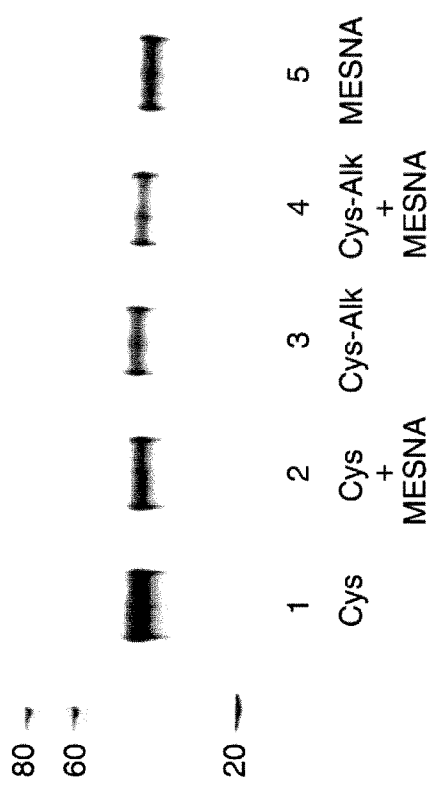
FIG. 2 shows the cleavage of TNR1B by (1) cysteine, (2) cysteine+mercaptoethane sulfonate (MESNA), (3) cystyl-propargylamide, (4) cystyl-propargylamide+MESNA, and (5) MESNA. All compounds were used at 50 mM concentration.

FIG. 2 shows SDS-polyacrylamide gel electrophoresis (SDS-PAGE) analysis of the alkyne-modified TNR1B, compared with cysteine-modified TNR1B (SEQ ID NO: 108) prepared using 50 mM cysteine instead of cystyl-propargylamide. SDS-PAGE was carried out using NuPAGEO Novex Bis-Tris Midi Gels (10%) obtained from Invitrogen (Carlsbad, Calif.). Proteins were visualized using Silver Stain Plus or Bio-Safe Coomassie Stain obtained from Bio-Rad (Hercules, Calif.). The alkyne-modified TNR1B (lane 3) and the cysteine-modified TNR1B (lane 1) had the same Mr ~43,000. In addition, the alkyne-modified TNR1B had comparable biological activity to cysteine-modified TNR1B as measured using a Human sTNFRII/TNFRSFlB Quantikine ELISA obtained from R&D Systems (Minneapolis, Minn.). Preparations of the cysteine-modified TNR1B (lane 2), alkyne-modified TNR1B (lane 4), or thioester-modified TNR1B (SEQ ID NO: 109) (lane 5) made in the presence of 50 mM MESNA had a similar Mr, but had less than 5% of the biological activity observed for preparations made in the absence of MESNA. Thus, alkyne-modified TNR1B prepared in the absence of MESNA was employed in further studies.

Figure 3:
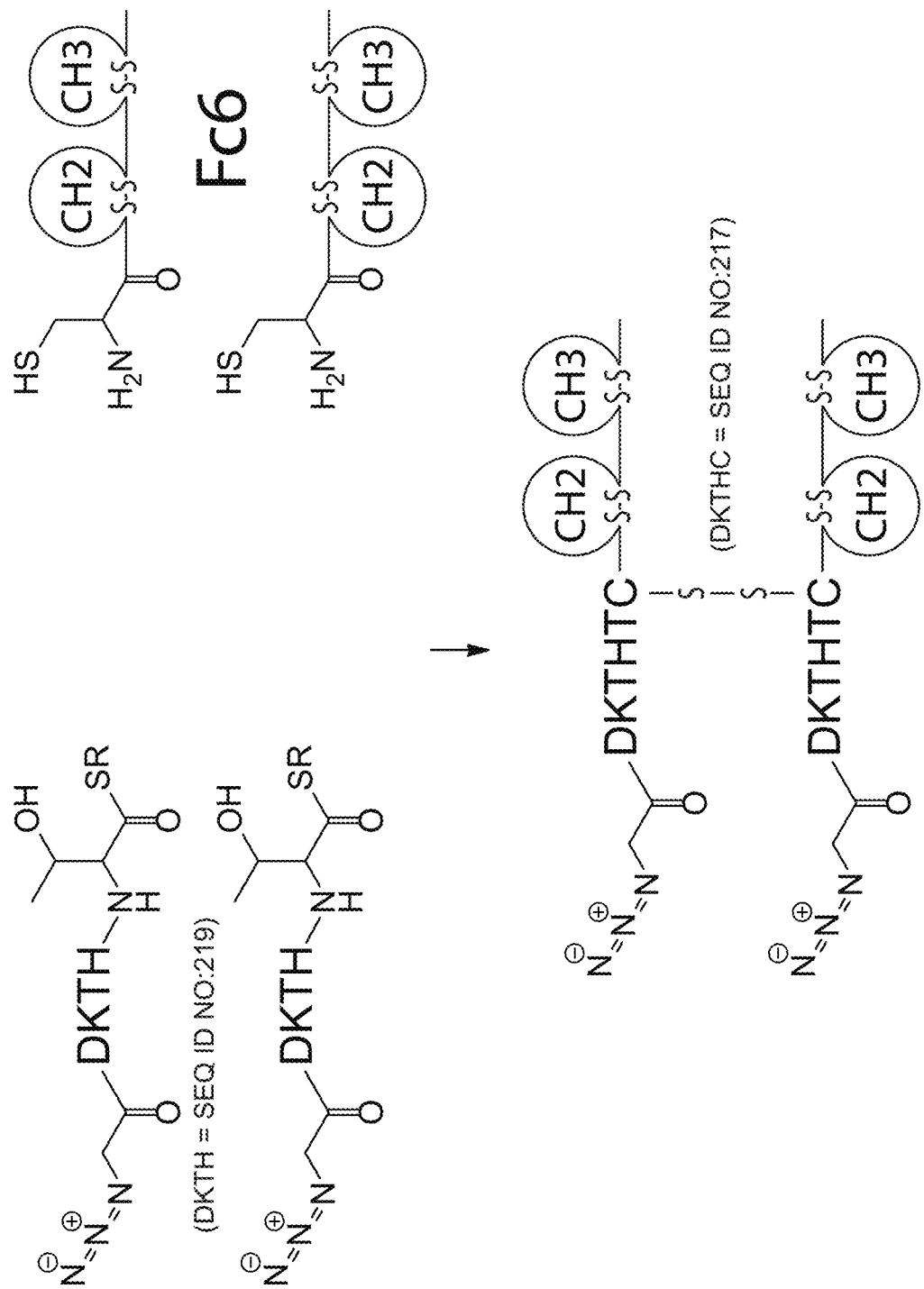
FIG. 3 shows the preparation of azide-modified Fc6 by ligation (peptidyl) of the Fc6 dimer and azide-DKTHT-thioester (Table 1). DKTHT is SEQ ID NO: 220.
Figure 4:
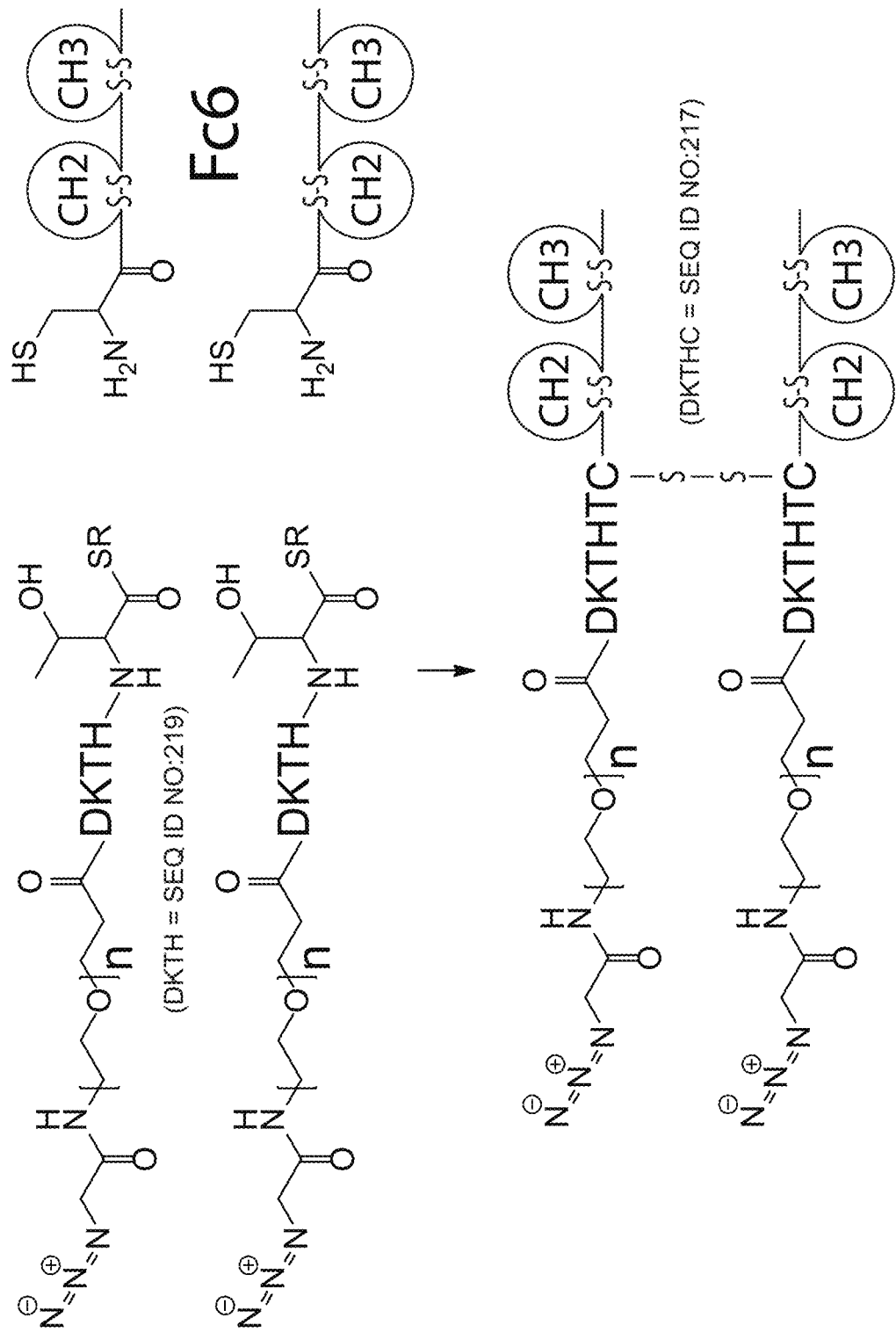
FIG. 4 shows the preparation of azide-modified Fc6 by ligation (peptidyl) of the Fc6 dimer and azide-PEG-DKTHT-thioester (Table 1). Cycloalkyne-modified Fc is similarly prepared by using DIBAC-PEG$_{12}$-thioester. DKTHT is SEQ ID NO: 220.

Azide-modified Fc6 (Az-Fc6) was prepared by the reaction of Fc6 protein with various azide-containing peptide thioesters (FIG. 3) and azide-containing PEG thioesters (FIG. 4). Alkyne-modified Fc6 (Alk-Fc6) was prepared by the reaction of alkyne-containing thioesters with Fc6 protein.

Recombinant Fc6 protein was expressed in Chinese hamster ovary (CHO) cells as described for TNR1B-intein (see above) and purified by Protein A affinity chromatography. The culture supernatant was applied to a column packed with rProtein A Fast Flow from Pharmacia (Uppsala, Sweden) pre-equilibrated with PBS. The column was washed extensively with PBS and the Fc6 protein then eluted with 0.1 M glycine buffer pH 2.7. Fractions were collected into tubes containing 0.05 vol/vol of 1.0 M Tris-HCl pH 9.0 (giving a final pH of 7.5), pooled, dialyzed against PBS, and stored at 4° C. prior to use.

Table 1 shows representative azide-containing and alkyne-containing peptide/PEG thioesters. Thioesters were synthesized by an Fmoc/t-Butyl solid-phase strategy on a 2-chlorotrityl chloride resin preloaded with the Fmoc-Thr (tBu)—OH. Amino acid derivatives were obtained from CPC Scientific (Sunnyvale, Calif.), Fmoc-PEG-OH derivatives were obtained from Quanta BioDesign (Powell, Ohio), and 2-(1H-benzotriazole-1-yl)-1,1,3,3-tetramethylaminium hexafluorophosphate (HBTU), dichloromethane (DCM), trichloroacetic acid (TFA), N, N'-diisopropylcarbodiimide (DIC), 1-hydroxybenzotriazole (HOBt), N,N'-diisopropylethylamine (DIEA) and triisopropylsilane (TIS) were obtained from Sigma (St. Louis, Mo.). The standard HBTU activation was employed for peptide elongation. Peptides containing PEG required the insertion of a Fmoc-PEG-OH. As a final step in peptide elongation, the terminal α-Fmoc (9-fluorenylmethoxycarbonyl) protecting group was converted to Boc (tert-butoxycarbonyl). The peptide resin was washed with DCM and cleaved with 1% TFA/DCM to yield the fully protected peptide with a free carboxylic acid on the C-terminus. The thioester of the peptides was formed by treating the crude protected peptide with DIC/HOBt/DIEA and benzyl mercaptan or thiophenol in DCM overnight. After concentration, the crude protected peptide thioester was precipitated by multiple triturations with cold ether followed by centrifugation. Deprotection was carried out by treatment of the crude protected product with 95:2.5:2.5 TFA/TIS/H$_2$O for 2 hours at room temperature. After precipitation with ice-cold ether the deprotected peptide thioester was purified by preparative RP-HPLC in a H$_2$O-acetonitrile (0.1% TFA) system to afford the final product with 91-95% purity and the desired MS.

Azide-modified Fc6 and alkyne-modified Fc6 were prepared by native chemical ligation as follows. 2-(N-morpholino)ethanesulfonic acid (MES) was obtained from Acros (Morris Plains, N.J.), tris(2-carboxyethyl)phosphine (TCEP) was obtained from Pierce (Rockford, Ill.), and 4-mercaptophenylacetic acid (MPAA) was obtained from Sigma-Aldrich (St. Louis, Mo.). Reactions were carried out by ligating the various thioesters shown in Table 1 with the Fc6 protein as follows. Reactions (100 uL) contained 50 mM MES buffer, pH 6.5, 0.8 mM TCEP, 10 mM MPAA, 4 mg/ml of the peptide thioester, and 0.5 mg/ml of the Fc6 protein. Following overnight incubation at room temperature, reactions were adjusted to pH 7.0 with 0.05 vol/vol of 1.0 M Tris-HCl pH 9.0, purified using Protein A Magnetic Beads from New England BioLabs, dialyzed in 0.1 M phosphate pH 8.0, and concentrated.

Figure 5:
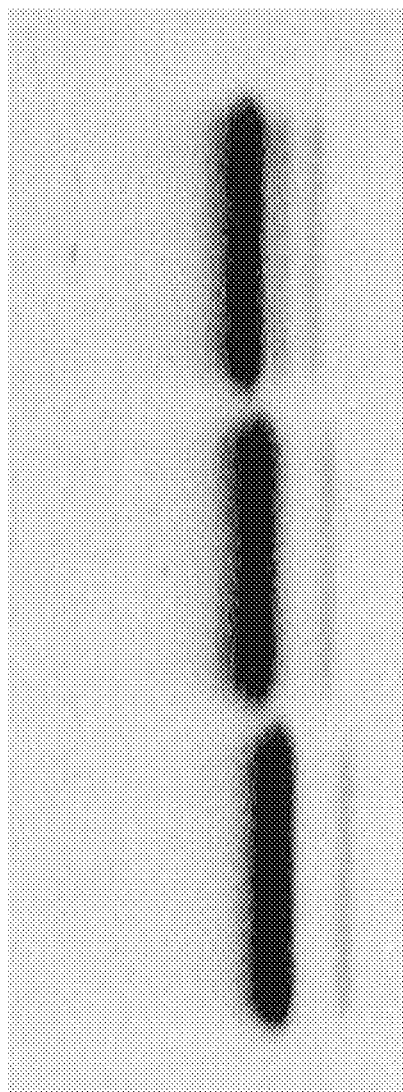
FIG. 5 shows SDS-PAGE analysis (reducing conditions) of (1) unmodified Fc6, (2) the Az-DKTHT-Fc6 reaction product of FIG. 3, and (3) the Az-PEG$_4$-DKTHT-Fc6 reaction product of FIG. 4.

FIG. 5 shows SDS-PAGE analysis demonstrating that Fc6 protein (lane 1) reacted quantitatively with azide-DKTHT-thioester to yield the Az-DKTHT-Fc6 protein (lane 2) and azide-PEG$_4$-DKTHT-thioester to yield the Az-PEG$_4$-DKTHT-Fc6 protein (lane 3). DKTHT is SEQ ID NO: 220. The sequence of the Az-DKTHT-Fc6 protein is shown in SEQ ID NO: 110 and the sequence of the Az-PEG$_4$-DKTHT-Fc6 is shown in SEQ ID NO: 111. The PEG$_4$ oligomer gave an incremental size increase comparable to the 5 amino acid DKTHT sequence (SEQ ID NO:220). This shows that a single oxyethylene monomer unit makes a contribution to contour length similar to a single amino acid residue, consistent with their having comparable fully extended conformations of ~3.5 to 4Å (Flory (1969) Statistical Mechanics of Chain Molecules (Interscience Publishers, New York).

Figure 6:
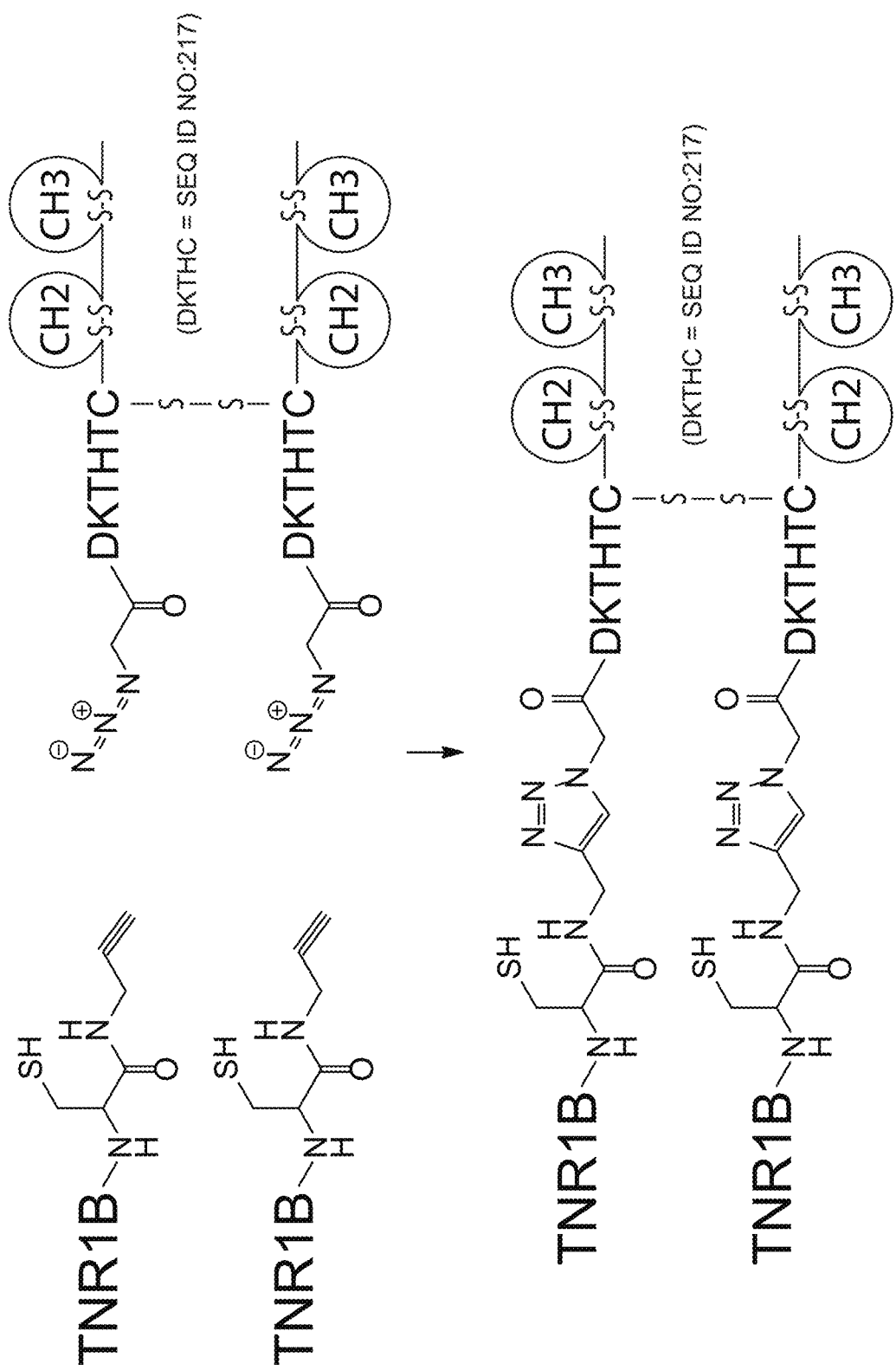
FIG. 6 shows the synthesis of TNR1B-alkyne-azide-Fc6 by ligation (non-peptidyl) of alkyne-modified TNR1B and Az-DKTHT-Fc6. DKTHT is SEQ ID NO: 220.
Figure 7:
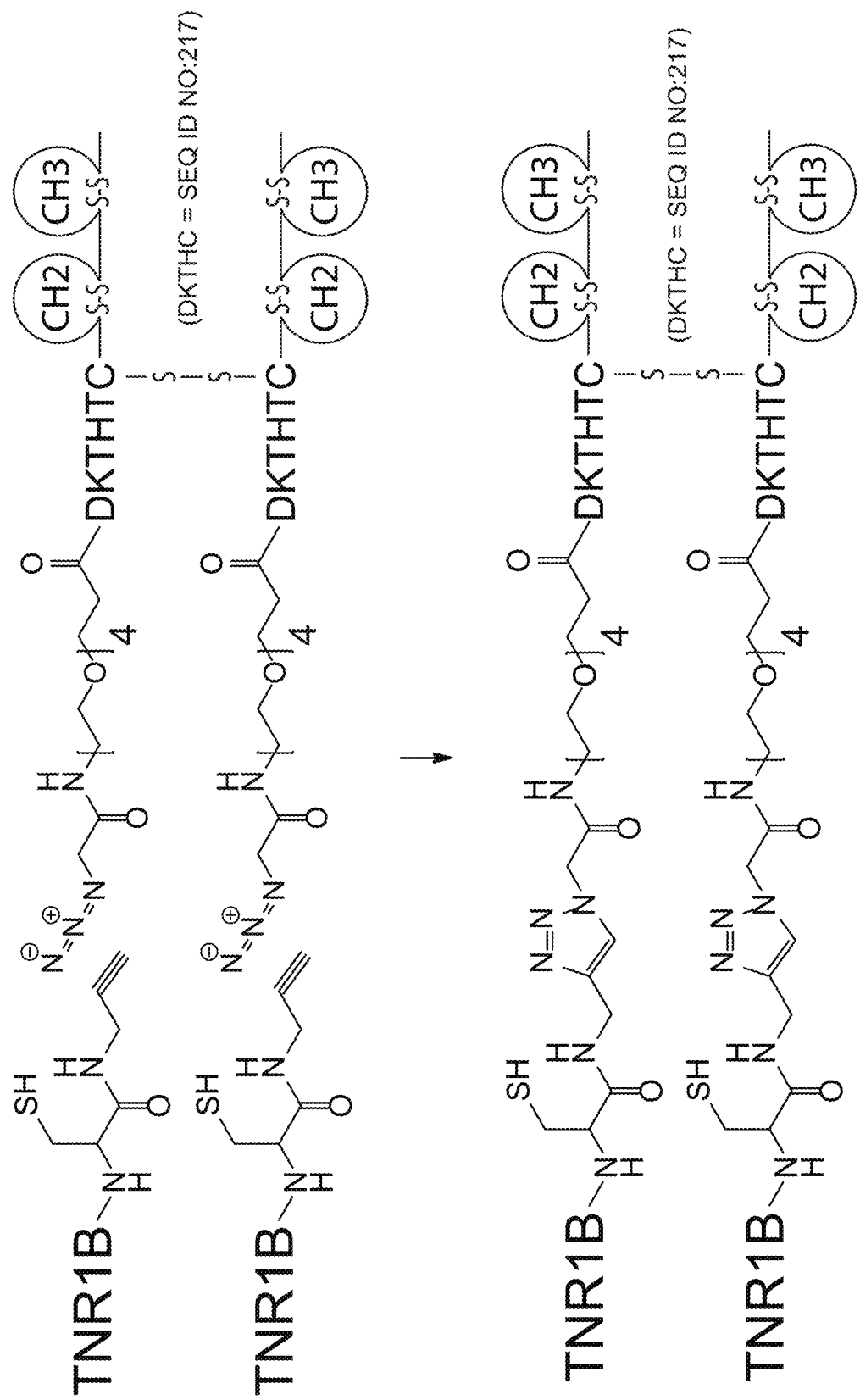
FIG. 7 shows the synthesis of TNR1B-alkyne-azide-PEG$_n$-Fc6 by ligation (non-peptidyl) of alkyne-modified TNR1B and azide-PEG$_n$-DKTHT-Fc6. In this example, n=4. DKTHT is SEQ ID NO: 220.

TNR1B-alkyne-azide-Fc6 was prepared via the reaction of the alkyne-modified TNR1B with the Az-DKTHT-Fc6 protein (FIG. 6) and the Az-PEG$_4$-DKTHT-Fc6 protein (FIG. 7). DKTHT is SEQ ID NO: 220. Sodium phosphate, dibasic (anhydrous) and sodium phosphate, monobasic (monohydrate) were obtained from Acros, TCEP was from Pierce, CuSO$_4$ (pentahydrate) was from Sigma-Aldrich, and Tris[1-benzyl-1H-1,2,3-triazol-4-yl)methyl]amine (TBTA) from AnaSpec (Freemont, Calif.). Reactions (60 uL) contained 0.1 M sodium phoshate, pH 8.0, 1.0 M CuSO$_4$, 2.0 M TBTA, the alkyne-modified TNR1B (30 ug), and either the unmodified Fc6 protein, the Az-DKTHT-Fc6 protein, or the Az-PEG$_4$-DKTHT-Fc6 protein (10 ug). DKTHT is SEQ ID NO: 220. Reactions were initiated by the addition of 2.0 mM TCEP, and incubated overnight at room temperature. The reaction products were purified using Protein A Magnetic Beads to remove any unreacted alkyne-modified TNR1B.

Figure 8:
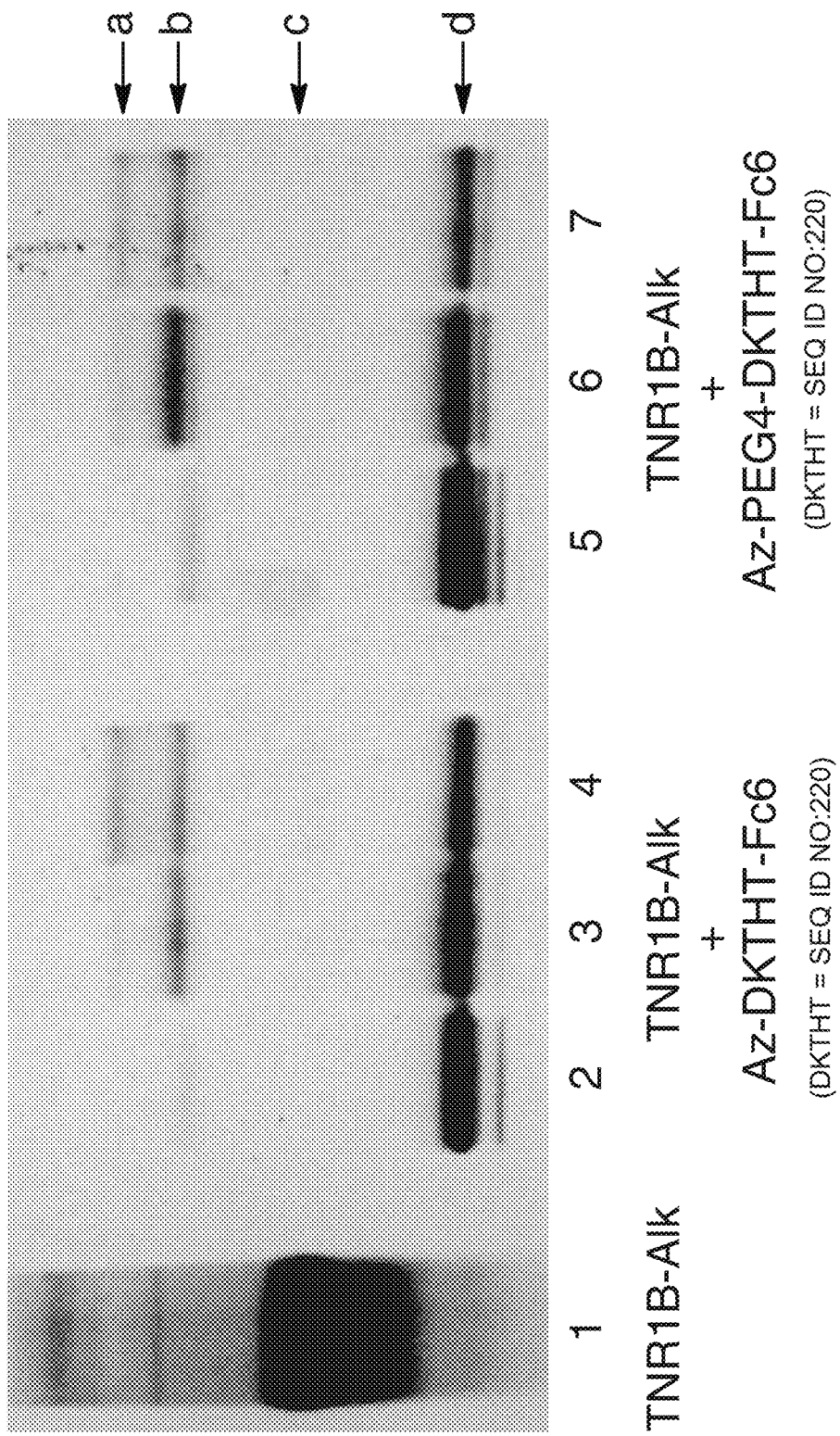
FIG. 8 shows SDS-PAGE analysis (reducing conditions) of (1) alkyne-modified TNR1B alone, (2) alkyne-modified TNR1B+Az-DKTHT-Fc6 in the absence of catalyst, (3) alkyne-modified TNR1B+Az-DKTHT-Fc6+catalyst leading to the product of FIG. 6, and (4) dialyzed alkyne-modified TNR1B+Az-DKTHT-Fc6+catalyst leading to increased formation of the product of FIG. 6 (5) alkyne-modified TNR1B+Az-PEG$_4$-DKTHT-Fc6 in the absence of catalyst, (6) alkyne-modified TNR1B+Az-PEG$_4$-DKTHT-Fc6+catalyst leading to the product of FIG. 7, and (7) dialyzed alkyne-modified TNR1B+Az-PEG$_4$-DKTHT-Fc6+catalyst leading to increased formation of the product of FIG. 7. The arrows correspond to (a) Mr ~75,000, (b) Mr ~65,000, (c) Mr ~43,000, and (d) Mr ~28,000. DKTHT is SEQ ID NO: 220.

FIG. 8 shows SDS-PAGE analysis of the TNR1B-alkyne-azide-Fc6 products under reducing conditions. In the absence of CuSO$_4$, TBTA and TCEP, both Az-DKTHT-Fc6 (lane 2) and Az-PEG$_4$-DKTHT-Fc6 (lane 5) gave a single band of Mr ~28-30,000 daltons (arrow d) corresponding to the input azide-modified Fc6 proteins, with no sign of any product formation. DKTHT is SEQ ID NO: 220. In addition, there was no evidence of any carryover of the input alkyne-modified TNR1B (shown in lane 1) following the Protein A purification. However, in the presence of CuSO$_4$, TBTA and TCEP, the reaction between alkyne-modified TNR1B and Az-DKTHT-Fc6 (lane 3) and the reaction between alkyne-modified TNR1B and Az-PEG$_4$-DKTHT-Fc6 (lane 6) both yielded two new products of Mr ~75,000 daltons (arrow a) and ~65,000 daltons (arrow b). DKTHT is SEQ ID NO: 220. Reactions carried out using a preparation of alkyne-modified TNR1B following buffer-exchange in 0.1 M phosphate pH 8.0 to remove salt gave essentially similar reaction products with both Az-DKTHT-Fc6 (lane 4) and Az-PEG$_4$-DKTHT-Fc6 (lane 6), although there was a significant increase in the yield of the Mr ~75,000 dalton product over the Mr ~65,000 dalton product. DKTHT is SEQ ID NO: 220.

Figure 9:
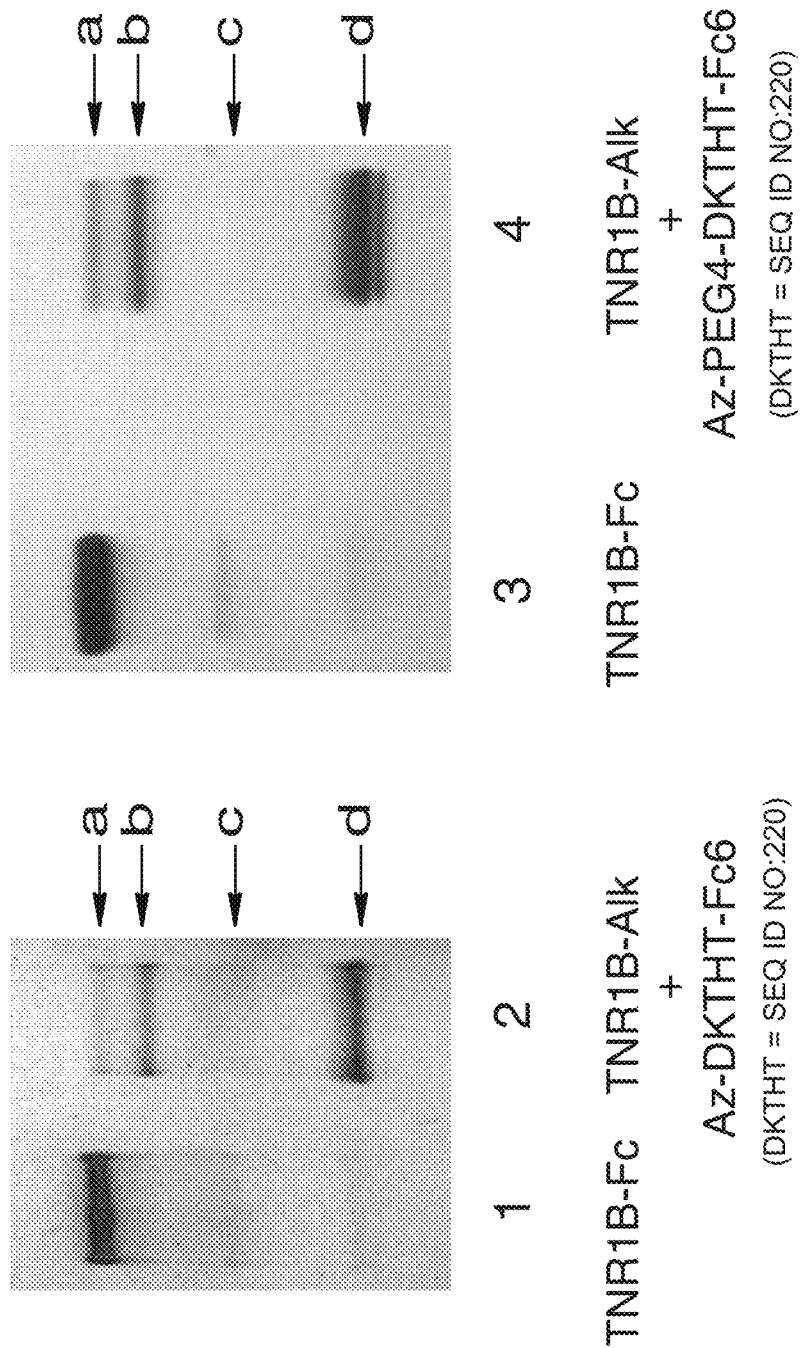
FIG. 9 shows SDS-PAGE analysis (reducing conditions) of (1) TNF1B-Fc fusion protein (etanercept) alone, (2) alkyne-modified TNR1B+Az-DKTHT-Fc6+catalyst leading to the product of FIG. 6, (3) TNF1B-Fc fusion protein (etanercept), and (4) alkyne-modified TNR1B+Az-PEG$_4$-DKTHT-Fc6 leading to the product of FIG. 7. DKTHT is SEQ ID NO: 220. The arrows correspond to (a) Mr ~75,000, (b) Mr ~65,000, (c) Mr ~43,000, and (d) Mr ~28,000.

FIG. 9 shows SDS-PAGE analysis comparing the TNR1B-alkyne-azide-Fc6 reaction products (left panel) and the TNR1B-alkyne-azide-PEG$_4$-Fc6 reaction products (right panel) with TNR1B-Fc fusion protein (etanercept). The TNR1B-alkyne-azide-Fc6 product of Mr ~75,000 daltons (lane 2), having the predicted sequence shown in SEQ ID NO: 112, and the TNR1B-alkyne-azide-PEG$_4$-Fc6 product of Mr ~75,000 daltons (lane 4), having the predicted sequence of shown in SEQ ID NO: 113, are essentially indistinguishable in size from etanercept (lanes 1, 3), the sequence of which is shown in SEQ ID NO: 114.

Figure 10:
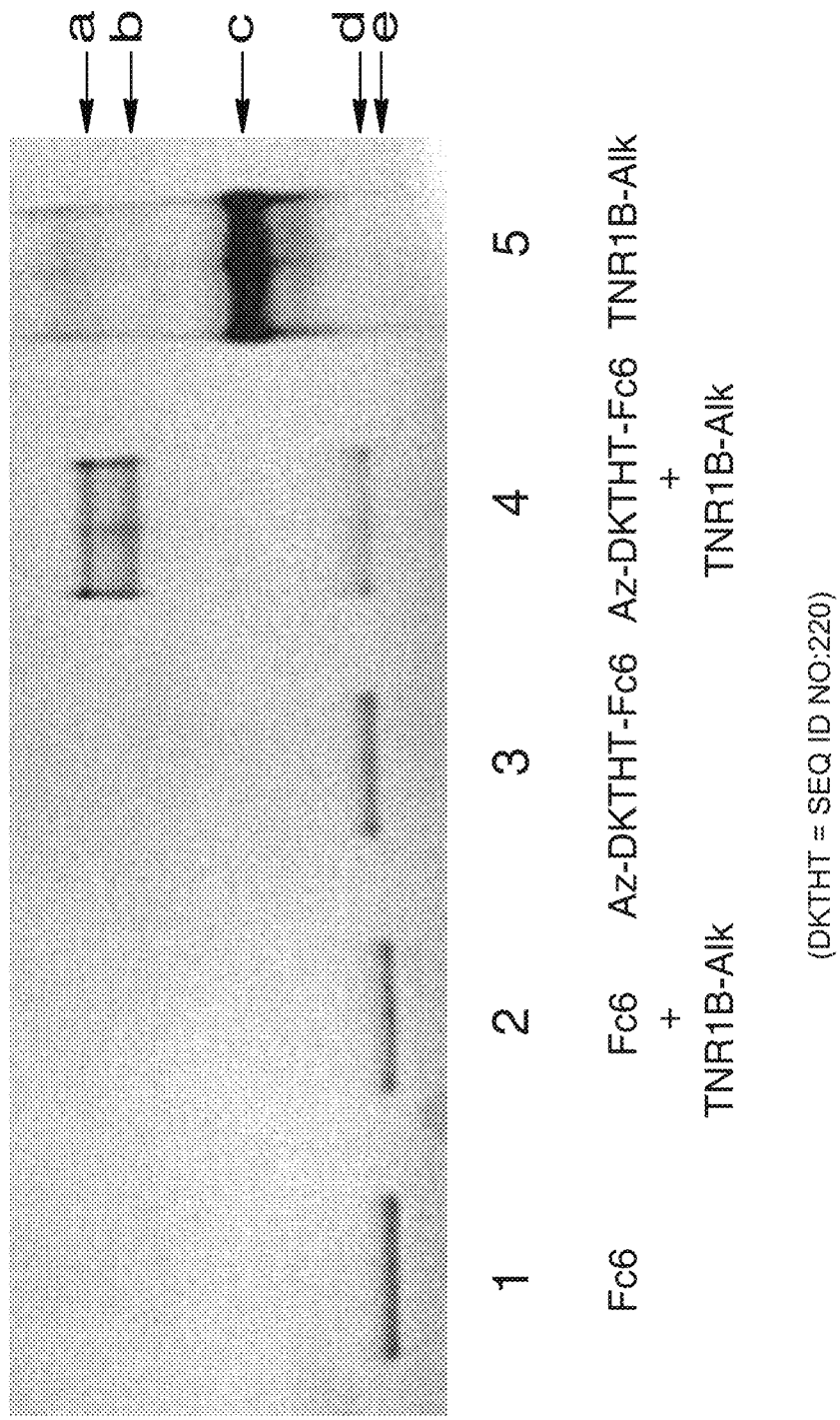
FIG. 10 shows SDS-PAGE analysis (reducing conditions) of (1) unmodified Fc6+catalyst, (2) alkyne-modified TNR1B+unmodified Fc6+catalyst (3) Az-DKTHT-Fc6+catalyst, (4) alkyne-modified TNR1B+Az-DKTHT-Fc6+catalyst leading to the product of FIG. 6, and (5) alkyne-modified TNR1B alone. The arrows correspond to (a) Mr ~75,000, (b) Mr ~65,000, (c) Mr ~43,000, (d) Mr ~28,000, and (e) Mr ~27,000. DKTHT is SEQ ID NO: 220.

FIG. 10 shows SDS-PAGE analysis providing further evidence confirming the requirement of the alkyne and azide groups for reactivity. Reaction mixtures that contained alkyne-modified TNR1B with unmodified Fc6 protein gave no reaction product (lane 2) compared with Fc6 alone (lane 1), while alkyne-modified TNR1B with Az-DKTHT-Fc6 gave the expected products (lane 4) compared with Az-DKTHT-Fc6 alone (lane 3). Again, no carryover of the input alkyne-modified TNR1B (shown in lane 5) was apparent following the Protein A purification. DKTHT is SEQ ID NO: 220.

The TNR1B-alkyne-azide-Fc6 products of FIG. 10 were further characterized by sequencing of their tryptic peptide by LC-MS.

Following SDS-PAGE, the gel was Coomassie stained and four gel regions were excised, corresponding to the Mr ~75,000 product (arrow a), the Mr ~65,000 product (arrow b), the unstained region where alkyne-modified TNR1B would migrate (arrow c), and the unreacted Az-DKTHT-Fc6 protein of Mr ~28,000 (arrow d). DKTHT is SEQ ID NO: 220. The four gel slices were diced into small small pieces (~0.5-1.0 mm$^3$) and processed as follows. Ammonium bicarbonate, acetonitrile, dithiothreitol, and iodoacetamide were obtained from Sigma-Aldrich, formic acid was obtained from Pierce, and porcine trypsin (sequencing grade) was obtained from Promega (Madison, Wis.). To remove the Coomassie stain, each gel slice was extracted with 200 uL of 25 mM $NH_4HCO_3$ in 50% acetonitrile by vortexing, centrifuged to remove the supernatant, and dehydrated by adding acetonitrile for a few minutes until the gel pieces shrank and turned white. The acetonitrile was discarded, and the gel slices dried in a Speed Vac (Savant Instruments, Farmingdale, N.Y.). Reduction and alkylation was then carried out by rehydrating the gel slices in 40 ul of 10 mM dithiothreitol in 25 mM $NH_4HCO_3$, vortexing, and incubated at 56° C. for 45 minutes. The supernatant was then discarded, 40 uL of 55 mM iodoacetamide in 25 mM $NH_4HCO_3$ was added, the gel slices vortexed and incubated in the dark for 30 minutes at room temperature. The supernatant was discarded, the gel slices again dehydrated in acetonitrile and dried in a Speed Vac. Trypsin digestion was then carried out by rehydrating the gel slices in 25 uL of trypsin (12.5 ug/mL) in 25 mM $NH_4HCO_3$ on ice for 60 minutes. Excess trypsin solution was then removed, the gel slices covered with 25 mM $NH_4HCO_3$ and incubated at 37° C. overnight. The supernatant was removed, and the gel then extracted twice with 30 uL of 50% acetonitrile/0.1% formic acid in water. The organic extracts were combined with the aqueous supernatant, reduced to a volume of 10 uL in a Speed Vac, then analysed by LC-MS using a Q-Star Elite mass spectrometer (AB SCIEX, Foster City, Calif.).

FIG. 11 summarizes the characterization of the structure of the TNR1B-alkyne-azide-Fc6 reaction product by mass spectrometry. The Mr ~75,000 product, as expected for the full-length TNR1B-alkyne-azide-Fc6 product, contained peptides from both the alkyne-modified TNR1B and azide-modified Fc6 parent proteins. In addition, the peptide coverage of the alkyne-modified TNR1B sequence (upper panel) extended from the N-terminal region (EYYDQTAQMCCSK—SEQ ID NO: 221) to the C-terminal region (SMAPGAVHLPQPVST—SEQ ID NO: 222). Similarly, the peptide coverage of the azide-modified Fc6 protein sequence (lower panel) extended from the N-terminal region (DTLMISR—SEQ ID NO: 223) to the C-terminal region (TTPPPVLDSDGSFFLYSK—SEQ ID NO: 224). In contrast, the Mr ~65,000 lacked the EYYDQTAQMCCSK (SEQ ID NO: 221) peptide, suggesting it was an N-terminally deleted version of the expected full-length TNR1B-alkyne-azide-Fc6 product. Sequences derived from the TNR1B protein were not detected in the unstained region of Mr ~43,000 where the alkyne-modified TNR1B would normally migrate (arrow c), while only sequences derived from the Fc6 protein were detected in the unreacted Az-DKTHT-Fc6 protein of Mr ~28,000 (arrow d).

The TNR1B-alkyne-azide-Fc6 and TNR1B-alkyne-azide-$PEG_4$-Fc6 products of FIG. 10 were further characterized for their biological activity by measuring their ability to bind TNF-α using surface plasmon resonance (SPR). Recombinant human TNF-α protein (carrier-free) was obtained from R&D Systems and reconstituted in PBS. SPR studies were carried out using a Biacore T100 instrument from Biacore AB (Uppsala, Sweden).

The surface-bound ligands, TNR1B-alkyne-azide-Fc6 and TNR1B-alkyne-azide-$PEG_4$-Fc6, were immobilized onto a CM5 sensor chip, Series S, using a Amine Coupling Kit (BR-1000-50) obtained from GE Healthcare (Piscataway, N.J.) according to the manufacturer's instructions. Binding of TNF-α was carried out at 25° C. in 10 mM Hepes buffer pH 7.4, 150 mM NaCl, 3 mM EDTA, and 0.005% Tween-20. Binding was evaluated in duplicate at TNF-α concentrations of 0.156 nM, 0.312 nM, 0.625 nM, 1.25 nM, 2.5 nM, 5.0 nM, 10.0 nM, 20.0 nM and 40 nM. Data was evaluated using Biacore T100 Evaluation Software, version 2.0.3.

Figure 12:
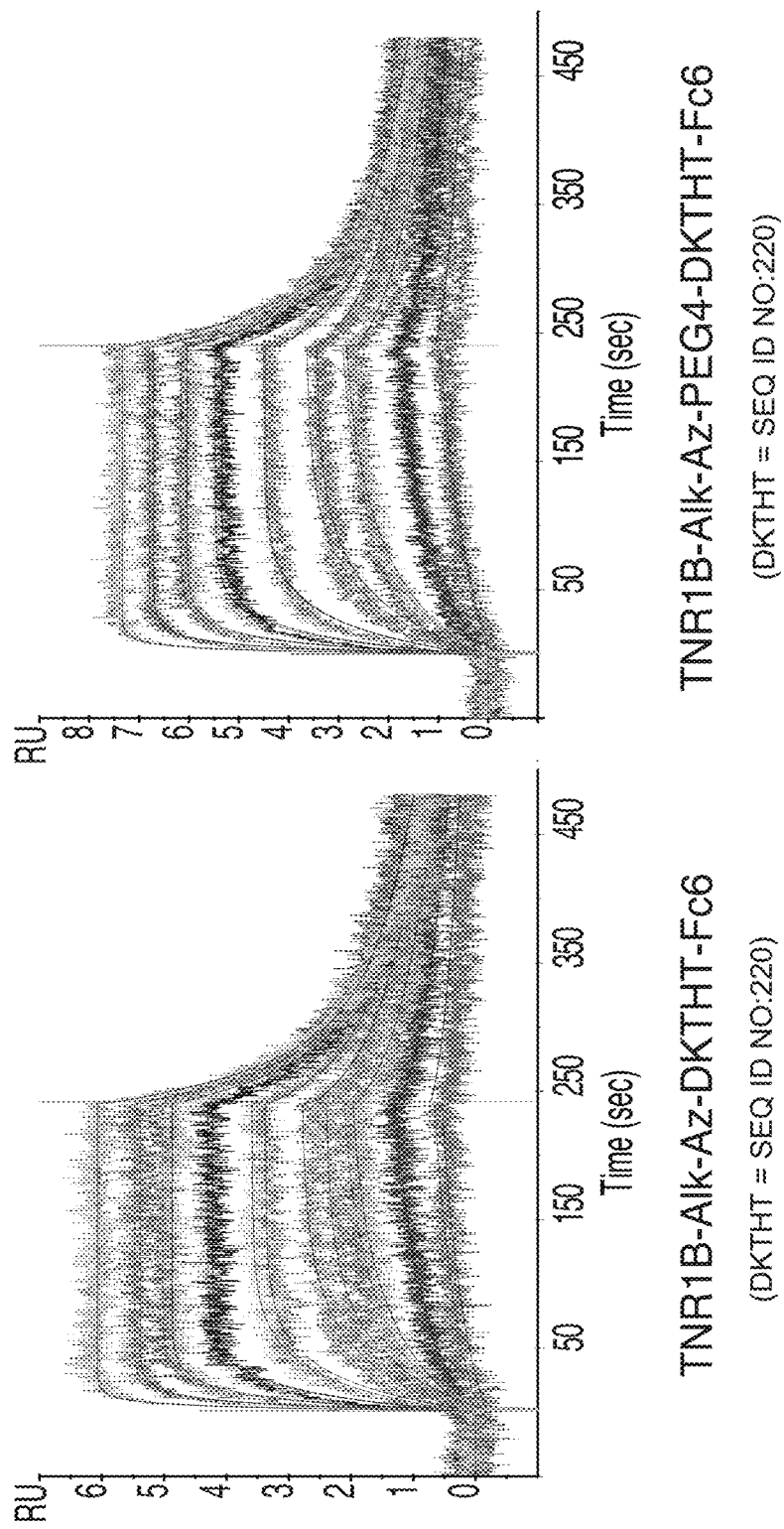
FIG. 12 shows SPR analysis of TNF-α binding by the TNR1B-alkyne-azide-DKTHT-Fc6 (left panel) and TNR1B-alkyne-azide-PEG$_4$-DKTHT-Fc6 (right panel) reaction products of FIG. 9. The kinetic binding data are summarized in Table 2. DKTHT is SEQ ID NO: 220.

FIG. 12 shows the kinetic binding curves for TNR1B-alkyne-azide-Fc6 (left panel) and TNR1B-alkyne-azide-PEG-Fc6 (right panel). Both products showed saturable TNF-α binding, and an excellent fit was obtained employing a two-exponential model ($Chi^2$ ~0.05). Table 2 summarizes the kinetic binding data.

Approximately 40% of the binding sites for each product were higher affinity, with a 1.6-fold greater dissociation constant for TNR1B-alkyne-azide-$PEG_4$-Fc6 ($K_D$=1.86× $10^{-10}$ M) than for TNR1B-alkyne-azide-Fc6 ($K_D$=2.99× $10^{-10}$ M). The remaining 60% of the binding sites were of lower affinity, with the dissociation constants about the same for TNR1B-alkyne-azide-$PEG_4$-Fc6 ($K_D$=5.12×$10^{-9}$ M) and TNR1B-alkyne-azide-Fc6 ($K_D$=5.17×$10^{-9}$ M). The association of the $PEG_4$ linker with increased high affinity binding, but equal low affinity binding, provides compelling evidence for a higher degree of cooperative (two-handed) binding of TNF-α by TNR1B-alkyne-azide-$PEG_4$-Fc6 compared with TNR1B-alkyne-azide-Fc6.

TABLE 1

Azide-containing and Alkyne-Containing Thioesters

| Name | Formula | Mr | MH+ | Sequence |
| --- | --- | --- | --- | --- |
| Az-DKTHT | $C_{33}H_{47}O_{10}N_{11}S$ | 789.86 | 780.60 | Azide-DKTHT-thioester |
| Az-$PEG_4$-DKTHT | $C_{44}H_{68}O_{15}N_{12}S$ | 1037.14 | 1038.20 | Azide-$PEG_4$-DKTHT-thioester |
| Az-$PEG_{12}$-DKTHT | $C_{59}H_{98}O_{23}N_{12}S$ | 1375.55 | 1376.26 | Azide-$PEG_{12}$-DKTHT-thioester |
| Az-$PEG_{24}$-DKTHT | $C_{83}H_{146}O_{35}N_{12}S$ | 1904.18 | 1904.80 | Azide- $PEG_{24}$-DKTHT-thioester |
| Az-$PEG_{36}$-DKTHT | $C_{107}H_{194}O_{47}N_{12}S$ | 2432.82 | 2434.40 | Azide-$PEG_{36}$-DKTHT-thioester |
| Alk-$PEG_{12}$ | $C_{53}H_{74}O_{15}N_2S$ | 1011.22 | 1011.80 | DIBAC-$PEG_{12}$-thioester |

Mr, relative molecular mass;

MH+, monoisotypic mass value.

DKTHT = SEQ ID NO: 220

TABLE 2

| Surface-bound ligand | ka1 (1/Ms) | kd1 (1/s) | KD1 (M) | Rmax1 | ka2 (1/Ms) | kd2 (1/s) | KD2 (M) | Rmax2 | Chi$^2$ |
|---|---|---|---|---|---|---|---|---|---|
| TNF-α binding measured by surface plasmon resonance | | | | | | | | | |
| TNR1B-Alk-Az-DKTHT-Fc6 | 1.252E+7 | 0.003744 | 2.990E−10 | 2.5 | 5.176E+6 | 0.03392 | 6.553E−9 | 3.9 | 0.0514 |
| TNR1B-Alk-Az-PEG4-DKTHT-Fc6 | 1.400E+7 | 0.002613 | 1.866E−10 | 3.0 | 5.129E+6 | 0.03021 | 5.890E−9 | 4.8 | 0.0503 |

Abbreviations:
ka, on-rate (measured);
kd, off-rate (measured);
KD, dissociation constant (calculated).
DKTHT = SEQ ID NO: 220

Example 2: Fab'-alkyne-azide-Fc6

Fab'-alkyne-azide-Fc6 was prepared via the reaction of cycloalkyne-modified Fab' with azide-modified Fc6 as follows.

Figure 13:
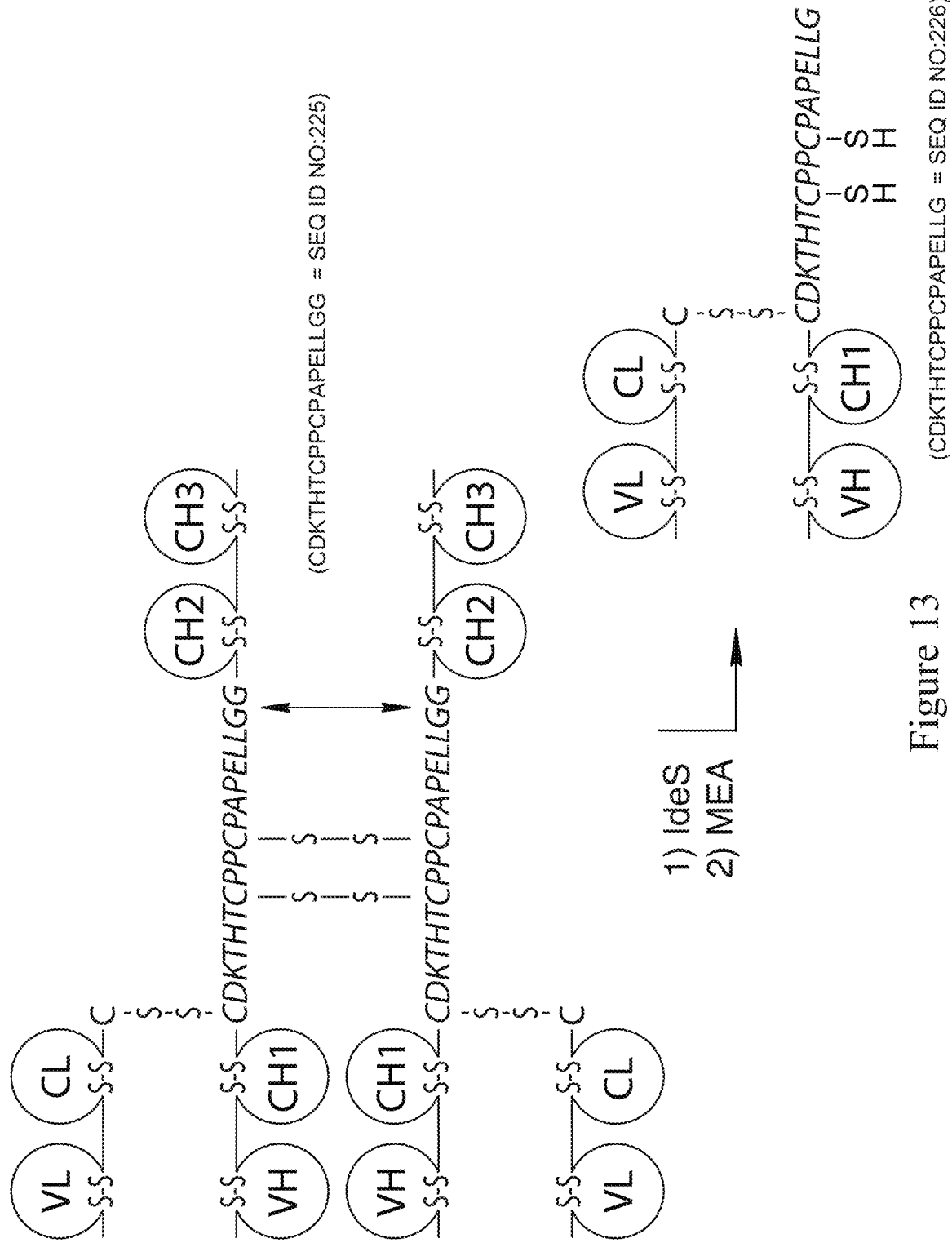
FIG. 13 shows the preparation of adalimumab Fab' in a three-step process: 1) IdeS cleavage to the Fab'2+Fc' fragments, 2) Protein A chromatography to remove the Fc' fragment, and 3) mild reduction of the Fab'2 fragment to the Fab' fragment with 2-mercaptoethylamine (MEA).

Adalimumab (Humira) was obtained as a liquid formulation (50 mg/ml) from Abbott (Abbott Park, Ill.). The Fab' fragment was prepared using IdesS protease to first generate Fab'2 fragment followed by selective reduction of the interchain disulfides with 2-mercaptoethylamine (FIG. 13). Antibody (10 mg) was exchanged into cleavage buffer (50 mM sodium phosphate, 150 mM NaCl, pH 6.6) using a Slide-A-Lyzer Mini Dialysis Unit, 10K MWCO from Pierce (Rockford, Ill.), then incubated with his-tagged recombinant IdeS immobilized on agarose beads (FragIT MidiSpin column) from Genovis (Lund, Sweden) for 1 hour at room temperature with constant mixing. The beads were removed from the digest solution by centrifugation, washed twice with cleavage buffer, and the digest and wash solutions then combined and applied to a HiTrap Protein A HP column from GE Life Sciences (Piscataway, N.J.) to remove Fc' fragment and undigested antibody. Flow-through fractions containing the Fab'2 fragment were reduced to the Fab' fragment by adding 1 mL aliquots to a vial containing 6 mg 2-mercaptoethylamine (MEA) from Pierce. Reductions were carried out with 10 mM EDTA to minimize re-oxidation of the interchain disulfides. Following incubation at 37° C. for 110 min, excess MEA was removed by buffer-exchange into PBS containing 10 mM EDTA using a PD-10 desalting column from GE Life Sciences (Piscataway, N.J.). The eluate containing the Fab' fragment was concentrated using an Amicon Ultracel-3 Centrifugal Filter Unit from Millipore (Billerica, Mass.).

Figure 14:
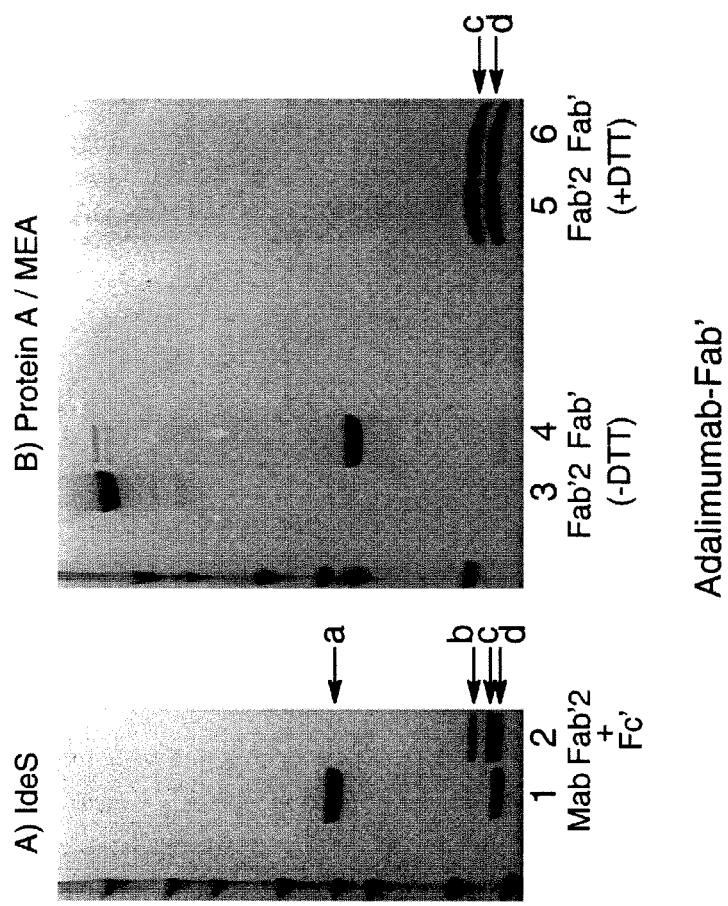
FIG. 14 shows SDS-PAGE analysis of (1) adalimumab, (2) adalimumab after IdeS cleavage, (3) adalimumab Fab'2 after Protein A purification, (4) adalimumab Fab' after MEA treatment of the Protein A purified Fab'2, (5) adalimumab Fab'2 after Protein A purification, and (6) adalimumab Fab' after MEA treatment of the Protein A purified Fab'2. The samples in lanes 1, 2, 5 and 6 were analysis under reducing conditions; while the samples in lanes 3 and 4 were analyzed under non-reducing conditions. The arrows correspond to the (a) heavy chain, (b) heavy chain Fc' fragment, (c) heavy chain Fd' (variable region-containing) fragment, and (d) light chain.

FIG. 14 shows SDS-PAGE analysis of adalimumab after cleavage with IdeS (panel A), followed by Protein A chromatography and mild reduction with MEA (panel B). In the presence of a strong reducing agent (dithiothreitol) in the polyacrylamide gel, the whole antibody (lane 1) migrated as a heavy chain of Mr ~55,000 (arrow a) and a light chain of Mr ~25,000 (arrow d). IdeS cleaved the heavy chain (lane 2) into a C-terminal fragment of Mr ~29,000 (arrow b) and an N-terminal fragment of Mr ~26,000 (arrow c). The light chain and the N-terminal heavy chain fragment comprise the Fab'2 domain, while the C-terminal heavy chain fragment comprises the Fc' domain. The Protein A column efficiently removed the Fc' domain from the Fab' domain (compare lane 2 with lanes 5 and 6). Under non-reducing conditions, the Fab'2 domain migrated as a single species of Mr ~110,000 (lane 3), while the Fab' domain produced by mild reduction with MEA migrated as a single species of Mr ~55,000 (lane 4). Under reducing conditions, the Fab'2 domain (lane 5) and the Fab' domain (lane 6) both yielded the same light chain (arrow d) and N-terminal heavy chain fragment (arrow c), as expected. Thus, the Fab' domain obtained by this procedure was essentially free of the Fab'2 and Fc' domains.

Figure 15:
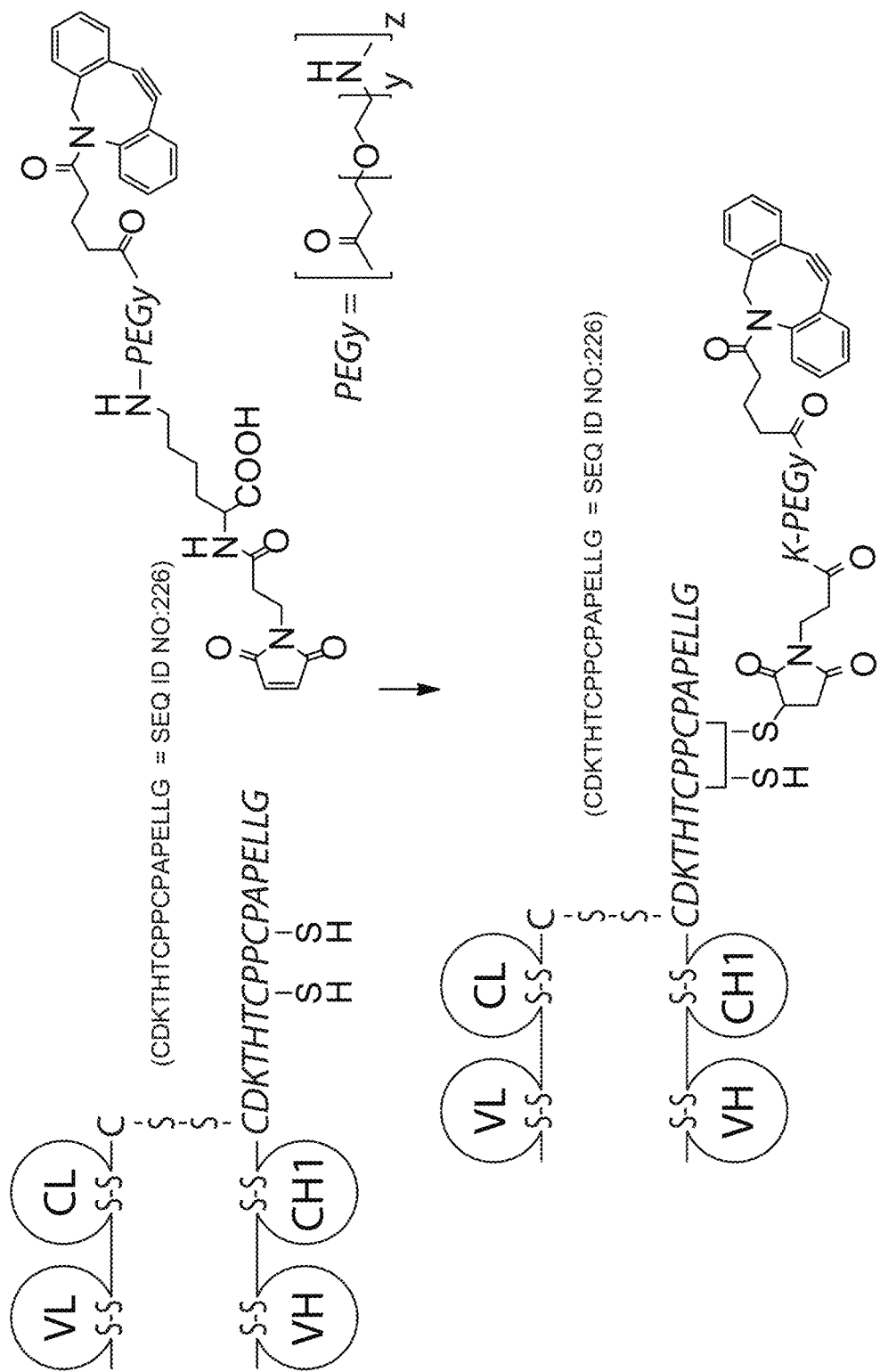
FIG. 15 shows the preparation of cycloalkyne-modified Fab' by the reaction of adalimumab Fab' with DIBAC-PEG$_y$-Lys(Mal). In this example, PEGy-PEG$_{12}$.

Cycloalkyne-modified Fab' was prepared from the adalimumab Fab' domain using a bifunctional linker, DIBAC-PEG$_{12}$-Lys (Mal), which contains a maleimide group capable of reacting with the free thiol groups on the Fab' fragment (FIG. 15). DIBAC-PEG$_{12}$-Lys(Mal) was prepared using an Fmoc solid-phase synthesis strategy. Lys(Mtt)-Wang resin and succinimido 3-maleimidopropanoate (Mpa-OSu) were obtained from CPC Scientific (Sunnyvale, Calif.), Fmoc-N-amido-dPEG$_{12}$-acid was obtained from Quanta BioDesign (Powell, Ohio), and 5-(11,12-Didehydrodibenzo[b,f]azocin-5(6H)-yl)-5-oxopentanoic acid, an acid-functionalised aza-dibenzocyclooctyne (DIBAC-acid), was synthesized as described by Debets, M. F. et al., *Chem. Commun.* 46, 97-99 (2010). Fmoc-N-amido-dPEG$_{12}$-acid and DIBAC-acid were sequentially reacted with Lys(Mtt)-Wang resin to obtain DIBAC-PEG$_{12}$-Lys (Mtt)-Wang resin, then treated with TFA/DCM/TIS(1:96:3) to remove the Mtt group. The deprotected resin was reacted with Mpa-OSu on the free amino group on the lysine side chain to obtain DIBAC-PEG12-Lys (Mpa)-Wang resin. Following cleavage with TFA/water (95:5), the crude product was purified by preparative RP-HPLC to afford the DIBAC-PEG$_{12}$-Lys (Mal) product (DPKM) with 93% purity and the desired MS spectra.

Figure 16:
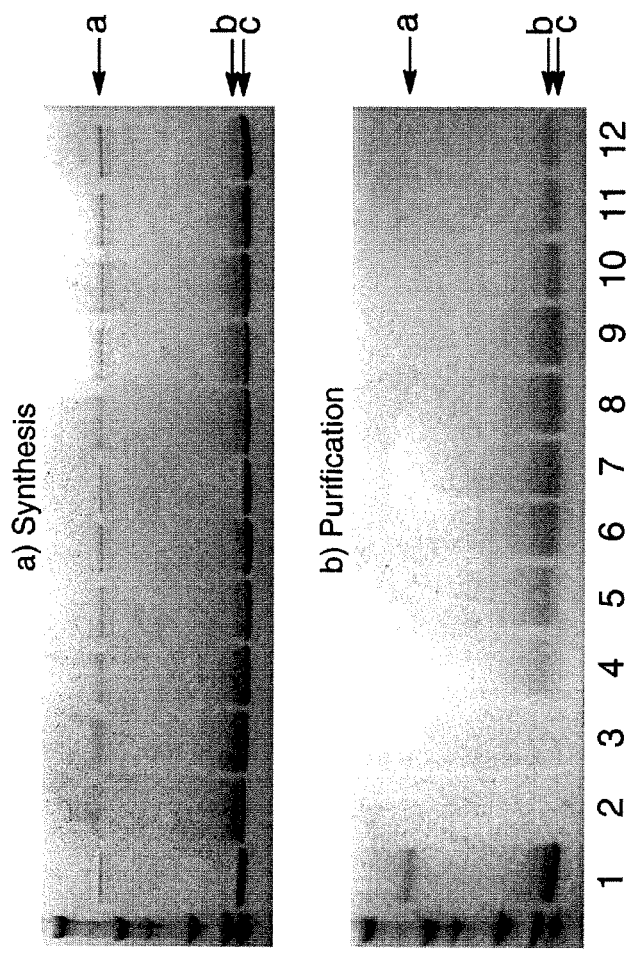
FIG. 16 shows SDS-PAGE analysis (non-reducing conditions) of the synthesis and purification of cycloalkyne-modified adalimumab Fab'. Upper panel shows the reaction at (1-6) pH 7.4 and (7-12) pH 7.0. The DIBAC-PEG$_y$-Lys (Mal) to Fab' ration was (1) 0, (2) 10:1, (3) 5:1, (4) 2.5:1, (5) 1.2:1, (6) 0.6:1, (7) 0, (8) 10, (9) 5, (10) 2.5, (11) 1.2, and (12) 0.6:1. The lower panel shows (1) unreacted Fab', (2) through (12) Protein L flow-through fractions containing only the cycloalkyne-modified Fab'.

FIG. 16 shows the chemical modification of adalimumab Fab' fragment with the DIBAC-PEG$_{12}$-Lys (Mal) linker and the purification of the resulting cycloalkyne-modified Fab'. For purification, reactions (0.535 mL) were carried out in 0.1 M sodium phosphate at pH 7.0 and pH 7.4, each containing 5 mg of Fab' fragment and 10 mg of DIBAC-PEG$_{12}$-Lys (Mal). After 30 hours incubation at room temperature, the two reactions were combined and buffered-exchanged into 20 mM sodium acetate, 20 mM NaCl, pH 5.5 using a PD-10 column. The eluate (3.5 mL) was applied to a HiTrap SP HP cation-exchange column from GE Life Sciences which retained all the unmodified Fab' and residual Fab'2. The flow-through fractions (5.5 mL) containing the purified cycloalkyne-modified Fab' (FIG. 16b) were pooled, adjusted to pH 7.0 with 10×PBS (0.55 mL), and concentrated by affinity chromatography on a Protein L column (Capto L) from GE Life Sciences. The cycloalkyne-modified Fab' was eluted from the Protein L column with 0.1 M glycine HCl pH 2.7 (2.4 mL), neutralized with 1/20 volume 1.0 M Tris HCl pH 9.0, buffered-exchanged into PBS using a PD-10 column (3.5 mL) and concentrated using Amicon Ultracel-3 Centrifugal Filter Unit to a final volume of 70 uL at a concentration of 9.5 mg/mL.

Various azide-modified Fc6 proteins with PEG linkers of different lengths were used in the preparation of the adalimumab Fab'-cycloalkyne-azide-Fc6. Az-DKTHT-Fc6 (FIG. 3) and Az-DKTHT-PEGx-Fc6 derivatives with x=12, 24, and 36 (FIG. 4) were prepared in reactions (2 ml) that contained 50 mM MES pH 6.5, 0.8 mM TCEP, 10 mM MPAA, 5 mg/ml of each of the four Az-DKTHT-PEGx-thioesters, and 2.36 mg/ml of Fc6 protein. DKTHT is SEQ ID NO: 220. After 20 hours at room temperature, the reactions were neutralized with 100 uL of Tris HCl pH 9.0, clarified by centrigugation at 12,000×g, and applied to a 1 ml HiTrap Protein A HP column. The columns were washed with 12 vol of PBS, the azide-modified Fc6 proteins were then eluted with 0.1 M glycine HCl pH 2.7 (2.0 mL), neutralized with ½0 volume 1.0 M Tris HCl pH 9.0, dialysed against three changes of PBS for 12 hours each using a Slide-A-Lyzer Mini Dialysis Unit, 10K MWCO, and concentrated using Amicon Ultracel-3 Centrifugal Filter Units.

Figure 17:
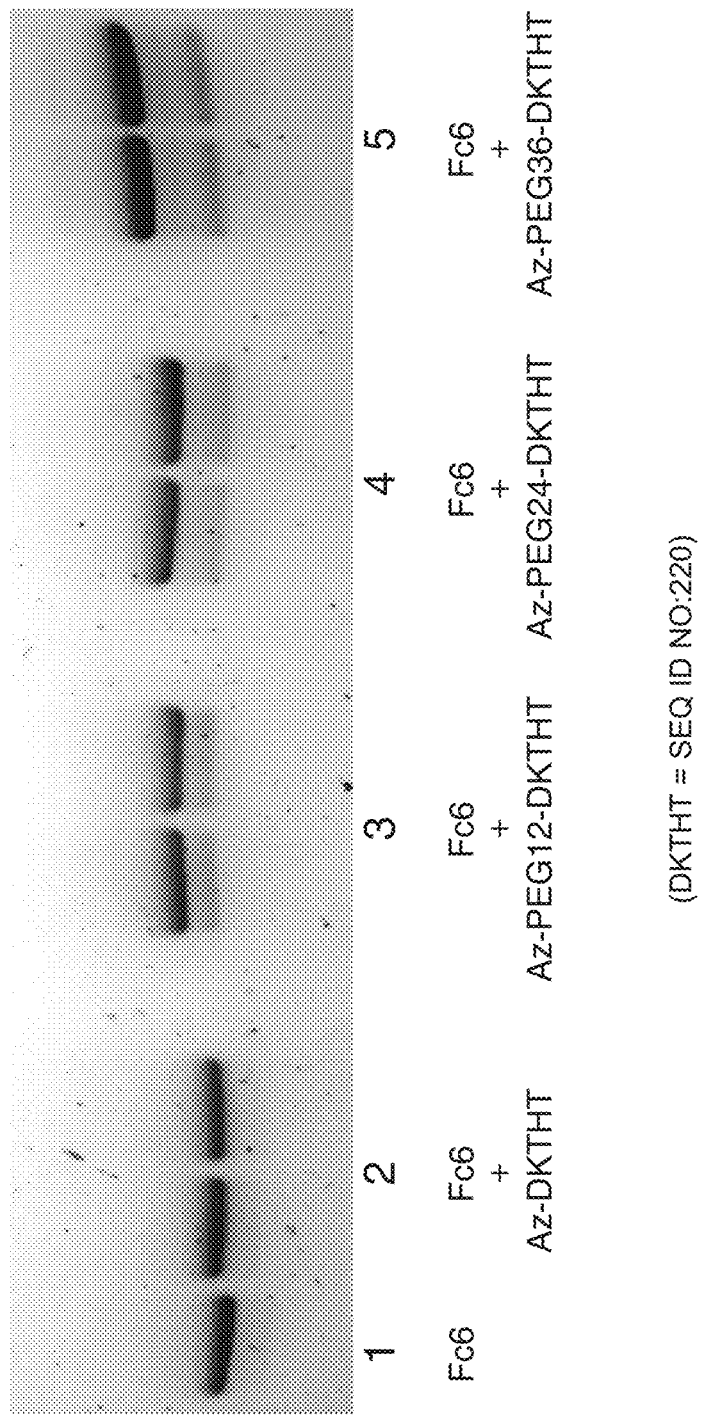
FIG. 17 shows SDS-PAGE analysis (reducing conditions) of (1) Fc6, (2) Az-DKTHT-Fc6, (3) Az-PEG$_{12}$-DKTHT-Fc6, (4) Az-PEG$_{24}$-DKTHT-Fc6, and (5) Az-PEG$_{36}$-DKTHT-Fc6. DKTHT is SEQ ID NO: 220.

FIG. 17 shows analysis by SDS-PAGE under reducing conditions of the Fc6 (lane 1) Az-DKTHT-Fc6 (lane 2), Az-DKTHT-PEG$_{12}$-Fc6 (lane 3), Az-DKTHT-PEG$_{24}$-Fc6 (lane 4), and Az-DKTHT-PEG$_{36}$-Fc6 (lane 5) proteins by SDS-PAGE. The Fc6 protein reacted quantitatively (>90%) with all four thioesters, yielding a ladder of products of increasing size. DKTHT is SEQ ID NO: 220.

Figure 18:
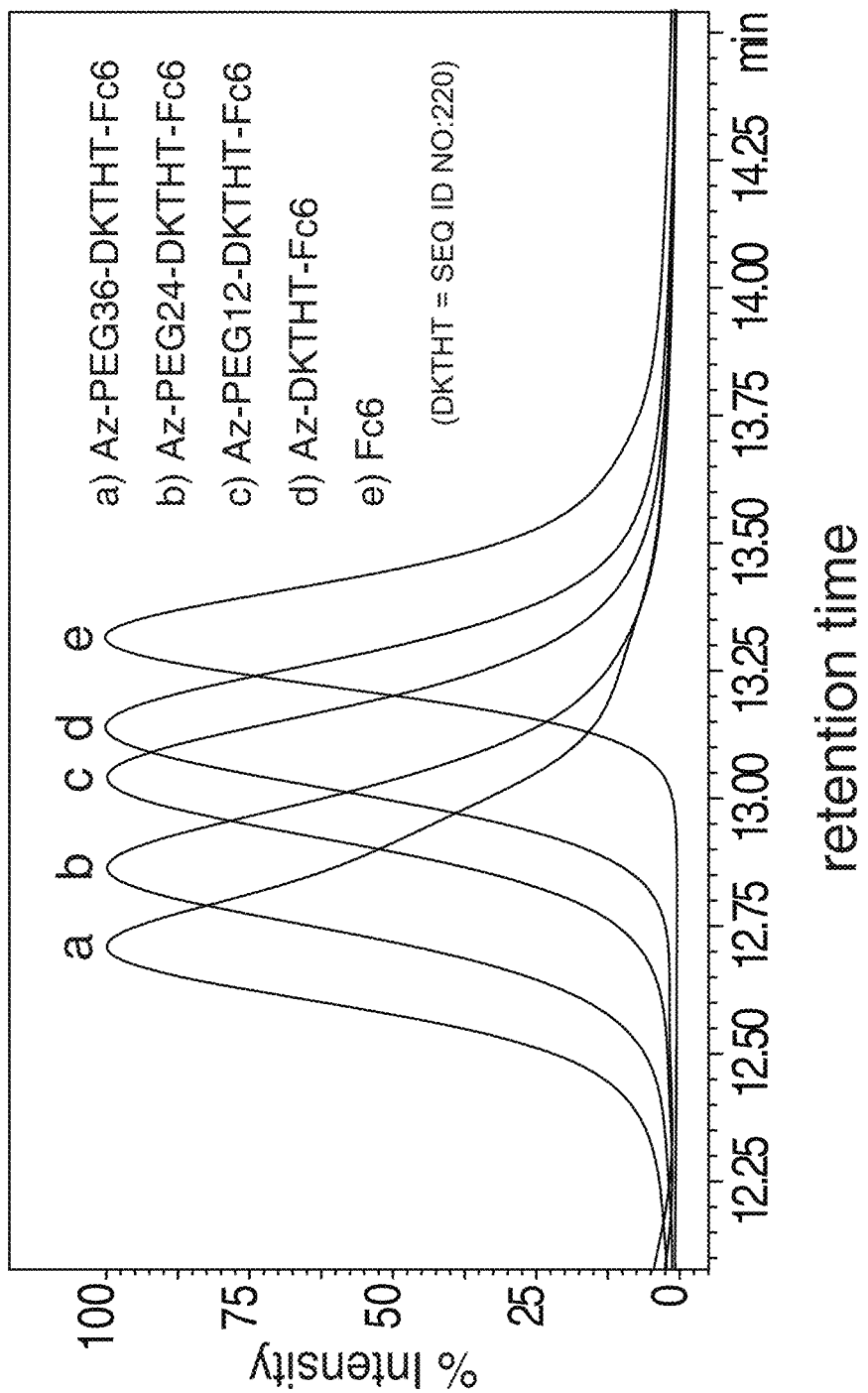
FIG. 18 shows size-exclusion chromatography of (a) Az-PEG$_{36}$-DKTHT-Fc6, (b) Az-PEG$_{24}$-DKTHT-Fc6, (c) Az-PEG$_{12}$-DKTHT-Fc6, (d) Az-DKTHT-Fc6, and (e) Fc6. DKTHT is SEQ ID NO: 220.

FIG. 18 shows analysis by size-exclusion chromatography (SEC) to confirm that the four azide-modified Fc6 protein products had the same dimeric structure as the parent Fc6 molecule. SEC was carried out using a Prominence HPLC System (Shimadzu Corp, Kyoto, Japan). TSKgel Super SW3000 columns (4.6 mm×30 cm column, 4.6 mm×5 cm guard column) were obtained from TOSOH Bioscience (Tokyo, Japan). Mobile phase, flow rate, column temperature, and detection wavelength used were 50 mM sodium phosphate, 300 mM NaCl, pH 7.4, 0.35 mL/min., 30° C., and 280 nm, respectively. The four azide-modified Fc6 protein products displayed a retention time that decreased as the size of PEG linker increased, confirming their dimer structure. All four products also gave essentially a single peak, demonstrating a two-handed structure in which both N-termini of the parent Fc6 dimer were modified by the PEG linker that was confirmed by SDS-PAGE analysis under non-reducing conditions (see below).

Figure 19:
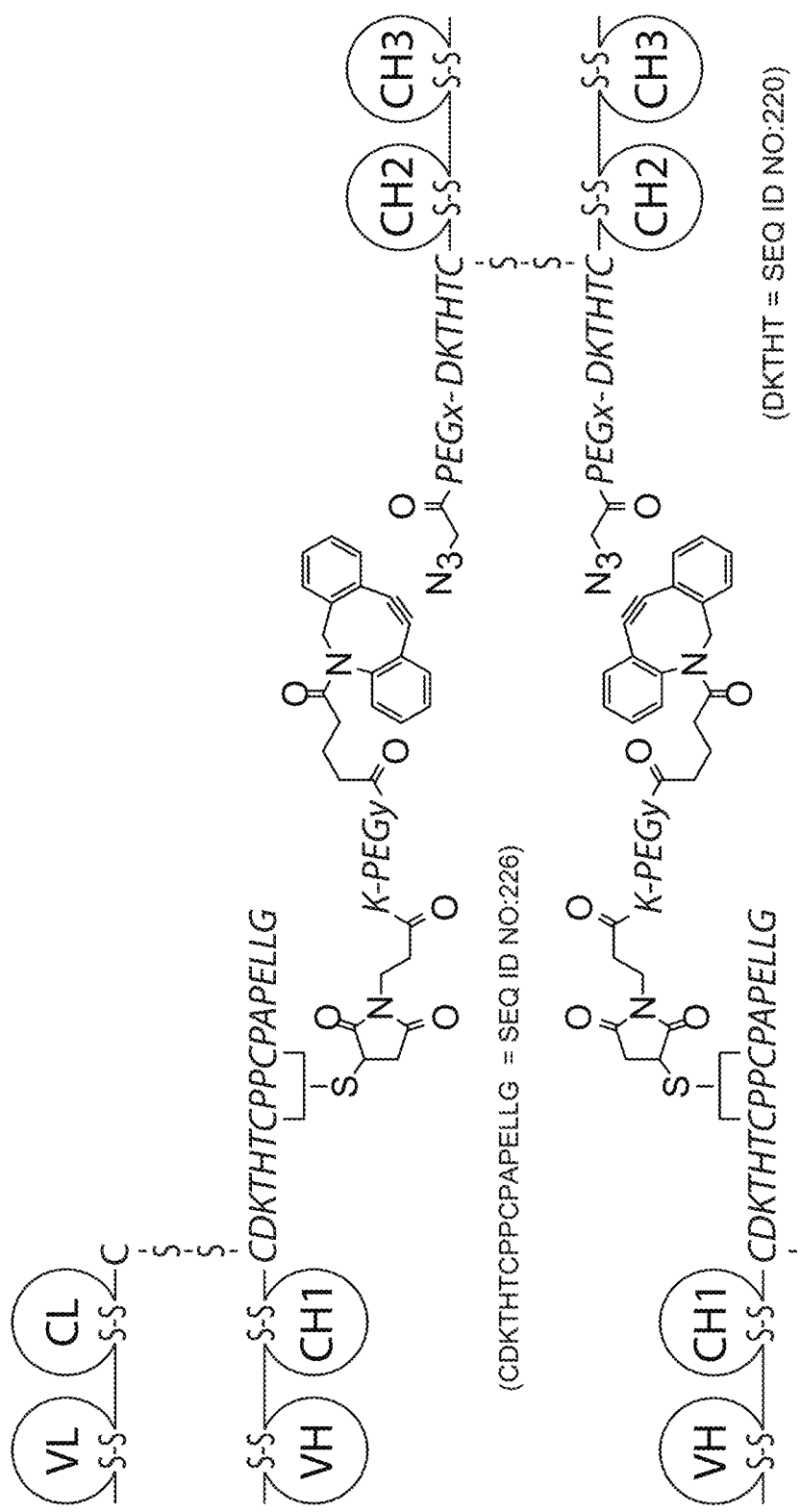
FIG. 19 shows the synthesis of Fab'-PEGy-alkyne-azide-PEGx-Fc6 by ligation (non-peptidyl) of cycloalkyne-modified adalimumab Fab' and azide-modified Fc6.
Figure 20:
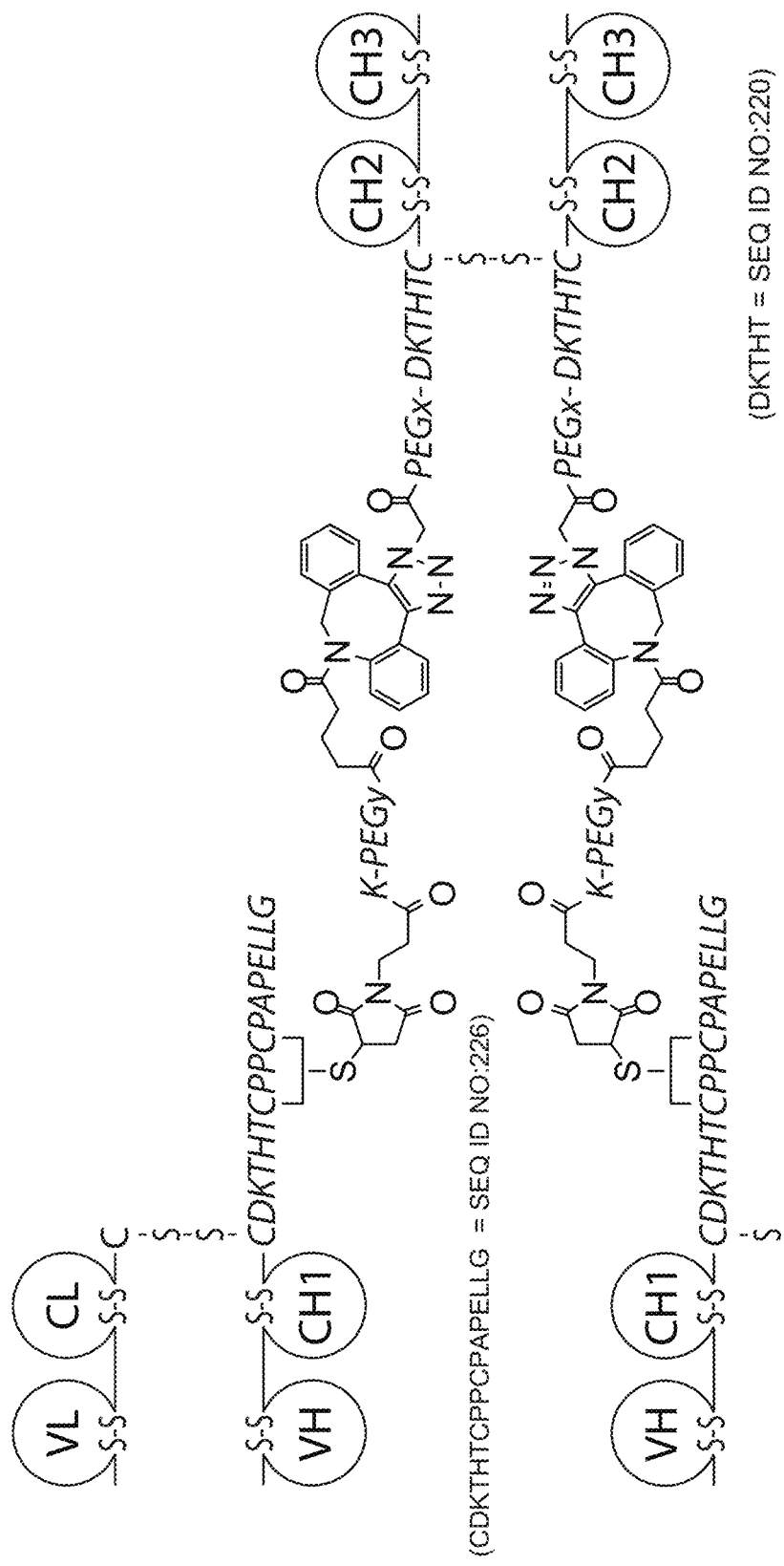
FIG. 20 shows the Fab'-PEGy-alkyne-azide-PEGx-Fc6 product series.

The cyclooctyne-modified Fab' was reacted with all four azide-modified Fc6 molecules (FIG. 19), yielding a family of Fab'-PEGy-cycloalkyne-azide-PEGx-Fc6 structures with arms of increasing length (FIG. 20). The overall lengths of the resulting arms were Fab'-PEG$_{12}$-Fc6 (for x=0, y=12), Fab'-PEG$_{24}$-Fc6 (for x=12, y=12), Fab'-PEG$_{36}$-Fc6 (for x=24, y=12), and Fab'-PEG$_{48}$-Fc6 (for x=36, y=12). The reactions (8 uL) were carried out in 0.1 M sodium phosphate pH 7.0 overnight at room temperature with each of the four azide-modified Fc6 proteins (2.5 mg/ml) in the presence or the absence of the cycloalkyne-modified Fab' (5 mg/ml).

Figure 21:
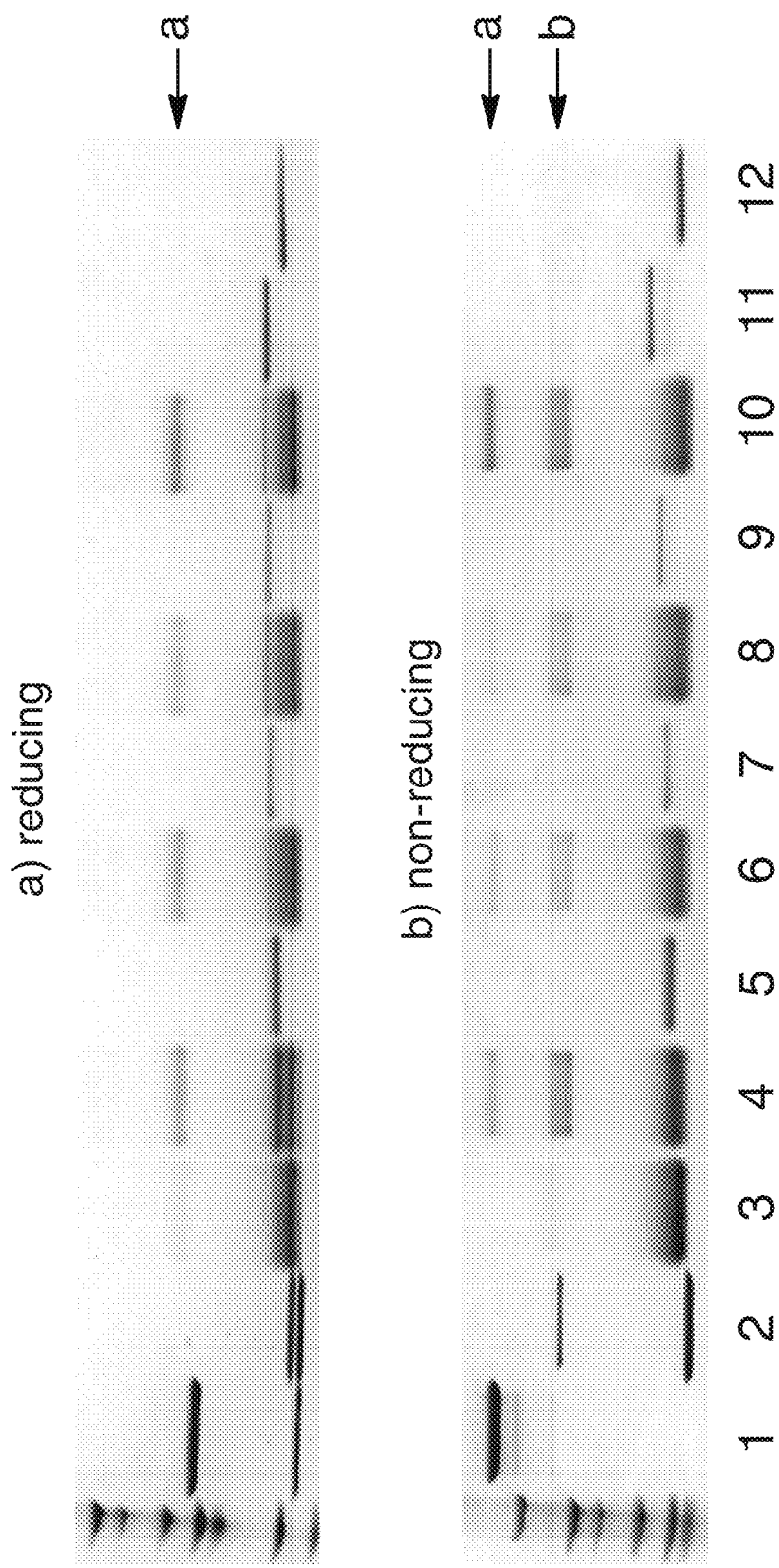
FIG. 21 shows SDS-PAGE analysis of (1) adalimumab whole antibody, (2) adalimumab Fab', (3) Fab'-PEG$_{12}$-alkyne, (4) Fab'-PEG$_{12}$-alkyne+Az-DKTHT-Fc6, (5) Az-DKTHT-Fc6, (6) Fab'-PEG$_{12}$-alkyne+Az-PEG$_{12}$-DKTHT- Fc6, (7) Az-PEG$_{12}$-DKTHT-Fc6, (8) Fab'-PEG$_{12}$-alkyne+ Az-PEG$_{24}$-DKTHT-Fc6, (9) Az-PEG$_{24}$-DKTHT-Fc6 alone, (10) Fab'-PEG$_{12}$-alkyne+Az-PEG$_{36}$-DKTHT-Fc6, (11) Az-PEG$_{36}$-DKTHT-Fc6, and (12) Fc6. Samples were run under reducing conditions (upper panel) and non-reducing conditions (lower panel). In the upper panel the arrow shows (a) Fab'-PEGy-alkyne-azide-PEGx-Fc6 heavy chain. In the lower panels the arrows show (a) two-handed Fab'-PEGy-alkyne-azide-PEGx-Fc6 molecules, and (b) one-handed Fab'-PEGy-alkyne-azide-PEGx-Fc6 molecules. DKTHT is SEQ ID NO: 220.

FIG. 21 shows SDS-PAGE analysis of the Fab'-cycloalkyne-azide-Fc6 reaction under reducing and non-reducing conditions. In the absence of the cycloalkyne-modified Fab' (lanes 5, 7, 9, and 11), all four of the azide-modified Fc6 proteins gave a single band on both reducing and non-reducing gels, confirming their dimeric, two-handed handed structure. In the presence of the cycloalkyne-modified Fab' (lanes 4, 6, 8, and 10), all four of the azide-modified Fc6 proteins were largely consumed in the resulting reaction. Under reducing conditions, all four reactions gave a product with Mr ~57,000 to 62,000 (arrow a). The size of the Fab'-PEG$_{12}$-Fc6 product (lane 4) was approximately 1-2 kD greater than the wild-type adalimumab heavy chain (lane 1), while the sizes of the Fab'-PEG$_{24}$-Fc6 (lane 6), Fab'-PEG$_{36}$-Fc6 (lane 8), and Fab'-PEG$_{48}$-Fc6 (lane 10) products further increased with the overall length of the PEG linker. Under non-reducing conditions, two products were observed, a first product of Mr ~155,000 to 160,000 (arrow a), and a second of Mr ~110,000 to 115,000 (arrow b). The larger Fab'-PEG$_{12}$-Fc6 product (lane 4) was approximately 5 kD greater than the adalimumab whole antibody (lane 1), consistent with the expected two-handed product, while the larger Fab'-PEG$_{24}$-Fc6 (lane 6), Fab'-PEG$_{36}$-Fc6 (lane 8), and Fab'-PEG$_{48}$-Fc6 (lane 10) products still further increased in size as the overall length of the PEG linker increased.

Figure 22:
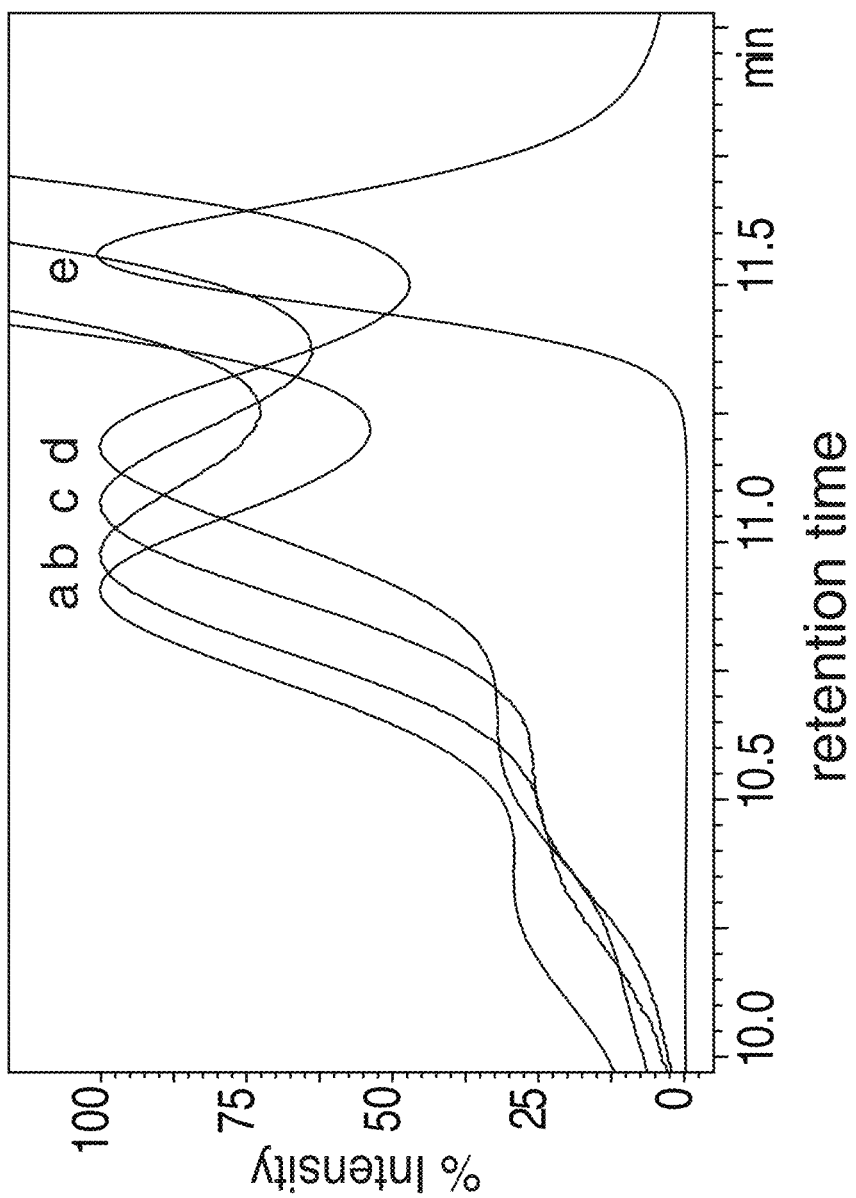
FIG. 22 shows size-exclusion chromatography (SEC) of two-handed reaction products: (a) Fab'-PEG$_{12}$-alkyne-azide-PEGa$_6$-DKTHT-Fc6, (b) Fab'-PEG$_{12}$-alkyne-azide-PEG$_{24}$-DKTHT-Fc6, (c) Fab'-PEG$_{12}$-alkyne-azide-PEG$_{12}$-DKTHT-Fc6, (d) Fab'-PEG$_{12}$-alkyne-azide-DKTHT-Fc6, and (e) whole adalimumab. DKTHT is SEQ ID NO: 220.

FIG. 22 shows analysis by SEC to confirm the two-handed structure (ie, two Fab' hands attached to one Fc6 domain) of the larger reaction product with Mr ~155,000 to 160,000 of the Fab'-PEG$_{12}$-Fc6, Fab'-PEG$_{24}$-Fc6, Fab'-PEG$_{36}$-Fc6, and Fab'-PEG$_{49}$-Fc6 reactions. All four reaction products displayed a shorter retention time than the adalimumab whole antibody that further decreased as the size of PEG linker increased, confirming the two-handed structure observed by SDS-PAGE analysis.

The biological activity of the Fab'-cycloalkyne-azide-Fc6 products evaluated by their ability to neutralize TNF-α-mediated cytotoxicity on murine WEHI cells treated with actinomycin D. The mouse WEHI-13VAR cell line (ATCC CRL-2148) was obtained from the American Type Culture Collection (Rockville, Md.) and grown in Gibco RPMI media 1640 (RPMI-1640) supplemented with 10% fetal bovine serum (FBS) and penicillin and streptomycin (10 U/ml), obtained from Life Technologies (Grand Island, N.Y.). TNF-α cytotoxity assays were carried out as follows. WEHI-13VAR cells were plated in 96-well Nunc white cell culture plates obtained from Thermo Fisher (Waltham, Mass.) at 2×10$^4$ cells per well overnight and then treated with actinomycin D (0.5 µg/ml) obtained from Sigma (St Louis, Mo.) and TNF-α (0.2 ng/ml) in the absence or presence of TNFR-IgG or other inhibitors. After 24 hr of incubation at 37° C./5% CO2, the cell viability was determined with CellTiter-Glo Luminescent Cell Viability Assay Systems (Promega, Madison, Wis.) measuring the quantity of the ATP present in metabolically active cells and luminescence measured using a POLARstar luminometer (BMG LABTECH Inc., Cary, N.C.). Each inhibitor was diluted by ten 3-fold serial dilutions starting at 10 µg/ml and measured in duplicate or triplicate. Cytotoxicity data were calculated using the following equations: (1-sample luciferase reading/luciferase reading from cells treated with actinomycin D alone)×100%, and presented as the mean±standard deviation. Enbrel was used as a cytotoxicity positive control and Fc6 as a negative control.

Figure 23:
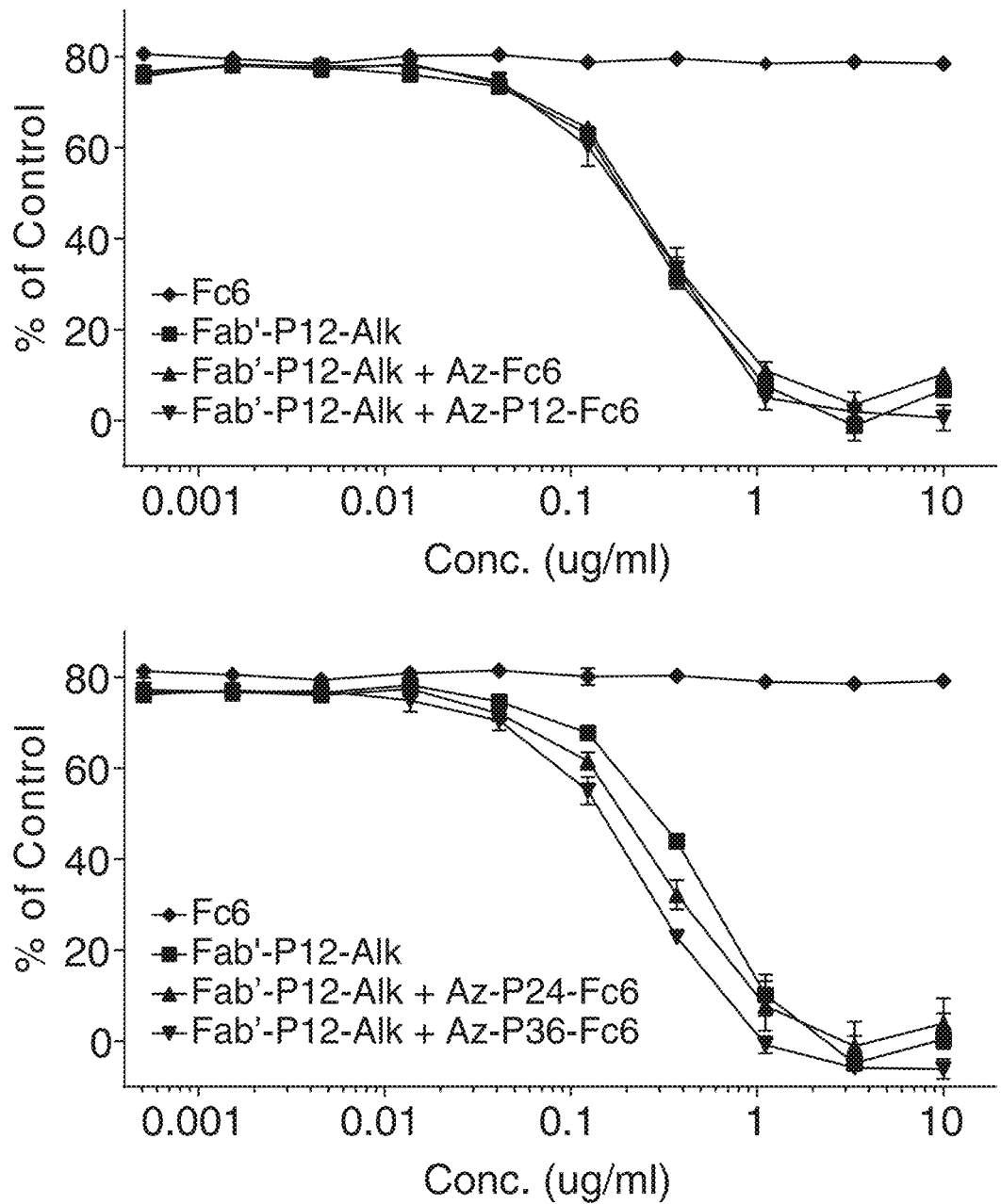
FIG. 23 shows the inhibition of TNF-α cytotoxity on WEHI cells by reaction products. The upper panel shows the (a) Fc6 control, (b) cycloalkyne-modified Fab', (c) Fab'-PEG$_{12}$-alkyne-azide-DKTHT-Fc6, and (d) Fab'-PEG$_{12}$-alkyne-azide-PEG$_{12}$-DKTHT-Fc6. The lower panel shows (a) Fc6 control, (b) cycloalkyne-modified Fab', (c) Fab'-PEG$_{12}$-alkyne-azide-PEG$_{24}$-DKTHT-Fc6, and (d) Fab'-PEG$_{12}$-alkyne-azide-PEGa$_6$-DKTHT-Fc6. DKTHT is SEQ ID NO: 220.

FIG. 23 shows the neutralization of TNF-α-mediated cytotoxicity by Fab'-PEG$_{12}$-Fc6, Fab'-PEG$_{24}$-Fc6, Fab'-PEG$_{36}$-Fc6, and Fab'-PEG$_{48}$-Fc6 reaction mixtures compared with the cycloalkyne-modified Fab' (based upon an equal amounts of input cycloalkyne-modified Fab'). The Fab'-PEG$_{12}$-Fc6 and Fab'-PEG$_{24}$-Fc6 reaction mixtures both displayed comparable TNF-α neutralization activity compared with that of the input cycloalkyne-modified Fab' (upper panel), whereas the Fab'-PEG$_{36}$-Fc6 and Fab'-PEG$_{48}$-Fc6 reaction mixtures displayed a 1.5-fold and 2.0-fold increase, respectively, in their TNF-α neutralization activity compared with the input cycloalkyne-modified Fab' (lower panel). Since the amount of two-handed product represented only 10-20% of the total cycloalkyne-modified Fab' in each reaction as estimated by SDS-PAGE (FIG. 22), the two-handed products of the Fab'-PEG$_{36}$-Fc6 and Fab'-

PEG$_{48}$-Fc6 reactions are estimated to be at least 7.5-fold and 10-fold greater than the input cycloalkyne-modified Fab', respectively.

Example 3: Fab-alkyne-azide-Fc6

Fab-alkyne-azide-Fc6 is prepared by reacting azide-modified Fc6 with an alkyne-modified or cycloalkyne-modified Fab protein that is produced by cleavage of an Fab-intein fusion protein as follows. Similarly, Fab-azide-alkyne-Fc6 is prepared by reacting alkyne-modified or cycloalkyne-modified Fc6 with an azide-modified Fab protein that is produced by cleavage of an Fab-intein fusion protein.

Adalimumab Fab-intein fusion protein is produced by cotransfecting expression vector pFUSE2ss-DE27-VIC-CLIg-hk (SEQ ID NO: 115) with pPUSEss-DE27-Vyl-CHIg-hG1-Mth-1 (SEQ ID NO: 116) or pFUSEss-DE27-Vyl-CHIg-hG1-Mth-2 (SEQ ID NO: 117).

Vector pFUSE2ss-DE27-VK-CLIg-hk directs the expression of the pre-kappa light chain of adalimumab shown in SEQ ID NO: 118. Cleavage of the heterologous IL-2 signal sequence by the cellular signal peptidase provides the mature kappa light chain of adalimumab shown in SEQ ID NO: 119.

Vector pFUSEss-DE27-Vγ1-CHIg-hG1-Mth-1 directs the expression of a first type of pre-heavy chain-intein chimeric polypeptide shown in SEQ ID NO: 120, in which the adalimumab heavy chain VH and CH1 domains are joined at their C-terminus to the N-terminus of an RIR1 self-splicing intein at the autocleavage site. Cleavage of the heterologous IL-2 signal sequence by the cellular signal peptidase provides the mature heavy chain-intein fusion protein shown in SEQ ID NO: 121. Together, the proteins of SEQ ID NO: 119 and SEQ ID NO: 121 comprise the adalimumab Fab-1-intein fusion protein that is secreted into the cell culture fluid.

Vector pFUSEss-DE27-Vyl-CHIg-hG1-Mth-2 directs the expression of a second type of pre-heavy chain-intein chimeric polypeptide shown in SEQ ID NO: 122, in which the adalimumab heavy chain VH and CH1 domains are joined at their C-terminus to the N-terminus of an RIR1 self-splicing intein at the autocleavage site. Cleavage of the heterologous IL-2 signal sequence by the cellular signal peptidase provides the mature heavy chain-intein fusion protein shown in SEQ ID NO: 123. Together, the proteins of SEQ ID NO: 119 and SEQ ID NO: 123 comprise the adalimumab Fab-2-intein fusion protein that is secreted into the cell culture fluid.

Protein production is executed by transient expression in CHO-DG44 cells essentially as described in Example 1, by the cotransfection of SEQ ID NO: 115 with SEQ ID NO: 116 to produce the adalimumab Fab-1-intein fusion protein, and by cotransfection of SEQ ID NO: 115 with SEQ ID NO: 117 to produce adalimumab Fab-2-intein fusion protein.

Alkyne-modified adalimumab Fab proteins are produced by cleavage of adalimumab Fab-intein fusion proteins with 50 mM cystyl-propargylamide essentially as described in Example 1. The adalimumab Fab-1-intein fusion protein is cleaved with cystyl-propargylamide to produce alkyne-modified adalimumab Fab-1 protein which is a heterodimer protein of SEQ ID NO: 119 and SEQ ID NO: 124. The adalimumab Fab-2-intein fusion protein is cleaved with cystyl-propargylamide to produce alkyne-modified adalimumab Fab-2 protein which is a heterodimer protein of SEQ ID NO: 119 and SEQ ID NO: 125.

Azide-modified adalimumab Fab proteins are produced by cleavage of adalimumab Fab-intein fusion proteins with 50 mM cystyl-3-azidopropylamide essentially as described in Example 1. The adalimumab Fab-1-intein fusion protein is cleaved with cystyl-3-azidopropylamide to produce azide-modified adalimumab Fab-1 protein which is a heterodimer protein of SEQ ID NO: 119 and SEQ ID NO: 126. The adalimumab Fab-2-intein fusion protein is cleaved with cystyl-3-azidopropylamide to produce azide-modified adalimumab Fab-2 protein which is a heterodimer protein of SEQ ID NO: 119 and SEQ ID NO: 127.

Adalimumab Fab-1-alkyne-azide-Fc6 and Adalimumab Fab-2-alkyne-azide-Fc6 are prepared via the reaction of alkyne-modified adalimumab Fab-1 protein or alkyne-modified adalimumab Fab-2 protein with Az-DKTHT-Fc6 protein (FIG. 6) or Az-PEGx-DKTHT-Fc6 proteins (FIG. 7). DKTHT is SEQ ID NO: 220.

Tris (3-hydroxypropyltriazolylmethyl)amine (THTPA) is prepared as described by Hong et al., Angew. Chem. Int. Ed. 48, 1-7 (2009). Reactions are carried out in 0.1 M sodium phosphate, pH 7.0, with the Linker-Fc at a concentration of 5 mgs/mL or greater, and a molar ratio of >2:1 of Fab-A:Linker-Fc. To the reaction is added a final concentration of 0.0001 M CuSO$_4$, 0.0005 M THTPA. The reaction is initiated by adding to a final concentration 0.005 M aminoguanidine and 0.005 M sodium ascorbate. Following incubation at room temperature for 12-18 hours in a closed tube, the reaction mixture is applied to a chromatographic column packed with Protein A (GE Lifesciences, NJ) to remove excess reagent and unreacted Fab-A, washed with PBS, eluted with 0.1 M Glycine-HCl, pH 2.7, and immediately neutralized by adding 1.0 M Tris-HCl, pH 9.0. The eluted Adalimumab Fab-1-alkyne-azide-Fc6 and Adalimumab Fab-2-alkyne-azide-Fc6 products are dialysed against PBS.

Adalimumab Fab-1-azide-alkyne-Fc6 and Adalimumab Fab-2-azide-alkyne-Fc6 are prepared via the reaction of azide-modified adalimumab Fab-1 protein or azide-modified adalimumab Fab-2 protein with cycloalkyne-modified Fc6 protein.

Cycloalkyne-modified Fc6 proteins are prepared essentially as described in Example 1 using DIBAC-PEG$_{12}$-thioester (Table 1) and other DIBAC-PEGx-thioesters and DIBAC-PEGx-DKTHT-thioesters similarly prepared. DKTHT is SEQ ID NO: 220.

Example 4: N-Terminal Azide-Modified Pc Protein

A series of azide-modified Fc proteins (N$_3$-Px-Fc), each having an azide functional group at its N-terminus, and optionally a PEG linker, was prepared by reacting the Fc6 protein with five thioesters having the sequence azidoacetyl-Px-DKTHT-thiophenol (x=0, 12, 24, 36, 48). Reactions were carried out in the absence of TCEP to minimize any reduction of the azide group to a primary amine. The azidoacetyl-Px-DKTHT-thiophenol thioesters with x=12, 24, 36 are shown in Table 1. Azidoacetyl-DKTHT-thiophenol was prepared as described in Example 1 (calculated for $C_{32}H_{45}O_{10}N_{11}S$ [M+H]$^+$776.8, found 776.3). DKTHT is SEQ ID NO: 220. Azidoacetyl-PEG48-DKTHT-thiophenol was prepared by solid-phase by the sequential condensation of Fmoc-PEG12-OH and Fmoc-PEG36-OH obtained from Quanta BioDesign (calculated for $C_{134}H_{247}N_{13}O_{60}S$ [M+H]+ 3032.5, found 3032.8). The structural formulas are as follows:

Each reaction (2 mL) contained 50 mM MES pH 6.5, 10 mM mercaptophenylacetic acid, 2.2 mg of Fc6, and one of the five thioesters as follows: azidoacetyl-DKTHT-thiophenol (5 mg), azidoacetyl-PEG12-DKTHT-thiophenol (5 mg), azidoacetyl-PEG24-DKTHT-thiophenol (10 mg), azidoacetyl-PEG36-DKTHT-thiophenol (10 mg), or azidoacetyl-PEG48-DKTHT-thiophenol (20 mg). DKTHT is SEQ ID NO: 220. Reactions were carried out for 20 hours at room temperature, neutralized with 0.1 mL of Tris HCl pH 9.0, centrifuged at 12,000×g, and applied to a HiTrap Protein A HP column. The columns were washed with 12 vol of PBS, and the $N_3$-Px-Fc proteins were then eluted with 0.1 M glycine HCl pH 2.7 and neutralized with 1/20 volume of 1.0 M Tris HCl pH 9.0. The peak fractions by A280 were combined, desalted on PD-10 columns, and concentrated using Amicon Ultracel-3 Centrifugal Filter Units.

Figure 24:
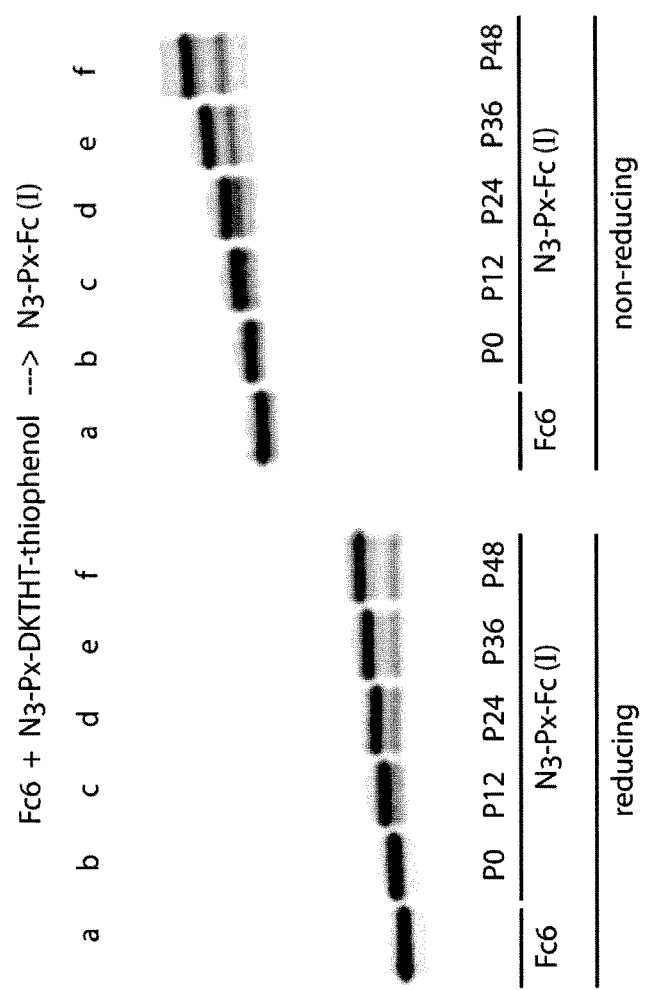
FIG. 24 shows the purified N3-Px-Fc proteins by SDS-PAGE under reducing (left) and non-reducing conditions (right): Fc6 control (lanes a), N3-P0-Fc (lanes b), N3-P12-Fc (lanes c), N3-P24-Fc (lanes d), N3-P36-Fc (lanes e), and N3-P48-Fc (lanes f).

FIG. 24 shows the purified $N_3$-Px-Fc proteins by SDS-PAGE under reducing (left) and non-reducing conditions (right): Fc6 control (lanes a), $N_3$—P0-Fc (lanes b), $N_3$—P12-Fc (lanes c), $N_3$—P24-Fc (lanes d), $N_3$—P36-Fc (lanes e), and $N_3$—P48-Fc (lanes f). The size of $N_3$-Px-Fc proteins increased with PEG linker length. In addition, the size of $N_3$-Px-Fc proteins prepared without TCEP (FIG. 24) were indistinguishable by SDS-PAGE from the size of $N_3$-Px-Fc proteins prepared with TCEP (FIG. 17).

Example 5: GLP1-triazole-Fc Hybrid Noglobulins

A series of GLP1-triazole-Fc hybrid immunoglobulins (GLP1-P4-DN-Px-Fc) were prepared by reacting a GLP-1 (glucagon-like peptide 1) analog, further modified to have a cyclooctyne functional group, with each of the five $N_3$-Px-Fc proteins of Example 4. The sequence of the GLP-1 analog, HGEGTFTSDVSSYLEEQAAKEFIAWLVKGRG-PEG$_3$-C—NH$_2$ (HGEGTFTSDVSSYLEEQAAKEFI-AWLVKGRG is SEQ ID NO:202), corresponds to residues 7-37 of the native GLP-1 peptide, in which glycine is substituted for alanine at position 8 and glutamic acid is substituted for glycine at position 22. In addition, the GLP-1 analog has a PEG3 linker and cysteine residue at its C-terminus used to attach the cyclooctyne functional group. This GLP-1 analog, gly8-glu22-GLP-1(7-37)-PEG3-cys-NH$_2$, was prepared by SPPS (calculated for $C_{165}H_{253}N_{43}O_{53}S$ [M+H]$^+$3720.3, found 3721.3).

Figure 25:
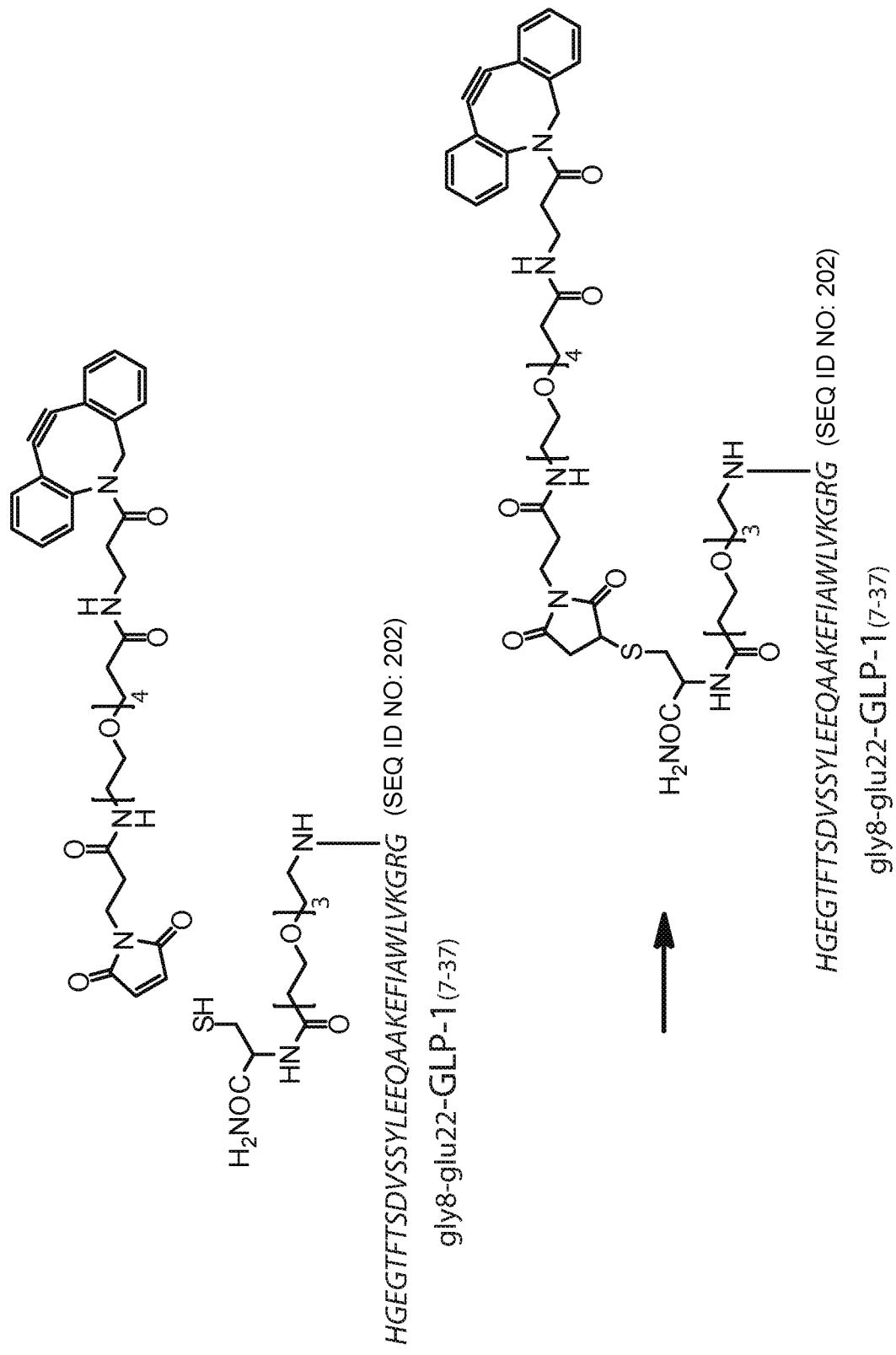
FIG. 25 shows shows the structure and synthesis of the cyclooctyne-modified GLP-1 analog (GLP1-P7-DBCO).

A cyclooctyne functional group was added to gly8-glu22-GLP-1(7-37)-PEG3-cys-NH$_2$ using a heterobifunctional linker, DBCO-PEG4-Maleimide, containing a maleimide group capable of reacting with the free thiol group on the C-terminal cysteine residue (FIG. 25). DBCO-PEG4-Maleimide (C$_{50}$H$_{54}$N$_4$O$_9$, mol weight 854.92), was obtained from Click Chemistry Tools (Scottsdale, Ariz.). Prior to use, the linker was dissolved at a concentration of 25 mg/mL in dimethysulfoxide (DMSO) obtained from Sigma-Aldrich (St. Louis, Mo.). Reactions (0.4 mL) contained 50 mM MES pH 6.5, 5 mM EDTA, 0.45 mg of gly8-glu22-GLP-1(7-37)-PEG3-cys-NH$_2$ peptide and 0.9 mg/mL of the DBCO-PEG4-Maleimide linker. Reactions were carried out for 30 minutes at room temperature. Excess unreacted linker was removed using a 5 mL HiTrap Desalting Column obtained from GE Life Sciences. FIG. 25 shows the structure of the resulting cyclooctyne-modified GLP-1 analog reaction product (GLP1-P7-DBCO).

Figure 26:
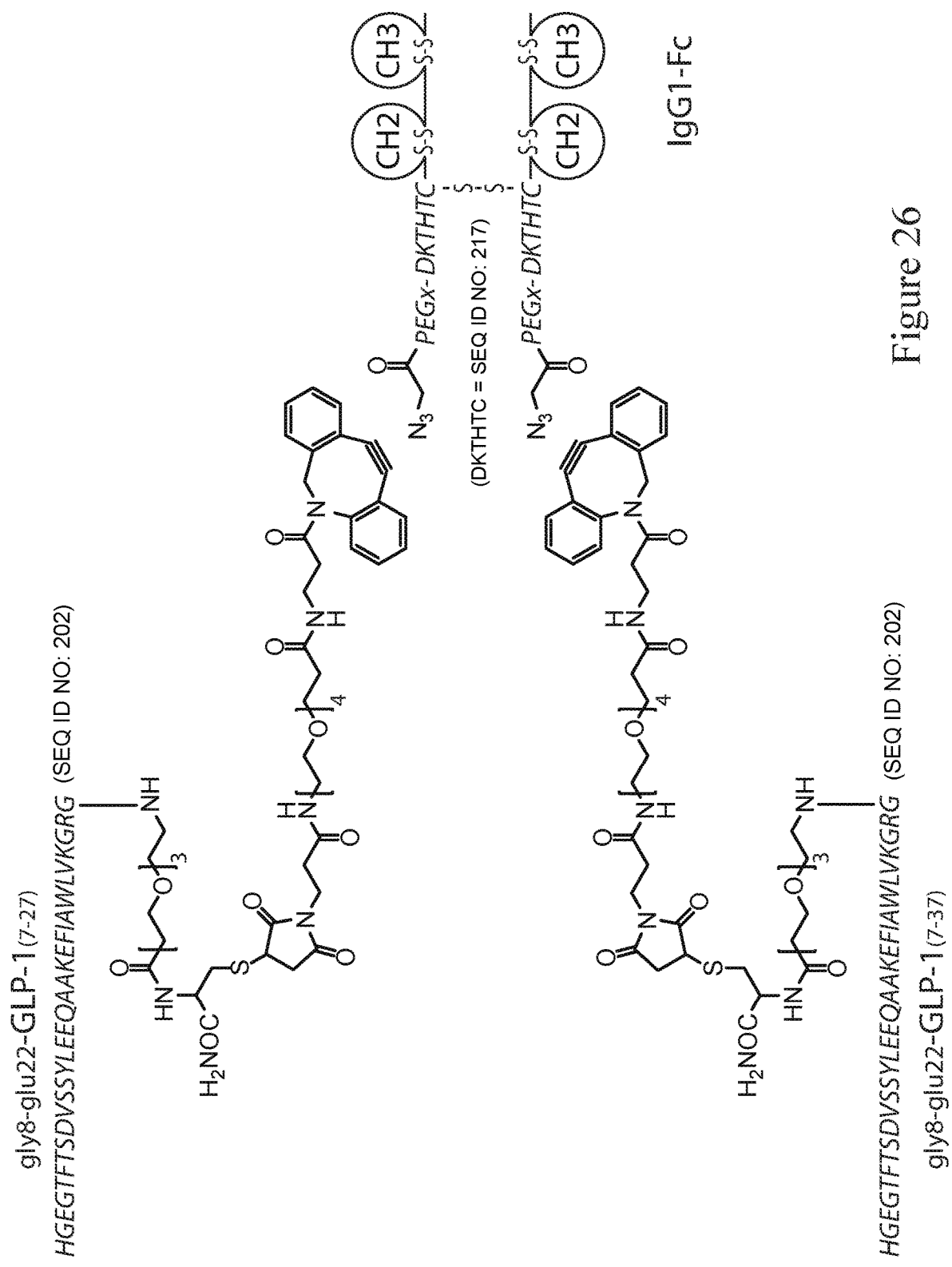
FIG. 26 shows the reaction between GLP1-P7-DBCO and the N3-Px-Fc proteins.
Figure 27:
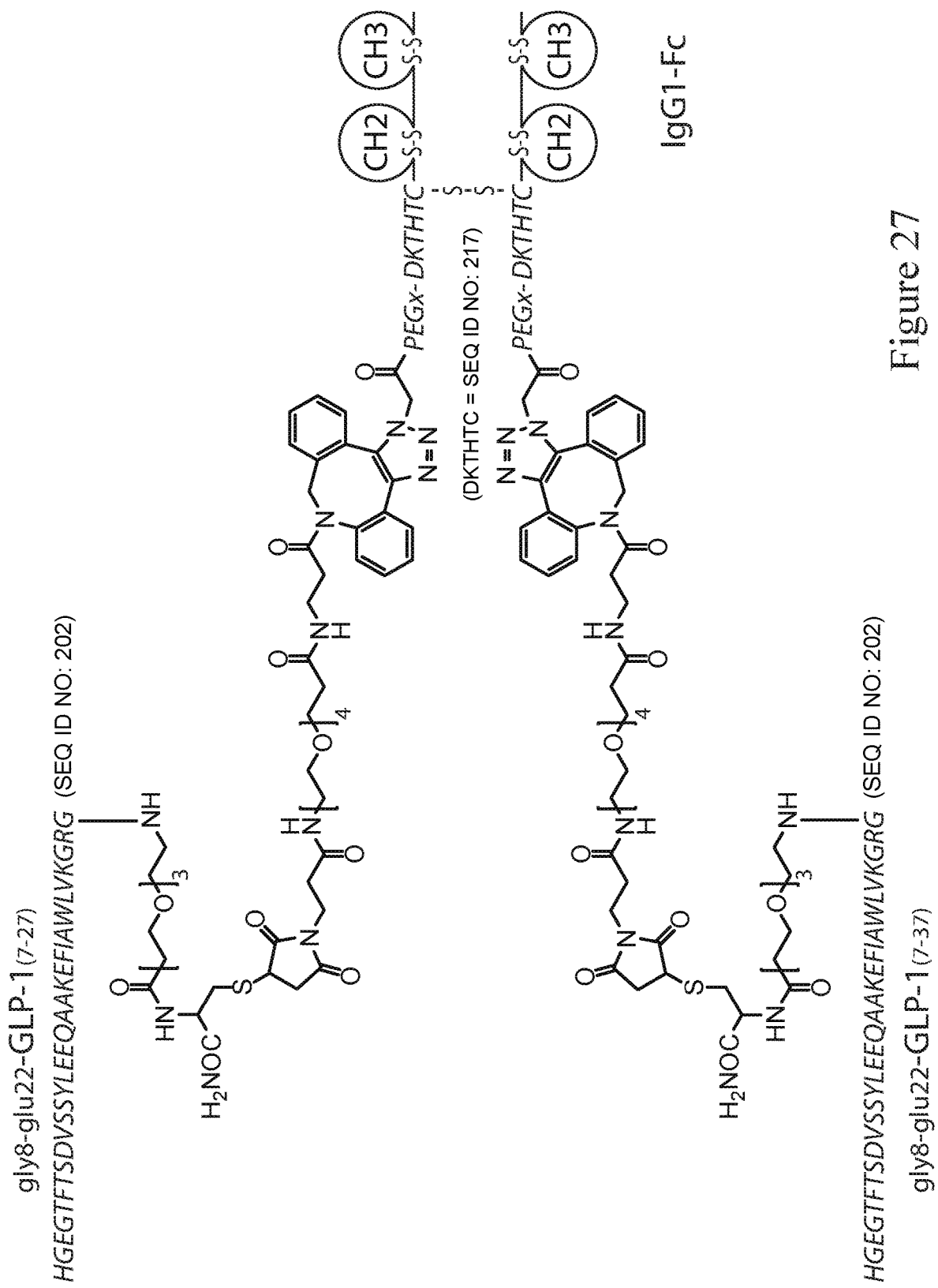
FIG. 27 shows the structure of GLP1-triazole-Fc hybrid immunoglobulins.

GLP1-P7-DBCO was reacted individually with each one of the five $N_3$-Px-Fc proteins (FIG. 26), to generate a series of GLP1-P7-triazole-Px-Fc hybrid immunoglobulins (FIG. 27). Each reaction (1.5 mL) contained 0.1 M sodium phosphate pH 7.0, 0.375 mg of the GLP1-P7-DBCO peptide, and 0.5 mg of one of the five $N_3$-Px-Fc proteins. Reactions were carried out for 3.5 hours at room temperature, the reactions were purified by HiTrap Protein A HP chromatography, desalted and concentrated as described in Example 4.

Figure 28:
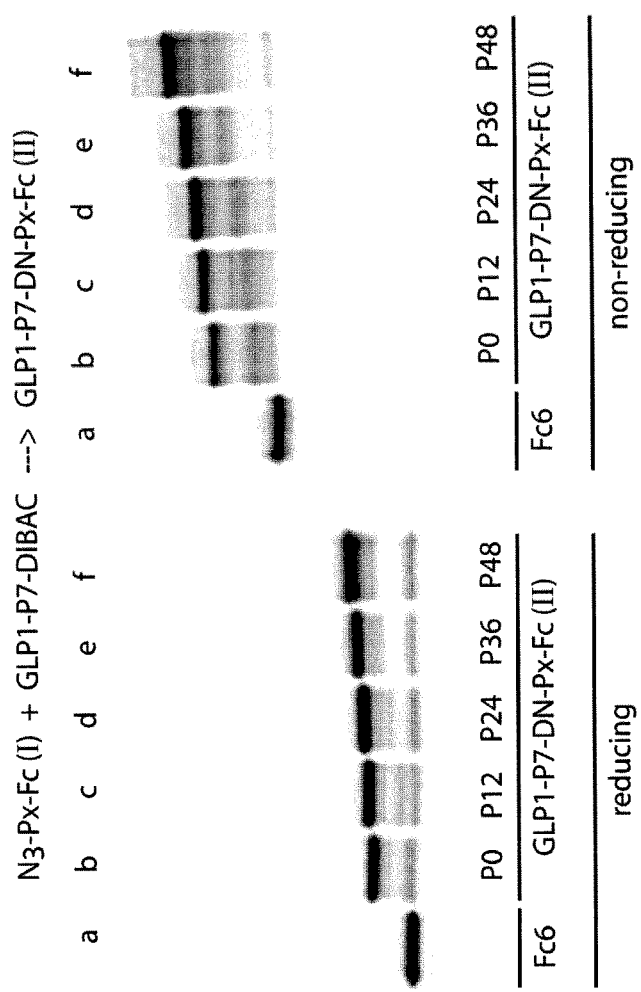
FIG. 28 shows the purified GLP1-triazole-Fc hybrid immunoglobulins by SDS-PAGE under reducing conditions (left) and non-reducing conditions (right): Fc6 control (lanes a), GLP1-P4-DN-P0-Fc (lanes b), GLP1-P4-DN-P12-Fc (lanes c), GLP1-P4-DN-P24-Fc (lanes d), GLP1-P4-DN-P36-Fc (lanes e), and GLP1-P4-DN-P48-Fc (lanes f).

FIG. 28 shows the purified GLP1-triazole-Fc hybrid immunoglobulins by SDS-PAGE under reducing conditions (left) and non-reducing conditions (right): Fc6 control (lanes a), GLP1-P4-DN—P0-Fc (lanes b), GLP1-P4-DN-P12-Fc (lanes c), GLP1-P4-DN-P24-Fc (lanes d), GLP1-P4-DN-P36-Fc (lanes e), and GLP1-P4-DN-P48-Fc (lanes f). The size of GLP1-triazole-Fc hybrid immunoglobulins increased with PEG linker length comparable to the $N_3$-Px-Fc proteins.

Figure 29:
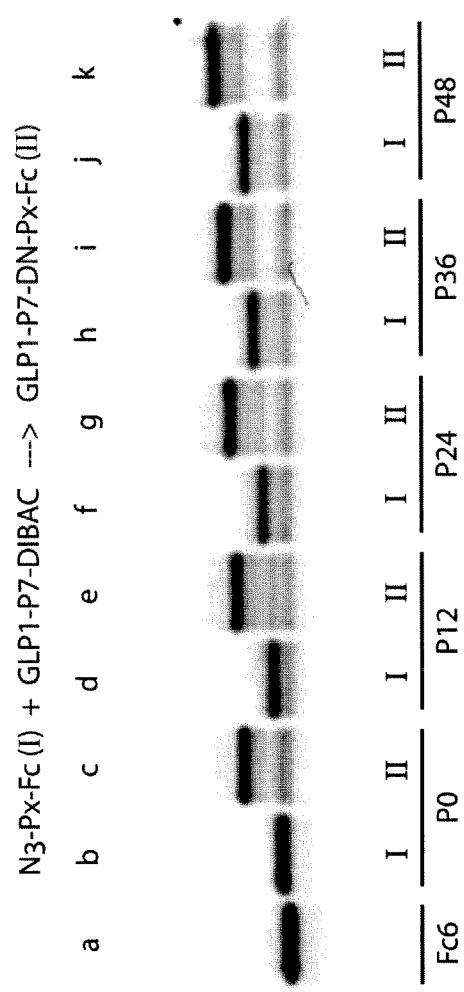
FIG. 29 directly compares the GLP1-triazole-Fc hybrid immunoglobulins and N3-Px-Fc proteins by SDS-PAGE under reducing conditions: Fc6 control (lane a), N3-P0-Fc (lane b), GLP1-P4-DN-P0-Fc (lane c), N3-P12-Fc (lane d), GLP1-P4-DN-P12-Fc (lane e), N3-P24-Fc (lane f), GLP1-P4-DN-P24-Fc (lane g), N3-P36-Fc (lane h), GLP1-P4-DN-P36-Fc (lane i), N3-P48-Fc (lane j), GLP1-P4-DN-P48-Fc (lane k).

FIG. 29 directly compares the GLP1-triazole-Fc hybrid immunoglobulins and $N_3$-Px-Fc proteins by SDS-PAGE under reducing conditions: Fc6 control (lane a), $N_3$—P0-Fc (lane b), GLP1-P4-DN—P0-Fc (lane c), $N_3$—P12-Fc (lane d), GLP1-P4-DN-P12-Fc (lane e), $N_3$—P24-Fc (lane f), GLP1-P4-DN-P24-Fc (lane g), $N_3$—P36-Fc (lane h), GLP1-P4-DN-P36-Fc (lane i), $N_3$—P48-Fc (lane j), GLP1-P4-DN-P48-Fc (lane k). The conversion of each $N_5$-Px-Fc protein to the corresponding GLP1-P4-DN-Px-Fc hybrid immunoglobulin was approximately 95%.

Example 6: Biological Activity of GLP1-Triazole-Fc Hybrid Immunoglobulins

The biological activity of the GLP1-P7-triazole-Px-Fc hybrid immunoglobulins was evaluated in a cell-based assay that measured the induction of cAMP synthesis in cells expressing the human GLP-1 receptor (GLP-1R). For isolation of GLP-1R expressing cells, Dulbecco's Modified Eagle Medium (DMEM) from Invitrogen (Grand Island, N.Y.), fetal bovine serum (FBS), penicillin, streptomycin, and geneticin sulfate (G418) were obtained from Corning (Manassas, Va.), the CalPhos transfection kit was obtained from Clontech (Mountain View, Calif.), human GLP-1 receptor expression plasmid was obtained from GeneCopoeia (Rockville, Md.), and anti-human GLP-1R-phycoerythrin monoclonal antibody was obtained from R&D Systems (Minneapolis, Minn.). For cAMP assays, 3-isobutyl-1-methylxanthine (IBMX) was obtained from Sigma-Aldrich (No. I5879), the cAMP dynamic 2 kit was obtained from Cisbio Bioassays (Bedford, Mass.), and the GLP-1(7-37) peptide was obtained from AnaSpec (No. 20761).

GLP-1R-expressing cells were prepared by transfecting a GLP-1R expression vector (EX-A0510-M02) into human 293T embryonic kidney cells using a CalPho mammalian transfection kit. Transfected cells were grown in DMEM supplemented with 10% FBS and penicillin and streptomycin (10 IU/ml), and selection for stable transfectants was carried out in same media containing 2 mg/ml G418. GLP-1R expression was evaluated by flow cytometric analysis using a anti-human GLP-1R-phycoerythrin monoclonal antibody.

For cAMP assays, 293T-GLP-1R cells were plated overnight into 384-well tissue culture treated white microtiter plates (Corning No. 3704) at a density of 5,000, 8,000 or 10,000 cells/well in 20 uL medium/well. The following day, serial dilutions of agonist (GLP-1 peptide or the GLP1-triazole-Fc hybrid immunoglobulins) in 20 uL PBS containing 0.5 mM IBMX were added to the cells, and the cells then incubated at 37° C. for 1, 4 or 24 hours. Following stimulation, cAMP levels were determined by Homogeneous Time-Resolved Fluorescence (HTRF) in a ClarioStar microplate reader (BMG Labtech) using a Cisbio cAMP dynamic 2 kit according to the manufacturer's instructions. Following addition of HTRF detection reagents, anti-cAMP Mab labeled with Cryptate (20 uL) and the cAMP labeled with d2 dye (20 uL), the plates were incubated for 1 hour at room temperature and the fluorescence ratio (665 nm/620 nm) calculated and used to determine the cAMP concentration in the cell lysates by four-parameter fit to a cAMP standard curve.

Figure 30:
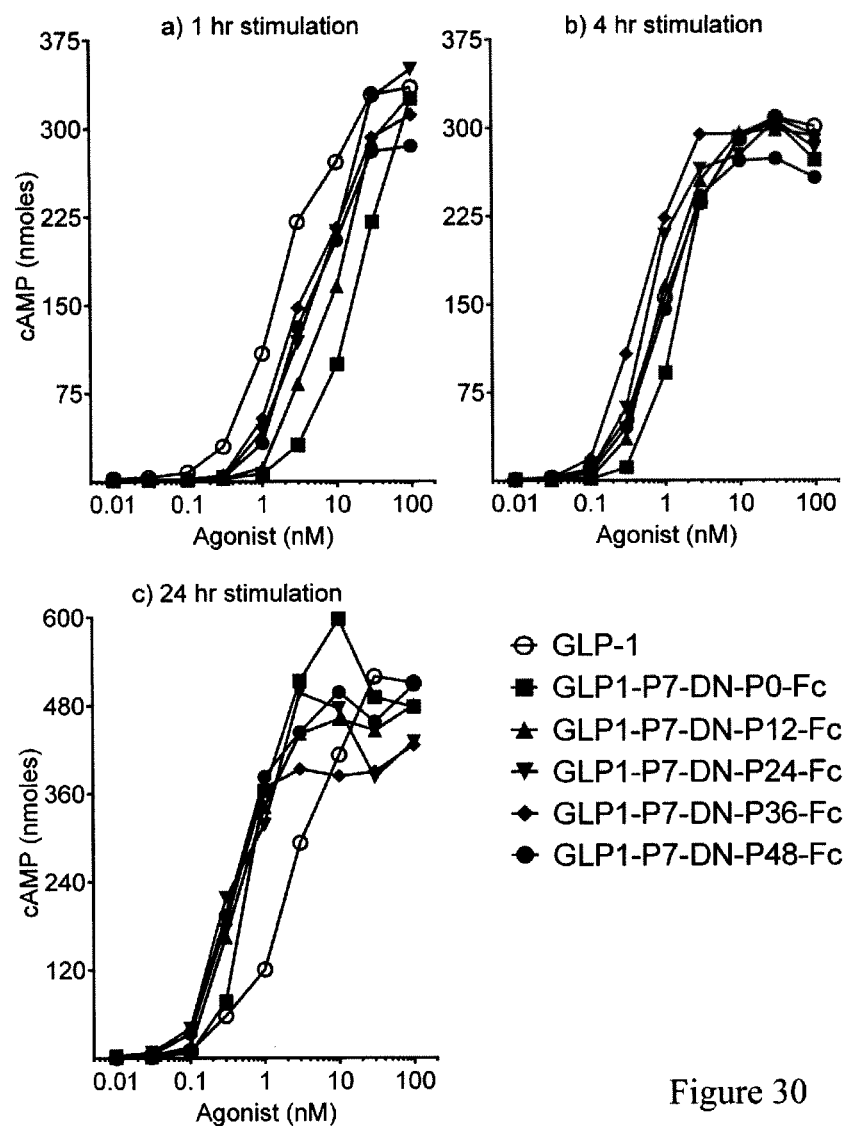
FIG. 30 compares the induction of cAMP synthesis in GLP-1 receptor expressing cells by GLP1-triazole-Fc hybrid immunoglobulins and GLP-1.

FIG. 30 shows the results for GLP-1(7-37) peptide and the GLP1-P7-DN-Px-Fc proteins (x=0, 12, 24, 36, 48). All five GLP1-triazole-Fc hybrid immunoglobulins induced cAMP levels comparable to GLP-1(7-37) peptide. Stimulation by GLP-1(7-37) was similar whether cells were exposed to agonist for 1, 4 or 24 hours, with an EC50 of ~2 nM at 24 hours, whereas stimulation by the GLP1-triazole-Fc hybrid immunoglobulins increased dramatically as cells were exposed to agonist for longer times, with an EC50 of ~0.4 nM at 24 hours.

Example 7: N-Terminal Cyclooctyne-Fc Proteins

Figure 31:
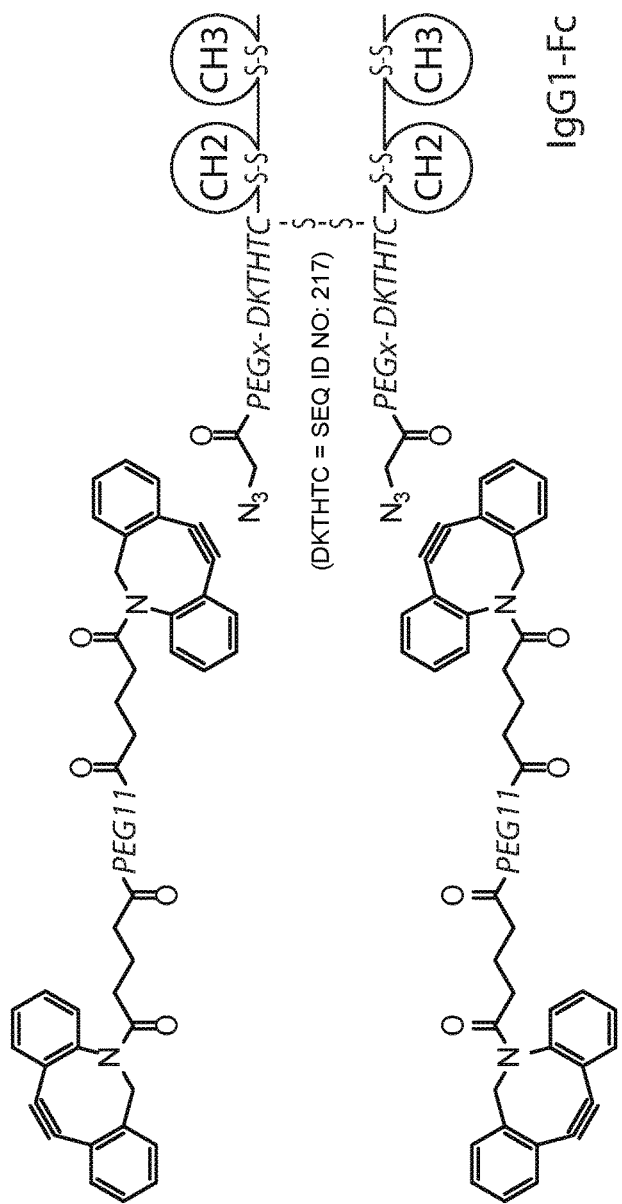
FIG. 31 shows the reaction between DIBAC-PEG11-DIBAC and the N3-Px-Fc proteins.

A series of cyclooctyne-modified Fc proteins (DIBAC-P11-DN-Px-Fc), each having a cyclooctyne functional group at its N-terminus is prepared by reacting a homobifunctional cyclooctyne linker with the azide-modified $N_3$-Px-Fc proteins of Example 4. The linker, DIBAC-PEG11-DIBAC, shown in FIG. 31, was obtained from CPC Scientific (calculated for $C_{74}H_{102}N_6O_{17}$ [M+H]+ 1346.6, found 1346.4). The PEG11 portion of this linker was derived from diamido-dPEG11-diamine (Quanta Biodesigns No. 10361) having the structure: [—NH—$CH_2$—($CH_2$—$CH_2$—O)$_3$—($CH_2$)$_3$—CO—NH—($CH_2$—$CH_2$—O)—($CH_2$)$_2$—CO—NH—$CH_2$—($CH_2$—$CH_2$—O)$_3$—($CH_2$)$_3$—NH—].

Figure 32:
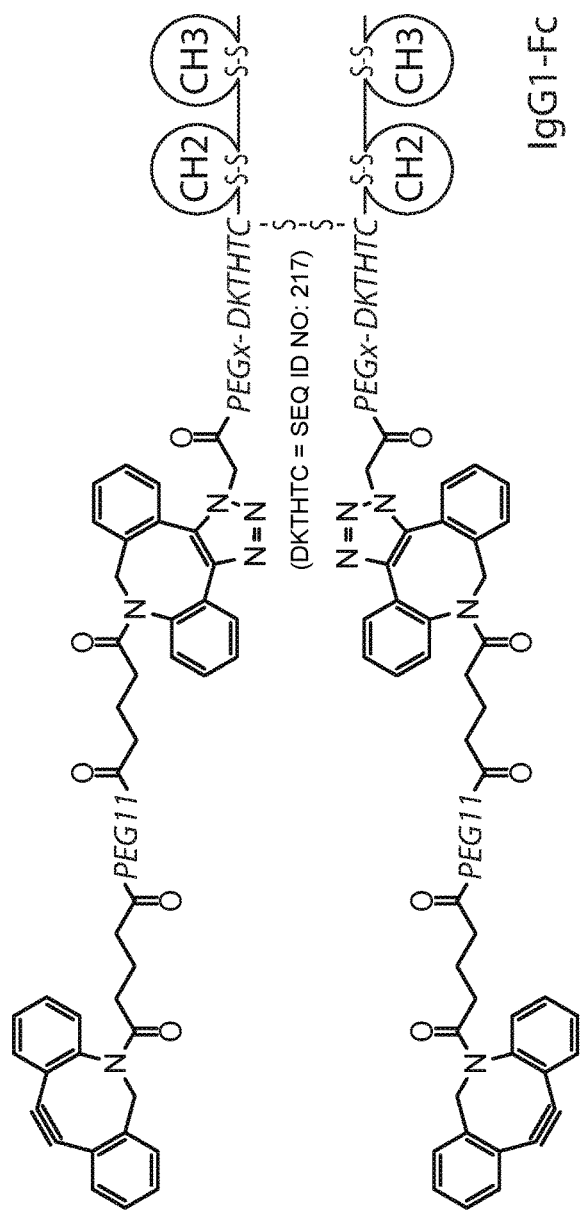
FIG. 32 shows the structure of the cyclooctyne-Px-Fc proteins.

DIBAC-PEG11-DIBAC is reacted individually with each one of the five $N_3$-Px-Fc proteins (FIG. 31), to generate a series of DIBAC-P11-DN-Px-Fc proteins (FIG. 32). Representative results are shown for the reaction of DIBAC-PEG11-DIBAC with the $N_3$-P0-Fc protein to generate DIBAC-P11-DN—P0-Fc. The reaction (1 mL) was initiated by adding 84 mg of the $N_3$-Px-Fc protein to 11.25 mg of the DIBAC-PEG11-DIBAC linker in 0.02 M sodium phosphate pH 7.0 in water-ethanol (0.64:0.36 vol/vol). The reaction was carried out for 12 hours at room temperature, and the DIBAC-PEG11-DIBAC linker was then extracted by adding 1 mL of PBS, mixing well, and centrifuging at 12,000×g which separated out the linker as an denser, oily phase. The desired DIBAC-P11-DN—P0-Fc product contained within the upper aqueous phase was purified by HiTrap Protein A HP chromatography, desalted and concentrated as described in Example 4.

Figure 33:
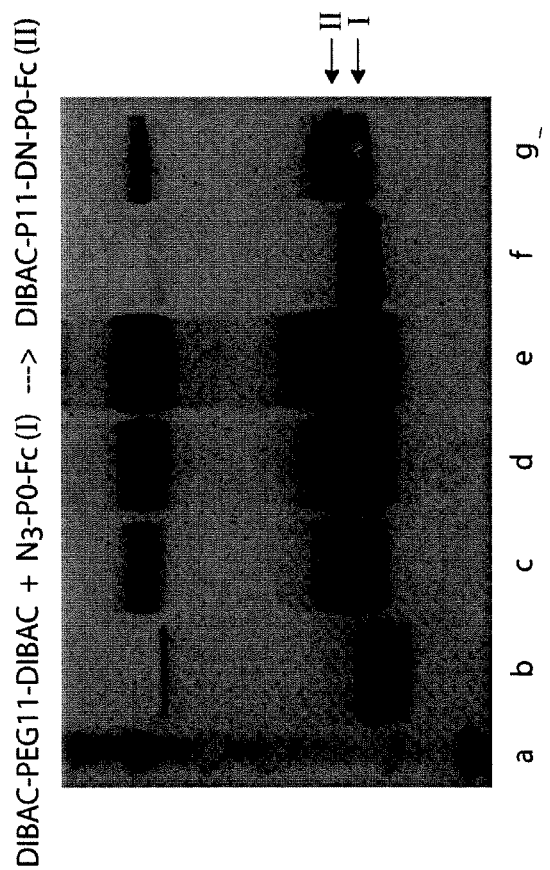
FIG. 33 shows the DIBAC-P11-DN—P0-Fc reaction product by SDS-PAGE under reducing conditions: Fc6 control (lane b), unpurified reaction product (lanes c-e), the purified N3-P0-Fc protein (lane f), and the purified DIBAC-P11-DN—P0-Fc protein (lane g).

FIG. 33 shows the DIBAC-P11-DN—P0-Fc reaction product by SDS-PAGE under reducing conditions: Fc6 control (lane b), unpurified reaction product (lanes c-e), the purified $N_3$-P0-Fc protein (lane f), and the purified DIBAC-P11-DN—P0-Fc protein (lane g). Approximately, 70% of the $N_3$-P0-Fc (I) protein was converted into a product having the expected size of the DIBAC-P11-DN—P0-Fc (II) protein.

Example 8: DNA-Triazole-Fc Hybrid Immunoglobulins

Figure 34:
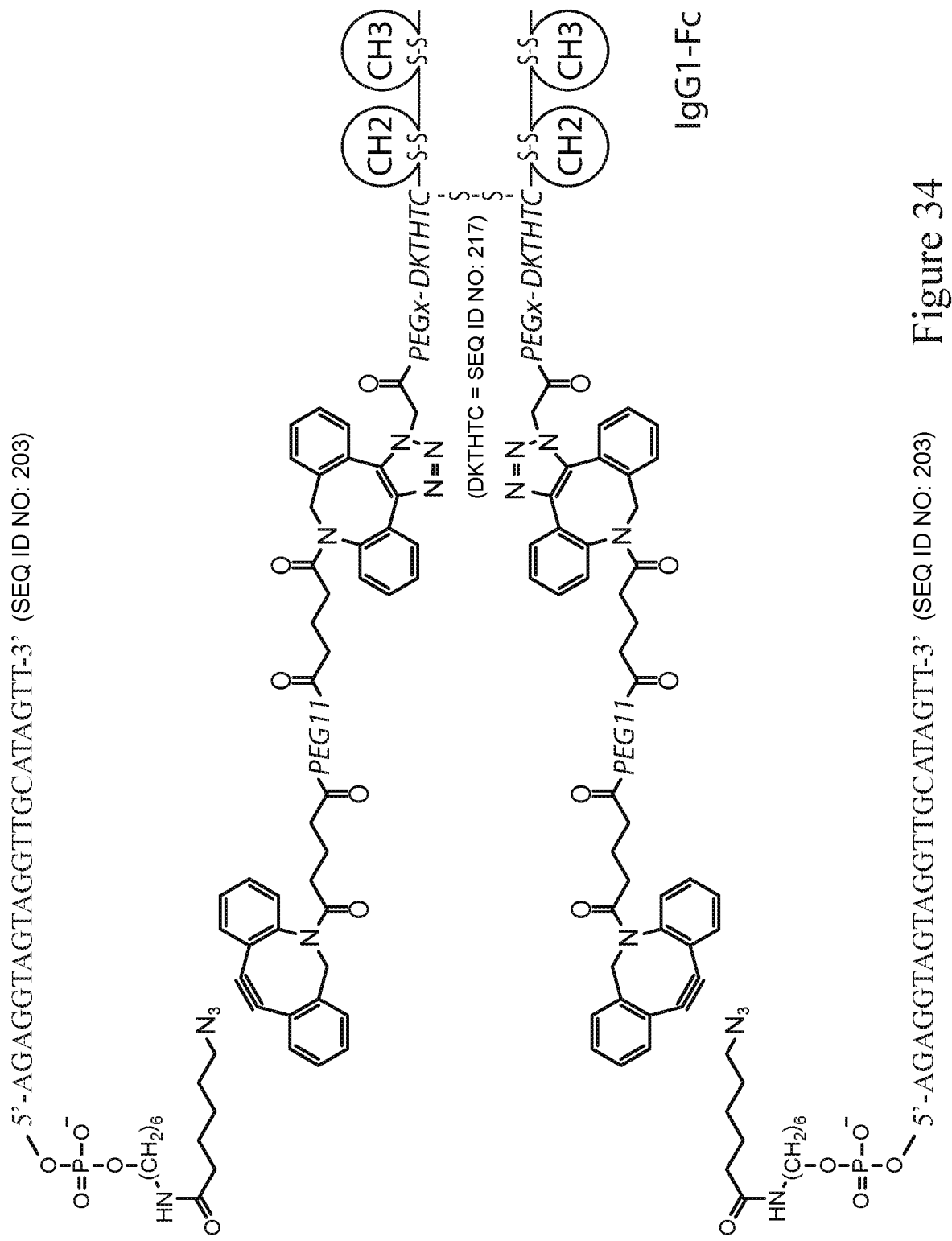
FIG. 34 shows the reaction between azide-modified DNA and the cyclooctyne-Px-Fc proteins.

A series of DNA-triazole-Fc hybrid immunoglobulins (DNA-P11-DN-Px-Fc) are prepared by reacting an azide-modified DNA or RNA, with each of the five DIBAC-P11-DN-Px-Fc proteins of Example 7. FIG. 34 shows the structure of the azide-modified DNA, 5AzD-let7d, having the sequence 5'-AGAGGTAGTAGGTTGCATAGTT-3' (SEQ ID NO:203) of the DNA coding strand for the mature human hsa-let-7d-5p miRNA (www.mirbase.org, Accession No. MIMAT0000065). The 5AzD-let7d oligonucleotide (5AzD-let7d) was obtained from Integrated DNA Technologies (Coralville, Iowa). Prior to use, 5AzD-let7d (molecular weight 7187.8) was dissolved in 10 mM Tris HCl, 1 mM EDTA.

Figure 35:
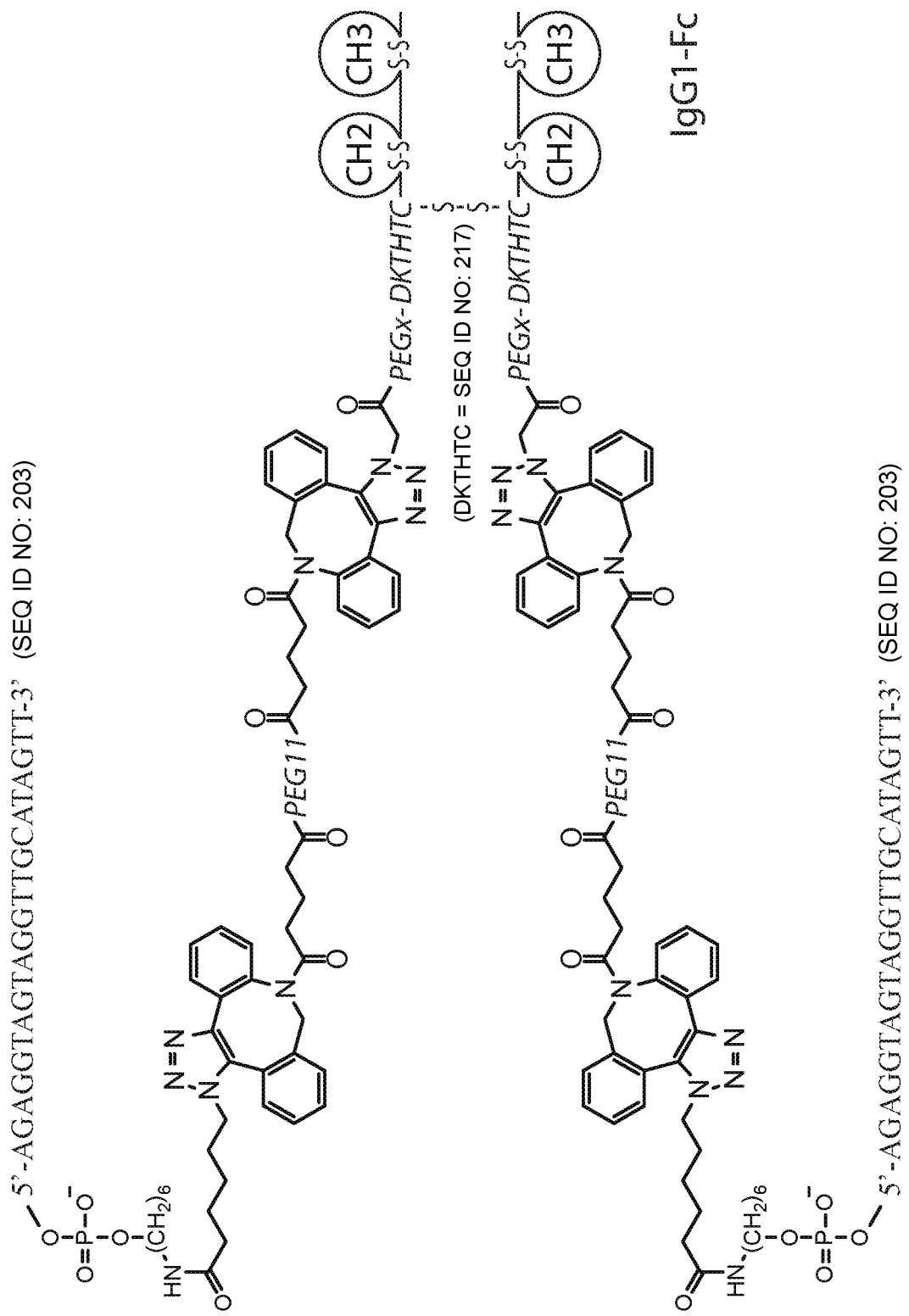
FIG. 35 shows the structure of DNA-triazole-Fc hybrid immunoglobulins.

5AzD-let7d was reacted individually with each of the DIBAC-P11-DN-Px-Fc proteins (FIG. 34) to generate a series of DNA-triazole-Fc hybrid immunoglobulins (FIG. 35). Representative results are shown for the reaction of 5AzD-let7d with the DIBAC-P11-DN—P0-Fc protein. Reactions (20 ul) contained 0.1 M sodium phosphate pH 7.0, 50 ug of 5AzD-let7d or a series of two-fold dilutions thereof, and 5.7 ug of the DNA-P11-DN-Px-Fc protein. Reactions were carried out at room temperature for 2 hours.

Figure 36:
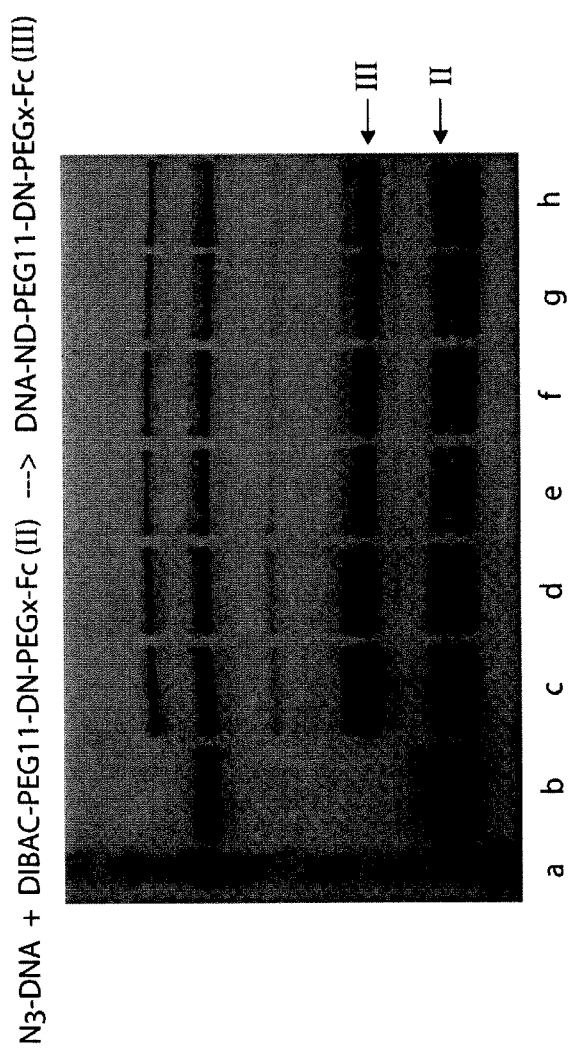
FIG. 36 shows the DNA-triazole-Fc hybrid immunoglobulins reaction products by SDS-PAGE under reducing conditions: the 5AzD-let7d oligonucleotide concentration (mg/ml) was as follows: markers (lane a), 0 (lane b), 2.5 (lane c), 1.25 (lane d), 0.063 (lane e), 0.031 (lane f), 0.016 (lane g), 0.08 (lane h).

FIG. 36 shows the reaction products by SDS-PAGE under reducing conditions: the 5AzD-let7d oligonucleotide concentration (mg/ml) was as follows: markers (lane a), 0 (lane b), 2.5 (lane c), 1.25 (lane d), 0.063 (lane e), 0.031 (lane f), 0.016 (lane g), 0.08 (lane h). Approximately 90% of the DIBAC-P11-DN—P0-Fc (II) protein was converted into a product having the expected size of the DNA-ND-P11-DN-PEG0-Fc (III) hybrid immunoglobulin.

Example 9: N-Terminal Azide-Mab Proteins

Figure 37:
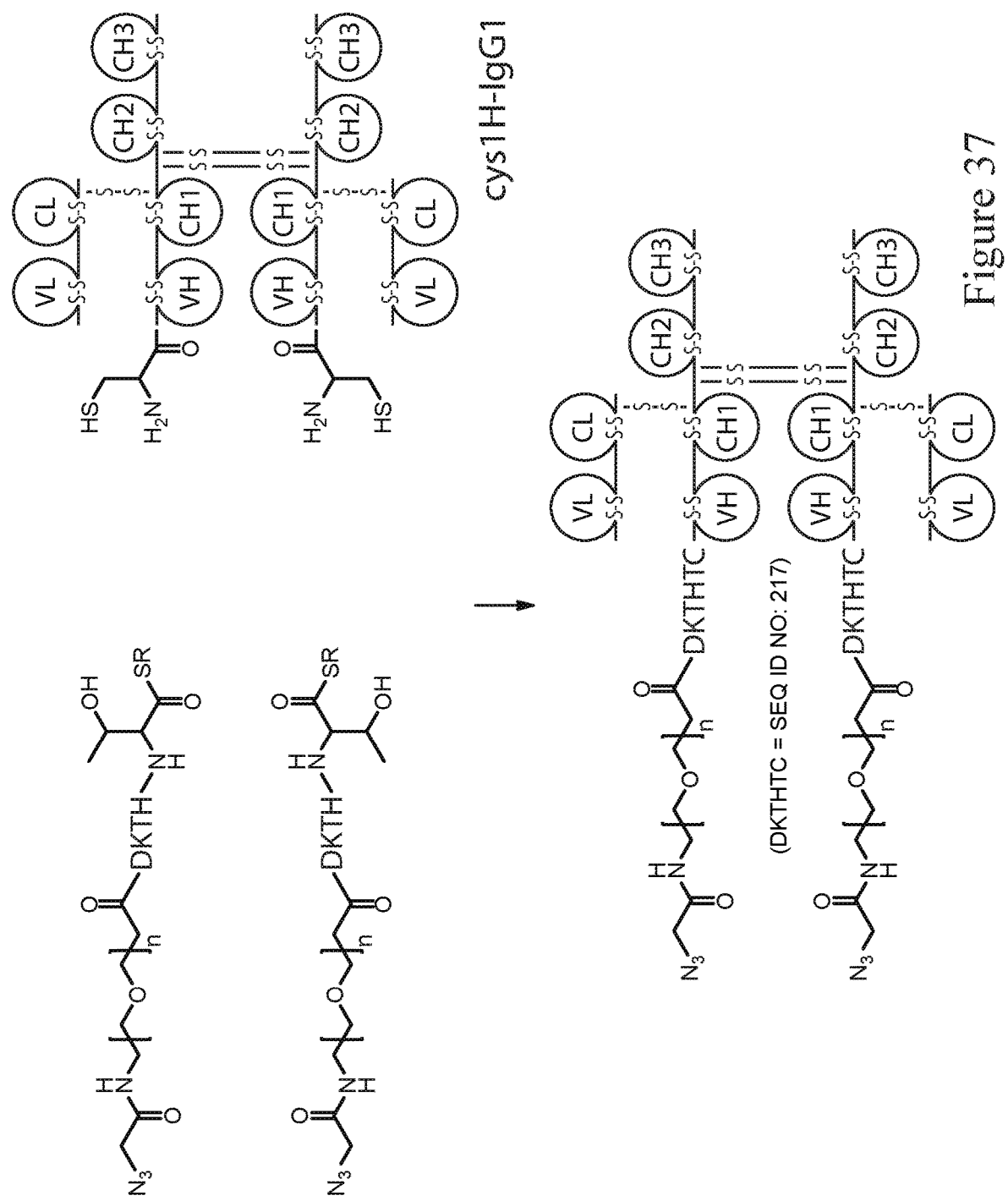
FIG. 37 shows the structure and synthesis of the trastuzumab variant, cys1H-IgG1, and the azide-modified trastuzumab heavy chain (N$_3$-Px-Hc).

A series of azide-modified trastuzumab proteins ($N_3$-Px-Hc), each having an azide functional group at the N-terminus of its heavy chain, and optionally a PEG linker, is prepared by reacting a trastuzumab protein variant, cys1H-IgG1, with thioesters having the sequence azidoacetyl-Px-DKTHT-thiophenol (FIG. 37). DKTHT is SEQ ID NO: 220.

Cys1H-IgG1 consists of the wild-type trastuzumab light chain shown in SEQ ID NO: 128, and a variant trastuzumab heavy chain, having at its heavy chain N-terminus a cysteine residue. The cys1H-IgG1 heavy chain is initially initially expressed as the variant trastuzumab pre-heavy chains shown in SEQ ID NO: 167, SEQ ID NO: 168, and SEQ ID NO: 169, having a SHH signal peptide, IFN signal peptide, and CETP signal peptide, respectively. Cleavage of the heterologous signal sequences by the cellular signal peptidase provides the mature heavy chain protein having an N-terminal cysteine, the sequence of which is shown in SEQ ID NO: 166.

Figure 38:
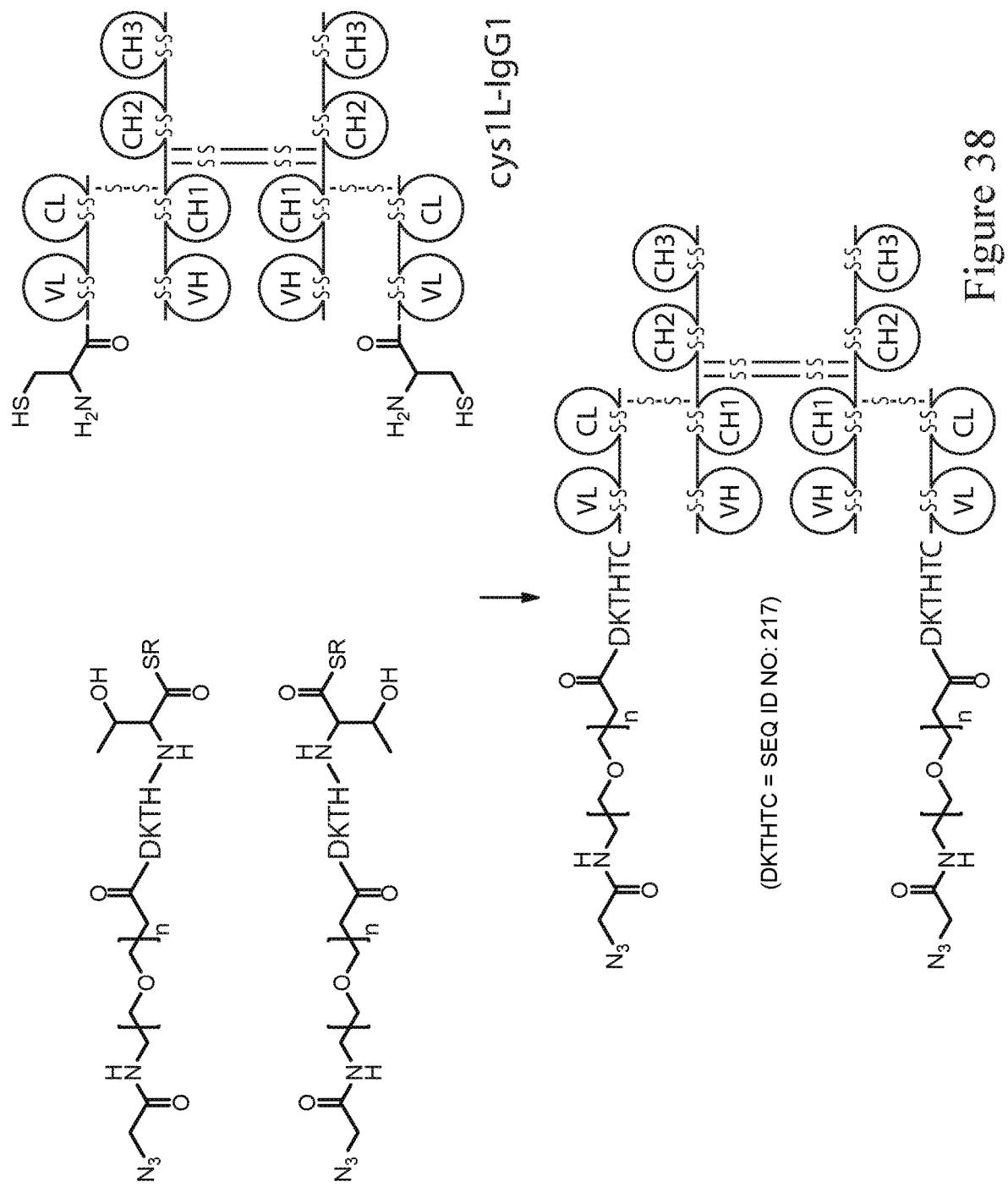
FIG. 38 shows the structure and synthesis of the trastuzumab variant, cyslL-IgG1, the azide-modified trastuzumab light chain (N$_3$-Px-Lc).

A second series of azide-modified trastuzumab proteins (N3-Px-Lc), each having an azide functional group at the N-terminus of its light chain, and optionally a PEG linker, is prepared by reacting a trastuzumab protein variant, cys1L-IgG1, with thioesters having the sequence azidoacetyl-Px-DKTHT-thiophenol (FIG. 38). DKTHT is SEQ ID NO: 220.

Cys1L-IgG1 consists of the wild-type trastuzumab heavy chain shown in SEQ ID NO: 129, and a variant trastuzumab light chain, having at its heavy chain N-terminus a cysteine residue. The cys1L-IgG1 light chain is initially initially expressed as the variant trastuzumab pre-light chains shown in SEQ ID NO: 131, SEQ ID NO: 132, and SEQ ID NO: 133 having a SHH signal peptide, IFN signal peptide, and CETP signal peptide, respectively. Cleavage of the heterologous signal sequences by the cellular signal peptidase provides the mature light chain protein having an N-terminal cysteine, the sequence of which is shown in SEQ ID NO: 130.

Appropriate light and heavy chain expression vectors are co-transfected to produce the cys1H-IgG1 and cysL-IgG proteins. Protein production is executed by transient expression in CHO-DG44 cells, adapted to serum-free suspension culture followed by Protein A purification, as described in Example 1.

Example 10: Mertansine-Triazole-Trastuzumab Hybrid Immunoglobulins

A series of mertansine-triazole-trastuzumab hybrid immunoglobulins are prepared by reacting the maytansinoid DM1 (mertansine), further modified to have a cyclooctyne functional group, with each of the $N_3$-Px-Hc and $N_3$-Px-Lc proteins of Example 9.

Figure 39:
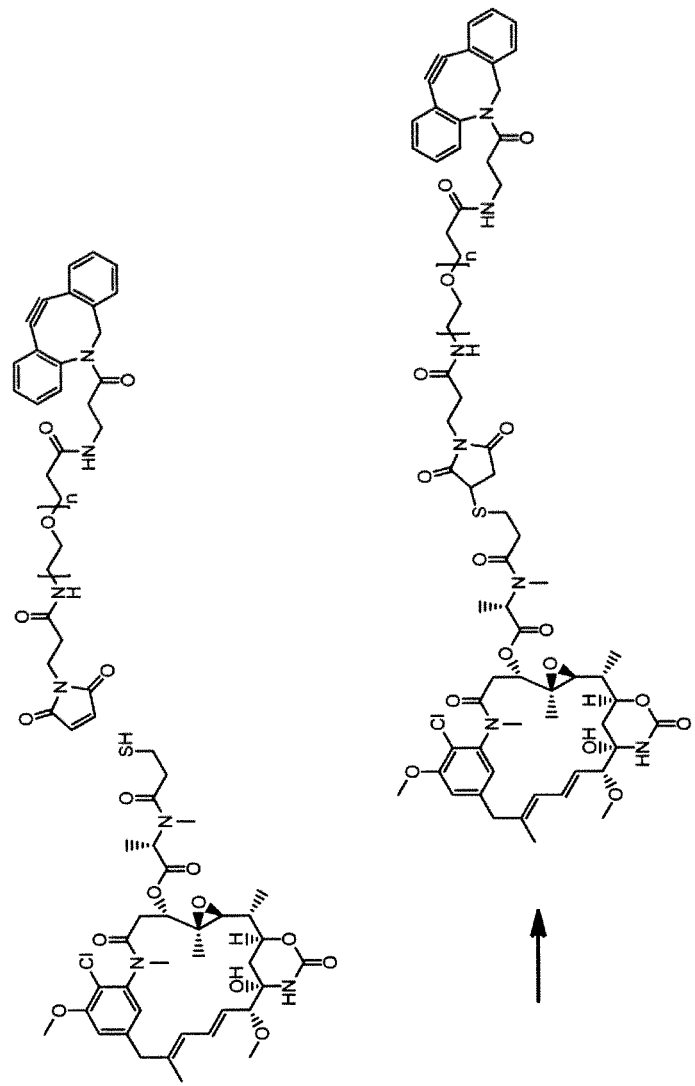
FIG. 39 shows the structure and synthesis of cyclooctyne-modified DM-1 (DM1-P4-DBCO).

DM1 (free thiol form; M. W. 737.5 g/mole) is prepared as described previously in U.S. Pat. Nos. 5,208,020 and 6,333,410 B1, which are hereby incorporated by reference. A cyclooctyne functional group is added to DM1 using the DBCO-PEG4-Maleimide heterobifunctional linker which contains a maleimide group capable of reacting with the free thiol group of DM1 (FIG. 39). DM1 is reacted with DBCO-PEG4-Maleimide in DMSO using the procedures of Example 5. The cycloctyne-modified-DM1 product (DM1-P4-DBCO) is purified by HPLC, and dissolved in DMSO prior to use.

Figure 40:
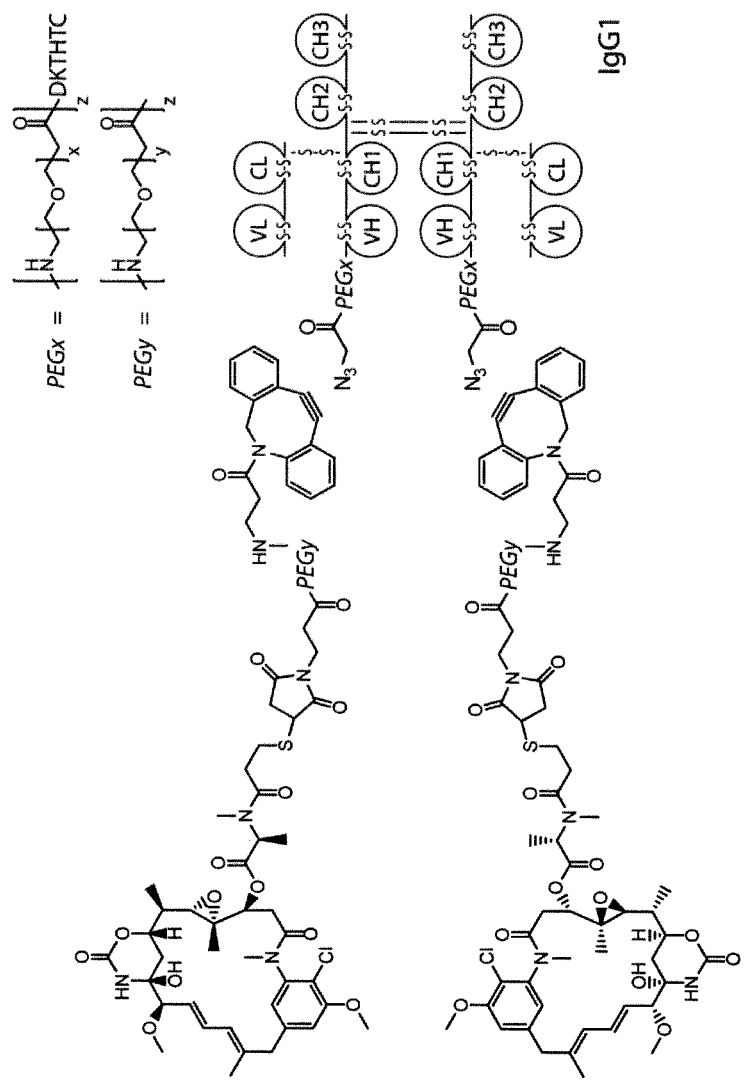
FIG. 40 shows the reaction between cyclooctyne-modified DM-1 and the N$_3$-Px-Hc proteins.
Figure 41:
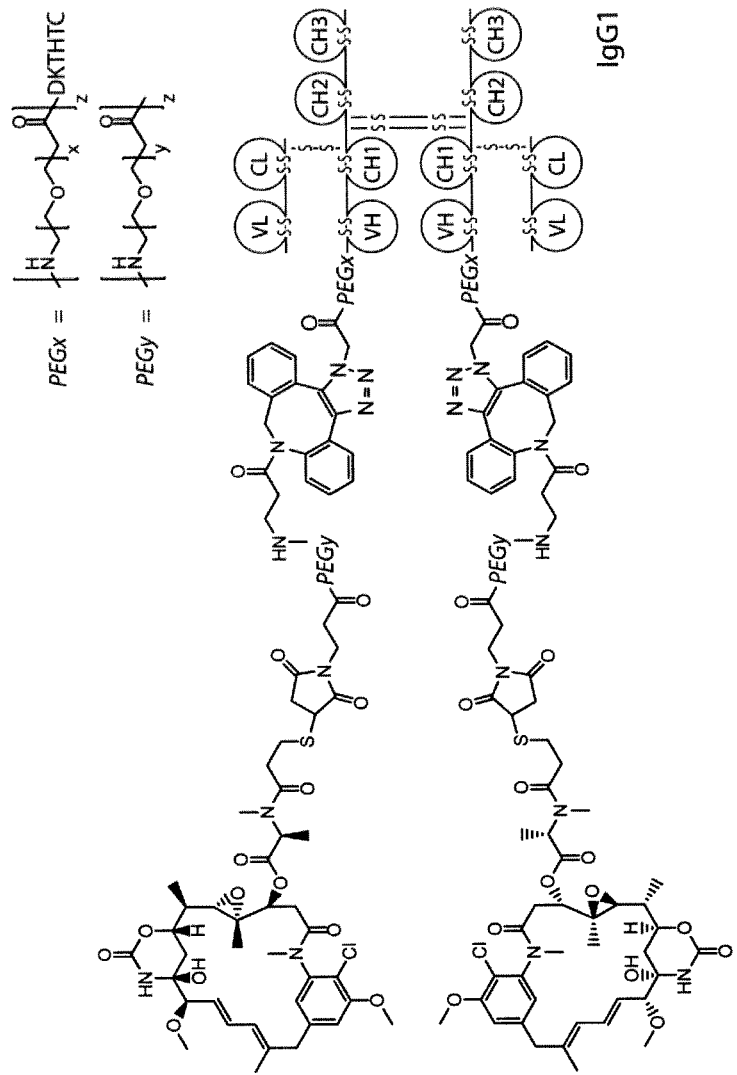
FIG. 41 shows the structure of DM1-P4-triazole-Px-Hc hybrid immunoglobulins.

DM1-P4-DBCO is reacted individually with each one of the five N3-Px-Hc proteins (FIG. 40), to generate a series of mertansine-triazole-trastuzumab hybrid immunoglobulins modified with DM1 at the N-terminus of the trastuzumab heavy chain (DM1-P4-triazole-Px-Hc) (FIG. 41).

Figure 42:
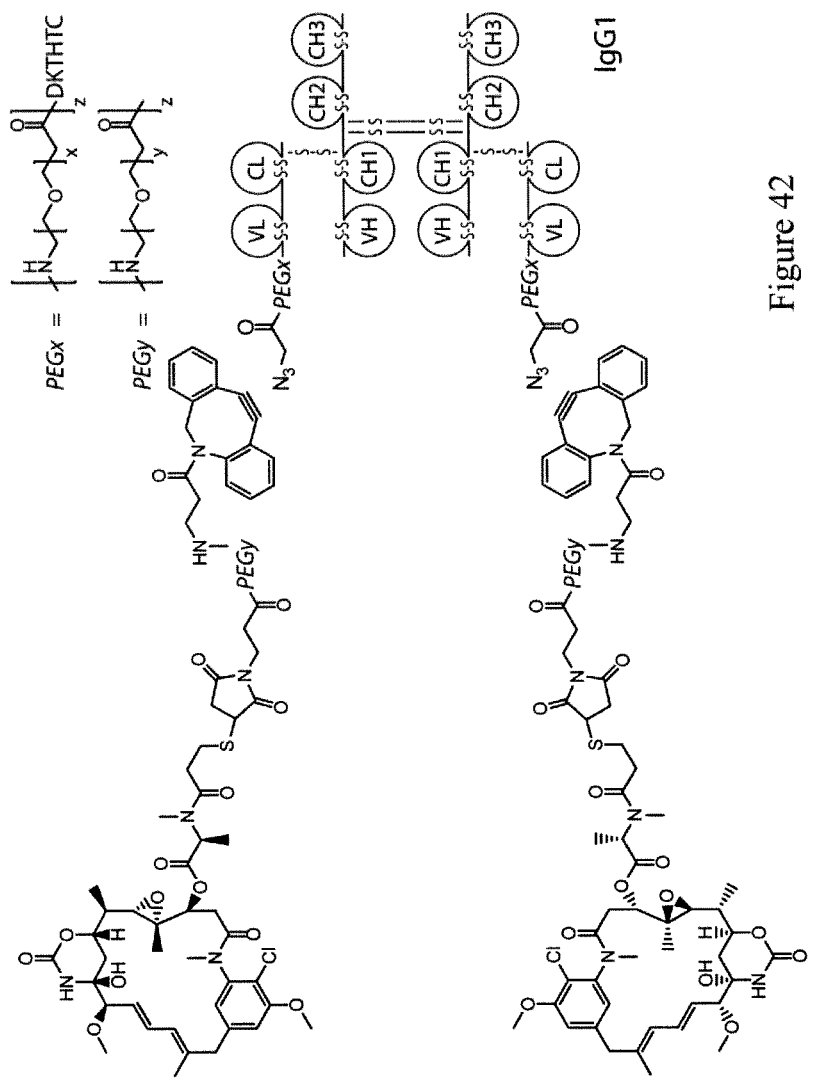
FIG. 42 shows the reaction between cyclooctyne-modified DM-1 and the N$_3$-Px-Lc proteins.
Figure 43:
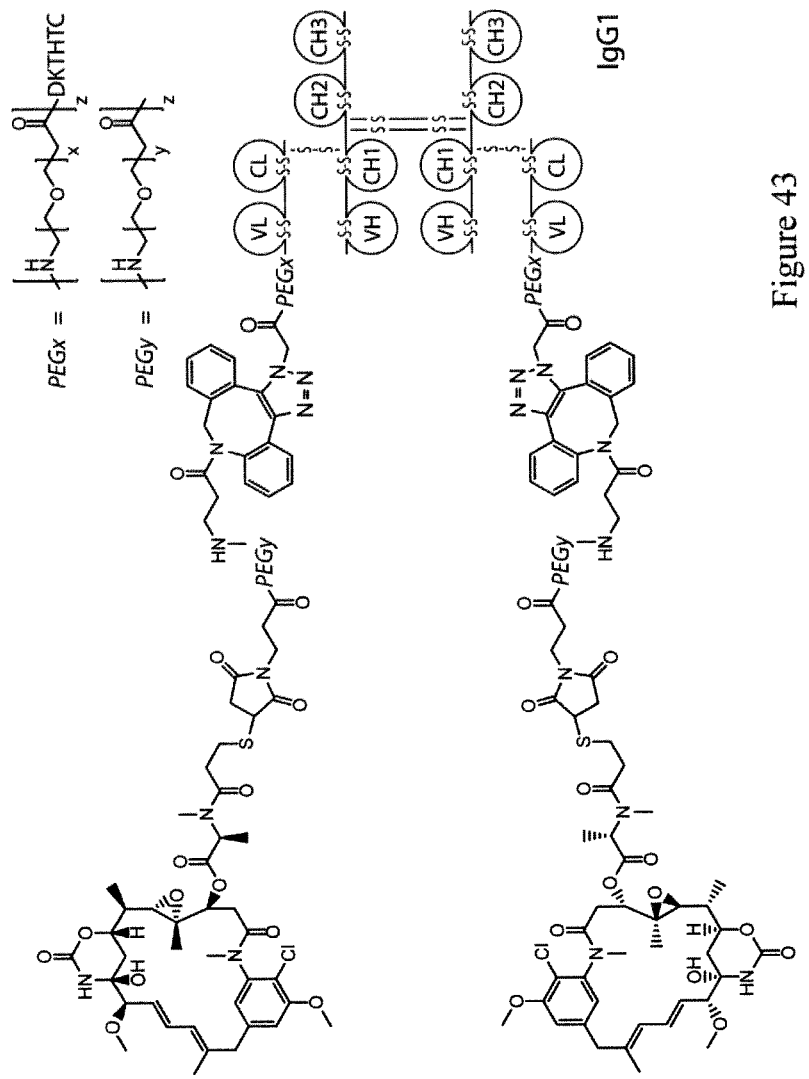
FIG. 43 shows the structure of DM1-P4-triazole-Px-Lc hybrid immunoglobulins.

DM1-P4-DBCO is reacted individually with each one of the five N3-Px-Lc proteins (FIG. 42), to generate a series of mertansine-triazole-trastuzumab hybrid immunoglobulins modified with DM1 at the N-terminus of the trastuzumab light chain (DM1-P4-triazole-Px-Lc) (FIG. 43).

The efficacy of the mertansine-triazole-trastuzumab hybrid immunoglobulins as novel antibody drug conjugates is evaluated and compared with ado-trastuzumab emtansine, obtained from Genentech (South San Francisco, Calif.), using in vitro cell proliferation assays and in vivo tumor growth inhibition assays as described in U.S. Pat. No. 7,521,541B2, which is hereby incorporated by reference.

Example 11: N-Terminal Tetrazine-Fc Proteins

Figure 44:
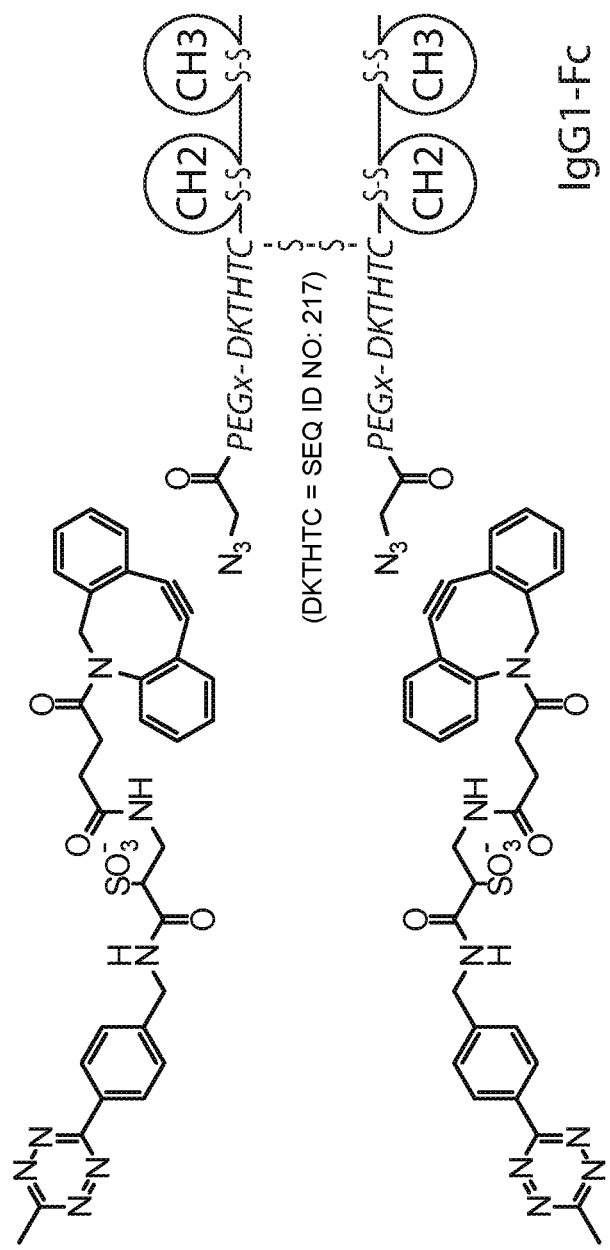
FIG. 44 shows the reaction between Tetrazine-DBCO and the N$_3$-Px-Fc proteins.

A series of tetrazine-modified Fc proteins (Tet-Px-Fc), each having a tetrazine group at its N-terminus and optionally a PEGx linker was prepared by reacting a heterobifunctional linker with the azide-modified $N_3$-Px-Fc proteins of Example 4. FIG. 44 shows the Tetrazine-DBCO heterobifunctional linker, which has a cyclooctyne group at one end capable reacting with the azide group of the $N_3$-Px-Fc proteins, and a tetrazine group at the other end. The Tetrazine-DBCO linker was obtained from Click Chemistry Tools (Item No. 1022; $C_{32}H_{29}N_7O_6S$, protonated; molecular weight 639.68, protonated). Prior to use, Tetrazine-DBCO was dissolved at a concentration of 25 mg/mL in water.

Figure 45:
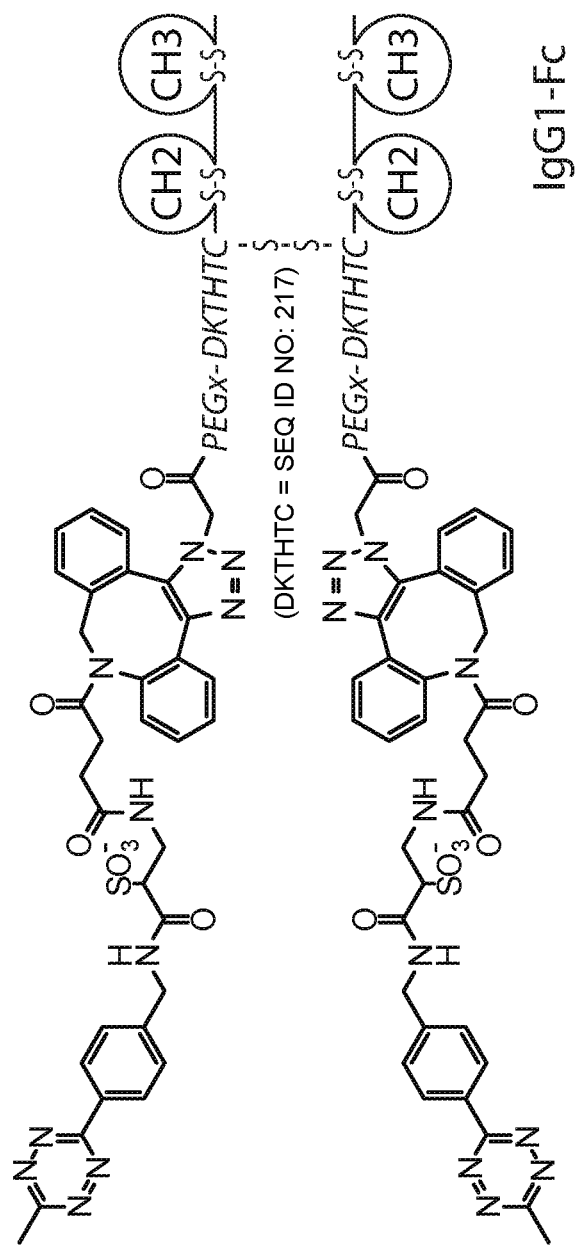
FIG. 45 shows the structure of tetrazine-modified Fc proteins (Tet-Px-Fc).

Tetrazine-DBCO was reacted individually with each $N_5$-Px-Fc protein (FIG. 44) to generate the corresponding series of Tet-Px-Fc proteins (FIG. 45). Reactions (0.72 mL) contained 0.1 M sodium phosphate pH 7.0, 0.1875 mg of the Tetrazine-DBCO linker, and 0.6 mg of the $N_3$-Px-Fc protein. Reactions were carried out for 3.5 hours at room temperature. Excess unreacted linker was removed by HiTrap ProteinA HP chromatography.

Figure 46:
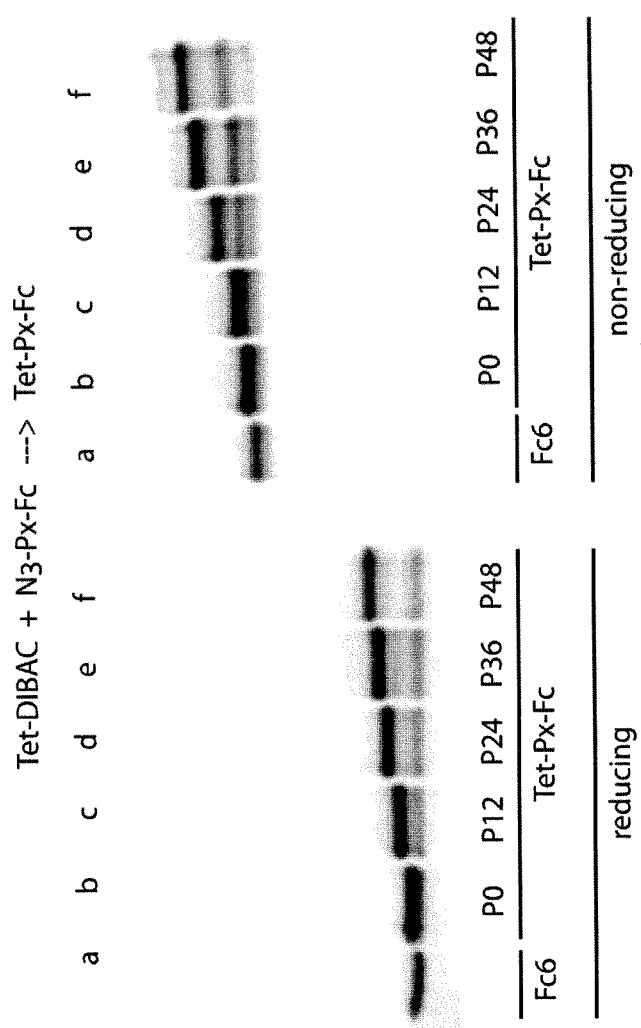
FIG. 46 shows the purified Tet-Px-Fc proteins by SDS-PAGE under reducing (left) and non-reducing conditions (right): Fc6 control (lanes a), Tet-P0-Fc (lanes b), Tet-P12-Fc (lanes c), Tet-P24-Fc (lanes d), Tet-P36-Fc (lanes e), and Tet-P48-Fc (lanes f).
Figure 50:
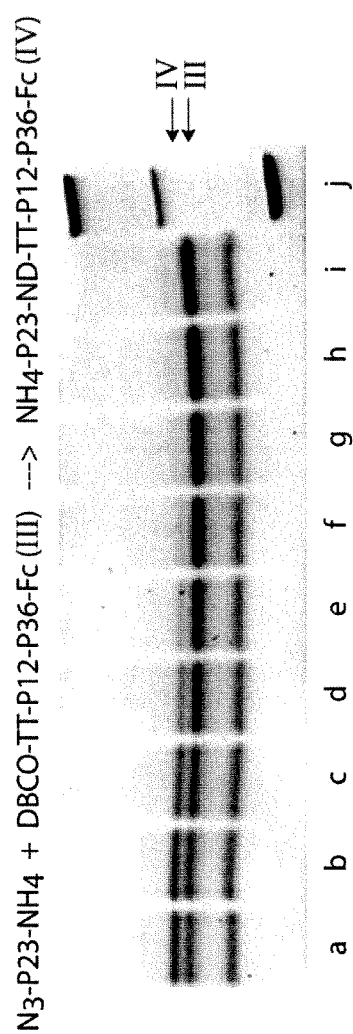
FIG. 50 shows the reaction products between NH2-PEG23-N3 and DBCO-TT-P12-P36-Fc protein by SDS-PAGE under reducing conditions: the NH2-PEG23-N3 linker concentration (mg/ml) was as follows: 0.12 (lane a), 0.06 (lane b), 0.03 (lane c), 0.015 (lane d), 0.0075 (lane e), 0.0038 (lane f), 0.002 (lane g), 0.001 (lane h), 0 (lane i).

FIG. 46 shows the purified Tet-Px-Fc proteins by SDS-PAGE under reducing (left) and non-reducing conditions (right): Fc6 control (lanes a), Tet-P0-Fc (lanes b), Tet-P12-Fc (lanes c), Tet-P24-Fc (lanes d), Tet-P36-Fc (lanes e), and Tet-P48-Fc (lanes f). The size on SDS-PAGE of the Tet-Px-Fc proteins increased as the PEG linker length increased, under both reducing and non-reducing conditions. In addition, each of the Tet-Px-Fc proteins was larger than the corresponding $N_5$-Px-Fc protein by SDS-PAGE under reducing conditions (FIG. 50).

Example 12: N-Terminal Trancyclooctene-Fc Proteins

Figure 47:
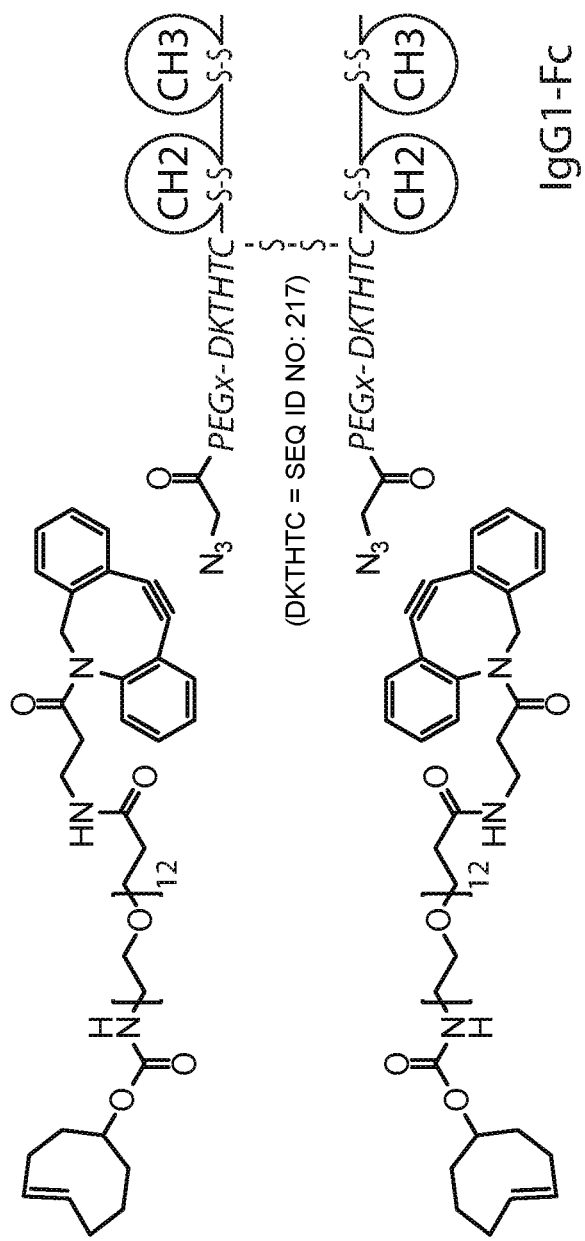
FIG. 47 shows the reaction between TCO-PEG12-DBCO and the N$_3$-Px-Fc proteins.

A series of transcyclooctene-modified Fc proteins (Tco-Px-Fc), each having a transcyclooctene group at its N-terminus and optionally a PEGx linker, is prepared by reacting a heterobifunctional linker with the azide-modified $N_5$-Px-Fc proteins of Example 4. FIG. 47 shows the TCO-PEG12-DBCO heterobifunctional linker, which has a cycloctyne group at one end capable reacting with the azide group of the $N_3$-Px-Fc proteins, and a transcyclooctene group at the other end. The TCO-PEG12-DBCO linker was obtained from Click Chemistry Tools (Item No. 1005; $C_{54}H_{81}N_3O_{16}$; molecular weight 1028.23). Prior to use, TCO-PEG12-DBCO was dissolved at a concentration of 100 mg/mL in DMSO.

Figure 48:
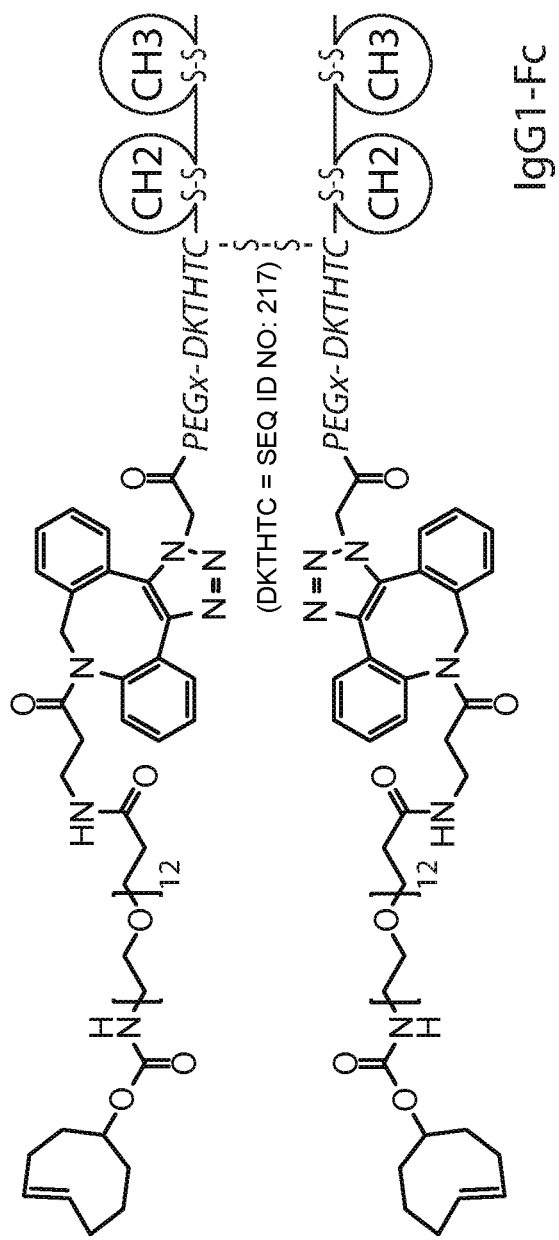
FIG. 48 shows the structure of transcyclooctene-modified Fc proteins (Tco-Px-Fc).

TCO-PEG12-DBCO is reacted individually with each $N_5$-Px-Fc protein (FIG. 47) to generate the corresponding series of Tco-P12-Px-Fc proteins (FIG. 48). Representative results are shown for the reaction of TCO-PEG12-DBCO with the $N_3$-P36-Fc protein. Reactions (6 uL) contained 0.1 M sodium phosphate pH 7.0, 0.2 mg of the TCO-PEG12-DBCO linker or a series of two-fold dilutions thereof in DMSO, and 5 ug of the $N_3$-P36-Fc protein. Reactions were carried out for 3.5 hours at room temperature.

Figure 49:
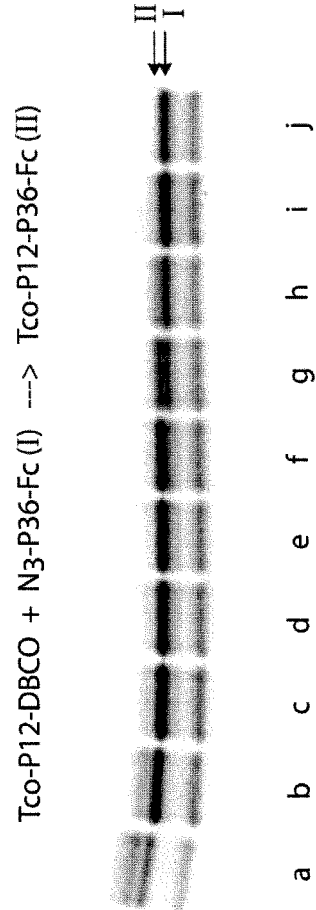
FIG. 49 shows the Tco-P12-Px-Fc proteins by SDS-PAGE under reducing conditions: the Tco-P12-DBCO linker concentration (mg/ml) was as follows: 32 (lane a), 16 (lane b), 8 (lane c), 4 (lane d), 2 (lane e), 1 (lane f), 0.5 (lane g), 0.25 (lane h), 0.125 (lane i), and 0 (lane j).

FIG. 49 shows the Tco-P12-Px-Fc proteins by SDS-PAGE under reducing conditions: the Tco-P12-DBCO linker concentration (mg/ml) was as follows: 32 (lane a), 16 (lane b), 8 (lane c), 4 (lane d), 2 (lane e), 1 (lane f), 0.5 (lane g), 0.25 (lane h), 0.125 (lane i), and 0 (lane j). The conversion the $N_3$-P36-Fc (I) protein into the Tco-P12-P36-Fc (II) protein was essentially complete at a Tco-P12-DBCO linker concentration of 1 mg/ml (lane f). In further studies, the Tco-P12-P36-Fc protein thereby obtained was purified by HiTrap ProteinA HP chromatography, desalted and concentrated as described in Example 4.

To test the reactivity of the Tco-P12-P36-Fc protein with a tetrazine functional group, purified Tco-P12-P36-Fc protein was first reacted with the heterobifunctional Tetrazine-DBCO linker to prepare DBCO-TT-P12-P36-Fc protein, which was purified by Protein A and then tested for its ability to react with an azido-PEG-amine linker, $NH_2$—PEG23-$N_3$, obtained from Quanta Biodesigns (Item No. 10525, $C_{48}H_{98}N_4O_{23}$, molecular weight 1099.30). The test reactions (6 uL) contained 0.1 M sodium phosphate pH 7.0, 0.2 mg of the $NH_2$—PEG23-$N_3$ linker or a series of two-fold dilutions thereof, and 5 ug of the DBCO-TT-P12-P36-Fc protein. Reactions were carried out for 1 hour at room temperature.

FIG. 50 shows the reaction products by SDS-PAGE under reducing conditions: the $NH_2$—PEG23-$N_3$ linker concentration (mg/ml) was as follows: 0.12 (lane a), 0.06 (lane b), 0.03 (lane c), 0.015 (lane d), 0.0075 (lane e), 0.0038 (lane f), 0.002 (lane g), 0.001 (lane h), 0 (lane i). The DBCO-TT-P12-P36-Fc (III) protein, but not the Tco-P12-P36-Fc protein (not shown), was converted into the expected $NH_2$—P23-ND-TT-P12-P36-Fc (IV) protein, confirming the reactivity of the Tco-P12-P36-Fc protein with a tetrazine functional group.

Example 13: GLP1-Dihydropyridizine-Fc Hybrid Immunoglobulins

A series of GLP1-dihydropyridizine-Fc hybrid immunoglobulins (GLP1-P3-TT-Px-Fc) were prepared by reacting a transcyclooctene-modified GLP-1 analog with the Tet-Px-Fc proteins of Example 11. GLP1-dihydropyridizine-Fc hybrid immunoglobulins are also prepared by reacting a tetrazine-modified GLP-1 analog with the Tco-Px-Fc proteins of Example 12.

Figure 51:
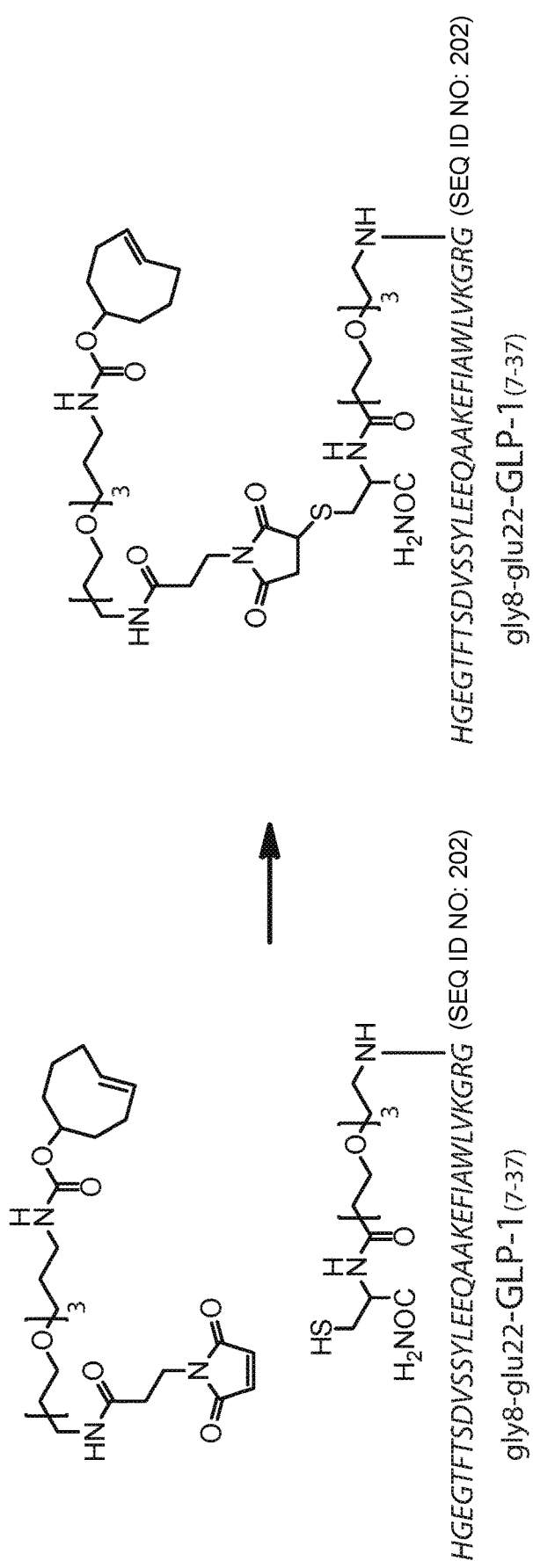
FIG. 51 shows the structure and synthesis of the transcyclooctene-modified GLP-1 analog (GLP1-P6-Tco).

To prepare the transcyclooctene-modified GLP-1 analog, the glyB-glu22-GLP-1(7-37)-PEG3-cys-NH2 peptide was reacted with a heterobifunctional linker, TCO-PEG3-Maleimide, which contains a maleimide group capable of reacting with the free thiol group on the C-terminal cysteine residue (FIG. 51). TCO-PEG3-Maleimide ($C_{26}H_{41}N_3O_8$, mol weight 523.62) was obtained from Click Chemistry Tools (Item No. 1002). Prior to use, the linker was dissolved at a concentration of 25 mg/mL in DMSO. Reactions (0.42 ml) contained 50 mM MES pH 6.5, 5 mM EDTA, 0.45 mg of glyB-glu22-GLP-1(7-37)-PEG3-cys-$NH_2$ peptide and 0.375 mg of the TCO-PEG3-Maleimide linker. Reactions were carried out at room temperature for 60 minutes. Excess unreacted linker was removed by buffer-exchange into 0.02 M sodium phosphate pH 7.0 using a 5 mL HiTrap Desalting Column. FIG. 51 shows the structure of the transcyclooctene-modified GLP-1 analog (GLP1-P6-Tco).

Figure 52:
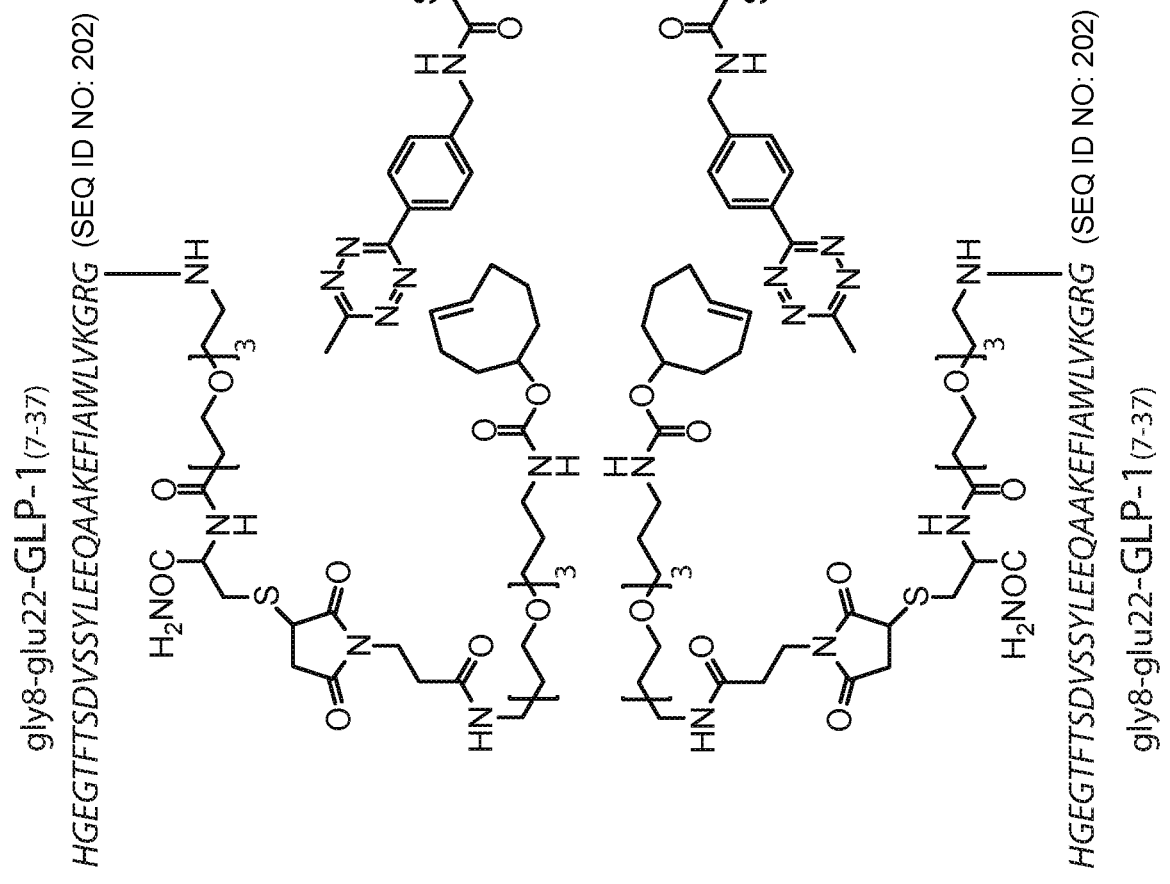
FIG. 52 shows the reaction between GLP1-P6-Tco peptide and the Tet-Px-Fc proteins.
Figure 53:
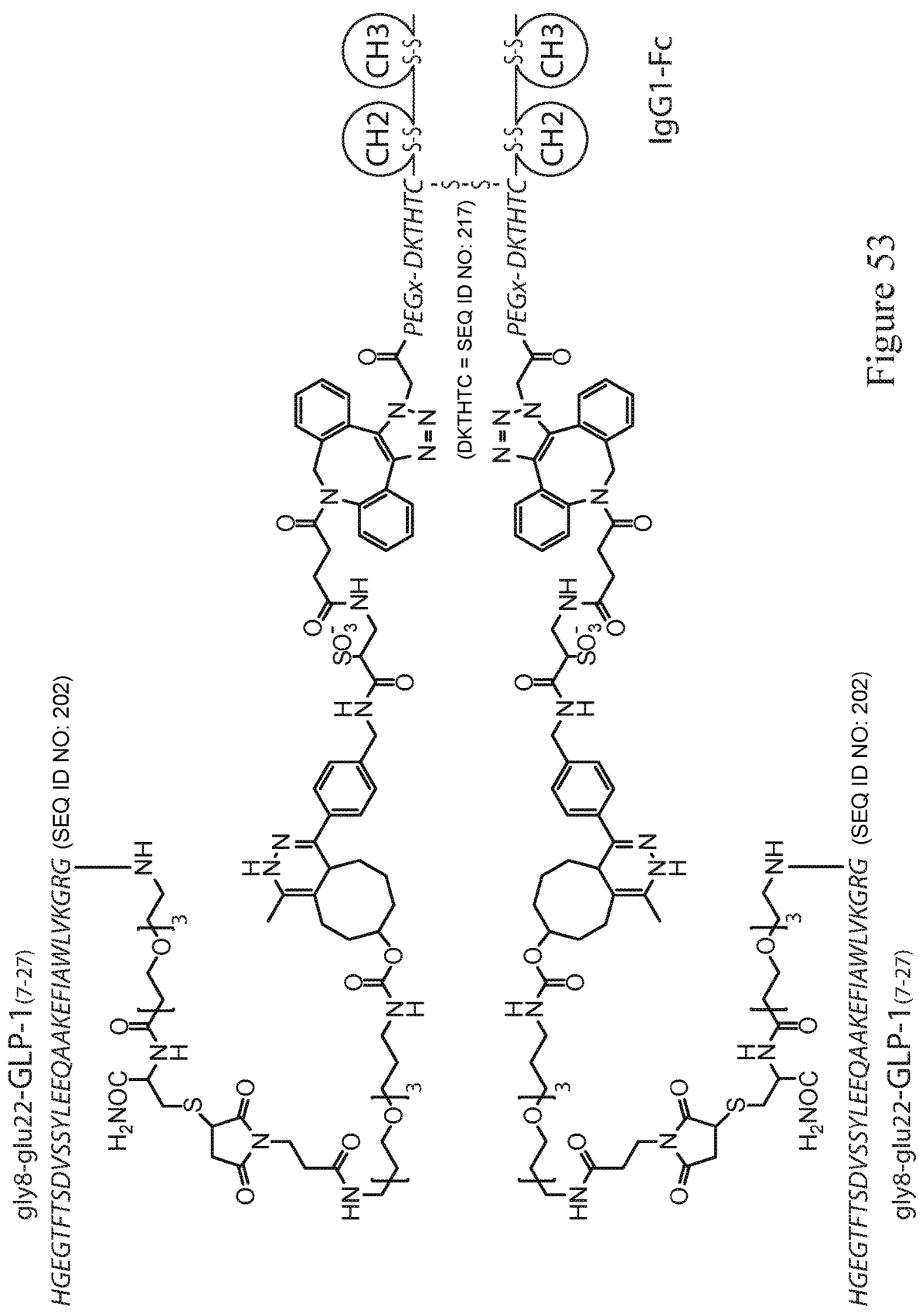
FIG. 53 shows the structure of the GLP1-dihydropyridizine-Fc hybrid immunoglobulins.

The GLP1-P6-Tco peptide was reacted individually with each of the Tet-Px-Fc proteins (FIG. 52), to generate the GLP1-P3-TT-Px-Fc series of hybrid immunoglobulins (FIG. 53). Reactions (0.99 ml) contained 0.1 M sodium phosphate pH 7.0, 0.145 mg of GLP1-P6-Tco peptide and 0.33 mg of each Tet-Px-Fc proteins. Reactions were carried out at room temperature for 30 minutes. The GLP1-P6-TT-Px-Fc hybrid immunoglobulins were then purified by chromatography on HiTrap Protein A HP.

Figure 54:
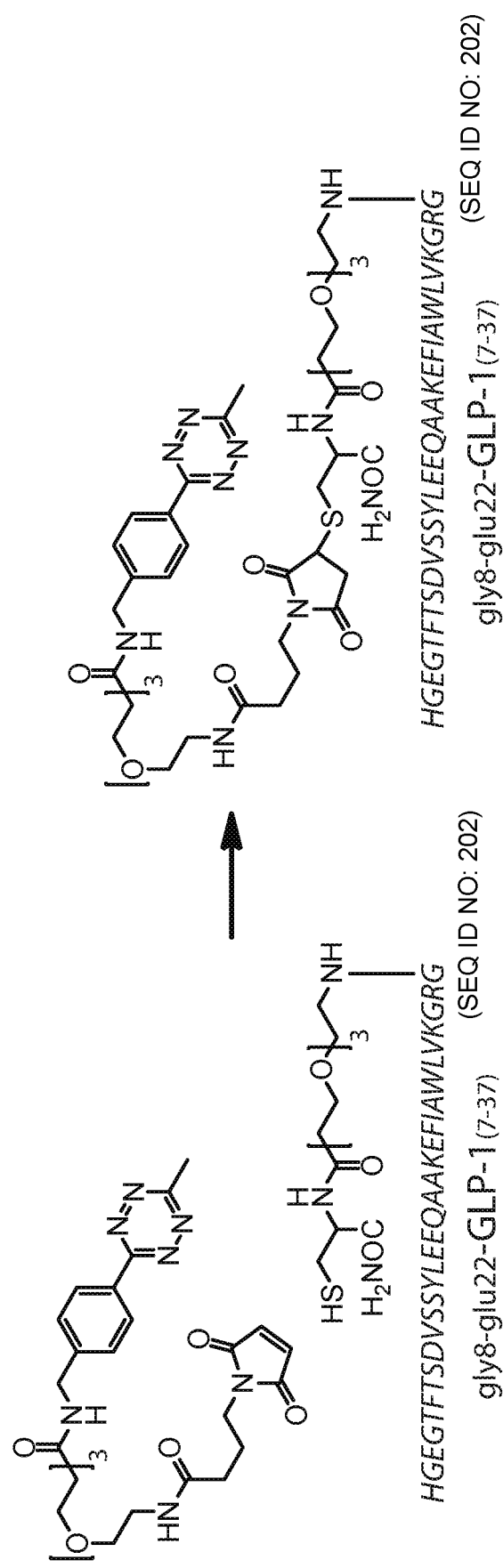
FIG. 54 shows the structure and synthesis of the tetrazine-modified GLP-1 analog (GLP1-P6-Tet).

To prepare the tetrazine-modified GLP-1 analog, the gly8-glu22-GLP-1(7-37)-PEG3-cys-NH2 peptide is reacted with a heterobifunctional linker, Tetrazine-PEG4-Maleimide, which contains a maleimide group capable of reacting with the free thiol group on the C-terminal cysteine residue (FIG. 54). Tetrazine-PEG4-Maleimide ($C_{29}H_{39}N_7O$, mol weight 613.66) was obtained from Click Chemistry Tools (Item No. A139). Prior to use, the linker is dissolved at a concentration of 25 mg/mL in DMSO. Reactions (0.42 ml) contain 50 mM MES pH 6.5, 5 mM EDTA, 0.45 mg of gly8-glu22-GLP-1(7-37)-PEG3-cys-NH2 peptide and 0.375 mg of the Tetrazine-PEG4-Maleimide linker. Reactions are carried out at room temperature for 60 minutes. Excess unreacted linker is removed by buffer-exchange into 0.02 M sodium phosphate pH 7.0 using a 5 mL HiTrap Desalting Column. FIG. 54 shows the structure of the tetrazine-modified GLP-1 analog (GLP1-P7-Tet).

Figure 55:
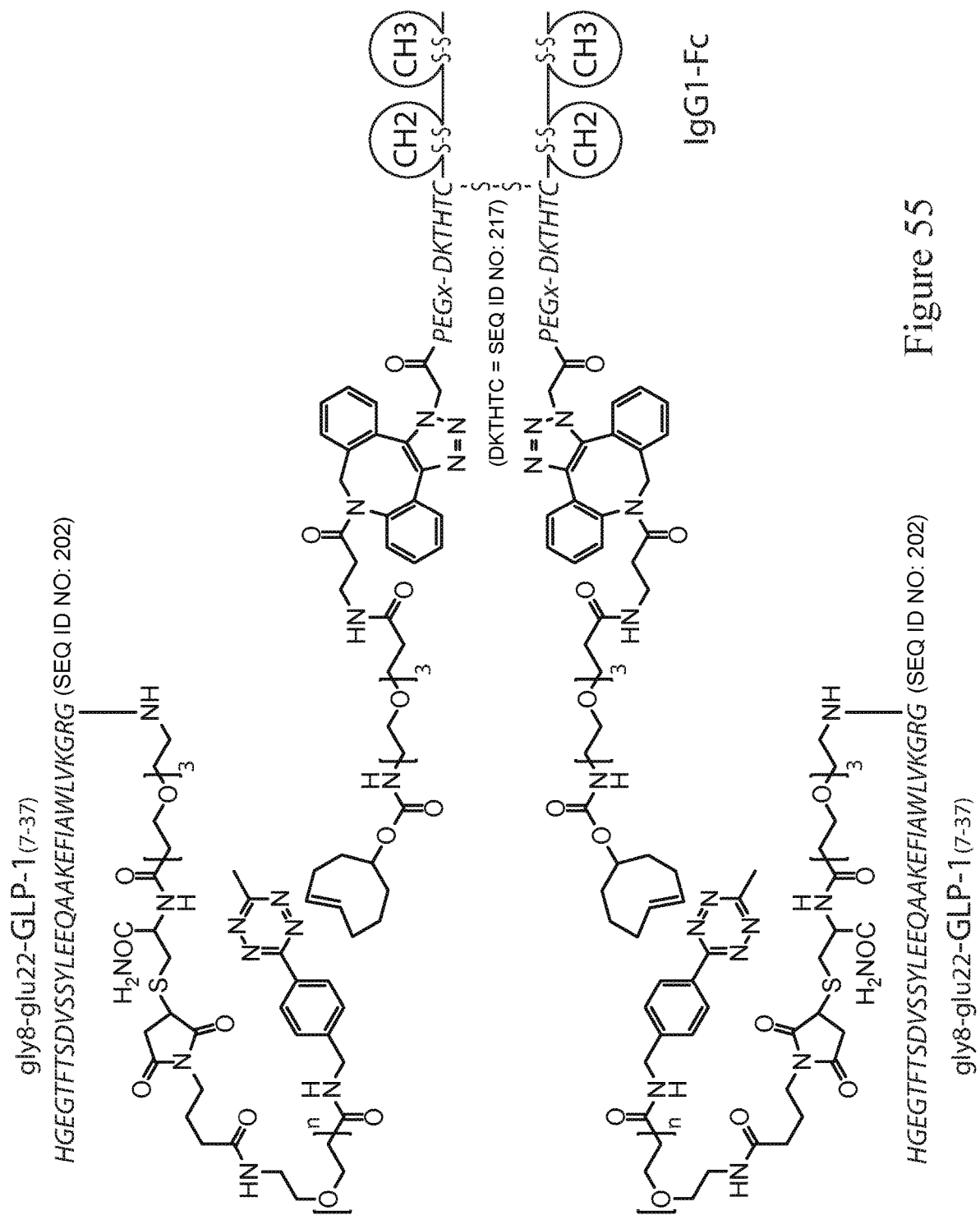
FIG. 55 shows the reaction between GLP1-P6-Tet peptide and the Tco-Px-Fc proteins.
Figure 56:
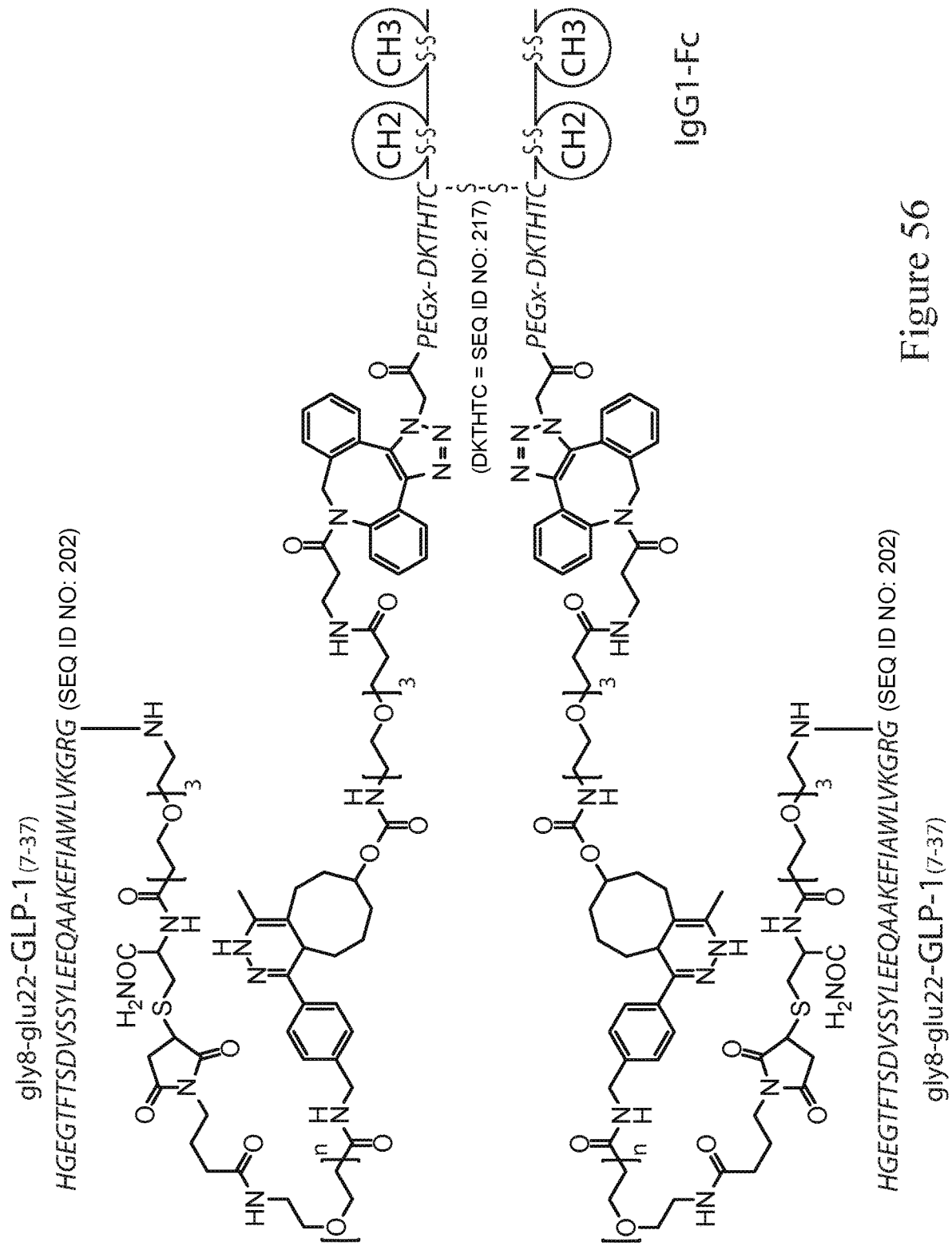
FIG. 56 shows the structure of the GLP1-P6-TT-Px-Fc hybrid immunoglobulins.

The GLP1-P7-Tet peptide is reacted individually with each of the Tco-Px-Fc proteins (FIG. 55), to generate the GLP1-P7-TetTco-Px-Fc series of hybrid immunoglobulins (FIG. 56). Reactions (0.99 ml) contain 0.1 M sodium phosphate pH 7.0, 0.145 mg of GLP1-P7-Tet peptide and 0.33 mg of each Tco-Px-Fc protein. Reactions are carried out at room temperature for 30 minutes. The GLP1-P7-Tet/Tco-Px-Fc hybrid immunoglobulins are then purified by chromatography on HiTrap Protein A HP.

Figure 57:
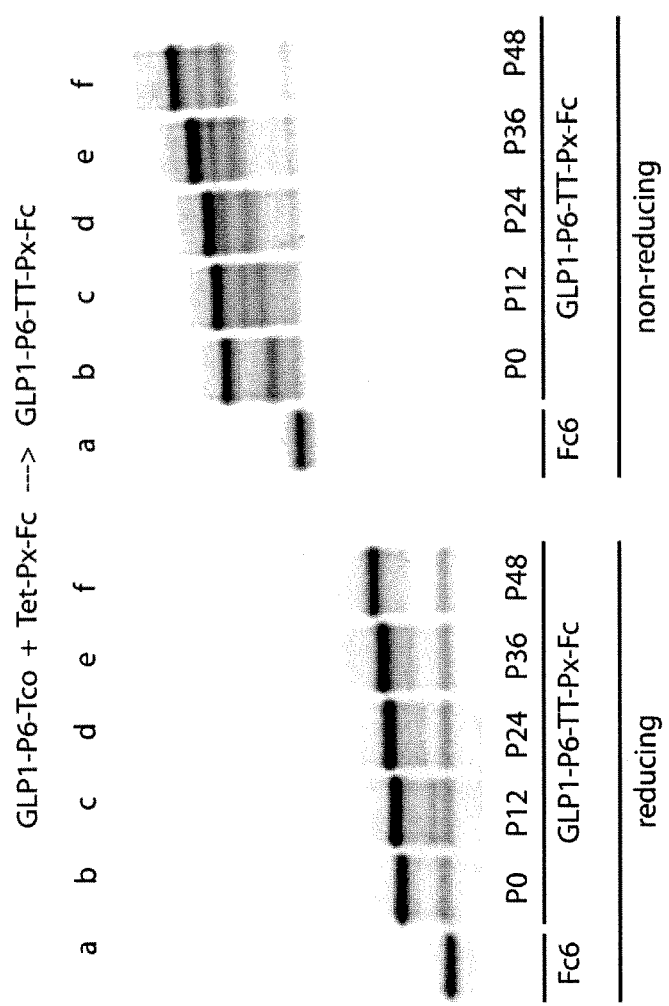
FIG. 57 shows the purified GLP1-dihydropyridizine-Fc hybrid immunoglobulins by SDS-PAGE under reducing conditions (left) and non-reducing conditions (right): Fc6 control (lanes a), GLP1-P6-TT-P0-Fc (lanes b), GLP1-P6-TT-P12-Fc (lanes c), GLP1-P6-TT-P24-Fc (lanes d), GLP1-P6-TT-P36-Fc (lanes e), and GLP1-P6-TT-P48-Fc (lanes f).

FIG. 57 shows the purified GLP1-dihydropyridizine-Fc hybrid immunoglobulins by SDS-PAGE under reducing conditions (left) and non-reducing conditions (right): Fc6 control (lanes a), GLP1-P6-TT-P0-Fc (lanes b), GLP1-TT-P12-Fc (lanes c), GLP1-P6-TT-P24-Fc (lanes d), GLP1-P6-TT-P36-Fc (lanes e), and GLP1-P6-TT-P48-Fc (lanes f). The size of GLP1-dihydropyridizine-Fc hybrid immunoglobulins increased with PEG linker length comparable to the Tet-Px-Fc proteins.

Figure 58:
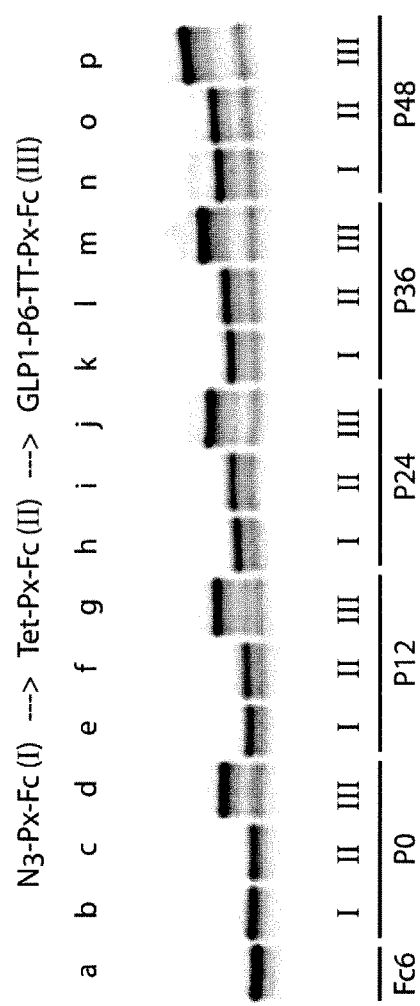
FIG. 58 directly compares the N3-Px-Fc (I) proteins, the Tet-Px-Fc (II) proteins, and the GLP1-dihydropyridizine-Fc (III) hybrid immunoglobulins by SDS-PAGE under reducing conditions: Fc6 control (lane a), N3-P0-Fc (lane b), Tet-P0-Fc (lane c), GLP1-P6-TT-P0-Fc (lane d), N3-P12-Fc (lane e), Tet-P12-Fc (lane f), GLP1-P6-TT-P12-Fc (lane g), N3-P24-Fc (lane h), Tet-P24-Fc (lane i), GLP1-P6-TT-P24-Fc (lane j), N3-P36-Fc (lane k), Tet-P36-Fc (lane l), GLP1-P6-TT-P36-Fc (lane m), N3-P48-Fc (lane n), Tet-P48-Fc (lane o), GLP1-P6-TT-P48-Fc (lane p).

FIG. 58 directly compares the N3-Px-Fc (I) proteins, the Tet-Px-Fc (II) proteins, and the GLP1-dihydropyridizine-Fc (III) hybrid immunoglobulins by SDS-PAGE under reducing conditions: Fc6 control (lane a), $N_3$—P0-Fc (lane b), Tet-P0-Fc (lane c), GLP1-P6-TT-P0-Fc (lane d), $N_3$—P12-Fc (lane e), Tet-P12-Fc (lane f), GLP1-P6-TT-P12-Fc (lane g), $N_3$—P24-Fc (lane h), Tet-P24-Fc (lane i), GLP1-P6-TT-P24-Fc (lane j), $N_3$—P36-Fc (lane k), Tet-P36-Fc (lane 1), GLP1-P6-TT-P36-Fc (lane m), $N_3$-P48-Fc (lane n), Tet-P48-Fc (lane o), GLP1-P6-TT-P48-Fc (lane p). The conversion of each Tet-Px-Fc protein to the corresponding GLP1-P6-TT-Px-Fc hybrid immunoglobulin was approximately 92%.

Figure 59:
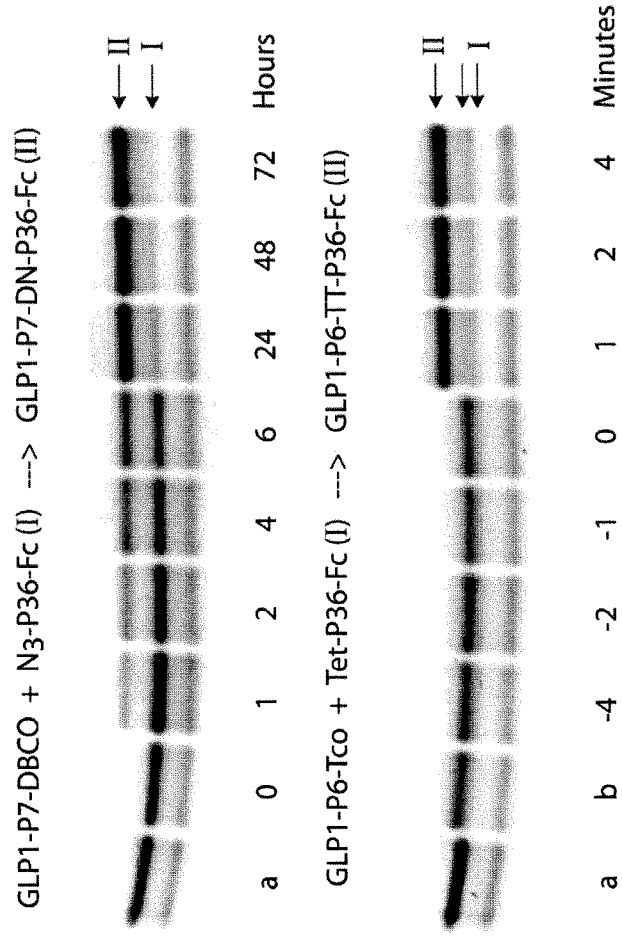
FIG. 59 shows a time course for the reaction of GLP1-P7-DBCO with N3-P36-Fc and a time course for the reaction of GLP1-P6-Tco with Tet-P36-Fc.

FIG. 59 shows a time course for the reaction of GLP1-P7-DBCO with $N_3$-P36-Fc and a time course for the reaction of GLP1-P6-Tco with Tet-P36-Fc. Reactions were carried out as described above for the various times indicated, except that each reaction was terminated by the addition of an excess of competitor. For the reaction of GLP1-P7-DBCO with $N_3$-P36-Fc, sodium azide was added to a final concentration of 0.1%; for the reaction of GLP1-P6-Tco with Tet-P36-Fc, TCO-PEG3-Maleimide was added to a final concentration of 3.5 mg/ml. Each reaction was analyzed SDS-PAGE under reducing conditions: (upper panel) $N_3$-P36-Fc alone (lane a), $N_3$—P36-Fc+GLP1-P7-DBCO for the following times, 0, 1, 2, 4, 6, 24, 48, 72 hours; (lower panel) Tet-P36-Fc alone (lane a), Tet-P36-Fc+TCO-PEG3-Maleimide alone (lane b), Tet-P36-Fc+GLP1-P6-Tco for the following times, −4, −2, −1, 0, 1, 2, 4 minutes. The reaction of GLP1-P6-Tco with Tet-P36-Fc (I) leading to the formation of GLP1-P7-DN-P36-Fc (II) is much faster, reaching completion within 1 minute, whereas the reaction of the GLP1-P7-DBCO with $N_3$-P36-Fc (I) leading to the formation of GLP1-P7-DN-P36-Fc (II) is only 50% complete after 6 hours.

Figure 60:
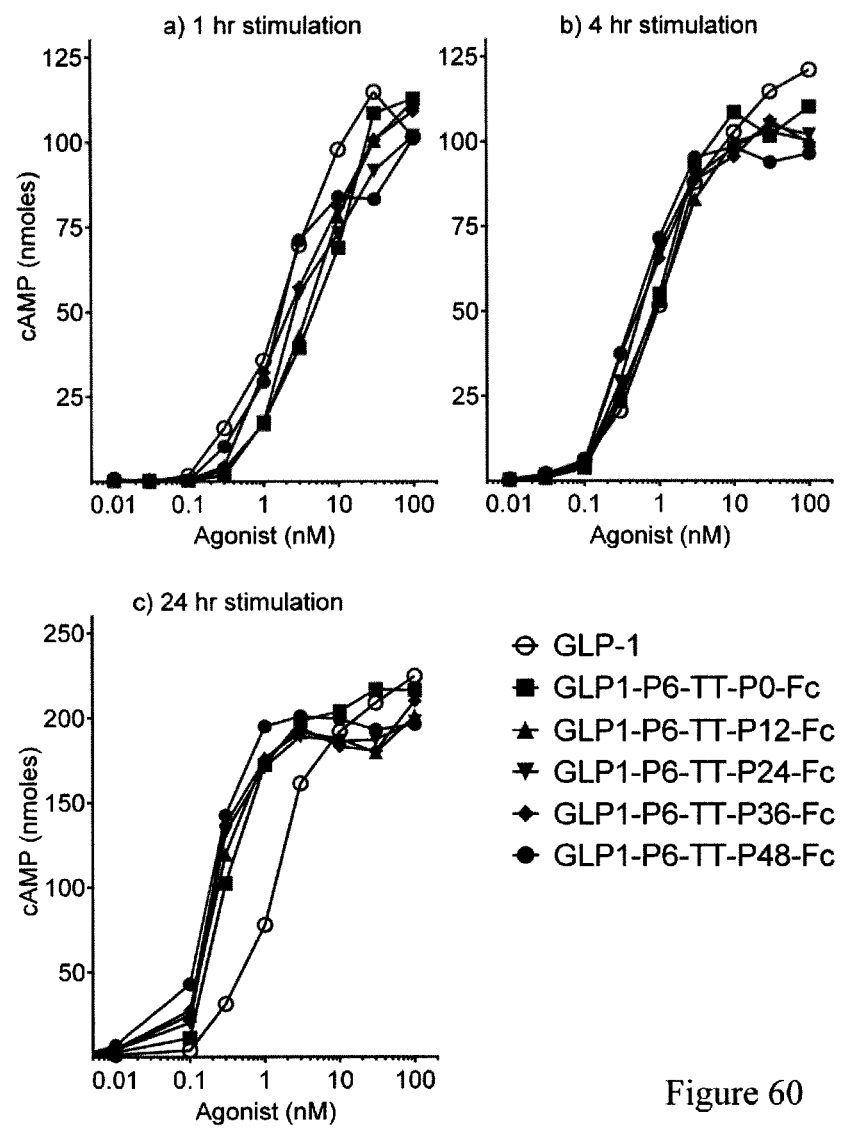
FIG. 60 compares the induction of cAMP synthesis in GLP-1 receptor expressing cells by GLP1-dihydropyridizine-Fc hybrid immunoglobulins and GLP-1.

The biological activity of GLP1-P6-dihydropyridizine-Px-Fc hybrid immunoglobulins was evaluated in a cell-based assay as described in Example 6. FIG. 60 shows the results for GLP-1(7-37) peptide and the GLP1-P6-TT-Px-Fc proteins (x=0, 12, 24, 36, 48). All five GLP1-dihydropyridizine-Fc hybrid immunoglobulins induced cAMP levels comparable to GLP-1(7-37) peptide. Stimulation by GLP-1 (7-37) was similar whether cells were exposed to agonist for 1, 4 or 24 hours, with an EC50 of ~2 nM at 24 hours, whereas stimulation by the GLP1-dihydropyridizine-Fc hybrid immunoglobulins increased dramatically as cells were exposed to agonist for longer times, with an EC50 of ~0.2 nM at 24 hours.

Example 14: Adalilimumab Fab-Dihydropyridizine-Fc Hybrid Immunoglobulins

A series of Fab-dihydropyridizine-Fc hybrid immunoglobulins (Fab-P3-TT-Px-Fc) were prepared by reacting a transcycloctene-modified Fab fragment with the Tet-Px-Fc proteins of Example 11. Fab-dihydropyridizine-Fc hybrid immunoglobulins are also prepared by reacting a a tetrazine-modified Fab fragment with the Tco-Px-Fc proteins of Example 12.

Figure 61:
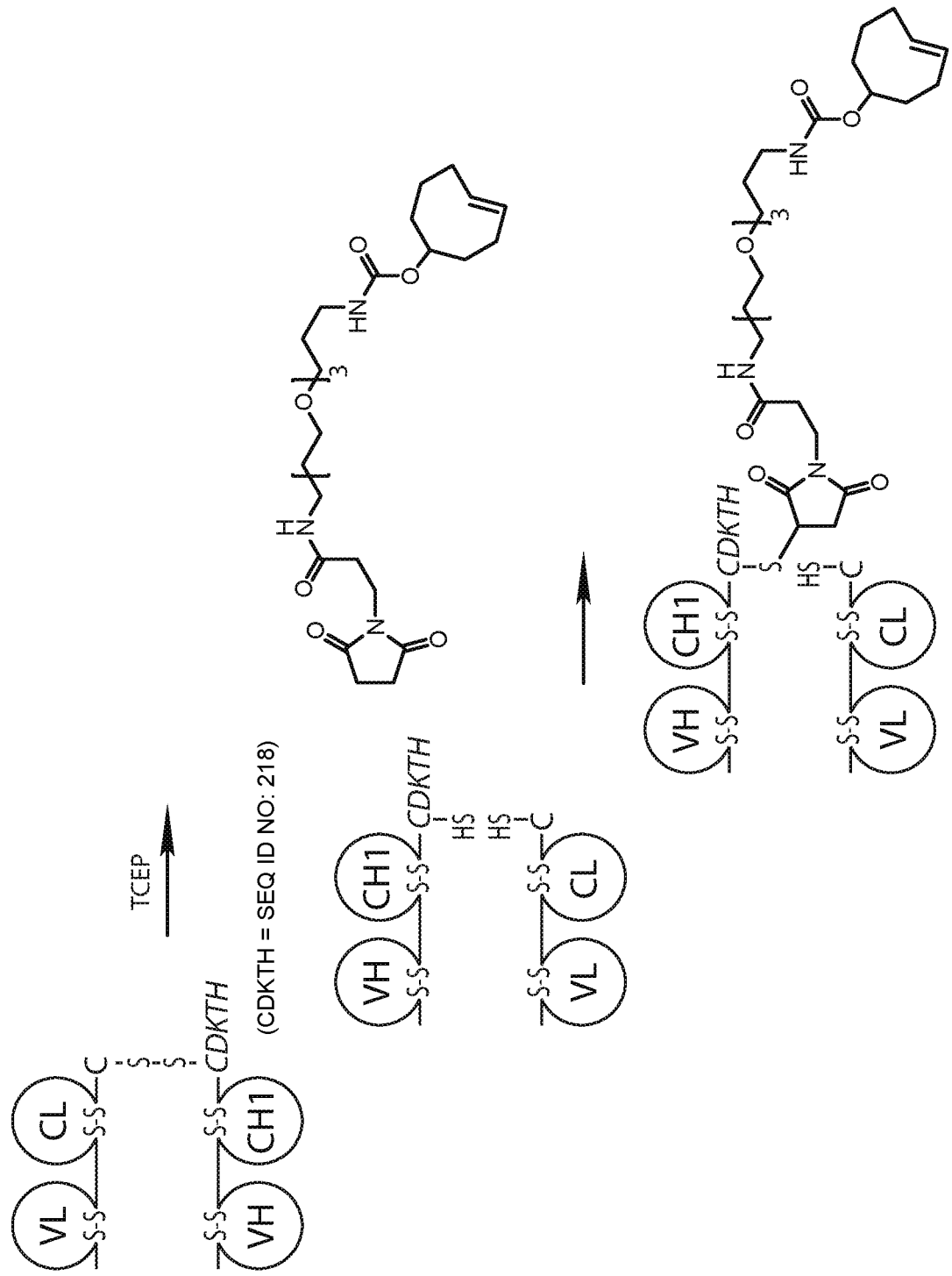
FIG. 61 shows the structure and synthesis of the transcyclooctene-modified adalimumab Fab (Fab-P3-Tco).

To prepare the transcyclooctene-modified Fab, TCEP-treated Fab was reacted with a heterobifunctional linker, TCO-PEG3-Maleimide, which contains a maleimide group capable of reacting with a free thiol group on the TCEP-treated Fab (FIG. 61). The Fab fragment was generated by papain digestion of 10 mg of adalimumab (Humira™) obtained from Abbott using a Pierce™ Fab Preparation Kit (Cat. No. 44985) according to the manufacturer's instructions. Following digestion, the Fab fragment was purified by chromatography on HiTrap Protein A HP to remove the Fc fragment and undigested antibody. The flow-through fractions, containing the Fab fragment, were buffer-exchanged into PBS, and concentrated to 5 mg/ml.

For the partial reduction of the Fab fragment with TCEP, reactions (0.26 ml) contained 0.1 M sodium phosphate pH 7.0, 0.5 mg of Fab, and 0.08 mg/ml TCEP. Following incubation for at room temperature for 60 minutes, the reaction was brought to 0.72 ml with the addition of 0.24 ml of 0.3 M sodium phosphate pH 7.0 and 0.22 ml of water. The TCO-PEG3-Maleimide linker was then added to the reaction (0.12 ml of at a concentration of 50 ug/ml in DMSO) and the reaction incubated for 20 minutes at room temperature. The transcyclooctene-modified Fab was buffered-exchanged on a PD-10 column into 0.02 M sodium phosphate pH 7.0 to remove excess linker, and the final product concentrated to 2.7 mg/ml. Under these conditions, greater than 90% of the Fab heavy chain and less than 10% of the Fab light chain was modified by the TCO-PEG3-Maleimide linker. FIG. 61 shows the structure of the transcyclooctene-modified Fab protein (Fab-P3-Tco).

Figure 62:
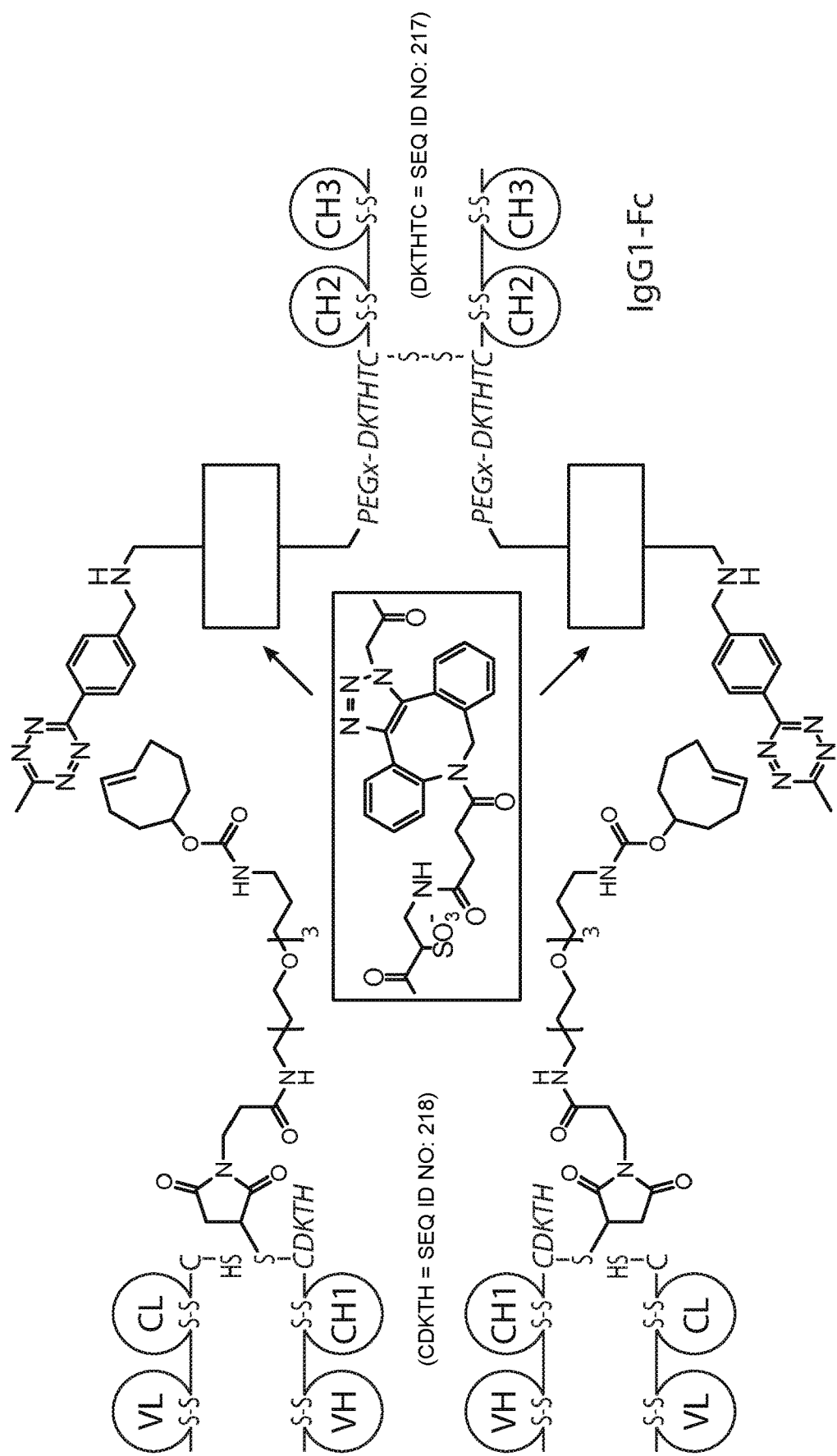
FIG. 62 shows the reaction between Fab-P3-Tco protein and the Tet-Px-Fc proteins.
Figure 63:
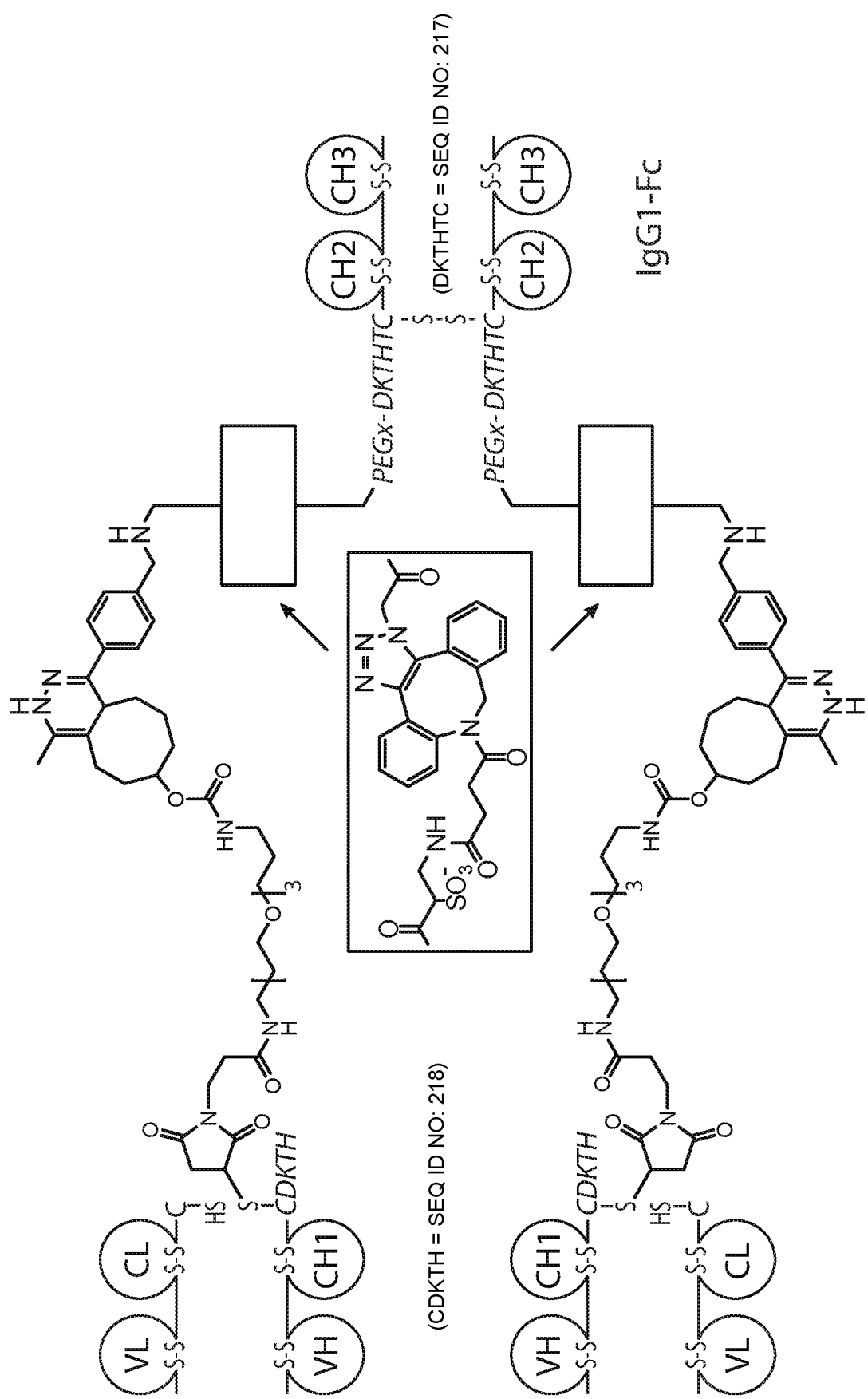
FIG. 63 shows the structure of the Fab-dihydropyridizine-Fc hybrid immunoglobulins.

The Fab-P3-Tco protein was reacted individually with each of the Tet-Px-Fc proteins (FIG. 62), to generate the Fab-P3-TT-Px-Fc series of hybrid immunoglobulins (FIG. 63). Reactions (6 ul) contained 0.1 M sodium phosphate pH 7.0, 3.6 ug of the Fab-P3-Tco protein and 1ug of each Tet-Px-Fc protein. Reactions were carried out at room temperature for 60 minutes.

Figure 64:
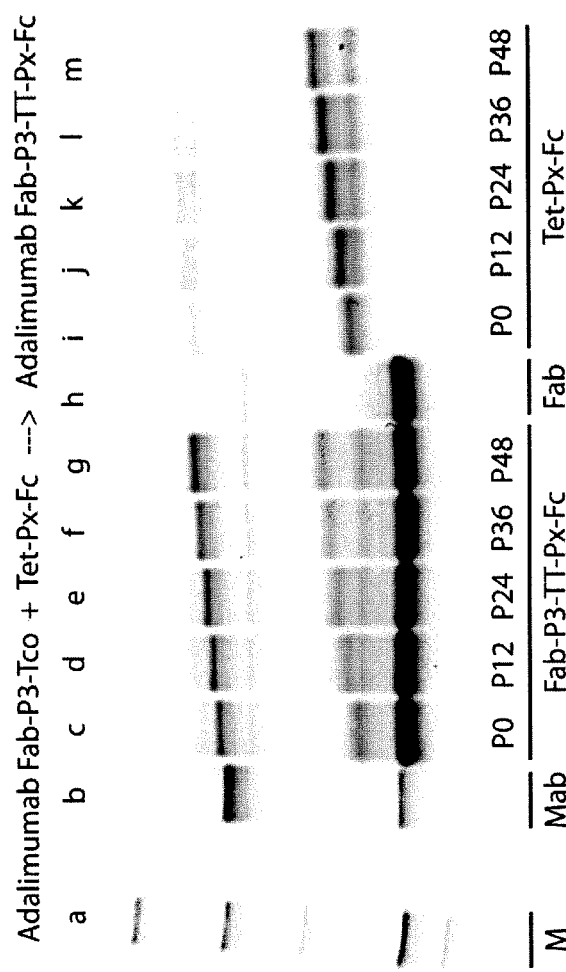
FIG. 64 shows the Fab-dihydropyridizine-Fc hybrid immunoglobulins by SDS-PAGE under reducing conditions: markers (lanes a), adalimumab (lane b), Fab-P3-TT-P0-Fc (lane c), Fab-P3-TT-P12-Fc (lane d), Fab-P3-TT-P24-Fc (lanes e), Fab-P3-TT-P36-Fc (lanes f), Fab-P3-TT-P48-Fc (lane g), Fab-P3-Tco (lane h), Tet-P0-Fc (lane i), Tet-P12-Fc (lane j), Tet-P24-Fc (lane k), Tet-P36-Fc (lane l)m Tet-P48-Fc (lane m).

FIG. 64 shows the Fab-dihydropyridizine-Fc hybrid immunoglobulins by SDS-PAGE under reducing conditions: markers (lanes a), adalimumab (lane b), Fab-P3-TT-P0-Fc (lane c), Fab-P3-TT-P12-Fc (lane d), Fab-P3-TT-P24-Fc (lanes e), Fab-P3-TT-P36-Fc (lanes f), Fab-P3-TT-P48-Fc (lane g), Fab-P3-Tco (lane h), Tet-P0-Fc (lane i), Tet-P12-Fc (lane j), Tet-P24-Fc (lane k), Tet-P36-Fc (lane 1)m Tet-P48-Fc (lane m). By comparison with adalimumab (lane b), the Fab-dihydropyridizine-Fc hybrid immunoglobulins had the expected size, showing an increase with PEG linker length comparable to the Tet-Px-Fc proteins. The conversion of each Tet-Px-Fc protein to the corresponding Fab-P3-TT-Px-Fc hybrid immunoglobulin was approximately 75%.

Example 15: Olanzapine-Dihydropyridizine-Fc Hybrid Immunoglobulins

In this example, hybrid immunoglobulins are prepared with an azide-derivative of a primary amine, secondary amine or alcohol compound. The azide-derivatized compond may be prepared as described in Pothukanuri, S. and Winssinger, N., Org Lett. 2007; 9(11):2223-5, hereby incorporated by reference. The primary amine, secondary amine or alcohol compound is first reacted with chloroalkyl chloroformate to obtain the chloroalkyl carbamate, followed by an azide displacement of the chloride, affording the azidoalkyl carbamate. All chemicals are obtained from Sigma-Aldrich.

Olanzapine (Sigma Cat. No. 01141) is first reacted with chloromethyl chloroformate as described in U.S. patent application Ser. No. 13/801,344, published Oct. 10, 2013, Publication No. US20130267505 A1, hereby incorporated by reference. A solution of olazapine (60 mmoles) and triethylamine (120 mmoles) in anhydrous dichloromethane (250 ml) is warmed to 35° C. until a clear solution is formed, then cooled to 5° C. Chloromethyl chloroformate (90 mmoles) is then added over 20 minutes. Other suitable chloroalkyl chloroformates include 2-chloroethyl chloroformate, 3-chloropropyl chloroformate, and 4-chlorobutyl chloroformate. The reaction is stirred at room temperature for 30 min and allowed to warm to room temperature. After 15 min at room temperature the reaction mixture is diluted with dichloromethane (100 ml) then washed with aqueous saturated $NaHCO_3$ (75 ml) and water (350 ml). The organic phase is dried over MgSO4 and filtered. The organic phase is then concentrated under vacuum at 45° C. to a volume of 150 ml. The mixture is diluted with 30 ml ethyl acetate and is further evaporated (20-30 ml) under vacuum. The mixture is cooled to room temperature and the resulting solid precipitate is filtered and washed with ethyl acetate. After drying under vacuum at 35° C. for 90 min, chloromethyl 2-methyl-4-(4-methylpiperazin-1-yl)-5H-benzo[b]thieno[2,3-e][1,4]diazepine-5-carboxylate is obtained. This compound (1.5 eq) is then treated with $NaN_3$ (1.5 eq) in $CH_3CN:H2O$ (1:1, 0.3 M) at room temperature for 8 to 36 hours. The reaction mixture is diluted with ethyl acetate and the organic phase is washed with water, brine then dried over $Na_2SO_4$ and concentrated in vacuo. Purification by HPLC affords the azide-olanzapine derivative, azidomethyl 2-methyl-4-(4-methylpiperazin-1-yl)-5H-benzo[b]thieno[2,3-e][1,4]diazepine-5-carboxylate (FIG. 65).

The azide-olanzapine derivative is then used to prepare series of olanzapine-dihydropyridizine-Fc hybrid immunoglobulins (Ola-P12-TT-Px-Fc) as follows. In a first step, the azide-olanzapine derivative is modified with a transcyclooctene functional group using a heterobifunctional linker. In a second step, the transcycloctene-modified olanzapine is reacted with the Tet-Px-Fc proteins of Example 11.

Figure 65:
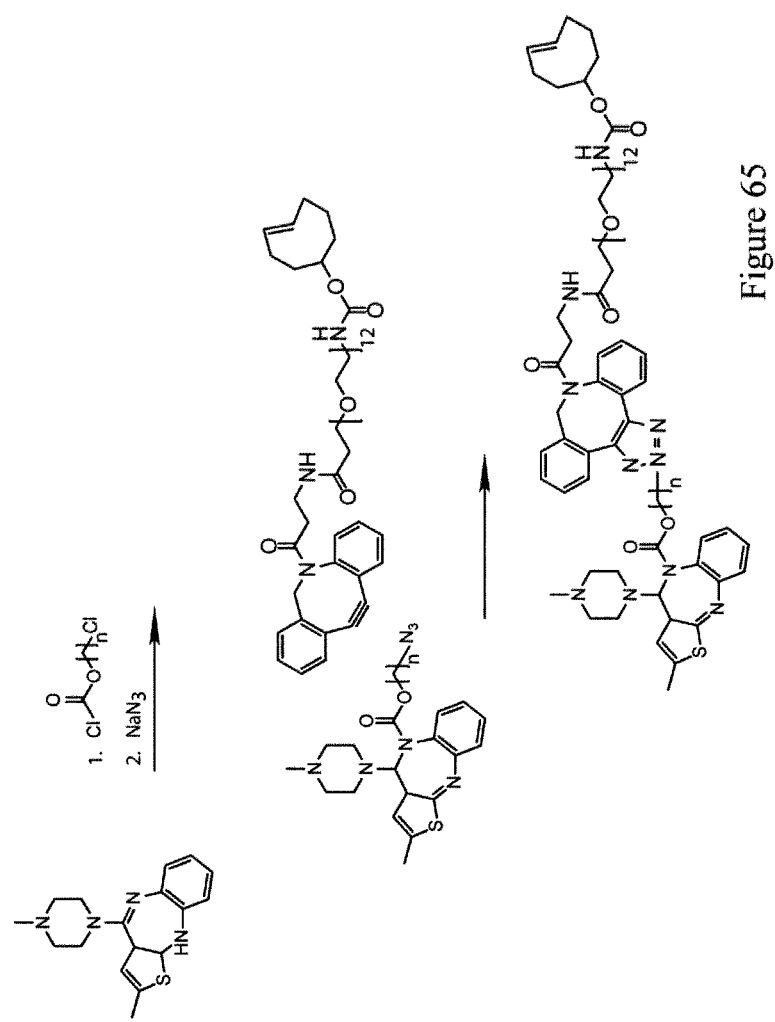
FIG. 65 shows the structure and synthesis of azide-modified and transcyclooctene-modified olanzapine (Ola-P12-Tco).

To prepare the transcyclooctene-modified olanzapine, the azide-olanzapine derivative is reacted with the heterobifunctional linker TCO-PEG12-DBCO which contains a cyclooctyne group capable of reacting with the azide group (FIG. 65). Reactions (1 ml) contain 0.5 mg of the azide-olanzapine deivative and 5 mg of the TCO-PEG12-DBCO linker in DMSO. Reactions are carried out at room temperature for 3 to 20 hours. The transcycloctene-modified olanzapine (Ola-P12-Tco) is purified by HPLC to remove excess unreacted TCO-PEG12-DBCO linker. Prior to use, Ola-P12-Tco is dissolved at a concentration of 1 mg/mL in DMSO.

Figure 66:
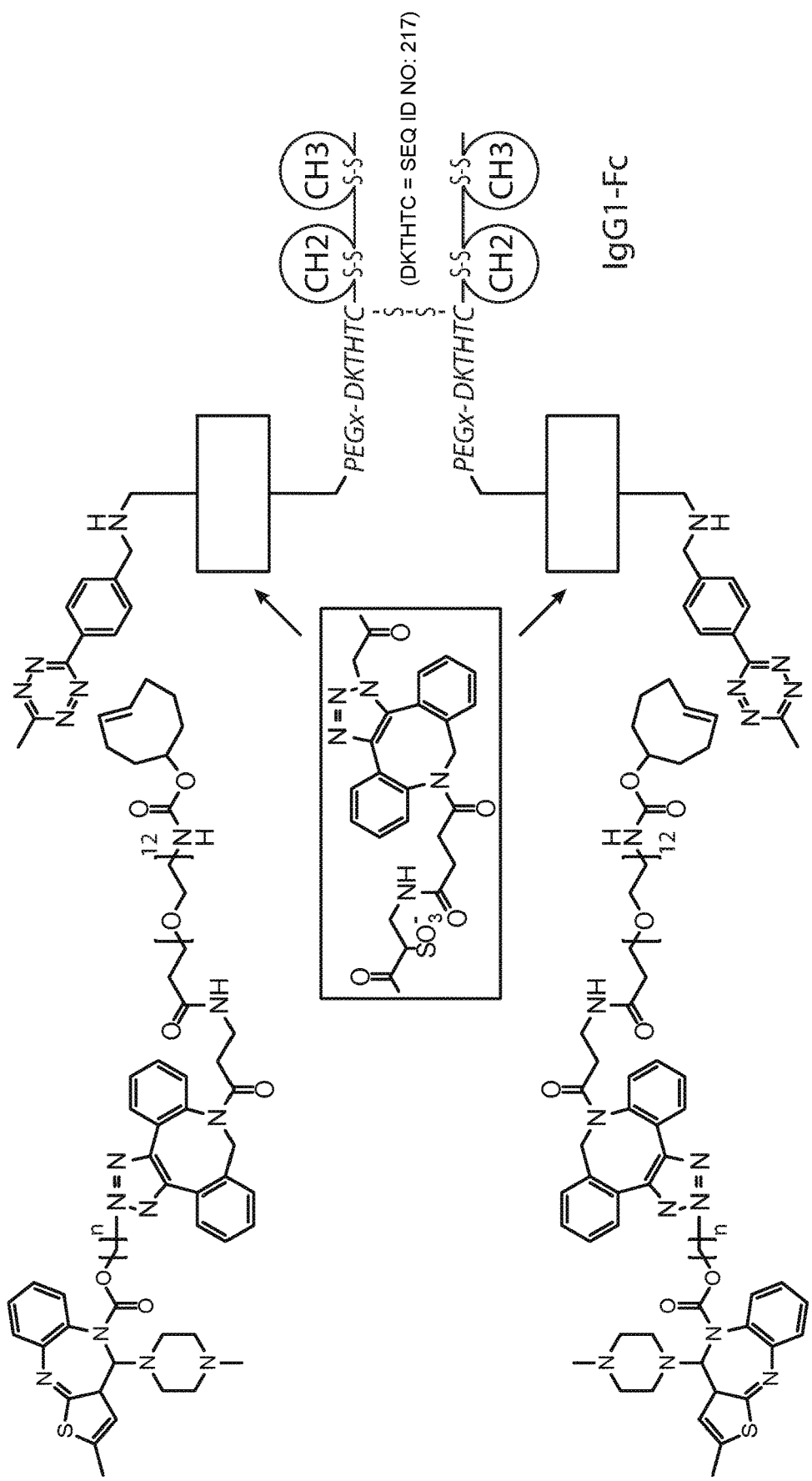
FIG. 66 shows the reaction between Ola-P12-Tco and the Tet-Px-Fc proteins.
Figure 67:
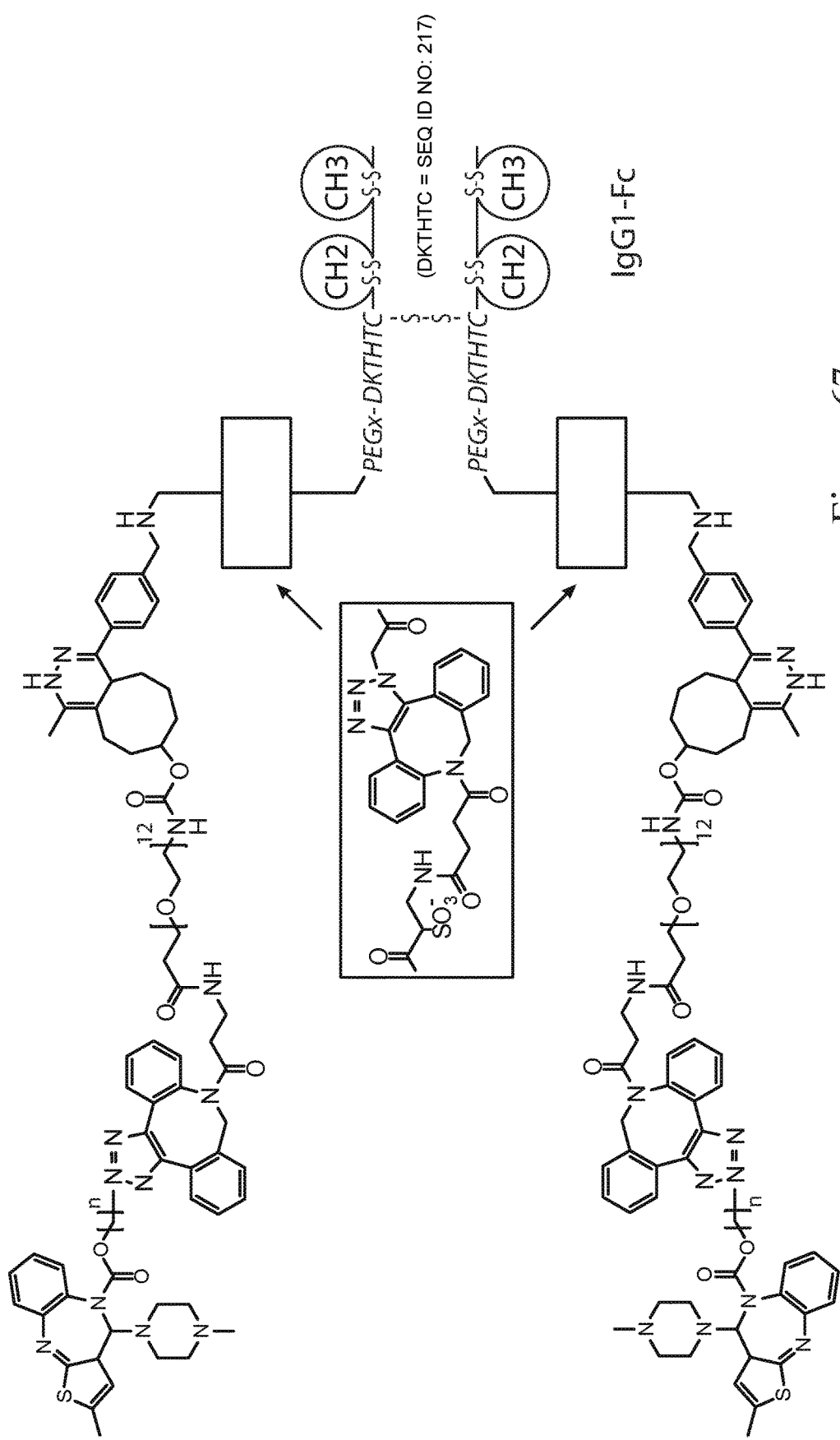
FIG. 67 shows the structure of olanzapine-dihydropyridizine-Fc hybrid immunoglobulins.

Ola-P12-Tco is reacted individually with each of the Tet-Px-Fc proteins (FIG. 66), to generate the Ola-P12-TT-Px-Fc series of hybrid immunoglobulins (FIG. 67). Reactions (1 ml) contain 0.1 mg of GLP1-P7-Tet peptide and 0.33 mg of each Tco-Px-Fc protein in DMSO. Reactions are carried out at room temperature for 60 minutes. The Ola-P12-TT-Px-Fc hybrid immunoglobulins are then purified by chromatography on HiTrap Protein A HP.

DISCUSSION

Aspects of the present invention provide the chemical semisynthesis of antibodies with nonprotein hinges that incorporate large binding domains such as the Fab itself or receptor extracellular domains. The present invention relates to the identification of ligation reactions that are compatible with the native structure and function of the cognate proteins and proceed efficiently. Aspects of the present invention provide compounds having nonprotein chains that are both flexible and extendible. Antibody-like molecules provided in embodiments of the invention have enormous potential as therapeutic candidates with improved binding affinity for their disease targets.

What is claimed is:

1. A compound having the structure:

A-B - - - Z wherein A is a biologically active structure of the compound;

wherein Z is a protein component of the compound, which protein component comprises one or more polypeptides, wherein at least one of the one or more polypeptides comprises consecutive amino acids which (i) are identical to a stretch of consecutive amino acids present in a chain of an $F_c$ domain of an antibody; (ii) bind to an $F_c$ receptor; and (iii) have at their N-terminus a cysteine or a selenocysteine;

wherein B is (a) an organic acid residue or (b) a stretch of consecutive amino acid residues which is, or is present in any of the following sequences: EPKSCDKTH-TCPPCP (SEQ ID NO: 213), ERKCCVECPPCP (SEQ ID NO: 214), ELKTPLGDTTHTCPRCP (EPKSCDTPPPCPRCP)3 (SEQ ID NO: 215), or ESKYGPPCPSC (SEQ ID NO: 216);

wherein the dashed line between B and Z represents a peptidyl linkage between the N-terminal cysteine or selenocysteine of Z and an amino acid residue or an organic acid residue of B; and wherein the solid line between A and B represents a nonpeptidyl linkage comprising the structure:

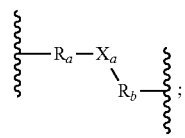

wherein $X_a$ is a chemical structure containing a cyclooctane fused to a dihydropyridazine; and wherein $R_a$ represents an organic structure which connects to A and $R_b$ represents an organic structure which comprises

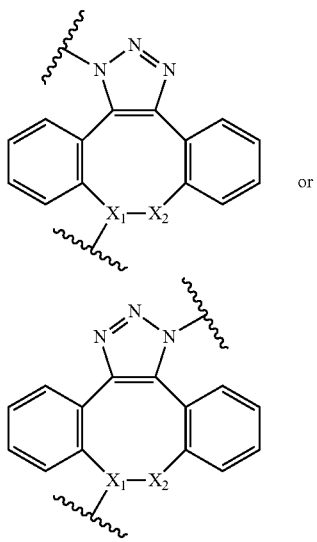

or and connects to B, wherein $X_1$ is CH or N, and $X_2$ is $CH_2$ or a carbonyl group.

2. The compound according to claim 1, wherein $X_a$ has the structure:

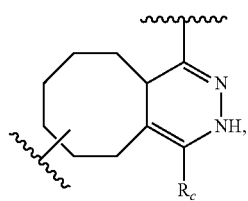

wherein $R_c$ is H, alkyl or aryl;
or a tautomer thereof.

3. The compound according to claim 1, wherein $R_a$ is connected to the cyclooctane and $R_b$ is connected to the dihydropyridazine.

4. The compound according to claim 1, wherein the solid line between A and B represents a nonpeptidyl linkage comprising the structure:

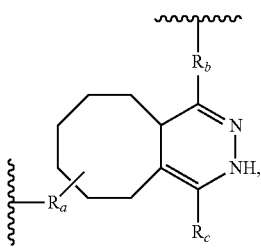

wherein $R_c$ is H, alkyl or aryl;
or a tautomer thereof.

5. The compound according to claim 1, wherein $R_a$ is a bond or an organic structure comprising or consisting of a chain of 1, 2, 3, 4, 5, 6, 7, 8, 9, 10 or more moieties, wherein each moiety is independently selected from the group consisting of [PEG(y)]z, polyalkylene glycol, polyoxyalkylated polyol, polyvinyl alcohol, polyvinyl alkyl ether, poly(lactic acid), poly(lactic-glycolic acid), polysaccharide, a branched residue, $C_1$-$C_{10}$ alkyl, $C_3$-$C_{10}$ cycloalkane, $C_2$-$C_{10}$ alkene, $C_5$-$C_{10}$ cycloalkene, amine, sulfur, oxygen, succinimide, maleimide, glycerol, triazole, isoxazolidine, $C_2$-$C_5$ acyl, $C_2$-$C_5$ acylamino, $C_2$-$C_5$ acyloxy, succinyl, malonyl, glutaryl, phthalyl, adipoyl, an amino acid, an aryl group, a heteroaryl group, a carbamate, a chemical structure containing a cyclooctane fused to a dihydropyridazine, a chemical structure containing a cyclooctene fused to a triazole, a chemical structure containing a cyclooctene fused to a isoxazolidine, a dibenzocyclooctene, a dibenzoazacyclooctene,

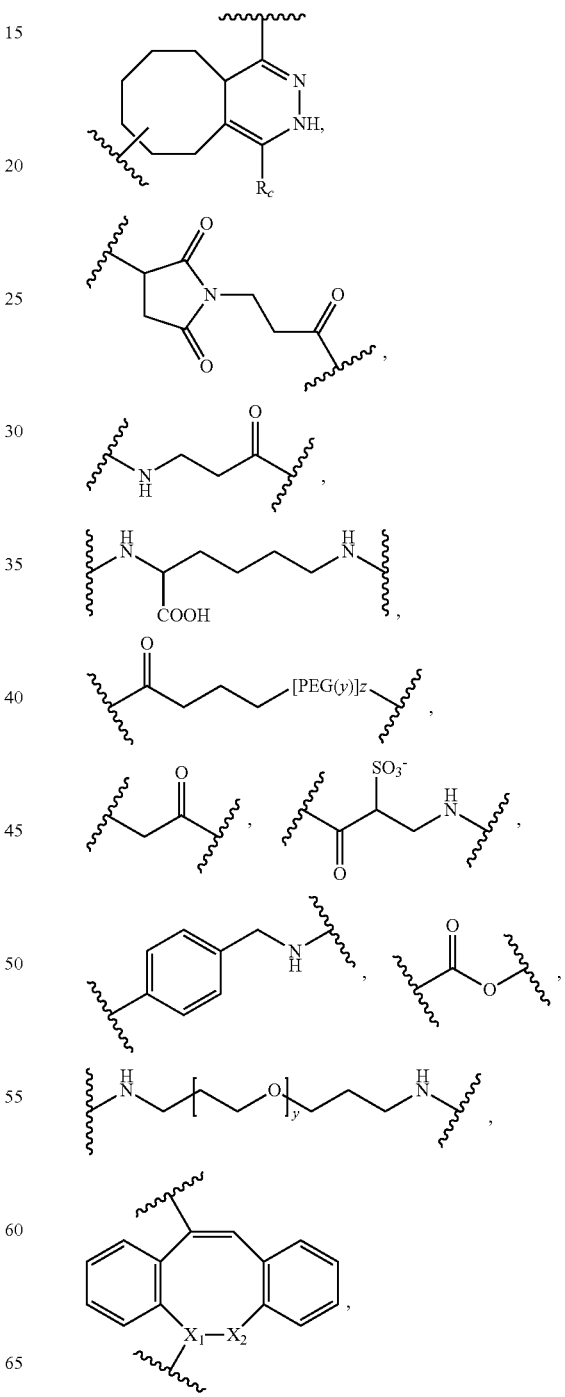

-continued

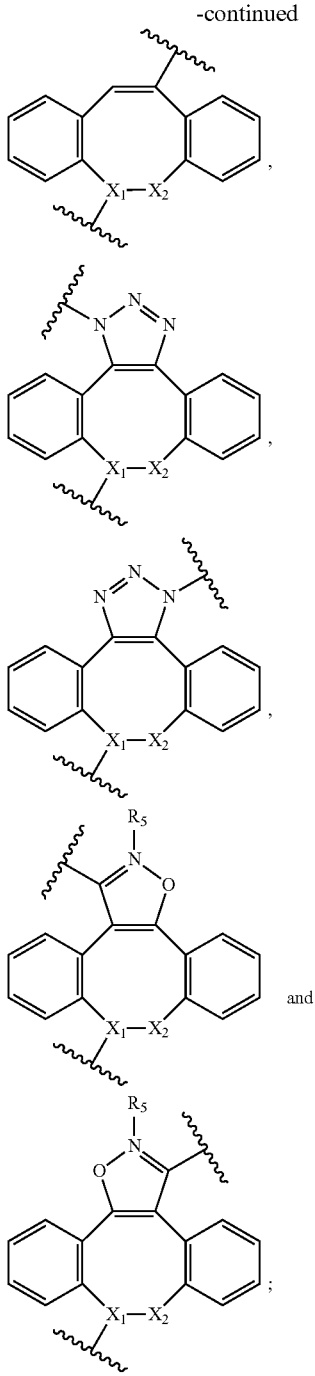

wherein $X_1$ is CH or N, $X_2$ is $CH_2$ or a carbonyl group, and $R_5$ is an aryl or alkyl group;
wherein [PEG(y)]z is:

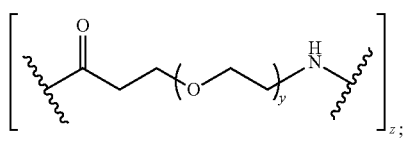

wherein y=1-100 and z=1-10.

6. The compound according to claim 1, wherein $R_a$
   i) is attached to A via a carbon-nitrogen bond or a carbon-sulfur bond;
   ii) is attached to A via a carbon-nitrogen bond;
   iii) is attached to A via a carbon-nitrogen bond, wherein the carbon-nitrogen bond is an amide bond;
   iv) is attached to A via a biologically labile bond;
   v) is attached to A via an amide bond between the C-terminal amino acid of A and an amino group in B;
   vi) is attached to A via an amide bond between the C-terminal amino acid of A and an amino group in B, wherein the terminal amino acid is cysteine;
   vii) is attached to A via a carbon-sulfur bond;
   viii) is attached to A via a carbon-sulfur bond formed between $R_2$ and a free thiol;
   ix) is is attached to A via a succinimide-sulfur bond;
   x) comprises a branched residue; or
   xi) is attached to more than one A via the branched residue.

7. The compound according to claim 1, wherein A
   i) comprises the structure of a compound that is a drug approved for treating a subject afflicted with a disease;
   ii) comprises the structure of an organic compound having a molecular weight less than 1000 Daltons, a DNA aptamer, an RNA aptamer, an oligonucleotide, or a protein that is biologically active;
   iii) comprises a primary or a secondary amine;
   iv) is linked to B via the primary or secondary amine;
   v) is aripiprazole or oseltamivir;
   vi) comprises a secondary amine;
   vii) is a respiratory drug, an antiasthmatic agent, an analgesic agent, an antidepressant, an antianginal agent, an antiarrhythmic agent, an antihypertensive agent, an antidiabetic agent, an antihistamine, an anti-infective agent, an antibiotic, an antiinflamatory agent, an antiparkinsonism drug, an antipsychotics, an antipyretic agent, an antiulcer agent, an attention deficit hyperactivity disorder (ADHD) drug, a central nervous system stimulant, a decongestant, or a psychostimulant;
   viii) is alprenolol, acebutolol, amidephrine, amineptine, amosulalol, amoxapine, amphetaminil, atenolol, atomoxetine, balofloxacin, bamethan, befunolol, benazepril, benfluorex, benzoctamine, betahistine, betaxolol, bevantolol, bifemelane, bisoprolol, brinzolamide, bufeniode, butethamine, camylofine, carazolol, carticaine, carvedilol, cephaeline, ciprofloxacin, clozapine, clobenzorex, clorprenaline, cyclopentamine, delapril, demexiptiline, denopamine, desipramine, desloratadine, diclofenac, dimetofrine, dioxadrol, dobutamine, dopexamine, doripenem, dorzolamide, droprenilamine, duloxetine, eltopraZine, enalapril, enoxacin, epinephrine, ertapenem, esapraZole, esmolol, etoxadrol, fasudil, fendiline, fenethylline, fenfluramine, fenoldopam, fenoterol, fenproporex, flecamide, fluoxetine, formoterol, frovatriptan, gaboxadol, garenoxacin, gatifloxacin, grepafloxacin, hexoprenaline, imidapril, indalpine, indecainide, indeloxazine hydrochloride, isoxsuprine, ispronicline, labetalol, landiolol, lapatinib, levophacetoperane, lisinopril, lomefloxacin, lotrafiban, maprotiline, mecamylamine, mefloquine, mepindolol, meropenem, metapramine, metaproterenol, methoxyphenamine, dextrorotary methylphenidate, methylphenidate, metipranolol, metoprolol, mitoxantrone, mivazerol, moexipril, moprolol, moxifloxacin, nebivolol, nifenalol, nipradilol, norfloxacin, nortriptyline, nylidrin, olanZapine, oxamniquine, oxprenolol, oxyfedrine, paroxetine, perhexyline, phenmetrazine, phenylephrine, phenylpropylmethylamine, pholedrine, picilorex, pimethylline, pindolol, pipemidic acid, piridocaine, practolol, pradofloxacin, pramipexole, pramiverin, prenalterol, prenylamine, prilocalne, procaterol, pronethalol, propafenone, propranolol, propylhexedrine, protokylol, protriptyline, pseudoephedrine, reboxetine, rasagiline, (r)-rasagiline, repinotan, reproterol, rimiterol, ritodrine, safinamide, salbutamol/albuterol, salmeterol, sarizotan, sertraline, silodosin, sotalol, soterenol, sparfloxacin, spirapril, sulfinalol, synephrine, tamsulosin, tebanicline, tianeptine, tirofiban, tretoquinol, trimetazidine, troxipide, varenicline, vildagliptin, viloxazine, viquidil or xamoterol;

ix) comprises a protein that is biologically active;

x) comprises a secreted protein;

xi) comprises an extracellular domain of a protein xii) is biologically active such that it has target-binding activity;

xiii) is an independently-folding protein or a portion thereof;

xiv) is a glycosylated protein;

xv) comprises intra-chain disulfide bonds;

xvi) binds a cytokine;

xvii) binds to a cytokine, wherein the cytokine is TNFα;

xviii) comprises Atrial Natriuretic Peptide (ANP), Calcitonin, Corticotropin Releasing Hormone (CRH), Endothelin, Exenatide, Gastric Inhibitory Peptide (GIP), Glucagon-Like Peptide-1 (GLP-1), Glucagon-Like Peptide-2 (GLP-2), an analog of GLP-1 or GLP-2, Glucagon Vasoactive Intestinal Peptide (GVIP), Ghrelin, Peptide YY or Secretin, or a portion thereof;

xix) comprises a stretch of consecutive amino acids in the sequence HGEGTFTSDVSSYLEEQAAKEFIAWLVKGRG (SEQ ID NO: 202);

xx) comprises at least one stretch of consecutive amino acids which are identical to a stretch of consecutive amino acids present in the heavy chain of a Fab or a Fab' of an antibody;

xxi) comprises at least one at least one stretch of consecutive amino acids which are identical to a stretch of consecutive amino acids present in the light chain of a Fab or a Fab' of an antibody;

xxii) comprises at least one Fab or Fab' of an antibody, or a portion of at least one Fab or Fab';

xxiii) comprises Fab-1 or Fab'1, or a portion thereof of an antibody;

xxiv) comprises Fab-2 or Fab'2, or a portion thereof of an antibody;

xxv) comprises two Fab or Fab' hands of an antibody;

xxvi) comprises at least one stretch of consecutive amino acids which are identical to a stretch of consecutive amino acids present in a single chain antibody; or xxvii) comprises at least one stretch of consecutive amino acids which are identical to a stretch of consecutive amino acids present in a TNFα receptor.

8. The compound according to claim 1, wherein Z comprises one C, wherein C is a first polypeptide, which first polypeptide comprises consecutive amino acids which (i) are identical to a stretch of consecutive amino acids present in a chain of an $F_c$ domain of an antibody; (ii) bind to an $F_e$ receptor; and (iii) have at their N-terminus a sequence selected from the group consisting of a cysteine, selenocysteine, CP, CPXCP (where X=P, R, or S) (SEQ ID NOs: 206-208), CDKTHTCPPCP (SEQ ID NO: 209), CVECPPCP (SEQ ID NO: 210), CCVECPPCP(SEQ ID NO: 211) and CDTPPPCPRCP (SEQ ID NO: 212), and wherein B is linked to Z via a peptidyl linkage between the N-terminal cysteine or selenocysteine of first polypeptide component C and an amino acid residue or an organic acid residue of B.

9. The compound according to claim 8, wherein C i) comprises consecutive amino acids which (i) are identical to a stretch of consecutive amino acids present in a chain of an $F_c$ domain of an antibody; (ii) bind to an $F_c$ receptor; and (iii) have at their N-terminus a sequence comprising a naturally occurring cysteine selected from the group consisting of CP, CPXCP (where X=P, R, or S) (SEQ ID NOs: 206-208), CDKTHTCPPCP (SEQ ID NO: 209), CVECPPCP (SEQ ID NO: 210), CCVECPPCP (SEQ ID NO: 211) and CDTPPPCPRCP (SEQ ID NO: 212);

ii) is a polypeptide component of the compound, which polypeptide component comprises consecutive amino acids which (i) are identical to a stretch of consecutive amino acids present in a chain of an $F_c$ domain of an antibody;

(ii) bind to an $F_c$ receptor; and (iii) have at their N-terminus a sequence comprising a non-naturally occurring cysteine or selenocysteine;

iii) comprises consecutive amino acids which are identical to a stretch of consecutive amino acids present in the chain of an Fc domain of an antibody selected from the group consisting of IgG, IgM, IgA, IgD, and IgE;

iv) comprises consecutive amino acids which are identical to a stretch of consecutive amino acids present in the chain of an Fc6 domain of an antibody vi) comprises consecutive amino acids which are identical to a stretch of consecutive amino acids present in a chain of an antibody other than a chain of a Fc domain of the antibody;

vi) consecutive amino acids which are identical to a stretch of consecutive amino acids present in a heavy chain of a Fab or a Fab' of an antibody; or vii) comprises consecutive amino acids which are identical to a stretch of consecutive amino acids present in the light chain of a Fab or a Fab' of an antibody.

10. The compound according to claim 8, wherein Z further comprises a second polypeptide, which second polypeptide comprises consecutive amino acids which are identical to a stretch of consecutive amino acids present in a chain of an antibody other than a chain of a Fc domain of the antibody.

11. The compound according to claim 10, wherein the second polypeptide comprises i) consecutive amino acids which are identical to a stretch of consecutive amino acids present in a heavy chain of a Fab or a Fab' of an antibody; or ii) consecutive amino acids which are identical to a stretch of consecutive amino acids present in the light chain of a Fab or a Fab' of an antibody.

12. The compound according to claim 1, wherein Z i) comprises an antibody or a portion thereof;

ii) comprises at least one Fab or Fab' of an antibody, or a portion of the at least one Fab or Fab' iii) comprises Fab-1 or Fab'1, or a portion thereof of an antibody;

iv) comprises Fab-2 or Fab'2, or a portion thereof of an antibody;

v) comprises two Fab or Fab' hands of an antibody;

vi) comprises at least one stretch of consecutive amino acids which are identical to a stretch of consecutive amino acids present in a single chain antibody; or vii) comprises a second polypeptide, and B is linked to Z via a peptidyl linkage between the N-terminal cysteine or selenocysteine of the second polypeptide of Z and an amino acid residue or an organic acid residue of B.

13. The compound according to claim 8, wherein the C-terminus of C
   i) comprises a stretch of consecutive amino acids present in a chain of an $F_c$ domain of an antibody that has been modified; or
   ii) is a cysteine, selenocysteine, homocysteine, or homoselenosysteine, or a derivative of cysteine, selenocysteine, homocysteine, or homoselenosysteine.

14. A homodimer or a heterodimer comprising the compound of claim 1.

15. The homodimer or heterodimer of claim 14, wherein each compound of the homodimer or heterodimer
   i) is capable of binding to the other by at least one disulfide bond;
   ii) is capable of binding to the other by at least one disulfide bond between the C or the second polypeptide of each compound;
   iii) is bound to the other by at least one disulfide bond;
   iv) is bound to the other by at least one disulfide bond between the C or the second polypeptide of each compound.

* * * * *

SEQUENCE LISTING

<160> NUMBER OF SEQ ID NOS: 226

<210> SEQ ID NO 1
<211> LENGTH: 228
<212> TYPE: PRT
<213> ORGANISM: Artificial Sequence
<220> FEATURE:
<223> OTHER INFORMATION: Human IgG1 Fc domain having the N-terminal
      sequence CDKTHTCPPCPAPE

<400> SEQUENCE: 1

Cys Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 2
<211> LENGTH: 684
<212> TYPE: DNA
<213> ORGANISM: Artificial Sequence
<220> FEATURE:
<223> OTHER INFORMATION: DNA encoding human IgG1 Fc domain having the
      N-terminal sequence CDKTHTCPPCPAPE

<400> SEQUENCE: 2
tgtgacaaaa ctcacacatg cccaccgtgc ccagcacctg aactcctggg ggggccctca      60
gtcttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300

-continued

```
aagtgcaagg tctccaacaa agccctccca gccccatcg agaaaaccat ctccaaagcc      360
aaagggcagc cccgagaacc acaggtgtac accctgcccc catcccggga tgagctgacc      420
aagaaccagg tcagcctgac ctgcctggtc aaaggcttct atcccagcga catcgccgtg      480
gagtgggaga gcaatgggca gccggagaac aactacaaga ccacgcctcc cgtgctggac      540
tccgacggct ccttcttcct ctacagcaag ctcaccgtgg acaagagcag gtggcagcag      600
gggaacgtct tctcatgctc cgtgatgcat gaggctctgc acaaccacta cacgcagaag      660
agcctctccc tgtctccggg taaa                                              684
```

<210> SEQ ID NO 3
<211> LENGTH: 251
<212> TYPE: PRT
<213> ORGANISM: Artificial Sequence
<220> FEATURE:
<223> OTHER INFORMATION: pre-Fc chimeric polypeptide having SHH signal peptide

<400> SEQUENCE: 3

```
Met Leu Leu Leu Ala Arg Cys Leu Leu Val Leu Val Ser Ser Leu
1               5                   10                  15

Leu Val Cys Ser Gly Leu Ala Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250
```

<210> SEQ ID NO 4
<211> LENGTH: 785
<212> TYPE: DNA
<213> ORGANISM: Artificial Sequence
<220> FEATURE:

<223> OTHER INFORMATION: DNA encoding pre-Fc chimeric polypeptide having SHH signal peptide

<400> SEQUENCE: 4

```
aagcttgaat tcccaccatg ctgctgctgg cgagatgtct gctgctagtc ctcgtctcct      60
cgctgctggt atgctcggga ctggcgtgtg acaaaactca cacatgccca ccgtgcccag     120
cacctgaact cctgggggg ccctcagtct tcctcttccc cccaaaaccc aaggacaccc      180
tcatgatctc ccggaccct gaggtcacat gcgtggtggt ggacgtgagc cacgaagacc      240
ctgaggtcaa gttcaactgg tacgtggacg gcgtggaggt gcataatgcc aagacaaagc      300
cgcgggagga gcagtacaac agcacgtacc gtgtggtcag cgtcctcacc gtcctgcacc     360
aggactggct gaatggcaag gagtacaagt gcaaggtctc caacaaagcc ctcccagccc     420
ccatcgagaa aaccatctcc aaagccaaag gcagccccg agaaccacag gtgtacaccc      480
tgcccccatc ccgggatgag ctgaccaaga accaggtcag cctgacctgc ctggtcaaag     540
gcttctatcc cagcgacatc gccgtggagt gggagagcaa tgggcagccg gagaacaact      600
acaagaccac gcctcccgtg ctggactccg acggctcctt cttcctctac agcaagctca     660
ccgtggacaa gagcaggtgg cagcagggga acgtcttctc atgctccgtg atgcatgagg     720
ctctgcacaa ccactacacg cagaagagcc tctccctgtc tccgggtaaa tgactcgagc     780
ggccg                                                                 785
```

<210> SEQ ID NO 5
<211> LENGTH: 251
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 5

```
Met Ala Leu Thr Phe Ala Leu Leu Val Ala Leu Leu Val Leu Ser Cys
1               5                   10                  15

Lys Ser Ser Cys Ser Val Gly Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190
```

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
            210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
            245                 250

<210> SEQ ID NO 6
<211> LENGTH: 785
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 6
aagcttgaat tcccaccatg gccttgacct ttgctttact ggtggccctc ctggtgctca      60
gctgcaagtc aagctgctct gtgggctgtg acaaaactca cacatgccca ccgtgcccag     120
cacctgaact cctgggggg ccctcagtct tcctcttccc cccaaaaccc aaggacaccc      180
tcatgatctc ccggaccccc tgaggtcaca tgcgtggtgg tggacgtgag cacgaagacc    240
ctgaggtcaa gttcaactgg tacgtggacg gcgtggaggt gcataatgcc aagacaaagc    300
cgcgggagga gcagtacaac agcacgtacc gtgtggtcag cgtcctcacc gtcctgcacc    360
aggactggct gaatggcaag gagtacaagt gcaaggtctc caacaaagcc ctcccagccc    420
ccatcgagaa aaccatctcc aaagccaaag gcagccccg agaaccacag gtgtacaccc     480 tgccccccatc ccgggatgag ctgaccaaga accaggtcag cctgacctgc ctggtcaaag    540
gcttctatcc cagcgacatc gccgtggagt gggagagcaa tgggcagccg gagaacaact    600
acaagaccac gcctcccgtg ctggactccg acggctcctt cttcctctac agcaagctca    660
ccgtggacaa gagcaggtgg cagcagggga acgtcttctc atgctccgtg atgcatgagg    720
ctctgcacaa ccactacacg cagaagagcc tctccctgtc tccgggtaaa tgactcgagc    780
ggccg                                                                 785

<210> SEQ ID NO 7
<211> LENGTH: 245
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 7

Met Leu Ala Ala Thr Val Leu Thr Leu Ala Leu Leu Gly Asn Ala His
1               5                   10                  15

Ala Cys Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser

```
                    85                  90                  95
Thr Tyr Arg Val Val Ser Val Leu Thr Val Leu His Gln Asp Trp Leu
                100                 105                 110

Asn Gly Lys Glu Tyr Lys Cys Lys Val Ser Asn Lys Ala Leu Pro Ala
            115                 120                 125

Pro Ile Glu Lys Thr Ile Ser Lys Ala Lys Gly Gln Pro Arg Glu Pro
        130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
210                 215                 220

Val Met His Glu Ala Leu His Asn His Tyr Thr Gln Lys Ser Leu Ser
225                 230                 235                 240

Leu Ser Pro Gly Lys
            245

<210> SEQ ID NO 8
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 8
aagcttgaat tcccaccatg ctggctgcca cagtcctgac cctggccctg ctgggcaatg     60
cccatgcctg tgacaaaact cacacatgcc caccgtgccc agcacctgaa ctcctggggg    120
ggcccctcag tcttcctctt cccccaaaac ccaaggacac cctcatgatc tcccggaccc    180
ctgaggtcac atgcgtggtg gtggacgtga gccacgaaga ccctgaggtc aagttcaact    240
ggtacgtgga cggcgtggag gtgcataatg ccaagacaaa gccgcgggag gagcagtaca    300
acagcacgta ccgtgtggtc agcgtcctca ccgtcctgca ccaggactgg ctgaatggca    360
aggagtacaa gtgcaaggtc tccaacaaag ccctcccagc ccccatcgag aaaaccatct    420
ccaaagccaa agggcagccc cgagaaccac aggtgtacac cctgccccca tcccgggatg    480
agctgaccaa gaaccaggtc agcctgacct gcctggtcaa aggcttctat cccagcgaca    540
tcgccgtgga gtgggagagc aatgggcagc cggagaacaa ctacaagacc acgcctcccg    600
tgctggactc cgacggctcc ttcttcctct acagcaagct caccgtggac aagagcaggt    660
ggcagcaggg gaacgtcttc tcatgctccg tgatgcatga ggctctgcac aaccactaca    720
cgcagaagag cctctccctg tctccgggta aatgactcga gcggccg                  767

<210> SEQ ID NO 9
<211> LENGTH: 222
<212> TYPE: PRT
<213> ORGANISM: Artificial Sequence
<220> FEATURE:
<223> OTHER INFORMATION: Human IgG1 Fc domain having the N-terminal
      sequence CPPCPAPE

<400> SEQUENCE: 9
```

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
        50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Arg Asp Glu Leu Thr Lys Asn Gln Val Ser Leu Thr Cys Leu Val
        130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys
        210                 215                 220

<210> SEQ ID NO 10
<211> LENGTH: 666
<212> TYPE: DNA
<213> ORGANISM: Artificial Sequence
<220> FEATURE:
<223> OTHER INFORMATION: DNA encoding human IgG1 Fc domain having the
      N-terminal sequence CPPCPAPE

<400> SEQUENCE: 10
tgcccaccgt gcccagcacc tgaactcctg gggggacct cagtcttcct cttccccca      60 aaacccaagg acaccctcat gatctcccgg acccctgagg tcacatgcgt ggtggtggac    120
gtgagccacg aagaccctga ggtcaagttc aactggtacg tggacggcgt ggaggtgcat    180
aatgccaaga caaagccgcg ggaggagcag tacaacagca cgtaccgtgt ggtcagcgtc    240
ctcaccgtcc tgcaccagga ctggctgaat ggcaaggagt acaagtgcaa ggtctccaac    300
aaagccctcc cagcccccat cgagaaaacc atctccaaag ccaaaggca gccccgagaa     360 ccacaggtgt acaccctgcc cccatcccgg gatgagctga ccaagaacca ggtcagcctg    420
acctgcctgg tcaaaggctt ctatcccagc gacatcgccg tggagtggga gagcaatggg    480
cagccggaga acaactacaa gaccacgcct cccgtgctgg actccgacgg ctccttcttc    540
ctctacagca agctcaccgt ggacaagagc aggtggcagc aggggaacgt cttctcatgc    600
tccgtgatgc atgaggctct gcacaaccac tacacgcaga gagcctctc cctgtctccg     660 ggtaaa                                                               666

<210> SEQ ID NO 11
<211> LENGTH: 245
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 11

```
Met Leu Leu Leu Ala Arg Cys Leu Leu Leu Val Leu Val Ser Ser Leu
1               5                   10                  15

Leu Val Cys Ser Gly Leu Ala Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245
```

<210> SEQ ID NO 12
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 12

```
aagcttgaat tcccaccatg ctgctgctgg cgagatgtct gctgctagtc ctcgtctcct      60
cgctgctggt atgctcggga ctggcgtgcc caccgtgccc agcacctgaa ctcctggggg     120
ggcccctcag tcttcctctt ccccccaaaa ccaaggacac cctcatgatc tcccggaccc     180
ctgaggtcac atgcgtggtg gtggacgtga gccacgaaga ccctgaggtc aagttcaact     240
ggtacgtgga cggcgtggag gtgcataatg ccaagacaaa gccgcgggag gagcagtaca     300
```

```
acagcacgta ccgtgtggtc agcgtcctca ccgtcctgca ccaggactgg ctgaatggca    360
aggagtacaa gtgcaaggtc tccaacaaag ccctcccagc ccccatcgag aaaaccatct    420
ccaaagccaa agggcagccc cgagaaccac aggtgtacac cctgccccca tcccgggatg    480
agctgaccaa gaaccaggtc agcctgacct gcctggtcaa aggcttctat cccagcgaca    540
tcgccgtgga gtgggagagc aatgggcagc cggagaacaa ctacaagacc acgcctcccg    600
tgctggactc cgacggctcc ttcttcctct acagcaagct caccgtggac aagagcaggt    660
ggcagcaggg gaacgtcttc tcatgctccg tgatgcatga ggctctgcac aaccactaca    720
cgcagaagag cctctcccctg tctccgggta atgactcga gcggccg                 767
```

<210> SEQ ID NO 13
<211> LENGTH: 245
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 13

```
Met Ala Leu Thr Phe Ala Leu Leu Val Ala Leu Leu Val Leu Ser Cys
1               5                   10                  15

Lys Ser Ser Cys Ser Val Gly Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245
```

<210> SEQ ID NO 14
<211> LENGTH: 767
<212> TYPE: DNA

<213> ORGANISM: Artificial Sequence
<220> FEATURE:
<223> OTHER INFORMATION: DNA encoding pre-Fc chimeric polypeptide having IFN signal peptide

<400> SEQUENCE: 14

```
aagcttgaat tcccaccatg gccttgacct ttgctttact ggtggccctc ctggtgctca      60
gctgcaagtc aagctgctct gtgggctgcc caccgtgccc agcacctgaa ctcctggggg     120
ggccctcagt cttcctcttc ccccaaaaac ccaaggacac cctcatgatc tcccggaccc     180
ctgaggtcac atgcgtggtg gtggacgtga gccacgaaga ccctgaggtc aagttcaact     240
ggtacgtgga cggcgtggag gtgcataatg ccaagacaaa gccgcgggag gagcagtaca     300
acagcacgta ccgtgtggtc agcgtcctca ccgtcctgca ccaggactgg ctgaatggca     360
aggagtacaa gtgcaaggtc tccaacaaag ccctcccagc ccccatcgag aaaaccatct     420
ccaaagccaa agggcagccc cgagaaccac aggtgtacac cctgcccca tcccgggatg      480
agctgaccaa gaaccaggtc agcctgacct gcctggtcaa aggcttctat cccagcgaca     540
tcgccgtgga gtgggagagc aatgggcagc cggagaacaa ctacaagacc acgcctcccg     600
tgctggactc cgacggctcc ttcttcctct acagcaagct caccgtggac aagagcaggt     660
ggcagcaggg gaacgtcttc tcatgctccg tgatgcatga ggctctgcac aaccactaca     720
cgcagaagag cctctccctg tctccgggta atgactcga gcggccg                    767
```

<210> SEQ ID NO 15
<211> LENGTH: 239
<212> TYPE: PRT
<213> ORGANISM: Artificial Sequence
<220> FEATURE:
<223> OTHER INFORMATION: pre-Fc chimeric polypeptide having CETP signal peptide

<400> SEQUENCE: 15

```
Met Leu Ala Ala Thr Val Leu Thr Leu Ala Leu Leu Gly Asn Ala His
1               5                   10                  15

Ala Cys Pro Pro Cys Pro Ala Pro Glu Leu Leu Gly Gly Pro Ser Val
                20                  25                  30

Phe Leu Phe Pro Pro Lys Pro Lys Asp Thr Leu Met Ile Ser Arg Thr
            35                  40                  45

Pro Glu Val Thr Cys Val Val Val Asp Val Ser His Glu Asp Pro Glu
        50                  55                  60

Val Lys Phe Asn Trp Tyr Val Asp Gly Val Glu Val His Asn Ala Lys
65                  70                  75                  80

Thr Lys Pro Arg Glu Glu Gln Tyr Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Arg Asp Glu Leu Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Val Leu Asp Ser
            180                 185                 190
```

Asp Gly Ser Phe Phe Leu Tyr Ser Lys Leu Thr Val Asp Lys Ser Arg
            195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys
225                 230                 235

<210> SEQ ID NO 16
<211> LENGTH: 749
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 16
aagcttgaat tcccaccatg ctggctgcca cagtcctgac cctggccctg ctgggcaatg      60
cccatgcctg cccaccgtgc ccagcacctg aactcctggg ggggcccctca gtcttcctct     120 tccccccaaa acccaaggac accctcatga tctcccggac ccctgaggtc acatgcgtgg     180
tggtggacgt gagccacgaa gaccctgagg tcaagttcaa ctggtacgtg gacggcgtgg     240
aggtgcataa tgccaagaca aagccgcggg aggagcagta caacagcacg taccgtgtgg     300
tcagcgtcct caccgtcctg caccaggact ggctgaatgg caaggagtac aagtgcaagg     360
tctccaacaa agccctccca gcccccatcg agaaaaccat ctccaaagcc aaagggcagc     420
cccgagaacc acaggtgtac accctgcccc catcccggga tgagctgacc aagaaccagg     480
tcagcctgac ctgcctggtc aaaggcttct atcccagcga catcgccgtg gagtgggaga     540
gcaatgggca gccggagaac aactacaaga ccacgcctcc cgtgctggac tccgacggct     600
ccttcttcct ctacagcaag ctcaccgtgg acaagagcag gtggcagcag gggaacgtct     660
tctcatgctc cgtgatgcat gaggctctgc acaaccacta cacgcagaag agcctctccc     720
tgtctccggg taaatgactc gagcggccg                                        749

<210> SEQ ID NO 17
<211> LENGTH: 219
<212> TYPE: PRT
<213> ORGANISM: Artificial Sequence
<220> FEATURE:
<223> OTHER INFORMATION: Human IgG1 Fc domain having the N-terminal
      sequence CPAPE

<400> SEQUENCE: 17

Cys Pro Ala Pro Glu Leu Leu Gly Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Lys Phe Asn
        35                  40                  45

Trp Tyr Val Asp Gly Val Glu Val His Asn Ala Lys Thr Lys Pro Arg
    50                  55                  60

Glu Glu Gln Tyr Asn Ser Thr Tyr Arg Val Val Ser Val Leu Thr Val
65                  70                  75                  80

Leu His Gln Asp Trp Leu Asn Gly Lys Glu Tyr Lys Cys Lys Val Ser
                85                  90                  95

Asn Lys Ala Leu Pro Ala Pro Ile Glu Lys Thr Ile Ser Lys Ala Lys
            100                 105                 110

```
Gly Gln Pro Arg Glu Pro Gln Val Tyr Thr Leu Pro Pro Ser Arg Asp
            115                 120                 125

Glu Leu Thr Lys Asn Gln Val Ser Leu Thr Cys Leu Val Lys Gly Phe
    130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Val Leu Asp Ser Asp Gly Ser Phe
                165                 170                 175

Phe Leu Tyr Ser Lys Leu Thr Val Asp Lys Ser Arg Trp Gln Gln Gly
            180                 185                 190

Asn Val Phe Ser Cys Ser Val Met His Glu Ala Leu His Asn His Tyr
            195                 200                 205

Thr Gln Lys Ser Leu Ser Leu Ser Pro Gly Lys
    210                 215
```

<210> SEQ ID NO 18
<211> LENGTH: 657
<212> TYPE: DNA
<213> ORGANISM: Artificial Sequence
<220> FEATURE:
<223> OTHER INFORMATION: DNA encoding human IgG1 Fc domain having the
      N-terminal sequence CPAPE

<400> SEQUENCE: 18

```
tgcccagcac ctgaactcct ggggggggccc tcagtcttcc tcttccccccc aaaacccaag    60 gacacccctca tgatctcccg gacccctgag gtcacatgcg tggtggtgga cgtgagccac   120
gaagaccctg aggtcaagtt caactggtac gtggacggcg tggaggtgca taatgccaag   180
acaaagccgc gggaggagca gtacaacagc acgtaccgtg tggtcagcgt cctcaccgtc   240
ctgcaccagg actggctgaa tggcaaggag tacaagtgca aggtctccaa caaagccctc   300 ccagcccccca tcgagaaaac catctccaaa gccaaagggc agccccgaga accacaggtg   360
tacaccctgc cccatccccg ggatgagctg accaagaacc aggtcagcct gacctgcctg   420
gtcaaaggct tctatcccag cgacatcgcc gtggagtggg agagcaatgg gcagccggag   480
aacaactaca agaccacgcc tcccgtgctg gactccgacg gctccttctt cctctacagc   540
aagctcaccg tggacaagag caggtggcag caggggaacg tcttctcatg ctccgtgatg   600
catgaggctc tgcacaacca ctacacgcag aagagcctct ccctgtctcc gggtaaa      657
```

<210> SEQ ID NO 19
<211> LENGTH: 242
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 19

```
Met Leu Leu Leu Ala Arg Cys Leu Leu Leu Val Leu Val Ser Ser Leu
1               5                   10                  15

Leu Val Cys Ser Gly Leu Ala Cys Pro Ala Pro Glu Leu Leu Gly Gly
            20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80
```

```
Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 20
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 20
aagcttgaat cccaccatg ctgctgctgg cgagatgtct gctgctagtc ctcgtctcct      60
cgctgctggt atgctcggga ctggcgtgcc cagcacctga actcctgggg gggccctcag    120
tcttcctctt cccccccaaaa cccaaggaca ccctcatgat ctcccggacc cctgaggtca    180
catgcgtggt ggtggacgtg agccacgaag accctgaggt caagttcaac tggtacgtgg    240
acggcgtgga ggtgcataat gccaagacaa agccgcggga ggagcagtac aacagcacgt    300
accgtgtggt cagcgtcctc accgtcctgc accaggactg gctgaatggc aaggagtaca    360
agtgcaaggt ctccaacaaa gcccteccag ccccatcga aaaaccatc tccaaagcca     420 aagggcagcc ccgagaacca caggtgtaca ccctgccccc atcccgggat gagctgacca    480
agaaccaggt cagcctgacc tgcctggtca aaggcttcta tcccagcgac atcgccgtgg    540
agtgggagag caatgggcag ccggagaaca actacaagac cacgcctccc gtgctggact    600
ccgacggctc cttcttcctc tacagcaagc tcaccgtgga caagagcagg tggcagcagg    660
ggaacgtctt ctcatgctcc gtgatgcatg aggctctgca caaccactac acgcagaaga    720
gcctctccct gtctccgggt aaatgactcg agcggccg                            758

<210> SEQ ID NO 21
<211> LENGTH: 242
<212> TYPE: PRT
<213> ORGANISM: Artificial Sequence
<220> FEATURE:
<223> OTHER INFORMATION: pre-Fc chimeric polypeptide having IFN signal
      peptide
```

<400> SEQUENCE: 21

Met Ala Leu Thr Phe Ala Leu Leu Val Ala Leu Leu Val Leu Ser Cys
1               5                   10                  15

Lys Ser Ser Cys Ser Val Gly Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 22
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 22

```
aagcttgaat tcccaccatg gccttgacct ttgctttact ggtggccctc ctggtgctca    60
gctgcaagtc aagctgctct gtgggctgcc cagcacctga actcctgggg gggccctcag   120
tcttcctctt ccccccaaaa cccaaggaca ccctcatgat ctcccggacc cctgaggtca   180
catgcgtggt ggtggacgtg agccacgaag accctgaggt caagttcaac tggtacgtgg   240
acggcgtgga ggtgcataat gccaagacaa agccgcggga ggagcagtac aacagcacgt   300
accgtgtggt cagcgtcctc accgtcctgc accaggactg gctgaatggc aaggagtaca   360
agtgcaaggt ctccaacaaa gccctcccag cccccatcga aaaaccatc tccaaagcca   420 aagggcagcc ccgagaacca caggtgtaca ccctgccccc atcccgggat gagctgacca   480
agaaccaggt cagcctgacc tgcctggtca aaggcttcta tcccagcgac atcgccgtgg   540
agtgggagag caatgggcag ccggagaaca actacaagac cacgcctccc gtgctggact   600
```

```
ccgacggctc cttcttcctc tacagcaagc tcaccgtgga caagagcagg tggcagcagg    660
ggaacgtctt ctcatgctcc gtgatgcatg aggctctgca caaccactac acgcagaaga    720
gcctctccct gtctccgggt aaatgactcg agcggccg                            758
```

<210> SEQ ID NO 23
<211> LENGTH: 236
<212> TYPE: PRT
<213> ORGANISM: Artificial Sequence
<220> FEATURE:
<223> OTHER INFORMATION: pre-Fc chimeric polypeptide having CETP signal peptide

<400> SEQUENCE: 23

```
Met Leu Ala Ala Thr Val Leu Thr Leu Ala Leu Leu Gly Asn Ala His
1               5                   10                  15

Ala Cys Pro Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Asp Glu Leu Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235
```

<210> SEQ ID NO 24
<211> LENGTH: 740
<212> TYPE: DNA
<213> ORGANISM: Artificial Sequence
<220> FEATURE:
<223> OTHER INFORMATION: DNA encoding pre-Fc chimeric polypeptide having CETP signal peptide

<400> SEQUENCE: 24

```
aagcttgaat tcccaccatg ctggctgcca cagtcctgac cctggccctg ctgggcaatg    60
cccatgcctg cccagcacct gaactcctgg ggggcccctc agtcttcctc ttccccccaa    120
aacccaagga caccctcatg atctcccgga cccctgaggt cacatgcgtg gtggtggacg    180
```

```
tgagccacga agaccctgag gtcaagttca actggtacgt ggacggcgtg gaggtgcata    240
atgccaagac aaagccgcgg gaggagcagt acaacagcac gtaccgtgtg gtcagcgtcc    300
tcaccgtcct gcaccaggac tggctgaatg gcaaggagta caagtgcaag gtctccaaca    360
aagccctccc agccccatc gagaaaacca tctccaaagc caagggcag ccccgagaac     420 cacaggtgta caccctgccc ccatcccggg atgagctgac caagaaccag gtcagcctga    480
cctgcctggt caaaggcttc tatcccagcg acatcgccgt ggagtgggag agcaatgggc    540
agccggagaa caactacaag accacgcctc ccgtgctgga ctccgacggc tccttcttcc    600
tctacagcaa gctcaccgtg gacaagagca ggtggcagca ggggaacgtc ttctcatgct    660
ccgtgatgca tgaggctctg cacaaccact acacgcagaa gagcctctcc ctgtctccgg    720
gtaaatgact cgagcggccg                                                740
```

<210> SEQ ID NO 25
<211> LENGTH: 225
<212> TYPE: PRT
<213> ORGANISM: Artificial Sequence
<220> FEATURE:
<223> OTHER INFORMATION: Human IgG2 Fc domain having the N-terminal
      sequence CCVECPPCPAPE

<400> SEQUENCE: 25

```
Cys Cys Val Glu Cys Pro Pro Cys Pro Ala Pro Pro Val Ala Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Phe Arg Val
65                  70                  75                  80

Val Ser Val Leu Thr Val Val His Gln Asp Trp Leu Asn Gly Lys Glu
                85                  90                  95

Tyr Lys Cys Lys Val Ser Asn Lys Gly Leu Pro Ala Pro Ile Glu Lys
            100                 105                 110

Thr Ile Ser Lys Thr Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Met Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 26

<211> LENGTH: 675
<212> TYPE: DNA
<213> ORGANISM: Artificial Sequence
<220> FEATURE:
<223> OTHER INFORMATION: DNA encoding human IgG2 Fc domain having the
      N-terminal sequence CCVECPPCPAPE

<400> SEQUENCE: 26

```
tgttgtgtcg agtgcccacc gtgcccagca ccacctgtgg caggaccgtc agtcttcctc      60
ttccccccaa acccaaggac accctcatg atctcccgga ccctgaggt cacgtgcgtg      120
gtggtggacg tgagccacga agaccccgag gtccagttca actggtacgt ggacggcgtg     180
gaggtgcata atgccaagac aaagccacgg gaggagcagt tcaacagcac gttccgtgtg     240
gtcagcgtcc tcaccgttgt gcaccaggac tggctgaacg gcaaggagta caagtgcaag     300
gtctccaaca aaggcctccc agcccccatc gagaaaacca tctccaaaac caaagggcag     360
ccccgagaac cacaggtgta caccctgccc ccatcccggg aggagatgac caagaaccag     420
gtcagcctga cctgcctggt caaaggcttc taccccagcg acatcgccgt ggagtgggag     480
agcaatgggc agccggagaa caactacaag accacacctc ccatgctgga ctccgacggc     540
tccttcttcc tctacagcaa gctcaccgtg gacaagagca ggtggcagca ggggaacgtc     600
ttctcatgct ccgtgatgca tgaggctctg cacaaccact acacgcagaa gagcctctcc     660
ctgtctccgg gtaaa                                                       675
```

<210> SEQ ID NO 27
<211> LENGTH: 248
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 27

```
Met Leu Leu Leu Ala Arg Cys Leu Leu Leu Val Leu Val Ser Ser Leu
1               5                   10                  15

Leu Val Cys Ser Gly Leu Ala Cys Cys Val Glu Cys Pro Pro Cys Pro
                20                  25                  30

Ala Pro Pro Val Ala Gly Pro Ser Val Phe Leu Phe Pro Pro Lys Pro
                35                  40                  45

Lys Asp Thr Leu Met Ile Ser Arg Thr Pro Glu Val Thr Cys Val Val
            50                  55                  60

Val Asp Val Ser His Glu Asp Pro Glu Val Gln Phe Asn Trp Tyr Val
65                  70                  75                  80

Asp Gly Val Glu Val His Asn Ala Lys Thr Lys Pro Arg Glu Glu Gln
                85                  90                  95

Phe Asn Ser Thr Phe Arg Val Val Ser Val Leu Thr Val Val His Gln
                100                 105                 110

Asp Trp Leu Asn Gly Lys Glu Tyr Lys Cys Lys Val Ser Asn Lys Gly
            115                 120                 125

Leu Pro Ala Pro Ile Glu Lys Thr Ile Ser Lys Thr Lys Gly Gln Pro
        130                 135                 140

Arg Glu Pro Gln Val Tyr Thr Leu Pro Pro Ser Arg Glu Glu Met Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190
```

```
Lys Thr Thr Pro Pro Met Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys
                245
```

<210> SEQ ID NO 28
<211> LENGTH: 776
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 28

```
aagcttgaat tcccaccatg ctgctgctgg cgagatgtct gctgctagtc ctcgtctcct      60
cgctgctggt atgctcggga ctggcgtgtt gtgtcgagtg cccaccgtgc ccagcaccac     120
ctgtggcagg accgtcagtc ttcctcttcc ccccaaaacc caaggacacc ctcatgatct     180
cccggacccc tgaggtcacg tgcgtggtgg tggacgtgag ccacgaagac cccgaggtcc     240
agttcaactg gtacgtggac ggcgtggagg tgcataatgc caagacaaag ccacgggagg     300
agcagttcaa cagcacgttc cgtgtggtca gcgtcctcac cgttgtgcac caggactggc     360
tgaacggcaa ggagtacaag tgcaaggtct ccaacaaagg cctcccagcc cccatcgaga     420
aaaccatctc caaaaccaaa gggcagcccc gagaaccaca ggtgtacacc ctgcccccat     480
cccgggagga gatgaccaag aaccaggtca gcctgacctg cctggtcaaa ggcttctacc     540
ccagcgacat cgccgtggag tgggagagca atgggcagcc ggagaacaac tacaagacca     600
cacctcccat gctggactcc gacggctcct tcttcctcta cagcaagctc accgtggaca     660
agagcaggtg gcagcagggg aacgtcttct catgctccgt gatgcatgag gctctgcaca     720
accactacac gcagaagagc ctctccctgt ctccgggtaa atgactcgag cggccg        776
```

<210> SEQ ID NO 29
<211> LENGTH: 248
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 29

```
Met Ala Leu Thr Phe Ala Leu Leu Val Ala Leu Leu Val Leu Ser Cys
1               5                   10                  15

Lys Ser Ser Cys Ser Val Gly Cys Cys Val Glu Cys Pro Cys Pro
            20                  25                  30

Ala Pro Pro Val Ala Gly Pro Ser Val Phe Leu Phe Pro Pro Lys Pro
            35                  40                  45

Lys Asp Thr Leu Met Ile Ser Arg Thr Pro Glu Val Thr Cys Val Val
    50                  55                  60

Val Asp Val Ser His Glu Asp Pro Glu Val Gln Phe Asn Trp Tyr Val
65                  70                  75                  80

Asp Gly Val Glu Val His Asn Ala Lys Thr Lys Pro Arg Glu Glu Gln
                85                  90                  95
```

```
Phe Asn Ser Thr Phe Arg Val Val Ser Val Leu Thr Val Val His Gln
            100                 105                 110
Asp Trp Leu Asn Gly Lys Glu Tyr Lys Cys Lys Val Ser Asn Lys Gly
        115                 120                 125
Leu Pro Ala Pro Ile Glu Lys Thr Ile Ser Lys Thr Lys Gly Gln Pro
    130                 135                 140
Arg Glu Pro Gln Val Tyr Thr Leu Pro Pro Ser Arg Glu Glu Met Thr
145                 150                 155                 160
Lys Asn Gln Val Ser Leu Thr Cys Leu Val Lys Gly Phe Tyr Pro Ser
                165                 170                 175
Asp Ile Ala Val Glu Trp Glu Ser Asn Gly Gln Pro Glu Asn Asn Tyr
            180                 185                 190
Lys Thr Thr Pro Pro Met Leu Asp Ser Asp Gly Ser Phe Phe Leu Tyr
        195                 200                 205
Ser Lys Leu Thr Val Asp Lys Ser Arg Trp Gln Gln Gly Asn Val Phe
    210                 215                 220
Ser Cys Ser Val Met His Glu Ala Leu His Asn His Tyr Thr Gln Lys
225                 230                 235                 240
Ser Leu Ser Leu Ser Pro Gly Lys
                245

<210> SEQ ID NO 30
<211> LENGTH: 776
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 30
aagcttgaat tcccaccatg gccttgacct ttgctttact ggtggccctc ctggtgctca      60
gctgcaagtc aagctgctct gtgggctgtt gtgtcgagtg cccaccgtgc ccagcaccac     120
ctgtggcagg accgtcagtc ttcctcttcc ccccaaaacc caaggacacc ctcatgatct     180
cccggacccc tgaggtcacg tgcgtggtgg tggacgtgag ccacgaagac cccgaggtcc     240
agttcaactg gtacgtggac ggcgtggagg tgcataatgc caagacaaag ccacgggagg     300
agcagttcaa cagcacgttc cgtgtggtca gcgtcctcac cgttgtgcac caggactggc     360
tgaacggcaa ggagtacaag tgcaaggtct ccaacaaagg cctcccagcc cccatcgaga     420
aaaccatctc caaaaccaaa gggcagcccc gagaaccaca ggtgtacacc ctgcccccat     480
cccgggagga gatgaccaag aaccaggtca gcctgacctg cctggtcaaa ggcttctacc     540
ccagcgacat cgccgtggag tgggagagca atgggcagcc ggagaacaac tacaagacca     600
cacctcccat gctggactcc gacggctcct tcttcctcta cagcaagctc accgtggaca     660
agagcaggtg gcagcagggg aacgtcttct catgctccgt gatgcatgag gctctgcaca     720
accactacac gcagaagagc ctctccctgt ctccgggtaa atgactcgag cggccg        776

<210> SEQ ID NO 31
<211> LENGTH: 242
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 31

Met Leu Ala Ala Thr Val Leu Thr Leu Ala Leu Leu Gly Asn Ala His
```

```
             1               5                  10                 15
          Ala Cys Cys Val Glu Cys Pro Pro Cys Pro Ala Pro Pro Val Ala Gly
                          20                 25                 30
          Pro Ser Val Phe Leu Phe Pro Pro Lys Pro Lys Asp Thr Leu Met Ile
                          35                 40                 45
          Ser Arg Thr Pro Glu Val Thr Cys Val Val Val Asp Val Ser His Glu
              50                 55                 60
          Asp Pro Glu Val Gln Phe Asn Trp Tyr Val Asp Gly Val Glu Val His
          65                 70                 75                 80
          Asn Ala Lys Thr Lys Pro Arg Glu Glu Gln Phe Asn Ser Thr Phe Arg
                          85                 90                 95
          Val Val Ser Val Leu Thr Val Val His Gln Asp Trp Leu Asn Gly Lys
                         100                105                110
          Glu Tyr Lys Cys Lys Val Ser Asn Lys Gly Leu Pro Ala Pro Ile Glu
                         115                120                125
          Lys Thr Ile Ser Lys Thr Lys Gly Gln Pro Arg Glu Pro Gln Val Tyr
                         130                135                140
          Thr Leu Pro Pro Ser Arg Glu Glu Met Thr Lys Asn Gln Val Ser Leu
          145                150                155                160
          Thr Cys Leu Val Lys Gly Phe Tyr Pro Ser Asp Ile Ala Val Glu Trp
                         165                170                175
          Glu Ser Asn Gly Gln Pro Glu Asn Asn Tyr Lys Thr Thr Pro Pro Met
                         180                185                190
          Leu Asp Ser Asp Gly Ser Phe Phe Leu Tyr Ser Lys Leu Thr Val Asp
                         195                200                205
          Lys Ser Arg Trp Gln Gln Gly Asn Val Phe Ser Cys Ser Val Met His
                         210                215                220
          Glu Ala Leu His Asn His Tyr Thr Gln Lys Ser Leu Ser Leu Ser Pro
          225                230                235                240
          Gly Lys

<210> SEQ ID NO 32
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 32
aagcttgaat tcccaccatg ctggctgcca cagtcctgac cctggccctg ctgggcaatg     60
cccatgcctg ttgtgtcgag tgcccaccgt gcccagcacc acctgtggca ggaccgtcag    120
tcttcctctt cccccaaaa cccaaggaca ccctcatgat ctcccggacc cctgaggtca    180
cgtgcgtggt ggtggacgtg agccacgaag accccgaggt ccagttcaac tggtacgtgg    240
acggcgtgga ggtgcataat gccaagacaa agccacggga ggagcagttc aacagcacgt    300
tccgtgtggt cagcgtcctc accgttgtgc accaggactg gctgaacggc aaggagtaca    360
agtgcaaggt ctccaacaaa ggcctcccag cccccatcga gaaaaccatc tccaaaacca    420
aagggcagcc ccgagaacca caggtgtaca ccctgccccc atcccgggag gagatgacca    480
agaaccaggt cagcctgacc tgcctggtca aaggcttcta ccccagcgac atcgccgtgg    540
agtgggagag caatgggcag ccggagaaca actacaagac cacacctccc atgctggact    600
ccgacggctc cttcttcctc tacagcaagc tcaccgtgga caagagcagg tggcagcagg    660
```

-continued

```
ggaacgtctt ctcatgctcc gtgatgcatg aggctctgca caaccactac acgcagaaga    720
gcctctccct gtctccgggt aaatgactcg agcggccg                            758
```

<210> SEQ ID NO 33
<211> LENGTH: 224
<212> TYPE: PRT
<213> ORGANISM: Artificial Sequence
<220> FEATURE:
<223> OTHER INFORMATION: Human IgG2 Fc domain having the N-terminal
      sequence CVECPPCPAPE

<400> SEQUENCE: 33

```
Cys Val Glu Cys Pro Pro Cys Pro Ala Pro Val Ala Gly Pro Ser
1               5                  10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220
```

<210> SEQ ID NO 34
<211> LENGTH: 672
<212> TYPE: DNA
<213> ORGANISM: Artificial Sequence
<220> FEATURE:
<223> OTHER INFORMATION: DNA encoding human IgG2 Fc domain having the
      N-terminal sequence CVECPPCPAPE

<400> SEQUENCE: 34

```
tgtgtcgagt gcccaccgtg cccagcacca cctgtggcag gaccgtcagt cttcctcttc    60
cccccaaaac ccaaggacac cctcatgatc tcccggaccc ctgaggtcac gtgcgtggtg   120
gtggacgtga gccacgaaga ccccgaggtc cagttcaact ggtacgtgga cggcgtggag   180
gtgcataatg ccaagacaaa gccacgggag gagcagttca acagcacgtt ccgtgtggtc   240
agcgtcctca ccgttgtgca ccaggactgg ctgaacggca aggagtacaa gtgcaaggtc   300
tccaacaaag gcctcccagc ccccatcgag aaaaccatct ccaaaaccaa agggcagccc   360
```

-continued

```
cgagaaccac aggtgtacac cctgccccca tcccgggagg agatgaccaa gaaccaggtc      420
agcctgacct gcctggtcaa aggcttctac cccagcgaca tcgccgtgga gtgggagagc      480
aatgggcagc cggagaacaa ctacaagacc acacctccca tgctggactc cgacggctcc      540
ttcttcctct acagcaagct caccgtggac aagagcaggt ggcagcaggg gaacgtcttc      600
tcatgctccg tgatgcatga ggctctgcac aaccactaca cgcagaagag cctctccctg      660
tctccgggta aa                                                          672
```

```
<210> SEQ ID NO 35
<211> LENGTH: 247
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 35
```

Met Leu Leu Leu Ala Arg Cys Leu Leu Val Leu Val Ser Ser Leu
1               5                   10                  15

Leu Val Cys Ser Gly Leu Ala Cys Val Glu Cys Pro Pro Cys Pro Ala
            20                  25                  30

Pro Pro Val Ala Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser His Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Phe Arg Val Val Ser Val Leu Thr Val Val His Gln Asp
            100                 105                 110

Trp Leu Asn Gly Lys Glu Tyr Lys Cys Lys Val Ser Asn Lys Gly Leu
        115                 120                 125

Pro Ala Pro Ile Glu Lys Thr Ile Ser Lys Thr Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Met Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

```
<210> SEQ ID NO 36
<211> LENGTH: 773
<212> TYPE: DNA
<213> ORGANISM: Artificial Sequence
<220> FEATURE:
<223> OTHER INFORMATION: DNA encoding pre-Fc chimeric polypeptide having
```

SHH signal peptide

<400> SEQUENCE: 36

```
aagcttgaat tcccaccatg ctgctgctgg cgagatgtct gctgctagtc ctcgtctcct      60
cgctgctggt atgctcggga ctggcgtgtg tcgagtgccc accgtgccca gcaccacctg     120
tggcaggacc gtcagtcttc ctcttccccc caaaacccaa ggacaccctc atgatctccc     180
ggacccctga ggtcacgtgc gtggtggtgg acgtgagcca cgaagacccc gaggtccagt     240
tcaactggta cgtggacggc gtggaggtgc ataatgccaa gacaaagcca cgggaggagc     300
agttcaacag cacgttccgt gtggtcagcg tcctcaccgt tgtgcaccag gactggctga     360
acggcaagga gtacaagtgc aaggtctcca acaaaggcct cccagccccc atcgagaaaa     420
ccatctccaa aaccaaaggg cagccccgag aaccacaggt gtacaccctg cccccatccc     480
gggaggagat gaccaagaac caggtcagcc tgacctgcct ggtcaaaggc ttctacccca     540
gcgacatcgc cgtggagtgg gagagcaatg ggcagccgga gaacaactac aagaccacac     600
ctcccatgct ggactccgac ggctccttct tcctctacag caagctcacc gtggacaaga     660
gcaggtggca gcaggggaac gtcttctcat gctccgtgat gcatgaggct ctgcacaacc     720
actacacgca gaagagcctc tccctgtctc cgggtaaatg actcgagcgg ccg            773
```

<210> SEQ ID NO 37
<211> LENGTH: 247
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 37

```
Met Ala Leu Thr Phe Ala Leu Leu Val Ala Leu Leu Val Leu Ser Cys
  1               5                  10                  15

Lys Ser Ser Cys Ser Val Gly Cys Val Glu Cys Pro Pro Cys Pro Ala
             20                  25                  30

Pro Pro Val Ala Gly Pro Ser Val Phe Leu Phe Pro Pro Lys Pro Lys
         35                  40                  45

Asp Thr Leu Met Ile Ser Arg Thr Pro Glu Val Thr Cys Val Val Val
     50                  55                  60

Asp Val Ser His Glu Asp Pro Glu Val Gln Phe Asn Trp Tyr Val Asp
 65                  70                  75                  80

Gly Val Glu Val His Asn Ala Lys Thr Lys Pro Arg Glu Glu Gln Phe
                 85                  90                  95

Asn Ser Thr Phe Arg Val Val Ser Val Leu Thr Val Val His Gln Asp
            100                 105                 110

Trp Leu Asn Gly Lys Glu Tyr Lys Cys Lys Val Ser Asn Lys Gly Leu
        115                 120                 125

Pro Ala Pro Ile Glu Lys Thr Ile Ser Lys Thr Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Met Leu Asp Ser Asp Gly Ser Phe Phe Leu Tyr Ser
        195                 200                 205
```

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
            245

<210> SEQ ID NO 38
<211> LENGTH: 773
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 38

```
aagcttgaat tcccaccatg gccttgacct ttgctttact ggtggccctc ctggtgctca      60
gctgcaagtc aagctgctct gtgggctgtg tcgagtgccc accgtgccca gcaccacctg    120
tggcaggacc gtcagtcttc ctcttccccc caaaacccaa ggacaccctc atgatctccc    180
ggacccctga ggtcacgtgc gtggtggtgg acgtgagcca cgaagacccc gaggtccagt    240
tcaactggta cgtggacggc gtggaggtgc ataatgccaa gacaaagcca cgggaggagc    300
agttcaacag cacgttccgt gtggtcagcg tcctcaccgt tgtgcaccag gactggctga    360
acggcaagga gtacaagtgc aaggtctcca acaaggcct cccagccccc atcgagaaaa     420
ccatctccaa aaccaaaggg cagccccgag aaccacaggt gtacaccctg cccccatccc    480
gggaggagat gaccaagaac caggtcagcc tgacctgcct ggtcaaaggc ttctacccca    540
gcgacatcgc cgtggagtgg gagagcaatg ggcagccgga gaacaactac aagaccacac    600
ctcccatgct ggactccgac ggctccttct tcctctacag caagctcacc gtggacaaga    660
gcaggtggca gcaggggaac gtcttctcat gctccgtgat gcatgaggct ctgcacaacc    720
actacacgca gaagagcctc tccctgtctc cgggtaaatg actcgagcgg ccg           773
```

<210> SEQ ID NO 39
<211> LENGTH: 241
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 39

Met Leu Ala Ala Thr Val Leu Thr Leu Ala Leu Leu Gly Asn Ala His
1               5                   10                  15

Ala Cys Val Glu Cys Pro Pro Cys Pro Ala Pro Pro Val Ala Gly Pro
                20                  25                  30

Ser Val Phe Leu Phe Pro Pro Lys Pro Lys Asp Thr Leu Met Ile Ser
            35                  40                  45

Arg Thr Pro Glu Val Thr Cys Val Val Val Asp Val Ser His Glu Asp
        50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
                85                  90                  95

Val Ser Val Leu Thr Val Val His Gln Asp Trp Leu Asn Gly Lys Glu
            100                 105                 110

Tyr Lys Cys Lys Val Ser Asn Lys Gly Leu Pro Ala Pro Ile Glu Lys
            115                 120                 125

Thr Ile Ser Lys Thr Lys Gly Gln Pro Arg Glu Pro Gln Val Tyr Thr
        130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Met Leu
            180                 185                 190

Asp Ser Asp Gly Ser Phe Phe Leu Tyr Ser Lys Leu Thr Val Asp Lys
        195                 200                 205

Ser Arg Trp Gln Gln Gly Asn Val Phe Ser Cys Ser Val Met His Glu
    210                 215                 220

Ala Leu His Asn His Tyr Thr Gln Lys Ser Leu Ser Leu Ser Pro Gly
225                 230                 235                 240

Lys

<210> SEQ ID NO 40
<211> LENGTH: 755
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 40

```
aagcttgaat tcccaccatg ctggctgcca cagtcctgac cctggccctg ctgggcaatg      60
cccatgcctg tgtcgagtgc ccaccgtgcc cagcaccacc tgtggcagga ccgtcagtct     120
tcctcttccc cccaaaaccc aaggacaccc tcatgatctc ccggacccct gaggtcacgt     180
gcgtggtggt ggacgtgagc cacgaagacc ccgaggtcca gttcaactgg tacgtggacg     240
gcgtggaggt gcataatgcc aagacaaagc cacgggagga gcagttcaac agcacgttcc     300
gtgtggtcag cgtcctcacc gttgtgcacc aggactggct gaacggcaag gagtacaagt     360
gcaaggtctc caacaaaggc ctcccagccc ccatcgagaa aaccatctcc aaaaccaaag     420
ggcagccccg agaaccacag gtgtacaccc tgcccccatc ccgggaggag atgaccaaga     480
accaggtcag cctgacctgc ctggtcaaag gcttctaccc cagcgacatc gccgtggagt     540
gggagagcaa tgggcagccg gagaacaact acaagaccac acctcccatg ctggactccg     600
acggctcctt cttcctctac agcaagctca ccgtggacaa gagcaggtgg cagcagggga     660
acgtcttctc atgctccgtg atgcatgagg ctctgcacaa ccactacacg cagaagagcc     720
tctccctgtc tccgggtaaa tgactcgagc ggccg                                755
```

<210> SEQ ID NO 41
<211> LENGTH: 221
<212> TYPE: PRT
<213> ORGANISM: Artificial Sequence
<220> FEATURE:
<223> OTHER INFORMATION: Human IgG2 Fc domain having the N-terminal
      sequence CPPCPAPE

<400> SEQUENCE: 41

Cys Pro Pro Cys Pro Ala Pro Val Ala Gly Pro Ser Val Phe Leu
1               5                   10                  15

Phe Pro Pro Lys Pro Lys Asp Thr Leu Met Ile Ser Arg Thr Pro Glu
                20                  25                  30

Val Thr Cys Val Val Val Asp Val Ser His Glu Asp Pro Glu Val Gln
            35                  40                  45

Phe Asn Trp Tyr Val Asp Gly Val Glu Val His Asn Ala Lys Thr Lys
 50                  55                  60

Pro Arg Glu Glu Gln Phe Asn Ser Thr Phe Arg Val Val Ser Val Leu
 65                  70                  75                  80

Thr Val Val His Gln Asp Trp Leu Asn Gly Lys Glu Tyr Lys Cys Lys
                85                  90                  95

Val Ser Asn Lys Gly Leu Pro Ala Pro Ile Glu Lys Thr Ile Ser Lys
                100                 105                 110

Thr Lys Gly Gln Pro Arg Glu Pro Gln Val Tyr Thr Leu Pro Pro Ser
            115                 120                 125

Arg Glu Glu Met Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Met Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
            195                 200                 205

His Tyr Thr Gln Lys Ser Leu Ser Leu Ser Pro Gly Lys
            210                 215                 220

<210> SEQ ID NO 42
<211> LENGTH: 663
<212> TYPE: DNA
<213> ORGANISM: Artificial Sequence
<220> FEATURE:
<223> OTHER INFORMATION: DNA encoding human IgG2 Fc domain having the
      N-terminal sequence CPPCPAPE

<400> SEQUENCE: 42
tgcccaccgt gcccagcacc acctgtggca ggaccgtcag tcttcctctt ccccccaaaa        60
cccaaggaca ccctcatgat ctcccggacc cctgaggtca cgtgcgtggt ggtggacgtg       120
agccacgaag accccgaggt ccagttcaac tggtacgtgg acggcgtgga ggtgcataat       180
gccaagacaa agccacggga ggagcagttc aacagcacgt tccgtgtggt cagcgtcctc       240
accgttgtgc accaggactg gctgaacggc aaggagtaca agtgcaaggt ctccaacaaa       300
ggcctcccag cccccatcga gaaaaccatc tccaaaacca agggcagcc  cgagaacca       360 caggtgtaca ccctgccccc atcccgggag gagatgacca agaaccaggt cagcctgacc       420
tgcctggtca aaggcttcta ccccagcgac atcgccgtgg agtgggagag caatgggcag       480
ccggagaaca actacaagac cacacctccc atgctggact ccgacggctc cttcttcctc       540
tacagcaagc tcaccgtgga caagagcagg tggcagcagg ggaacgtctt ctcatgctcc       600
gtgatgcatg aggctctgca caaccactac acgcagaaga gcctctccct gtctccgggt       660
aaa                                                                    663

<210> SEQ ID NO 43
<211> LENGTH: 244
<212> TYPE: PRT
<213> ORGANISM: Artificial Sequence
<220> FEATURE:
<223> OTHER INFORMATION: pre-Fc chimeric polypeptide having SHH signal

```
peptide

<400> SEQUENCE: 43

Met Leu Leu Leu Ala Arg Cys Leu Leu Val Leu Val Ser Ser Leu
1               5                   10                  15

Leu Val Cys Ser Gly Leu Ala Cys Pro Pro Cys Pro Ala Pro Pro Val
            20                  25                  30

Ala Gly Pro Ser Val Phe Leu Phe Pro Pro Lys Pro Lys Asp Thr Leu
                35                  40                  45

Met Ile Ser Arg Thr Pro Glu Val Thr Cys Val Val Val Asp Val Ser
        50                  55                  60

His Glu Asp Pro Glu Val Gln Phe Asn Trp Tyr Val Asp Gly Val Glu
65                  70                  75                  80

Val His Asn Ala Lys Thr Lys Pro Arg Glu Glu Gln Phe Asn Ser Thr
                85                  90                  95

Phe Arg Val Val Ser Val Leu Thr Val Val His Gln Asp Trp Leu Asn
                100                 105                 110

Gly Lys Glu Tyr Lys Cys Lys Val Ser Asn Lys Gly Leu Pro Ala Pro
            115                 120                 125

Ile Glu Lys Thr Ile Ser Lys Thr Lys Gly Gln Pro Arg Glu Pro Gln
        130                 135                 140

Val Tyr Thr Leu Pro Pro Ser Arg Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Met Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Lys

<210> SEQ ID NO 44
<211> LENGTH: 764
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 44
aagcttgaat tcccaccatg ctgctgctgg cgagatgtct gctgctagtc ctcgtctcct      60
cgctgctggt atgctcggga ctggcgtgcc caccgtgccc agcaccacct gtggcaggac     120
cgtcagtctt cctcttcccc ccaaaaccca aggacaccct catgatctcc cggacccctg     180
aggtcacgtg cgtggtggtg gacgtgagcc acgaagaccc gaggtccag ttcaactggt     240 acgtggacgg cgtggaggtg cataatgcca agacaaagcc acgggaggag cagttcaaca     300
gcacgttccg tgtggtcagc gtcctcaccg ttgtgcacca ggactggctg aacggcaagg     360
agtacaagtg caaggtctcc aacaaaggcc tcccagcccc catcgagaaa accatctcca     420
aaaccaaagg gcagccccga gaaccacagg tgtacaccct gcccccatcc cgggaggaga     480
tgaccaagaa ccaggtcagc ctgacctgcc tggtcaaagg cttctacccc agcgacatcg     540
```

```
ccgtggagtg ggagagcaat gggcagccgg agaacaacta caagaccaca cctcccatgc    600
tggactccga cggctccttc ttcctctaca gcaagctcac cgtggacaag agcaggtggc    660 agcagggaa cgtcttctca tgctccgtga tgcatgaggc tctgcacaac cactacacgc     720
agaagagcct ctccctgtct ccgggtaaat gactcgagcg gccg                    764
```

<210> SEQ ID NO 45
<211> LENGTH: 244
<212> TYPE: PRT
<213> ORGANISM: Artificial Sequence
<220> FEATURE:
<223> OTHER INFORMATION: pre-Fc chimeric polypeptide having IFN signal peptide

<400> SEQUENCE: 45

```
Met Ala Leu Thr Phe Ala Leu Leu Val Ala Leu Leu Val Leu Ser Cys
1               5                   10                  15

Lys Ser Ser Cys Ser Val Gly Cys Pro Pro Cys Pro Ala Pro Pro Val
            20                  25                  30

Ala Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

His Glu Asp Pro Glu Val Gln Phe Asn Trp Tyr Val Asp Gly Val Glu
65                  70                  75                  80

Val His Asn Ala Lys Thr Lys Pro Arg Glu Glu Gln Phe Asn Ser Thr
                85                  90                  95

Phe Arg Val Val Ser Val Leu Thr Val Val His Gln Asp Trp Leu Asn
            100                 105                 110

Gly Lys Glu Tyr Lys Cys Lys Val Ser Asn Lys Gly Leu Pro Ala Pro
        115                 120                 125

Ile Glu Lys Thr Ile Ser Lys Thr Lys Gly Gln Pro Arg Glu Pro Gln
    130                 135                 140

Val Tyr Thr Leu Pro Pro Ser Arg Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Met Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Lys
```

<210> SEQ ID NO 46
<211> LENGTH: 764
<212> TYPE: DNA
<213> ORGANISM: Artificial Sequence
<220> FEATURE:
<223> OTHER INFORMATION: DNA encoding pre-Fc chimeric polypeptide having IFN signal peptide

<400> SEQUENCE: 46

```
aagcttgaat tcccaccatg gccttgacct ttgctttact ggtggccctc ctggtgctca    60
```

```
gctgcaagtc aagctgctct gtgggctgcc caccgtgccc agcaccacct gtggcaggac      120
cgtcagtctt cctcttcccc ccaaaaccca aggacaccct catgatctcc cggacccctg      180
aggtcacgtg cgtggtggtg gacgtgagcc acgaagaccc cgaggtccag ttcaactggt      240
acgtggacgg cgtggaggtg cataatgcca agacaaagcc acgggaggag cagttcaaca      300
gcacgttccg tgtggtcagc gtcctcaccg ttgtgcacca ggactggctg aacggcaagg      360
agtacaagtg caaggtctcc aacaaaggcc tcccagcccc catcgagaaa accatctcca      420
aaaccaaagg gcagccccga gaaccacagg tgtacaccct gcccccatcc cgggaggaga      480
tgaccaagaa ccaggtcagc ctgacctgcc tggtcaaagg cttctacccc agcgacatcg      540
ccgtggagtg ggagagcaat gggcagccgg agaacaacta caagaccaca cctcccatgc      600
tggactccga cggctccttc ttcctctaca gcaagctcac cgtggacaag agcaggtggc      660
agcaggggaa cgtcttctca tgctccgtga tgcatgaggc tctgcacaac cactacacgc      720
agaagagcct ctccctgtct ccgggtaaat gactcgagcg gccg                      764
```

```
<210> SEQ ID NO 47
<211> LENGTH: 238
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 47
```

```
Met Leu Ala Ala Thr Val Leu Thr Leu Ala Leu Leu Gly Asn Ala His
1               5                   10                  15

Ala Cys Pro Pro Cys Pro Ala Pro Val Ala Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Gln Phe Asn Trp Tyr Val Asp Gly Val Glu Val His Asn Ala Lys Thr
65                  70                  75                  80

Lys Pro Arg Glu Glu Gln Phe Asn Ser Thr Phe Arg Val Val Ser Val
                85                  90                  95

Leu Thr Val Val His Gln Asp Trp Leu Asn Gly Lys Glu Tyr Lys Cys
            100                 105                 110

Lys Val Ser Asn Lys Gly Leu Pro Ala Pro Ile Glu Lys Thr Ile Ser
        115                 120                 125

Lys Thr Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
```

<210> SEQ ID NO 48
<211> LENGTH: 746
<212> TYPE: DNA
<213> ORGANISM: Artificial Sequence
<220> FEATURE:
<223> OTHER INFORMATION: DNA encoding pre-Fc chimeric polypeptide having CETP signal peptide

<400> SEQUENCE: 48

```
aagcttgaat tcccaccatg ctggctgcca cagtcctgac cctggccctg ctgggcaatg    60
cccatgcctg ccaccgtgc ccagcaccac ctgtggcagg accgtcagtc ttcctcttcc   120
ccccaaaacc caaggacacc ctcatgatct cccggacccc tgaggtcacg tgcgtggtgg   180
tggacgtgag ccacgaagac cccgaggtcc agttcaactg gtacgtggac ggcgtggagg   240
tgcataatgc caagacaaag ccacgggagg agcagttcaa cagcacgttc cgtgtggtca   300
gcgtcctcac cgttgtgcac caggactggc tgaacggcaa ggagtacaag tgcaaggtct   360
ccaacaaagg cctcccagcc cccatcgaga aaaccatctc caaaaccaaa gggcagcccc   420
gagaaccaca ggtgtacacc ctgcccccat cccgggagga gatgaccaag aaccaggtca   480
gcctgacctg cctggtcaaa ggcttctacc ccagcgacat cgccgtggag tgggagagca   540
atgggcagcc ggagaacaac tacaagacca cacctcccat gctggactcc gacggctcct   600
tcttcctcta cagcaagctc accgtggaca agagcaggtg gcagcagggg aacgtcttct   660
catgctccgt gatgcatgag gctctgcaca accactacac gcagaagagc ctctccctgt   720
ctccgggtaa atgactcgag cggccg                                        746
```

<210> SEQ ID NO 49
<211> LENGTH: 218
<212> TYPE: PRT
<213> ORGANISM: Artificial Sequence
<220> FEATURE:
<223> OTHER INFORMATION: Human IgG2 Fc domain having the N-terminal sequence CPAPE

<400> SEQUENCE: 49

Cys Pro Ala Pro Pro Val Ala Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Phe Arg Val Val Ser Val Leu Thr Val Val
65                  70                  75                  80

His Gln Asp Trp Leu Asn Gly Lys Glu Tyr Lys Cys Lys Val Ser Asn
                85                  90                  95

Lys Gly Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Met Leu Asp Ser Asp Gly Ser Phe Phe
            165                 170                 175

Leu Tyr Ser Lys Leu Thr Val Asp Lys Ser Arg Trp Gln Gln Gly Asn
        180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 50
<211> LENGTH: 654
<212> TYPE: DNA
<213> ORGANISM: Artificial Sequence
<220> FEATURE:
<223> OTHER INFORMATION: DNA encoding human IgG2 Fc domain having the
      N-terminal sequence CPAPE

<400> SEQUENCE: 50
tgcccagcac cacctgtggc aggaccgtca gtcttcctct tccccccaaa acccaaggac      60
accctcatga tctcccggac ccctgaggtc acgtgcgtgg tggtggacgt gagccacgaa     120
gaccccgagg tccagttcaa ctggtacgtg acggcgtgg aggtgcataa tgccaagaca      180
aagccacggg aggagcagtt caacagcacg ttccgtgtgg tcagcgtcct caccgttgtg     240
caccaggact ggctgaacgg caaggagtac aagtgcaagg tctccaacaa aggcctccca    300
gcccccatcg agaaaaccat ctccaaaacc aaagggcagc cccgagaacc acaggtgtac    360
accctgcccc catcccggga ggagatgacc aagaaccagg tcagcctgac ctgcctggtc    420
aaaggcttct accccagcga catcgccgtg gagtgggaga gcaatgggca gccggagaac    480
aactacaaga ccacacctcc catgctggac tccgacggct ccttcttcct ctacagcaag    540
ctcaccgtgg acaagagcag gtggcagcag gggaacgtct tctcatgctc cgtgatgcat    600
gaggctctgc acaaccacta cacgcagaag agcctctccc tgtctccggg taaa          654

<210> SEQ ID NO 51
<211> LENGTH: 241
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 51

Met Leu Leu Leu Ala Arg Cys Leu Leu Val Leu Val Ser Ser Leu
1               5                   10                  15

Leu Val Cys Ser Gly Leu Ala Cys Pro Ala Pro Pro Val Ala Gly Pro
            20                  25                  30

Ser Val Phe Leu Phe Pro Pro Lys Pro Lys Asp Thr Leu Met Ile Ser
        35                  40                  45

Arg Thr Pro Glu Val Thr Cys Val Val Val Asp Val Ser His Glu Asp
    50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
                85                  90                  95

Val Ser Val Leu Thr Val Val His Gln Asp Trp Leu Asn Gly Lys Glu
            100                 105                 110

Tyr Lys Cys Lys Val Ser Asn Lys Gly Leu Pro Ala Pro Ile Glu Lys

```
                115                 120                 125
Thr Ile Ser Lys Thr Lys Gly Gln Pro Arg Glu Pro Gln Val Tyr Thr
            130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Met Leu
            180                 185                 190

Asp Ser Asp Gly Ser Phe Phe Leu Tyr Ser Lys Leu Thr Val Asp Lys
            195                 200                 205

Ser Arg Trp Gln Gln Gly Asn Val Phe Ser Cys Ser Val Met His Glu
            210                 215                 220

Ala Leu His Asn His Tyr Thr Gln Lys Ser Leu Ser Leu Ser Pro Gly
225                 230                 235                 240

Lys

<210> SEQ ID NO 52
<211> LENGTH: 755
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 52
aagcttgaat  tcccaccatg  ctgctgctgg  cgagatgtct  gctgctagtc  ctcgtctcct     60
cgctgctggt  atgctcggga  ctggcgtgcc  cagcaccacc  tgtggcagga  ccgtcagtct    120
tcctcttccc  cccaaaaccc  aaggacaccc  tcatgatctc  ccggaccccc  gaggtcacgt    180
gcgtggtggt  ggacgtgagc  cacgaagacc  ccgaggtcca  gttcaactgg  tacgtggacg    240
gcgtggaggt  gcataatgcc  aagacaaagc  cacgggagga  gcagttcaac  agcacgttcc    300
gtgtggtcag  cgtcctcacc  gttgtgcacc  aggactggct  gaacggcaag  gagtacaagt    360
gcaaggtctc  caacaaaggc  ctcccagccc  catcgagaa   aaccatctcc  aaaaccaaag    420
ggcagccccg  agaaccacag  gtgtacaccc  tgccccatc   ccgggaggag  atgaccaaga    480
accaggtcag  cctgacctgc  ctggtcaaag  gcttctaccc  cagcgacatc  gccgtggagt    540
gggagagcaa  tgggcagccg  gagaacaact  acaagaccac  acctcccatg  ctggactccg    600
acggctcctt  cttcctctac  agcaagctca  ccgtggacaa  gagcaggtgg  cagcagggga    660
acgtcttctc  atgctccgtg  atgcatgagg  ctctgcacaa  ccactacacg  cagaagagcc    720
tctccctgtc  tccgggtaaa  tgactcgagc  ggccg                                 755

<210> SEQ ID NO 53
<211> LENGTH: 241
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 53

Met Ala Leu Thr Phe Ala Leu Leu Val Ala Leu Leu Val Leu Ser Cys
1               5                   10                  15

Lys Ser Ser Cys Ser Val Gly Cys Pro Ala Pro Pro Val Ala Gly Pro
            20                  25                  30
```

| Ser | Val | Phe | Leu | Phe | Pro | Pro | Lys | Pro | Lys | Asp | Thr | Leu | Met | Ile | Ser |
|---|---|---|---|---|---|---|---|---|---|---|---|---|---|---|---|
| | | 35 | | | | 40 | | | | | 45 | | | | |

| Arg | Thr | Pro | Glu | Val | Thr | Cys | Val | Val | Val | Asp | Val | Ser | His | Glu | Asp |
|---|---|---|---|---|---|---|---|---|---|---|---|---|---|---|---|
| 50 | | | | | 55 | | | | | 60 | | | | | |

| Pro | Glu | Val | Gln | Phe | Asn | Trp | Tyr | Val | Asp | Gly | Val | Glu | Val | His | Asn |
|---|---|---|---|---|---|---|---|---|---|---|---|---|---|---|---|
| 65 | | | | | 70 | | | | | 75 | | | | | 80 |

| Ala | Lys | Thr | Lys | Pro | Arg | Glu | Glu | Gln | Phe | Asn | Ser | Thr | Phe | Arg | Val |
|---|---|---|---|---|---|---|---|---|---|---|---|---|---|---|---|
| | | | | 85 | | | | | 90 | | | | | 95 | |

| Val | Ser | Val | Leu | Thr | Val | Val | His | Gln | Asp | Trp | Leu | Asn | Gly | Lys | Glu |
|---|---|---|---|---|---|---|---|---|---|---|---|---|---|---|---|
| | | | 100 | | | | | 105 | | | | | 110 | | |

| Tyr | Lys | Cys | Lys | Val | Ser | Asn | Lys | Gly | Leu | Pro | Ala | Pro | Ile | Glu | Lys |
|---|---|---|---|---|---|---|---|---|---|---|---|---|---|---|---|
| | | 115 | | | | | 120 | | | | | 125 | | | |

| Thr | Ile | Ser | Lys | Thr | Lys | Gly | Gln | Pro | Arg | Glu | Pro | Gln | Val | Tyr | Thr |
|---|---|---|---|---|---|---|---|---|---|---|---|---|---|---|---|
| | 130 | | | | | 135 | | | | | 140 | | | | |

| Leu | Pro | Pro | Ser | Arg | Glu | Glu | Met | Thr | Lys | Asn | Gln | Val | Ser | Leu | Thr |
|---|---|---|---|---|---|---|---|---|---|---|---|---|---|---|---|
| 145 | | | | | 150 | | | | | 155 | | | | | 160 |

| Cys | Leu | Val | Lys | Gly | Phe | Tyr | Pro | Ser | Asp | Ile | Ala | Val | Glu | Trp | Glu |
|---|---|---|---|---|---|---|---|---|---|---|---|---|---|---|---|
| | | | | 165 | | | | | 170 | | | | | 175 | |

| Ser | Asn | Gly | Gln | Pro | Glu | Asn | Asn | Tyr | Lys | Thr | Thr | Pro | Pro | Met | Leu |
|---|---|---|---|---|---|---|---|---|---|---|---|---|---|---|---|
| | | | 180 | | | | | 185 | | | | | 190 | | |

| Asp | Ser | Asp | Gly | Ser | Phe | Phe | Leu | Tyr | Ser | Lys | Leu | Thr | Val | Asp | Lys |
|---|---|---|---|---|---|---|---|---|---|---|---|---|---|---|---|
| | 195 | | | | | 200 | | | | | 205 | | | | |

| Ser | Arg | Trp | Gln | Gln | Gly | Asn | Val | Phe | Ser | Cys | Ser | Val | Met | His | Glu |
|---|---|---|---|---|---|---|---|---|---|---|---|---|---|---|---|
| | 210 | | | | | 215 | | | | | 220 | | | | |

| Ala | Leu | His | Asn | His | Tyr | Thr | Gln | Lys | Ser | Leu | Ser | Leu | Ser | Pro | Gly |
|---|---|---|---|---|---|---|---|---|---|---|---|---|---|---|---|
| 225 | | | | | 230 | | | | | 235 | | | | | 240 |

Lys

```
<210> SEQ ID NO 54
<211> LENGTH: 755
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 54
aagcttgaat tcccaccatg gccttgacct ttgctttact ggtggccctc ctggtgctca        60
gctgcaagtc aagctgctct gtgggctgcc agcaccacc tgtggcagga ccgtcagtct       120
tcctcttccc cccaaaaccc aaggacaccc tcatgatctc ccggacccct gaggtcacgt       180
gcgtggtggt ggacgtgagc cacgaagacc ccgaggtcca gttcaactgg tacgtggacg       240
gcgtggaggt gcataatgcc aagacaaagc cacgggagga gcagttcaac agcacgttcc       300
gtgtggtcag cgtcctcacc gttgtgcacc aggactggct gaacggcaag gagtacaagt       360
gcaaggtctc caacaaaggc ctcccagccc ccatcgagaa aaccatctcc aaaaccaaag       420
ggcagccccg agaaccacag gtgtacaccc tgcccccatc ccgggaggag atgaccaaga       480
accaggtcag cctgacctgc ctggtcaaag gcttctaccc cagcgacatc gccgtggagt       540
gggagagcaa tgggcagccg gagaacaact acaagaccac acctcccatg ctggactccg       600
acggctcctt cttcctctac agcaagctca ccgtggacaa gagcaggtgg cagcagggga       660
acgtcttctc atgctccgtg atgcatgagg ctctgcacaa ccactacacg cagaagagcc       720
tctccctgtc tccgggtaaa tgactcgagc ggccg                                 755
```

<210> SEQ ID NO 55
<211> LENGTH: 235
<212> TYPE: PRT
<213> ORGANISM: Artificial Sequence
<220> FEATURE:
<223> OTHER INFORMATION: pre-Fc chimeric polypeptide having CETP signal peptide

<400> SEQUENCE: 55

```
Met Leu Ala Ala Thr Val Leu Thr Leu Ala Leu Leu Gly Asn Ala His
1               5                   10                  15

Ala Cys Pro Ala Pro Pro Val Ala Gly Pro Ser Val Phe Leu Phe Pro
                20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
        50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
        115                 120                 125

Gly Gln Pro Arg Glu Pro Gln Val Tyr Thr Leu Pro Pro Ser Arg Glu
130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Ser Leu Ser Leu Ser Pro Gly Lys
225                 230                 235
```

<210> SEQ ID NO 56
<211> LENGTH: 737
<212> TYPE: DNA
<213> ORGANISM: Artificial Sequence
<220> FEATURE:
<223> OTHER INFORMATION: DNA encoding pre-Fc chimeric polypeptide having CETP signal peptide

<400> SEQUENCE: 56

```
aagcttgaat tcccaccatg ctggctgcca cagtcctgac cctggccctg ctgggcaatg      60
cccatgcctg cccagcacca cctgtggcag gaccgtcagt cttcctcttc cccccaaaac     120
ccaaggacac cctcatgatc tcccggaccc ctgaggtcac gtgcgtggtg gtggacgtga     180
gccacgaaga ccccgaggtc cagttcaact ggtacgtgga cggcgtggag gtgcataatg     240
ccaagacaaa gccacgggag gagcagttca acagcacgtt ccgtgtggtc agcgtcctca     300
ccgttgtgca ccaggactgg ctgaacggca aggagtacaa gtgcaaggtc tccaacaaag     360
gcctcccagc ccccatcgag aaaaccatct ccaaaaccaa agggcagccc cgagaaccac     420
```

```
aggtgtacac cctgccccca tcccgggagg agatgaccaa gaaccaggtc agcctgacct    480
gcctggtcaa aggcttctac cccagcgaca tcgccgtgga gtgggagagc aatgggcagc    540
cggagaacaa ctacaagacc acacctccca tgctggactc cgacggctcc ttcttcctct    600
acagcaagct caccgtggac aagagcaggt ggcagcaggg gaacgtcttc tcatgctccg    660
tgatgcatga ggctctgcac aaccactaca cgcagaagag cctctccctg tctccgggta    720
aatgactcga gcggccg                                                   737
```

<210> SEQ ID NO 57
<211> LENGTH: 267
<212> TYPE: PRT
<213> ORGANISM: Artificial Sequence
<220> FEATURE:
<223> OTHER INFORMATION: Human IgG3 Fc domain having the N-terminal
      sequence (CPRCPEPKSDTPPP)3-CPRCPAPE

<400> SEQUENCE: 57

```
Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro Ala Pro Glu Leu Leu Gly Gly Pro Ser Val Phe Leu Phe Pro
    50                  55                  60

Pro Lys Pro Lys Asp Thr Leu Met Ile Ser Arg Thr Pro Glu Val Thr
65                  70                  75                  80

Cys Val Val Val Asp Val Ser His Glu Asp Pro Glu Val Gln Phe Lys
                85                  90                  95

Trp Tyr Val Asp Gly Val Glu Val His Asn Ala Lys Thr Lys Pro Arg
            100                 105                 110

Glu Glu Gln Tyr Asn Ser Thr Phe Arg Val Val Ser Val Leu Thr Val
        115                 120                 125

Leu His Gln Asp Trp Leu Asn Gly Lys Glu Tyr Lys Cys Lys Val Ser
    130                 135                 140

Asn Lys Ala Leu Pro Ala Pro Ile Glu Lys Thr Ile Ser Lys Thr Lys
145                 150                 155                 160

Gly Gln Pro Arg Glu Pro Gln Val Tyr Thr Leu Pro Pro Ser Arg Glu
                165                 170                 175

Glu Met Thr Lys Asn Gln Val Ser Leu Thr Cys Leu Val Lys Gly Phe
            180                 185                 190

Tyr Pro Ser Asp Ile Ala Val Glu Trp Glu Ser Ser Gly Gln Pro Glu
        195                 200                 205

Asn Asn Tyr Asn Thr Thr Pro Pro Met Leu Asp Ser Asp Gly Ser Phe
    210                 215                 220

Phe Leu Tyr Ser Lys Leu Thr Val Asp Lys Ser Arg Trp Gln Gln Gly
225                 230                 235                 240

Asn Ile Phe Ser Cys Ser Val Met His Glu Ala Leu His Asn Arg Phe
                245                 250                 255

Thr Gln Lys Ser Leu Ser Leu Ser Pro Gly Lys
            260                 265
```

<210> SEQ ID NO 58
<211> LENGTH: 801
<212> TYPE: DNA

<213> ORGANISM: Artificial Sequence
<220> FEATURE:
<223> OTHER INFORMATION: DNA encoding human IgG3 Fc domain having the N-terminal sequence (CPRCPEPKSDTPPP)3-CPRCPAPE

<400> SEQUENCE: 58

```
tgcccacggt gcccagagcc caaatcttgt gacacacctc ccccgtgccc acggtgccca      60
gagcccaaat cttgtgacac acctccccca tgcccacggt gcccagagcc caaatcttgt     120
gacacacctc ccccgtgccc aaggtgccca gcacctgaac tcctgggagg accgtcagtc     180
ttcctcttcc ccccaaaacc caaggatacc cttatgattt cccggacccc tgaggtcacg     240
tgcgtggtgg tggacgtgag ccacgaagac cccgaggtcc agttcaagtg gtacgtggac     300
ggcgtggagg tgcataatgc caagacaaag ccgcgggagg agcagtacaa cagcacgttc     360
cgtgtggtca gcgtcctcac cgtcctgcac caggactggc tgaacggcaa ggagtacaag     420
tgcaaggtct ccaacaaagc cctcccagcc cccatcgaga aaaccatctc caaaaccaaa     480
ggacagcccc gagaaccaca ggtgtacacc ctgcccccat cccgggagga tgaccaag      540
aaccaggtca gcctgacctg cctggtcaaa ggcttctacc ccagcgacat cgccgtggag     600
tgggagagca atgggcagcc ggagaacaac tacaacacca cgcctcccat gctggactcc     660
gacggctcct tcttcctcta cagcaagctc accgtggaca agagcaggtg gcagcagggg     720
aacatcttct catgctccgt gatgcatgag gctctgcaca accgcttcac gcagaagagc     780
ctctccctgt ctccgggtaa a                                                801
```

<210> SEQ ID NO 59
<211> LENGTH: 290
<212> TYPE: PRT
<213> ORGANISM: Artificial Sequence
<220> FEATURE:
<223> OTHER INFORMATION: pre-Fc chimeric polypeptide having SHH signal peptide

<400> SEQUENCE: 59

```
Met Leu Leu Leu Ala Arg Cys Leu Leu Val Leu Val Ser Ser Leu
1               5                   10                  15

Leu Val Cys Ser Gly Leu Ala Cys Pro Arg Cys Pro Glu Pro Lys Ser
            20                  25                  30

Cys Asp Thr Pro Pro Pro Cys Pro Arg Cys Pro Glu Pro Lys Ser Cys
        35                  40                  45

Asp Thr Pro Pro Pro Cys Pro Arg Cys Pro Glu Pro Lys Ser Cys Asp
    50                  55                  60

Thr Pro Pro Pro Cys Pro Arg Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Gln Phe Lys Trp Tyr Val Asp Gly Val Glu Val His
        115                 120                 125

Asn Ala Lys Thr Lys Pro Arg Glu Glu Gln Tyr Asn Ser Thr Phe Arg
    130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175
```

Lys Thr Ile Ser Lys Thr Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
        210                 215                 220

Glu Ser Ser Gly Gln Pro Glu Asn Asn Tyr Lys Thr Thr Pro Pro Met
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Ile Phe Ser Cys Ser Val Met His
            260                 265                 270

Glu Ala Leu His Asn Arg Phe Thr Gln Lys Ser Leu Ser Leu Ser Pro
        275                 280                 285

Gly Lys
    290

<210> SEQ ID NO 60
<211> LENGTH: 902
<212> TYPE: DNA
<213> ORGANISM: Artificial Sequence
<220> FEATURE:
<223> OTHER INFORMATION: DNA encoding pre-Fc chimeric polypeptide
      having SHH signal peptide

<400> SEQUENCE: 60
aagcttgaat tcccaccatg ctgctgctgg cgagatgtct gctgctagtc ctcgtctcct    60
cgctgctggt atgctcggga ctggcgtgcc cacggtgccc agagcccaaa tcttgtgaca   120
cacctccccc gtgcccacgg tgcccagagc ccaaatcttg tgacacacct cccccatgcc   180
cacggtgccc agagcccaaa tcttgtgaca cacctccccc gtgcccaagg tgcccagcac   240
ctgaactcct ggaggaccg tcagtcttcc tcttccccc aaaacccaag gatacccta    300 tgatttcccg gacccctgag gtcacgtgcg tggtggtgga cgtgagccac gaagaccccg   360
aggtccagtt caagtggtac gtggacggcg tggaggtgca taatgccaag acaaagccgc   420
gggaggagca gtacaacagc acgttccgtg tggtcagcgt cctcaccgtc ctgcaccagg   480
actggctgaa cggcaaggag tacaagtgca aggtctccaa caaagccctc cagcccccca   540
tcgagaaaac catctccaaa accaaggac agccccgaga ccacaggtg tacacccgc   600 ccccatcccg ggaggagatg accaagaacc aggtcagcct gacctgcctg gtcaaaggct   660
tctaccccag cgacatcgcc gtggagtggg agagcagcgg cagccggag aacaactaca   720 acaccacgcc tcccatgctg gactccgacg gctccttctt cctctacagc aagctcaccg   780
tggacaagag caggtggcag caggggaaca tcttctcatg ctccgtgatg catgaggctc   840
tgcacaaccg cttcacgcag aagagcctct ccctgtctcc gggtaaatga ctcgagcggc   900
cg                                                                 902

<210> SEQ ID NO 61
<211> LENGTH: 290
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 61

Met Ala Leu Thr Phe Ala Leu Leu Val Ala Leu Leu Val Leu Ser Cys

```
  1               5                  10                 15
Lys Ser Ser Cys Ser Val Gly Cys Pro Arg Cys Pro Glu Pro Lys Ser
                 20                 25                 30

Cys Asp Thr Pro Pro Cys Pro Arg Cys Pro Glu Pro Lys Ser Cys
                 35                 40                 45

Asp Thr Pro Pro Pro Cys Pro Arg Cys Pro Glu Pro Lys Ser Cys Asp
                 50                 55                 60

Thr Pro Pro Pro Cys Pro Arg Cys Pro Ala Pro Glu Leu Leu Gly Gly
 65              70                 75                 80

Pro Ser Val Phe Leu Phe Pro Pro Lys Pro Lys Asp Thr Leu Met Ile
                 85                 90                 95

Ser Arg Thr Pro Glu Val Thr Cys Val Val Val Asp Val Ser His Glu
                100                105                110

Asp Pro Glu Val Gln Phe Lys Trp Tyr Val Asp Gly Val Glu Val His
                115                120                125

Asn Ala Lys Thr Lys Pro Arg Glu Glu Gln Tyr Asn Ser Thr Phe Arg
                130                135                140

Val Val Ser Val Leu Thr Val Leu His Gln Asp Trp Leu Asn Gly Lys
145              150                155                160

Glu Tyr Lys Cys Lys Val Ser Asn Lys Ala Leu Pro Ala Pro Ile Glu
                165                170                175

Lys Thr Ile Ser Lys Thr Lys Gly Gln Pro Arg Glu Pro Gln Val Tyr
                180                185                190

Thr Leu Pro Pro Ser Arg Glu Glu Met Thr Lys Asn Gln Val Ser Leu
                195                200                205

Thr Cys Leu Val Lys Gly Phe Tyr Pro Ser Asp Ile Ala Val Glu Trp
                210                215                220

Glu Ser Ser Gly Gln Pro Glu Asn Asn Tyr Asn Thr Thr Pro Pro Met
225              230                235                240

Leu Asp Ser Asp Gly Ser Phe Phe Leu Tyr Ser Lys Leu Thr Val Asp
                245                250                255

Lys Ser Arg Trp Gln Gln Gly Asn Ile Phe Ser Cys Ser Val Met His
                260                265                270

Glu Ala Leu His Asn Arg Phe Thr Gln Lys Ser Leu Ser Leu Ser Pro
                275                280                285

Gly Lys
   290

<210> SEQ ID NO 62
<211> LENGTH: 902
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 62
aagcttgaat tcccaccatg gccttgacct ttgctttact ggtggccctc ctggtgctca    60
gctgcaagtc aagctgctct gtgggctgcc cacggtgccc agagcccaaa tcttgtgaca   120
cacctccccc gtgcccacgg tgcccagagc ccaaatcttg tgacacacct ccccatgcc    180 cacggtgccc agagcccaaa tcttgtgaca cacctccccc gtgcccaagg tgcccagcac   240
ctgaactcct gggaggaccg tcagtcttcc tcttcccccc aaaacccaag gatacccta    300 tgatttcccg gaccctgag gtcacgtgcg tggtggtgga cgtgagccac gaagacccg    360
```

```
aggtccagtt caagtggtac gtggacggcg tggaggtgca taatgccaag acaaagccgc    420
gggaggagca gtacaacagc acgttccgtg tggtcagcgt cctcaccgtc ctgcaccagg    480
actggctgaa cggcaaggag tacaagtgca aggtctccaa caaagccctc ccagccccca    540
tcgagaaaac catctccaaa accaaggac agccccgaga ccacaggtg tacaccctgc      600 ccccatcccg ggaggagatg accaagaacc aggtcagcct gacctgcctg gtcaaaggct    660
tctaccccag cgacatcgcc gtggagtggg agagcagcgg gcagccggag aacaactaca    720
acaccacgcc tcccatgctg gactccgacg gctccttctt cctctacagc aagctcaccg    780
tggacaagag caggtggcag caggggaaca tcttctcatg ctccgtgatg catgaggctc    840
tgcacaaccg cttcacgcag aagagcctct ccctgtctcc gggtaaatga ctcgagcggc    900
cg                                                                  902
```

```
<210> SEQ ID NO 63
<211> LENGTH: 284
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 63

Met Leu Ala Ala Thr Val Leu Thr Leu Ala Leu Leu Gly Asn Ala His
1               5                   10                  15

Ala Cys Pro Arg Cys Pro Glu Pro Lys Ser Cys Asp Thr Pro Pro Pro
                20                  25                  30

Cys Pro Arg Cys Pro Glu Pro Lys Ser Cys Asp Thr Pro Pro Pro Cys
            35                  40                  45

Pro Arg Cys Pro Glu Pro Lys Ser Cys Asp Thr Pro Pro Pro Cys Pro
        50                  55                  60

Arg Cys Pro Ala Pro Glu Leu Leu Gly Gly Pro Ser Val Phe Leu Phe
65                  70                  75                  80

Pro Pro Lys Pro Lys Asp Thr Leu Met Ile Ser Arg Thr Pro Glu Val
                85                  90                  95

Thr Cys Val Val Val Asp Val Ser His Glu Asp Pro Glu Val Gln Phe
                100                 105                 110

Lys Trp Tyr Val Asp Gly Val Glu Val His Asn Ala Lys Thr Lys Pro
            115                 120                 125

Arg Glu Glu Gln Tyr Asn Ser Thr Phe Arg Val Val Ser Val Leu Thr
        130                 135                 140

Val Leu His Gln Asp Trp Leu Asn Gly Lys Glu Tyr Lys Cys Lys Val
145                 150                 155                 160

Ser Asn Lys Ala Leu Pro Ala Pro Ile Glu Lys Thr Ile Ser Lys Thr
                165                 170                 175

Lys Gly Gln Pro Arg Glu Pro Gln Val Tyr Thr Leu Pro Pro Ser Arg
            180                 185                 190

Glu Glu Met Thr Lys Asn Gln Val Ser Leu Thr Cys Leu Val Lys Gly
        195                 200                 205

Phe Tyr Pro Ser Asp Ile Ala Val Glu Trp Glu Ser Ser Gly Gln Pro
    210                 215                 220

Glu Asn Asn Tyr Asn Thr Thr Pro Pro Met Leu Asp Ser Asp Gly Ser
225                 230                 235                 240

Phe Phe Leu Tyr Ser Lys Leu Thr Val Asp Lys Ser Arg Trp Gln Gln
                245                 250                 255
```

Gly Asn Ile Phe Ser Cys Ser Val Met His Glu Ala Leu His Asn Arg
            260                 265                 270

Phe Thr Gln Lys Ser Leu Ser Leu Ser Pro Gly Lys
        275                 280

<210> SEQ ID NO 64
<211> LENGTH: 884
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 64
aagcttgaat tcccaccatg ctggctgcca cagtcctgac cctggccctg ctgggcaatg      60
cccatgcctg cccacggtgc ccagagccca atcttgtga cacacctccc ccgtgcccac     120
ggtgcccaga gcccaaatct tgtgacacac ctcccccatg cccacggtgc ccagagccca     180
aatcttgtga cacacctccc ccgtgcccaa ggtgcccagc acctgaactc ctgggaggac     240
cgtcagtctt cctcttcccc ccaaaaccca aggataccct tatgatttcc cggacccctg     300
aggtcacgtg cgtggtggtg gacgtgagcc acgaagaccc cgaggtccag ttcaagtggt     360
acgtggacgg cgtggaggtg cataatgcca agacaaagcc gcgggaggag cagtacaaca     420
gcacgttccg tgtggtcagc gtcctcaccg tcctgcacca ggactggctg aacggcaagg     480
agtacaagtg caaggtctcc aacaaagccc tcccagcccc catcgagaaa accatctcca     540
aaaccaaagg acagcccga gaaccacagg tgtacaccct gcccccatcc cgggaggaga     600
tgaccaagaa ccaggtcagc ctgacctgcc tggtcaaagg cttctacccc agcgacatcg     660
ccgtggagtg ggagagcagc gggcagccgg agaacaacta caacaccacg cctcccatgc     720
tggactccga cggctccttc ttcctctaca gcaagctcac cgtggacaag agcaggtggc     780
agcaggggaa catcttctca tgctccgtga tgcatgaggc tctgcacaac cgcttcacgc     840
agaagagcct ctccctgtct ccgggtaaat gactcgagcg gccg                      884

<210> SEQ ID NO 65
<211> LENGTH: 222
<212> TYPE: PRT
<213> ORGANISM: Artificial Sequence
<220> FEATURE:
<223> OTHER INFORMATION: Human IgG3 Fc domain having the N-terminal
      sequence CPRCPAPE

<400> SEQUENCE: 65

Cys Pro Arg Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Gln Phe Lys Trp Tyr Val Asp Gly Val Glu Val His Asn Ala Lys Thr
    50                  55                  60

Lys Pro Arg Glu Glu Gln Tyr Asn Ser Thr Phe Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Thr Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Ser Gly
145                 150                 155                 160

Gln Pro Glu Asn Asn Tyr Asn Thr Thr Pro Pro Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Ile Phe Ser Cys Ser Val Met His Glu Ala Leu His
        195                 200                 205

Asn Arg Phe Thr Gln Lys Ser Leu Ser Leu Ser Pro Gly Lys
210                 215                 220

<210> SEQ ID NO 66
<211> LENGTH: 681
<212> TYPE: DNA
<213> ORGANISM: Artificial Sequence
<220> FEATURE:
<223> OTHER INFORMATION: DNA encoding human IgG3 Fc domain having the
      N-terminal sequence CPRCPAPE

<400> SEQUENCE: 66
tgcccaaggt gcccagcacc tgaactcctg ggaggaccgt cagtcttcct cttcccccca      60
aaacccaagg ataccttat gatttcccgg acccctgagg tcacgtgcgt ggtggtggac     120
gtgagccacg aagaccccga ggtccagttc aagtggtacg tggacggcgt ggaggtgcat     180
aatgccaaga caaagccgcg ggaggagcag tacaacagca cgttccgtgt ggtcagcgtc     240
ctcaccgtcc tgcaccagga ctggctgaac ggcaaggagt acaagtgcaa ggtctccaac     300
aaagccctcc cagcccccat cgagaaaacc atctccaaaa ccaaaggaca gccccgagaa     360
ccacaggtgt acaccctgcc cccatcccgg gaggagatga ccaagaacca ggtcagcctg     420
acctgcctgg tcaaaggctt ctaccccagc gacatcgccg tggagtggga gagcagcggg     480
cagccggaga acaactacaa caccacgcct cccatgctgg actccgacgg ctccttcttc     540
ctctacagca agctcaccgt ggacaagagc aggtggcagc aggggaacat cttctcatgc     600
tccgtgatgc atgaggctct gcacaaccgc ttcacgcaga gagcctctc cctgtctccg      660 ggtaaatgac tcgagcggcc g                                                681

<210> SEQ ID NO 67
<211> LENGTH: 245
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 67

Met Leu Leu Leu Ala Arg Cys Leu Leu Leu Val Leu Val Ser Ser Leu
1               5                   10                  15

Leu Val Cys Ser Gly Leu Ala Cys Pro Arg Cys Pro Ala Pro Glu Leu
                20                  25                  30

Leu Gly Gly Pro Ser Val Phe Leu Phe Pro Pro Lys Pro Lys Asp Thr
            35                  40                  45

Leu Met Ile Ser Arg Thr Pro Glu Val Thr Cys Val Val Val Asp Val
        50                  55                  60

```
Ser His Glu Asp Pro Glu Val Gln Phe Lys Trp Tyr Val Asp Gly Val
 65                  70                  75                  80

Glu Val His Asn Ala Lys Thr Lys Pro Arg Glu Glu Gln Tyr Asn Ser
                 85                  90                  95

Thr Phe Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Ser Gly Gln Pro Glu Asn Asn Tyr Asn Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Ile Phe Ser Cys Ser
    210                 215                 220

Val Met His Glu Ala Leu His Asn Arg Phe Thr Gln Lys Ser Leu Ser
225                 230                 235                 240

Leu Ser Pro Gly Lys
                245

<210> SEQ ID NO 68
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 68
aagcttgaat tcccaccatg ctgctgctgg cgagatgtct gctgctagtc ctcgtctcct      60
cgctgctggt atgctcggga ctggcgtgcc caaggtgccc agcacctgaa ctcctgggag     120
gaccgtcagt cttcctcttc cccccaaaac ccaaggatac ccttatgatt tcccggaccc     180
ctgaggtcac gtgcgtggtg gtggacgtga gccacgaaga ccccgaggtc cagttcaagt     240
ggtacgtgga cggcgtggag gtgcataatg ccaagacaaa gccgcgggag gagcagtaca     300
acagcacgtt ccgtgtggtc agcgtcctca ccgtcctgca ccaggactgg ctgaacggca     360
aggagtacaa gtgcaaggtc tccaacaaag ccctcccagc ccccatcgag aaaaccatct     420
ccaaaaccaa aggacagccc cgagaaccac aggtgtacac cctgccccca tcccgggagg     480
agatgaccaa gaaccaggtc agcctgacct gcctggtcaa aggcttctac ccagcgaca     540 tcgccgtgga gtgggagagc agcgggcagc cggagaacaa ctacaacacc acgcctccca     600
tgctggactc cgacggctcc ttcttcctct acagcaagct caccgtggac aagagcaggt     660
ggcagcaggg gaacatcttc tcatgctccg tgatgcatga ggctctgcac aaccgcttca     720
cgcagaagag cctctccctg tctccgggta aatgactcga gcggccg                   767

<210> SEQ ID NO 69
<211> LENGTH: 245
<212> TYPE: PRT
<213> ORGANISM: Artificial Sequence
<220> FEATURE:
```

<223> OTHER INFORMATION: pre-Fc chimeric polypeptide having IFN signal peptide

<400> SEQUENCE: 69

| | | | | | | | | | | | | | | | |
|---|---|---|---|---|---|---|---|---|---|---|---|---|---|---|---|
| Met | Ala | Leu | Thr | Phe | Ala | Leu | Leu | Val | Ala | Leu | Leu | Val | Leu | Ser | Cys |
| 1 | | | | 5 | | | | | 10 | | | | | 15 | |
| Lys | Ser | Ser | Cys | Ser | Val | Gly | Cys | Pro | Arg | Cys | Pro | Ala | Pro | Glu | Leu |
| | | | 20 | | | | | 25 | | | | | 30 | | |
| Leu | Gly | Gly | Pro | Ser | Val | Phe | Leu | Phe | Pro | Pro | Lys | Pro | Lys | Asp | Thr |
| | | | | 35 | | | | | 40 | | | | | 45 | |
| Leu | Met | Ile | Ser | Arg | Thr | Pro | Glu | Val | Thr | Cys | Val | Val | Val | Asp | Val |
| | 50 | | | | | 55 | | | | | 60 | | | | |
| Ser | His | Glu | Asp | Pro | Glu | Val | Gln | Phe | Lys | Trp | Tyr | Val | Asp | Gly | Val |
| 65 | | | | | 70 | | | | | 75 | | | | | 80 |
| Glu | Val | His | Asn | Ala | Lys | Thr | Lys | Pro | Arg | Glu | Glu | Gln | Tyr | Asn | Ser |
| | | | | 85 | | | | | 90 | | | | | 95 | |
| Thr | Phe | Arg | Val | Val | Ser | Val | Leu | Thr | Val | Leu | His | Gln | Asp | Trp | Leu |
| | | | 100 | | | | | 105 | | | | | 110 | | |
| Asn | Gly | Lys | Glu | Tyr | Lys | Cys | Lys | Val | Ser | Asn | Lys | Ala | Leu | Pro | Ala |
| | | | | 115 | | | | | 120 | | | | | 125 | |
| Pro | Ile | Glu | Lys | Thr | Ile | Ser | Lys | Thr | Lys | Gly | Gln | Pro | Arg | Glu | Pro |
| | 130 | | | | | 135 | | | | | 140 | | | | |
| Gln | Val | Tyr | Thr | Leu | Pro | Pro | Ser | Arg | Glu | Glu | Met | Thr | Lys | Asn | Gln |
| 145 | | | | | 150 | | | | | 155 | | | | | 160 |
| Val | Ser | Leu | Thr | Cys | Leu | Val | Lys | Gly | Phe | Tyr | Pro | Ser | Asp | Ile | Ala |
| | | | | 165 | | | | | 170 | | | | | 175 | |
| Val | Glu | Trp | Glu | Ser | Ser | Gly | Gln | Pro | Glu | Asn | Asn | Tyr | Asn | Thr | Thr |
| | | | 180 | | | | | 185 | | | | | 190 | | |
| Pro | Pro | Met | Leu | Asp | Ser | Asp | Gly | Ser | Phe | Phe | Leu | Tyr | Ser | Lys | Leu |
| | | | | 195 | | | | | 200 | | | | | 205 | |
| Thr | Val | Asp | Lys | Ser | Arg | Trp | Gln | Gln | Gly | Asn | Ile | Phe | Ser | Cys | Ser |
| | 210 | | | | | 215 | | | | | 220 | | | | |
| Val | Met | His | Glu | Ala | Leu | His | Asn | Arg | Phe | Thr | Gln | Lys | Ser | Leu | Ser |
| 225 | | | | | 230 | | | | | 235 | | | | | 240 |
| Leu | Ser | Pro | Gly | Lys | | | | | | | | | | | |
| | | | | 245 | | | | | | | | | | | |

<210> SEQ ID NO 70
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having IFN signal peptide

<400> SEQUENCE: 70

```
aagcttgaat tcccaccatg gccttgacct ttgctttact ggtggccctc ctggtgctca    60
gctgcaagtc aagctgctct gtgggctgcc caaggtgccc agcacctgaa ctcctgggag   120
gaccgtcagt cttcctcttc cccccaaaac ccaaggatac ccttatgatt tcccggaccc   180
ctgaggtcac gtgcgtggtg gtggacgtga gccacgaaga ccccgaggtc cagttcaagt   240
ggtacgtgga cggcgtggag gtgcataatg ccaagacaaa gccgcgggag gagcagtaca   300
acagcacgtt ccgtgtggtc agcgtcctca ccgtcctgca ccaggactgg ctgaacggca   360
aggagtacaa gtgcaaggtc tccaacaaag ccctcccagc ccccatcgag aaaaccatct   420
ccaaaaccaa aggacagccc cgagaaccac aggtgtacac cctgccccca tcccgggagg   480
```

```
agatgaccaa gaaccaggtc agcctgacct gcctggtcaa aggcttctac cccagcgaca      540
tcgccgtgga gtgggagagc agcgggcagc cggagaacaa ctacaacacc acgcctccca      600
tgctggactc cgacggctcc ttcttcctct acagcaagct caccgtggac aagagcaggt      660
ggcagcaggg gaacatcttc tcatgctccg tgatgcatga ggctctgcac aaccgcttca      720
cgcagaagag cctctccctg tctccgggta atgactcga gcggccg                    767
```

```
<210> SEQ ID NO 71
<211> LENGTH: 239
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 71
```

```
Met Leu Ala Ala Thr Val Leu Thr Leu Ala Leu Leu Gly Asn Ala His
1               5                   10                  15

Ala Cys Pro Arg Cys Pro Ala Pro Glu Leu Leu Gly Gly Pro Ser Val
                20                  25                  30

Phe Leu Phe Pro Pro Lys Pro Lys Asp Thr Leu Met Ile Ser Arg Thr
            35                  40                  45

Pro Glu Val Thr Cys Val Val Val Asp Val Ser His Glu Asp Pro Glu
        50                  55                  60

Val Gln Phe Lys Trp Tyr Val Asp Gly Val Glu Val His Asn Ala Lys
65                  70                  75                  80

Thr Lys Pro Arg Glu Glu Gln Tyr Asn Ser Thr Phe Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Ala Leu Pro Ala Pro Ile Glu Lys Thr Ile
        115                 120                 125

Ser Lys Thr Lys Gly Gln Pro Arg Glu Pro Gln Val Tyr Thr Leu Pro
    130                 135                 140

Pro Ser Arg Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Ser
                165                 170                 175

Gly Gln Pro Glu Asn Asn Tyr Asn Thr Thr Pro Pro Met Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Ile Phe Ser Cys Ser Val Met His Glu Ala Leu
    210                 215                 220

His Asn Arg Phe Thr Gln Lys Ser Leu Ser Leu Ser Pro Gly Lys
225                 230                 235
```

```
<210> SEQ ID NO 72
<211> LENGTH: 749
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 72
```

```
aagcttgaat tcccaccatg ctggctgcca cagtcctgac cctggccctg ctgggcaatg       60
```

-continued

```
cccatgcctg cccaaggtgc ccagcacctg aactcctggg aggaccgtca gtcttcctct      120 tcccccaaa  acccaaggat  acccttatga  tttcccggac  ccctgaggtc  acgtgcgtgg    180
tggtggacgt  gagccacgaa  gaccccgagg  tccagttcaa  gtggtacgtg  gacggcgtgg   240
aggtgcataa  tgccaagaca  aagccgcggg  aggagcagta  caacagcacg  ttccgtgtgg   300
tcagcgtcct  caccgtcctg  caccaggact  ggctgaacgg  caaggagtac  aagtgcaagg   360
tctccaacaa  agccctccca  gcccccatcg  agaaaaccat  ctccaaaacc  aaaggacagc   420
cccgagaacc  acaggtgtac  accctgcccc  catcccggga  ggagatgacc  aagaaccagg   480
tcagcctgac  ctgcctggtc  aaaggcttct  accccagcga  catcgccgtg  gagtgggaga   540
gcagcgggca  gccggagaac  aactacaaca  ccacgcctcc  catgctggac  tccgacggct   600
ccttcttcct  ctacagcaag  ctcaccgtgg  acaagagcag  gtggcagcag  gggaacatct   660
tctcatgctc  cgtgatgcat  gaggctctgc  acaaccgctt  cacgcagaag  agcctctccc   720
tgtctccggg  taaatgactc  gagcggccg                                       749
```

<210> SEQ ID NO 73
<211> LENGTH: 219
<212> TYPE: PRT
<213> ORGANISM: Artificial Sequence
<220> FEATURE:
<223> OTHER INFORMATION: Human IgG3 Fc domain having the N-terminal sequence CPAPE

<400> SEQUENCE: 73

```
Cys Pro Ala Pro Glu Leu Leu Gly Gly Pro Ser Val Phe Leu Phe Pro
  1               5                  10                  15

Pro Lys Pro Lys Asp Thr Leu Met Ile Ser Arg Thr Pro Glu Val Thr
             20                  25                  30

Cys Val Val Asp Val Ser His Glu Asp Pro Glu Val Gln Phe Lys
         35                  40                  45

Trp Tyr Val Asp Gly Val Glu Val His Asn Ala Lys Thr Lys Pro Arg
     50                  55                  60

Glu Glu Gln Tyr Asn Ser Thr Phe Arg Val Val Ser Val Leu Thr Val
 65                  70                  75                  80

Leu His Gln Asp Trp Leu Asn Gly Lys Glu Tyr Lys Cys Lys Val Ser
                 85                  90                  95

Asn Lys Ala Leu Pro Ala Pro Ile Glu Lys Thr Ile Ser Lys Thr Lys
            100                 105                 110

Gly Gln Pro Arg Glu Pro Gln Val Tyr Thr Leu Pro Pro Ser Arg Glu
        115                 120                 125

Glu Met Thr Lys Asn Gln Val Ser Leu Thr Cys Leu Val Lys Gly Phe
    130                 135                 140

Tyr Pro Ser Asp Ile Ala Val Glu Trp Glu Ser Ser Gly Gln Pro Glu
145                 150                 155                 160

Asn Asn Tyr Asn Thr Thr Pro Pro Met Leu Asp Ser Asp Gly Ser Phe
                165                 170                 175

Phe Leu Tyr Ser Lys Leu Thr Val Asp Lys Ser Arg Trp Gln Gln Gly
            180                 185                 190

Asn Ile Phe Ser Cys Ser Val Met His Glu Ala Leu His Asn Arg Phe
        195                 200                 205

Thr Gln Lys Ser Leu Ser Leu Ser Pro Gly Lys
    210                 215
```

<210> SEQ ID NO 74
<211> LENGTH: 672
<212> TYPE: DNA
<213> ORGANISM: Artificial Sequence
<220> FEATURE:
<223> OTHER INFORMATION: DNA encoding human IgG3 Fc domain having the
      N-terminal sequence CPAPE

<400> SEQUENCE: 74

```
tgcccagcac ctgaactcct gggaggaccg tcagtcttcc tcttcccccc aaaacccaag      60
gatacccttA tgatttcccg gaccCctgag gtcacgtgcg tggtggtgga cgtgagccac     120
gaagaccccg aggtccagtt caagtggtac gtggacggcg tggaggtgca taatgccaag     180
acaaagccgc gggaggagca gtacaacagc acgttccgtg tggtcagcgt cctcaccgtc     240
ctgcaccagg actggctgaa cggcaaggag tacaagtgca aggtctccaa caaagccctc     300
ccagccccca tcgagaaaac catctccaaa accaaggac agccccgaga ccacaggtg      360
tacaccctgc ccccatcccg ggaggagatg accaagaacc aggtcagcct gacctgcctg     420
gtcaaaggct tctaccccag cgacatcgcc gtggagtggg agagcagcgg gcagccggag     480
aacaactaca acaccacgcc tcccatgctg gactccgacg gctccttctt cctctacagc     540
aagctcaccg tggacaagag caggtggcag caggggaaca tcttctcatg ctccgtgatg     600
catgaggctc tgcacaaccg cttcacgcag aagagcctct ccctgtctcc gggtaaatga     660
ctcgagcggc cg                                                         672
```

<210> SEQ ID NO 75
<211> LENGTH: 242
<212> TYPE: PRT
<213> ORGANISM: Artificial Sequence
<220> FEATURE:
<223> OTHER INFORMATION: pre-Fc chimeric polypeptide having SHH signal
      peptide

<400> SEQUENCE: 75

```
Met Leu Leu Leu Ala Arg Cys Leu Leu Leu Val Leu Val Ser Ser Leu
1               5                   10                  15

Leu Val Cys Ser Gly Leu Ala Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Gln Phe Lys Trp Tyr Val Asp Gly Val Glu Val His
65                  70                  75                  80

Asn Ala Lys Thr Lys Pro Arg Glu Glu Gln Tyr Asn Ser Thr Phe Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Thr Lys Gly Gln Pro Arg Glu Pro Gln Val Tyr
    130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Ser Gly Gln Pro Glu Asn Asn Tyr Asn Thr Thr Pro Pro Met
```

```
                        180                 185                 190

Leu Asp Ser Asp Gly Ser Phe Phe Leu Tyr Ser Lys Leu Thr Val Asp
                195                 200                 205

Lys Ser Arg Trp Gln Gln Gly Asn Ile Phe Ser Cys Ser Val Met His
            210                 215                 220

Glu Ala Leu His Asn Arg Phe Thr Gln Lys Ser Leu Ser Leu Ser Pro
225                 230                 235                 240

Gly Lys

<210> SEQ ID NO 76
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      SHH signal peptide

<400> SEQUENCE: 76
aagcttgaat tccaccatg ctgctgctgg cgagatgtct gctgctagtc ctcgtctcct        60
cgctgctggt atgctcggga ctggcgtgcc cagcacctga actcctggga ggaccgtcag      120
tcttcctctt cccccaaaa cccaaggata cccttgatgt tcccggacc cctgaggtca       180 cgtgcgtggt ggtggacgtg agccacgaag accccgaggt ccagttcaag tggtacgtgg      240
acggcgtgga ggtgcataat gccaagacaa agccgcggga ggagcagtac aacagcacgt      300
tccgtgtggt cagcgtcctc accgtcctgc accaggactg gctgaacggc aaggagtaca      360
agtgcaaggt ctccaacaaa gccctcccag ccccatcga gaaaaccatc tccaaaacca      420
aaggacagcc ccgagaacca caggtgtaca ccctgccccc atcccgggag gagatgacca      480
agaaccaggt cagcctgacc tgcctggtca aaggcttcta ccccagcgac atcgccgtgg      540
agtgggagag cagcgggcag ccggagaaca actacaacac cacgcctccc atgctggact      600
ccgacggctc cttcttcctc tacagcaagc tcaccgtgga caagagcagg tggcagcagg      660
ggaacatctt ctcatgctcc gtgatgcatg aggctctgca caaccgcttc acgcagaaga      720
gcctctccct gtctccgggt aaatgactcg agcggccg                              758

<210> SEQ ID NO 77
<211> LENGTH: 242
<212> TYPE: PRT
<213> ORGANISM: Artificial Sequence
<220> FEATURE:
<223> OTHER INFORMATION: pre-Fc chimeric polypeptide having IFN signal
      peptide

<400> SEQUENCE: 77

Met Ala Leu Thr Phe Ala Leu Leu Val Ala Leu Leu Val Leu Ser Cys
1               5                   10                  15

Lys Ser Ser Cys Ser Val Gly Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Gln Phe Lys Trp Tyr Val Asp Gly Val Glu Val His
65                  70                  75                  80

Asn Ala Lys Thr Lys Pro Arg Glu Glu Gln Tyr Asn Ser Thr Phe Arg
                85                  90                  95
```

```
Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Thr Lys Gly Gln Pro Arg Glu Pro Gln Val Tyr
    130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Ser Gly Gln Pro Glu Asn Asn Tyr Asn Thr Thr Pro Pro Met
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Ile Phe Ser Cys Ser Val Met His
    210                 215                 220

Glu Ala Leu His Asn Arg Phe Thr Gln Lys Ser Leu Ser Leu Ser Pro
225                 230                 235                 240

Gly Lys

<210> SEQ ID NO 78
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      IFN signal peptide

<400> SEQUENCE: 78
aagcttgaat cccaccatg gccttgacct ttgctttact ggtggccctc ctggtgctca      60
gctgcaagtc aagctgctct gtgggctgcc agcacctga actcctggga ggaccgtcag    120
tcttcctctt cccccaaaa cccaaggata cccttatgat ttcccggacc cctgaggtca    180
cgtgcgtggt ggtggacgtg agccacgaag accccgaggt ccagttcaag tggtacgtgg    240
acggcgtgga ggtgcataat gccaagacaa agccgcggga ggagcagtac aacagcacgt    300
tccgtgtggt cagcgtcctc accgtcctgc accaggactg gctgaacggc aaggagtaca    360
agtgcaaggt ctccaacaaa gccctcccag ccccatcga gaaaaccatc tccaaaacca    420
aaggacagcc ccgagaacca caggtgtaca ccctgccccc atcccgggag gagatgacca    480
agaaccaggt cagcctgacc tgcctggtca aaggcttcta ccccagcgac atcgccgtgg    540
agtgggagag cagcgggcag ccggagaaca actacaacac cacgcctccc atgctggact    600
ccgacggctc cttcttcctc tacagcaagc tcaccgtgga caagagcagg tggcagcagg    660
ggaacatctt ctcatgctcc gtgatgcatg aggctctgca caaccgcttc acgcagaaga    720
gcctctccct gtctccgggt aaatgactcg agcggccg                           758

<210> SEQ ID NO 79
<211> LENGTH: 235
<212> TYPE: PRT
<213> ORGANISM: Artificial Sequence
<220> FEATURE:
<223> OTHER INFORMATION: pre-Fc chimeric polypeptide having CETP signal
      peptide

<400> SEQUENCE: 79

Met Leu Ala Ala Thr Val Leu Thr Leu Ala Leu Leu Gly Asn Ala His
1               5                   10                  15
```

```
Ala Cys Pro Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Gln Phe
    50                  55                  60

Lys Trp Tyr Val Asp Gly Val Glu Val His Asn Ala Lys Thr Lys Pro
65                  70                  75                  80

Arg Glu Glu Gln Tyr Asn Ser Thr Phe Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Thr
        115                 120                 125

Lys Gly Gln Pro Arg Glu Pro Gln Val Tyr Thr Leu Pro Pro Ser Arg
130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Ser Gly Gln Pro
                165                 170                 175

Glu Asn Asn Tyr Asn Thr Thr Pro Pro Met Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Ile Phe Ser Cys Ser Val Met His Glu Ala Leu His Asn Arg
    210                 215                 220

Phe Thr Gln Lys Ser Leu Ser Leu Ser Pro Gly
225                 230                 235

<210> SEQ ID NO 80
<211> LENGTH: 740
<212> TYPE: DNA
<213> ORGANISM: Artificial Sequence
<220> FEATURE:
<223> OTHER INFORMATION: DNA encoding pre-Fc chimeric polypeptide having
      CETP signal peptide

<400> SEQUENCE: 80
aagcttgaat tcccaccatg ctggctgcca cagtcctgac cctggccctg ctgggcaatg      60
cccatgcctg cccagcacct gaactcctgg gaggaccgtc agtcttcctc ttccccccaa    120
aacccaagga taccttatg atttccggga cccctgaggt cacgtgcgtg gtggtggacg     180
tgagccacga agaccccgag gtccagttca gtggtacgt ggacggcgtg gaggtgcata     240
atgccaagac aaagccgcgg gaggagcagt acaacagcac gttccgtgtg gtcagcgtcc    300
tcaccgtcct gcaccaggac tggctgaacg gcaaggagta caagtgcaag gtctccaaca    360
aagccctccc agcccccatc gagaaaacca tctccaaaac caaaggacag ccccgagaac    420
cacaggtgta caccctgccc ccatcccggg aggagatgac caagaaccag gtcagcctga    480
cctgcctggt caaaggcttc taccccagcg acatcgccgt ggagtgggag agcagcgggc    540
agccggagaa caactacaac accacgcctc ccatgctgga ctccgacggc tccttcttcc    600
tctacagcaa gctcaccgtg gacaagagca ggtggcagca ggggaacatc ttctcatgct    660
ccgtgatgca tgaggctctg cacaaccgct tcacgcagaa gagcctctcc ctgtctccgg    720
gtaaatgact cgagcggccg                                                740
```

<210> SEQ ID NO 81
<211> LENGTH: 222
<212> TYPE: PRT
<213> ORGANISM: Artificial Sequence
<220> FEATURE:
<223> OTHER INFORMATION: Human IgG4 Fc domain having the N-terminal
      sequence CPSCPAPE

<400> SEQUENCE: 81

Cys Pro Ser Cys Pro Ala Pro Glu Phe Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Gln Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Gly Leu Pro Ser Ser Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Gln Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Arg Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Leu Gly Lys
    210                 215                 220

<210> SEQ ID NO 82
<211> LENGTH: 666
<212> TYPE: DNA
<213> ORGANISM: Artificial Sequence
<220> FEATURE:
<223> OTHER INFORMATION: DNA encoding human IgG4 Fc domain having the
      N-terminal sequence CPSCPAPE

<400> SEQUENCE: 82
tgcccatcat gcccagcacc tgagttcctg gggggaccat cagtcttcct gttccccca        60 aaacccaagg acactctcat gatctcccgg acccctgagg tcacgtgcgt ggtggtggac      120
gtgagccagg aagaccccga ggtccagttc aactggtacg tggatggcgt ggaggtgcat      180
aatgccaaga caaagccgcg ggaggagcag ttcaacagca cgtaccgtgt ggtcagcgtc      240
ctcaccgtcc tgcaccagga ctggctgaac ggcaaggagt acaagtgcaa ggtctccaac      300
aaaggcctcc cgtcctccat cgagaaaacc atctccaaag ccaaagggca gccccgagag      360
ccacaggtgt acaccctgcc cccatcccag gaggagatga ccaagaacca ggtcagcctg      420

```
acctgcctgg tcaaaggctt ctaccccagc gacatcgccg tggagtggga gagcaatggg      480
cagccggaga caactacaa gaccacgcct cccgtgctgg actccgacgg ctccttcttc       540
ctctacagca ggctaaccgt ggacaagagc aggtggcagg aggggaatgt cttctcatgc     600
tccgtgatgc atgaggctct gcacaaccac tacacacaga gagcctctc cctgtctctg      660 ggtaaa                                                                666
```

<210> SEQ ID NO 83
<211> LENGTH: 245
<212> TYPE: PRT
<213> ORGANISM: Artificial Sequence
<220> FEATURE:
<223> OTHER INFORMATION: pre-Fc chimeric polypeptide having a SHH signal
      peptide

<400> SEQUENCE: 83

```
Met Leu Leu Leu Ala Arg Cys Leu Leu Val Leu Val Ser Ser Leu
1               5                   10                  15

Leu Val Cys Ser Gly Leu Ala Cys Pro Ser Cys Pro Ala Pro Glu Phe
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245
```

<210> SEQ ID NO 84
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      a SHH signal peptide

<400> SEQUENCE: 84

```
aagcttgaat tcccaccatg ctgctgctgg cgagatgtct gctgctagtc ctcgtctcct    60
cgctgctggt atgctcggga ctggcgtgcc catcatgccc agcacctgag ttcctggggg   120
gaccatcagt cttcctgttc cccccaaaac ccaaggacac tctcatgatc tcccggaccc   180
ctgaggtcac gtgcgtggtg gtggacgtga gccaggaaga ccccgaggtc cagttcaact   240
ggtacgtgga tggcgtggag gtgcataatg ccaagacaaa gccgcgggag gagcagttca   300
acagcacgta ccgtgtggtc agcgtcctca ccgtcctgca ccaggactgg ctgaacggca   360
aggagtacaa gtgcaaggtc tccaacaaag gcctcccgtc ctccatcgag aaaaccatct   420
ccaaagccaa agggcagccc cgagagccac aggtgtacac cctgccccca tcccaggagg   480
agatgaccaa gaaccaggtc agcctgacct gcctggtcaa aggcttctac cccagcgaca   540
tcgccgtgga gtgggagagc aatgggcagc cggagaacaa ctacaagacc acgcctcccg   600
tgctggactc cgacggctcc ttcttcctct acagcaggct aaccgtggac aagagcaggt   660
ggcaggaggg gaatgtcttc tcatgctccg tgatgcatga ggctctgcac aaccactaca   720
cacagaagag cctctccctg tctctgggta aatgactcga gcggccg            767

<210> SEQ ID NO 85
<211> LENGTH: 245
<212> TYPE: PRT
<213> ORGANISM: Artificial Sequence
<220> FEATURE:
<223> OTHER INFORMATION: pre-Fc chimeric polypeptide having a IFN signal
      peptide

<400> SEQUENCE: 85

Met Ala Leu Thr Phe Ala Leu Leu Val Ala Leu Leu Val Leu Ser Cys
1               5                   10                  15

Lys Ser Ser Cys Ser Val Gly Cys Pro Ser Cys Pro Ala Pro Glu Phe
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220
```

Val Met His Glu Ala Leu His Asn His Tyr Thr Gln Lys Ser Leu Ser
225                 230                 235                 240

Leu Ser Leu Gly Lys
            245

<210> SEQ ID NO 86
<211> LENGTH: 767
<212> TYPE: DNA
<213> ORGANISM: Artificial Sequence
<220> FEATURE:
<223> OTHER INFORMATION: DNA encoding pre-Fc chimeric polypeptide having
      a IFN signal peptide

<400> SEQUENCE: 86

```
aagcttgaat cccaccatg gccttgacct tgctttact ggtggccctc ctggtgctca      60
gctgcaagtc aagctgctct gtgggctgcc catcatgccc agcacctgag ttcctggggg    120
gaccatcagt cttcctgttc cccccaaaac ccaaggacac tctcatgatc tcccggaccc    180
ctgaggtcac gtgcgtggtg gtggacgtga gccaggaaga ccccgaggtc cagttcaact    240
ggtacgtgga tggcgtggag gtgcataatg ccaagacaaa gccgcgggag gagcagttca    300
acagcacgta ccgtgtggtc agcgtcctca ccgtcctgca ccaggactgg ctgaacggca    360
aggagtacaa gtgcaaggtc tccaacaaag cctcccgtc ctccatcgag aaaaccatct    420
ccaaagccaa agggcagccc cgagagccac aggtgtacac cctgccccca tcccaggagg    480
agatgaccaa gaaccaggtc agcctgacct gcctggtcaa aggcttctac cccagcgaca    540
tcgccgtgga gtgggagagc aatgggcagc cggagaacaa ctacaagacc acgcctcccg    600
tgctggactc cgacggctcc ttcttcctct acagcaggct aaccgtggac aagagcaggt    660
ggcaggaggg gaatgtcttc tcatgctccg tgatgcatga ggctctgcac aaccactaca    720
cacagaagag cctctccctg tctctgggta atgactcga gcggccg                 767
```

<210> SEQ ID NO 87
<211> LENGTH: 239
<212> TYPE: PRT
<213> ORGANISM: Artificial Sequence
<220> FEATURE:
<223> OTHER INFORMATION: pre-Fc chimeric polypeptide having a CETP
      signal peptide

<400> SEQUENCE: 87

Met Leu Ala Ala Thr Val Leu Thr Leu Ala Leu Leu Gly Asn Ala His
1               5                   10                  15

Ala Cys Pro Ser Cys Pro Ala Pro Glu Phe Leu Gly Gly Pro Ser Val
                20                  25                  30

Phe Leu Phe Pro Pro Lys Pro Lys Asp Thr Leu Met Ile Ser Arg Thr
            35                  40                  45

Pro Glu Val Thr Cys Val Val Val Asp Val Ser Gln Glu Asp Pro Glu
    50                  55                  60

Val Gln Phe Asn Trp Tyr Val Asp Gly Val Glu Val His Asn Ala Lys
65                  70                  75                  80

Thr Lys Pro Arg Glu Glu Gln Phe Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Gly Leu Pro Ser Ser Ile Glu Lys Thr Ile
        115                 120                 125

```
Ser Lys Ala Lys Gly Gln Pro Arg Glu Pro Gln Val Tyr Thr Leu Pro
    130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
        195                 200                 205

Trp Gln Glu Gly Asn Val Phe Ser Cys Ser Val Met His Glu Ala Leu
    210                 215                 220

His Asn His Tyr Thr Gln Lys Ser Leu Ser Leu Ser Leu Gly Lys
225                 230                 235
```

<210> SEQ ID NO 88
<211> LENGTH: 749
<212> TYPE: DNA
<213> ORGANISM: Artificial Sequence
<220> FEATURE:
<223> OTHER INFORMATION: DNA encoding pre-Fc chimeric polypeptide having
    a CETP signal peptide

<400> SEQUENCE: 88

```
aagcttgaat tcccaccatg ctggctgcca cagtcctgac cctggccctg ctgggcaatg      60
cccatgcctg cccatcatgc ccagcacctg agttcctggg gggaccatca gtcttcctgt     120
tccccccaaa acccaaggac actctcatga tctcccggac ccctgaggtc acgtgcgtgg     180
tggtggacgt gagccaggaa gaccccgagg tccagttcaa ctggtacgtg gatggcgtgg     240
aggtgcataa tgccaagaca aagccgcggg aggagcagtt caacagcacg taccgtgtgg     300
tcagcgtcct caccgtcctg caccaggact ggctgaacgg caaggagtac aagtgcaagg     360
tctccaacaa aggcctcccg tcctccatcg agaaaaccat ctccaaagcc aaagggcagc     420
cccgagagcc acaggtgtac accctgcccc catcccagga ggagatgacc aagaaccagg     480
tcagcctgac ctgcctggtc aaaggcttct accccagcga catcgccgtg gagtgggaga     540
gcaatgggca gccggagaac aactacaaga ccacgcctcc cgtgctggac tccgacggct     600
ccttcttcct ctacagcagg ctaaccgtgg acaagagcag gtggcaggag gggaatgtct     660
tctcatgctc cgtgatgcat gaggctctgc acaaccacta cacacagaag agcctctccc     720
tgtctctggg taaatgactc gagcggccg                                       749
```

<210> SEQ ID NO 89
<211> LENGTH: 219
<212> TYPE: PRT
<213> ORGANISM: Artificial Sequence
<220> FEATURE:
<223> OTHER INFORMATION: Human IgG4 Fc domain having the N-terminal
    sequence CPAPE

<400> SEQUENCE: 89

```
Cys Pro Ala Pro Glu Phe Leu Gly Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser Gln Glu Asp Pro Glu Val Gln Phe Asn
        35                  40                  45

Trp Tyr Val Asp Gly Val Glu Val His Asn Ala Lys Thr Lys Pro Arg
```

```
                     50                  55                  60

Glu Glu Gln Phe Asn Ser Thr Tyr Arg Val Val Ser Val Leu Thr Val
 65                  70                  75                  80

Leu His Gln Asp Trp Leu Asn Gly Lys Glu Tyr Lys Cys Lys Val Ser
                     85                  90                  95

Asn Lys Gly Leu Pro Ser Ser Ile Glu Lys Thr Ile Ser Lys Ala Lys
                100                 105                 110

Gly Gln Pro Arg Glu Pro Gln Val Tyr Thr Leu Pro Pro Ser Gln Glu
            115                 120                 125

Glu Met Thr Lys Asn Gln Val Ser Leu Thr Cys Leu Val Lys Gly Phe
        130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Val Leu Asp Ser Asp Gly Ser Phe
                165                 170                 175

Phe Leu Tyr Ser Arg Leu Thr Val Asp Lys Ser Arg Trp Gln Glu Gly
            180                 185                 190

Asn Val Phe Ser Cys Ser Val Met His Glu Ala Leu His Asn His Tyr
        195                 200                 205

Thr Gln Lys Ser Leu Ser Leu Ser Leu Gly Lys
    210                 215

<210> SEQ ID NO 90
<211> LENGTH: 657
<212> TYPE: DNA
<213> ORGANISM: Artificial Sequence
<220> FEATURE:
<223> OTHER INFORMATION: DNA encoding human IgG4 Fc domain having the
      N-terminal sequence CPAPE

<400> SEQUENCE: 90
tgcccagcac ctgagttcct ggggggacca tcagtcttcc tgttcccccc aaaacccaag      60
gacactctca tgatctcccg gacccctgag gtcacgtgcg tggtggtgga cgtgagccag     120
gaagaccccg aggtccagtt caactggtac gtggatggcg tggaggtgca taatgccaag     180
acaaagccgc gggaggagca gttcaacagc acgtaccgtg tggtcagcgt cctcaccgtc     240
ctgcaccagg actggctgaa cggcaaggag tacaagtgca aggtctccaa caaaggcctc     300
ccgtcctcca tcgagaaaac catctccaaa gccaaagggc agccccgaga gccacaggtg     360
tacaccctgc ccccatccca ggaggagatg accaagaacc aggtcagcct gacctgcctg     420
gtcaaaggct tctaccccag cgacatcgcc gtggagtggg agagcaatgg gcagccggag     480
aacaactaca agaccacgcc tcccgtgctg gactccgacg gctccttctt cctctacagc     540
aggctaaccg tggacaagag caggtggcag gaggggaatg tcttctcatg ctccgtgatg     600
catgaggctc tgcacaacca ctacacacag aagagcctct ccctgtctct gggtaaa       657

<210> SEQ ID NO 91
<211> LENGTH: 242
<212> TYPE: PRT
<213> ORGANISM: Artificial Sequence
<220> FEATURE:
<223> OTHER INFORMATION: pre-Fc chimeric polypeptide having a SHH signal
      peptide

<400> SEQUENCE: 91

Met Leu Leu Leu Ala Arg Cys Leu Leu Leu Val Leu Val Ser Ser Leu
  1               5                  10                  15
```

| | | | | | | | | | | |
|---|---|---|---|---|---|---|---|---|---|---|
|Leu|Val|Cys|Ser 20|Gly|Leu|Ala|Cys 25|Pro|Ala|Pro|Glu|Phe 30|Leu|Gly|Gly|
|Pro|Ser|Val 35|Phe|Leu|Phe|Pro 40|Pro|Lys|Pro|Lys 45|Asp|Thr|Leu|Met|Ile|
|Ser|Arg 50|Thr|Pro|Glu|Val 55|Thr|Cys|Val|Val 60|Asp|Val|Ser|Gln|Glu|
|Asp 65|Pro|Glu|Val|Gln 70|Phe|Asn|Trp|Tyr 75|Val|Asp|Gly|Val|Glu|Val|His 80|
|Asn|Ala|Lys|Thr 85|Lys|Pro|Arg|Glu 90|Glu|Gln|Phe|Asn|Ser 95|Thr|Tyr|Arg|
|Val|Val 100|Ser|Val|Leu|Thr 105|Val|Leu|His|Gln|Asp 110|Trp|Leu|Asn|Gly|Lys|
|Glu 115|Tyr|Lys|Cys|Lys 120|Val|Ser|Asn|Lys 125|Gly|Leu|Pro|Ser|Ser|Ile|Glu|
|Lys 130|Thr|Ile|Ser|Lys 135|Ala|Lys|Gly|Gln 140|Pro|Arg|Glu|Pro|Gln|Val|Tyr|
|Thr 145|Leu|Pro|Pro|Ser 150|Gln|Glu|Glu|Met 155|Thr|Lys|Asn|Gln|Val|Ser|Leu 160|
|Thr|Cys|Leu|Val|Lys 165|Gly|Phe|Tyr|Pro 170|Ser|Asp|Ile|Ala|Val|Glu 175|Trp|
|Glu|Ser|Asn|Gly 180|Gln|Pro|Glu|Asn 185|Asn|Tyr|Lys|Thr|Thr 190|Pro|Pro|Val|
|Leu|Asp|Ser 195|Asp|Gly|Ser|Phe 200|Phe|Leu|Tyr|Ser|Arg 205|Leu|Thr|Val|Asp|
|Lys|Ser|Arg 210|Trp|Gln|Glu|Gly 215|Asn|Val|Phe|Ser|Cys 220|Ser|Val|Met|His|
|Glu 225|Ala|Leu|His|Asn 230|His|Tyr|Thr|Gln 235|Lys|Ser|Leu|Ser|Leu|Ser|Leu 240|
|Gly|Lys|

```
<210> SEQ ID NO 92
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      a SHH signal peptide

<400> SEQUENCE: 92
aagcttgaat tcccaccatg ctgctgctgg cgagatgtct gctgctagtc ctcgtctcct      60
cgctgctggt atgctcggga ctggcgtgcc cagcacctga gttcctgggg ggaccatcag     120
tcttcctgtt cccccaaaa  cccaaggaca ctctcatgat ctcccggacc cctgaggtca     180
cgtgcgtggt ggtggacgtg agccaggaag accccgaggt ccagttcaac tggtacgtgg     240
atggcgtgga ggtgcataat gccaagacaa agccgcggga ggagcagttc aacagcacgt     300
accgtgtggt cagcgtcctc accgtcctgc accaggactg gctgaacggc aaggagtaca     360
agtgcaaggt ctccaacaaa ggcctcccgt cctccatcga gaaaaccatc tccaaagcca     420
aagggcagcc ccgagagcca caggtgtaca ccctgccccc atcccaggag gagatgacca     480
agaaccaggt cagcctgacc tgcctggtca aaggcttcta ccccagcgac atcgccgtgg     540
agtgggagag caatgggcag ccggagaaca actacaagac cacgcctccc gtgctggact     600
ccgacggctc cttcttcctc tacagcaggc taaccgtgga caagagcagg tggcaggagg     660
gaatgtcttc tcatgctccg tgatgcatg aggctctgca caaccactac acacagaaga     720
```
gcctctccct gtctctgggt aaatgactcg agcggccg        758

<210> SEQ ID NO 93
<211> LENGTH: 242
<212> TYPE: PRT
<213> ORGANISM: Artificial Sequence
<220> FEATURE:
<223> OTHER INFORMATION: pre-Fc chimeric polypeptide having a IFN signal
      peptide

<400> SEQUENCE: 93

Met Ala Leu Thr Phe Ala Leu Leu Val Ala Leu Leu Val Leu Ser Cys
1               5                   10                  15

Lys Ser Ser Cys Ser Val Gly Cys Pro Ala Pro Glu Phe Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser Gln Glu
    50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Gly Leu Pro Ser Ser Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Arg Leu Thr Val Asp
        195                 200                 205

Lys Ser Arg Trp Gln Glu Gly Asn Val Phe Ser Cys Ser Val Met His
    210                 215                 220

Glu Ala Leu His Asn His Tyr Thr Gln Lys Ser Leu Ser Leu Ser Leu
225                 230                 235                 240

Gly Lys

<210> SEQ ID NO 94
<211> LENGTH: 758
<212> TYPE: DNA
<213> ORGANISM: Artificial Sequence
<220> FEATURE:
<223> OTHER INFORMATION: DNA encoding pre-Fc chimeric polypeptide having
      a IFN signal peptide

<400> SEQUENCE: 94
aagcttgaat tcccaccatg gccttgacct tgctttact ggtggccctc ctggtgctca        60
gctgcaagtc aagctgctct gtgggctgcc cagcacctga gttcctgggg ggaccatcag      120
tcttcctgtt cccccaaaa cccaaggaca ctctcatgat ctcccggacc ctgaggtca        180 cgtgcgtggt ggtggacgtg agccaggaag acccgaggt ccagttcaac tggtacgtgg       240

```
atggcgtgga ggtgcataat gccaagacaa agccgcggga ggagcagttc aacagcacgt    300
accgtgtggt cagcgtcctc accgtcctgc accaggactg gctgaacggc aaggagtaca    360
agtgcaaggt ctccaacaaa ggcctcccgt cctccatcga aaaaccatc tccaaagcca     420 aaggcagcc ccgagagcca caggtgtaca ccctgccccc atcccaggag gagatgacca    480
agaaccaggt cagcctgacc tgcctggtca aaggcttcta ccccagcgac atcgccgtgg    540
agtgggagag caatgggcag ccggagaaca actacaagac cacgcctccc gtgctggact    600
ccgacggctc cttcttcctc tacagcaggc taaccgtgga caagagcagg tggcaggagg    660
ggaatgtctt ctcatgctcc gtgatgcatg aggctctgca caaccactac acacagaaga    720 gcctctcccct gtctctgggt aaatgactcg agcggccg                            758
```

<210> SEQ ID NO 95
<211> LENGTH: 236
<212> TYPE: PRT
<213> ORGANISM: Artificial Sequence
<220> FEATURE:
<223> OTHER INFORMATION: pre-Fc chimeric polypeptide having a CETP
       signal peptide

<400> SEQUENCE: 95

```
Met Leu Ala Ala Thr Val Leu Thr Leu Ala Leu Leu Gly Asn Ala His
1               5                   10                  15

Ala Cys Pro Ala Pro Glu Phe Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser Gln Glu Asp Pro Glu Val Gln Phe
    50                  55                  60

Asn Trp Tyr Val Asp Gly Val Glu Val His Asn Ala Lys Thr Lys Pro
65                  70                  75                  80

Arg Glu Glu Gln Phe Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Gly Leu Pro Ser Ser Ile Glu Lys Thr Ile Ser Lys Ala
        115                 120                 125

Lys Gly Gln Pro Arg Glu Pro Gln Val Tyr Thr Leu Pro Pro Ser Gln
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Arg Leu Thr Val Asp Lys Ser Arg Trp Gln Glu
        195                 200                 205

Gly Asn Val Phe Ser Cys Ser Val Met His Glu Ala Leu His Asn His
    210                 215                 220

Tyr Thr Gln Lys Ser Leu Ser Leu Ser Leu Gly Lys
225                 230                 235
```

<210> SEQ ID NO 96
<211> LENGTH: 740
<212> TYPE: DNA
<213> ORGANISM: Artificial Sequence

```
<220> FEATURE:
<223> OTHER INFORMATION: DNA encoding pre-Fc chimeric polypeptide having
      a CETP signal peptide

<400> SEQUENCE: 96
aagcttgaat tcccaccatg ctggctgcca cagtcctgac cctggccctg ctgggcaatg      60
cccatgcctg cccagcacct gagttcctgg ggggaccatc agtcttcctg ttcccccaa     120 aacccaagga cactctcatg atctcccgga cccctgaggt cacgtgcgtg gtggtggacg     180
tgagccagga agaccccgag gtccagttca actggtacgt ggatggcgtg gaggtgcata     240
atgccaagac aaagccgcgg gaggagcagt tcaacagcac gtaccgtgtg gtcagcgtcc     300
tcaccgtcct gcaccaggac tggctgaacg gcaaggagta caagtgcaag gtctccaaca     360
aaggcctccc gtcctccatc gagaaaacca tctccaaagc caaagggcag ccccgagagc     420
cacaggtgta caccctgccc ccatcccagg aggagatgac caagaaccag gtcagcctga     480
cctgcctggt caaaggcttc taccccagca catcgccgt ggagtgggag agcaatgggc     540
agccggagaa caactacaag accacgcctc ccgtgctgga ctccgacggc tccttcttcc     600
tctacagcag gctaaccgtg gacaagagca ggtggcagga ggggaatgtc ttctcatgct     660
ccgtgatgca tgaggctctg cacaaccact acacacagaa gagcctctcc ctgtctctgg     720
gtaaatgact cgagcggccg                                                  740

<210> SEQ ID NO 97
<211> LENGTH: 5428
<212> TYPE: DNA
<213> ORGANISM: Artificial Sequence
<220> FEATURE:
<223> OTHER INFORMATION: pCDNA3.1(+)

<400> SEQUENCE: 97
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ggctaact agagaaccca     840 ctgcttactg gcttatcgaa attaatacga ctcactatag ggagacccaa gctggctagc     900
gtttaaactt aagcttggta ccgagctcgg atccactagt ccagtgtggt ggaattctgc     960
agatatccag cacagtggcg gccgctcgag tctagagggc cgtttaaac ccgctgatca    1020 gcctcgactg tgccttctag ttgccagcca tctgttgttt gccccctccc cgtgccttcc    1080
ttgaccctgg aaggtgccac tcccactgtc ctttcctaat aaaatgagga aattgcatcg    1140
```

```
cattgtctga gtaggtgtca ttctattctg gggggtgggg tggggcagga cagcaagggg      1200
gaggattggg aagacaatag caggcatgct ggggatgcgg tgggctctat ggcttctgag      1260
gcggaaagaa ccagctgggg ctctaggggg tatccccacg cgccctgtag cggcgcatta      1320
agcgcggcgg gtgtggtggt tacgcgcagc gtgaccgcta cacttgccag cgccctagcg      1380
cccgctcctt tcgctttctt cccttccttt ctcgccacgt tcgccggctt tccccgtcaa      1440
gctctaaatc gggggctccc tttagggttc cgatttagtg ctttacggca cctcgacccc      1500
aaaaaacttg attagggtga tggttcacgt agtgggccat cgccctgata cacggttttt      1560 cgcccttttga cgttggagtc cacgttcttt aatagtggac tcttgttcca aactggaaca      1620
acactcaacc ctatctcggt ctattctttt gatttataag ggattttgcc gatttcggcc      1680
tattggttaa aaaatgagct gatttaacaa aaatttaacg cgaattaatt ctgtggaatg      1740
tgtgtcagtt agggtgtgga agtccccag gctccccagc aggcagaagt atgcaaagca      1800
tgcatctcaa ttagtcagca accaggtgtg gaaagtcccc aggctcccca gcaggcagaa      1860
gtatgcaaag catgcatctc aattagtcag caaccatagt cccgccccta actccgccca      1920
tcccgcccct aactccgccc agttccgccc attctccgcc ccatggctga ctaatttttt      1980
ttatttatgc agaggccgag gccgcctctg cctctgagct attccagaag tagtgaggag      2040
gcttttttgg aggcctaggc ttttgcaaaa agctcccggg agcttgtata tccatttccg      2100
gatctgatca agagacagga tgaggatcgt ttcgcatgat tgaacaagat ggattgcacg      2160
caggttctcc ggccgcttgg gtggagaggc tattcggcta tgactgggca acagacaa      2220 tcggctgctc tgatgccgcc gtgttccggc tgtcagcgca ggggcgcccg gttcttttttg      2280 tcaagaccga cctgtccggt gccctgaatg aactgcagga cgaggcagcg cggctatcgt      2340
ggctggccac gacgggcgtt ccttgcgcag ctgtgctcga cgttgtcact gaagcgggaa      2400
gggactggct gctattgggc gaagtgccgg gcaggatct cctgtcatct caccttgctc      2460
ctgccgagaa agtatccatc atggctgatg caatgcggcg gctgcatacg cttgatccgg      2520
ctacctgccc attcgaccac caagcgaaac atcgcatcga gcgagcacgt actcggatgg      2580
aagccggtct tgtcgatcag gatgatctgg acgaagagca tcaggggctc gcgccagccg      2640
aactgttcgc caggctcaag gcgcgcatgc ccgacggcga ggatctcgtc gtgacccatg      2700
gcgatgcctg cttgccgaat atcatggtgg aaaatggccg cttttctgga ttcatcgact      2760
gtggccggct gggtgtggcg gaccgctatc aggacatagc gttggctacc cgtgatattg      2820
ctgaagagct tggcggcgaa tgggctgacc gcttcctcgt gctttacggt atcgccgctc      2880
ccgattcgca gcgcatcgcc ttctatcgcc ttcttgacga gttcttctga gcgggactct      2940
ggggttcgaa atgaccgacc aagcgacgcc caacctgcca tcacgagatt tcgattccac      3000
cgccgccttc tatgaaaggt tgggcttcgg aatcgttttc cgggacgccg gctggatgat      3060
cctccagcgc ggggatctca tgctggagtt cttcgcccac cccaacttgt ttattgcagc      3120
ttataatggt tacaaataaa gcaatagcat cacaaatttc acaaataaag catttttttc      3180
actgcattct agttgtggtt tgtccaaact catcaatgta tcttatcatg tctgtatacc      3240
gtcgacctct agctagagct tggcgtaatc atggtcatag ctgtttcctg tgtgaaattg      3300
ttatccgctc acaattccac acaacatacg agccggaagc ataaagtgta aagcctgggg      3360
tgcctaatga gtgagctaac tcacattaat tgcgttgcgc tcactgcccg ctttccagtc      3420
gggaaacctg tcgtgccagc tgcattaatg aatcggccaa cgcgcgggga gaggcggttt      3480
```

```
gcgtattggg cgctcttccg cttcctcgct cactgactcg ctgcgctcgg tcgttcggct    3540
gcggcgagcg gtatcagctc actcaaaggc ggtaatacgg ttatccacag aatcaggggga   3600 taacgcagga agaacatgt gagcaaaagg ccagcaaaag gccaggaacc gtaaaaaggc    3660
cgcgttgctg gcgttttttcc ataggctccg ccccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg gaaaaagagt tggtagctct tgatccggca acaaaccac     4200 cgctggtagc ggtttttttg tttgcaagca gcagattacg cgcagaaaaa aaggatctca    4260
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact ttaaaagtgc tcatcattgg    5100
aaaacgttct cggggcgaaa actctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc ttttccaata ttattgaagc atttatcagg gttattgtct    5340
catgagcgga tacatatttg aatgtattta gaaaaataaa caaatagggg ttccgcgcac    5400
atttccccga aaagtgccac ctgacgtc                                       5428
```

<210> SEQ ID NO 98
<211> LENGTH: 4195
<212> TYPE: DNA
<213> ORGANISM: Artificial Sequence
<220> FEATURE:
<223> OTHER INFORMATION: pSA

<400> SEQUENCE: 98

```
ctaaattgta agcgttaata ttttgttaaa attcgcgtta aatttttgtt aaatcagctc      60
attttttaac caataggccg aaatcggcaa aatcccttat aaatcaaaag aatagaccga     120
```

```
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc  ctaaagggag    300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcaagcgg ccgcaacccg ggaaaagctt ggccattgca    660
tacgttgtat ccatatcata atatgtacat ttatattggc tcatgtccaa cattaccgcc    720
atgttgacat tgattattga ctagttatta atagtaatca attacggggt cattagttca    780
tagcccatat atggagttcc gcgttacata acttacggta atggcccgc  ctggctgacc    840 gcccaacgac ccccgcccat tgacgtcaat aatgacgtat gttcccatag taacgccaat    900
agggactttc cattgacgtc aatgggtgga gtatttacgg taaactgccc acttggcagt    960
acatcaagtg tatcatatgc caagtacgcc ccctattgac gtcaatgacg gtaaatggcc    1020
cgcctggcat tatgcccagt acatgacctt atgggacttt cctacttggc agtacatcta    1080
cgtattagtc atcgctatta ccatggtgat gcggttttgg cagtacatca atgggcgtgg    1140
atagcggttt gactcacggg gatttccaag tctccacccc attgacgtca atgggagttt    1200
gttttggcac caaaatcaac gggactttcc aaaatgtcgt aacaactccg ccccattgac    1260
gcaaatgggc ggtaggcgtg tacggtggga ggtctatata agcagagctc gtttagtgaa    1320
ccgtcagatc gcctggagac gccatccacg ctgttttgac ctccatagaa gacaccggga    1380
ccgatccagc ctccgcggcc gggaacggtg cattggaacg cggattcccc gtgccaagag    1440
tgacgtaagt accgcctata gagtctatag gcccaccccc ttggcttctt atgcatgctc    1500
ccctgctccg acccgggctc ctcgcccgcc cggaccacca ggccaccctc aaccgtcctg    1560
gccccggacc caaaccccac ccctcactct gcttctcccc gcaggagaat tcaatcgcga    1620
aagggcccaa agatctgcca taccacattt gtagaggttt tacttgcttt aaaaaacctc    1680
ccacacctcc ccctgaacct gaaacataaa atgaatgcaa ttgttgttgt taacttgttt    1740
attgcagctt ataatggtta caaataaagc aatagcatca caaatttcac aaataaagca    1800 ttttttcac  tgcattctag ttgtggtttg tccaaactca tcaatgtatc ttatcatgtc    1860
tggagctagc atcccgcccc taactccgcc ctgttccgcc cattctccgc cccatggctg    1920 actaatttt  tttatttatg cagaggccga ggccgcctcg gcctctgagc tattccagaa    1980
gtagtgagga ggcttttttg gaggcctagg cttttgcgtc gagaagcgcg cttggcgtaa    2040
tcatggtcat agctgtttcc tgtgtgaaat tgttatccgc tcacaattcc acacaacata    2100
cgagccggaa gcataaagtg taaagcctgg ggtgcctaat gagtgagcta actcacatta    2160
attgcgttgc gctcactgcc cgcttttcca tcgggaaacc tgtcgtgcca gctgcattaa    2220
tgaatcggcc aacgcgcggg gagaggcggt ttgcgtattg ggcgctcttc cgcttcctcg    2280
ctcactgact cgctgcgctc ggtcgttcgg ctgcggcgag cggtatcagc tcactcaaag    2340
gcggtaatac ggttatccac agaatcaggg gataacgcag gaaagaacat gtgagcaaaa    2400
ggccagcaaa aggccaggaa ccgtaaaaag gccgcgttgc tggcgttttt ccataggctc    2460
```

-continued

| | |
|---|---|
| cgcccccctg acgagcatca caaaaatcga cgctcaagtc agaggtggcg aaacccgaca | 2520 |
| ggactataaa gataccaggc gtttccccct ggaagctccc tcgtgcgctc tcctgttccg | 2580 |
| accctgccgc ttaccggata cctgtccgcc tttctccctt cgggaagcgt ggcgctttct | 2640 |
| catagctcac gctgtaggta tctcagttcg gtgtaggtcg ttcgctccaa gctgggctgt | 2700 |
| gtgcacgaac ccccgttca gcccgaccgc tgcgccttat ccggtaacta tcgtcttgag | 2760 |
| tccaacccgg taagacacga cttatcgcca ctggcagcag ccactggtaa caggattagc | 2820 |
| agagcgaggt atgtaggcgg tgctacagag ttcttgaagt ggtggcctaa ctacggctac | 2880 |
| actagaagga cagtatttgg tatctgcgct ctgctgaagc cagttacctt cggaaaaaga | 2940 |
| gttggtagct cttgatccgg caaacaaacc accgctggta gcggtggttt ttttgtttgc | 3000 |
| aagcagcaga ttacgcgcag aaaaaaagga tctcaagaag atcctttgat ctttctacg | 3060 |
| gggtctgacg ctcagtggaa cgaaaactca cgttaaggga ttttggtcat gagattatca | 3120 |
| aaaaggatct tcacctagat ccttttaaat taaaatgaa gttttaaatc aatctaaagt | 3180 |
| atatatgagt aaacttggtc tgacagttac caatgcttaa tcagtgaggc acctatctca | 3240 |
| gcgatctgtc tatttcgttc atccatagtt gcctgactcc ccgtcgtgta gataactacg | 3300 |
| atacgggagg gcttaccatc tggccccagt gctgcaatga taccgcgaga cccacgctca | 3360 |
| ccggctccag atttatcagc aataaaccag ccagccggaa gggccgagcg cagaagtggt | 3420 |
| cctgcaactt tatccgcctc catccagtct attaattgtt gccgggaagc tagagtaagt | 3480 |
| agttcgccag ttaatagttt gcgcaacgtt gttgccattg ctacaggcat cgtggtgtca | 3540 |
| cgctcgtcgt ttggtatggc ttcattcagc tccggttccc aacgatcaag gcgagttaca | 3600 |
| tgatccccca tgttgtgcaa aaaagcggtt agctccttcg gtcctccgat cgttgtcaga | 3660 |
| agtaagttgg ccgcagtgtt atcactcatg gttatggcag cactgcataa ttctcttact | 3720 |
| gtcatgccat ccgtaagatg cttttctgtg actggtgagt actcaaccaa gtcattctga | 3780 |
| gaatagtgta tgcggcgacc gagttgctct tgcccggcgt caatacggga taataccgcg | 3840 |
| ccacatagca gaactttaaa agtgctcatc attggaaaac gttcttcggg gcgaaaactc | 3900 |
| tcaaggatct taccgctgtt gagatccagt tcgatgtaac ccactcgtgc acccaactga | 3960 |
| tcttcagcat cтттттacттт caccagcgtt tctgggtgag caaaaacagg aaggcaaaat | 4020 |
| gccgcaaaaa agggaataag ggcgacacgg aaatgttgaa tactcatact cttcctttt | 4080 |
| caatattatt gaagcattta tcagggttat tgtctcatga gcggatacat atttgaatgt | 4140 |
| atttagaaaa ataaacaaat aggggttccg cgcacatttc cccgaaaagt gccac | 4195 |

<210> SEQ ID NO 99
<211> LENGTH: 824
<212> TYPE: DNA
<213> ORGANISM: Artificial Sequence
<220> FEATURE:
<223> OTHER INFORMATION: Artificial Construct

<400> SEQUENCE: 99

| | |
|---|---|
| gttaacgaat tcccaccatg attgaacaag atggattgca cgcaggttct ccggccgctt | 60 |
| gggtggagag gctattcggc tatgactggg cacaacagac aatcggctgc tctgatgccg | 120 |
| ccgtgttccg gctgtcagcg caggggcgcc cggttctttt tgtcaagacc gacctgtccg | 180 |
| gtgccctgaa tgaactgcag gacgaggcag cgcggctatc gtggctggcc acgacgggcg | 240 |
| ttccttgcgc agctgtgctc gacgttgtca ctgaagcggg aagggactgg ctgctattgg | 300 |
| gcgaagtgcc ggggcaggat ctcctgtcat ctcaccttgc tcctgccgag aaagtatcca | 360 |

```
tcatggctga tgcaatgcgg cggctgcata cgcttgatcc ggctacctgc ccattcgacc      420
accaagcgaa acatcgcatc gagcgagcac gtactcggat ggaagccggt cttgtcgatc      480
aggatgatct ggacgaagag catcaggggc tcgcgccagc cgaactgttc gccaggctca      540
aggcgcgcat gcccgacggc gaggatctcg tcgtgaccca tggcgatgcc tgcttgccga      600
atatcatggt ggaaaatggc cgcttttctg gattcatcga ctgtggccgg ctgggtgtgg      660
cggaccgcta tcaggacata gcgttggcta cccgtgatat tgctgaagag cttggcggcg      720
aatgggctga ccgcttcctc gtgctttacg gtatcgccgc tcccgattcg cagcgcatcg      780
ccttctatcg ccttcttgac gagttcttct gaagatctgt taac                      824
```

<210> SEQ ID NO 100
<211> LENGTH: 6739
<212> TYPE: DNA
<213> ORGANISM: Artificial Sequence
<220> FEATURE:
<223> OTHER INFORMATION: pCDNA3-TNR1B-Mth

<400> SEQUENCE: 100

```
gacggatcgg gagatctccc gatccctat ggtgcactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgcc ccattgacgc aaatgggcg       780 gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttgaat tcccaccatg gcgcccgtcg ccgtctgggc cgcgctggcc      960
gtcggactgg agctctgggc tgcggcgcac gccttgcccg cccaggtggc atttacaccc     1020
tacgccccgg agcccgggag cacatgccgg ctcagagaat actatgacca gacagctcag     1080
atgtgctgca gcaaatgctc gccgggccaa catgcaaaag tcttctgtac caagacctcg     1140
gacaccgtgt gtgactcctg tgaggacagc acatacaccc agctctggaa ctgggttccc     1200
gagtgcttga gctgtggctc cgctgtagc tctgaccagg tggaaactca agcctgcact     1260
cgggaacaga accgcatctg cacctgcagg cccggctggt actgcgcgct gagcaagcag     1320
gaggggtgcc ggctgtgcgc gccgctgcgc aagtgccgcc cgggcttcgg cgtggccaga     1380
ccaggaactg aaacatcaga cgtggtgtgc aagccctgtg ccccggggac gttctccaac     1440
acgacttcat ccacggatat ttgcaggccc caccagatct gtaacgtggt ggccatccct     1500
gggaatgcaa gcatggatgc agtctgcacg tccacgtccc ccaccggag tatggcccca     1560
```

```
gggggcagtac acttaccccca gccagtgtcc acacgatccc aacacacgca gccaactcca    1620
gaacccagca ctgctccaag cacctccttc ctgctcccaa tggggcccag ccccccagct    1680
gaagggagca ctggcgacgg gtgcgtatcc ggtgacacca ttgtaatgac tagtggcggg    1740
ccccgcactg tggctgaact ggagggcaaa ccgttcaccg cactgattcg cggctctggc    1800
tacccatgcc cctcaggttt cttccgcacc tgtgaacgtg acgtatatga tctgcgtaca    1860
cgtgagggtc attgcttacg tttgacccat gatcaccgtg ttctggtgat ggatggtggc    1920
ctggaatggc gtgccgcggg tgaactggaa cgcggcgacc gcctggtgat ggatgatgca    1980
gctggcgagt ttccggcact ggcaaccttc cgtggcctgc gtggcgctgg ccgccaggat    2040
gtttatgacg ctactgttta cggtgctagc gcattcactg ctaatggctt cattgtacac    2100
gcatgtggcg agcagcccgg gaccggtctg aactcaggcc tcacgacaaa tcctggtgta    2160
tccgcttggc aggtcaacac agcttatact gcgggacaat tggtcacata taacggcaag    2220
acgtataaat gtttgcagcc ccacacctcc ttggcaggat gggaaccatc caacgttcct    2280
gccttgtggc agcttcaatg actcgagcgg cccgtttaaa cccgctgatc agcctcgact    2340
gtgccttcta gttgccagcc atctgttgtt tgcccctccc ccgtgccttc cttgaccctg    2400
gaaggtgcca ctcccactgt cctttcctaa taaaatgagg aaattgcatc gcattgtctg    2460
agtaggtgtc attctattct ggggggtggg gtggggcagg acagcaaggg ggaggattgg    2520
gaagacaata gcaggcatgc tggggatgcg gtgggctcta tggcttctga ggcggaaaga    2580
accagctggg gctctagggg gtatccccac gcgccctgta gcggcgcatt aagcgcggcg    2640
ggtgtggtgg ttacgcgcag cgtgaccgct acacttgcca gcgccctagc gcccgctcct    2700
ttcgctttct tcccttcctt tctcgccacg ttcgccggct ttccccgtca agctctaaat    2760
cgggggctcc ctttagggtt ccgatttagt gctttacggc acctcgaccc caaaaaactt    2820
gattagggtg atggttcacg tagtgggcca tcgccctgat agacggtttt tcgccctttg    2880
acgttggagt ccacgttctt taatagtgga ctcttgttcc aaactggaac aacactcaac    2940
cctatctcgg tctattcttt tgatttataa gggattttgc cgatttcggc ctattggtta    3000
aaaaatgagc tgatttaaca aaaatttaac gcgaattaat tctgtggaat gtgtgtcagt    3060
tagggtgtgg aaagtcccca ggctccccag caggcagaag tatgcaaagc atgcatctca    3120
attagtcagc aaccaggtgt ggaaagtccc caggctcccc agcaggcaga agtatgcaaa    3180
gcatgcatct caattagtca gcaaccatag tccgcccct aactccgccc atcccgcccc    3240
taactccgcc cagttccgcc cattctccgc cccatggctg actaattttt tttatttatg    3300
cagaggccga ggccgcctct gcctctgagc tattccagaa gtagtgagga ggcttttttg    3360
gaggcctagg cttttgcaaa aagctcccgg gagcttgtat atccatttc ggatctgatc    3420
aagagacagg atgaggatcg tttcgcatga ttgaacaaga tggattgcac gcaggttctc    3480
cggccgcttg ggtggagagg ctattcggct atgactgggc acaacagaca atcggctgct    3540
ctgatgccgc cgtgttccgg ctgtcagcgc agggggcgccc ggttcttttt gtcaagaccg    3600
acctgtccgg tgccctgaat gaactgcagg acgaggcagc gcggctatcg tggctggcca    3660
cgacgggcgt tccttgcgca gctgtgctcg acgttgtcac tgaagcggga agggactggc    3720
tgctattggg cgaagtgccg gggcaggatc tcctgtcatc tcaccttgct cctgccgaga    3780
aagtatccat catggctgat gcaatgcggc ggctgcatac gcttgatccg gctacctgcc    3840
cattcgacca ccaagcgaaa catcgcatcg agcgagcacg tactcggatg gaagccggtc    3900
ttgtcgatca ggatgatctg gacgaagagc atcaggggct cgcgccagcc gaactgttcg    3960
```

```
ccaggctcaa ggcgcgcatg cccgacggcg aggatctcgt cgtgacccat ggcgatgcct    4020
gcttgccgaa tatcatggtg gaaaatggcc gcttttctgg attcatcgac tgtgccggc     4080 tgggtgtggc ggaccgctat caggacatag cgttggctac ccgtgatatt gctgaagagc    4140
ttggcggcga atgggctgac cgcttcctcg tgctttacgg tatcgccgct cccgattcgc    4200
agcgcatcgc cttctatcgc cttcttgacg agttcttctg agcgggactc tggggttcga    4260
aatgaccgac caagcgacgc ccaacctgcc atcacgagat ttcgattcca ccgccgcctt    4320
ctatgaaagg ttgggcttcg gaatcgtttt ccgggacgcc ggctggatga tcctccagcg    4380
cggggatctc atgctggagt tcttcgccca ccccaacttg tttattgcag cttataatgg    4440
ttacaaataa agcaatagca tcacaaattt cacaaataaa gcattttttt cactgcattc    4500
tagttgtggt ttgtccaaac tcatcaatgt atcttatcat gtctgtatac cgtcgacctc    4560
tagctagagc ttggcgtaat catggtcata gctgtttcct gtgtgaaatt gttatccgct    4620
cacaattcca cacaacatac gagccggaag cataaagtgt aaagcctggg gtgcctaatg    4680
agtgagctaa ctcacattaa ttgcgttgcg ctcactgccc gctttccagt cgggaaacct    4740
gtcgtgccag ctgcattaat gaatcggcca acgcgcgggg agaggcggtt tgcgtattgg    4800
gcgctcttcc gcttcctcgc tcactgactc gctgcgctcg gtcgttcggc tgcggcgagc    4860
ggtatcagct cactcaaagg cggtaatacg gttatccaca gaatcagggg ataacgcagg    4920
aaagaacatg tgagcaaaag gccagcaaaa ggccaggaac cgtaaaaagg ccgcgttgct    4980
ggcgtttttc cataggctcc gcccccctga cgagcatcac aaaaatcgac gctcaagtca    5040
gaggtggcga aacccgacag gactataaag ataccaggcg tttccccctg gaagctccct    5100
cgtgcgctct cctgttccga ccctgccgct taccggatac ctgtccgcct ttctcccttc    5160
gggaagcgtg gcgctttctc atagctcacg ctgtaggtat ctcagttcgg tgtaggtcgt    5220
tcgctccaag ctgggctgtg tgcacgaacc ccccgttcag cccgaccgct gcgccttatc    5280
cggtaactat cgtcttgagt ccaacccggt aagacacgac ttatcgccac tggcagcagc    5340
cactggtaac aggattagca gagcgaggta tgtaggcggt gctacagagt tcttgaagtg    5400
gtggcctaac tacggctaca ctagaagaac agtatttggt atctgcgctc tgctgaagcc    5460
agttaccttc ggaaaaagag ttggtagctc ttgatccggc aaacaaacca ccgctggtag    5520
cggttttttt gtttgcaagc agcagattac gcgcagaaaa aaaggatctc aagaagatcc    5580
tttgatcttt tctacggggt ctgacgctca gtggaacgaa aactcacgtt aagggatttt    5640
ggtcatgaga ttatcaaaaa ggatcttcac ctagatcctt ttaaattaaa aatgaagttt    5700
taaatcaatc taaagtatat atgagtaaac ttggtctgac agttaccaat gcttaatcag    5760
tgaggcacct atctcagcga tctgtctatt tcgttcatcc atagttgcct gactccccgt    5820
cgtgtagata actacgatac gggagggctt accatctggc cccagtgctg caatgatacc    5880
gcgagaccca cgctcaccgg ctccagattt atcagcaata aaccagccag ccggaagggc    5940
cgagcgcaga agtggtcctg caactttatc cgcctccatc cagtctatta attgttgccg    6000
ggaagctaga gtaagtagtt cgccagttaa tagtttgcgc aacgttgttg ccattgctac    6060
aggcatcgtg gtgtcacgct cgtcgtttgg tatggcttca ttcagctccg gttcccaacg    6120
atcaaggcga gttacatgat cccccatgtt gtgcaaaaaa gcggttagct ccttcggtcc    6180
tccgatcgtt gtcagaagta agttggccgc agtgttatca ctcatggtta tggcagcact    6240
gcataattct cttactgtca tgccatccgt aagatgcttt tctgtgactg gtgagtactc    6300
```

```
aaccaagtca ttctgagaat agtgtatgcg gcgaccgagt tgctcttgcc cggcgtcaat    6360
acgggataat accgcgccac atagcagaac tttaaaagtg ctcatcattg gaaaacgttc    6420 ttcgggcga aaactctcaa ggatcttacc gctgttgaga tccagttcga tgtaacccac    6480
tcgtgcaccc aactgatctt cagcatcttt tactttcacc agcgtttctg ggtgagcaaa    6540
aacaggaagg caaatgccg caaaaaggg aataagggcg acacggaaat gttgaatact     6600
catactcttc ctttttcaat attattgaag catttatcag ggttattgtc tcatgagcgg    6660
atacatattt gaatgtattt agaaaaataa acaaataggg gttccgcgca catttccccg    6720
aaaagtgcca cctgacgtc                                                 6739
```

<210> SEQ ID NO 101
<211> LENGTH: 457
<212> TYPE: PRT
<213> ORGANISM: Artificial Sequence
<220> FEATURE:
<223> OTHER INFORMATION: pre-TNR1B-intein chimeric polypeptide

<400> SEQUENCE: 101

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Gly Cys Val Ser Gly Asp Thr Ile Val Met Thr Ser Gly Gly Pro
            260                 265                 270

Arg Thr Val Ala Glu Leu Glu Gly Lys Pro Phe Thr Ala Leu Ile Arg
        275                 280                 285
```

Gly Ser Gly Tyr Pro Cys Pro Ser Gly Phe Phe Arg Thr Cys Glu Arg
            290                 295                 300

Asp Val Tyr Asp Leu Arg Thr Arg Glu Gly His Cys Leu Arg Leu Thr
305                 310                 315                 320

His Asp His Arg Val Leu Val Met Asp Gly Gly Leu Glu Trp Arg Ala
            325                 330                 335

Ala Gly Glu Leu Glu Arg Gly Asp Arg Leu Val Met Asp Asp Ala Ala
            340                 345                 350

Gly Glu Phe Pro Ala Leu Ala Thr Phe Arg Gly Leu Arg Gly Ala Gly
            355                 360                 365

Arg Gln Asp Val Tyr Asp Ala Thr Val Tyr Gly Ala Ser Ala Phe Thr
370                 375                 380

Ala Asn Gly Phe Ile Val His Ala Cys Gly Glu Gln Pro Gly Thr Gly
385                 390                 395                 400

Leu Asn Ser Gly Leu Thr Thr Asn Pro Gly Val Ser Ala Trp Gln Val
            405                 410                 415

Asn Thr Ala Tyr Thr Ala Gly Gln Leu Val Thr Tyr Asn Gly Lys Thr
            420                 425                 430

Tyr Lys Cys Leu Gln Pro His Thr Ser Leu Ala Gly Trp Glu Pro Ser
            435                 440                 445

Asn Val Pro Ala Leu Trp Gln Leu Gln
    450                 455

<210> SEQ ID NO 102
<211> LENGTH: 435
<212> TYPE: PRT
<213> ORGANISM: Artificial Sequence
<220> FEATURE:
<223> OTHER INFORMATION: mature TNR1B-intein fusion protein

<400> SEQUENCE: 102

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Cys Val Ser Gly
225                 230                 235                 240

Asp Thr Ile Val Met Thr Ser Gly Gly Pro Arg Thr Val Ala Glu Leu
                245                 250                 255

Glu Gly Lys Pro Phe Thr Ala Leu Ile Arg Gly Ser Gly Tyr Pro Cys
            260                 265                 270

Pro Ser Gly Phe Phe Arg Thr Cys Glu Arg Asp Val Tyr Asp Leu Arg
        275                 280                 285

Thr Arg Glu Gly His Cys Leu Arg Leu Thr His Asp His Arg Val Leu
    290                 295                 300

Val Met Asp Gly Gly Leu Glu Trp Arg Ala Ala Gly Glu Leu Glu Arg
305                 310                 315                 320

Gly Asp Arg Leu Val Met Asp Asp Ala Ala Gly Glu Phe Pro Ala Leu
                325                 330                 335

Ala Thr Phe Arg Gly Leu Arg Gly Ala Gly Arg Gln Asp Val Tyr Asp
            340                 345                 350

Ala Thr Val Tyr Gly Ala Ser Ala Phe Thr Ala Asn Gly Phe Ile Val
        355                 360                 365

His Ala Cys Gly Glu Gln Pro Gly Thr Gly Leu Asn Ser Gly Leu Thr
    370                 375                 380

Thr Asn Pro Gly Val Ser Ala Trp Gln Val Asn Thr Ala Tyr Thr Ala
385                 390                 395                 400

Gly Gln Leu Val Thr Tyr Asn Gly Lys Thr Tyr Lys Cys Leu Gln Pro
                405                 410                 415

His Thr Ser Leu Ala Gly Trp Glu Pro Ser Asn Val Pro Ala Leu Trp
            420                 425                 430

Gln Leu Gln
        435

<210> SEQ ID NO 103
<211> LENGTH: 6103
<212> TYPE: DNA
<213> ORGANISM: Artificial Sequence
<220> FEATURE:
<223> OTHER INFORMATION: pCDNA3-SHH-IgG1-Fc11

<400> SEQUENCE: 103
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca caaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttgaat cccaccatg ctgctgctgg cgagatgtct gctgctagtc    960
ctcgtctcct cgctgctggt atgctcggga ctggcgtgcc caccgtgccc agcacctgaa   1020
ctcctggggg ggcccctcagt cttcctcttc cccccaaaac ccaaggacac cctcatgatc   1080
tcccggaccc ctgaggtcac atgcgtggtg gtggacgtga gccacgaaga ccctgaggtc   1140
aagttcaact ggtacgtgga cggcgtggag gtgcataatg ccaagacaaa gccgcgggag   1200
gagcagtaca acagcacgta ccgtgtggtc agcgtcctca ccgtcctgca ccaggactgg   1260
ctgaatggca aggagtacaa gtgcaaggtc tccaacaaag ccctcccagc ccccatcgag   1320
aaaaccatct ccaaagccaa agggcagccc cgagaaccac aggtgtacac cctgccccca   1380
tcccgggatg agctgaccaa gaaccaggtc agcctgacct gcctggtcaa aggcttctat   1440
cccagcgaca tcgccgtgga gtgggagagc aatgggcagc cggagaacaa ctacaagacc   1500
acgcctcccg tgctggactc cgacggctcc ttcttcctct acagcaagct caccgtggac   1560
aagagcaggt ggcagcaggg gaacgtcttc tcatgctccg tgatgcatga ggctctgcac   1620
aaccactaca cgcagaagag cctctccctg tctccgggta aatgactcga gcggccgtt   1680 taaacccgct gatcagcctc gactgtgcct tctagttgcc agccatctgt tgtttgcccc   1740
tcccccgtgc cttccttgac cctggaaggt gccactccca ctgtcctttc ctaataaaat   1800
gaggaaattg catcgcattg tctgagtagg tgtcattcta ttctgggggg tggggtgggg   1860
caggacagca agggggagga ttgggaagac aatagcaggc atgctgggga tgcggtgggc   1920
tctatggctt ctgaggcgga aagaaccagc tggggctcta gggggtatcc ccacgcgccc   1980
tgtagcggcg cattaagcgc ggcgggtgtg gtggttacgc gcagcgtgac cgctacactt   2040
gccagcgccc tagcgcccgc tcctttcgct ttcttccctt cctttctcgc cacgttcgcc   2100
ggctttcccc gtcaagctct aaatcggggg ctccctttag ggttccgatt tagtgcttta   2160
cggcacctcg accccaaaaa acttgattag ggtgatggtt cacgtagtgg gccatcgccc   2220
tgatagacgg ttttttcgccc tttgacgttg gagtccacgt tctttaatag tggactcttg   2280
ttccaaactg gaacaacact caaccctatc tcggtctatt cttttgattt ataagggatt   2340
ttgccgattt cggcctattg gttaaaaaat gagctgattt aacaaaaatt taacgcgaat   2400
taattctgtg gaatgtgtgt cagttagggt gtggaaagtc ccaggctccc cagcaggca   2460 gaagtatgca aagcatgcat ctcaattagt cagcaaccag gtgtggaaag tccccaggct   2520
ccccagcagg cagaagtatg caaagcatgc atctcaatta gtcagcaacc atagtcccgc   2580
ccctaactcc gcccatcccg ccctaactc gcccagttc gcccattct ccgccccatg   2640 gctgactaat ttttttatt tatgcagagg ccgaggccgc ctctgcctct gagctattcc   2700
agaagtagtg aggaggcttt tttggaggcc taggcttttg caaaaagctc ccgggagctt   2760
gtatatccat tttcggatct gatcaagaga caggatgagg atcgtttcgc atgattgaac   2820
aagatggatt gcacgcaggt tctccggccg cttgggtgga gaggctattc ggctatgact   2880
gggcacaaca gacaatcggc tgctctgatg ccgccgtgtt ccggctgtca gcgcaggggc   2940
gcccggttct ttttgtcaag accgacctgt ccggtgccct gaatgaactg caggacgagg   3000
```

```
cagcgcggct atcgtggctg gccacgacgg gcgttccttg cgcagctgtg ctcgacgttg    3060
tcactgaagc gggaagggac tggctgctat tgggcgaagt gccggggcag gatctcctgt    3120
catctcacct tgctcctgcc gagaaagtat ccatcatggc tgatgcaatg cggcggctgc    3180
atacgcttga tccggctacc tgcccattcg accaccaagc gaaacatcgc atcgagcgag    3240
cacgtactcg gatggaagcc ggtcttgtcg atcaggatga tctggacgaa gagcatcagg    3300
ggctcgcgcc agccgaactg ttcgccaggc tcaaggcgcg catgcccgac ggcgaggatc    3360
tcgtcgtgac ccatggcgat gcctgcttgc cgaatatcat ggtggaaaat ggccgctttt    3420
ctggattcat cgactgtggc cggctgggtg tggcggaccg ctatcaggac atagcgttgg    3480
ctacccgtga tattgctgaa gagcttggcg gcgaatgggc tgaccgcttc ctcgtgcttt    3540
acggtatcgc cgctcccgat tcgcagcgca tcgccttcta tcgccttctt gacgagttct    3600
tctgagcggg actctggggt tcgaaatgac cgaccaagcg acgcccaacc tgccatcacg    3660
agatttcgat tccaccgccg ccttctatga aggttgggc ttcggaatcg ttttccggga    3720
cgccggctgg atgatcctcc agcgcgggga tctcatgctg gagttcttcg cccacccaa    3780 cttgtttatt gcagcttata atggttacaa ataaagcaat agcatcacaa atttcacaaa    3840
taaagcattt ttttcactgc attctagttg tggtttgtcc aaactcatca atgtatctta    3900
tcatgtctgt ataccgtcga cctctagcta gagcttggcg taatcatggt catagctgtt    3960
tcctgtgtga aattgttatc cgctcacaat tccacacaac atacgagccg aagcataaa    4020 gtgtaaagcc tggggtgcct aatgagtgag ctaactcaca ttaattgcgt tgcgctcact    4080
gcccgctttc cagtcgggaa acctgtcgtg ccagctgcat taatgaatcg gccaacgcgc    4140
ggggagaggc ggtttgcgta ttgggcgctc ttccgcttcc tcgctcactg actcgctgcg    4200
ctcggtcgtt cggctgcggc gagcggtatc agctcactca aaggcggtaa tacggttatc    4260
cacagaatca ggggataacg caggaaagaa catgtgagca aaaggccagc aaaaggccag    4320
gaaccgtaaa aaggccgcgt tgctggcgtt tttccatagg ctccgccccc ctgacgagca    4380
tcacaaaaat cgacgctcaa gtcagaggtg gcgaaacccg acaggactat aaagatacca    4440
ggcgtttccc cctggaagct ccctcgtgcg ctctcctgtt ccgaccctgc cgcttaccgg    4500
atacctgtcc gcctttctcc cttcgggaag cgtggcgctt tctcatagct cacgctgtag    4560
gtatctcagt tcggtgtagg tcgttcgctc caagctgggc tgtgtgcacg aaccccccgt    4620
tcagcccgac cgctgcgcct tatccggtaa ctatcgtctt gagtccaacc cggtaagaca    4680
cgacttatcg ccactggcag cagccactgg taacaggatt agcagagcga ggtatgtagg    4740
cggtgctaca gagttcttga agtggtggcc taactacggc tacactagaa gaacagtatt    4800
tggtatctgc gctctgctga agccagttac cttcggaaaa agagttggta gctcttgatc    4860
cggcaaacaa accaccgctg gtagcggttt ttttgtttgc aagcagcaga ttacgcgcag    4920
aaaaaaagga tctcaagaag atcctttgat cttttctacg gggtctgacg ctcagtggaa    4980
cgaaaactca cgttaaggga ttttggtcat gagattatca aaaaggatct tcacctagat    5040
ccttttaaat taaaaatgaa gttttaaatc aatctaaagt atatatgagt aaacttggtc    5100
tgacagttac caatgcttaa tcagtgaggc acctatctca gcgatctgtc tatttcgttc    5160
atccatagtt gcctgactcc ccgtcgtgta gataactacg atacgggagg gcttaccatc    5220
tggccccagt gctgcaatga taccgcgaga cccacgctca ccggctccag atttatcagc    5280
aataaaccag ccagccggaa gggccgagcg cagaagtggt cctgcaactt tatccgcctc    5340
```

```
catccagtct attaattgtt gccgggaagc tagagtaagt agttcgccag ttaatagttt    5400
gcgcaacgtt gttgccattg ctacaggcat cgtggtgtca cgctcgtcgt ttggtatggc    5460
ttcattcagc tccggttccc aacgatcaag gcgagttaca tgatccccca tgttgtgcaa    5520
aaaagcggtt agctccttcg gtcctccgat cgttgtcaga agtaagttgg ccgcagtgtt    5580
atcactcatg gttatggcag cactgcataa ttctcttact gtcatgccat ccgtaagatg    5640
cttttctgtg actggtgagt actcaaccaa gtcattctga aatagtgta tgcggcgacc    5700 gagttgctct tgcccggcgt caatacggga taataccgcg ccacatagca gaactttaaa    5760
agtgctcatc attggaaaac gttcttcggg gcgaaaactc tcaaggatct taccgctgtt    5820
gagatccagt tcgatgtaac ccactcgtgc acccaactga tcttcagcat ctttactttt    5880
caccagcgtt tctgggtgag caaaaacagg aaggcaaaat gccgcaaaaa agggaataag    5940
ggcgacacgg aaatgttgaa tactcatact cttcctttt caatattatt gaagcattta     6000
tcagggttat tgtctcatga gcggatacat atttgaatgt atttagaaaa ataaacaaat    6060 agggggttccg cgcacatttc cccgaaaagt gccacctgac gtc                    6103
```

<210> SEQ ID NO 104
<211> LENGTH: 245
<212> TYPE: PRT
<213> ORGANISM: Artificial Sequence
<220> FEATURE:
<223> OTHER INFORMATION: pre-Fc6 polypeptide

<400> SEQUENCE: 104

```
Met Leu Leu Leu Ala Arg Cys Leu Leu Leu Val Leu Val Ser Ser Leu
1               5                   10                  15

Leu Val Cys Ser Gly Leu Ala Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
```

-continued

```
                225                 230                 235                 240

Leu Ser Pro Gly Lys
            245

<210> SEQ ID NO 105
<211> LENGTH: 222
<212> TYPE: PRT
<213> ORGANISM: Artificial Sequence
<220> FEATURE:
<223> OTHER INFORMATION: mature Fc6 protein

<400> SEQUENCE: 105

Cys Pro Pro Cys Pro Ala Pro Glu Leu Leu Gly Gly Pro Ser Val Phe
1               5                  10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 106
<211> LENGTH: 237
<212> TYPE: PRT
<213> ORGANISM: Artificial Sequence
<220> FEATURE:
<223> OTHER INFORMATION: cleaved alkyne-modified TNR1B
<220> FEATURE:
<221> NAME/KEY: SITE
<222> LOCATION: (237)..(237)
<223> OTHER INFORMATION: Xaa = cysteine-alkyne

<400> SEQUENCE: 106

Leu Pro Ala Gln Val Ala Phe Thr Pro Tyr Ala Pro Glu Pro Gly Ser
1               5                  10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45
```

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Xaa
225                 230                 235

<210> SEQ ID NO 107
<211> LENGTH: 237
<212> TYPE: PRT
<213> ORGANISM: Artificial Sequence
<220> FEATURE:
<223> OTHER INFORMATION: azide-modified TNR1B protein
<220> FEATURE:
<221> NAME/KEY: SITE
<222> LOCATION: (237)..(237)
<223> OTHER INFORMATION: Xaa = cysteine-azide

<400> SEQUENCE: 107

Leu Pro Ala Gln Val Ala Phe Thr Pro Tyr Ala Pro Glu Pro Gly Ser
1                5                  10                  15

Thr Cys Arg Leu Arg Glu Tyr Tyr Asp Gln Thr Ala Gln Met Cys Cys
             20                  25                  30

Ser Lys Cys Ser Pro Gly Gln His Ala Lys Val Phe Cys Thr Lys Thr
         35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His

```
145                 150                 155                 160
Gln Ile Cys Asn Val Val Ala Ile Pro Gly Asn Ala Ser Met Asp Ala
                165                 170                 175
Val Cys Thr Ser Thr Ser Pro Thr Arg Ser Met Ala Pro Gly Ala Val
                180                 185                 190
His Leu Pro Gln Pro Val Ser Thr Arg Ser Gln His Thr Gln Pro Thr
                195                 200                 205
Pro Glu Pro Ser Thr Ala Pro Ser Thr Ser Phe Leu Leu Pro Met Gly
        210                 215                 220
Pro Ser Pro Pro Ala Glu Gly Ser Thr Gly Asp Gly Xaa
225                 230                 235

<210> SEQ ID NO 108
<211> LENGTH: 237
<212> TYPE: PRT
<213> ORGANISM: Artificial Sequence
<220> FEATURE:
<223> OTHER INFORMATION: cysteine-modified TNR1B

<400> SEQUENCE: 108

Leu Pro Ala Gln Val Ala Phe Thr Pro Tyr Ala Pro Glu Pro Gly Ser
1               5                   10                  15
Thr Cys Arg Leu Arg Glu Tyr Tyr Asp Gln Thr Ala Gln Met Cys Cys
                20                  25                  30
Ser Lys Cys Ser Pro Gly Gln His Ala Lys Val Phe Cys Thr Lys Thr
                35                  40                  45
Ser Asp Thr Val Cys Asp Ser Cys Glu Asp Ser Thr Tyr Thr Gln Leu
        50                  55                  60
Trp Asn Trp Val Pro Glu Cys Leu Ser Cys Gly Ser Arg Cys Ser Ser
65                  70                  75                  80
Asp Gln Val Glu Thr Gln Ala Cys Thr Arg Glu Gln Asn Arg Ile Cys
                85                  90                  95
Thr Cys Arg Pro Gly Trp Tyr Cys Ala Leu Ser Lys Gln Glu Gly Cys
                100                 105                 110
Arg Leu Cys Ala Pro Leu Arg Lys Cys Arg Pro Gly Phe Gly Val Ala
                115                 120                 125
Arg Pro Gly Thr Glu Thr Ser Asp Val Val Cys Lys Pro Cys Ala Pro
        130                 135                 140
Gly Thr Phe Ser Asn Thr Thr Ser Ser Thr Asp Ile Cys Arg Pro His
145                 150                 155                 160
Gln Ile Cys Asn Val Val Ala Ile Pro Gly Asn Ala Ser Met Asp Ala
                165                 170                 175
Val Cys Thr Ser Thr Ser Pro Thr Arg Ser Met Ala Pro Gly Ala Val
                180                 185                 190
His Leu Pro Gln Pro Val Ser Thr Arg Ser Gln His Thr Gln Pro Thr
                195                 200                 205
Pro Glu Pro Ser Thr Ala Pro Ser Thr Ser Phe Leu Leu Pro Met Gly
        210                 215                 220
Pro Ser Pro Pro Ala Glu Gly Ser Thr Gly Asp Gly Cys
225                 230                 235

<210> SEQ ID NO 109
<211> LENGTH: 236
<212> TYPE: PRT
<213> ORGANISM: Artificial Sequence
<220> FEATURE:
<223> OTHER INFORMATION: thioester-modified TNR1B
```

```
<220> FEATURE:
<221> NAME/KEY: SITE
<222> LOCATION: (236)..(236)
<223> OTHER INFORMATION: Xaa = glycine-thioester

<400> SEQUENCE: 109
```

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Xaa
225                 230                 235

```
<210> SEQ ID NO 110
<211> LENGTH: 227
<212> TYPE: PRT
<213> ORGANISM: Artificial Sequence
<220> FEATURE:
<223> OTHER INFORMATION: Az-DKTHT-Fc6 protein
<220> FEATURE:
<221> NAME/KEY: SITE
<222> LOCATION: (1)..(1)
<223> OTHER INFORMATION: Xaa = azide-aspartic acid

<400> SEQUENCE: 110
```

Xaa Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr

```
                65                  70                  75                  80
Arg Val Val Ser Val Leu Thr Val Leu His Gln Asp Trp Leu Asn Gly
                        85                  90                  95
Lys Glu Tyr Lys Cys Lys Val Ser Asn Lys Ala Leu Pro Ala Pro Ile
                        100                 105                 110
Glu Lys Thr Ile Ser Lys Ala Lys Gly Gln Pro Arg Glu Pro Gln Val
                        115                 120                 125
Tyr Thr Leu Pro Pro Ser Arg Asp Glu Leu Thr Lys Asn Gln Val Ser
                130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                        165                 170                 175
Val Leu Asp Ser Asp Gly Ser Phe Phe Leu Tyr Ser Lys Leu Thr Val
                        180                 185                 190
Asp Lys Ser Arg Trp Gln Gln Gly Asn Val Phe Ser Cys Ser Val Met
                        195                 200                 205
His Glu Ala Leu His Asn His Tyr Thr Gln Lys Ser Leu Ser Leu Ser
                        210                 215                 220

Pro Gly Lys
225

<210> SEQ ID NO 111
<211> LENGTH: 227
<212> TYPE: PRT
<213> ORGANISM: Artificial Sequence
<220> FEATURE:
<223> OTHER INFORMATION: Az-PEG4-DKTHT-Fc6
<220> FEATURE:
<221> NAME/KEY: SITE
<222> LOCATION: (1)..(1)
<223> OTHER INFORMATION: Xaa = azide-PEG4-aspartic acid

<400> SEQUENCE: 111

Xaa Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                        85                  90                  95
Lys Glu Tyr Lys Cys Lys Val Ser Asn Lys Ala Leu Pro Ala Pro Ile
                        100                 105                 110
Glu Lys Thr Ile Ser Lys Ala Lys Gly Gln Pro Arg Glu Pro Gln Val
                        115                 120                 125
Tyr Thr Leu Pro Pro Ser Arg Asp Glu Leu Thr Lys Asn Gln Val Ser
                130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                        165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 112
<211> LENGTH: 465
<212> TYPE: PRT
<213> ORGANISM: Artificial Sequence
<220> FEATURE:
<223> OTHER INFORMATION: Polypeptide with internal non-peptidyl moiety.
      TNR1B-alkyne-azide-Fc6
<220> FEATURE:
<221> NAME/KEY: SITE
<222> LOCATION: (238)..(238)
<223> OTHER INFORMATION: Xaa = non-peptidyl moiety

<400> SEQUENCE: 112

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
            85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
            130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
            210                 215                 220

Pro Ser Pro Pro Ala Glu Gly Ser Thr Gly Asp Gly Cys Xaa Asp Lys
225                 230                 235                 240

Thr His Thr Cys Pro Pro Cys Pro Ala Pro Glu Leu Leu Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
```

```
            275                 280                 285
Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465

<210> SEQ ID NO 113
<211> LENGTH: 465
<212> TYPE: PRT
<213> ORGANISM: Artificial Sequence
<220> FEATURE:
<223> OTHER INFORMATION: Polypeptide with internal non-peptidyl moiety.
      TNR1B-alkyne-azide-PEG4-Fc6
<220> FEATURE:
<221> NAME/KEY: SITE
<222> LOCATION: (238)..(238)
<223> OTHER INFORMATION: Xaa = non-peptidyl moiety containing PEG4
      linker

<400> SEQUENCE: 113

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
```

```
              130                 135                 140
Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Cys Xaa Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
    450                 455                 460

Lys
465

<210> SEQ ID NO 114
<211> LENGTH: 467
<212> TYPE: PRT
<213> ORGANISM: Artificial Sequence
<220> FEATURE:
<223> OTHER INFORMATION: Etanercept

<400> SEQUENCE: 114

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
```

-continued

```
                20                  25                  30
Ser Lys Cys Ser Pro Gly Gln His Ala Lys Val Phe Cys Thr Lys Thr
            35                  40                  45
Ser Asp Thr Val Cys Asp Ser Cys Glu Asp Ser Thr Tyr Thr Gln Leu
        50                  55                  60
Trp Asn Trp Val Pro Glu Cys Leu Ser Cys Gly Ser Arg Cys Ser Ser
65                  70                  75                  80
Asp Gln Val Glu Thr Gln Ala Cys Thr Arg Glu Gln Asn Arg Ile Cys
                    85                  90                  95
Thr Cys Arg Pro Gly Trp Tyr Cys Ala Leu Ser Lys Gln Glu Gly Cys
                100                 105                 110
Arg Leu Cys Ala Pro Leu Arg Lys Cys Arg Pro Gly Phe Gly Val Ala
            115                 120                 125
Arg Pro Gly Thr Glu Thr Ser Asp Val Val Cys Lys Pro Cys Ala Pro
        130                 135                 140
Gly Thr Phe Ser Asn Thr Thr Ser Ser Thr Asp Ile Cys Arg Pro His
145                 150                 155                 160
Gln Ile Cys Asn Val Val Ala Ile Pro Gly Asn Ala Ser Met Asp Ala
                165                 170                 175
Val Cys Thr Ser Thr Ser Pro Thr Arg Ser Met Ala Pro Gly Ala Val
                180                 185                 190
His Leu Pro Gln Pro Val Ser Thr Arg Ser Gln His Thr Gln Pro Thr
            195                 200                 205
Pro Glu Pro Ser Thr Ala Pro Ser Thr Ser Phe Leu Leu Pro Met Gly
        210                 215                 220
Pro Ser Pro Pro Ala Glu Gly Ser Thr Gly Asp Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
        290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Asp Glu Leu Thr Lys Asn Gln Val Ser
        370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Tyr Lys Thr Thr Pro Pro
                405                 410                 415
Val Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
            435                 440                 445
```

His Glu Ala Leu His Asn His Tyr Thr Gln Lys Ser Leu Ser Leu Ser
    450                 455                 460

Pro Gly Lys
465

<210> SEQ ID NO 115
<211> LENGTH: 4175
<212> TYPE: DNA
<213> ORGANISM: Artificial Sequence
<220> FEATURE:
<223> OTHER INFORMATION: pFUSE2ss-DE27-V -CLIg-hk

<400> SEQUENCE: 115

| | | | | | | |
|---|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gcctttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccgttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaacatgta | caggatgcaa | ctcctgtctt | gcattgcact | aagtcttgca | 600 |
| cttgtcacga | attcagacat | ccagatgacc | cagtctccat | cctccctgtc | tgcatctgta | 660 |
| ggggacagag | tcaccatcac | ttgtcgggca | agtcagggca | tcagaaatta | cttagcctgg | 720 |
| tatcagcaaa | aaccagggaa | agcccctaag | ctcctgatct | atgctgcatc | cactttgcaa | 780 |
| tcaggggtcc | catctcggtt | cagtggcagt | ggatctggga | cagatttcac | tctcaccatc | 840 |
| agcagcctac | agcctgaaga | tgttgcaact | tattactgtc | aaaggtataa | ccgtgcaccg | 900 |
| tatactttg | gccaggggac | caaggtggaa | atcaaacgta | cggtggctgc | accatctgtc | 960 |
| ttcatcttcc | cgccatctga | tgagcagttg | aaatctggaa | ctgcctctgt | tgtgtgcctg | 1020 |
| ctgaataact | tctatcccag | agaggccaaa | gtacagtgga | aggtggataa | cgccctccaa | 1080 |
| tcgggtaact | cccaggagag | tgtcacagag | caggacagca | aggacagcac | ctacagcctc | 1140 |
| agcagcaccc | tgacgctgag | caaagcagac | tacgagaaac | acaaagtcta | cgcctgcgaa | 1200 |
| gtcacccatc | agggcctgag | ctcgcccgtc | acaaagagct | tcaacagggg | agagtgttag | 1260 |
| agggagctag | ctcgacatga | taagatacat | tgatgagttt | ggacaaacca | caactagaat | 1320 |
| gcagtgaaaa | aaatgcttta | tttgtgaaat | ttgtgatgct | attgctttat | ttgtaaatt | 1380 |
| tgtgatgcta | ttgctttatt | tgtaaccatt | ataagctgca | ataaacaagt | taacaacaac | 1440 |
| aattgcattc | attttatgtt | tcaggttcag | ggggaggtgt | gggaggtttt | ttaaagcaag | 1500 |
| taaaacctct | acaaatgtgg | tatggaatta | attctaaaat | acagcatagc | aaaactttaa | 1560 |
| cctccaaatc | aagcctctac | ttgaatcctt | ttctgaggga | tgaataaggc | ataggcatca | 1620 |
| ggggctgttg | ccaatgtgca | ttagctgttt | gcagcctcac | cttctttcat | ggagtttaag | 1680 |
| atatagtgta | ttttcccaag | gtttgaacta | gctcttcatt | tctttatgtt | ttaaatgcac | 1740 |
| tgacctccca | cattcccttt | ttagtaaaat | attcagaaat | aatttaaata | catcattgca | 1800 |
| atgaaaataa | atgttttta | ttaggcagaa | tccagatgct | caaggcccctt | cataatatcc | 1860 |

```
cccagtttag tagttggact tagggaacaa aggaaccttt aatagaaatt ggacagcaag     1920
aaagcgagct tctagcttta gttcctggtg tacttgaggg ggatgagttc ctcaatggtg     1980
gttttgacca gcttgccatt catctcaatg agcacaaagc agtcaggagc atagtcagag     2040
atgagctctc tgcacatgcc acaggggctg accaccctga tggatctgtc cacctcatca     2100
gagtaggggt gcctgacagc acaatggtg tcaaagtcct tctgcccgtt gctcacagca      2160
gacccaatgg caatggcttc agcacagaca gtgaccctgc caatgtaggc ctcaatgtgg     2220
acagcagaga tgatctcccc agtcttggtc ctgatggccg ccccgacatg gtgcttgttg     2280
tcctcataga gcatggtgat cttctcagtg gcgacctcca ccagctccag atcctgctga     2340
gagatgttga aggtcttcat gatggctcct cctgtcagga gaggaaagag aagaaggtta     2400
gtacaattgc tatagtgagt tgtattatac tatgcttatg attaattgtc aaactagggc     2460
tgcagggttc atagtgccac ttttcctgca ctgcccatc tcctgccac cctttcccag       2520
gcatagacag tcagtgactt accaaactca caggagggag aaggcagaag cttgagacag     2580
acccgcggga ccgccgaact gcgaggggac gtggctaggg cggcttcttt tatggtgcgc     2640
cggccctcgg aggcagggcg ctcggggagg cctagcggcc aatctgcggt ggcaggaggc     2700
ggggccgaag gccgtgcctg accaatccgg agcacatagg agtctcagcc ccccgccccca    2760
aagcaagggg aagtcacgcg cctgtagcgc cagcgtgttg tgaaatgggg cttgggggg      2820
gttggggccc tgactagtca aaacaaactc ccattgacgt caatggggtg gagacttgga    2880
aatccccgtg agtcaaaccg ctatccacgc ccattgatgt actgccaaaa ccgcatcatc     2940
atggtaaatag cgatgactaa tacgtagatg tactgccaag taggaaagtc ccataaggtc    3000
atgtactggg cataatgcca ggcgggccat ttaccgtcat tgacgtcaat aggggggcgta    3060
cttggcatat gatacacttg atgtactgcc aagtgggcag tttaccgtaa atactccacc    3120
cattgacgtc aatggaaagt ccctattggc gttactatgg aacatacgt cattattgac     3180
gtcaatgggc gggggtcgtt gggcggtcag ccaggcgggc catttaccgt aagttatgta    3240
acgcctgcag gttaattaag aacatgtgag caaaaggcca gcaaaggcc aggaaccgta     3300
aaaaggccgc gttgctggcg ttttttccata ggctccgccc ccctgacgag catcacaaaa   3360
atcgacgctc aagtcagagg tggcgaaacc cgacaggact ataaagatac caggcgtttc    3420
ccctggaag ctccctcgtg cgctctcctg ttccgaccct gccgcttacc ggatacctgt     3480
ccgcctttct cccttcggga agcgtggcgc tttctcatag ctcacgctgt aggtatctca    3540
gttcggtgta ggtcgttcgc tccaagctgg gctgtgtgca cgaacccccc gttcagcccg    3600
accgctgcgc cttatccggt aactatcgtc ttgagtccaa cccggtaaga cacgacttat    3660
cgccactggc agcagccact ggtaacagga ttagcagagc gaggtatgta ggcggtgcta    3720
cagagttctt gaagtggtgg cctaactacg gctacactag aagaacagta tttggtatct    3780
gcgctctgct gaagccagtt accttcggaa aaagagttgg tagctcttga tccggcaaac    3840
aaaccaccgc tggtagcggt ggtttttttg tttgcaagca gcagattacg cgcagaaaaa    3900
aaggatctca agaagatcct ttgatctttt ctacgggtc tgacgctcag tggaacgaaa     3960
actcacgtta agggatttg gtcatggcta gttaattaac atttaaatca gcggccgcaa    4020
taaaatatct ttattttcat tacatctgtg tgttggtttt ttgtgtgaat cgtaactaac    4080
atacgctctc catcaaaaca aaacgaaaca aaacaaacta gcaaaatagg ctgtccccag    4140
tgcaagtgca ggtgccagaa catttctcta tcgaa                               4175
```

<210> SEQ ID NO 116
<211> LENGTH: 4776
<212> TYPE: DNA
<213> ORGANISM: Artificial Sequence
<220> FEATURE:
<223> OTHER INFORMATION: pPUSEss-DE27-V 1-CHIg-hG1-Mth-1

<400> SEQUENCE: 116

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | cgggtgccta | gagaaggtgg | cgcggggtaa | 120 |
| actgggaaag | tgatgtcgtg | tactggctcc | gcctttttcc | cgagggtggg | ggagaaccgt | 180 |
| atataagtgc | agtagtcgcc | gtgaacgttc | tttttcgcaa | cgggtttgcc | gccagaacac | 240 |
| agctgaagct | cgaggggct | cgcatctctc | cttcacgcgc | ccgccgccct | acctgaggcc | 300 |
| gccatccacg | ccggttgagt | cgcgttctgc | cgcctcccgc | ctgtggtgcc | tcctgaactg | 360 |
| cgtccgccgt | ctaggtaagt | ttaaagctca | ggtcgagacc | gggcctttgt | ccggcgctcc | 420 |
| cttggagcct | acctagactc | agccggctct | ccacgctttg | cctgaccctg | cttgctcaac | 480 |
| tctacgtctt | tgtttcgttt | tctgttctgc | gccgttacag | atccaagctg | tgaccggcgc | 540 |
| ctacctgaga | tcaccggcga | aggagggcca | ccatgtacag | gatgcaactc | ctgtcttgca | 600 |
| ttgcactaag | tcttgcactt | gtcacgaatt | cggaggtgca | gctggtggag | tctgggggag | 660 |
| gcttggtaca | gcccggcagg | tccctgagac | tctcctgtgc | ggcctctgga | ttcacctttg | 720 |
| atgattatgc | catgcactgg | gtccggcaag | ctccagggaa | gggcctggaa | tgggtctcag | 780 |
| ctatcacttg | gaatagtggt | cacatagact | atgcggactc | tgtggagggc | cgattcacca | 840 |
| tctccagaga | caacgccaag | aactccctgt | atctgcaaat | gaacagtctg | agagctgagg | 900 |
| atacggccgt | atattactgt | gcgaaagtct | cgtaccttag | caccgcgtcc | tcccttgact | 960 |
| attggggcca | aggtaccctg | gtcaccgtct | cgagtgctag | caccaagggc | ccatcggtct | 1020 |
| tcccctggc | accctcctcc | aagagcacct | ctggggcac | agcggccctg | ggctgcctgg | 1080 |
| tcaaggacta | cttccccgaa | ccggtgacgg | tgtcgtggaa | ctcaggcgcc | ctgaccagcg | 1140 |
| gcgtgcacac | cttcccggct | gtcctacagt | cctcaggact | ctactccctc | agcagcgtgg | 1200 |
| tgaccgtgcc | ctccagcagc | ttgggcaccc | agacctacat | ctgcaacgtg | aatcacaagc | 1260 |
| ccagcaacac | caaggtggac | aagaaagttg | agcccaaatc | ttgtgacaaa | actcacacat | 1320 |
| gcgtatccgg | tgacaccatt | gtaatgacta | gtggcgggcc | ccgcactgtg | ctgaactgg | 1380 |
| agggcaaacc | gttcaccgca | ctgattcgcg | gctctggcta | cccatgcccc | tcaggtttct | 1440 |
| tccgcacctg | tgaacgtgac | gtatatgatc | tgcgtacacg | tgagggtcat | tgcttacgtt | 1500 |
| tgacccatga | tcaccgtgtt | ctggtgatgg | atggtggcct | ggaatggcgt | gccgcgggtg | 1560 |
| aactggaacg | cggcgaccgc | ctggtgatgg | atgatgcagc | tggcgagttt | ccggcactgg | 1620 |
| caaccttccg | tggcctgcgt | ggcgctggcc | gccaggatgt | tatgacgct | actgtttacg | 1680 |
| gtgctagcgc | attcactgct | aatggcttca | ttgtacacgc | atgtggcgag | cagcccggga | 1740 |
| ccggtctgaa | ctcaggcctc | acgacaaatc | ctggtgtatc | cgcttggcag | gtcaacacag | 1800 |
| cttatactgc | gggacaattg | gtcacatata | acggcaagac | gtataaatgt | ttgcagcccc | 1860 |
| acacctcctt | ggcaggatgg | gaaccatcca | acgttcctgc | cttgtggcag | cttcaatgag | 1920 |
| tcctagctgg | ccagacatga | taagatacat | tgatgagttt | ggacaaacca | caactagaat | 1980 |
| gcagtgaaaa | aaatgcttta | tttgtgaaat | ttgtgatgct | attgctttat | ttgtaaccat | 2040 |
| tataagctgc | aataaacaag | ttaacaacaa | caattgcatt | cattttatgt | ttcaggttca | 2100 |

```
gggggaggtg tgggaggttt tttaaagcaa gtaaaacctc tacaaatgtg gtatggaatt    2160
aattctaaaa tacagcatag caaaacttta acctccaaat caagcctcta cttgaatcct    2220
tttctgaggg atgaataagg cataggcatc aggggctgtt gccaatgtgc attagctgtt    2280
tgcagcctca ccttctttca tggagtttaa gatatagtgt atttttcccaa ggtttgaact    2340 agctcttcat ttctttatgt tttaaatgca ctgacctccc acattccctt tttagtaaaa    2400
tattcagaaa taatttaaat acatcattgc aatgaaaata aatgtttttt attaggcaga    2460
atccagatgc tcaaggccct tcataatatc ccccagttta gtagttggac ttagggaaca    2520
aaggaacctt taatagaaat tggacagcaa gaaagcgagc ttctagctta tcctcagtcc    2580
tgctcctctg ccacaaagtg cacgcagttg ccggccgggt cgcgcagggc gaactcccgc    2640
ccccacggct gctcgccgat ctcggtcatg gccggcccgg aggcgtcccg gaagttcgtg    2700
gacacgacct ccgaccactc ggcgtacagc tcgtccaggc cgcgcaccca cacccaggcc    2760
agggtgttgt ccggcaccac ctggtcctgg accgcgctga tgaacagggt cacgtcgtcc    2820
cggaccacac cggcgaagtc gtcctccacg aagtcccggg agaacccgag ccggtcggtc    2880
cagaactcga ccgctccggc gacgtcgcgc gcggtgagca ccggaacggc actggtcaac    2940
ttggccatga tggctcctcc tgtcaggaga ggaaagagaa gaaggttagt acaattgcta    3000
tagtgagttg tattatacta tgcagatata ctatgccaat gattaattgt caaactaggg    3060
ctgcagggtt catagtgcca cttttcctgc actgccccat ctcctgccca cccttttccca   3120 ggcatagaca gtcagtgact taccaaactc acaggaggga gaaggcagaa gcttgagaca    3180
gacccgcggg accgccgaac tgcgagggga cgtggctagg gcggcttctt ttatggtgcg    3240
ccggccctcg gaggcagggc gctcggggag gcctagcggc caatctgcgg tggcaggagg    3300
cggggccgaa ggccgtgcct gaccaatccg gagcacatag gagtctcagc cccccgcccc    3360
aaagcaaggg gaagtcacgc gcctgtagcg ccagcgtgtt gtgaaatggg ggcttggggg    3420
ggttggggcc ctgactagtc aaaacaaact cccattgacg tcaatggggt ggagacttgg    3480
aaatccccgt gagtcaaacc gctatccacg cccattgatg tactgccaaa accgcatcat    3540
catggtaata gcgatgacta atacgtagat gtactgccaa gtaggaaagt cccataaggt    3600
catgtactgg gcataatgcc aggcgggcca tttaccgtca ttgacgtcaa tagggggcgt    3660
acttggcata tgatacactt gatgtactgc caagtgggca gtttaccgta aatactccac    3720
ccattgacgt caatggaaag tccctattgg cgttactatg ggaacatacg tcattattga    3780
cgtcaatggg cggggtcgt tgggcggtca gccaggcggg ccatttaccg taagttatgt    3840
aacgcctgca ggttaattaa gaacatgtga gcaaaaggcc agcaaaaggc caggaaccgt    3900
aaaaaggccg cgttgctggc gttttttccat aggctccgcc cccctgacga gcatcacaaa    3960
aatcgacgct caagtcagag gtggcgaaac ccgacaggac tataaagata ccaggcgttt    4020 cccccctggaa gctccctcgt gcgctctcct gttccgaccc tgccgcttac cggatacctg    4080
tccgcctttc tcccttcggg aagcgtggcg ctttctcata gctcacgctg taggtatctc    4140
agttcggtgt aggtcgttcg ctccaagctg ggctgtgtgc acgaaccccc cgttcagccc    4200
gaccgctgcg ccttatccgg taactatcgt cttgagtcca acccggtaag acacgactta    4260
tcgccactgg cagcagccac tggtaacagg attagcagag cgaggtatgt aggcggtgct    4320
acagagttct tgaagtggtg gcctaactac ggctacacta agaacagt atttggtatc     4380 tgcgctctgc tgaagccagt taccttcgga aaaagagttg gtagctcttg atccggcaaa    4440
caaaccaccg ctggtagcgg tggtttttttt gtttgcaagc agcagattac gcgcagaaaa    4500
```

| | |
|---|---:|
| aaaggatctc aagaagatcc tttgatctttt tctacggggt ctgacgctca gtggaacgaa | 4560 |
| aactcacgtt aagggatttt ggtcatggct agtaattaa catttaaatc agcggccgca | 4620 |
| ataaaatatc tttatttttca ttacatctgt gtgttggttt tttgtgtgaa tcgtaactaa | 4680 |
| catacgctct ccatcaaaac aaaacgaaac aaaacaaact agcaaaatag gctgtcccca | 4740 |
| gtgcaagtgc aggtgccaga acatttctct atcgaa | 4776 |

<210> SEQ ID NO 117
<211> LENGTH: 4779
<212> TYPE: DNA
<213> ORGANISM: Artificial Sequence
<220> FEATURE:
<223> OTHER INFORMATION: pFUSEss-DE27-V 1-CHIg-hG1-Mth-2

<400> SEQUENCE: 117

| | |
|---|---:|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc tttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggcga aggagggcca ccatgtacag gatgcaactc ctgtcttgca | 600 |
| ttgcactaag tcttgcactt gtcacgaatt cggaggtgca gctggtggag tctgggggag | 660 |
| gcttggtaca gccggcagg tccctgagac tctcctgtgc ggcctctgga ttcacctttg | 720 |
| atgattatgc catgcactgg gtccggcaag ctccagggaa gggcctggaa tgggtctcag | 780 |
| ctatcacttg gaatagtggt cacatagact atgcggactc tgtggagggc cgattcacca | 840 |
| tctccagaga caacgccaag aactccctgt atctgcaaat gaacagtctg agagctgagg | 900 |
| atacggccgt atattactgt gcgaaagtct cgtaccttag caccgcgtcc tcccttgact | 960 |
| attggggcca aggtaccctg gtcaccgtct cgagtgctag caccaagggc ccatcggtct | 1020 |
| tccccctggc accctcctcc aagagcacct ctgggggcac agcggccctg ggctgcctgg | 1080 |
| tcaaggacta cttccccgaa ccggtgacgg tgtcgtggaa ctcaggcgcc ctgaccagcg | 1140 |
| gcgtgcacac cttcccggct gtcctacagt cctcaggact ctactccctc agcagcgtgg | 1200 |
| tgaccgtgcc ctcagcagc ttgggcaccc agacctacat ctgcaacgtg aatcacaagc | 1260 |
| ccagcaacac caaggtggac aagaaagttg agcccaaatc ttgtgacaaa actcacacag | 1320 |
| ggtgcgtatc cggtgacacc attgtaatga ctagtggcgg gccccgcact gtggctgaac | 1380 |
| tggagggcaa accgttcacc gcactgattc gcggctctgg ctacccatgc ccctcaggtt | 1440 |
| tcttccgcac ctgtgaacgt gacgtatatg atctgcgtac acgtgagggt cattgcttac | 1500 |
| gtttgaccca tgatcaccgt gttctggtga tggtggtgg cctggaatgg cgtgccgcgg | 1560 |
| gtgaactgga acgcggcgac cgcctggtga tgatgatgc agctggcgag tttccggcac | 1620 |
| tgcaaccttt ccgtggcctg cgtggcgctg ccgccagga tgtttatgac gctactgttt | 1680 |
| acggtgctag cgcattcact gctaatggct tcattgtaca cgcatgtggc gagcagcccg | 1740 |

```
ggaccggtct gaactcaggc ctcacgacaa atcctggtgt atccgcttgg caggtcaaca    1800
cagcttatac tgcgggacaa ttggtcacat ataacggcaa gacgtataaa tgtttgcagc    1860
cccacacctc cttggcagga tgggaaccat ccaacgttcc tgccttgtgg cagcttcaat    1920
gagtcctagc tggccagaca tgataagata cattgatgag tttggacaaa ccacaactag    1980
aatgcagtga aaaaaatgct ttatttgtga aatttgtgat gctattgctt tatttgtaac    2040
cattataagc tgcaataaac aagttaacaa caacaattgc attcatttta tgtttcaggt    2100
tcaggggag gtgtgggagg ttttttaaag caagtaaaac ctctacaaat gtggtatgga    2160
attaattcta aaatacagca tagcaaaact ttaacctcca aatcaagcct ctacttgaat    2220
cctttttctga gggatgaata aggcataggc atcaggggct gttgccaatg tgcattagct    2280
gtttgcagcc tcaccttctt tcatggagtt taagatatag tgtattttcc caaggtttga    2340
actagctctt catttctttta tgttttaaat gcactgacct cccacattcc cttttagta    2400
aaatattcag aaataattta aatacatcat tgcaatgaaa ataaatgttt tttattaggc    2460
agaatccaga tgctcaaggc ccttcataat atccccagt ttagtagttg gacttaggga    2520
acaaaggaac ctttaataga aattggacag caagaaagcg agcttctagc ttatcctcag    2580
tcctgctcct ctgccacaaa gtgcacgcag ttgccggccg ggtcgcgcag ggcgaactcc    2640
cgcccccacg gctgctcgcc gatctcggtc atggccggcc cggaggcgtc ccggaagttc    2700
gtggacacga cctccgacca ctcggcgtac agctcgtcca ggccgcgcac ccacacccag    2760
gccagggtgt tgtccggcac cacctggtcc tggaccgcgc tgatgaacag ggtcacgtcg    2820
tcccggacca caccggcgaa gtcgtcctcc acgaagtccc gggagaaccc gagccggtcg    2880
gtccagaact cgaccgctcc ggcgacgtcg cgcgcggtga gcaccggaac ggcactggtc    2940
aacttggcca tgatggctcc tcctgtcagg agaggaaaga gaagaaggtt agtacaattg    3000
ctatagtgag ttgtattata ctatgcagat atactatgcc aatgattaat tgtcaaacta    3060
gggctgcagg gttcatagtg ccacttttcc tgcactgccc catctcctgc ccacccttc    3120
ccaggcatag acagtcagtg acttaccaaa ctcacaggag ggagaaggca gaagcttgag    3180
acagacccgc gggaccgccg aactgcgagg ggacgtggct agggcggctt cttttatggt    3240
gcgccggccc tcggaggcag ggcgctcggg gaggcctagc ggccaatctg cggtggcagg    3300
aggcggggcc gaaggccgtg cctgaccaat ccggagcaca taggagtctc agccccccgc    3360
cccaaagcaa ggggaagtca cgcgcctgta gcgccagcgt gttgtgaaat gggggcttgg    3420
gggggttggg gccctgacta gtcaaaacaa actcccattg acgtcaatgg ggtggagact    3480
tggaaatccc cgtgagtcaa accgctatcc acgcccattg atgtactgcc aaaaccgcat    3540
catcatggta atagcgatga ctaatacgta gatgtactgc caagtaggaa agtcccataa    3600
ggtcatgtac tgggcataat gccaggcggg ccatttaccg tcattgacgt caataggggg    3660
cgtacttggc atatgataca cttgatgtac tgccaagtgg gcagtttacc gtaaatactc    3720
cacccattga cgtcaatgga aagtccctat tggcgttact atgggaacat acgtcattat    3780
tgacgtcaat gggcgggggt cgttgggcgg tcagccaggc gggccattta ccgtaagtta    3840
tgtaacgcct gcaggttaat taagaacatg tgagcaaaag ccagcaaaa ggccaggaac    3900
cgtaaaaagg ccgcgttgct ggcgtttttc cataggctcc gcccccctga cgagcatcac    3960
aaaaatcgac gctcaagtca gaggtggcga acccgacag gactataaag ataccaggcg    4020
tttccccctg gaagctccct cgtgcgctct cctgttccga ccctgccgct taccggatac    4080
ctgtccgcct ttctcccttc gggaagcgtg gcgctttctc atagctcacg ctgtaggtat    4140
```

```
ctcagttcgg tgtaggtcgt tcgctccaag ctgggctgtg tgcacgaacc ccccgttcag    4200
cccgaccgct gcgccttatc cggtaactat cgtcttgagt ccaacccggt aagcacgac    4260 ttatcgccac tggcagcagc cactggtaac aggattagca gagcgaggta tgtaggcggt    4320
gctacagagt tcttgaagtg gtggcctaac tacggctaca ctagaagaac agtatttggt    4380
atctgcgctc tgctgaagcc agttaccttc ggaaaaagag ttggtagctc ttgatccggc    4440
aaacaaacca ccgctggtag cggtggtttt tttgtttgca agcagcagat tacgcgcaga    4500
aaaaaaggat ctcaagaaga tcctttgatc ttttctacgg ggtctgacgc tcagtggaac    4560
gaaaactcac gttaagggat tttggtcatg ctagttaat taacatttaa atcagcggcc    4620
gcaataaaat atctttattt tcattacatc tgtgtgttgg ttttttgtgt gaatcgtaac    4680
taacatacgc tctccatcaa aacaaaacga aacaaaacaa actagcaaaa taggctgtcc    4740
ccagtgcaag tgcaggtgcc agaacatttc tctatcgaa                          4779
```

<210> SEQ ID NO 118
<211> LENGTH: 234
<212> TYPE: PRT
<213> ORGANISM: Artificial Sequence
<220> FEATURE:
<223> OTHER INFORMATION: pre-kappa light chain of adalimumab

<400> SEQUENCE: 118

```
Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Arg Asn Tyr Leu Ala Trp Tyr Gln Gln Lys Pro Gly Lys Ala Pro
    50                  55                  60

Lys Leu Leu Ile Tyr Ala Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Arg Tyr Asn
            100                 105                 110

Arg Ala Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 119
<211> LENGTH: 214
<212> TYPE: PRT
<213> ORGANISM: Artificial Sequence
<220> FEATURE:
<223> OTHER INFORMATION: mature kappa light chain of adalimumab

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 120
<211> LENGTH: 448
<212> TYPE: PRT
<213> ORGANISM: Artificial Sequence
<220> FEATURE:
<223> OTHER INFORMATION: pre-heavy chain-intein chimeric polypeptide

<400> SEQUENCE: 120

Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Arg Ser Leu Arg Leu Ser Cys Ala Ala Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Ala Ile Thr Trp Asn Ser Gly His Ile Asp Tyr
65                  70                  75                  80

Ala Asp Ser Val Glu Gly Arg Phe Thr Ile Ser Arg Asp Asn Ala Lys
                85                  90                  95
```

```
Asn Ser Leu Tyr Leu Gln Met Asn Ser Leu Arg Ala Glu Asp Thr Ala
            100                 105                 110

Val Tyr Tyr Cys Ala Lys Val Ser Tyr Leu Ser Thr Ala Ser Ser Leu
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Val Ser Gly Asp Thr Ile
                245                 250                 255

Val Met Thr Ser Gly Gly Pro Arg Thr Val Ala Glu Leu Glu Gly Lys
            260                 265                 270

Pro Phe Thr Ala Leu Ile Arg Gly Ser Gly Tyr Pro Cys Pro Ser Gly
        275                 280                 285

Phe Phe Arg Thr Cys Glu Arg Asp Val Tyr Leu Arg Thr Arg Glu
    290                 295                 300

Gly His Cys Leu Arg Leu Thr His Asp His Arg Val Leu Val Met Asp
305                 310                 315                 320

Gly Gly Leu Glu Trp Arg Ala Ala Gly Glu Leu Arg Gly Asp Arg
                325                 330                 335

Leu Val Met Asp Asp Ala Ala Gly Glu Phe Pro Ala Leu Ala Thr Phe
            340                 345                 350

Arg Gly Leu Arg Gly Ala Gly Arg Gln Asp Val Tyr Asp Ala Thr Val
        355                 360                 365

Tyr Gly Ala Ser Ala Phe Thr Ala Asn Gly Phe Ile Val His Ala Cys
    370                 375                 380

Gly Glu Gln Pro Gly Thr Gly Leu Asn Ser Gly Leu Thr Thr Asn Pro
385                 390                 395                 400

Gly Val Ser Ala Trp Gln Val Asn Thr Ala Tyr Thr Ala Gly Gln Leu
                405                 410                 415

Val Thr Tyr Asn Gly Lys Thr Tyr Lys Cys Leu Gln Pro His Thr Ser
            420                 425                 430

Leu Ala Gly Trp Glu Pro Ser Asn Val Pro Ala Leu Trp Gln Leu Gln
        435                 440                 445

<210> SEQ ID NO 121
<211> LENGTH: 428
<212> TYPE: PRT
<213> ORGANISM: Artificial Sequence
<220> FEATURE:
<223> OTHER INFORMATION: mature heavy chain-intein fusion protein

<400> SEQUENCE: 121

Glu Val Gln Leu Val Glu Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Val Ser Gly Asp Thr Ile Val Met Thr Ser
225                 230                 235                 240

Gly Gly Pro Arg Thr Val Ala Glu Leu Glu Gly Lys Pro Phe Thr Ala
                245                 250                 255

Leu Ile Arg Gly Ser Gly Tyr Pro Cys Pro Ser Gly Phe Phe Arg Thr
            260                 265                 270

Cys Glu Arg Asp Val Tyr Asp Leu Arg Thr Arg Glu Gly His Cys Leu
        275                 280                 285

Arg Leu Thr His Asp His Arg Val Leu Val Met Asp Gly Gly Leu Glu
    290                 295                 300

Trp Arg Ala Ala Gly Glu Leu Glu Arg Gly Asp Arg Leu Val Met Asp
305                 310                 315                 320

Asp Ala Ala Gly Glu Phe Pro Ala Leu Ala Thr Phe Arg Gly Leu Arg
                325                 330                 335

Gly Ala Gly Arg Gln Asp Val Tyr Asp Ala Thr Val Tyr Gly Ala Ser
            340                 345                 350

Ala Phe Thr Ala Asn Gly Phe Ile Val His Ala Cys Gly Glu Gln Pro
        355                 360                 365

Gly Thr Gly Leu Asn Ser Gly Leu Thr Thr Asn Pro Gly Val Ser Ala
    370                 375                 380

Trp Gln Val Asn Thr Ala Tyr Thr Ala Gly Gln Leu Val Thr Tyr Asn
385                 390                 395                 400

Gly Lys Thr Tyr Lys Cys Leu Gln Pro His Thr Ser Leu Ala Gly Trp
                405                 410                 415

Glu Pro Ser Asn Val Pro Ala Leu Trp Gln Leu Gln
            420                 425
```

<210> SEQ ID NO 122
<211> LENGTH: 449
<212> TYPE: PRT
<213> ORGANISM: Artificial Sequence
<220> FEATURE:
<223> OTHER INFORMATION: pre-heavy chain-intein chimeric polypeptide

<400> SEQUENCE: 122

```
Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Pro Gly Arg Ser Leu Arg Leu Ser Cys Ala Ala Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Ala Ile Thr Trp Asn Ser Gly His Ile Asp Tyr
65                  70                  75                  80

Ala Asp Ser Val Glu Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Lys Val Ser Tyr Leu Ser Thr Ala Ser Ser Leu
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Gly Cys Val Ser Gly Asp Thr
                245                 250                 255

Ile Val Met Thr Ser Gly Gly Pro Arg Thr Val Ala Glu Leu Glu Gly
            260                 265                 270

Lys Pro Phe Thr Ala Leu Ile Arg Gly Ser Gly Tyr Pro Cys Pro Ser
        275                 280                 285

Gly Phe Phe Arg Thr Cys Glu Arg Asp Val Tyr Asp Leu Arg Thr Arg
    290                 295                 300

Glu Gly His Cys Leu Arg Leu Thr His Asp His Arg Val Leu Val Met
305                 310                 315                 320

Asp Gly Gly Leu Glu Trp Arg Ala Ala Gly Glu Leu Glu Arg Gly Asp
                325                 330                 335

Arg Leu Val Met Asp Asp Ala Ala Gly Glu Phe Pro Ala Leu Ala Thr
            340                 345                 350

Phe Arg Gly Leu Arg Gly Ala Gly Arg Gln Asp Val Tyr Asp Ala Thr
        355                 360                 365

Val Tyr Gly Ala Ser Ala Phe Thr Ala Asn Gly Phe Ile Val His Ala
```

```
                370             375             380
Cys Gly Glu Gln Pro Gly Thr Gly Leu Asn Ser Gly Leu Thr Thr Asn
385             390             395             400

Pro Gly Val Ser Ala Trp Gln Val Asn Thr Ala Tyr Thr Ala Gly Gln
            405             410             415

Leu Val Thr Tyr Asn Gly Lys Thr Tyr Lys Cys Leu Gln Pro His Thr
            420             425             430

Ser Leu Ala Gly Trp Glu Pro Ser Asn Val Pro Ala Leu Trp Gln Leu
            435             440             445

Gln

<210> SEQ ID NO 123
<211> LENGTH: 429
<212> TYPE: PRT
<213> ORGANISM: Artificial Sequence
<220> FEATURE:
<223> OTHER INFORMATION: mature heavy chain-intein fusion protein

<400> SEQUENCE: 123

Glu Val Gln Leu Val Glu Ser Gly Gly Gly Leu Val Gln Pro Gly Arg
1               5               10              15

Ser Leu Arg Leu Ser Cys Ala Ala Ser Gly Phe Thr Phe Asp Asp Tyr
            20              25              30

Ala Met His Trp Val Arg Gln Ala Pro Gly Lys Gly Leu Glu Trp Val
        35              40              45

Ser Ala Ile Thr Trp Asn Ser Gly His Ile Asp Tyr Ala Asp Ser Val
    50              55              60

Glu Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Val Tyr Tyr Cys
            85              90              95

Ala Lys Val Ser Tyr Leu Ser Thr Ala Ser Ser Leu Asp Tyr Trp Gly
        100             105             110

Gln Gly Thr Leu Val Thr Val Ser Ser Ala Ser Thr Lys Gly Pro Ser
    115             120             125

Val Phe Pro Leu Ala Pro Ser Ser Lys Ser Thr Ser Gly Gly Thr Ala
    130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
        180             185             190

Pro Ser Ser Ser Leu Gly Thr Gln Thr Tyr Ile Cys Asn Val Asn His
    195             200             205

Lys Pro Ser Asn Thr Lys Val Asp Lys Lys Val Glu Pro Lys Ser Cys
    210             215             220

Asp Lys Thr His Thr Gly Cys Val Ser Gly Asp Thr Ile Val Met Thr
225             230             235             240

Ser Gly Gly Pro Arg Thr Val Ala Glu Leu Glu Gly Lys Pro Phe Thr
            245             250             255

Ala Leu Ile Arg Gly Ser Gly Tyr Pro Cys Pro Ser Gly Phe Phe Arg
        260             265             270

Thr Cys Glu Arg Asp Val Tyr Asp Leu Arg Thr Arg Glu Gly His Cys
    275             280             285
```

```
Leu Arg Leu Thr His Asp His Arg Val Leu Val Met Asp Gly Gly Leu
        290                 295                 300

Glu Trp Arg Ala Ala Gly Glu Leu Glu Arg Gly Asp Arg Leu Val Met
305                 310                 315                 320

Asp Asp Ala Ala Gly Glu Phe Pro Ala Leu Ala Thr Phe Arg Gly Leu
                325                 330                 335

Arg Gly Ala Gly Arg Gln Asp Val Tyr Asp Ala Thr Val Tyr Gly Ala
                340                 345                 350

Ser Ala Phe Thr Ala Asn Gly Phe Ile Val His Ala Cys Gly Glu Gln
            355                 360                 365

Pro Gly Thr Gly Leu Asn Ser Gly Leu Thr Thr Asn Pro Gly Val Ser
        370                 375                 380

Ala Trp Gln Val Asn Thr Ala Tyr Thr Ala Gly Gln Leu Val Thr Tyr
385                 390                 395                 400

Asn Gly Lys Thr Tyr Lys Cys Leu Gln Pro His Thr Ser Leu Ala Gly
                405                 410                 415

Trp Glu Pro Ser Asn Val Pro Ala Leu Trp Gln Leu Gln
                420                 425

<210> SEQ ID NO 124
<211> LENGTH: 230
<212> TYPE: PRT
<213> ORGANISM: Artificial Sequence
<220> FEATURE:
<223> OTHER INFORMATION: Part of alkyne-modified adalimumab Fab-1
      protein. Modified at C-Terminus.
<220> FEATURE:
<221> NAME/KEY: SITE
<222> LOCATION: (230)..(230)
<223> OTHER INFORMATION: Xaa = cysteine-alkyne

<400> SEQUENCE: 124

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Xaa
225             230

<210> SEQ ID NO 125
<211> LENGTH: 231
<212> TYPE: PRT
<213> ORGANISM: Artificial Sequence
<220> FEATURE:
<223> OTHER INFORMATION: Part of alkyne-modified adalimumab Fab-2
      protein. Motified at C-Terminus
<220> FEATURE:
<221> NAME/KEY: SITE
<222> LOCATION: (131)..(131)
<223> OTHER INFORMATION: Xaa = cysteine-alkyne
<220> FEATURE:
<221> NAME/KEY: misc_feature
<222> LOCATION: (231)..(231)
<223> OTHER INFORMATION: Xaa can be any naturally occurring amino acid

<400> SEQUENCE: 125

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Gly Xaa
225             230

<210> SEQ ID NO 126
<211> LENGTH: 230
<212> TYPE: PRT
<213> ORGANISM: Artificial Sequence
<220> FEATURE:
```

```
<223> OTHER INFORMATION: Part of azide-modified adalimumab Fab-1
      protein. Modified C-Terminus
<220> FEATURE:
<221> NAME/KEY: SITE
<222> LOCATION: (230)..(230)
<223> OTHER INFORMATION: Xaa = cysteine-azide

<400> SEQUENCE: 126
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Xaa
225                 230

```
<210> SEQ ID NO 127
<211> LENGTH: 231
<212> TYPE: PRT
<213> ORGANISM: Artificial Sequence
<220> FEATURE:
<223> OTHER INFORMATION: Part of azide-modified adalimumab Fab-2
      protein. Modified C-Terminus
<220> FEATURE:
<221> NAME/KEY: SITE
<222> LOCATION: (231)..(231)
<223> OTHER INFORMATION: Xaa = cysteine-azide

<400> SEQUENCE: 127
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val

```
                50                  55                  60
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
                210                 215                 220

Asp Lys Thr His Thr Gly Xaa
225                 230

<210> SEQ ID NO 128
<211> LENGTH: 214
<212> TYPE: PRT
<213> ORGANISM: Homo sapiens

<400> SEQUENCE: 128

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
                 35                  40                  45

Tyr Ser Ala Ser Phe Leu Tyr Ser Gly Val Pro Ser Arg Phe Ser Gly
             50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 129
<211> LENGTH: 450
<212> TYPE: PRT
<213> ORGANISM: Homo sapiens

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 130
<211> LENGTH: 215
<212> TYPE: PRT
<213> ORGANISM: Artificial Sequence
<220> FEATURE:
<223> OTHER INFORMATION: Trastuzumab light chain having the N-terminal
      sequence C

<400> SEQUENCE: 130

Cys Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 131
<211> LENGTH: 238
<212> TYPE: PRT
```

<213> ORGANISM: Artificial Sequence
<220> FEATURE:
<223> OTHER INFORMATION: pre-light chimeric polypeptide having SHH signal peptide

<400> SEQUENCE: 131

Met Leu Leu Leu Ala Arg Cys Leu Leu Leu Val Leu Val Ser Ser Leu
1               5                   10                  15

Leu Val Cys Ser Gly Leu Ala Cys Asp Ile Gln Met Thr Gln Ser Pro
            20                  25                  30

Ser Ser Leu Ser Ala Ser Val Gly Asp Arg Val Thr Ile Thr Cys Arg
        35                  40                  45

Ala Ser Gln Asp Val Asn Thr Ala Val Ala Trp Tyr Gln Gln Lys Pro
    50                  55                  60

Gly Lys Ala Pro Lys Leu Leu Ile Tyr Ser Ala Ser Phe Leu Tyr Ser
65                  70                  75                  80

Gly Val Pro Ser Arg Phe Ser Gly Ser Arg Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln His Tyr Thr Thr Pro Pro Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 132
<211> LENGTH: 238
<212> TYPE: PRT
<213> ORGANISM: Artificial Sequence
<220> FEATURE:
<223> OTHER INFORMATION: pre-light chimeric polypeptide having IFN signal peptide

<400> SEQUENCE: 132

Met Ala Leu Thr Phe Ala Leu Leu Val Ala Leu Leu Val Leu Ser Cys
1               5                   10                  15

Lys Ser Ser Cys Ser Val Gly Cys Asp Ile Gln Met Thr Gln Ser Pro
            20                  25                  30

Ser Ser Leu Ser Ala Ser Val Gly Asp Arg Val Thr Ile Thr Cys Arg
        35                  40                  45

Ala Ser Gln Asp Val Asn Thr Ala Val Ala Trp Tyr Gln Gln Lys Pro
    50                  55                  60

Gly Lys Ala Pro Lys Leu Leu Ile Tyr Ser Ala Ser Phe Leu Tyr Ser
65                  70                  75                  80

Gly Val Pro Ser Arg Phe Ser Gly Ser Arg Ser Gly Thr Asp Phe Thr

```
                    85                  90                  95
Leu Thr Ile Ser Ser Leu Gln Pro Glu Asp Phe Ala Thr Tyr Tyr Cys
                100                 105                 110

Gln Gln His Tyr Thr Thr Pro Pro Thr Phe Gly Gln Gly Thr Lys Val
                115                 120                 125

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 133
<211> LENGTH: 232
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 133

Met Leu Ala Ala Thr Val Leu Thr Leu Ala Leu Leu Gly Asn Ala His
1               5                   10                  15

Ala Cys Asp Ile Gln Met Thr Gln Ser Pro Ser Ser Leu Ser Ala Ser
            20                  25                  30

Val Gly Asp Arg Val Thr Ile Thr Cys Arg Ala Ser Gln Asp Val Asn
        35                  40                  45

Thr Ala Val Ala Trp Tyr Gln Gln Lys Pro Gly Lys Ala Pro Lys Leu
    50                  55                  60

Leu Ile Tyr Ser Ala Ser Phe Leu Tyr Ser Gly Val Pro Ser Arg Phe
65                  70                  75                  80

Ser Gly Ser Arg Ser Gly Thr Asp Phe Thr Leu Thr Ile Ser Ser Leu
                85                  90                  95

Gln Pro Glu Asp Phe Ala Thr Tyr Tyr Cys Gln Gln His Tyr Thr Thr
            100                 105                 110

Pro Pro Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205
```

```
Val Tyr Ala Cys Glu Val Thr His Gln Gly Leu Ser Ser Pro Val Thr
    210                 215                 220
Lys Ser Phe Asn Arg Gly Glu Cys
225                 230

<210> SEQ ID NO 134
<211> LENGTH: 216
<212> TYPE: PRT
<213> ORGANISM: Artificial Sequence
<220> FEATURE:
<223> OTHER INFORMATION: Trastuzumab light chain having the N-terminal
      sequence CP

<400> SEQUENCE: 134

Cys Pro Asp Ile Gln Met Thr Gln Ser Pro Ser Ser Leu Ser Ala Ser
1               5                   10                  15
Val Gly Asp Arg Val Thr Ile Thr Cys Arg Ala Ser Gln Asp Val Asn
            20                  25                  30
Thr Ala Val Ala Trp Tyr Gln Gln Lys Pro Gly Lys Ala Pro Lys Leu
        35                  40                  45
Leu Ile Tyr Ser Ala Ser Phe Leu Tyr Ser Gly Val Pro Ser Arg Phe
    50                  55                  60
Ser Gly Ser Arg Ser Gly Thr Asp Phe Thr Leu Thr Ile Ser Ser Leu
65                  70                  75                  80
Gln Pro Glu Asp Phe Ala Thr Tyr Tyr Cys Gln Gln His Tyr Thr Thr
                85                  90                  95
Pro Pro Thr Phe Gly Gln Gly Thr Lys Val Glu Ile Lys Arg Thr Val
            100                 105                 110
Ala Ala Pro Ser Val Phe Ile Phe Pro Pro Ser Asp Glu Gln Leu Lys
        115                 120                 125
Ser Gly Thr Ala Ser Val Val Cys Leu Leu Asn Asn Phe Tyr Pro Arg
    130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
            180                 185                 190
Val Tyr Ala Cys Glu Val Thr His Gln Gly Leu Ser Ser Pro Val Thr
        195                 200                 205
Lys Ser Phe Asn Arg Gly Glu Cys
    210                 215

<210> SEQ ID NO 135
<211> LENGTH: 239
<212> TYPE: PRT
<213> ORGANISM: Artificial Sequence
<220> FEATURE:
<223> OTHER INFORMATION: pre-light chimeric polypeptide having SHH
      signal peptide

<400> SEQUENCE: 135

Met Leu Leu Leu Ala Arg Cys Leu Leu Leu Val Leu Val Ser Ser Leu
1               5                   10                  15
Leu Val Cys Ser Gly Leu Ala Cys Pro Asp Ile Gln Met Thr Gln Ser
            20                  25                  30
Pro Ser Ser Leu Ser Ala Ser Val Gly Asp Arg Val Thr Ile Thr Cys
        35                  40                  45
```

```
Arg Ala Ser Gln Asp Val Asn Thr Ala Val Ala Trp Tyr Gln Gln Lys
 50                  55                  60

Pro Gly Lys Ala Pro Lys Leu Leu Ile Tyr Ser Ala Ser Phe Leu Tyr
 65                  70                  75                  80

Ser Gly Val Pro Ser Arg Phe Ser Gly Ser Arg Ser Gly Thr Asp Phe
                 85                  90                  95

Thr Leu Thr Ile Ser Ser Leu Gln Pro Glu Asp Phe Ala Thr Tyr Tyr
            100                 105                 110

Cys Gln Gln His Tyr Thr Thr Pro Pro Thr Phe Gly Gln Gly Thr Lys
            115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 136
<211> LENGTH: 239
<212> TYPE: PRT
<213> ORGANISM: Artificial Sequence
<220> FEATURE:
<223> OTHER INFORMATION: pre-light chimeric polypeptide having IFN
      signal peptide

<400> SEQUENCE: 136

Met Ala Leu Thr Phe Ala Leu Leu Val Ala Leu Leu Val Leu Ser Cys
 1               5                  10                  15

Lys Ser Ser Cys Ser Val Gly Cys Pro Asp Ile Gln Met Thr Gln Ser
                 20                  25                  30

Pro Ser Ser Leu Ser Ala Ser Val Gly Asp Arg Val Thr Ile Thr Cys
            35                  40                  45

Arg Ala Ser Gln Asp Val Asn Thr Ala Val Ala Trp Tyr Gln Gln Lys
 50                  55                  60

Pro Gly Lys Ala Pro Lys Leu Leu Ile Tyr Ser Ala Ser Phe Leu Tyr
 65                  70                  75                  80

Ser Gly Val Pro Ser Arg Phe Ser Gly Ser Arg Ser Gly Thr Asp Phe
                 85                  90                  95

Thr Leu Thr Ile Ser Ser Leu Gln Pro Glu Asp Phe Ala Thr Tyr Tyr
            100                 105                 110

Cys Gln Gln His Tyr Thr Thr Pro Pro Thr Phe Gly Gln Gly Thr Lys
            115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175
```

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 137
<211> LENGTH: 233
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 137

Met Leu Ala Ala Thr Val Leu Thr Leu Ala Leu Leu Gly Asn Ala His
1               5                   10                  15

Ala Cys Pro Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 138
<211> LENGTH: 217
<212> TYPE: PRT
<213> ORGANISM: Artificial Sequence
<220> FEATURE:
<223> OTHER INFORMATION: Trastuzumab light chain having the N-terminal
      sequence CPP

<400> SEQUENCE: 138

Cys Pro Pro Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
            20                  25                  30

Asn Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 139
<211> LENGTH: 240
<212> TYPE: PRT
<213> ORGANISM: Artificial Sequence
<220> FEATURE:
<223> OTHER INFORMATION: pre-light chimeric polypeptide having SHH
      signal peptide

<400> SEQUENCE: 139

Met Leu Leu Leu Ala Arg Cys Leu Leu Val Leu Val Ser Ser Leu
1               5                   10                  15

Leu Val Cys Ser Gly Leu Ala Cys Pro Pro Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
    50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
        115                 120                 125

Lys Val Glu Ile Lys Arg Thr Val Ala Ala Pro Ser Val Phe Ile Phe

```
            130                 135                 140
Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240

<210> SEQ ID NO 140
<211> LENGTH: 240
<212> TYPE: PRT
<213> ORGANISM: Artificial Sequence
<220> FEATURE:
<223> OTHER INFORMATION: pre-light chimeric polypeptide having IFN
      signal peptide

<400> SEQUENCE: 140

Met Ala Leu Thr Phe Ala Leu Leu Val Ala Leu Leu Val Leu Ser Cys
1               5                   10                  15

Lys Ser Ser Cys Ser Val Gly Cys Pro Pro Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln His Tyr Thr Thr Pro Pro Thr Phe Gly Gln Gly Thr
            115                 120                 125

Lys Val Glu Ile Lys Arg Thr Val Ala Ala Pro Ser Val Phe Ile Phe
            130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240

<210> SEQ ID NO 141
<211> LENGTH: 234
```

```
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 141
```

| | | | | | | | | | | | | | | | |
|---|---|---|---|---|---|---|---|---|---|---|---|---|---|---|---|
|Met|Leu|Ala|Ala|Thr|Val|Leu|Thr|Leu|Ala|Leu|Leu|Gly|Asn|Ala|His|
|1| | | |5| | | | |10| | | | |15| |
|Ala|Cys|Pro|Pro|Asp|Ile|Gln|Met|Thr|Gln|Ser|Pro|Ser|Ser|Leu|Ser|
| | | | |20| | | | |25| | | | |30| |
|Ala|Ser|Val|Gly|Asp|Arg|Val|Thr|Ile|Thr|Cys|Arg|Ala|Ser|Gln|Asp|
| | | | |35| | | | |40| | | | |45| |
|Val|Asn|Thr|Ala|Val|Ala|Trp|Tyr|Gln|Gln|Lys|Pro|Gly|Lys|Ala|Pro|
| |50| | | | |55| | | | |60| | | | |
|Lys|Leu|Leu|Ile|Tyr|Ser|Ala|Ser|Phe|Leu|Tyr|Ser|Gly|Val|Pro|Ser|
|65| | | | |70| | | | |75| | | | |80|
|Arg|Phe|Ser|Gly|Ser|Arg|Ser|Gly|Thr|Asp|Phe|Thr|Leu|Thr|Ile|Ser|
| | | | |85| | | | |90| | | | |95| |
|Ser|Leu|Gln|Pro|Glu|Asp|Phe|Ala|Thr|Tyr|Tyr|Cys|Gln|Gln|His|Tyr|
| | | | |100| | | | |105| | | | |110| |
|Thr|Thr|Pro|Pro|Thr|Phe|Gly|Gln|Gly|Thr|Lys|Val|Glu|Ile|Lys|Arg|
| | | | |115| | | | |120| | | | |125| |
|Thr|Val|Ala|Ala|Pro|Ser|Val|Phe|Ile|Phe|Pro|Pro|Ser|Asp|Glu|Gln|
| |130| | | | |135| | | | |140| | | | |
|Leu|Lys|Ser|Gly|Thr|Ala|Ser|Val|Val|Cys|Leu|Leu|Asn|Asn|Phe|Tyr|
|145| | | | |150| | | | |155| | | | |160|
|Pro|Arg|Glu|Ala|Lys|Val|Gln|Trp|Lys|Val|Asp|Asn|Ala|Leu|Gln|Ser|
| | | | |165| | | | |170| | | | |175| |
|Gly|Asn|Ser|Gln|Glu|Ser|Val|Thr|Glu|Gln|Asp|Ser|Lys|Asp|Ser|Thr|
| | | | |180| | | | |185| | | | |190| |
|Tyr|Ser|Leu|Ser|Ser|Thr|Leu|Thr|Leu|Ser|Lys|Ala|Asp|Tyr|Glu|Lys|
| | | | |195| | | | |200| | | | |205| |
|His|Lys|Val|Tyr|Ala|Cys|Glu|Val|Thr|His|Gln|Gly|Leu|Ser|Ser|Pro|
| |210| | | | |215| | | | |220| | | | |
|Val|Thr|Lys|Ser|Phe|Asn|Arg|Gly|Glu|Cys| | | | | | |
|225| | | | |230| | | | | | | | | | |

```
<210> SEQ ID NO 142
<211> LENGTH: 217
<212> TYPE: PRT
<213> ORGANISM: Artificial Sequence
<220> FEATURE:
<223> OTHER INFORMATION: Trastuzumab light chain having the N-terminal
      sequence CPR

<400> SEQUENCE: 142
```

| | | | | | | | | | | | | | | | |
|---|---|---|---|---|---|---|---|---|---|---|---|---|---|---|---|
|Cys|Pro|Arg|Asp|Ile|Gln|Met|Thr|Gln|Ser|Pro|Ser|Ser|Leu|Ser|Ala|
|1| | | |5| | | | |10| | | | |15| |
|Ser|Val|Gly|Asp|Arg|Val|Thr|Ile|Thr|Cys|Arg|Ala|Ser|Gln|Asp|Val|
| | | | |20| | | | |25| | | | |30| |
|Asn|Thr|Ala|Val|Ala|Trp|Tyr|Gln|Gln|Lys|Pro|Gly|Lys|Ala|Pro|Lys|
| | | | |35| | | | |40| | | | |45| |
|Leu|Leu|Ile|Tyr|Ser|Ala|Ser|Phe|Leu|Tyr|Ser|Gly|Val|Pro|Ser|Arg|
| |50| | | | |55| | | | |60| | | | |
|Phe|Ser|Gly|Ser|Arg|Ser|Gly|Thr|Asp|Phe|Thr|Leu|Thr|Ile|Ser|Ser|
|65| | | | |70| | | | |75| | | | |80|

```
Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
210                 215

<210> SEQ ID NO 143
<211> LENGTH: 240
<212> TYPE: PRT
<213> ORGANISM: Artificial Sequence
<220> FEATURE:
<223> OTHER INFORMATION: pre-light chimeric polypeptide having SHH
      signal peptide

<400> SEQUENCE: 143

Met Leu Leu Leu Ala Arg Cys Leu Leu Leu Val Leu Val Ser Ser Leu
1               5                   10                  15

Leu Val Cys Ser Gly Leu Ala Cys Pro Arg Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220
```

```
Gln Gly Leu Ser Ser Pro Val Thr Lys Ser Phe Asn Arg Gly Glu Cys
225                 230                 235                 240
```

<210> SEQ ID NO 144
<211> LENGTH: 240
<212> TYPE: PRT
<213> ORGANISM: Artificial Sequence
<220> FEATURE:
<223> OTHER INFORMATION: pre-light chimeric polypeptide having IFN
      signal peptide

<400> SEQUENCE: 144

```
Met Ala Leu Thr Phe Ala Leu Leu Val Ala Leu Leu Val Leu Ser Cys
1               5                   10                  15

Lys Ser Ser Cys Ser Val Gly Cys Pro Arg Asp Ile Gln Met Thr Gln
                20                  25                  30

Ser Pro Ser Ser Leu Ser Ala Ser Val Gly Asp Arg Val Thr Ile Thr
            35                  40                  45

Cys Arg Ala Ser Gln Asp Val Asn Thr Ala Val Ala Trp Tyr Gln Gln
    50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 145
<211> LENGTH: 234
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 145

```
Met Leu Ala Ala Thr Val Leu Thr Leu Ala Leu Leu Gly Asn Ala His
1               5                   10                  15

Ala Cys Pro Arg Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45
```

```
Val Asn Thr Ala Val Ala Trp Tyr Gln Gln Lys Pro Gly Lys Ala Pro
         50                  55                  60

Lys Leu Leu Ile Tyr Ser Ala Ser Phe Leu Tyr Ser Gly Val Pro Ser
 65                  70                  75                  80

Arg Phe Ser Gly Ser Arg Ser Gly Thr Asp Phe Thr Leu Thr Ile Ser
                 85                  90                  95

Ser Leu Gln Pro Glu Asp Phe Ala Thr Tyr Tyr Cys Gln Gln His Tyr
                100                 105                 110

Thr Thr Pro Pro Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 146
<211> LENGTH: 217
<212> TYPE: PRT
<213> ORGANISM: Artificial Sequence
<220> FEATURE:
<223> OTHER INFORMATION: Trastuzumab light chain having the N-terminal
      sequence CPS

<400> SEQUENCE: 146

Cys Pro Ser Asp Ile Gln Met Thr Gln Ser Pro Ser Ser Leu Ser Ala
  1               5                  10                  15

Ser Val Gly Asp Arg Val Thr Ile Thr Cys Arg Ala Ser Gln Asp Val
             20                  25                  30

Asn Thr Ala Val Ala Trp Tyr Gln Gln Lys Pro Gly Lys Ala Pro Lys
         35                  40                  45

Leu Leu Ile Tyr Ser Ala Ser Phe Leu Tyr Ser Gly Val Pro Ser Arg
 50                  55                  60

Phe Ser Gly Ser Arg Ser Gly Thr Asp Phe Thr Leu Thr Ile Ser Ser
 65                  70                  75                  80

Leu Gln Pro Glu Asp Phe Ala Thr Tyr Tyr Cys Gln Gln His Tyr Thr
                 85                  90                  95

Thr Pro Pro Thr Phe Gly Gln Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 147
<211> LENGTH: 240
<212> TYPE: PRT
<213> ORGANISM: Artificial Sequence
<220> FEATURE:
<223> OTHER INFORMATION: pre-light chimeric polypeptide having SHH
      signal peptide

<400> SEQUENCE: 147

Met Leu Leu Leu Ala Arg Cys Leu Leu Leu Val Leu Val Ser Ser Leu
1               5                   10                  15

Leu Val Cys Ser Gly Leu Ala Cys Pro Ser Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 148
<211> LENGTH: 240
<212> TYPE: PRT
<213> ORGANISM: Artificial Sequence
<220> FEATURE:
<223> OTHER INFORMATION: pre-light chimeric polypeptide having IFN
      signal peptide

<400> SEQUENCE: 148

Met Ala Leu Thr Phe Ala Leu Leu Val Ala Leu Leu Val Leu Ser Cys

```
1               5                   10                  15
Lys Ser Ser Cys Ser Val Gly Cys Pro Ser Asp Ile Gln Met Thr Gln
                20                  25                  30

Ser Pro Ser Ser Leu Ser Ala Ser Val Gly Asp Arg Val Thr Ile Thr
                35                  40                  45

Cys Arg Ala Ser Gln Asp Val Asn Thr Ala Val Ala Trp Tyr Gln Gln
        50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln His Tyr Thr Thr Pro Pro Thr Phe Gly Gln Gly Thr
                115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240
```

<210> SEQ ID NO 149
<211> LENGTH: 234
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 149

```
Met Leu Ala Ala Thr Val Leu Thr Leu Ala Leu Leu Gly Asn Ala His
1               5                   10                  15

Ala Cys Pro Ser Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
                35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
                100                 105                 110

Thr Thr Pro Pro Thr Phe Gly Gln Gly Thr Lys Val Glu Ile Lys Arg
        115                 120                 125
```

```
Thr Val Ala Ala Pro Ser Val Phe Ile Phe Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 150
<211> LENGTH: 218
<212> TYPE: PRT
<213> ORGANISM: Artificial Sequence
<220> FEATURE:
<223> OTHER INFORMATION: Trastuzumab light chain having the N-terminal
      sequence CDKT

<400> SEQUENCE: 150

Cys Asp Lys Thr Asp Ile Gln Met Thr Gln Ser Pro Ser Ser Leu Ser
1               5                   10                  15

Ala Ser Val Gly Asp Arg Val Thr Ile Thr Cys Arg Ala Ser Gln Asp
                20                  25                  30

Val Asn Thr Ala Val Ala Trp Tyr Gln Gln Lys Pro Gly Lys Ala Pro
            35                  40                  45

Lys Leu Leu Ile Tyr Ser Ala Ser Phe Leu Tyr Ser Gly Val Pro Ser
50                  55                  60

Arg Phe Ser Gly Ser Arg Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 151
<211> LENGTH: 241
<212> TYPE: PRT
<213> ORGANISM: Artificial Sequence
```

<220> FEATURE:
<223> OTHER INFORMATION: pre-light chimeric polypeptide having SHH
     signal peptide

<400> SEQUENCE: 151

Met Leu Leu Leu Ala Arg Cys Leu Leu Leu Val Leu Val Ser Ser Leu
1               5                   10                  15

Leu Val Cys Ser Gly Leu Ala Cys Asp Lys Thr Asp Ile Gln Met Thr
            20                  25                  30

Gln Ser Pro Ser Ser Leu Ser Ala Ser Val Gly Asp Arg Val Thr Ile
        35                  40                  45

Thr Cys Arg Ala Ser Gln Asp Val Asn Thr Ala Val Ala Trp Tyr Gln
    50                  55                  60

Gln Lys Pro Gly Lys Ala Pro Lys Leu Leu Ile Tyr Ser Ala Ser Phe
65                  70                  75                  80

Leu Tyr Ser Gly Val Pro Ser Arg Phe Ser Gly Ser Arg Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln His Tyr Thr Thr Pro Pro Thr Phe Gly Gln Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 152
<211> LENGTH: 241
<212> TYPE: PRT
<213> ORGANISM: Artificial Sequence
<220> FEATURE:
<223> OTHER INFORMATION: pre-light chimeric polypeptide having IFN
     signal peptide

<400> SEQUENCE: 152

Met Ala Leu Thr Phe Ala Leu Leu Val Ala Leu Leu Val Leu Ser Cys
1               5                   10                  15

Lys Ser Ser Cys Ser Val Gly Cys Asp Lys Thr Asp Ile Gln Met Thr
            20                  25                  30

Gln Ser Pro Ser Ser Leu Ser Ala Ser Val Gly Asp Arg Val Thr Ile
        35                  40                  45

Thr Cys Arg Ala Ser Gln Asp Val Asn Thr Ala Val Ala Trp Tyr Gln
    50                  55                  60

Gln Lys Pro Gly Lys Ala Pro Lys Leu Leu Ile Tyr Ser Ala Ser Phe
65                  70                  75                  80

```
Leu Tyr Ser Gly Val Pro Ser Arg Phe Ser Gly Ser Arg Ser Gly Thr
                85                  90                  95

Asp Phe Thr Leu Thr Ile Ser Ser Leu Gln Pro Glu Asp Phe Ala Thr
            100                 105                 110

Tyr Tyr Cys Gln Gln His Tyr Thr Thr Pro Pro Thr Phe Gly Gln Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 153
<211> LENGTH: 235
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 153

Met Leu Ala Ala Thr Val Leu Thr Leu Ala Leu Leu Gly Asn Ala His
1               5                   10                  15

Ala Cys Asp Lys Thr Asp Ile Gln Met Thr Gln Ser Pro Ser Ser Leu
                20                  25                  30

Ser Ala Ser Val Gly Asp Arg Val Thr Ile Thr Cys Arg Ala Ser Gln
            35                  40                  45

Asp Val Asn Thr Ala Val Ala Trp Tyr Gln Gln Lys Pro Gly Lys Ala
        50                  55                  60

Pro Lys Leu Leu Ile Tyr Ser Ala Ser Phe Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln His
            100                 105                 110

Tyr Thr Thr Pro Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190
```

```
Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 154
<211> LENGTH: 220
<212> TYPE: PRT
<213> ORGANISM: Artificial Sequence
<220> FEATURE:
<223> OTHER INFORMATION: Trastuzumab light chain having the N-terminal
      sequence CDKTHT

<400> SEQUENCE: 154

Cys Asp Lys Thr His Thr Asp Ile Gln Met Thr Gln Ser Pro Ser Ser
1               5                   10                  15

Leu Ser Ala Ser Val Gly Asp Arg Val Thr Ile Thr Cys Arg Ala Ser
            20                  25                  30

Gln Asp Val Asn Thr Ala Val Ala Trp Tyr Gln Gln Lys Pro Gly Lys
        35                  40                  45

Ala Pro Lys Leu Leu Ile Tyr Ser Ala Ser Phe Leu Tyr Ser Gly Val
    50                  55                  60

Pro Ser Arg Phe Ser Gly Ser Arg Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Thr Thr Pro Pro Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 155
<211> LENGTH: 243
<212> TYPE: PRT
<213> ORGANISM: Artificial Sequence
<220> FEATURE:
<223> OTHER INFORMATION: pre-light chimeric polypeptide having SHH
      signal peptide

<400> SEQUENCE: 155

Met Leu Leu Leu Ala Arg Cys Leu Leu Leu Val Leu Val Ser Ser Leu
1               5                   10                  15

Leu Val Cys Ser Gly Leu Ala Cys Asp Lys Thr His Thr Asp Ile Gln
            20                  25                  30
```

Met Thr Gln Ser Pro Ser Ser Leu Ser Ala Ser Val Gly Asp Arg Val
                35                  40                  45

Thr Ile Thr Cys Arg Ala Ser Gln Asp Val Asn Thr Ala Val Ala Trp
 50                  55                  60

Tyr Gln Gln Lys Pro Gly Lys Ala Pro Lys Leu Leu Ile Tyr Ser Ala
 65                  70                  75                  80

Ser Phe Leu Tyr Ser Gly Val Pro Ser Arg Phe Ser Gly Ser Arg Ser
                85                  90                  95

Gly Thr Asp Phe Thr Leu Thr Ile Ser Ser Leu Gln Pro Glu Asp Phe
                    100                 105                 110

Ala Thr Tyr Tyr Cys Gln Gln His Tyr Thr Thr Pro Pro Thr Phe Gly
                115                 120                 125

Gln Gly Thr Lys Val Glu Ile Lys Arg Thr Val Ala Ala Pro Ser Val
                130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175

Trp Lys Val Asp Asn Ala Leu Gln Ser Gly Asn Ser Gln Glu Ser Val
                180                 185                 190

Thr Glu Gln Asp Ser Lys Asp Ser Thr Tyr Ser Leu Ser Ser Thr Leu
                195                 200                 205

Thr Leu Ser Lys Ala Asp Tyr Glu Lys His Lys Val Tyr Ala Cys Glu
                210                 215                 220

Val Thr His Gln Gly Leu Ser Ser Pro Val Thr Lys Ser Phe Asn Arg
225                 230                 235                 240

Gly Glu Cys

<210> SEQ ID NO 156
<211> LENGTH: 243
<212> TYPE: PRT
<213> ORGANISM: Artificial Sequence
<220> FEATURE:
<223> OTHER INFORMATION: pre-light chimeric polypeptide having IFN
      signal peptide

<400> SEQUENCE: 156

Met Ala Leu Thr Phe Ala Leu Leu Val Ala Leu Leu Val Leu Ser Cys
 1               5                  10                  15

Lys Ser Ser Cys Ser Val Gly Cys Asp Lys Thr His Thr Asp Ile Gln
                20                  25                  30

Met Thr Gln Ser Pro Ser Ser Leu Ser Ala Ser Val Gly Asp Arg Val
                35                  40                  45

Thr Ile Thr Cys Arg Ala Ser Gln Asp Val Asn Thr Ala Val Ala Trp
 50                  55                  60

Tyr Gln Gln Lys Pro Gly Lys Ala Pro Lys Leu Leu Ile Tyr Ser Ala
 65                  70                  75                  80

Ser Phe Leu Tyr Ser Gly Val Pro Ser Arg Phe Ser Gly Ser Arg Ser
                85                  90                  95

Gly Thr Asp Phe Thr Leu Thr Ile Ser Ser Leu Gln Pro Glu Asp Phe
                    100                 105                 110

Ala Thr Tyr Tyr Cys Gln Gln His Tyr Thr Thr Pro Pro Thr Phe Gly
                115                 120                 125

Gln Gly Thr Lys Val Glu Ile Lys Arg Thr Val Ala Ala Pro Ser Val
                130                 135                 140

```
Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
            165                 170                 175

Trp Lys Val Asp Asn Ala Leu Gln Ser Gly Asn Ser Gln Glu Ser Val
        180                 185                 190

Thr Glu Gln Asp Ser Lys Asp Ser Thr Tyr Ser Leu Ser Ser Thr Leu
    195                 200                 205

Thr Leu Ser Lys Ala Asp Tyr Glu Lys His Lys Val Tyr Ala Cys Glu
    210                 215                 220

Val Thr His Gln Gly Leu Ser Ser Pro Val Thr Lys Ser Phe Asn Arg
225                 230                 235                 240

Gly Glu Cys

<210> SEQ ID NO 157
<211> LENGTH: 237
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 157

Met Leu Ala Ala Thr Val Leu Thr Leu Ala Leu Leu Gly Asn Ala His
1               5                   10                  15

Ala Cys Asp Lys Thr His Thr Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 158
<211> LENGTH: 217
```

```
<212> TYPE: PRT
<213> ORGANISM: Artificial Sequence
<220> FEATURE:
<223> OTHER INFORMATION: Trastuzumab light chain having the N-terminal
      sequence CVE

<400> SEQUENCE: 158
```

Cys Val Glu Asp Ile Gln Met Thr Gln Ser Pro Ser Ser Leu Ser Ala
1               5                   10                  15

Ser Val Gly Asp Arg Val Thr Ile Thr Cys Arg Ala Ser Gln Asp Val
            20                  25                  30

Asn Thr Ala Val Ala Trp Tyr Gln Gln Lys Pro Gly Lys Ala Pro Lys
        35                  40                  45

Leu Leu Ile Tyr Ser Ala Ser Phe Leu Tyr Ser Gly Val Pro Ser Arg
    50                  55                  60

Phe Ser Gly Ser Arg Ser Gly Thr Asp Phe Thr Leu Thr Ile Ser Ser
65                  70                  75                  80

Leu Gln Pro Glu Asp Phe Ala Thr Tyr Tyr Cys Gln Gln His Tyr Thr
                85                  90                  95

Thr Pro Pro Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

```
<210> SEQ ID NO 159
<211> LENGTH: 240
<212> TYPE: PRT
<213> ORGANISM: Artificial Sequence
<220> FEATURE:
<223> OTHER INFORMATION: pre-light chimeric polypeptide having SHH
      signal peptide

<400> SEQUENCE: 159
```

Met Leu Leu Leu Ala Arg Cys Leu Leu Leu Val Leu Val Ser Ser Leu
1               5                   10                  15

Leu Val Cys Ser Gly Leu Ala Cys Val Glu Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
    50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

```
Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 160
<211> LENGTH: 240
<212> TYPE: PRT
<213> ORGANISM: Artificial Sequence
<220> FEATURE:
<223> OTHER INFORMATION: pre-light chimeric polypeptide having IFN
      signal peptide

<400> SEQUENCE: 160

Met Ala Leu Thr Phe Ala Leu Leu Val Ala Leu Leu Val Leu Ser Cys
1               5                   10                  15

Lys Ser Ser Cys Ser Val Gly Cys Val Glu Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
    50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220
```

```
Gln Gly Leu Ser Ser Pro Val Thr Lys Ser Phe Asn Arg Gly Glu Cys
225                 230                 235                 240
```

<210> SEQ ID NO 161
<211> LENGTH: 234
<212> TYPE: PRT
<213> ORGANISM: Artificial Sequence
<220> FEATURE:
<223> OTHER INFORMATION: pre-light chimeric polypeptide having CETP
      signal peptide

<400> SEQUENCE: 161

```
Met Leu Ala Ala Thr Val Leu Thr Leu Ala Leu Leu Gly Asn Ala His
1               5                   10                  15

Ala Cys Val Glu Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 162
<211> LENGTH: 220
<212> TYPE: PRT
<213> ORGANISM: Artificial Sequence
<220> FEATURE:
<223> OTHER INFORMATION: Trastuzumab light chain having the N-terminal
      sequence CDTPPP

<400> SEQUENCE: 162

```
Cys Asp Thr Pro Pro Asp Ile Gln Met Thr Gln Ser Pro Ser Ser
1               5                   10                  15

Leu Ser Ala Ser Val Gly Asp Arg Val Thr Ile Thr Cys Arg Ala Ser
                20                  25                  30

Gln Asp Val Asn Thr Ala Val Ala Trp Tyr Gln Gln Lys Pro Gly Lys
            35                  40                  45
```

```
Ala Pro Lys Leu Leu Ile Tyr Ser Ala Ser Phe Leu Tyr Ser Gly Val
        50                  55                  60

Pro Ser Arg Phe Ser Gly Ser Arg Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Thr Thr Pro Pro Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 163
<211> LENGTH: 243
<212> TYPE: PRT
<213> ORGANISM: Artificial Sequence
<220> FEATURE:
<223> OTHER INFORMATION: pre-light chimeric polypeptide having SHH
      signal peptide

<400> SEQUENCE: 163

Met Leu Leu Leu Ala Arg Cys Leu Leu Leu Val Leu Val Ser Ser Leu
1               5                   10                  15

Leu Val Cys Ser Gly Leu Ala Cys Asp Thr Pro Pro Asp Ile Gln
            20                  25                  30

Met Thr Gln Ser Pro Ser Ser Leu Ser Ala Ser Val Gly Asp Arg Val
        35                  40                  45

Thr Ile Thr Cys Arg Ala Ser Gln Asp Val Asn Thr Ala Val Ala Trp
    50                  55                  60

Tyr Gln Gln Lys Pro Gly Lys Ala Pro Lys Leu Leu Ile Tyr Ser Ala
65                  70                  75                  80

Ser Phe Leu Tyr Ser Gly Val Pro Ser Arg Phe Ser Gly Ser Arg Ser
                85                  90                  95

Gly Thr Asp Phe Thr Leu Thr Ile Ser Ser Leu Gln Pro Glu Asp Phe
            100                 105                 110

Ala Thr Tyr Tyr Cys Gln Gln His Tyr Thr Thr Pro Pro Thr Phe Gly
        115                 120                 125

Gln Gly Thr Lys Val Glu Ile Lys Arg Thr Val Ala Ala Pro Ser Val
130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175

Trp Lys Val Asp Asn Ala Leu Gln Ser Gly Asn Ser Gln Glu Ser Val
```

```
                        180                 185                 190
Thr Glu Gln Asp Ser Lys Asp Ser Thr Tyr Ser Leu Ser Ser Thr Leu
                195                 200                 205

Thr Leu Ser Lys Ala Asp Tyr Glu Lys His Lys Val Tyr Ala Cys Glu
            210                 215                 220

Val Thr His Gln Gly Leu Ser Ser Pro Val Thr Lys Ser Phe Asn Arg
225                 230                 235                 240

Gly Glu Cys

<210> SEQ ID NO 164
<211> LENGTH: 243
<212> TYPE: PRT
<213> ORGANISM: Artificial Sequence
<220> FEATURE:
<223> OTHER INFORMATION: pre-light chimeric polypeptide having IFN
      signal peptide

<400> SEQUENCE: 164

Met Ala Leu Thr Phe Ala Leu Leu Val Ala Leu Leu Val Leu Ser Cys
1               5                   10                  15

Lys Ser Ser Cys Ser Val Gly Cys Asp Thr Pro Pro Asp Ile Gln
            20                  25                  30

Met Thr Gln Ser Pro Ser Ser Leu Ser Ala Ser Val Gly Asp Arg Val
            35                  40                  45

Thr Ile Thr Cys Arg Ala Ser Gln Asp Val Asn Thr Ala Val Ala Trp
        50                  55                  60

Tyr Gln Gln Lys Pro Gly Lys Ala Pro Lys Leu Leu Ile Tyr Ser Ala
65                  70                  75                  80

Ser Phe Leu Tyr Ser Gly Val Pro Ser Arg Phe Ser Gly Ser Arg Ser
                85                  90                  95

Gly Thr Asp Phe Thr Leu Thr Ile Ser Ser Leu Gln Pro Glu Asp Phe
            100                 105                 110

Ala Thr Tyr Tyr Cys Gln Gln His Tyr Thr Thr Pro Pro Thr Phe Gly
            115                 120                 125

Gln Gly Thr Lys Val Glu Ile Lys Arg Thr Val Ala Ala Pro Ser Val
        130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175

Trp Lys Val Asp Asn Ala Leu Gln Ser Gly Asn Ser Gln Glu Ser Val
            180                 185                 190

Thr Glu Gln Asp Ser Lys Asp Ser Thr Tyr Ser Leu Ser Ser Thr Leu
            195                 200                 205

Thr Leu Ser Lys Ala Asp Tyr Glu Lys His Lys Val Tyr Ala Cys Glu
        210                 215                 220

Val Thr His Gln Gly Leu Ser Ser Pro Val Thr Lys Ser Phe Asn Arg
225                 230                 235                 240

Gly Glu Cys

<210> SEQ ID NO 165
<211> LENGTH: 237
<212> TYPE: PRT
<213> ORGANISM: Artificial Sequence
<220> FEATURE:
<223> OTHER INFORMATION: pre-light chimeric polypeptide having CETP
      signal peptide
```

<400> SEQUENCE: 165

```
Met Leu Ala Ala Thr Val Leu Thr Leu Ala Leu Leu Gly Asn Ala His
1               5                   10                  15

Ala Cys Asp Thr Pro Pro Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Asn Thr Ala Val Ala Trp Tyr Gln Gln Lys Pro Gly
    50                  55                  60

Lys Ala Pro Lys Leu Leu Ile Tyr Ser Ala Ser Phe Leu Tyr Ser Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 166
<211> LENGTH: 451
<212> TYPE: PRT
<213> ORGANISM: Artificial Sequence
<220> FEATURE:
<223> OTHER INFORMATION: Trastuzumab heavy chain having the N-terminal sequence C

<400> SEQUENCE: 166

```
Cys Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110
```

```
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 167
<211> LENGTH: 474
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 167

Met Leu Leu Leu Ala Arg Cys Leu Leu Leu Val Leu Val Ser Ser Leu
```

-continued

```
  1               5               10              15
Leu Val Cys Ser Gly Leu Ala Cys Glu Val Gln Leu Val Glu Ser Gly
                 20              25              30
Gly Gly Leu Val Gln Pro Gly Gly Ser Leu Arg Leu Ser Cys Ala Ala
                 35              40              45
Ser Gly Phe Asn Ile Lys Asp Thr Tyr Ile His Trp Val Arg Gln Ala
             50              55              60
Pro Gly Lys Gly Leu Glu Trp Val Ala Arg Ile Tyr Pro Thr Asn Gly
 65              70              75              80
Tyr Thr Arg Tyr Ala Asp Ser Val Lys Gly Arg Phe Thr Ile Ser Ala
                 85              90              95
Asp Thr Ser Lys Asn Thr Ala Tyr Leu Gln Met Asn Ser Leu Arg Ala
                100             105             110
Glu Asp Thr Ala Val Tyr Tyr Cys Ser Arg Trp Gly Gly Asp Gly Phe
                115             120             125
Tyr Ala Met Asp Tyr Trp Gly Gln Gly Thr Leu Val Thr Val Ser Ser
                130             135             140
Ala Ser Thr Lys Gly Pro Ser Val Phe Pro Leu Ala Pro Ser Ser Lys
145             150             155             160
Ser Thr Ser Gly Gly Thr Ala Ala Leu Gly Cys Leu Val Lys Asp Tyr
                165             170             175
Phe Pro Glu Pro Val Thr Val Ser Trp Asn Ser Gly Ala Leu Thr Ser
                180             185             190
Gly Val His Thr Phe Pro Ala Val Leu Gln Ser Ser Gly Leu Tyr Ser
                195             200             205
Leu Ser Ser Val Val Thr Val Pro Ser Ser Ser Leu Gly Thr Gln Thr
210             215             220
Tyr Ile Cys Asn Val Asn His Lys Pro Ser Asn Thr Lys Val Asp Lys
225             230             235             240
Lys Val Glu Pro Lys Ser Cys Asp Lys Thr His Thr Cys Pro Pro Cys
                245             250             255
Pro Ala Pro Glu Leu Leu Gly Gly Pro Ser Val Phe Leu Phe Pro Pro
                260             265             270
Lys Pro Lys Asp Thr Leu Met Ile Ser Arg Thr Pro Glu Val Thr Cys
                275             280             285
Val Val Val Asp Val Ser His Glu Asp Pro Glu Val Lys Phe Asn Trp
                290             295             300
Tyr Val Asp Gly Val Glu Val His Asn Ala Lys Thr Lys Pro Arg Glu
305             310             315             320
Glu Gln Tyr Asn Ser Thr Tyr Arg Val Val Ser Val Leu Thr Val Leu
                325             330             335
His Gln Asp Trp Leu Asn Gly Lys Glu Tyr Lys Cys Lys Val Ser Asn
                340             345             350
Lys Ala Leu Pro Ala Pro Ile Glu Lys Thr Ile Ser Lys Ala Lys Gly
                355             360             365
Gln Pro Arg Glu Pro Gln Val Tyr Thr Leu Pro Pro Ser Arg Asp Glu
                370             375             380
Leu Thr Lys Asn Gln Val Ser Leu Thr Cys Leu Val Lys Gly Phe Tyr
385             390             395             400
Pro Ser Asp Ile Ala Val Glu Trp Glu Ser Asn Gly Gln Pro Glu Asn
                405             410             415
Asn Tyr Lys Thr Thr Pro Pro Val Leu Asp Ser Asp Gly Ser Phe Phe
                420             425             430
```

```
Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 168
<211> LENGTH: 474
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 168

```
Met Ala Leu Thr Phe Ala Leu Leu Val Ala Leu Leu Val Leu Ser Cys
1               5                   10                  15

Lys Ser Ser Cys Ser Val Gly Cys Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Asn Ile Lys Asp Thr Tyr Ile His Trp Val Arg Gln Ala
    50                  55                  60

Pro Gly Lys Gly Leu Glu Trp Val Ala Arg Ile Tyr Pro Thr Asn Gly
65                  70                  75                  80

Tyr Thr Arg Tyr Ala Asp Ser Val Lys Gly Arg Phe Thr Ile Ser Ala
                85                  90                  95

Asp Thr Ser Lys Asn Thr Ala Tyr Leu Gln Met Asn Ser Leu Arg Ala
            100                 105                 110

Glu Asp Thr Ala Val Tyr Tyr Cys Ser Arg Trp Gly Gly Asp Gly Phe
        115                 120                 125

Tyr Ala Met Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
```

```
              305                 310                 315                 320
Glu Gln Tyr Asn Ser Thr Tyr Arg Val Val Ser Val Leu Thr Val Leu
                    325                 330                 335

His Gln Asp Trp Leu Asn Gly Lys Glu Tyr Lys Cys Lys Val Ser Asn
                    340                 345                 350

Lys Ala Leu Pro Ala Pro Ile Glu Lys Thr Ile Ser Lys Ala Lys Gly
                    355                 360                 365

Gln Pro Arg Glu Pro Gln Val Tyr Thr Leu Pro Pro Ser Arg Asp Glu
            370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                    405                 410                 415

Asn Tyr Lys Thr Thr Pro Pro Val Leu Asp Ser Asp Gly Ser Phe Phe
                    420                 425                 430

Leu Tyr Ser Lys Leu Thr Val Asp Lys Ser Arg Trp Gln Gln Gly Asn
                    435                 440                 445

Val Phe Ser Cys Ser Val Met His Glu Ala Leu His Asn His Tyr Thr
                    450                 455                 460

Gln Lys Ser Leu Ser Leu Ser Pro Gly Lys
465                 470
```

<210> SEQ ID NO 169
<211> LENGTH: 468
<212> TYPE: PRT
<213> ORGANISM: Artificial Sequence
<220> FEATURE:
<223> OTHER INFORMATION: pre-heavy chain chimeric polypeptide having
      CETP signal peptide

<400> SEQUENCE: 169

```
Met Leu Ala Ala Thr Val Leu Thr Leu Ala Leu Leu Gly Asn Ala His
1               5                   10                  15

Ala Cys Glu Val Gln Leu Val Glu Ser Gly Gly Gly Leu Val Gln Pro
                    20                  25                  30

Gly Gly Ser Leu Arg Leu Ser Cys Ala Ala Ser Gly Phe Asn Ile Lys
            35                  40                  45

Asp Thr Tyr Ile His Trp Val Arg Gln Ala Pro Gly Lys Gly Leu Glu
        50                  55                  60

Trp Val Ala Arg Ile Tyr Pro Thr Asn Gly Tyr Thr Arg Tyr Ala Asp
65                  70                  75                  80

Ser Val Lys Gly Arg Phe Thr Ile Ser Ala Asp Thr Ser Lys Asn Thr
                    85                  90                  95

Ala Tyr Leu Gln Met Asn Ser Leu Arg Ala Glu Asp Thr Ala Val Tyr
                100                 105                 110

Tyr Cys Ser Arg Trp Gly Gly Asp Gly Phe Tyr Ala Met Asp Tyr Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190
```

```
Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 170
<211> LENGTH: 452
<212> TYPE: PRT
<213> ORGANISM: Artificial Sequence
<220> FEATURE:
<223> OTHER INFORMATION: Trastuzumab heavy chain having the N-terminal
      sequence CP

<400> SEQUENCE: 170

Cys Pro Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Asn Ile Lys
            20                  25                  30

Asp Thr Tyr Ile His Trp Val Arg Gln Ala Pro Gly Lys Gly Leu Glu
        35                  40                  45

Trp Val Ala Arg Ile Tyr Pro Thr Asn Gly Tyr Thr Arg Tyr Ala Asp
    50                  55                  60

Ser Val Lys Gly Arg Phe Thr Ile Ser Ala Asp Thr Ser Lys Asn Thr
65                  70                  75                  80
```

```
Ala Tyr Leu Gln Met Asn Ser Leu Arg Ala Glu Asp Thr Ala Val Tyr
                 85                  90                  95

Tyr Cys Ser Arg Trp Gly Gly Asp Gly Phe Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 171
<211> LENGTH: 475
<212> TYPE: PRT
<213> ORGANISM: Artificial Sequence
<220> FEATURE:
```

<223> OTHER INFORMATION: pre-heavy chain chimeric polypeptide having SHH signal peptide

<400> SEQUENCE: 171

```
Met Leu Leu Leu Ala Arg Cys Leu Leu Leu Val Leu Val Ser Ser Leu
1               5                   10                  15

Leu Val Cys Ser Gly Leu Ala Cys Pro Glu Val Gln Leu Val Glu Ser
            20                  25                  30

Gly Gly Gly Leu Val Gln Pro Gly Gly Ser Leu Arg Leu Ser Cys Ala
        35                  40                  45

Ala Ser Gly Phe Asn Ile Lys Asp Thr Tyr Ile His Trp Val Arg Gln
50                  55                  60

Ala Pro Gly Lys Gly Leu Glu Trp Val Ala Arg Ile Tyr Pro Thr Asn
65                  70                  75                  80

Gly Tyr Thr Arg Tyr Ala Asp Ser Val Lys Gly Arg Phe Thr Ile Ser
                85                  90                  95

Ala Asp Thr Ser Lys Asn Thr Ala Tyr Leu Gln Met Asn Ser Leu Arg
            100                 105                 110

Ala Glu Asp Thr Ala Val Tyr Tyr Cys Ser Arg Trp Gly Gly Asp Gly
        115                 120                 125

Phe Tyr Ala Met Asp Tyr Trp Gly Gln Gly Thr Leu Val Thr Val Ser
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400
```

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
        420                 425                 430

Phe Leu Tyr Ser Lys Leu Thr Val Asp Lys Ser Arg Trp Gln Gln Gly
    435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 172
<211> LENGTH: 475
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 172

Met Ala Leu Thr Phe Ala Leu Leu Val Ala Leu Leu Val Leu Ser Cys
1               5                   10                  15

Lys Ser Ser Cys Ser Val Gly Cys Pro Glu Val Gln Leu Val Glu Ser
            20                  25                  30

Gly Gly Gly Leu Val Gln Pro Gly Gly Ser Leu Arg Leu Ser Cys Ala
        35                  40                  45

Ala Ser Gly Phe Asn Ile Lys Asp Thr Tyr Ile His Trp Val Arg Gln
50                  55                  60

Ala Pro Gly Lys Gly Leu Glu Trp Val Ala Arg Ile Tyr Pro Thr Asn
65                  70                  75                  80

Gly Tyr Thr Arg Tyr Ala Asp Ser Val Lys Gly Arg Phe Thr Ile Ser
            85                  90                  95

Ala Asp Thr Ser Lys Asn Thr Ala Tyr Leu Gln Met Asn Ser Leu Arg
        100                 105                 110

Ala Glu Asp Thr Ala Val Tyr Tyr Cys Ser Arg Trp Gly Gly Asp Gly
    115                 120                 125

Phe Tyr Ala Met Asp Tyr Trp Gly Gln Gly Thr Leu Val Thr Val Ser
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
        180                 185                 190

Ser Gly Val His Thr Phe Pro Ala Val Leu Gln Ser Ser Gly Leu Tyr
    195                 200                 205

Ser Leu Ser Ser Val Val Thr Val Pro Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr

-continued

```
                275                 280                 285
Cys Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 173
<211> LENGTH: 469
<212> TYPE: PRT
<213> ORGANISM: Artificial Sequence
<220> FEATURE:
<223> OTHER INFORMATION: pre-heavy chain chimeric polypeptide having
      CETP signal peptide

<400> SEQUENCE: 173

Met Leu Ala Ala Thr Val Leu Thr Leu Ala Leu Leu Gly Asn Ala His
1               5                   10                  15

Ala Cys Pro Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
        50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
                100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160
```

```
Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 174
<211> LENGTH: 453
<212> TYPE: PRT
<213> ORGANISM: Artificial Sequence
<220> FEATURE:
<223> OTHER INFORMATION: Trastuzumab heavy chain having the N-terminal
      sequence CPP

<400> SEQUENCE: 174

Cys Pro Pro Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Ile
            20                  25                  30

Lys Asp Thr Tyr Ile His Trp Val Arg Gln Ala Pro Gly Lys Gly Leu
        35                  40                  45
```

-continued

```
Glu Trp Val Ala Arg Ile Tyr Pro Thr Asn Gly Tyr Thr Arg Tyr Ala
 50                  55                  60

Asp Ser Val Lys Gly Arg Phe Thr Ile Ser Ala Asp Thr Ser Lys Asn
 65                  70                  75                  80

Thr Ala Tyr Leu Gln Met Asn Ser Leu Arg Ala Glu Asp Thr Ala Val
                 85                  90                  95

Tyr Tyr Cys Ser Arg Trp Gly Asp Gly Phe Tyr Ala Met Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450
```

<210> SEQ ID NO 175
<211> LENGTH: 476
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 175

Met Leu Leu Ala Arg Cys Leu Leu Val Leu Val Ser Ser Leu
1               5                   10                  15

Leu Val Cys Ser Gly Leu Ala Cys Pro Pro Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Phe Asn Ile Lys Asp Thr Tyr Ile His Trp Val Arg
    50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
                85                  90                  95

Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
        115                 120                 125

Gly Phe Tyr Ala Met Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
            370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 176
<211> LENGTH: 476
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 176

Met Ala Leu Thr Phe Ala Leu Leu Val Ala Leu Leu Val Leu Ser Cys
1               5                   10                  15

Lys Ser Ser Cys Ser Val Gly Cys Pro Pro Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Phe Asn Ile Lys Asp Thr Tyr Ile His Trp Val Arg
    50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
                85                  90                  95

Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
        115                 120                 125

Gly Phe Tyr Ala Met Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro

```
                   245                 250                 255
Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
            290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Phe Leu Tyr Ser Lys Leu Thr Val Asp Lys Ser Arg Trp Gln Gln
                435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 177
<211> LENGTH: 470
<212> TYPE: PRT
<213> ORGANISM: Artificial Sequence
<220> FEATURE:
<223> OTHER INFORMATION: pre-heavy chain chimeric polypeptide having
      CETP signal peptide

<400> SEQUENCE: 177

Met Leu Ala Ala Thr Val Leu Thr Leu Ala Leu Leu Gly Asn Ala His
1               5                   10                  15

Ala Cys Pro Pro Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125
```

```
Tyr Trp Gly Gln Gly Thr Leu Val Thr Val Ser Ser Ala Ser Thr Lys
        130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 178
<211> LENGTH: 453
<212> TYPE: PRT
<213> ORGANISM: Artificial Sequence
<220> FEATURE:
<223> OTHER INFORMATION: Trastuzumab heavy chain having the N-terminal
      sequence CPR

<400> SEQUENCE: 178

Cys Pro Arg Glu Val Gln Leu Val Glu Ser Gly Gly Gly Leu Val Gln
1               5                   10                  15
```

```
Pro Gly Gly Ser Leu Arg Leu Ser Cys Ala Ala Ser Gly Phe Asn Ile
            20                  25                  30

Lys Asp Thr Tyr Ile His Trp Val Arg Gln Ala Pro Gly Lys Gly Leu
            35                  40                  45

Glu Trp Val Ala Arg Ile Tyr Pro Thr Asn Gly Tyr Thr Arg Tyr Ala
50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
            85                  90                  95

Tyr Tyr Cys Ser Arg Trp Gly Gly Asp Gly Phe Tyr Ala Met Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430
```

```
Val Met His Glu Ala Leu His Asn His Tyr Thr Gln Lys Ser Leu Ser
        435                 440                 445

Leu Ser Pro Gly Lys
    450

<210> SEQ ID NO 179
<211> LENGTH: 476
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 179

Met Leu Leu Leu Ala Arg Cys Leu Leu Leu Val Leu Val Ser Ser Leu
1               5                   10                  15

Leu Val Cys Ser Gly Leu Ala Cys Pro Arg Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Phe Asn Ile Lys Asp Thr Tyr Ile His Trp Val Arg
    50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
                85                  90                  95

Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
        115                 120                 125

Gly Phe Tyr Ala Met Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335
```

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
            450                 455                 460

Tyr Thr Gln Lys Ser Leu Ser Leu Ser Pro Gly Lys
465                 470                 475

<210> SEQ ID NO 180
<211> LENGTH: 476
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 180

Met Ala Leu Thr Phe Ala Leu Leu Val Ala Leu Leu Val Leu Ser Cys
1               5                   10                  15

Lys Ser Ser Cys Ser Val Gly Cys Pro Arg Glu Val Gln Leu Val Glu
            20                  25                  30

Ser Gly Gly Gly Leu Val Gln Pro Gly Gly Ser Leu Arg Leu Ser Cys
            35                  40                  45

Ala Ala Ser Gly Phe Asn Ile Lys Asp Thr Tyr Ile His Trp Val Arg
50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
            85                  90                  95

Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
            115                 120                 125

Gly Phe Tyr Ala Met Asp Tyr Trp Gly Gln Gly Thr Leu Val Thr Val
            130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
            165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
            195                 200                 205

Tyr Ser Leu Ser Ser Val Val Thr Val Pro Ser Ser Ser Leu Gly Thr

```
                  210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 181
<211> LENGTH: 470
<212> TYPE: PRT
<213> ORGANISM: Artificial Sequence
<220> FEATURE:
<223> OTHER INFORMATION: pre-heavy chain chimeric polypeptide having
      CETP signal peptide

<400> SEQUENCE: 181

Met Leu Ala Ala Thr Val Leu Thr Leu Ala Leu Leu Gly Asn Ala His
1               5                   10                  15

Ala Cys Pro Arg Glu Val Gln Leu Val Glu Ser Gly Gly Gly Leu Val
                20                  25                  30

Gln Pro Gly Gly Ser Leu Arg Leu Ser Cys Ala Ala Ser Gly Phe Asn
            35                  40                  45

Ile Lys Asp Thr Tyr Ile His Trp Val Arg Gln Ala Pro Gly Lys Gly
        50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95
```

Asn Thr Ala Tyr Leu Gln Met Asn Ser Leu Arg Ala Glu Asp Thr Ala
                100                 105                 110

Val Tyr Tyr Cys Ser Arg Trp Gly Gly Asp Gly Phe Tyr Ala Met Asp
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 182
<211> LENGTH: 453
<212> TYPE: PRT
<213> ORGANISM: Artificial Sequence
<220> FEATURE:
<223> OTHER INFORMATION: Trastuzumab heavy chain having the N-terminal sequence CPS

<400> SEQUENCE: 182

Cys Pro Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Ile
            20                  25                  30

Lys Asp Thr Tyr Ile His Trp Val Arg Gln Ala Pro Gly Lys Gly Leu
        35                  40                  45

Glu Trp Val Ala Arg Ile Tyr Pro Thr Asn Gly Tyr Thr Arg Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ser Arg Trp Gly Gly Asp Gly Phe Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

```
Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 183
<211> LENGTH: 476
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 183

Met Leu Leu Leu Ala Arg Cys Leu Leu Leu Val Leu Val Ser Ser Leu
1               5                   10                  15

Leu Val Cys Ser Gly Leu Ala Cys Pro Ser Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Phe Asn Ile Lys Asp Thr Tyr Ile His Trp Val Arg
    50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
                85                  90                  95

Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
        115                 120                 125

Gly Phe Tyr Ala Met Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300
```

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 184
<211> LENGTH: 476
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 184

Met Ala Leu Thr Phe Ala Leu Leu Val Ala Leu Leu Val Leu Ser Cys
1               5                   10                  15

Lys Ser Ser Cys Ser Val Gly Cys Pro Ser Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Phe Asn Ile Lys Asp Thr Tyr Ile His Trp Val Arg
    50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
                85                  90                  95

Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
        115                 120                 125

Gly Phe Tyr Ala Met Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu

```
            180                 185                 190
Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 185
<211> LENGTH: 470
<212> TYPE: PRT
<213> ORGANISM: Artificial Sequence
<220> FEATURE:
<223> OTHER INFORMATION: pre-heavy chain chimeric polypeptide having
      CETP signal peptide

<400> SEQUENCE: 185

Met Leu Ala Ala Thr Val Leu Thr Leu Ala Leu Leu Gly Asn Ala His
1               5                   10                  15

Ala Cys Pro Ser Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60
```

```
Leu Glu Trp Val Ala Arg Ile Tyr Pro Thr Asn Gly Tyr Thr Arg Tyr
 65                  70                  75                  80

Ala Asp Ser Val Lys Gly Arg Phe Thr Ile Ser Ala Asp Thr Ser Lys
             85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Asp Gly Phe Tyr Ala Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

```
<210> SEQ ID NO 186
<211> LENGTH: 454
<212> TYPE: PRT
<213> ORGANISM: Artificial Sequence
<220> FEATURE:
<223> OTHER INFORMATION: Trastuzumab heavy chain having the N-terminal
      sequence CDKT

<400> SEQUENCE: 186
```

```
Cys Asp Lys Thr Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Asn
            20                  25                  30

Ile Lys Asp Thr Tyr Ile His Trp Val Arg Gln Ala Pro Gly Lys Gly
        35                  40                  45

Leu Glu Trp Val Ala Arg Ile Tyr Pro Thr Asn Gly Tyr Thr Arg Tyr
    50                  55                  60

Ala Asp Ser Val Lys Gly Arg Phe Thr Ile Ser Ala Asp Thr Ser Lys
65                  70                  75                  80

Asn Thr Ala Tyr Leu Gln Met Asn Ser Leu Arg Ala Glu Asp Thr Ala
                85                  90                  95

Val Tyr Tyr Cys Ser Arg Trp Gly Gly Asp Gly Phe Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365
```

```
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 187
<211> LENGTH: 477
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 187

```
Met Leu Leu Leu Ala Arg Cys Leu Leu Val Leu Val Ser Ser Leu
1               5                   10                  15

Leu Val Cys Ser Gly Leu Ala Cys Asp Lys Thr Glu Val Gln Leu Val
                20                  25                  30

Glu Ser Gly Gly Gly Leu Val Gln Pro Gly Gly Ser Leu Arg Leu Ser
            35                  40                  45

Cys Ala Ala Ser Gly Phe Asn Ile Lys Asp Thr Tyr Ile His Trp Val
    50                  55                  60

Arg Gln Ala Pro Gly Lys Gly Leu Glu Trp Val Ala Arg Ile Tyr Pro
65                  70                  75                  80

Thr Asn Gly Tyr Thr Arg Tyr Ala Asp Ser Val Lys Gly Arg Phe Thr
                85                  90                  95

Ile Ser Ala Asp Thr Ser Lys Asn Thr Ala Tyr Leu Gln Met Asn Ser
            100                 105                 110

Leu Arg Ala Glu Asp Thr Ala Val Tyr Tyr Cys Ser Arg Trp Gly Gly
        115                 120                 125

Asp Gly Phe Tyr Ala Met Asp Tyr Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270
```

```
Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
        290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
450                 455                 460

His Tyr Thr Gln Lys Ser Leu Ser Leu Ser Pro Gly Lys
465                 470                 475

<210> SEQ ID NO 188
<211> LENGTH: 477
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 188

Met Ala Leu Thr Phe Ala Leu Leu Val Ala Leu Leu Val Leu Ser Cys
1               5                   10                  15

Lys Ser Ser Cys Ser Val Gly Cys Asp Lys Thr Glu Val Gln Leu Val
                20                  25                  30

Glu Ser Gly Gly Gly Leu Val Gln Pro Gly Gly Ser Leu Arg Leu Ser
            35                  40                  45

Cys Ala Ala Ser Gly Phe Asn Ile Lys Asp Thr Tyr Ile His Trp Val
        50                  55                  60

Arg Gln Ala Pro Gly Lys Gly Leu Glu Trp Val Ala Arg Ile Tyr Pro
65                  70                  75                  80

Thr Asn Gly Tyr Thr Arg Tyr Ala Asp Ser Val Lys Gly Arg Phe Thr
                85                  90                  95

Ile Ser Ala Asp Thr Ser Lys Asn Thr Ala Tyr Leu Gln Met Asn Ser
            100                 105                 110

Leu Arg Ala Glu Asp Thr Ala Val Tyr Tyr Cys Ser Arg Trp Gly Gly
        115                 120                 125

Asp Gly Phe Tyr Ala Met Asp Tyr Trp Gly Gln Gly Thr Leu Val Thr
130                 135                 140

Val Ser Ser Ala Ser Thr Lys Gly Pro Ser Val Phe Pro Leu Ala Pro
```

```
                145                 150                 155                 160
        Ser Ser Lys Ser Thr Ser Gly Gly Thr Ala Ala Leu Gly Cys Leu Val
                        165                 170                 175

Lys Asp Tyr Phe Pro Glu Pro Val Thr Val Ser Trp Asn Ser Gly Ala
                        180                 185                 190

Leu Thr Ser Gly Val His Thr Phe Pro Ala Val Leu Gln Ser Ser Gly
                        195                 200                 205

Leu Tyr Ser Leu Ser Ser Val Val Thr Val Pro Ser Ser Ser Leu Gly
                        210                 215                 220

Thr Gln Thr Tyr Ile Cys Asn Val Asn His Lys Pro Ser Asn Thr Lys
        225                 230                 235                 240

Val Asp Lys Lys Val Glu Pro Lys Ser Cys Asp Lys Thr His Thr Cys
                        245                 250                 255

Pro Pro Cys Pro Ala Pro Glu Leu Leu Gly Gly Pro Ser Val Phe Leu
                        260                 265                 270

Phe Pro Pro Lys Pro Lys Asp Thr Leu Met Ile Ser Arg Thr Pro Glu
                        275                 280                 285

Val Thr Cys Val Val Val Asp Val Ser His Glu Asp Pro Glu Val Lys
                        290                 295                 300

Phe Asn Trp Tyr Val Asp Gly Val Glu Val His Asn Ala Lys Thr Lys
        305                 310                 315                 320

Pro Arg Glu Glu Gln Tyr Asn Ser Thr Tyr Arg Val Val Ser Val Leu
                        325                 330                 335

Thr Val Leu His Gln Asp Trp Leu Asn Gly Lys Glu Tyr Lys Cys Lys
                        340                 345                 350

Val Ser Asn Lys Ala Leu Pro Ala Pro Ile Glu Lys Thr Ile Ser Lys
                        355                 360                 365

Ala Lys Gly Gln Pro Arg Glu Pro Gln Val Tyr Thr Leu Pro Pro Ser
                        370                 375                 380

Arg Asp Glu Leu Thr Lys Asn Gln Val Ser Leu Thr Cys Leu Val Lys
        385                 390                 395                 400

Gly Phe Tyr Pro Ser Asp Ile Ala Val Glu Trp Glu Ser Asn Gly Gln
                        405                 410                 415

Pro Glu Asn Asn Tyr Lys Thr Thr Pro Pro Val Leu Asp Ser Asp Gly
                        420                 425                 430

Ser Phe Phe Leu Tyr Ser Lys Leu Thr Val Asp Lys Ser Arg Trp Gln
                        435                 440                 445

Gln Gly Asn Val Phe Ser Cys Ser Val Met His Glu Ala Leu His Asn
                        450                 455                 460

His Tyr Thr Gln Lys Ser Leu Ser Leu Ser Pro Gly Lys
        465                 470                 475

<210> SEQ ID NO 189
<211> LENGTH: 471
<212> TYPE: PRT
<213> ORGANISM: Artificial Sequence
<220> FEATURE:
<223> OTHER INFORMATION: pre-heavy chain chimeric polypeptide having
      CETP signal peptide

<400> SEQUENCE: 189

Met Leu Ala Ala Thr Val Leu Thr Leu Ala Leu Leu Gly Asn Ala His
1               5                   10                  15

Ala Cys Asp Lys Thr Glu Val Gln Leu Val Glu Ser Gly Gly Gly Leu
                20                  25                  30
```

```
Val Gln Pro Gly Gly Ser Leu Arg Leu Ser Cys Ala Ala Ser Gly Phe
             35                  40                  45

Asn Ile Lys Asp Thr Tyr Ile His Trp Val Arg Gln Ala Pro Gly Lys
 50                  55                  60

Gly Leu Glu Trp Val Ala Arg Ile Tyr Pro Thr Asn Gly Tyr Thr Arg
 65                  70                  75                  80

Tyr Ala Asp Ser Val Lys Gly Arg Phe Thr Ile Ser Ala Asp Thr Ser
                 85                  90                  95

Lys Asn Thr Ala Tyr Leu Gln Met Asn Ser Leu Arg Ala Glu Asp Thr
                100                 105                 110

Ala Val Tyr Tyr Cys Ser Arg Trp Gly Gly Asp Gly Phe Tyr Ala Met
            115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
```

```
                450                 455                 460
Leu Ser Leu Ser Pro Gly Lys
465                 470

<210> SEQ ID NO 190
<211> LENGTH: 456
<212> TYPE: PRT
<213> ORGANISM: Artificial Sequence
<220> FEATURE:
<223> OTHER INFORMATION: Trastuzumab heavy chain having the N-terminal
      sequence CDKTHT

<400> SEQUENCE: 190

Cys Asp Lys Thr His Thr Glu Val Gln Leu Val Glu Ser Gly Gly Gly
1               5                   10                  15

Leu Val Gln Pro Gly Gly Ser Leu Arg Leu Ser Cys Ala Ala Ser Gly
            20                  25                  30

Phe Asn Ile Lys Asp Thr Tyr Ile His Trp Val Arg Gln Ala Pro Gly
        35                  40                  45

Lys Gly Leu Glu Trp Val Ala Arg Ile Tyr Pro Thr Asn Gly Tyr Thr
    50                  55                  60

Arg Tyr Ala Asp Ser Val Lys Gly Arg Phe Thr Ile Ser Ala Asp Thr
65                  70                  75                  80

Ser Lys Asn Thr Ala Tyr Leu Gln Met Asn Ser Leu Arg Ala Glu Asp
                85                  90                  95

Thr Ala Val Tyr Tyr Cys Ser Arg Trp Gly Gly Asp Gly Phe Tyr Ala
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335
```

```
Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
        450                 455

<210> SEQ ID NO 191
<211> LENGTH: 479
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 191

Met Leu Leu Leu Ala Arg Cys Leu Leu Leu Val Leu Val Ser Ser Leu
1               5                   10                  15

Leu Val Cys Ser Gly Leu Ala Cys Asp Lys Thr His Thr Glu Val Gln
            20                  25                  30

Leu Val Glu Ser Gly Gly Gly Leu Val Gln Pro Gly Gly Ser Leu Arg
        35                  40                  45

Leu Ser Cys Ala Ala Ser Gly Phe Asn Ile Lys Asp Thr Tyr Ile His
    50                  55                  60

Trp Val Arg Gln Ala Pro Gly Lys Gly Leu Glu Trp Val Ala Arg Ile
65                  70                  75                  80

Tyr Pro Thr Asn Gly Tyr Thr Arg Tyr Ala Asp Ser Val Lys Gly Arg
                85                  90                  95

Phe Thr Ile Ser Ala Asp Thr Ser Lys Asn Thr Ala Tyr Leu Gln Met
            100                 105                 110

Asn Ser Leu Arg Ala Glu Asp Thr Ala Val Tyr Tyr Cys Ser Arg Trp
        115                 120                 125

Gly Gly Asp Gly Phe Tyr Ala Met Asp Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240
```

```
Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 192
<211> LENGTH: 479
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 192

Met Ala Leu Thr Phe Ala Leu Leu Val Ala Leu Leu Val Leu Ser Cys
1               5                   10                  15

Lys Ser Ser Cys Ser Val Gly Cys Asp Lys Thr His Thr Glu Val Gln
            20                  25                  30

Leu Val Glu Ser Gly Gly Gly Leu Val Gln Pro Gly Gly Ser Leu Arg
        35                  40                  45

Leu Ser Cys Ala Ala Ser Gly Phe Asn Ile Lys Asp Thr Tyr Ile His
    50                  55                  60

Trp Val Arg Gln Ala Pro Gly Lys Gly Leu Glu Trp Val Ala Arg Ile
65                  70                  75                  80

Tyr Pro Thr Asn Gly Tyr Thr Arg Tyr Ala Asp Ser Val Lys Gly Arg
                85                  90                  95

Phe Thr Ile Ser Ala Asp Thr Ser Lys Asn Thr Ala Tyr Leu Gln Met
            100                 105                 110

Asn Ser Leu Arg Ala Glu Asp Thr Ala Val Tyr Tyr Cys Ser Arg Trp
```

```
            115                 120                 125
Gly Gly Asp Gly Phe Tyr Ala Met Asp Tyr Trp Gly Gln Gly Thr Leu
            130                 135                 140
Val Thr Val Ser Ser Ala Ser Thr Lys Gly Pro Ser Val Phe Pro Leu
145                 150                 155                 160
Ala Pro Ser Ser Lys Ser Thr Ser Gly Gly Thr Ala Ala Leu Gly Cys
                    165                 170                 175
Leu Val Lys Asp Tyr Phe Pro Glu Pro Val Thr Val Ser Trp Asn Ser
                180                 185                 190
Gly Ala Leu Thr Ser Gly Val His Thr Phe Pro Ala Val Leu Gln Ser
            195                 200                 205
Ser Gly Leu Tyr Ser Leu Ser Ser Val Val Thr Val Pro Ser Ser Ser
        210                 215                 220
Leu Gly Thr Gln Thr Tyr Ile Cys Asn Val Asn His Lys Pro Ser Asn
225                 230                 235                 240
Thr Lys Val Asp Lys Lys Val Glu Pro Lys Ser Cys Asp Lys Thr His
                    245                 250                 255
Thr Cys Pro Pro Cys Pro Ala Pro Glu Leu Leu Gly Gly Pro Ser Val
                260                 265                 270
Phe Leu Phe Pro Pro Lys Pro Lys Asp Thr Leu Met Ile Ser Arg Thr
            275                 280                 285
Pro Glu Val Thr Cys Val Val Val Asp Val Ser His Glu Asp Pro Glu
        290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                    325                 330                 335
Val Leu Thr Val Leu His Gln Asp Trp Leu Asn Gly Lys Glu Tyr Lys
                340                 345                 350
Cys Lys Val Ser Asn Lys Ala Leu Pro Ala Pro Ile Glu Lys Thr Ile
            355                 360                 365
Ser Lys Ala Lys Gly Gln Pro Arg Glu Pro Gln Val Tyr Thr Leu Pro
370                 375                 380
Pro Ser Arg Asp Glu Leu Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                    405                 410                 415
Gly Gln Pro Glu Asn Asn Tyr Lys Thr Thr Pro Pro Val Leu Asp Ser
                420                 425                 430
Asp Gly Ser Phe Phe Leu Tyr Ser Lys Leu Thr Val Asp Lys Ser Arg
            435                 440                 445
Trp Gln Gln Gly Asn Val Phe Ser Cys Ser Val Met His Glu Ala Leu
        450                 455                 460
His Asn His Tyr Thr Gln Lys Ser Leu Ser Leu Ser Pro Gly Lys
465                 470                 475

<210> SEQ ID NO 193
<211> LENGTH: 473
<212> TYPE: PRT
<213> ORGANISM: Artificial Sequence
<220> FEATURE:
<223> OTHER INFORMATION: pre-heavy chain chimeric polypeptide having
      CETP signal peptide

<400> SEQUENCE: 193
```

```
Met Leu Ala Ala Thr Val Leu Thr Leu Ala Leu Leu Gly Asn Ala His
1               5                   10                  15

Ala Cys Asp Lys Thr His Thr Glu Val Gln Leu Val Glu Ser Gly Gly
            20                  25                  30

Gly Leu Val Gln Pro Gly Gly Ser Leu Arg Leu Ser Cys Ala Ala Ser
            35                  40                  45

Gly Phe Asn Ile Lys Asp Thr Tyr Ile His Trp Val Arg Gln Ala Pro
        50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
            85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
            115                 120                 125

Ala Met Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
```

```
                420             425             430
Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470

<210> SEQ ID NO 194
<211> LENGTH: 453
<212> TYPE: PRT
<213> ORGANISM: Artificial Sequence
<220> FEATURE:
<223> OTHER INFORMATION: Trastuzumab heavy chain having the N-terminal
      sequence CVE

<400> SEQUENCE: 194

Cys Val Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Ile
                20                  25                  30

Lys Asp Thr Tyr Ile His Trp Val Arg Gln Ala Pro Gly Lys Gly Leu
            35                  40                  45

Glu Trp Val Ala Arg Ile Tyr Pro Thr Asn Gly Tyr Thr Arg Tyr Ala
50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ser Arg Trp Gly Gly Asp Gly Phe Tyr Ala Met Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 195
<211> LENGTH: 476
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 195

Met Leu Leu Leu Ala Arg Cys Leu Leu Leu Val Leu Val Ser Ser Leu
1               5                   10                  15

Leu Val Cys Ser Gly Leu Ala Cys Val Glu Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Phe Asn Ile Lys Asp Thr Tyr Ile His Trp Val Arg
    50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
                85                  90                  95

Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
        115                 120                 125

Gly Phe Tyr Ala Met Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

```
Tyr Ser Leu Ser Ser Val Val Thr Val Pro Ser Ser Leu Gly Thr
        210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
450                 455                 460

Tyr Thr Gln Lys Ser Leu Ser Leu Ser Pro Gly Lys
465                 470                 475

<210> SEQ ID NO 196
<211> LENGTH: 476
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 196

Met Ala Leu Thr Phe Ala Leu Leu Val Ala Leu Leu Val Leu Ser Cys
1               5                   10                  15

Lys Ser Ser Cys Ser Val Gly Cys Val Glu Val Gln Leu Val Glu
                20                  25                  30

Ser Gly Gly Gly Leu Val Gln Pro Gly Gly Ser Leu Arg Leu Ser Cys
            35                  40                  45

Ala Ala Ser Gly Phe Asn Ile Lys Asp Thr Tyr Ile His Trp Val Arg
        50                  55                  60

Gln Ala Pro Gly Lys Gly Leu Glu Trp Val Ala Arg Ile Tyr Pro Thr
65                  70                  75                  80

Asn Gly Tyr Thr Arg Tyr Ala Asp Ser Val Lys Gly Arg Phe Thr Ile
```

```
                85                  90                  95
Ser Ala Asp Thr Ser Lys Asn Thr Ala Tyr Leu Gln Met Asn Ser Leu
            100                 105                 110

Arg Ala Glu Asp Thr Ala Val Tyr Tyr Cys Ser Arg Trp Gly Gly Asp
        115                 120                 125

Gly Phe Tyr Ala Met Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 197
<211> LENGTH: 470
<212> TYPE: PRT
<213> ORGANISM: Artificial Sequence
```

<220> FEATURE:
<223> OTHER INFORMATION: pre-heavy chain chimeric polypeptide having CETP signal peptide

<400> SEQUENCE: 197

```
Met Leu Ala Ala Thr Val Leu Thr Leu Ala Leu Leu Gly Asn Ala His
1               5                   10                  15

Ala Cys Val Glu Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
```

```
                385                 390                 395                 400
Ala Val Glu Trp Glu Ser Asn Gly Gln Pro Glu Asn Asn Tyr Lys Thr
                    405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 198
<211> LENGTH: 456
<212> TYPE: PRT
<213> ORGANISM: Artificial Sequence
<220> FEATURE:
<223> OTHER INFORMATION: Trastuzumab heavy chain having the N-terminal
      sequence CDTPPP

<400> SEQUENCE: 198

Cys Asp Thr Pro Pro Glu Val Gln Leu Val Glu Ser Gly Gly Gly
1               5                   10                  15

Leu Val Gln Pro Gly Gly Ser Leu Arg Leu Ser Cys Ala Ala Ser Gly
            20                  25                  30

Phe Asn Ile Lys Asp Thr Tyr Ile His Trp Val Arg Gln Ala Pro Gly
        35                  40                  45

Lys Gly Leu Glu Trp Val Ala Arg Ile Tyr Pro Thr Asn Gly Tyr Thr
    50                  55                  60

Arg Tyr Ala Asp Ser Val Lys Gly Arg Phe Thr Ile Ser Ala Asp Thr
65                  70                  75                  80

Ser Lys Asn Thr Ala Tyr Leu Gln Met Asn Ser Leu Arg Ala Glu Asp
                85                  90                  95

Thr Ala Val Tyr Tyr Cys Ser Arg Trp Gly Gly Asp Gly Phe Tyr Ala
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270
```

```
Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
                435                 440                 445

Ser Leu Ser Leu Ser Pro Gly Lys
    450                 455

<210> SEQ ID NO 199
<211> LENGTH: 479
<212> TYPE: PRT
<213> ORGANISM: Artificial Sequence
<220> FEATURE:
<223> OTHER INFORMATION: pre-heavy chain chimeric polypeptide having SHH
      signal peptide

<400> SEQUENCE: 199

Met Leu Leu Leu Ala Arg Cys Leu Leu Leu Val Leu Val Ser Ser Leu
1               5                   10                  15

Leu Val Cys Ser Gly Leu Ala Cys Asp Thr Pro Pro Glu Val Gln
            20                  25                  30

Leu Val Glu Ser Gly Gly Gly Leu Val Gln Pro Gly Gly Ser Leu Arg
        35                  40                  45

Leu Ser Cys Ala Ala Ser Gly Phe Asn Ile Lys Asp Thr Tyr Ile His
    50                  55                  60

Trp Val Arg Gln Ala Pro Gly Lys Gly Leu Glu Trp Val Ala Arg Ile
65                  70                  75                  80

Tyr Pro Thr Asn Gly Tyr Thr Arg Tyr Ala Asp Ser Val Lys Gly Arg
                85                  90                  95

Phe Thr Ile Ser Ala Asp Thr Ser Lys Asn Thr Ala Tyr Leu Gln Met
            100                 105                 110

Asn Ser Leu Arg Ala Glu Asp Thr Ala Val Tyr Tyr Cys Ser Arg Trp
        115                 120                 125

Gly Gly Asp Gly Phe Tyr Ala Met Asp Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175
```

```
Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 200
<211> LENGTH: 479
<212> TYPE: PRT
<213> ORGANISM: Artificial Sequence
<220> FEATURE:
<223> OTHER INFORMATION: pre-heavy chain chimeric polypeptide having IFN
      signal peptide

<400> SEQUENCE: 200

Met Ala Leu Thr Phe Ala Leu Leu Val Ala Leu Leu Val Leu Ser Cys
1               5                   10                  15

Lys Ser Ser Cys Ser Val Gly Cys Asp Thr Pro Pro Glu Val Gln
            20                  25                  30

Leu Val Glu Ser Gly Gly Gly Leu Val Gln Pro Gly Gly Ser Leu Arg
        35                  40                  45

Leu Ser Cys Ala Ala Ser Gly Phe Asn Ile Lys Asp Thr Tyr Ile His
```

-continued

```
                50                  55                  60
Trp Val Arg Gln Ala Pro Gly Lys Gly Leu Glu Trp Val Ala Arg Ile
 65                  70                  75                  80
Tyr Pro Thr Asn Gly Tyr Thr Arg Tyr Ala Asp Ser Val Lys Gly Arg
                     85                  90                  95
Phe Thr Ile Ser Ala Asp Thr Ser Lys Asn Thr Ala Tyr Leu Gln Met
                100                 105                 110
Asn Ser Leu Arg Ala Glu Asp Thr Ala Val Tyr Tyr Cys Ser Arg Trp
                115                 120                 125
Gly Gly Asp Gly Phe Tyr Ala Met Asp Tyr Trp Gly Gln Gly Thr Leu
            130                 135                 140
Val Thr Val Ser Ser Ala Ser Thr Lys Gly Pro Ser Val Phe Pro Leu
145                 150                 155                 160
Ala Pro Ser Ser Lys Ser Thr Ser Gly Gly Thr Ala Ala Leu Gly Cys
                165                 170                 175
Leu Val Lys Asp Tyr Phe Pro Glu Pro Val Thr Val Ser Trp Asn Ser
                180                 185                 190
Gly Ala Leu Thr Ser Gly Val His Thr Phe Pro Ala Val Leu Gln Ser
                195                 200                 205
Ser Gly Leu Tyr Ser Leu Ser Ser Val Val Thr Val Pro Ser Ser Ser
            210                 215                 220
Leu Gly Thr Gln Thr Tyr Ile Cys Asn Val Asn His Lys Pro Ser Asn
225                 230                 235                 240
Thr Lys Val Asp Lys Lys Val Glu Pro Lys Ser Cys Asp Lys Thr His
                245                 250                 255
Thr Cys Pro Pro Cys Pro Ala Pro Glu Leu Leu Gly Gly Pro Ser Val
                260                 265                 270
Phe Leu Phe Pro Pro Lys Pro Lys Asp Thr Leu Met Ile Ser Arg Thr
                275                 280                 285
Pro Glu Val Thr Cys Val Val Val Asp Val Ser His Glu Asp Pro Glu
            290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Glu Tyr Lys
                340                 345                 350
Cys Lys Val Ser Asn Lys Ala Leu Pro Ala Pro Ile Glu Lys Thr Ile
                355                 360                 365
Ser Lys Ala Lys Gly Gln Pro Arg Glu Pro Gln Val Tyr Thr Leu Pro
370                 375                 380
Pro Ser Arg Asp Glu Leu Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
                420                 425                 430
Asp Gly Ser Phe Phe Leu Tyr Ser Lys Leu Thr Val Asp Lys Ser Arg
            435                 440                 445
Trp Gln Gln Gly Asn Val Phe Ser Cys Ser Val Met His Glu Ala Leu
            450                 455                 460
His Asn His Tyr Thr Gln Lys Ser Leu Ser Leu Ser Pro Gly Lys
465                 470                 475
```

<210> SEQ ID NO 201
<211> LENGTH: 473
<212> TYPE: PRT
<213> ORGANISM: Artificial Sequence
<220> FEATURE:
<223> OTHER INFORMATION: pre-heavy chain chimeric polypeptide having CETP signal peptide

<400> SEQUENCE: 201

```
Met Leu Ala Ala Thr Val Leu Thr Leu Ala Leu Leu Gly Asn Ala His
1               5                   10                  15

Ala Cys Asp Thr Pro Pro Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asn Ile Lys Asp Thr Tyr Ile His Trp Val Arg Gln Ala Pro
    50                  55                  60

Gly Lys Gly Leu Glu Trp Val Ala Arg Ile Tyr Pro Thr Asn Gly Tyr
65                  70                  75                  80

Thr Arg Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ser Arg Trp Gly Gly Asp Gly Phe Tyr
        115                 120                 125

Ala Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
```

```
                355                 360                 365
Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470

<210> SEQ ID NO 202
<211> LENGTH: 31
<212> TYPE: PRT
<213> ORGANISM: Homo sapiens

<400> SEQUENCE: 202

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 203
<211> LENGTH: 22
<212> TYPE: DNA
<213> ORGANISM: Homo sapiens

<400> SEQUENCE: 203
agaggtagta ggttgcatag tt                                          22

<210> SEQ ID NO 204
<211> LENGTH: 237
<212> TYPE: PRT
<213> ORGANISM: Artificial Sequence
<220> FEATURE:
<223> OTHER INFORMATION: TNR1B

<400> SEQUENCE: 204

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
```

```
            115                 120                 125
Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Cys
225                 230                 235
```

<210> SEQ ID NO 205
<211> LENGTH: 222
<212> TYPE: PRT
<213> ORGANISM: Artificial Sequence
<220> FEATURE:
<223> OTHER INFORMATION: Fc6

<400> SEQUENCE: 205

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 206
<211> LENGTH: 5
<212> TYPE: PRT

```
<213> ORGANISM: Artificial Sequence
<220> FEATURE:
<223> OTHER INFORMATION: N-Terminus Sequence

<400> SEQUENCE: 206

Cys Pro Pro Cys Pro
1               5

<210> SEQ ID NO 207
<211> LENGTH: 5
<212> TYPE: PRT
<213> ORGANISM: Artificial Sequence
<220> FEATURE:
<223> OTHER INFORMATION: N-Terminal Sequence

<400> SEQUENCE: 207

Cys Pro Arg Cys Pro
1               5

<210> SEQ ID NO 208
<211> LENGTH: 5
<212> TYPE: PRT
<213> ORGANISM: Artificial Sequence
<220> FEATURE:
<223> OTHER INFORMATION: N-Terminal Sequence

<400> SEQUENCE: 208

Cys Pro Ser Cys Pro
1               5

<210> SEQ ID NO 209
<211> LENGTH: 11
<212> TYPE: PRT
<213> ORGANISM: Artificial Sequence
<220> FEATURE:
<223> OTHER INFORMATION: N-Terminal Sequence

<400> SEQUENCE: 209

Cys Asp Lys Thr His Thr Cys Pro Pro Cys Pro
1               5                   10

<210> SEQ ID NO 210
<211> LENGTH: 8
<212> TYPE: PRT
<213> ORGANISM: Artificial Sequence
<220> FEATURE:
<223> OTHER INFORMATION: N-Terminal Sequence

<400> SEQUENCE: 210

Cys Val Glu Cys Pro Pro Cys Pro
1               5

<210> SEQ ID NO 211
<211> LENGTH: 9
<212> TYPE: PRT
<213> ORGANISM: Artificial Sequence
<220> FEATURE:
<223> OTHER INFORMATION: N-Terminal Sequence

<400> SEQUENCE: 211

Cys Cys Val Glu Cys Pro Pro Cys Pro
1               5

<210> SEQ ID NO 212
<211> LENGTH: 11
<212> TYPE: PRT
<213> ORGANISM: Artificial Sequence
```

<220> FEATURE:
<223> OTHER INFORMATION: N-Terminal Sequence

<400> SEQUENCE: 212

Cys Asp Thr Pro Pro Cys Pro Arg Cys Pro
1               5                   10

<210> SEQ ID NO 213
<211> LENGTH: 15
<212> TYPE: PRT
<213> ORGANISM: Artificial
<220> FEATURE:
<223> OTHER INFORMATION: Sequence of component "B"

<400> SEQUENCE: 213

Glu Pro Lys Ser Cys Asp Lys Thr His Thr Cys Pro Pro Cys Pro
1               5                   10                  15

<210> SEQ ID NO 214
<211> LENGTH: 12
<212> TYPE: PRT
<213> ORGANISM: Artificial
<220> FEATURE:
<223> OTHER INFORMATION: Sequence of component "B"

<400> SEQUENCE: 214

Glu Arg Lys Cys Cys Val Glu Cys Pro Pro Cys Pro
1               5                   10

<210> SEQ ID NO 215
<211> LENGTH: 62
<212> TYPE: PRT
<213> ORGANISM: Artificial
<220> FEATURE:
<223> OTHER INFORMATION: Sequence of component "B"

<400> SEQUENCE: 215

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
    50                  55                  60

<210> SEQ ID NO 216
<211> LENGTH: 12
<212> TYPE: PRT
<213> ORGANISM: Artificial
<220> FEATURE:
<223> OTHER INFORMATION: Sequence of component "B"

<400> SEQUENCE: 216

Glu Ser Lys Tyr Gly Pro Pro Cys Pro Ser Cys Pro
1               5                   10

<210> SEQ ID NO 217
<211> LENGTH: 6
<212> TYPE: PRT
<213> ORGANISM: Artificial
<220> FEATURE:
<223> OTHER INFORMATION: Sequence in linker

<400> SEQUENCE: 217

```
Asp Lys Thr His Thr Cys
1               5
```

<210> SEQ ID NO 218
<211> LENGTH: 5
<212> TYPE: PRT
<213> ORGANISM: Artificial
<220> FEATURE:
<223> OTHER INFORMATION: Sequence in adalimumab Fab

<400> SEQUENCE: 218

```
Cys Asp Lys Thr His
1               5
```

<210> SEQ ID NO 219
<211> LENGTH: 4
<212> TYPE: PRT
<213> ORGANISM: Artificial
<220> FEATURE:
<223> OTHER INFORMATION: Hinge sequence

<400> SEQUENCE: 219

```
Asp Lys Thr His
1
```

<210> SEQ ID NO 220
<211> LENGTH: 5
<212> TYPE: PRT
<213> ORGANISM: Artificial
<220> FEATURE:
<223> OTHER INFORMATION: Hinge sequence

<400> SEQUENCE: 220

```
Asp Lys Thr His Thr
1               5
```

<210> SEQ ID NO 221
<211> LENGTH: 13
<212> TYPE: PRT
<213> ORGANISM: Artificial
<220> FEATURE:
<223> OTHER INFORMATION: N-terminal region of alkyne-modified TNR1B
      sequence

<400> SEQUENCE: 221

```
Glu Tyr Tyr Asp Gln Thr Ala Gln Met Cys Cys Ser Lys
1               5                   10
```

<210> SEQ ID NO 222
<211> LENGTH: 15
<212> TYPE: PRT
<213> ORGANISM: Artificial
<220> FEATURE:
<223> OTHER INFORMATION: C-terminal region of alkyne-modified TNR1B
      sequence

<400> SEQUENCE: 222

```
Ser Met Ala Pro Gly Ala Val His Leu Pro Gln Pro Val Ser Thr
1               5                   10                  15
```

<210> SEQ ID NO 223
<211> LENGTH: 7
<212> TYPE: PRT
<213> ORGANISM: Artificial
<220> FEATURE:
<223> OTHER INFORMATION: N-terminal region of azide-modified Fc6 protein
      sequence

```
<400> SEQUENCE: 223

Asp Thr Leu Met Ile Ser Arg
1               5

<210> SEQ ID NO 224
<211> LENGTH: 18
<212> TYPE: PRT
<213> ORGANISM: Artificial
<220> FEATURE:
<223> OTHER INFORMATION: C-terminal region of azide-modified Fc6 protein
      sequence

<400> SEQUENCE: 224

Thr Thr Pro Pro Pro Val Leu Asp Ser Asp Gly Ser Phe Phe Leu Tyr
1               5                   10                  15

Ser Lys

<210> SEQ ID NO 225
<211> LENGTH: 18
<212> TYPE: PRT
<213> ORGANISM: Artificial
<220> FEATURE:
<223> OTHER INFORMATION: Portion of adalimumab Fab

<400> SEQUENCE: 225

Cys Asp Lys Thr His Thr Cys Pro Pro Cys Pro Ala Pro Glu Leu Leu
1               5                   10                  15

Gly Gly

<210> SEQ ID NO 226
<211> LENGTH: 17
<212> TYPE: PRT
<213> ORGANISM: Artificial
<220> FEATURE:
<223> OTHER INFORMATION: Portion of adalimumab Fab

<400> SEQUENCE: 226

Cys Asp Lys Thr His Thr Cys Pro Pro Cys Pro Ala Pro Glu Leu Leu
1               5                   10                  15

Gly
```